US010482997B2

(12) United States Patent
Blundell et al.

(10) Patent No.: US 10,482,997 B2
(45) Date of Patent: Nov. 19, 2019

(54) METHOD FOR DETERMINING THREE-DIMENSIONAL STRUCTURES OF DYNAMIC MOLECULES

(75) Inventors: Charles Douglas Blundell, Manchester (GB); Andrew Almond, Manchester (GB)

(73) Assignee: Conformetrix Limited, Manchester (GB)

( * ) Notice: Subject to any disclaimer, the term of this patent is extended or adjusted under 35 U.S.C. 154(b) by 916 days.

(21) Appl. No.: 12/677,726

(22) PCT Filed: Sep. 3, 2008

(86) PCT No.: PCT/GB2008/002973
§ 371 (c)(1),
(2), (4) Date: Mar. 11, 2010

(87) PCT Pub. No.: WO2009/034297
PCT Pub. Date: Mar. 19, 2009

(65) Prior Publication Data
US 2010/0191517 A1    Jul. 29, 2010

(30) Foreign Application Priority Data
Sep. 14, 2007    (GB) .................................. 0718027.6

(51) Int. Cl.
*G01N 31/00*    (2006.01)
*G16C 20/80*    (2019.01)
*G16B 15/00*    (2019.01)
*G16C 10/00*    (2019.01)

(52) U.S. Cl.
CPC ............. *G16C 20/80* (2019.02); *G16B 15/00* (2019.02); *G16C 10/00* (2019.02)

(58) Field of Classification Search
None
See application file for complete search history.

(56) References Cited

PUBLICATIONS

Brooks et al. "CHARMM: A Program for Macromolecular Energy, Minimization, and Dynamics Calculations" (Journal of Computational Chemistry, vol. 4 (1983) pp. 187-217).*
Bruschweiler et al. "Adding Harmonic Motion to the Karplus Relation for Spin-Spin Coupling" (J. Am. Chem. Soc. (1994) vol. 116,pp. 11199-11200).*
Kieffer et al. "Three-Dimensional Solution Structure of the Extracellular Region of the Complement Regulatory Protein CD59, a New Cell-Surface Protein Domain Related to Snake Venom Neurotoxinst" (Biochemistry vol. 33 (1994) 4471-4482).*
Zheng et al. "Molecular Simulation Study of Water Interactions with Oligo (Ethylene Glycol)-Terminated Alkanethiol Self-Assembled Monolayers" (Langmuir, vol. 20 (2004) pp. 8931-8938).*
Laskowski et al. "AQUA and PROCHECK-NMR: Programs for checking the quality of protein structures solved by NMR" (Journal of Biomolecular NMR, vol. 8 (1996) pp. 477-486).*
Cheng et al., "From Secondary Structure to Three-Dimensional Structure: Improved Dihedral Angle Probability Distribution Function for Use with Energy Searches for Native Structures of Polypeptides and Proteins," Journal of Computational Chemistry, vol. 17 (1996) pp. 1453-1480.*
Almond A et al: "Hyaluronan: The Local Solution Conformation Determined by NMR and Computer Modeling is Close to a Contracted Left-handed 4-Fold Helix" Journal of Molecular Biology, London, GB, vol. 358, No. 5, May 19, 2006 (May 19, 2006), pp. 1256-1269, XP024951008; ISSN: 0022-2836 [retrieved on May 19, 2006] p. 1257, left-hand column, line 35—right-hand column, line 59, p. 1258, right-hand column, lines 17-55, p. 1259, right-hand column, line 23—p. 1260, left-hand column, line 9, p. 1261, left-hand column, lines 19-24, p. 1261.
Guntert P et al: "Efficient computation of three-dimensional protein structures in solution from nuclear magnetic resonance data using the program DIANA and the supporting programs CALIBA, HABAS and GLOMSA" Journal of Molecular Biology, London, GB, vol. 217, No. 3, Feb. 5, 1991 (Feb. 5, 1991), pp. 517-530, XP024014293; ISSN: 0022-2836 [retrieved on Feb. 5, 1991] abstract p. 518, left-hand column, line 61—p. 519, left-hand column, line 4 p. 519, right-hand column, line 5—p. 520, left-hand column, line 3, figure 1, table 4.
Berndt Kurt D et al: "Conformational sampling by NMR solution structures calculated with the program DIANA evaluated by comparison with long-time molecular dynamics calculations in explicit water" Proteins Structure Function and Genetics, vol. 24, No. 3, 1996, pp. 304-313, XP002519007; ISSN: 0887-3585 abstract p. 305, right-hand column, lines 26-41, p. 306, right-hand column, lines 22-44, p. 309, left-hand column, line 41—right-hand column, line 24.
Guntert P et al: "Improved Efficiency of Protein Structure Calculations From NMR Data Using the Program Diana With Redundant Dihedral Angle Constraints" Journal of Biomolecular NMR, vol. 1, No. 4, 1991, pp. 447-456, XP008103443; ISSN: 0925-2738, p. 447, line 1—p. 449, line 10, p. 455, lines 1-5, table 2.
Leach, In Molecular Modelling: Principles and Applications, 2001, Second Edition, pp. 2-3, Pearson Education EMA.

(Continued)

*Primary Examiner* — Anna Skibinsky
(74) *Attorney, Agent, or Firm* — Michael Best & Friedrich LLP

(57) ABSTRACT

The present invention relates to a method for determining three-dimensional structures of molecules, particularly, but not exclusively, dynamic organic molecules of biological interest such as peptides, carbohydrates, proteins and drug molecules. A first aspect of the present invention provides a method for generating data representing an ensemble of three-dimensional structures of a molecule, the molecule comprising first and second atoms linked by at least one bond, said bond having an associated angle, and the angle varying to generate a plurality of three-dimensional structures of said molecule, the method comprising: receiving data representing said molecule, said data comprising data indicating variability of said angle; and generating an ensemble of structures such that the angle has an associated value selected based upon said variability. A second aspect of the present invention provides a computer implemented method for simulating the variability of the three-dimensional structure of a molecule.

23 Claims, 19 Drawing Sheets

(56) References Cited

PUBLICATIONS

Andreev et al., A general Monte Carlo approach to structure solution from powder-diffraction data, 1997, Journal of Applied Crystallography, 30, pp. 294-305.
Allinger, Conformational analysis. 130. MM2—hydrocarbon force-field utilizing v1 and v2 torisional terms, 1977, Journal of the American Chemical Society, 99, pp. 8127-8134.
Mandl, In Statistical physics., 1998, Second edition, pp. 31-67, Wiley.
Raeside, Monte-Carlo principles and applications, 1976, Physics in Medicine and Biology, 21, pp. 181-197.
Farrow et al., Backbone dynamics of a free and a phosphopeptide-complexed SRC homology-2 domain studied by 15N-NMR relaxation, 1994, Biochemistry, 33, 5984-6003.
Almond et al., Comparison of aqueous molecular dynamics with NMR relaxation and residual dipolar couplings favors internal motion in a mannose oligosaccharide, 2001, Journal of the American Chemical Society, 123, pp. 4792-4802.
Almond et al., Dynamics of hyaluronan oligosaccharides revealed by 15N relaxation, 2005, Journal of the American Chemical Society, 127, pp. 1086-1087.
Mackeen et al., The importance of including local correlation times in the calculation of inter-proton distances from NMR measurements: ignoring local correlation times leads to significant errors in the conformational analysis of the Glc alpha 1-2Glc alpha linkage by NMR spectroscopy, 2006, Organic and Biomolecular Chemistry, 4, pp. 2241-2246.
Noggle et al., The nuclear Overhauser effect: chemical applications, 1971, Academic Press, New York pp. 1-95.
Lipari et al., Model-free approach to the interpretation of nuclear magnetic resonance relaxation in macromolecules. 1. Theory and range of validity, 1982, Journal of the American Chemical Society, 104, pp. 4546-4559.
Günter, In NMR spectroscopy: basic principles, concepts and applications in chemistry, 1994, Second edition, pp. 115-117, John Wiley & sons, New York.
Prestegard et al., NMR structures of biomolecules using field oriented media and residual dipolar couplings, 2000, Quarterly Reviews of Biophysics, 33, pp. 371-424.
Sykes, In a guidebook to mechanism in organic chemistry, 1986, pp. 4-5, Wiley, New York.
Sykes, In a guidebook to mechanism in organic chemistry,1986, p. 7, Wiley, New York.
Campbell et al., Protein-structure determination by NMR. Trends in Biotechnology, 1987, 5, pp. 302-306.
Friebolin, In Basic one- and two-dimensional NMR spectroscopy, 1991, VCH, Weinheim, pp. 110-127, 160-169, 180-303.
Liu et al., Improved WATERGATE pulse sequences for solvent suppression in NMR spectroscopy, 1998, Journal of Magnetic Resonance, 132, pp. 125-129.
Griesinger et al., Practical aspects of the E.COSY technique. Measurement of scalar spin-spin coupling-constants in peptides, 1987, Journal of Magnetic Resonance, 75, pp. 474-492.
Kuboniwa et al., Measurement of Hn-Ha J couplings in calcium-free calmodulin using new 2D and 3D water-flip-back methods, 1994, Journal of Biomolecular NMR, 4, pp. 871-878.
Poveda et al., Solution conformation and dynamics of a tetrasaccharide related to the Lewis(X) antigen deduced by 1-H NMR NOESY, ROESY, and T-ROESY measurements, 1997, Carbohydrate Research, 300, pp. 3-10.
Lemieux et al., Observations on the Karplus curve in relation to conformation of 1,3-dioxolane ring, 1962, Canadian Journal of Chemistry-Revue Canadienne De Chimie., 40, pp. 1955-1959.
Haasnoot et al., The Relationship between Proton-Proton NMR Coupling-Constants and Substituent Electronegativities-I: An Empirical Generalization of the Karplus Equation, 1980, Tetrahedron, 36, pp. 2783-2792.
Deprex-Poulain et al., Facts, figures and trends in lead generation, 2004, Current Topics in Medicinal Chemistry, 4, pp. 569-580.
Banerji et al., Structures of the Cd44-hyaluronan complex provide insight into a fundamental carbohydrate-protein interaction, 2007, Nature Structural & Molecular Biology. 14, pp. 234-239.
Alonso et al., Combining docking and molecular dynamics simulations in drug design, 2006, Medical Research Reviews, 26, pp. 531-568.
Blundell et al., Enzymatic and chemical methods for the generation of pure hyaluronan oligosaccharides with both odd and even numbers of monosaccharide units, 2006, Analytical Biochemistry, 353, pp. 236-247.
Blundell et al., Use of 15-N-NMR to resolve molecular details in isotopically-enriched carbohydrates: sequence-specific observations in hyaluronan oligomers up to decasaccharides, 2004, Glycobiology, 14, pp. 999-1009.
Blundell et al., Complete assignment of hyaluronan oligosaccharides up to hexasaccharides, 2006, Carbohydrate Research, 341, pp. 2803-2815.
Blundell et al., Hyaluronan: the absence of amide-carboxylate hydrogen bonds and the chain conformation in aqueous solution are incompatible with stable secondary and tertiary structure models, 2006, Biochemical Journal, 396, pp. 487-498.
Mobli et al., N-Acetylated amino sugars: the dependence of NMR 3J(HNH2)-couplings on conformation, dynamics and solvent, 2007, Organic and Biomolecular Chemistry, 5, pp. 2243-2251.
Johnson, The crystal structure of N-acetyl-alpha-D-glucosamine, 1966, Acta Crystallographica, 21, pp. 885-891.
Perez et al., Self-consistent Karplus parametrization of (3)J couplings depending on the polypeptide side-chain torsion chi(1), 2001, Journal of the American Chemical Society, 123 , pp. 7081-7093.
Schubert et al., A software tool for the prediction of Xaa-Pro peptide bond conformations in proteins based on C-13 chemical shift statistics, 2002, Journal of Biomolecular NMR, 24, pp. 149-154.
Natesh et al., Crystal structure of the human angiotensin-converting enzyme-lisinopril complex, 2003, Nature, 421, pp. 551-554.
Cornilescu et al., Protein backbone angle restraints from searching a database for chemical shift and sequence homology, 1999, Journal of Biomolecular NMR, 13, pp. 289-302.
Blundell et al., Temperature dependencies of amide 1H- and 15N-chemical shifts in hyaluronan oligosaccharides, 2007, Magnetic Resonance Chemistry, 45, pp. 430-433.
Cierpicki et al., Amide proton temperature coefficients as hydrogen bond indicators in proteins, 2001, Journal of Biomolecular NMR, 21(3), pp. 249-261.
Bostrom et al., Conformational energy penalties of protein-bounds ligands, 1998, Journal of Computer-Aided Molecular Design, 12, pp. 383-396.
Mobli et al., The structural plasticity of heparin sulphate NA-domains and hence their role in mediating multivalent interactions is confirmed by high-accuracy 15N-NMR relaxation studies, 2008, Glycoconjugate Journal, 25, pp. 401-414.
Office Action from the Japanese Intellectual Property Office for Application No. 2010-524562 dated Aug. 6, 2013 (3 pages).
Meguro, et al., "New Structure Deformation Algorithm for Monte Carlo Simulation of Protein Folding," brochure (2002) 14 pages.

* cited by examiner

Simple scaling factor sets.
no scalar couplings
$c = 0$
$f = \{1\}$
one scalar coupling
$J_1 > \lambda$
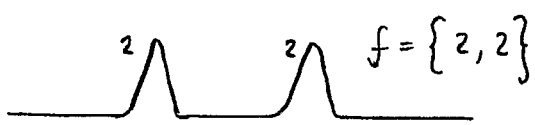
$f = \{2, 2\}$
two scalar couplings
$J_1 > \lambda$
$J_2 > \lambda$
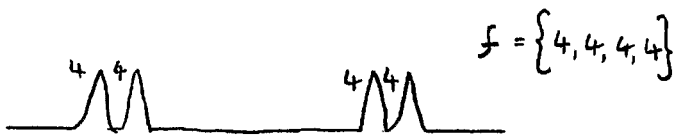
$f = \{4, 4, 4, 4\}$
three scalar couplings
$J_1 > \lambda$
$J_2 > \lambda$
$J_3 > \lambda$
$f = \{8, 8, 8, 8, 8, 8, 8, 8\}$
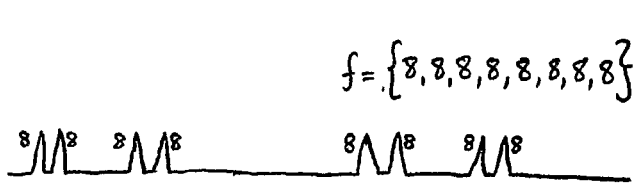
Figure 9

Ideal scaling factor sets.
one scalar coupling
$J > \lambda$
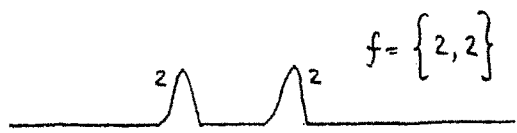
$f = \{2, 2\}$
two scalar couplings
$J_1 = J_2 > \lambda$
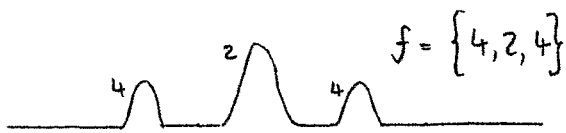
$f = \{4, 2, 4\}$
three scalar couplings
$J_1 = J_2 = J_3 > \lambda$
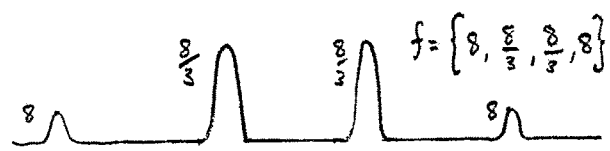
$f = \{8, \frac{8}{3}, \frac{8}{3}, 8\}$
four scalar couplings
$J_1 = J_2 = J_3 = J_4 > \lambda$
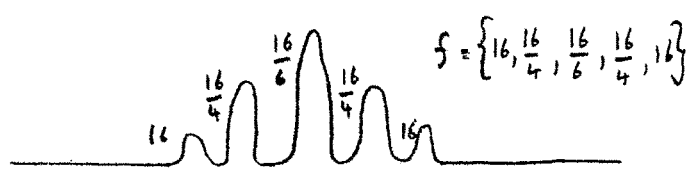
$f = \{16, \frac{16}{4}, \frac{16}{6}, \frac{16}{4}, 16\}$
Figure 10 no overlap, $\lambda \leq J$:

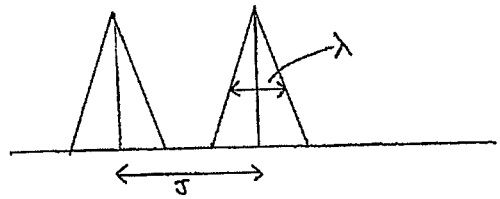

overlap due to J coupling $< \lambda$:

appearance in spectrum:
experimental height e

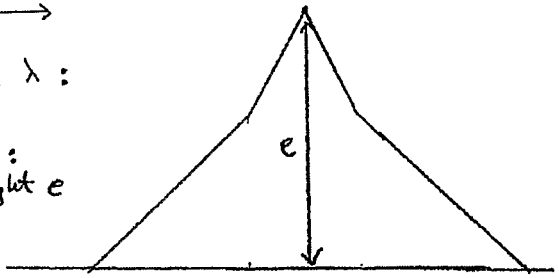

model with isosceles triangles:

$e = h + d$ by similar $\triangle s$,
$d = \frac{h}{\lambda}(\lambda - J)$ $\Rightarrow \frac{e}{h} = 1 + \left(\frac{\lambda - J}{\lambda}\right)$

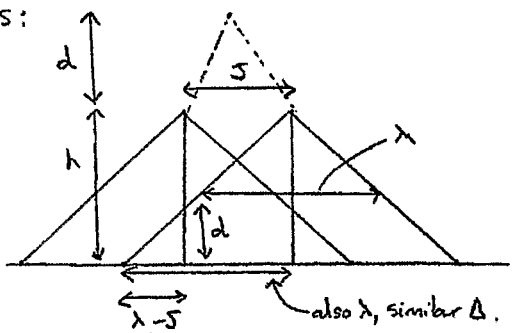

— also $\lambda$, similar $\triangle$.

for overlap factor, b, we want the value of $\frac{2h}{e}$ $b = 2 \cdot \frac{h}{e}$ $= \frac{2}{1 + \left(\frac{\lambda - J}{\lambda}\right)}$ $= \frac{2}{\left(\frac{2\lambda - J}{\lambda}\right)}$ $= \frac{2\lambda}{2\lambda - J} = \boxed{\frac{\lambda}{\lambda - \frac{J}{2}}}$

Figure 11

CD44 + hyaluronan
1.3 Å resolution
co-complex structure hyaluronan mean solution structure
vs
structure when bound to receptor CD44
RMSD all heavy atoms 2.3 Å

→ GlcNAc → GlcAc →

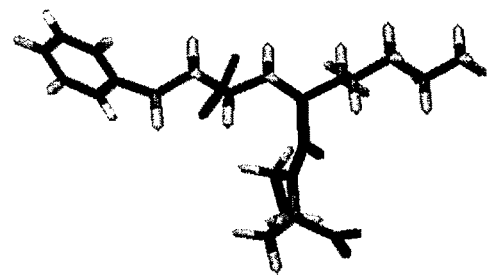
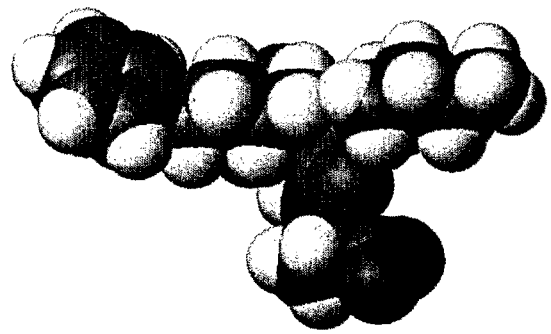
Figure 27
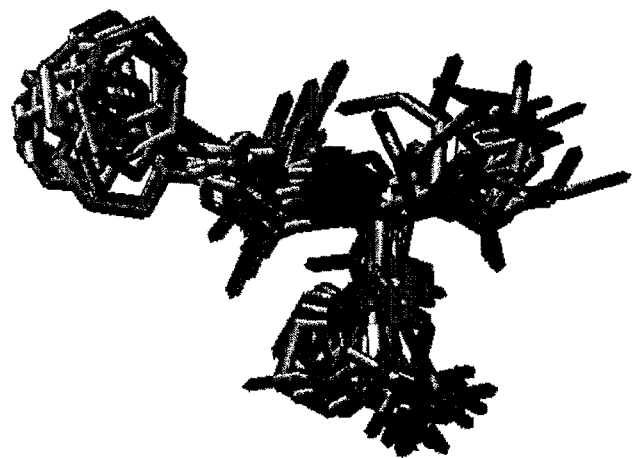
Figure 28

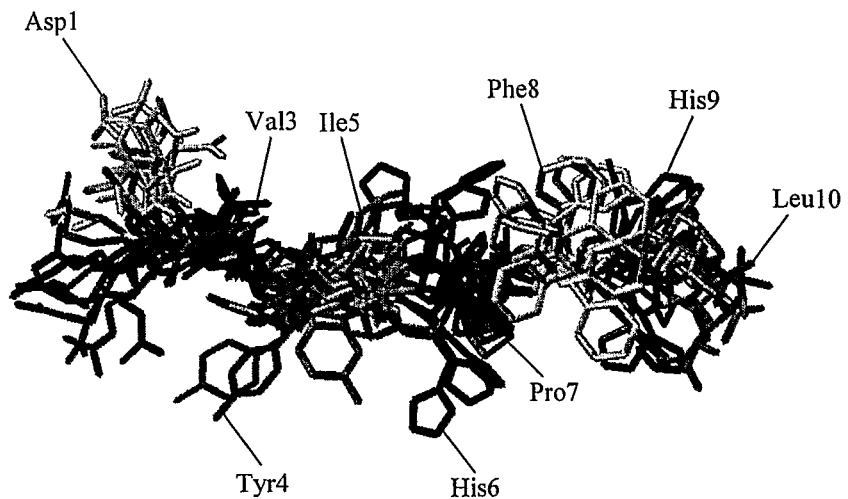
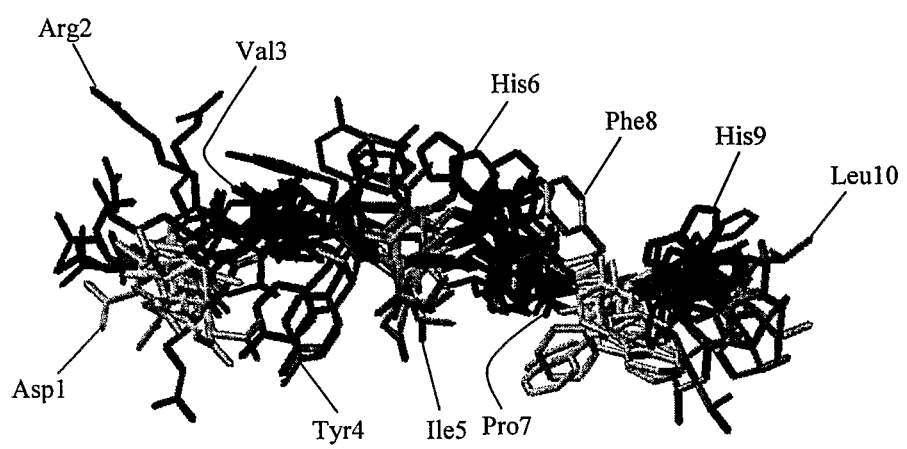
Figure 30

METHOD FOR DETERMINING THREE-DIMENSIONAL STRUCTURES OF DYNAMIC MOLECULES

The present invention relates to a method for determining three-dimensional structures of molecules, particularly, but not exclusively, dynamic organic molecules of biological interest such as peptides, carbohydrates, proteins and drug molecules.

Many important molecules have intrinsically flexible and dynamic structures, for example, peptides, carbohydrates, antibiotics, organic drug molecules and proteins. In many biochemical analyses a knowledge of the three-dimensional (3D) structure of such molecules in solution is desirable, in order to understand their physicochemical properties, the effect of chemical modifications or how they interact with other molecules, such as proteins.

Current approaches often solely use computational molecular modelling to understand 3D-structure of molecules, which has significant uncertainly because molecular potential energy surfaces are not well understood in solution and experimental data is rarely incorporated into models of the molecule component of a system under study. One of the significant challenges with using experimental data to define the 3D-structure of small molecules is that they are often relatively disordered in solution, meaning that dynamics has to be taken into account and has meant that the problem of determining their 3D-structure in solution has remained largely unsolved. A procedure that can accurately define the 3D-structure of small molecules would enable many processes that have so far been regarded as inaccurate, such as rational drug design and virtual screening.

An object of the present invention is to obviate or mitigate drawbacks associated with current methods for determining the 3D-structure of molecules.

A first aspect of the present invention provides a method for generating data representing an ensemble of three-dimensional structures of a molecule, the molecule comprising first and second atoms linked by at least one bond, said bond having an associated angle, and the angle varying to generate a plurality of three-dimensional structures of said molecule, the method comprising:
  receiving data representing said molecule, said data comprising data indicating variability of said angle; and
  generating an ensemble of structures such that the angle has an associated value selected based upon said variability.

This aspect of the present invention provides a computational method for generating an ensemble of 3D-structures of a molecule which can then be utilised in a number of further applications. For example, in one preferred embodiment the ensemble of structures can be analysed to provide one or more types of predicted experimental data which can then be compared to corresponding real experimental data. The comparison can be used to drive an optimisation procedure whereby the ensemble of structures is modified a number of times and the comparison of predicted to experimental data repeated for each ensemble until the optimum ensemble of structures is identified which provides the closest comparison of real to predicted experimental data.

An important feature of a preferred embodiment of the invention is that it facilitates optimisation of an ensemble of 3D-molecular structures against one or more types of real experimental data simultaneously, which can be particularly important when one type of experimental data alone would be insufficient to properly characterise a solution 3D-structure of a molecule. This is exemplified below in Examples 1, 2 and 3.

A second aspect of the present invention provides a computer implemented method for simulating the variability of the three-dimensional structure of a molecule, the molecule comprising first and second atoms linked by at least one bond, said bond having an associated angle, and the angle varying to generate a plurality of three-dimensional structures of said molecule, the method comprising:
  receiving data representing said molecule, said data comprising data indicating variability of said angle;
  simulating the variability of the three-dimensional structure of the molecule based upon said data indicating variability of said angle; and
  generating an ensemble of structures such that the angle has an associated value selected based upon said simulating.

The present invention has applicability to a wide range of molecules, such as, but not limited to the following examples:
  1) carbohydrate ligands and carbohydrate-mimetics (e.g., aminoglycoside antibiotics);
  2) peptides and artificial peptide mimetics;
  3) drug molecule molecular flexibilities;
  4) flexible protein sidechains within an enzyme/receptor active site or protein-protein interaction site;
  5) flexible bases within nucleic acid molecules, (e.g, RNA aptamers); and
  6) proteins with several conformational states (e.g., integrins) and intrinsically unfolded proteins.

Projects requiring structural information on flexible molecules will dramatically benefit from dynamic structures generated according to the present invention, particularly those involving ligand-protein interactions, such as rational drug design, which relies upon interaction-energy predictions. Such predictions based on prior art models are currently poor (only ~10% of predicted molecules successfully bind to their receptor), because although enthalpic contributions can be estimated well, entropic contributions cannot. Using both the drug molecule's preferred structure (internal enthalpy) and dynamic motions (entropy) determined using the methodology according to the present invention will therefore result in significant improvements in hit identification and lead optimisation via rational drug design approaches [30]. Moreover, the methods of the present invention and the dynamic 3D-structures that are produced from them can be used to calculate the deviation of a free solution structure from its bound form which can then be used as an accurate scoring function to compare and select candidate molecules.

Example 4 below presents a series of results for different organic molecules which demonstrates the accuracy with which the methods of the present invention can predict the bioactive (i.e. ligand-bound) conformation of those molecules. Example 5 below describes how a comparison of the dynamic 3D structures of lisinopril and AngiotensinI generated using methods according to the present invention suggested a modification to the chemical structure of lisinopril that anticipated structural features of the next-generation ACE-inhibitor Benazeprilat. This result clearly demonstrates how the methods of the present invention can provide dynamic 3D structures that will greatly aid lead optimisation decisions by medicinal chemists.

A further application for 3D dynamic structures generated according to the methods of the present invention is in improved virtual screening results. The 3D dynamic structure of a natural ligand or drug can be used as a more accurate 3D conformational template or pharmacophore map for the query compound than theoretically-generated 3D conformations in virtual screening techniques that search for other molecules in a database that can have a similar shape to the query compound. Typically, to overcome uncertainty over the query compound's preferred shapes, virtual screening strategies use many conformational variants for each query. By employing the methodology of the present invention, these many potential derivatives can be replaced by a single or, at most, several key preferred conformations determined directly from experiment—reducing the computational complexity and time of a search by several orders of magnitude. Molecules identified from such a virtual screen may be new hits or backbone scaffold-hops for the development of a new drug.

Another application of the present invention is to improve 3D-QSAR (quantitative structure activity relationships). The 3D dynamic structures of several molecules across a drug family determined with the methodology of the present invention are expected to provide a new level of rationalisation to the technique of 3D-QSAR (above that currently produced by traditional computational chemistry methodologies) because the 3D dynamic structures determined from experimental data with the methodology of the present invention will be much more realistic than theoretically-generated conformations.

The present invention thus facilitates the simulation or prediction of the dynamic structure of existing pharmaceutical molecules and will significantly aid the discovery of new drugs by rational drug design and chemical mimicry.

In addition to the above, other technical areas that can benefit from the methods of present invention include:
1) the generation of biomimetic molecules e.g., the design of heparin mimetics;
2) the analysis of molecular interactions using arrays of receptor molecules, e.g., in systems biology and proteomics;
3) the design of drug-libraries from predictions of likely reaction routes in combinatorial chemistry; and
4) the design and construction of molecular machines (nanotechnology).

A third aspect of the present invention provides a method for generating data representing an optimised ensemble of three-dimensional structures of a molecule selected from a plurality of ensembles of three-dimensional structures of said molecule, wherein each ensemble is generated according to a method according to the first and/or second aspects of the present invention.

A principal source of real experimental data is nuclear magnetic resonance (NMR) data from organic molecules in aqueous or organic solution, but data from other experimental techniques could also be used. As described more fully below, various NMR experiments can be used synergistically to sample the 3D-structure and dynamic motions of molecules. The data resulting from each NMR experiment is processed using methods particular to each experimental data-type, to prepare it for input into an optimisation algorithm which employs a series of ensembles of molecular structures, each ensemble generated according to the first and/or second aspects of the present invention.

A fourth aspect of the present invention provides a computer implemented method for processing NMR data indicative of the three-dimensional structures of a molecule from an NMR spectrum obtained in respect of said compound, the method comprising:

a. determining resonance frequencies, $v$, for resonance multiplet components in said spectrum;
b. identifying resonance multiplet components in said NMR spectrum which have a difference in resonance frequency ($\Delta v$) that is less than the intrinsic resonance linewidth at half maximum height, $\lambda$, of said multiplet spectrum;
c. determining the height, $h_i$, of each of i such multiplet components identified in step b. on said NMR spectrum;
d. determining a broadening factor, b, for each multiplet as follows:

$$b = \frac{\lambda}{\lambda - (\Delta v/2)}$$

e. analysing the multiplet structure to predict ideal resonance frequencies, $v_{ideal}$, for each of said multiplet components and determine if the ideal multiplet structure is a doublet or a triplet;
f. if the ideal multiplet structure is a doublet then determine a scaling factor, $f_i$, for each multiplet component as follows:

$f_i = 2 \cdot b$ and determine a height, $H_i$, of resonance multiplet component, i, at 1 mole abundance, as follows:

$H_i = h_i \times f_i$ g. if the ideal multiplet structure is a triplet then determine a scaling factor, $f_{i(outer)}$, for each outer multiplet component as follows:

$f_i(outer) = 4 \cdot b$ and determine a scaling factor $f_{i(inner)}$, for overlapped inner multiplet components as follows:

$f_{i(inner)} = 2 \cdot b$ h. determining the height, $H_i$, of resonance multiplet component, i, at 1 mole abundance, as follows:

$H_{i(inner)} = h_{i(inner)} \times f_{i(inner)}$ $H_{i(outer)} = h_{i(outer)} \times f_{i(outer)}$ This aspect of the present invention enables data to be derived from NMR spectra to be employed in the optimisation employing molecular ensembles generated according to the first or second aspects of the present invention.

With regard to the first and second aspects of the present invention the data representing the molecule preferably further comprises data indicating a mean angle for said bond. Preferably the data indicating variability of said angle comprises data related to said mean angle. The data indicating the variability of said bond may comprise data indicating a distribution of angles about said mean angle. Said distribution is preferably a probability distribution. Said probability distribution of angles may be symmetric about said mean angle. Preferably the data indicating the variability of said bond is a Gaussian distribution of angles about said mean angle.

In a preferred embodiment the data representing the molecule further comprises further data indicating a further mean angle for said bond. It is preferred that the data indicating variability of said angle comprises further data related to said further mean angle. The data indicating the variability of said bond may comprise a further probability distribution of angles about said further mean angle. Said further probability distribution of angles may be symmetric about said further mean angle. Preferably the data indicating the variability of said bond is a further Gaussian distribution of angles about said further mean angle.

While the first and second aspects of the present invention can be used to generate an ensemble of 3D-structures of a molecule containing a single pair of first and second atoms linked via a bond or sequence of bonds having a particular associated variability, it will be appreciated that the first and second aspects of the present invention is eminently suitable to generate an ensemble of 3D-structures of a molecule containing a plurality of pairs of interconnected first and second atoms, as exemplified below in Examples 1 to 5, in which the molecules subjected to the methods of the present invention each contain a relatively large number of flexible bonds (e.g. see FIGS. 16 and 17 relating to Example 1). Thus, where reference is made below to, "first and second atoms", it should be understood that any molecule of interest being interrogated using the methodology of the present invention may incorporate one, two or more pairs of "first and second atoms" linked via at least one bond with an associated angular variability.

Regarding the first and second aspects of the present invention the data representing the molecule preferably comprises data indicating the chemical nature of the first and second atoms. The data representing the molecule may further comprise data indicating the variability of said bond based on the chemical nature of the first and second atoms.

Said data indicating the variability of said bond may comprise data indicating that the variability of the bond is zero when the first and second atoms are linked via a double covalent bond, a triple covalent bond or when the first and second atoms are incorporated into an aromatic ring structure.

It may be the case that said data indicating the variability of said bond comprises data indicating that the variability of the bond is zero when one of the first and second atoms is a hydrogen atom or a halogen atom.

Said data indicating the variability of said bond may comprise data indicating that the variability of the bond is zero when the first and second atoms are incorporated into a three or four-membered ring structure.

Said data indicating the variability of said bond can comprise data indicating that the variability of the bond is non-zero and exhibits a unimodal variability of bond angles when the first and second atoms are linked via a single covalent bond and:
one of the first and second atoms is linked to a third atom via a double or triple covalent bond; or
the first and second atoms are oxygen atoms.

It may be the case that said data indicating the variability of said bond comprises data indicating that the variability of the bond is non-zero and exhibits a bimodal variability of bond angles when the first and second atoms are incorporated into a five or six-membered saturated alicyclic ring structure.

Said data indicating the variability of said bond may comprise data indicating that the variability of the bond is non-zero and exhibits a bimodal variability of bond angles when:
the first and second atoms are linked via a single covalent bond and one of the first and second atoms is $sp^3$-hybridised and the other of the first and second atoms is $sp^2$-hybridised; or the first and second atoms are linked via a single covalent bond and said single covalent bond is conjugated to at least one further double covalent bond in the molecule.

Said data indicating variability of said bond may comprise data indicating that the variability of the bond is non-zero and exhibits a trimodal variability of bond angles when the first and second atoms are linked via a single covalent bond and:
both of the first and second atoms are tetravalent and $sp^3$-hybridised; or
one of the first and second atoms is $sp^3$-hybridised and the other of the first and second atoms is an oxygen atom.

With reference to the first and second aspects of the present invention it is preferred that said angle is a dihedral angle defined between said first and second atoms.

In a preferred embodiment of the first and second aspects of the present invention the method further comprises predicting at least one experimental parameter from said generated ensemble of three-dimensional structures of said molecule.

Preferably the method further comprises a comparison of said at least one predicted experimental parameter to at least one further parameter derived from at least one physical experiment. That is, an experiment performed on a chemical corresponding to the molecule of interest.

It is preferred that the method further comprises determining an agreement function based on said comparison.

In further preferred embodiments the methods according to the first and/or second aspects of the present invention may further comprise:
generating further data representing a further ensemble of three-dimensional structures of said molecule;
predicting at least one further experimental parameter from said further generated ensemble of three-dimensional structures of said molecule;
comparing said at least one further predicted experimental parameter to said at least one parameter derived from at least one physical experiment;
determining a further agreement function based on said comparison of the at least one further experimental parameter to said at least one parameter derived from at least one physical experiment; and
generating data indicating the ensemble having the best agreement function.

The method may comprise generating a plurality of said further ensembles and selecting the ensemble having the best agreement function determined from said plurality of further ensembles.

Preferably the method further comprises predicting at least two experimental parameters from said generated ensemble of three-dimensional structures of said molecule.

The method may further comprise a comparison of said at least two predicted experimental parameters to at least two further parameters derived from at least two physical experiments. That is, at least two experiments performed on a chemical corresponding to the molecule of interest.

Preferably said at least two physical experiments provide data indicative of the three-dimensional structures of said molecule sampled over different time periods.

Said at least two physical experiments may provide data indicative of the three-dimensional structures of said molecule sampled over different ranges of movement of said molecule.

It is preferred that at least one of said predicted experimental parameters relates to NMR data indicative of the three-dimensional structures of said molecule.

Said NMR data may be selected from the group consisting of scalar-couplings, nuclear Overhauser enhancements (NOEs), rotating-frame NOEs (ROEs), residual dipolar couplings (RDCs), heteronuclear NOEs, and $T_1$ relaxation data.

The or at least one of said physical experiments may comprise ID NMR spectroscopy. Said ID NMR spectroscopy may be selected from the group consisting of [$^1$H]-1D spectroscopy, [$^{13}$C]-1D spectroscopy, [$^{13}$C]-filtered [$^1$H]-1D spectroscopy, [$^{15}$N]-1D spectroscopy and [$^{15}$N]-filtered [$^1$H]-1D spectroscopy.

Preferably the or at least one of said physical experiments comprises 2D NMR spectroscopy. Said 2D NMR spectroscopy may be selected from the group consisting of [$^1$H, $^1$H]-DQF-COSY spectroscopy, [$^1$H, $^1$H]-TOCSY spectroscopy, [$^1$H, $^{13}$C]-HSQC spectroscopy, [$^1$H, $^{13}$C]-HMBC spectroscopy and [$^1$H, $^{15}$N]-HSQC spectroscopy.

Preferably said molecule is an organic molecule.

Preferably said molecule is selected from the group consisting of a peptide, a carbohydrate, an antibiotic, a nucleic acid, a lipid, a metabolite, a drug molecule and a protein.

Said molecule is preferably selected from the group consisting of hyaluronan, lisinospril and angiotensinI.

Rotatable bonds within the molecule are assigned a number of dynamic parameters, including mean angle values and angle probability distributions about those means. The optimisation algorithm may be used to determine the value for each dynamic parameter that is the best fit to all the real experimental data. By repeated use of the algorithm with modifications to the dynamic parameters and the inclusion of more and more experimental data throughout the optimisation, the mean structure and dynamic motions of the flexible parts of the molecule can be accurately predicted. This methodology is explained in more detail below and demonstrated in Examples 1, 2 and 3 below for three organic molecules, namely a hyaluronan hexasaccharide (an oligosaccharide), lisinopril (a peptidomimetic drug molecule) and angiotensinI (a peptide).

Another aspect of the present invention provides use of an ensemble of three-dimensional structures of a molecule generated according to a method according to the first and/or second aspects of the present invention to predict NMR data indicative of the three-dimensional structures of said molecule.

A further aspect of the present invention provides a method for predicting NMR data using an ensemble of three-dimensional structures of a molecule generated using a method according to the first and/or second aspects of the present invention.

An aspect of the present invention provides use of a method according to the first and/or second aspects of the present invention to an ensemble of three-dimensional structures of a molecule generated according to predict NMR data indicative of the three-dimensional structures of said molecule.

A further aspect of the present invention provides a method for predicting NMR data using an ensemble of three-dimensional structures of a molecule generated using a method according to the first and/or second aspects of the present invention.

Another aspect of the present invention provides a method for simulating a bioactive conformation of a molecule by generating an ensemble of three-dimensional structures of said molecule using a method according to the first and/or second aspects of the present invention.

A further aspect of the present invention provides use of an ensemble of three-dimensional structures of a molecule generated according to a method set out in the first and/or second aspects of the present invention to simulate a bioactive conformation of said molecule.

Another aspect of the present invention provides a method for simulating a conformation of a molecule when bound to its intended target by generating an ensemble of three-dimensional structures of said molecule using a method according to the first and/or second aspect of the present invention.

The present invention further provides, in a further aspect, use of an ensemble of three-dimensional structures of a molecule generated according to a method set out in the first and/or second aspects of the present invention to simulate a conformation of said molecule when bound to its intended target.

In another aspect, the present invention provides a method for simulating a conformation of a ligand molecule when bound to its intended target by generating an ensemble of three-dimensional structures of said ligand molecule using a method according to the first and/or second aspects of the present invention.

A still further aspect of the present invention provides use of an ensemble of three-dimensional structures of a ligand molecule generated according to a method set out in the first and/or second aspects of the present invention to simulate a conformation of said ligand molecule when bound to its intended target.

A yet further aspect of the present invention provides a method for simulating a bioactive conformation of a peptide molecule by generating an ensemble of three-dimensional structures of said peptide molecule using a method according to the first and/or second aspects of the present invention.

The invention further provides, in another aspect, use of an ensemble of three-dimensional structures of a peptide molecule generated according to a method set out in the first and/or second aspects of the present invention to simulate a bioactive conformation of said peptide molecule.

A further aspect of the present invention provides a method for simulating a bioactive conformation of a carbohydrate molecule by generating an ensemble of three-dimensional structures of said carbohydrate molecule using a method according to the first and/or second aspects of the present invention.

The invention further provides, in another aspect, use of an ensemble of three-dimensional structures of a carbohydrate molecule generated according to a method set out in the first and/or second aspects of the present invention to simulate a bioactive conformation of said carbohydrate molecule.

A further aspect of the present invention provides a method for simulating a bioactive conformation of a drug molecule by generating an ensemble of three-dimensional structures of said drug molecule using a method according to the first and/or second aspects of the present invention.

The invention further provides, in another aspect, use of an ensemble of three-dimensional structures of a drug molecule generated according to a method set out in the first and/or second aspects of the present invention to simulate a bioactive conformation of said drug molecule.

An aspect of the present invention relates to a method for simulating the hydrogen bond occupancy in a molecule by generating an ensemble of three-dimensional structures of said peptide molecule using a method according to the first and/or second aspects of the present invention.

There is further provided, according to another aspect of the present invention, use of an ensemble of three-dimensional structures of a molecule generated according to a method set out in the first and/or second aspects of the present invention to simulate the hydrogen bond occupancy of said molecule.

According to a still further aspect of the present invention there is provided a data carrier carrying data usable to generate an ensemble of three-dimensional structures of a molecule, the molecule comprising first and second atoms linked by at least one bond, the data comprising data representing said molecule including data indicating variability of said angle.

A yet further aspect of the present invention provides a carrier medium carrying computer readable instructions configured to cause a computer to carry out a method according to the first and/or second aspects of the present invention.

According to another aspect of the present invention there is provided a computer apparatus for generating data representing an ensemble of three-dimensional structures of a molecule, the apparatus comprising:
- a memory storing processor readable instructions;
- a processor configured to read and execute instructions stored in said memory;
- wherein said processor readable instructions comprise instructions configured to cause the processor to carry out a method according to the first and/or second aspects of the present invention.

The starting point for generating a molecular ensemble according to the first and/or second aspects of the present invention is a description of molecular topology, which is dictated by the chemical formula of the molecule of interest and describes the number and type of bonds, their lengths, angles and torsional (dihedral) angles between them. This geometrical information can be conveniently described by a set of internal coordinates (also commonly known as a Z-matrix) [1]. The internal coordinates provide a description of each molecular atom in terms of bond lengths, bond angles, and dihedral angles, relative to other adjacent atoms. These internal coordinates can be used to specify a set of molecular (Cartesian) coordinates for the atoms in space, using standard geometrical arguments [2].

Due to the nature of covalent chemical bonds (e.g., σ-bond, π-bond) and orbital hybridisation ($sp^2$, $sp^3$), in the majority of cases bonds and angles can be assumed to maintain their average geometry while a molecules undergoes local dynamic motions in solution (to a good approximation), i.e., they can be kept constant. Therefore, to a first approximation local dynamic motions of molecules in solution occur by rotations about dihedral angles (see FIGS. 1a and 1b). Furthermore, these rotations usually occupy a limited set of possible angles about a mean angle (which will be described in more detail later), that is, the range of angles which a flexible bond can adopt can be characterised by defining a variability in bond angle associated with that bond.

A molecular ensemble of 3D-structures generated according to the first and/or second aspects of the present invention is a set of discrete molecular structures (which in itself is a set of atomic coordinates) that is intended to mirror as closely as possible the range of 3D-shapes that a solvated molecule undergoes while flexing. In a preferred embodiment of the present invention, a molecular ensemble is generated by varying specified dihedral angles (those that can rotate, also known as conformational degrees of freedom) according to well-established models of molecular motion, while keeping other conformational degrees of freedom fixed (angles, bonds and non-rotatable torsions).

Examples of conformational degrees of freedom are glycosidic, phosphodiester and peptide backbone dihedral angles. A series of rules relating to the dynamic behaviour of specific types of bonds in solution has been developed by the inventors and is set out below. These rules are used to establish which bonds in a molecule of interest are allowed to rotate and those which are not. Whether a bond should be allowed to rotate can be determined with the following considerations:

1) all single bonds within the molecule are rotatable, whereas no double-, triple- or aromatic bonds are rotatable;
2) the rotation of many single bonds has no effect on the relative positions of atoms in the molecule, and therefore these kinds of single bonds do not need to be rotated. Examples of such single bonds include bonds between a hydrogen atom and any other atom, or a halogen atom and any other atom; and
3) single bonds within some cyclic chemistries are unable to rotate because of the constrained geometry; an example of this would be the C—C bonds in cyclopropane.

For small librations (oscillations about a mean angle) of a dihedral angle, the molecular potential energy may be considered harmonic (i.e., depends on the square of the angular deviation from the mean) [3]. The distribution of angles about the mean from such a potential may be modelled using a Gaussian (also known as Normal) distribution (see FIG. 1c), although it will be appreciated that other models of bond angle variability may be adopted.

Once the chemical structure of the molecule of interest has been analysed and the appropriate conformational degree(s) of freedom of the molecule identified using standard methods together with the rules set out above, where appropriate, it is then necessary to establish a set of initial parameters to describe each bond within the molecule. By way of example only, the most simple case of a molecule of interest including only a single variable dihedral angle will be considered. In this case, the dihedral angle is allocated a mean bond angle (e.g. 40°) and a maximum variability in bond angle about the mean angle (e.g. 18°). The dihedral angle being modelled will therefore possess a mean value of 40° but can in fact vary between 22° and 58° across an ensemble of structures generated for that molecule. If the ensemble size is taken as, say 10, in this simple example, then when the ensemble is generated, it will consist of 10 discrete molecular structures, each structure including a specific value for the variable dihedral angle of between 22° and 58°, with the overall mean of all of the dihedral angles being 40°. The distribution of dihedral angles across the range from 22° to 58° is preferably controlled with use of some form of distribution function, such as a Gaussian probability distribution function. While a preferred embodiment of the present invention uses a canonical Gaussian spread of angles (equation (1)) other distributions could be readily implemented. Examples of other distributions include the top hat function (equation (2)) and the Weibull distribution (equation (3)).

$$p(x; \mu, \sigma) = \frac{1}{\sigma\sqrt{2\pi}} \exp\left(\frac{(x-\mu)^2}{2\sigma^2}\right) \quad (1)$$

$$p(x; \mu, \sigma) = \frac{1}{\sigma} \text{ for } \mu - 1/2\sigma \le x \le \mu + 1/2\sigma, \text{ otherwise} = 0 \quad (2)$$

-continued $$p(x; k, \lambda) = \frac{k}{\lambda}\left(\frac{x}{\lambda}\right)^{k-1} \exp\left\{-\left(\frac{x}{\lambda}\right)^k\right\} \quad (3)$$

In the preferred embodiment where the angular probability distribution is modelled as a Gaussian distribution, the distribution would be $p(\alpha)=G(\mu, \sigma)$, which is a Gaussian distributed angle ($\alpha$) with mean angle $\mu$ (average bond geometry) and a standard deviation angle of $\sigma$ (local libration), representing a single degree of freedom, see FIG. 1(c). This probability distribution will simulate libration about a single bond that corresponds to a 3D-distribution around a single conformer, see FIG. 2 for an example based on angiotensin-4, with zero, one and two degrees of freedom.

In commonly encountered $sp^2$ and $sp^3$ bond chemistries (planar and tetrahedral, respectively) there may be several distinct conformational states (e.g., alkane chains that can adopt g+, g− and t rotamer conformers at each carbon-carbon bond, cyclic rings that can adopt a range of conformations such as chair, boat and/or skew boat conformations, and functional groups, such as peptide bonds, which can adopt slowly-interconverting cis and trans conformations). In such cases, more complicated and more general expressions may be used for the probability distribution, such as $p(\alpha)=p_1 G(\mu_1, \sigma_1)+p_2 G(\mu_2, \sigma_2)+p_3 G(\mu_3, \sigma_3)$, which corresponds to a system with up to three librational states, where $p_1$, $p_2$ and $p_3$ are probabilities such that $p_1+p_2+p_3=1$ (specific examples are described in detail below). Furthermore, some of the probabilities and/or mean and standard deviation values may be coupled to one another, in order to model such cases as found in, e.g., peptides or puckering cyclohexane-type rings. For example, $\sigma_1=\sigma_2=\sigma_3$ (in the equation above) would indicate that each conformational substate has an identical range of librational motion.

Calculation of a dynamic ensemble in this manner may result in parts of the molecule accidentally clashing with one another. In order to avoid this situation, after generation of each single structure (within the ensemble) it may be tested to see whether any of the van der Waals active atoms (see below) are within a set distance (typically 0.1 nm). If this condition is met the 3D-structure can be deleted and recalculated. This process may be repeated until a sterically-acceptable 3D-structure is generated (up to a maximum number of tries, typically 50 times, after which the current 3D-structure is automatically accepted).

Once an ensemble of molecular structures has been generated it may be used to predict real experimental data, for example, but not limited to NMR data. The quality of the prediction, i.e. the closeness of fit of the predicted experimental data to the real experimental data, may then be used to assess how closely the ensemble of structures models the range of structures that the real molecules populate in solution.

It will be appreciated that it is theoretically possible to calculate more measurable molecular properties from a dynamic molecular ensemble than it would be from a static representation (assuming that a relevant physical theory correlating the two is known). This is a basic hypothesis of classical statistical physics, which says that a full description of a molecular system includes the states that it can occupy (macrostates) and the probability of their occurrence (statistical weights) [4]. Thus, in contrast to using just a single mean angle to represent each rotatable bond as in prior methods, the inclusion of a degree of variability at each conformational degree of freedom makes it is possible to simultaneously satisfy one or more different kinds of NMR experimental data, which each provide a different snapshot of the molecular flexibilities because they are averaged from the ensemble over different functions of molecular geometry, effectively increasing the amount of experimental information available to define the model. This facilitates the use of multiple NMR datasets, which allows the large number of restraints that are often necessary to define the conformation of dynamic molecules.

When a comparison to real experimental data is to be made, a molecular ensemble of structures is first generated according to the first and/or second aspects of the present invention. Standard methods (explained in more detail below) are then used to predict an experimental parameter for each member of the ensemble. The predicted values for each member of the ensemble are then averaged and the average value compared to the corresponding parameter derived from the real experimental data.

For example, nuclear Overhauser enhancements (NOEs) are known to average over distances raised to the power six. Standard methods may therefore be employed to determine a predicted NOE value for each member of the ensemble, this set of predicted NOEs averaged and this average value compared to the NOE calculated from the real experimental data. Further examples include residual dipolar couplings which average over squared cosine angles and scalar couplings which average over torsional angles.

Following the prediction of experimental parameters and the comparison of said predicted parameters to corresponding real parameters, one or more further ensembles can be generated according to the first and/or second aspects of the present invention and each further ensemble tested against the real experimental data in a similar manner as described above. In this way, an optimisation routine can be established (see FIG. 3) in which a series of ensembles of molecular structures are iteratively generated and compared to real experimental data to determine the ensemble which most closely matches the real experimental data, that is the ensemble which exhibits the highest correlation with the real experimental data.

At the heart of the algorithm is a conformational model generator that produces a dynamic molecular ensemble for each and every iteration of an optimisation routine. The generator derives the ensemble from a set of variable parameters (some that define conformation, while others define dynamic spread) as outlined above and described in more detail below. These parameters are then simultaneously optimised to fit real experimental data derived from one or more than one type of experiment (which preferably contain different kinds of NMR data), resulting in a best-fit dynamic ensemble for the molecule using the Monte-Carlo approach [5]. This process can be described algorithmically in the following way, which permits its implementation on a digital computer:

1) Generation of a dynamic ensemble based on the conformational degrees of freedom by a set of dynamic molecular variables. The conformational degrees of freedom are selected based on local chemistry considerations (see definitions later). In particular, the types and hybridisation of chemical bonds determine whether they will be rotatable.
2) Prediction of experimental data from the dynamic ensemble by use of a suitable physical theory and integration (averaging). By way of example, for the NMR experiments considered in detail below (nuclear Overhauser enhancement experiments (NOESY, ROESY), residual dipolar couplings, coupling constants and $^1$H-$^{15}$N heteronuclear enhancements) suitable physical theories have been derived and validated [6, 7-9].

3) Comparison of the predicted experimental data against the true experimental data and calculation of an agreement function. This is normally the square distance between the two (including experimental error), referred to as $\chi^2$.

4) If the $\chi^2$ is lower than that seen previously, this dynamic structure is accepted and becomes the new candidate best structure.

5) The molecular variables are changed randomly (both mean and dynamic spread) and we jump back to step 1 until a specified number of iterations have elapsed. The number of steps required is dependent on the complexity of the problem. In simple terms, this complexity can be estimated from the number of conformational degrees of freedom.

6) Once a suitable number of iterations have been performed, such that a well-defined final ensemble can be generated reproducibly, the current candidate structure represents a single solved dynamic structure. This structure can be assessed for goodness-of-fit to the experimental data by calculating the average $\chi^2$ per conformational restraint.

7) Many dynamic structures are generated and statistics are performed on them to determine the precision of the repeated structure determination. This determines the robustness of the experimental data in determining a single unique dynamic molecular conformation.

The chi-square least-squares measure ($\chi^2$) is used to determine the goodness of fit between the experimental data ($x_{exp}$) and the theoretical predictions ($x_{pred}$), which is the sum of the square distances between prediction and experiment, divided by the square of the estimated error ($\varepsilon^2_{exp}$) on each experimental measurement. Three measures are discussed herein, the least-squares fit for each individual restraint ($\chi^2_{restraint}$), sums of these values to make the least-squares fit for a dataset ($\chi^2_{dataset}$) and sums of these values to make the least-squares fit for all experimental data ($\chi^2_{total}$), see equations (4-6).

$$\chi^2_{restraint} = \frac{(x_{exp} - x_{exp})^2}{\varepsilon^2_{exp}} \quad (4)$$

$$\chi^2_{dataset} = \sum_{restraint} \chi^2_{restraint} \quad (5)$$

$$\chi^2_{total} = \sum_{dataset} \chi^2_{dataset} \quad (6)$$

At each iteration of the algorithm, the current dynamic molecular ensemble is used to make a prediction of one or more experimental data sets, which ideally average the ensemble over different functions of the molecular geometry (as discussed above). The $\chi^2$ fit of each data point is reported, from which statistics for each different kind of dataset can be calculated (exemplified in Examples 1, 2 and 3 below).

The mean, their spreads (also referred to herein as variability) and relative probability weightings of the Gaussian distributed angles are iteratively searched by repeated calculation of the dynamic molecular ensemble and comparison with experimental data, until a good fit to the experimental data is found (FIG. 3). In a preferred embodiment of the present invention, a Monte-Carlo iterative approach has been using to perform this search, but other iterative optimization procedures can also be used, such as, but not limited to the Levenberg-Marquardt algorithm or a Genetic algorithm.

Certain classes of molecular restraints can be added to the calculation that are not dependent on experimental data, but instead are regarded as fundamental molecular properties. The most obvious is the van der Waals energy, which can be implemented as a direct addition to $\chi^2$. The actual numerical value for the van der Waals force constant should be modified by a constant scaling factor (see below) chosen by the user so that it harmonises with the other experimental datasets.

In the following description examples of NMR experimental data that are sensitive to dynamic conformation are given, which will be used in Examples 1, 2 and 3 below and can be used to determine the dynamic structure of a variety of molecules, in particular organic molecules. The way in which the NMR experiments are performed and NMR datasets acquired is also described in detail below. Furthermore, the theory used to make predictions of these experimental NMR parameters is described, and how the structures are optimised by comparing experimental measurements against predictions. NMR is a particularly suitable method because it provides atomic-scale information in aqueous solution. However, it should be noted that other types of experimental data (that provide dynamic information) could be used, such as solution-state scattering and fluorescence energy transfer (specific examples of their use are not detailed in this application).

The first type of experimental data to be considered is produced by NMR experiments that are based on the nuclear Overhauser effect [10]. In this case, particularly useful experiments are NOESY and ROESY spectroscopy. An important advancement over standard NMR structure-calculation methods is the use of a full relaxation matrix [7] to theoretically predict the experimental data. Such a calculation method (as opposed to using the approximation of simply relating intensity to distance, r, through $r^{-6}$) is important because small molecules can contain many NMR-active nuclei in a small volume and mixing times are often relatively long. Therefore, there is the strong possibility of significant spin-diffusion, which can only be taken into account by calculation of a full relaxation matrix. Methods for performing this calculation by matrix diagonalisation have been published previously [7]. Ultimately, cross-peaks are represented by off-diagonal terms in the final matrix, while diagonal-peaks are found on the diagonal of the matrix. Different linear combinations of spectral density functions can be used to perform calculations of the different possible relaxation experiments (e.g., NOESY, ROESY and T-ROESY).

Other types of NMR relaxation experiments, such as heteronuclear $T_1$-relaxation and NOE data (typically between $^1$H and $^{13}$C or $^{15}$N), can be interpreted as order parameters ($S^2$), overall tumbling correlation times ($\tau_c$) and internal correlation times ($\tau_1$), as described previously [8]. These data are intimately related to local dynamics and can be used as a complement to other NMR measurements. In order to make predictions, all structures in the molecular ensemble may be overlaid such that they have the minimum root-mean-square deviation (RMSD) between them. The correlation functions for selected vectors are calculated in this molecular frame, which have been derived previously [11], resulting in an estimation of $S^2$.

NMR scalar coupling constants (J), and in particular three-bond couplings, are indicative of conformation via an empirical relationship, the Karplus curve [12]. For each dihedral angle, assuming that the Karplus equation is known, it is possible to calculate J by averaging over the dynamic ensemble and then directly comparing to the experimental data to determine $\chi^2$.

Residual dipolar couplings (RDCs) induced by an inert weakly-alighning co-solute can be calculated by methods that have been derived previously [7]. Other methods are available in the literature for the more generic case [13]. RDCs are an important complement to the total experimental data pool because they provide long-range conformational information rather than local information provided by relaxation data. Some data (e.g., scalar couplings) is directly comparable with theoretical calculations. However, in other cases (e.g., NOESY measurements) datasets need to be scaled by an arbitrary constant, which is dependent on sample concentration, spectrometer sensitivity etc. and can be calculated from the experimental data and their respective prediction by a straight-line fit (passing through zero). A suitable coefficient ($\kappa_{dataset}$) is shown in equation (7) and can be applied to all predictions such that a graph of $\{\kappa x_{pred}, x_{exp}\}$ has a unitary gradient (see below).

$$\kappa_{dataset} = \frac{\sum_{dataset} \frac{x_{pred} x_{exp}}{\varepsilon_{exp}^2}}{\sum_{dataset} \frac{x_{pred}^2}{\varepsilon_{exp}^2}} \quad (7)$$

An important consideration in equation (7) is the strong dependence on errors. If these are not quantified correctly then the resultant structure may be biased. While calculation of the experimental error ($\varepsilon_{exp}$) has been discussed above, errors due to the finite size of the ensemble has not. One case where this is particularly important (it is not considered for NOESY, ROESY or scalar couplings) is in making predictions of RDCs, which depends on the direction of the inter-nuclear vector within the molecular frame. Here the dependence on angle is highly non-linear and thus an extra error correction has to be applied. This is most suitably achieved by scaling the effective error. The scaling (to produce an effective error $\varepsilon_{exp}'$) can be derived in the following way. If $\theta$ is the angle between the major axis of alignment in the molecular frame, then starting from the equation defining residual dipolar couplings [13], equation (8) is obtained, which allows the calculation error to be obtained by differentiations, equation (9). Suitable approximations result in equation (10).

$$RDC \propto \cos^2\theta - 1 \quad (8)$$

$$\text{Calculation error} = \left|\frac{d}{d\theta}(\cos^2\theta - 1)\right| \quad (9)$$
$$= |2\sin\theta\cos\theta|$$
$$= |\sin 2\theta|$$
$$\approx \frac{1}{2}(1 - \cos 4\theta) \quad (10)$$

Substituting the identity: $\cos 4\theta = 8\cos^4\theta - 8\cos^2\theta + 1$ into (10) and dividing this into the experimental error, results in equations (11) and (12), the latter of which is almost identical to equation (11), but avoids division by zero by having a minimum value of ¼ in the denominator and is therefore used in practice.

$$\Rightarrow \varepsilon_{exp}' \approx \frac{\varepsilon_{exp}}{4(\cos^2\theta - \cos^4\theta)} \quad (11)$$

$$\Rightarrow \varepsilon_{exp}' \approx \frac{\varepsilon_{exp}}{0.25 + 3(\cos^4\theta - \cos^2\theta)} \quad (12)$$

Using equation (12), it is possible to increase the total experimental error estimate ($\varepsilon_{exp}$) to take into account errors associated with predictions of residual dipolar couplings, which can then be used to more-accurately assess the degree of fit with the experimental data.

A preferred embodiment of the present invention will now be described which will serve to further describe various preferred features of the present invention.

Before a first ensemble can be generated for a molecule of interest and structure calculations performed based on said ensemble, a variety of parameters are specified.

A series of solvent masks are specified for the molecule in each solvent used in the real experiments from which datasets of real experimental data have been derived. This comprises a list of hydrogen atoms that are NMR-active and inactive due to rapid exchange with the solvent. This information is important for the accuracy of the full-relaxation matrix calculation used in the calculation of NMR relaxation predictions (see above), which is very sensitive to the exact location of every proton in the molecule. All protons in the molecule that are NMR-inactive due to chemical exchange with the solvent must therefore be excluded from the calculations. For example, the solvent mask for a carbohydrate in H$_2$O would specify that all hydroxyl hydrogen atoms are NMR-inactive, but for the same carbohydrate in DMSO, the solvent mask would specify that the same hydroxyl protons are active. Each dataset has the appropriate solvent mask associated with it as an input parameter.

First the number of solvents required is specified, followed by the required number of solvents, listed by name (these are used later by the experimental data input files). The actual atoms that are included or excluded from the solvent mask are specified by either an add statement or an exc statement, which add atoms to the solvent mask or takes them away. The next two fields in each of these statements define the residue number and atom types. A wild-card asterisk is used to select all protons (H*) and take away all hydroxyls (HO*). A typical file is shown below:

```
conditions:

solvents 2
endsection
solvent:

name h2o
add * H*
exc * HO*
endsection
solvent:

name d2o
add * H*
exc * HO*
exc * H2N
endsection
```

A van der Waals mask is prepared according to the needs of the structure calculations, which is a global parameter set (i.e., is not specific to a particular dataset). This mask allows atoms to remain NMR-active but to be effectively transparent to van der Waals forces (calculated as an addition to $\chi^2$, see below), allowing them to overlap and clash with other portions of the molecule without penalty during structure calculations. The use of this mask is important in allowing atoms within the structure of undetermined orientation but arbitrary initial (and/or fixed) geometry to not bias the result from the structure calculations by unfortunate steric clashes. Examples of this case are hydroxyl protons and carboxylate group oxygen atoms, whose conformations cannot be easily investigated experimentally in water. This mask can also be used in the initial stages of 3D-structure determination, when one set of dynamic variables can be tested independently of another, by uncoupling them from another portion of the structure by allowing that other portion of the structure to adopt conformations and steric clashes without penalty. As the dynamic structure of the molecule is progressively defined, the van der Waals mask is appropriately updated, i.e., including all portions of the molecule that have currently been solved.

In the configuration section of the van der Waals input file the cut-off distance for calculation is specified (atoms that are separated by one or two covalent bonds are always excluded from the calculation) and a coupling constant is specified, which determines the scaling factor applied to the van der Waals calculation before it is included as a term in the overall $\chi^2$ calculation. The next section (the nonbonded section) defines the atomic radii and repulsion energy for each kind of atom (e.g. for hydrogen, vdw*H*0.016 0.60). Following this, a series of statements are listed detailing the atoms that are included and those that are excluded (without any statements all atoms are included). In the example input file shown below all the hydroxyl atoms are excluded (exc*HO*), while all other atoms are included. The nomenclature used in this specification is similar to that used in the solvent masks.

---
configuration:

vdw.cutoff 6.0
vdw.coupling 1e-4
endsection
nonbonded:

vdw * H* 0.016 0.60
vdw * C* 0.100 1.91
vdw * N* 0.170 1.82
vdw * O* 0.210 1.66
exc * HO*
endsection
---

For prediction of NMR relaxation data (NOESY, ROESY, T-ROESY) via the model-free approximation [11], a value must be specified for the molecular correlation time ($\tau_c$) at 298 K and 0.88 cP viscosity (i.e., $H_2O$ at 25° C.), which is a global parameter. The value of $\tau_c$ can be determined experimentally [8] or estimated in the first instance. To a reasonable first approximation, small molecules of molecular weight ~400 Da have a correlation time of 0.4 ns at 298 K, whereas a small protein of ~10 kDa has a correlation time of ~5 ns at 298 K. Occasionally, molecules are of sufficiently low molecular weight (around ~250 Da) that the NOE cross-peaks pass the threshold from being negative (normal for proteins) to positive (i.e., they have the opposite sign to the diagonal peaks), which allows $\tau_c$ to be estimated through the equation $\tau_c\omega \sim 1.12$ (the value of $\tau_c$ that causes the NOE cross-peaks to be zero, where $\omega$ is the proton-resonance angular frequency). It should be noted that ROEs do not have this zero point and thus can be very useful when $\tau_c\omega \sim 1.12$ [9].

The calculation of the spectral density used in prediction of relaxation data can be improved for molecules with a highly-anisotropic shape, by introducing a symmetric top model for molecular diffusion. In this case the single $|_c$ value is replaced by two correlation times (parallel and perpendicular to the axis of symmetry on the symmetric top). The resulting modifications to the spectral density function is described in [46], equations (3) to (9).

When the value for $\tau_c$ has not been determined experimentally, the initial estimated value can be reviewed after a few rounds of structure calculations (should this be deemed necessary), at the point when it is clear that the dynamic structure starts to have a good correlation with the experimental data. At this point, the $\tau_c$ value can be optimised by repeated calculations with the same datasets, but with different values of $\tau_c$ and taking the value that gives the best $\chi^2_{total}$ value to the experimental data.

While the value of $\tau_c$ is a global physical parameter that is fixed during structure calculations, variations in the actual value of $\tau_c$ in datasets due to differences in solvent viscosity (e.g., 100% $D_2O$ has ~1.25 the viscosity of 100% $H_2O$) or temperature (e.g., one relaxation dataset may have been recorded at 298 K, while another was at 278 K) is compensated for by using the simple Debye theory for rotational diffusion, which states that the value of $\tau_c$ is proportional to the temperature and inversely proportional to the solvent viscosity. Each relaxation dataset therefore has both a value for the NMR sample's viscosity (in cP) and the temperature at which the dataset was acquired (in K). The viscosity ($\zeta$) of 100% $H_2O$ at different temperatures (T1, T2; $\zeta_{298}$ of 100% $H_2O$=0.0088 P) can be calculated using equation (13). The viscosity of 100% $D_2O$ at a given temperature is related to that of 100% $H_2O$ via equation (14). By using equation (13) and linearly scaling equation (14) to a given percentage v/v of $H_2O/D_2O$, the viscosity of $H_2O/D_2O$ mixtures at any given temperature can be estimated.

$$\zeta_{T2}=\zeta_{T1} \times e^{(1/T1-1/T2)} \quad (13)$$

$$\zeta_{D_2O}=1.23 \times \zeta_{H_2O} \quad (14)$$

In the preferred embodiment described here, experimental data is input into the structure calculations via a series of text files that contain specific measurements, information about spectral overlaps and physical parameters that describe the experimental conditions. In all files a configuration section specifies the NMR magnetic-field strength (field 900 MHz), a name identifier for the dataset (ident NOESY) and the appropriate solvent mask to use (h2o). In the case of a relaxation dataset, the temperature (temp 298, in Kelvin), the solvent viscosity (visc 0.88, in cP) and the mixing time used (mixtime 400 ms) are also specified. An example input file specifying NOESY data is described below:

---
configuration:

field      750
solvent    h2o
ident      NOESY
temp       298
visc       0.88
mix_time   400 ms
endsection
data:

asgn    1    a    6    H1M    a    6    H2N    48.8    19.6    0
ovlp    1    a    6    H2M    a    6    H2N    48.8    19.6    0
---

-continued

```
ovlp   1  a  6  H3M  a  6  H2N  48.8  19.6  0
asgn   2  a  6  H3   a  6  H2N  34.2  13.7  0
...
endsection
```

The experimental data section has a format that is somewhat standard, but is also tailored to the specific type of experimental measurements. For example, in the NOESY data-input file above, the line asgn 2 a 6 H3 a 6 H2N 34.2 13.7 0 specifies restraint number 2, while the subsequent four fields define the two atoms, between which the NOE is observed (and should be calculated). The next two fields give the restraint intensity and its error (in the case of asgn 10, 34.2±13.7) and the final field is a flag (0) specifying that the $\chi^2_{restraint}$ value (comparison of the predicted value of this restraint to the experimentally-observed value) should be included in the total $\chi^2_{total}$ value for the dynamic ensemble (a value above 5 would indicate that it should not be used). Overlapped restraints are specified with the format ovlp 1 a 6 H2M a 6 H2N 48.8 19.6 0, where ovlp 1 indicates that the NOE between the atoms in this overlapped restraint needs to be combined with the NOE calculated from the primary restraint of the same number (i.e., asgn 1). Diagonal peaks in the spectrum are simply represented as NOEs between the same two atoms (see actual input data-files in Appendix A for examples of this).

```
configuration:

field     900
solvent   h2o
ident     RDC
endsection
data:

asgn    1   a   6   C1   a   6   H1   -5.85   0.35   0
...
endsection
```

The configuration section of a residual dipolar coupling (RDC) input file is directly analogous to that described above for relaxation data, see the example input file above. In the line asgn 1 a 6 C1 a 6 H1 −5.85 0.35 0, asgn 1 specifies that this line is restraint number 1. The subsequent a 6 C1 a 6 H1 characters define the two atom assignments, between which the residual dipolar coupling is to be calculated. Following this, the experimental measurements and their errors are listed (i.e., in the case of asgn 1, −5.85, 0.35 Hz) and a flag (0) specifying that the $\chi^2_{restraint}$ value of the comparison of the predicted value of this restraint to the experimentally observed value should be included in the total $\chi^2_{total}$ value for the dynamic ensemble (as described above).

```
configuration:

field     900
solvent   h2o
ident     JCOUP
endsection
data:

coup 1 2 H2 2 C2 2 N2 2 H2N 9.45 -2.08 0.63 0 9.67 0.5 0
endsection
```

Input data-files representing conformation-dependent scalar-couplings are similarly specified. A typical input file is shown directly above. In the line: coup 1 2H2 2 C2 2 N2 2H2N 9.45 −2.08 0.63 0 9.67 0.5 1, coup 1 specifies that this structural restraint is a coupling-constant type of data and is restraint number 1. The four fields: 9.45-2.08 0.63 0 specify the A, B and C and phase (ϕ) parameters to use in the generic Karplus equation $^3J_{HH}=A\cos^2(\theta+\phi)+B\cos(\theta+\phi)+C$, for the HCNH angle θ. Following this, the experimental measurement and its error is given (in the case of coup 1, 9.67±0.5 Hz) and a flag (0) specifying that the $\chi^2_{restraint}$ value of the comparison of the predicted value of this restraint to the experimentally observed value should be included in the total $\chi^2_{dataset}$ value for the ensemble (described above)

Dihedral angle structural restraints for peptides can be generated using chemical shifts and the program TALOS [42]. The program TALOS takes as input the peptide sequence and the chemical shifts for HN, HA, C, CA and CB nuclei for each residue within the molecule and outputs a predicted value with error for each backbone phi and psi angle. Since TALOS is actually designed for proteins, which are generally more rigid than peptides, the errors actually used for the $\chi^2$ calculation are taken as twice the error values predicted by TALOS (this value is based upon our current experience). An example format for a dihedral angle structural restraint file is as follows:

```
configuration:

remark   Angiotensin1, dihedral angle restraints
remark   given twice the error value from TALOS
field    600
solvent  h2o
temp     298
visc     0.88
ident    TDIHEDRALS
endsection
data:

remark  dihedral_no   dihedral_atom_identifiers(x8)          angle  error  code
remark  phi example
dihe    1    1   C    2   N    2   CA   2   C    -85    26    0
remark  psi example
dihe    9    2   N    2   CA   2   C    3   N    138    36    0
remark  omega example
dihe    17   3   CA   3   C    4   N    4   CA   180    20    0
endsection
```

In this file, the configuration: section follows the same format as other data types. In the data: section, each restraint is introduced by dihe and the subsequent field is the restraint number. The next 8 fields define the 4 atoms in the dihedral angle, in pairs of (residue number, atom name). Following these, the dihedral angle value is given and then its error.

The presence or absence of hydrogen bond interactions can be inferred from several kinds of experimental data, including amide proton exchange rates and temperature coefficients. Whether a hydrogen bond can be considered to be present or not depends on both angular and distance criteria. Typically the donor and acceptor electronegative atoms are separated by a distance of between 3.3 to 2.5 angstroms, the donor hydrogen and acceptor electronegative atoms by a distance of 2.5 to 1.5 angstroms and the angle between the three atoms is >110°. If all these three criteria within a structure are satisfied, a hydrogen bond can be considered to be present. In a flexible molecule, hydrogen bonds can be transiently formed and broken, giving them a percentage occupancy that may be estimated from experimental data (see [36]). By counting the number of molecules within the current best ensemble that satisfy these criteria, the percentage occupancy of the hydrogen bond within the ensemble can be calculated. Comparison of the calculated occupancy for the current ensemble with the experimental restraint occupancy value allows a $\chi^2_{restraint}$ score to be directly calculated.

An example format for a hydrogen bond structural restraint file is as follows:

```
remark hydrogen bond restraints file
configuration:

solvent   h2o
ident     HBOND
endsection
data:

remark atomsx3 d1 range d2 range ang percent perc_error start code
hbond 1 3 N 3 HN 1 OD1 2.9 0.4 2.0 0.5 110 0 10 0.0 0
hcomb 1 3 N 3 HN 1 OD2
endsection
```

In this file, the configuration: section follows the same format as other data types. In the data: section, each restraint is introduced by hbond and the subsequent field is the restraint number. The next 6 fields define the 3 atoms in the hydrogen bond (electronegative donor, hydrogen atom, electronegative acceptors, respectively), in pairs of (residue number, atom name). Following these, the next 5 fields specify the three criteria to judge by whether a hydrogen-bond is present in a structure or not. The first 2 values give a mean distance and range (e.g. for hbond 1, 2.9±0.4 angstroms) between which the two electronegative atoms must be found, the next 2 values give a mean distance and range between which the hydrogen and acceptor atoms must be found, and the last value is a minimum value for the angle between all three atoms. The next two values define the expected percentage occupancy and error of the hydrogen bond determined from the experimental data (e.g. for hbond 1, 0 and 10, meaning 0±10% occupancy). The last two fields define the point during each run of calculations at which the restraint is included in the $\chi^2_{total}$ score and the quality code, respectively. In cases where the hydrogen-bond acceptor atom can be more than one atom, other acceptor atoms can be included into the cumulative score for a restraint with lines beginning with hcomb, which behaves in an identical manner to the ovlp lines used in NOESY datasets (e.g., for hbond 1 in the example above the total occupancy of all hydrogen bond interactions for the amide proton of residue 3 with the two sidechain oxygen OD atoms of residue 1 should be 0±10).

```
configuration:

solvent  h2o
ident    ORDER
endsection
data:

hnoe 1 w 2 H2N w 2 N2 0.44 0.01 0
endsection
```

Order parameters (which are the result of Lipari-Szabo model-free analysis) are useful descriptors of local dynamics and a specific implementation and input datafile is described here. The configuration section of this input file is directly analogous to those described previously and an example is presented above. In the experimental data section the line hnoe 1 w 2 H2N w 2 N2 0.44 0.01 0, hnoe 1 specifies that this structural restraint is an order-parameter type of data and is restraint number 1. The subsequent fields: w 2 H2N w 2 N2 define the two atoms assignments, for which the order parameter is to be calculated. Following this, the experimental measurements and their errors are given (in the case of hnoe 1, 0.44±0.01) and a flag (0) specifying that the $\chi^2_{restraint}$ value of the comparison of the predicted value of this restraint to the experimentally observed value should be included in the total $\chi^2_{dataset}$ value for the dynamic ensemble (as described above).

In order to correctly calculate an ensemble of 3D-structures, the dynamic model for the molecule must be specified, which is another global parameter set. This dynamic model contains all the specifications for the variables of the rotatable bonds of interest within the molecule. Whether a bond should be allowed to rotate can be determined with the following considerations:

1) all single bonds within the molecule are rotatable, whereas no double-, triple- or aromatic bonds are rotatable;

2) the rotation of many single bonds has no effect on the relative positions of atoms in the molecule, and therefore these kinds of single bonds do not need to be rotated. Examples of such single bonds include bonds between a hydrogen atom and any other atom, or a halogen atom and any other atom; and 3) single bonds within some cyclic chemistries are unable to rotate because of the constrained geometry; an example of this would be the C—C bonds in cyclopropane.

Single bonds within the molecule that have been identified to require a dynamic model (in accordance with the above considerations) are now assigned a unimodal, bimodal or trimodal model. When there is no experimental data indicating the modality of the bond in question, the choice of modality of the dynamic model is determined using Table 1. This table shows the relationship between the bond modality to be used and the hybridisation state [14] of the two atoms in the single bond (atoms A and B).

TABLE 1

| Basic rules for determining the type of dynamic model at each rotatable bond. | | | | |
|---|---|---|---|---|
| | | Hybridisation state of atom A | | |
| | | $sp^1$ | $sp^2$ | $sp^3$ |
| Hybridisation state of atom B | $sp^1$ | not rotated | unimodal | unimodal |
| | $sp^2$ | unimodal | bimodal | bimodal |
| | $sp^3$ | unimodal | bimodal | trimodal |

In accordance with these specifications, the modal behaviour initially assigned to a wide variety of covalent bonds is set out below.

Examples of covalent bonds generally considered to have fixed internal coordinate geometries (covalent bonds in black are considered to be fixed).

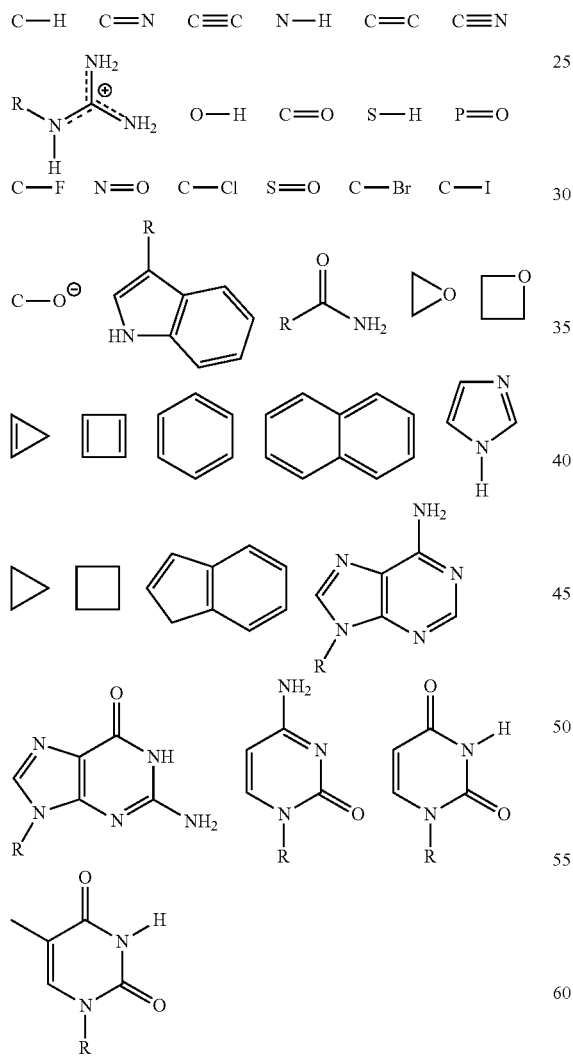

Examples of covalent bonds generally considered to prefer a unimodal distribution (covalent bonds in black are considered prefer a unimodal behaviour).

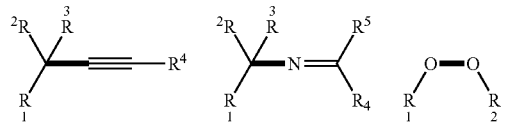

Examples of covalent bonds generally considered to prefer a bimodal distribution (covalent bonds in black are considered prefer a bimodal behaviour).

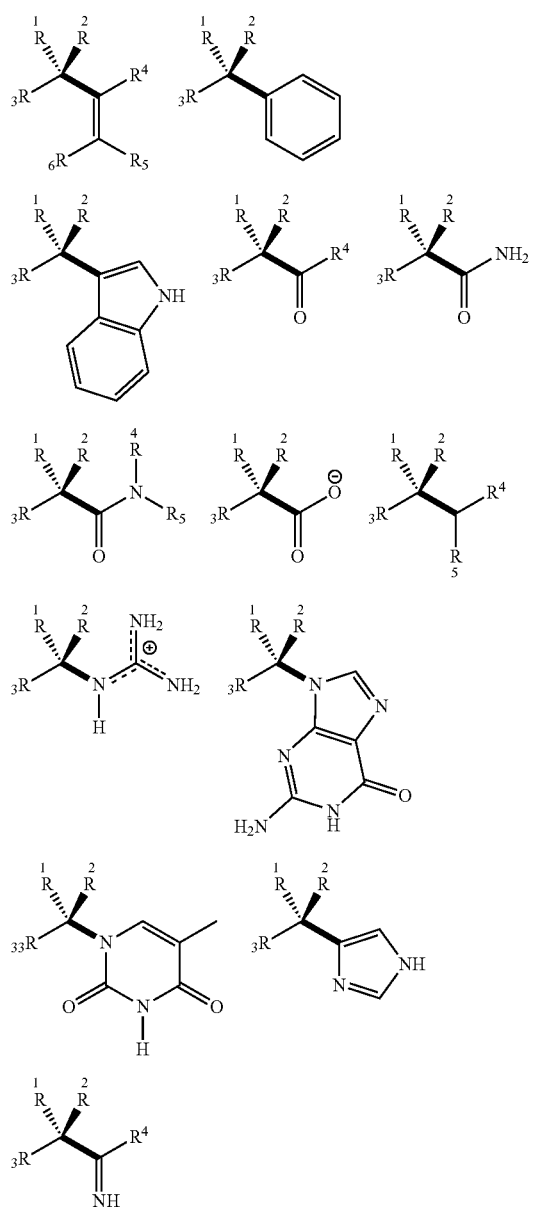

Examples of covalent bonds generally considered to prefer a bimodal distribution, that take cis and trans conformers due to electron conjugation (covalent bonds in black are considered prefer a cis/trans behaviour).

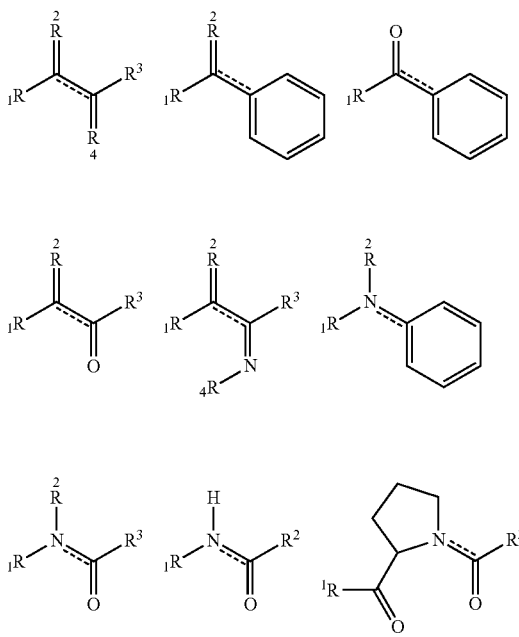

Examples of covalent bonds generally considered to prefer a trimodal distribution (covalent bonds in black are considered prefer a trimodal behaviour).

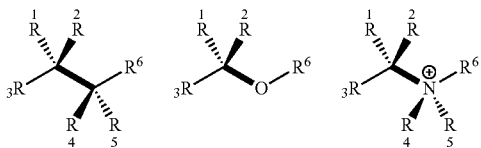

The initial values of the mean angles for each mode are set to values that are sterically favourable conformations. For example, in a trimodal model, the three mean angles would correspond to the fully staggered state for the bond [15]. Covalent bonds that have an intermediate character between a single and a double bond (due to electron conjugation) are given a bimodal model, where the two mean angles of the two conformations are given cis and trans dihedral geometries. Cyclic chemistries that interconvert between more than one conformation are given bi- or trimodal models as appropriate, where several dihedral angles are simultaneously moved together (see below for some examples).

Examples of cyclic chemistries that can adopt more than one conformation.

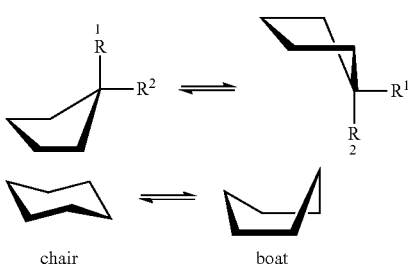

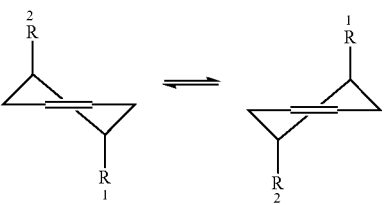

During the determination of a dynamic 3D-structure it may become apparent from the best-fit to the experimental data that a rotatable bond that was initially set to a bimodal or trimodal behaviour (according to the table and description above) is actually adopting a lower modal behaviour in the real molecule. In this case, the modal behaviour in the dynamic model file can be updated accordingly.

Where there is previous experimental data available for a rotatable bond's modal behaviour, this can be used to define the modal behaviour. Kinds of experimental data that can be used to define the modal behaviour for a given bond include NMR data (for example the cis/trans forms of a proline amide bond have distinct chemical shifts) or consideration of the range of conformations displayed for that bond (and substituents on atoms A and B) in the Cambridge Structural Database. Where molecular dynamics simulations have been performed, these may be also be used to decide upon the best modal behaviour for the bond.

Having decided upon which rotatable bonds are to be varied in order to find the best fit ensemble to the experimental data, there are two basic kinds of flexibilities defined, which are designated for each bond by a user:

1) gyrations define unimodal bond flexibilities
2) multigyrations define bimodal, trimodal and higher modal bond flexibilities.

As described below, in a preferred embodiment of the present invention rotatable bonds are designated with a gyration that has a single mean angular value ($\mu$) and a Gaussian spread of angle ($\sigma$), and these are optimised by a suitable optimisation algorithm which iteratively generates ensembles of molecular structures and tests each ensemble against real experimental data. Examples of bonds specified in this way are glycosidic linkage bonds in carbohydrates. A rotatable bond designated with a multigyration is assigned multiple geometries that it can adopt (typically related to 2 or 3 low-energy rotamer positions), each of which has an angular value and Gaussian spread of angle that can be optimised, and their relative proportions are specified with probability models (see below). These probabilities can be specified according to the relative intensity of local NOEs/ROEs or by conformational-dependent coupling constants (e.g., hydroxymethyl groups in pyranose rings), but they can also be optimised by the algorithm. An example of a bond typically described with a bimodal multigyration is a peptide $C^\alpha$—$C^O$ bond (i.e., the $\psi$ dihedral), which typically jumps between α-helical-like ($\psi \approx -60°$) and β-strand-like ($\psi \approx 120°$) geometries. The input data file shown below provides an example of how these modelling considerations can be implemented practically.

| variables: |
| --- |
| var 1 rand 0 360 jump 180 |
| var 2 rand 0 360 jump 180 |
| var 3 fix 18 jump 10.0 start 0.3 |

```
var 4 fix -60 jump 0.0 start 0.0
var 5 fix 60 jump 0.0 start 0.0
var 6 fix 15 jump 0.0 start 0.0
var 7 fix -120 jump 0.0 start 0.0
var 8 fix 120 jump 0.0 start 0.0
var 9 fix 0 jump 0.0 start 0.0
var 10 fix 30 jump 0.0 start 0.0
endsection
probabilities:

mode 1 2 0.5 0.0
mode 2 3 0.33 0.66 0.0
mode 3 4 0.33 0.1
endsection
dynamics:

gyrate 41 1 3
gyrate 42 2 3
multigyrate 48 1 4 6 5 6
multigyrate 35 2 7 10 8 10 9 10
multigyrate 55 3 7 10 8 10 9 10
endsection
```

In the variables section of this file, variables are defined using the var command, which each define either a mean value or a Gaussian spread for a rotatable bond's dihedral angle. Following the var command is a number representing the variable number (used to identify the variable later). The next option determines the initial starting value of the variable. For example, "rand 0 3 60" indicates that the initial configuration will be a random value between 0° and 360°, while "fix 18" indicates that the variable starts at 18°. The "jump" option specifies the initial value used for applying random changes to each variable in the optimisation. Large values (~180) are typically used for variables that will be used as angular degrees of freedom (ensuring that they sample their space effectively), while smaller values (~10) are used for variables that will be applied as dynamic spreads, which typically have final values up to 25° (see Examples 1, 2 and 3 below). Finally, the "start" option specifies the point at which optimisation will start. Using a value of 0.0 here indicates that optimisation will begin immediately, while a value of 0.5 would start optimisation half-way through the optimisation iterations.

The probabilities section is used to define bimodal and trimodal distributions. After the mode, command is the probability number (used to refer to it) and then a number, which is either 2 for a bimodal distribution, 3 for a trimodal distribution or 4 for a 'symmetric' trimodal distribution (where two of the probabilities are equal, see below). The next two or three numbers represent the cumulative probability, at which the different modes will be selected. The final number is a value that allows the probability to be optimised iteratively (a value of 0.0 indicates that the probability model should not change during optimisation). For example, in the above "mode 1 2 0.5" defines a bimodal model, where each conformation has a probability of 0.5 (0.5). The second mode 2 command above specifies a trimodal distribution (e.g., applied to a methyl-group). Both are set not to be optimised. The last mode 3 4 0.33 0.1 command specifies a trimodal distribution with only one degree of freedom, a single probability, $p_1$. (i.e. a symmetric trimodal model); the other two probabilities are exactly the same, i.e., $p_2=p_3=\frac{1}{2}(1-p_1)$. In this case $p_1$ has a floating probability, specified by the last column in this command being 0.1, which is a suitable iteration jump size.

In the dynamics section of this file, the relationship between the defined variables and the molecular dihedral bond angles is specified. A line beginning with gyrate specifies a unimodal probability distribution model, with the three attendant numbers specifying:
  1) the exact dihedral angle in the molecular structure
  2) the variable to use for the mean value for the dihedral angle (from the variables section) and
  3) the variable to use for the Gaussian spread of the dihedral angle.

For example, in the case above the line gyrate 41 1 3, 41 specifies a dihedral angle (41 is the value for a particular bond used in the internal coordinates table, see Appendices A, B and C associated with Examples 1, 2 and 3 respectively for example internal coordinate files), 1 specifies that var 1 should be used for the mean value and 3 specifies that var 3 should be used for the Gaussian spread.

A line beginning with multigyrate specifies a bimodal or trimodal angular model. In the line multigyrate 48 1 4 6 5 6, for example, the first number (48) specifies the molecular dihedral angle from the internal coordinates table to vary, the second number the probability model to use (1, from the probabilities section), and the subsequent numbers are the appropriate pairs of mean and Gaussian spreads (var 4 & 6 and var 5 & 6) for each of the modes. Probability models 2, 3 and 4 require 2, 3 and 2 pairs of variables respectively.

It should be noted that variables and probability models can be used repeatedly in several gyrate or multigyrate commands, allowing significant flexibility in the way that the dynamic model can be specified. For example, this allows certain rotatable bonds to be coupled (e.g., identical environments within a polymer) or allows multiple bonds to be moved in concert between major conformational states (e.g., cyclohexane ring). The general principles explained above are employed in Examples 1, 2 and 3 below.

Having defined the solvent masks, the van der Waals mask and the dynamic model it is now possible to use the optimisation algorithm to find the values for each of the, for example 10, unknown variables that give the best fit to the experimental data. This may be achieved using a process of repeated rounds of structure calculations. FIG. 4 shows a flowchart that is representative of a preferred embodiment of an overall ensemble generation and optimisation process.

During a round of structure calculations, the optimisation process may be run many times (e.g. around 40 times) to produce many optimised dynamic structures. Each individual run may have the same number of iterative optimisation steps (e.g. around 10,000, for the number of degrees of freedom typically found in a small dynamic molecule) and may employ the same number of structures in the dynamic ensemble (e.g. around 100). The number of optimisation steps and structures in the dynamic ensemble may be kept constant between successive rounds of structure calculations, allowing the results from different rounds to be directly compared, or alternatively the number of optimisation steps and/or the number of structures in the dynamic ensemble may be varied between one or more successive rounds of structure calculations.

In a preferred embodiment, experimental datasets can be progressively added to successive rounds of structure calculations. This may represent a practical limitation because in every dataset file there may be a variety of human and experimental sources of error in the initial restraint list. These sources of error may, for example, include:
  1) mis-assignment of structural restraints;
  2) incorrect application of scaling factors in determining structural-restraint intensities;
  3) incorrect calculation of restraint errors; and/or
  4) spectral artefacts.

In order to find and correct these mistakes, repeated rounds of structure calculations can be performed, in a manner similar to the determination of protein 3D-static structures by NMR [16]. By initially using a subset of the total dataset that has extremely high confidence of having few mistakes (typically 60-70% of the structural restraints 2D-NOESY and T-ROESY datasets), the few structural restraints that have high $\chi^2_{restraint}$ scores (i.e. $\chi^2_{restraint} \gg 10$) after a round of structure calculations can be easily identified as outliers. These outliers are fully reanalysed as described above, which is usually successful in determining the source of the inconsistencies and resolving them. In order to check that they have been resolved, another round of structure calculations may be performed with the revised measurements and scaling factors. Once a reasonable subset of the real experimental data (structural restraints) has been found to be consistent with the predicted experimental data, more structural restraints from the real experimental dataset can be included.

This process may be repeated until all the structural restraints in the real experimental dataset can be simultaneously satisfied. Use of a flag field in the structural restraint lists, described above, can be used to rapidly include or omit individual structural restraints in subsequent rounds of calculations. Having completed one real experimental dataset file, another real experimental dataset is included and further rounds of calculations performed, progressively correcting erroneous structural restraints in the new dataset as before, while also correcting erroneous structural restraints in the previous datasets that are now found to be in conflict with the new data.

It will be appreciated from the foregoing discussion that a sufficient number of correctly-measured structural restraints are required in the first instance to achieve rough convergence of the optimised dynamic structures in a round of structure calculation, and, moreover, before erroneous structural restraints inconsistent with that structure can be identified. The dynamic structure has been satisfactorily determined when the inclusion of more structural restraints or whole real experimental datasets of structural restraints results in no change in the final values for the dynamic variables or probabilities in the optimised dynamic structure.

It is preferred that the progress made in solving the dynamic structure is monitored by performing statistics on at least one run, and preferably more, for example, every round of structure calculations. Every run of the optimisation algorithm generates an optimised dynamic structure, which has associated with it the best-fit values for each of the variables and probabilities, the $\chi^2_{total}$ value for the dynamic ensemble, the $\chi^2_{restraint}$ value for every structural restraint used in the optimisation and a $\chi^2$ value for the van der Waals contribution. Using the best runs in the round of calculations (i.e., those with lowest $\chi^2_{total}$ values), mean values and standard deviations for each of these parameters is calculated; by way of example only, the best 10 runs out of 40 may be used. Mean values and the standard deviations for the $\chi^2_{dataset}$ values for each dataset file are preferably calculated. These data can be reported in a primary statistics table, which may take the following appearance:

|  | Mean | StDev | Ranked run no. | | | | | | | | | |
|---|---|---|---|---|---|---|---|---|---|---|---|---|
|  |  |  | 22 | 27 | 24 | 10 | 12 | 11 | 5 | 15 | 9 | 26 |
| Datasets |  |  |  |  |  |  |  |  |  |  |  |  |
| 15N-NOE | 108.3 | 4.3 | 98.6 | 103.2 | 106.8 | 110.5 | 111.0 | 112.5 | 107.5 | 112.1 | 108.2 | 112.4 |
| 2D-NOESY | 29.6 | 1.6 | 31.1 | 28.6 | 28.2 | 29.1 | 27.3 | 28.8 | 33.2 | 28.9 | 30.9 | 29.6 |
| JCOUP | 2.6 | 0.9 | 2.2 | 2.7 | 2.2 | 2.3 | 1.6 | 2.9 | 3.5 | 4.4 | 3.6 | 1.1 |
| ORDER | 2.2 | 1.5 | 2.0 | 2.2 | 1.5 | 1.1 | 2.5 | 0.2 | 2.0 | 0.4 | 4.5 | 5.3 |
| VDW | 1.3 | 0.9 | 2.5 | 1.9 | 2.6 | 0.5 | 1.7 | 1.7 | 0.2 | 1.0 | 0.5 | 0.3 |
| TotChi | 143.9 | 3.8 | 136.5 | 138.6 | 141.2 | 143.5 | 144.1 | 146.0 | 146.5 | 146.7 | 147.6 | 148.7 |
| Variables |  |  |  |  |  |  |  |  |  |  |  |  |
| var 1 | −83.4 | 8.9 | −95.2 | −74.3 | −88.5 | −76.4 | −92.8 | −96.2 | −75.7 | −73.2 | −74.8 | −87.1 |
| var 2 | −119.3 | 5.2 | −115.3 | −122.9 | −112.0 | −123.6 | −114.5 | −121.6 | −124.7 | −112.1 | −119.8 | −126.8 |
| var 3 | 20.9 | 5.5 | 18.8 | 24.4 | 11.5 | 25.1 | 16.3 | 23.2 | 25.9 | 12.4 | 27.5 | 23.9 |
| Probabilities |  |  |  |  |  |  |  |  |  |  |  |  |
| p1(1) | 0.33 | 0.0 | 0.33 | 0.31 | 0.33 | 0.33 | 0.34 | 0.33 | 0.32 | 0.33 | 0.33 | 0.35 |
| p2(1) | 0.66 | 0.0 | 0.66 | 0.66 | 0.66 | 0.68 | 0.66 | 0.65 | 0.66 | 0.67 | 0.64 | 0.66 |

In such primary statistics tables, the data from the runs with the best $\chi^2_{total}$ values are shown (in this case the runs were ranked in terms $\chi^2_{total}$ and the best 10 runs were selected). The TotChi line gives the $\chi^2_{total}$ value for each run, as well as the mean value and standard deviation (StDev) for these $\chi^2_{total}$ values. Above this line, the mean $\chi^2_{total}$ and its standard deviation are given for each individual dataset file (designated, in this case, 2D-NOESY, JCOUP, ORDER, 15N-NOESY-HSQC that were used in this round of calculations. The mean $\chi^2_{total}$ and standard deviation values are also given for the van der Waals (VDW) term in each run. Following the TotChi line are the results for the variables specified in the dynamic model file, and then the probabilities.

In a further preferred embodiment of the present invention, in order to determine if any one dataset file is unduly biasing the emerging dynamic structure, a secondary statistics table may also be produced that reports the $\chi^2_{dataset}$/restraint for each dataset (Chi/Res) from the number of structural restraints in each dataset file (Restraints) and the total $\chi^2_{dataset}$ value for the dataset (Tot chi):

| Dataset | Restraints | Tot Chi | Chi/Res | Viol(>10) | Percent |
|---|---|---|---|---|---|
| TOTAL | 107 | 142.3 | 1.3 | 0 | 0 |
| 2D-NOESY | 82 | 107.9 | 1.3 | 0 | 0 |
| JCOUP | 3 | 2.6 | 0.9 | 0 | 0 |
| 15N-NOESY-HSQC | 19 | 29.6 | 1.6 | 0 | 0 |
| ORDER | 3 | 2.2 | 0.7 | 0 | 0 |

When no one dataset is unduly biasing the emerging dynamic structure, all $\chi^2_{dataset}$/restraint values are ~1 and are comparable to each other. In the example above, it can be seen that this is indeed the case, although the 15N-NOESY-HSQC dataset might be biasing the structure a little ($\chi^2_{dataset}$/restraint=1.6). While the errors for order parameters (ORDER) and scalar coupling (JCOUP) kinds of data can be determined experimentally, the errors for NOESY and T-ROESY datasets depend upon the imprecisely known value m. Suitable values for m based upon experience have been given for the most common kinds of NOESY and T-ROESY experiments (see below), and these can be taken as a guide for other NOESY and T-ROESY experiments. To determine the value of m for other experiments more precisely, different m values can be tried until a $\chi^2_{dataset}$/restraint value of ~1 is achieved, this may be termed balancing. To avoid the process of balancing becoming too subjective, m values comparable to those given below should be used (i.e., between 0.1 and 0.8) and balancing should not be attempted until the base dataset has been determined for the dataset being balanced.

In a similar process to balancing, the most suitable value for $\tau_c$ can be found if it has not been precisely determined experimentally. An initial estimated value for $\tau_c$ can be used to allow structure calculations to be preformed and sufficient structural restraints to be used in the optimisation algorithm to produce loosely converging structures. At this point, several rounds of structure calculations that only differ in the value of $\tau_c$ can be performed, and the value of $\tau_c$ that gives the lowest mean $\chi^2_{total}$ value is taken to be the best value for $\tau_c$ (as described above).

Having determined an initial dynamic 3D-solution structure of a molecule which best fits real experimental data, in a still further preferred embodiment of the present invention the initial best 3D-solution structure is refined by a more extensive round of structure calculations to find the best possible fit to all available experimental data. This structure-refinement round may use some or all of the same real experimental datasets as were used in the previous rounds of structure calculations but, for example the ensemble size may be increased (e.g. to 250 structures), the number of iterative steps may be increased (e.g. to 15000) and/or more runs may be performed (e.g. 100). In addition or alternatively, the dynamic model file can be changed to set the molecule's starting point to be in the best conformation determined in the previous round of structure calculations (i.e., all variables starting in a random conformation are initially fixed to the best value previously determined), and/or only small jump sizes in dynamic parameters are permitted. This allows the known $\chi^2_{total}$ minimum to be locally searched until the best possible values of the experimental variables and probabilities are determined. Statistics may be performed on this refinement round, preferably in a similar manner to the statistics performed previously in the original dynamic structure calculation rounds which provided the initial ensemble or dynamic structure which best fit all of the real experimental data. Using the best runs from this refinement round, the mean optimised dynamic structure and mean optimised dynamic ensemble may be calculated (e.g. taking the mean values for the variables and probabilities from, for example the best 20 runs of the 100).

Referring now to FIG. 5, there are illustrated a plurality of components which cooperate to provide an implementation of the invention. A user interface component 1 provides an interface between a user and the programmed computer. The user interface component 1 communicates with a plurality of modules so as to process received data and output processed data. For example, a component 2 represents a flexible molecule which is processed by the embodiment of the invention. The flexible molecule represented by the flexible molecule component 2 is received by the user interface 1. Prediction and experimental calculation component 3 predicts experimental data values in the manner described above and uses those predicted values so as to update data associated with a flexible molecule component 2. The prediction and experimental calculation component 3 communicates with a molecular property averager component 4 arranged to produce averages of molecular properties from ensembles of structures. The prediction and experimental calculation component 3 further communicates with an iteration thread 5 configured to perform a plurality of iterations which affect the flexible molecule represented by the flexible molecule component 2. A data storage component 6 stores data required by the system and communicates with a plurality of the system components. A dynamic confirmation generator component 7 compares predictions of experimental data against real experimental data.

The flexible molecule represented by the flexible molecule component 2 is defined in terms of bonds, angles and torsional angles, rather than using Cartesian coordinates. Representation of the flexible molecule is achieved by using a plurality of classes shown in FIG. 6. A molecule class 8 acts as a super class for a flexible molecule class 9. The flexible molecule class 9 has an association with a topology class 10 which in turn has associations with an atom class 11 and a bond class 12. The atom class 11 and the bond class 12 respectively represent atoms and bonds included within molecules.

The data storage component 6 of FIG. 5 is shown in further detail in FIG. 7. A data storage class 13 has an association with a data file class 14 representing a data file. The data storage class 13 also has an association with an experimental data storage class 15 storing experimental data and a physical parameters class 16 storing physical parameters of the molecule of interest. A molecule property storage class 17 also interfaces with the data storage class 13 and stores data indicative of the molecular properties.

The experimental data storage class 15 interfaces with the data storage class in order to make predictions of experimental data chosen by the user and to report the $\chi^2$ measure for the agreement between predicted and real experimental measurements. The molecular-property-averger component 4 calculates statistics during generation of the dynamic molecular ensemble from the dynamic degrees of freedom that can be used to make predictions of experimental data. This is implemented as multiple instances of a polymorphic class structure that define each type of experimental data. Thus new types of experimental data can be readily added. This is illustrated in FIG. 5.

Referring to FIG. 8, it can be seen that the data_file class 14 has a plurality of subclasses representing different types of experimental data. More specifically, a relaxation_data class 18, an rdc_data class 19, a jcoup_data class 20, a hetnoe_data class 21, a hbond_data class 22, a dihedrals_data class 23 and vdw_data class 24 are all subclasses of the data_file class 14. It can be seen that the data_file class 14 exposes two parameters, an identity parameter identifying the file and a data type parameter being an integer value indicating the type of data. A number of methods are also exposed by the data_file class 14. Specifically, a read data method is arranged to read data from a data file, serialise and unserialise methods are respectfully arranged to serialise the contents of a class or unserialise its content, while a calculate chi-square method is arranged to perform a $\chi^2$-calculation. A return data type method returns the data type of the data file represented by the data_file class 14 while an output violations method outputs any violations which may have occurred to the class.

It can be seen that the relaxation_data class 18 has a noe_data class 25, a roe_data class 26 and a troe_data class 27 representing subtypes of relaxation data represented by the relaxation_data class 18.

The class structure described with reference to FIG. 8 allows a variety of different types of experimental data to be represented within a common structure. A plurality of different types of experimental data can be used together to produce a single dynamic model. This was described in further detail above.

It will be appreciated that the class structure described with reference to FIG. 8 provides considerable flexibility and allows any kind of dynamical data that can be related to a physical model to be used within the method described above. For example, NMR relaxation data, fluorescence resonance energy transfer (FRET) data, analytical ultracentrifugation (AUC) data and small-angle X-ray scattering (SAXS) data can all be used.

Where NMR data is employed in the optimisation the molecule under investigation will typically contain both carbon and hydrogen atoms (often referred to as organic molecules) and have one or more covalent bonds that are rotatable (i.e., do not have a fixed geometry). While a pure (>95% single molecular species) molecule may be studied, a mixture of related molecules (i.e., variants with a few atoms being different) or substantially different molecules (for example, in the presence of impurities) can also be used, provided that the experimental observable(s) being measured can be sufficiently resolved or deconvoluted. Molecules can also be analysed in the presence of receptor molecules (such as proteins or nucleic acids), if NMR data can be recorded.

In accordance with standard practice, NMR samples may be prepared by dissolving the molecule of interest in a solvent, typically water ($H_2O$, $D_2O$ and mixtures thereof) for molecules of biological interest, but organic solvents can also be used where appropriate. Samples are typically made at solute concentrations of 1-100 mM, at approximately neutral pH with up to 300 mM salt (e.g., sodium chloride, phosphate buffer), but are not restricted to these ranges of conditions. Samples typically contain an internal reference compound (e.g., DSS, dimethyl-2-silapentane-5-sulphonate) and an inorganic antibacterial (e.g., sodium azide), but neither of these conditions are mandatory. One or more samples of the molecule of interest with slightly different conditions (e.g., 10% $D_2O$/90% $H_2O$ v/v, 100% $D_2O$, presence of alignment media) may be prepared as desired. Molecules have no requirement to be isotopically-enriched (e.g., with $^{15}N$, $^{13}C$, $^{19}F$ or $^{31}P$) or depleted (e.g., replacement of natural-abundance $^{13}C$ with $^{12}C$, $^{15}N$ with $^{14}N$ or $^{1}H$ with $^{2}H$), but additional experiments can be performed and the data used in the optimisation should the molecule be so enriched or depleted. The NMR samples are used to record NMR datasets using standard pulse-sequences available on any modern NMR spectrometer.

NMR datasets may be recorded on molecular sample(s), prepared as described above, to allow $^{1}H$, $^{13}C$ and/or $^{15}N$ nuclei (and any other NMR-active nuclei present) to be assigned (i.e., their NMR chemical shifts determined) and proton-proton homonuclear scalar-coupling constants be measured. NMR spectra can be recorded at any temperature, provided that the molecule remains in solution. While spectra are typically recorded at a proton-resonance frequency of 600 MHz, higher or lower field-strengths can also be used, assuming suitable spectral resolution can be achieved. These assignment experiments [17, 18] typically comprise:

1) [$^{1}H$]-1D
2) [$^{1}H$, $^{1}H$]-DQF-COSY
3) [$^{1}H$, $^{1}H$]-TOCSY
4) [$^{1}H$, $^{13}C$]-HSQC
5) [$^{1}H$, $^{13}C$]
6) [$^{13}C$]-1D spectra
7) [$^{13}C$]-filtered [$^{1}H$]-1D spectra
8) [$^{1}H$, $^{15}N$]-HSQC
9) [$^{15}N$]-1D spectra
10) [$^{15}N$]-filtered [$^{1}H$]-1D spectra.

NMR experimental datasets may then be recorded, which allow for the measurement of parameters that are quantitatively indicative of molecular 3D-structural and dynamical information. The experiments typically performed to achieve this include, but are not limited to:

1) Nuclear Overhauser enhancements (NOEs) and rotating-frame NOEs (ROEs). NOE and ROE data are typically measured using experiments such as [$^{1}H$, $^{1}H$]-NOESY, [$^{1}H$, $^{15}N$]-NOESY-HSQC, [$^{1}H$, $^{13}C$]-NOESY-HSQC, [$^{1}H$, $^{1}H$]-T-ROESY and [$^{1}H$, $^{15}N$]-T-ROESY-HSQC [19, 20]. In the particular case where water is the solvent, the solvent signal is usually suppressed using presaturation or a dedicated pulse-sequence, e.g., one containing the WATERGATE filter [21].

2) Conformation-dependent scalar-couplings. Conformation-dependent scalar couplings (e.g., $^{3}J$) are typically measured using experiments such as [$^{1}H$]-1D spectra, quantitative E-COSY [22], HNHA [23] and J-modulated $^{15}N$-HSQC experiments [24].

3) Residual dipolar couplings (RDCs), which are typically measured from [$^{1}H$]-1D spectra and experiments such as [$^{1}H$, $^{13}C$]-HSQC and [$^{1}H$, $^{15}N$]-HSQC where broadband heteronuclear decoupling during acquisition has been disabled [13]. In the particular case where the molecule is $^{13}C$ and/or $^{15}N$-isotopically enriched, standard experiments such as those typically performed on proteins can also be used to measure RDCs and conformation-dependent scalar couplings (e.g., $^{3}J_{HC}$).

4) $T_1$- and $T_2$-relaxation data and heteronuclear (e.g., $^{1}H$—$^{13}C$ or $^{1}H$—$^{15}N$) NOEs [25], which are measured using pulse-sequences that have been derived previously [6].

5) Chemical shift anisotropy, paramagnetic-induced shifts, hydrogen-bonds (identified by determination of e.g., exchange rates, proton-carbonyl scalar-couplings, isotope effects or exchangeable proton temperature coefficients) and salt-bridges (identified by e.g., pH or NaCl titrations).

As mentioned above, the experimental datasets can be recorded at any NMR field-strength, at any temperature in which the molecule is still soluble and on samples of different compositions. All datasets should be recorded with a sufficient number of datapoints in the acquisition dimension to allow spectral features of interest be resolved (e.g., proton multiplet structure). In the case of NOESY and T-ROESY [26] spectra, the spectrum is preferably recorded with suitable parameters such that proton multiplet components are not resolved in the indirect proton dimension, since this significantly complicates the determination of scaling factors (see below). Spectra are also typically recorded with high signal-to-noise ratios to minimise errors on peak-height and chemical-shift (peak-centre) measurements.

In NOESY, ROESY and T-ROESY NMR datasets, the structural and dynamical information is encoded within the intensities of peaks (both diagonal and cross-peaks) of the respective spectra and therefore these peak intensities must be accurately determined (often achieved by measuring the maximum peak-heights). However, with the exception of those protons in the molecule that have no homonuclear scalar couplings (e.g, an aldehyde proton), each peak from a proton is multiply split into a resonance multiplet [27] in the acquisition dimension, according to the number and magnitudes of the scalar couplings associated with the proton, the NMR field-strength, and the difference in chemical shift between the proton and those protons scalar-coupled to it.

Since the true peak-height for one mole abundance of protons is required for input into the algorithm (described below with reference to FIGS. 9, 10 and 11), these splittings must be compensated for to allow the correct equivalent peak-height value for one mole abundance of protons to be calculated. This is achieved by the use of scaling factors, $f$. In brief, the scaling factor for each resonance in a resonance multiplet must be determined, which is a conversion factor that allows the observed height of a resonance in a resonance multiplet to be converted to the value for one mole abundance of protons. The set of scaling factors for the resonance multiplet of a particular proton is termed the scaling factor set, $f_i = \{i_i, \ldots, i_n\}$. It is therefore necessary to know the scaling factor set for the proton in the acquisition dimension of the observed NOE (or ROE) to determine the equivalent one mole abundance height of the observed NOE. The determination of scaling factor sets, and their use in calculating one mole abundance true peak heights, is detailed below.

Proton resonance multiplets arise from scalar-couplings between adjacent protons. In the first-order case, each scalar-coupling bifurcates the proton lineshape, and therefore for c scalar-couplings to a proton, the proton will have $2^c$ multiplet components. This first-order case occurs when the so-called weak-coupling limit is satisfied, which is when the difference in frequency between two nuclei I and S($\Delta N_{IS}$) is considerably greater than the scalar-coupling ($J_{IS}$) between them (a working definition would be that the frequency difference is ten times the scalar-coupling), described by equation (15).

$$\Delta N_{IS} = |N_I - N_S| \gg J_{IS} \qquad (15)$$

wherein $N_I$ is the measured resonance frequency for nucleus I, $N_S$ is the measured resonance frequency for nucleus S, ($\Delta N_{IS}$) is the difference in frequency between nuclei I and S, and ($J_{IS}$) is the scalar-coupling between nuclei I and S.

In the case of weakly-coupled protons and when the value of each homonuclear coupling-constant is known (described above), proton scaling factors can be explicitly and easily calculated (see below). However, when the weak coupling limit is not satisfied, the nuclei are said to be strongly-coupled, and distortions to resonance multiplet lineshapes occur that are not expected at first-order. These distortions prevent the easy calculation of scaling factors (see below) and therefore the scaling-factor sets for protons that are weakly- and strongly-coupled are determined with different methodologies. Since proton homonuclear coupling constants are typically less than 15 Hz ($J_{IS}$), it can be easily ascertained with equation (1) whether a proton is weakly coupled to the other protons that it is scalar-coupled to at a particular proton resonance frequency (Hz), once the protons' chemical shifts have been determined through the standard processes of assigning the protons in the molecule (described above).

When a proton satisfies the weak-coupling limit for all protons it is scalar-coupled to, the proton's scaling-factor set may be determined according to the following methodology. In the most simple case, all the multiplet components are resolved from each other, i.e., a proton with c scalar-couplings will have $2^c$ multiplet components uniquely visible in the spectrum as $2^c$ resonances in the resonance multiplet. In this case, all the resonances will theoretically have the same height as each other, and the scaling factor for each resonance in this case is therefore also $2^C$, as shown in FIG. 9. The scaling-factor sets for each peak produced by the presence of 0, 1, 2 or 3 homonuclear coupling constants are given explicitly in FIG. 9. Such scaling-factor sets are termed simple scaling-factor sets.

In more complex cases for protons obeying the weak-coupling limit, multiplet components overlap with each other to some degree, meaning that fewer distinct resonances (than the number of multiplet components, $2^c$) are observed in the spectrum. The extent and nature of the overlap depends upon both number and magnitude of the scalar-couplings to the proton and the intrinsic proton resonance linewidth at half-height in the spectrum ($\lambda$, which is itself dependent upon the temperature, the solvent conditions and the molecule's correlation time). Since $\lambda$ is a property of a particular spectrum, it is therefore clear that scaling-factor sets must be determined for each spectrum that will be quantified. The intrinsic proton resonance linewidth at half-height ($\lambda$) in a spectrum is measured by taking the mean of the linewidth at half-height from several resonances that are resolved from overlap with other resonances (e.g., an aldehyde proton, which has no homonuclear scalar couplings). Multiplet components will overlap (i.e., will not be individually resolved) when the difference in resonance frequency ($\Delta v$) between the components is less than or equal to the value of $\lambda$ (i.e., $\Delta v \leq \lambda$) and will manifest in the spectrum as a single resonance, which is higher than that expected for an individual multiplet component. Moreover, unless the multiplet components overlap exactly (i.e., $\Delta v = 0$) the resonance will be broader than the non-overlapped multiplet components in the spectrum.

The degree of overlap of a proton's multiplet components depends upon the values of the homonuclear scaling-couplings to that proton. Where the coupling constants all coincidentally have the same value (J), and that value is larger than the intrinsic proton resonance linewidth at half-height (i.e., J>$\lambda$), the multiplet components overlap perfectly (i.e., $\Delta v = 0$) and give ideal scaling-factor sets. The appearance of the proton lineshapes, and their associated scaling-factor sets, are shown in FIG. 10, for the cases of 1, 2, 3 and 4 identical homonuclear scaling coupling constants being present.

In the rather more common case where the coupling constants do not all have the same value, the multiplet components do not overlap perfectly (i.e., $\Delta v \neq 0$) and non-ideal lineshapes are observed. Such multiplet components may be analysed using a method according to the fourth aspect of the present invention as defined above, specific embodiments of which are now described in detail to demonstrate the application of that aspect of the present invention.

These non-ideal line-shapes will generally have an appearance similar to one of the resonance-multiplet patterns shown in FIGS. 9 and 10. In this case, the scaling factor set from the non-ideal proton is initially taken from the lineshape in FIG. 9 or 10, which is most similar to that observed in the spectrum. For each resonance in this multiplet that is broadened by non-perfect overlap of multiplet components, the value Δv between the overlapping components is explicitly calculated from the known values of the homonuclear coupling constants. For example, if a proton has a single scalar-coupling of 3 Hz (Δv=3 Hz) to a second proton and the spectrum's intrinsic line-width at half-height is 6 Hz (λ=6 Hz), the two multiplet components will not overlap perfectly with each other, and a single broad resonance will be observed in the spectrum, which has a height lower than that required for one mole abundance of protons, yet taller than half the value of one mole abundance protons. Since a single resonance is observed, this proton's multiplet pattern is most like the case shown in FIG. 9 (a proton with no scalar coupling) and the scaling factor set is initially taken to be $f=\{1\}$. However, the height of this single broadened resonance must be further scaled by the appropriate broadening adjustment (b) to determine the height that would have been observed for the overlapped resonance if the two components had overlapped perfectly. This broadening adjustment can be shown (see FIG. 11 for a schematic involving one scalar coupling, J) to be modelled suitably by equation (16).

$$b = \frac{\lambda}{\lambda - (\Delta v/2)} \text{ for } \Delta v \leq \lambda \quad (16)$$

Therefore, in the case of the proton described above with a single scalar-coupling constant of 3 Hz (Δv=3 Hz) in a spectrum with an intrinsic line-width at half-height of 6 Hz (λ=6 Hz), the broadened resonance with initial scaling-factor set $f=\{1\}$ is converted via broadening adjustment b=6/(6−(3/2))=1.3 to be $f=\{1.3\}$. This set of combined scaling factors is the correct scaling factor required to convert this resonance's experimentally-measured height into an equivalent height for one mole abundance protons. Each broadened resonance within a resonance multiplet may be similarly treated, to determine a set of combined scaling factors for a non-ideal weakly-coupled proton.

As a second, particularly common example, consider a proton with two scalar-couplings of 8 Hz and 10 Hz, in a spectrum with intrinsic line-width at half-height of 6 Hz (λ=6 Hz). The line-shape of this proton is most like that of a proton with two identical scaling coupling constants (FIG. 10), in which the two central multiplet components overlap and make a resonance approximately twice as high as the two outer resonances. The resonances are therefore given an initial scaling factor set of $f=\{4, 2, 4\}$. The separations between the multiplet components are clearly 8 Hz (first and second components, $\Delta v_{1,2}$=8 Hz), 2 Hz (second and third components, $\Delta v_{2,3}$=2 Hz) and 8 Hz (third and fourth components, $\Delta v_{3,4}$=8 Hz). Since the values of $\Delta v_{1,2}$ and $\Delta v_{3,4}$ are less than λ, the outer multiplet components do not overlap with any other multiplet components and therefore no broadening adjustment is required. However, for the two interior multiplet components (which non-perfectly overlap to give a single broad resonance, since $\Delta v_{2,3}$<λ) a broadening adjustment is applied. The combined scaling factor, $f$, for the central resonance in the multiplet is given by the initial value, i.e., 2×b, where b=5/(5−(2/2))=1.25 (since $\Delta v_{2,3}$=2, λ=5), which is 2×1.25=2.5. Therefore, the scaling factor set for this proton's resonance multiplet is $f_i=\{4, 2.5, 4\}$. By using these formulae and rules, it is possible to explicitly calculate the combined-scaling-factor sets for protons with different numbers and magnitudes of scalar-couplings in any given particular spectrum, as long as the weak-coupling rule applies. A variety of different examples are given in the worked example of a hyaluronan hexasaccharide (see worked examples below). More general rules for calculating multiplet patterns beyond the simple cases exhibited here have been published [27].

It can be readily seen from broadening adjustment equation (16) that when the value of Δv is equal to λ, then b=2 (i.e., the two multiplet components only just overlap and create a resonance appearing in the spectrum as a broad plateau at the same height as the individual multiplet components). It can also be seen that when the two multiplet components overlap perfectly (i.e., Δv=0), then b=1, which is equivalent to the numeric sum of the scaling factors of the multiplet component individually, and equivalent to the case of ideal scaling factors sets, where no broadening is present.

When a proton is strongly-coupled to other protons, i.e., it does not satisfy equation (15), the proton's scaling-factor set may be determined according to the following methodology. First a spectral-peak resulting from that proton (i.e., the chemical shift in the acquisition dimension corresponding to that proton) is sought (with strong signal intensity) that does not overlap any other peaks. In the selected peak, therefore, all the resonances in the multiplet can be clearly observed without being obscured by overlap from other peaks in the spectrum. The line-widths at half-height of the resonances in the multiplet are then measured directly from the spectrum, to determine whether any are particularly broader than any other in the resonance multiplet. When the resonances are indeed all approximately as broad as each other (which may be considered to be when the widest resonance is less than twice as wide as the narrowest resonance) the proton's scaling factor set can be determined as follows. The height of each resonance is measured directly from the spectrum ($h_i$), and the scaling factor for each resonance ($f_i$) is determined using equation (17).

$$f_i = \frac{\sum_{i=1}^{i=n} h_i}{h_i} \quad (17)$$

In this manner, a scaling-factor set can be determined for each strongly-coupled proton, provided a clearly-resolved peak can be identified in the spectrum. It is noted that equation (17) gives reasonably accurate results only when each resonance in the multiplet has approximately the same line-width at half-height and when the heights of all resonances in the resonance multiplets can be measured accurately. When the resonances do not have approximately the same line-width at half-height, volumes of each resonance ($v_i$) may be used instead of heights in equation (17), provided the volumes can be measured with sufficient accuracy.

The different NMR datasets containing information on the structure and dynamics of the molecule are analysed and datapoints within each spectrum are converted in particular ways, depending upon the kind of data contained in the spectrum. These procedures are required to convert the data into a form suitable for use by the dynamic structure calculation algorithm (described above). In addition to the measurement of each structural-restraint's value, the measurement's standard error must also be determined so that the algorithm can calculate how good a fit the dynamic model is to the experimental data.

Structural restraints from NOESY, ROESY and T-ROESY are derived by measuring both diagonal and cross-peak heights from the spectra. Having determined the scaling factor sets for the resonances in a proton's resonance multiplet (see above), the true peak height (H) for one mole abundance of protons from each resonance can be calculated as follows. The resonance height ($h_i$) of each resonance in the resonance multiplet is measured directly from the spectrum and multiplied by the relevant scaling factor $f_i$ from the scaling-factor set, giving an individual measure of the true peak height, $H_i$, equation (18).

$$H_i = h_i \times f_i \quad (18)$$

By measuring several resonance heights in the resonance multiplet and multiplying each by its associated scaling factor, several different values for the true peak-height (H) are therefore calculated. The best value to use for the true peak height is therefore the mean value ($<H>$) from these repeated measurements, equation (19).

$$\langle H \rangle = \frac{\sum_{i=1}^{i=n} H_i}{n} \quad (19)$$

Using formula (19), the true peak-height of every peak (both diagonal and cross-peaks) in the NOESY or ROESY spectrum may be calculated, for direct input into the algorithm. Each true peak-height is associated with a pair of protons, being the NOE or ROE assignment denoting the protons for which the NOE or ROE value should be predicted by the algorithm. Each true peak-height is also given a calculated standard error value (see below). The designation of the two protons experiencing the NOE/ROE effect, with true peak-height value and standard error on the true peak-height value, is termed an NOE or ROE structural restraint. In the case of overlapped NOE or ROE structural restraints (which occur particularly when the protons forming the peak in the spectrum have identical chemical shifts) several pairs of protons are together causing the peak in the spectrum, and the algorithm therefore calculates the combined predicted value for the true peak-height for this group of protons pairs. It is noted that cross-peaks in a homonuclear 2D-NOESY, ROESY or T-ROESY spectrum that are assigned to protons that are scalar-coupled to each other are generally not useful in the generation of accurate structural restraints. This is because the evolution of the scalar coupling(s) during the NOE or ROE mixing time significantly distorts the resonance multiplet lineshape and structure in non-trivial ways, making it intractable to analysis in this manner.

Having determined the mean true peak-height ($<H>$) of a peak, the estimated error ($\varepsilon_{exp}$) on this measurement must also be calculated. Sources of error in the calculated mean true peak height include the signal-to-noise of the spectrum, intrinsic non-idealities in the lineshape of each resonance due to phase-twists and spectral artefacts and the scaling of the error in each measured resonance height by the scaling factor applied to it. The signal-to-noise of the spectrum (s) is measured directly. Non-idealities in the lineshape of each resonance may be considered to give a uniform systematic error across NOESY, ROESY and T-ROESY spectra that is directly proportional to the height of the measured resonance. The constant of proportionality is termed m and may be considered to be approximately 0.4 (i.e., ~40% of the measured resonance height) in the case of 2D-NOESY spectra, 0.5 in the case of 2D-T-ROESY spectra, 0.2 in the case of $^{15}$N-T-ROESY-HSQC spectra, and 0.4 in the case of $^{15}$N-NOESY-HSQC spectra. Therefore, according to standard statistical procedures, the error $\varepsilon(h)$ in the measurement of each resonance height, h, from the spectrum that results from these two systematic errors is given by equation (20).

$$\varepsilon(h) = \sqrt{(m^2 h^2 + s^2)} \quad (20)$$

In determining the true peak-height, each measured resonance height is multiplied by the appropriate scaling factor ($f_i$). This results in an error $\varepsilon(H)$ on each individual measure of the true peak-height (H), which is given by equation (21).

$$\varepsilon(H)_i = f_i \sqrt{(m^2 h_i^2 + s^2)} \quad (21)$$

For a resonance multiplet of several resonances, therefore, each estimate of the true peak height ($H_1$) has an associated estimated standard error of $f_i \sqrt{(m^2 h_i^2 + s^2)}$. Just as a mean value for the true peak-height ($<H>$) was calculated, the appropriate single value to use for the estimated standard error ($\varepsilon_{exp}$) is given (according to standard statistical procedures) by equation (22).

$$\varepsilon_{exp} = \sqrt{\frac{1}{n} \sum_{i=1}^{i=n} f_i^2 (m^2 h_i^2 + s^2)} \quad (22)$$

A further complication that can occur in the determination of peak-heights in a NOESY or T-ROESY spectrum is that resonances from different peaks can overlap to greater or lesser extents, dependent upon the chemical shifts of the protons forming each peak. Where the difference in Hz between two overlapping resonances ($\Delta v$) of equivalent mole ratio (e.g., an overlap of two resonances from different doublets) can be precisely determined (using the known chemical shifts of each proton, and the frequency of each resonance in the resonance multiplet calculated from the scaling-factor sets and scalar-coupling), the above formula for broadening adjustments can be directly applied, resulting in a quantified overlapped NOE or ROE structural restraint (i.e., the true peak-height represents the sum of two or more NOEs/ROEs) for use in the algorithm. Where the overlap is caused by two components of non-equivalent mole ratio (e.g., a doublet resonance at 0.5 mole proton abundance, overlapping with an outer triplet resonance at 0.25 mole proton abundance), the overlap and broadening adjustments may be appropriately weighted to accommodate this non-equivalence.

In the case where a mixture of related molecular species (i.e., variants with a few atoms being different) is present in the NMR sample, some NOEs/ROEs will be from protons present at mole abundance (i.e., those in the parts of the molecule where there are no differences in chemical structures), whereas others will be at a significantly reduced mole abundance (i.e., NOEs between parts of the molecule that vary in chemical structure between the mixture of molecular species). For example, in the case of sugars with a reducing terminus, it is known that the reducing terminal ring exists in solution as a mixture of α- and β-anomers of typical relative abundances (r) 0.4 and 0.6 mole per mole, respectively, whereas the rest of the molecule is identical. NOEs between groups in the rest of the molecule will therefore be present at 1 mole abundance, whereas NOEs to protons in the α- or β-rings will have a reduced intensity. In the case of NOEs from a proton not in the reducing terminal ring to a proton in the α-reducing terminal ring, the intensity will therefore be 40% of what it would have been if the α-form was at 100% abundance. The true peak-height (determined from measured resonance heights from a resonance multiplet and scaled by scaling factors as above) must therefore be additionally multiplied by a factor of 1/r to determine the one mole value. The estimated standard error $\varepsilon_{exp}$ on the true peak-height in these cases is now therefore calculated by equation (23).

$$\varepsilon_{exp} = \sqrt{\frac{1}{n}\sum_{i=1}^{i=n}\frac{f_i^2(m^2h_i^2+s^2)}{r^2}} \quad (23)$$

A similar lack of protons behaving at one mole abundance can occur through non-uniform excitation of protons within the molecule due to the NMR pulse-sequence employed. This is especially true in the case of protons close to the water resonance in water samples, in which a WATERGATE excitation profile is used to minimise the signal from $H_2O$. To overcome this problem, resonance heights from protons in spectra, in which uniform excitation has been achieved (e.g., a 1D spectrum with light presaturation to reduce the water, or a $^{13}C$-filtered 1D spectrum), may be compared against resonances from spectra with non-uniform excitation (e.g., a 1D spectrum with WATERGATE) and the ratio of resonance heights can be used to provide the suitable rescaling factor for one mole abundance in all experiments employing the same excitation profile (e.g., 2D NOESY with WATERGATE). The errors on true peak-heights derived in this way are determined in the same fashion as for mixtures of molecules making non-mole-abundance protons, equation (9), caused by having a mixture of molecules. Clearly, since these excitation profiles introduce another source of error, uniform excitation of proton signals is to be preferred where experimentally possible.

The use of 'noNOEs' and 'noROEs' structural restraints from each NOESY and ROESY spectrum may be an important part of the analysis of each dataset. In addition to increasing the size of the dataset, the importance of noNOEs and noROEs lies in the restrictions they impose on the relative 3D-space that atoms in the molecule can occupy across the molecular ensemble to still remain consistent with the experimental data. A noNOE (or noROE) is assigned when there is no signal intensity above the noise of the spectrum at the chemical-shift coordinates (where a correlation may have been possible). Such noNOEs may be given a true peak-height of zero and their standard errors set to a third of the value of the intensity measured at the chemical-shift coordinates multiplied by the smallest scaling factor from the acquisition dimension proton's scaling-factor set (i.e. $\varepsilon_{exp}=(f_{min} \times h_{zero})/3$, where $f_{min}$ is the smallest scaling factor from the acquisition dimension proton's scaling-factor set and $h_{zero}$ is the intensity measured at the chemical-shift coordinates). As many noNOEs (and noROEs) as possible are assigned within each spectrum.

Another kind of NMR data that reports 3D-molecular structure and dynamics are conformation-dependent scalar-couplings. These are measured and their standard error determined from standard experiments such as those described above. Each scalar-coupling is related to an appropriate Karplus relation [28] for input into the algorithm; appropriate Karplus relations may be taken from published literature or explicitly calculated using quantum-mechanical approaches. In some specific cases, the measured coupling constant(s) can be directly related to a discrete molecular geometry or sets of molecular geometries. In these instances, the distinct bond rotamer states and their relative proportions may be explicitly expressed in the molecular internal coordinates model used by the algorithm. An example of this case is the hydroxylmethyl group of pyranose rings, where the relation of Hasnoot et al. can be used to explicitly calculate the relative proportions of gg and gt conformers [29].

A further kind of NMR data that reports 3D-molecular structure and dynamics are residual dipolar couplings (RDCs). Residual dipolar couplings are measured as the apparent change observed in a scalar-coupling when the molecule is in the presence of weak alignment media (e.g., phage, bicelles, gels) [13]. First, coupling constants (1-, 2- and 3-bond) in the molecule are measured from appropriate spectra recorded in the absence of alignment media, using standard methodologies. These same couplings are then measured in identical spectra recorded in the presence of alignment media, and the difference in Hz between the two measurements is the residual dipolar coupling (RDC). The error associated with determining this RDC may also be calculated, using standard statistical methods (such as that described below for the particular case of RDCs measured from a [$^1H$, $^{13}C$]-HSQC spectra).

A particular experiment which can be used to measure RDCs, when the molecule of interest is not isotopically-enriched, is a [$^1H$, $^{13}C$]-HSQC spectrum recorded at $^{13}C$-natural abundance without $^{13}C$-broadband decoupling during acquisition. This experiment not only allows $^1J_{CH}$ couplings to be directly measured, but allows sufficient data points in the acquisition dimension to be recorded so that the multiplet components caused by proton couplings are resolved. Each $^1J_{CH}$ coupling (J) can then be measured several (n) times as the separation in Hz between analogous resonances in each high- and low-field resonance multiplet, giving a mean value ($\mu_J$) and standard deviation ($\sigma_J$) associated with each measurement. The root-mean-square deviation (RMSD) of all $^1J_{CH}$ couplings within the dataset is then calculated, and this is taken to be the standard error associated with each individual $^1J_{CH}$ coupling ($\sigma_j$). Similarly, the mean value ($\mu_R$) and standard error ($\sigma_R$) of each $^1J_{CH}$ coupling is determined when in the presence of alignment media. The residual dipolar coupling (D) may then be calculated as the difference in Hz between the two mean values ($\mu_R-\mu_J$) and its standard error ($\sigma_D$) is given by the square root of sum of the squared standard errors ($\sqrt{(\sigma_D^2+\sigma_J^2)}$).

Compound RDCs (where compound RDCs are defined as the sum of two or more RDCs) for proton-proton RDCs can also be simultaneously measured from such a decoupled [$^1H$, $^{13}C$]-HSQC spectrum. These can be measured using the fact that the separation in Hz between the outermost components of each proton multiplet is equal to the sum of all the 2- and 3-bond proton scalar couplings forming that multiplet, when there is no strong-coupling present. Similarly, in the presence of alignment media, this separation is equal to the sum of all the 2- and 3-bond proton scalar-couplings combined with the proton-proton RDCs forming that multiplet. By subtraction of these two values and performing similar statistical analyses to those described above, a compound RDC and its standard error can be measured.

Having employed one or more of the processes described above, structural restraints with quantified errors will have been extracted and appropriately converted from NMR experiments that sample the molecular 3D-structure and dynamic motions of the molecule of interest. While the dynamic structure of a molecule can be determined from a single NMR dataset containing structural and dynamical data (e.g., a 2D-NOESY), significantly greater accuracy may be achieved when two or more real experimental datasets, that have different kinds of data (e.g., NOE data with RDC data), are used because the different kinds of experiment sample molecular motions in qualitatively different ways, i.e., by reporting various different averages of molecular distances and geometries, according to the physical theories that describe them. Where two or more experimental datasets contain the same type of data that was recorded in slightly different ways (e.g., 2D-NOESY and $^{13}$C-NOESY-HSQC datasets, or multiple 2D NOESY datasets with different NOE mixing times), there is an improvement to the accuracy of the determined structure, but it may not be as substantial. When more than one real experimental dataset is being used, each dataset is kept as a separate list of structural restraints for use by the algorithm as described above.

The methods described above permit the determination of the 3D-structure of dynamic molecules. Such structures are useful because they enable a multiplicity of analytical and computer modelling exercises to be undertaken that can predict experimental observables. The technology has applicability to a wide range of molecules, such as, but not limited to the following examples:
1) carbohydrate ligands and carbohydrate-mimetics (e.g., aminoglycoside antibiotics);
2) peptides and artificial peptide mimetics;
3) drug molecule molecular flexibilities;
4) flexible protein sidechains within an enzyme/receptor active site or protein-protein interaction site;
5) flexible bases within nucleic acid molecules, (e.g, RNA aptamers); and
6) proteins with several conformational states (e.g., integrins) and intrinsically unfolded proteins.

Any research and development project requiring structural information on flexible molecules will dramatically benefit from dynamic structures generated according to a preferred embodiment of the present invention, particularly those involving ligand-protein interactions. A further potentially important use of the dynamic structures generated according to the present invention is in rational drug design (RDD), i.e., using computers to design molecules that interact with target proteins in specific ways. Since RDD relies upon interaction-energy predictions, it requires detailed and accurate physical data for both drug and protein. Currently, predictions are poor, as seen by the fact that only ~10% of predicted molecules successfully bind to their receptor. To improve this, data is needed concerning both the enthalpic contribution to binding energy (formation of intermolecular bonds, governed by the molecular shape) and the entropic contribution to binding energy (change in disorder and flexibility on binding). Molecular bonding interactions (enthalpy) can be estimated well, but molecular flexibility (entropy) cannot, and without this flexibility information RDD is fundamentally limited in its predictive capability. Using both the drug molecule's preferred structure (internal enthalpy) and dynamic motions (entropy) determined with our methodology will therefore result in significant improvements in hit identification and lead optimisation via RDD approaches [30]. The methodology allows the dynamic structure of pharmaceutical molecules to be determined, which will significantly aid the discovery of new drugs by rational drug design and chemical mimicry.

Furthermore, the present invention and the dynamic 3D-structures that are produced from it can be used to calculate the deviation of a free solution structure from its bound form and used as an accurate scoring function (see FIG. 12). Dynamic structures therefore provide a significant advance in predictive power for understanding potential ligand-receptor interactions, compared with techniques that only consider enthalpic energy terms (e.g., hydrogen bonds, hydrophobics, etc.) or use molecular dynamics simulations. In particular, this will permit docking to be performed more accurately, with scoring functions that quantitatively fit to experimentally-measured binding constants and interaction energies [32]. Other areas that can benefit from the present invention include:
1) the generation of biomimetic molecules e.g., the design of heparin mimetics;
2) the analysis of molecular interactions using arrays of receptor molecules, e.g., in systems biology and proteomics;
3) the design of drug-libraries from predictions of likely reaction routes in combinatorial chemistry; and
4) design and construction of molecular machines (nanotechnology).

The present invention will now be further described with reference to the following non-limiting examples, in which:

FIG. 1. (a/b) shows the dihedral angle α, (a) from the side & (b) looking down the central bond, while (c) shows the Gaussian distribution of a that is used to generate the dynamic ensemble;

FIG. 2. Models for the angiotensin-4 peptide (VAL-TYR-ILE-HIS-PRO-PHE). Left: static structure for angiotensin-4. Middle: ensemble made by applying the Gaussian distribution G(−57°,20°), as described above, to the φ-angle between TYR and ILE (C[2]-N[3]-Cα[3]-C[3]). Right: ensemble made by applying the distribution) G(−57°,20°) to the φ-angle between TYR and ILE and G(−20°,20°) to the ψ angle between ILE and HIS (N[3]-Cα[3]-C[3]-N[4]);

FIG. 3. A schematic flowchart representation of a dynamic-structure determination method in accordance with a preferred embodiment of the present invention;

FIG. 4. Flowchart showing the overall process used to determine the 3D-structure of a dynamic molecule in accordance with a preferred embodiment of the present invention;

Figure 1:
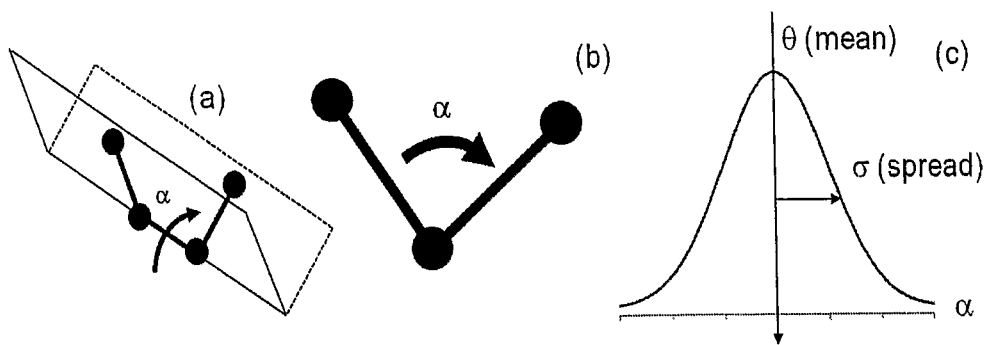
Figure 2:
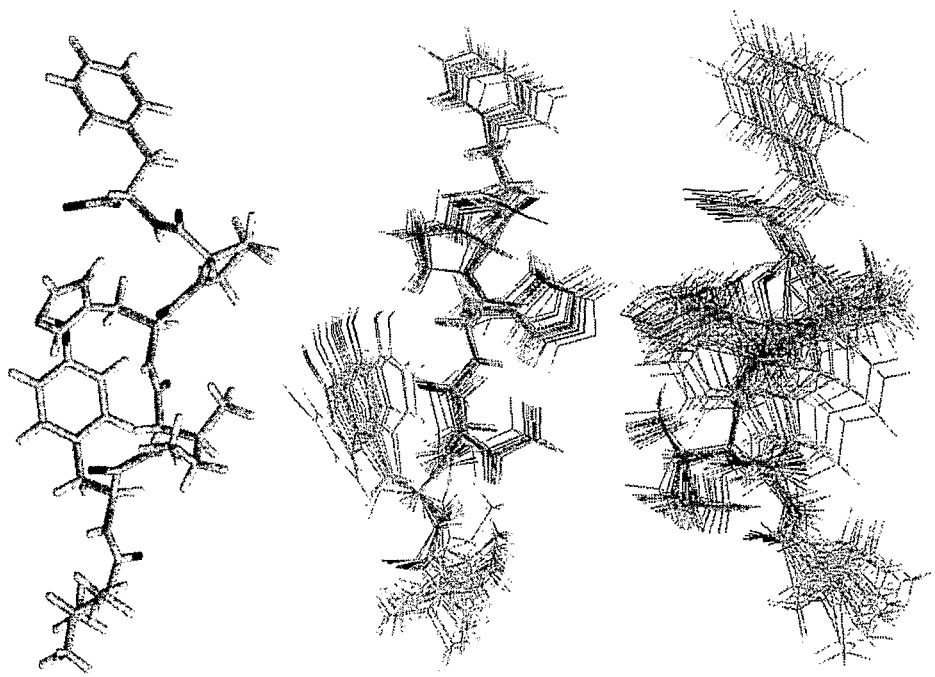
Figure 3:
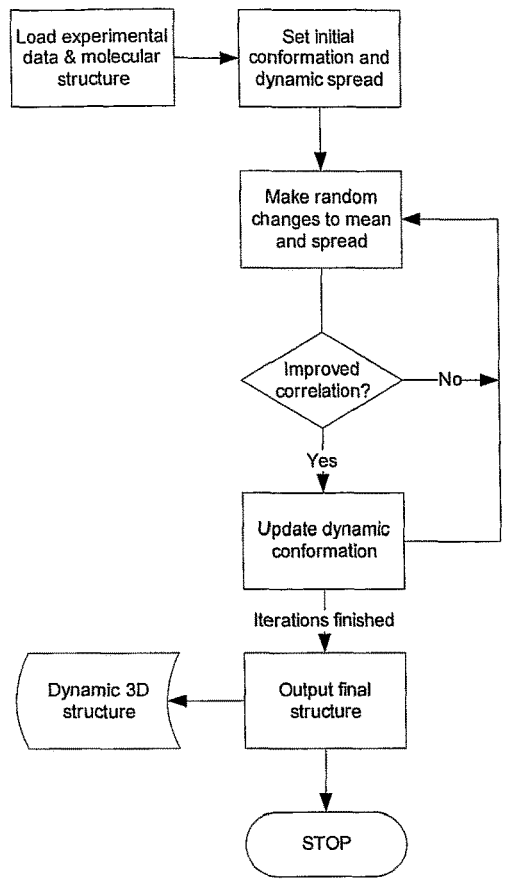
Figure 4:
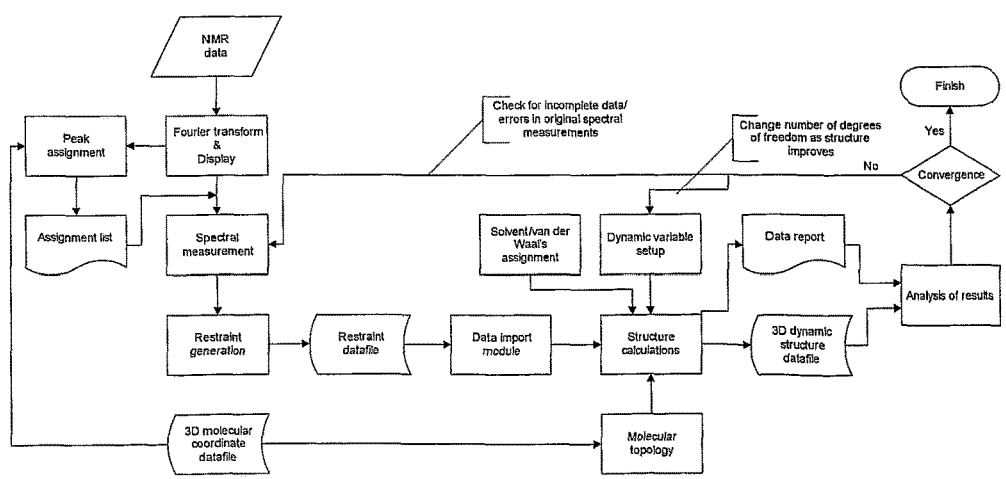
Figure 5:
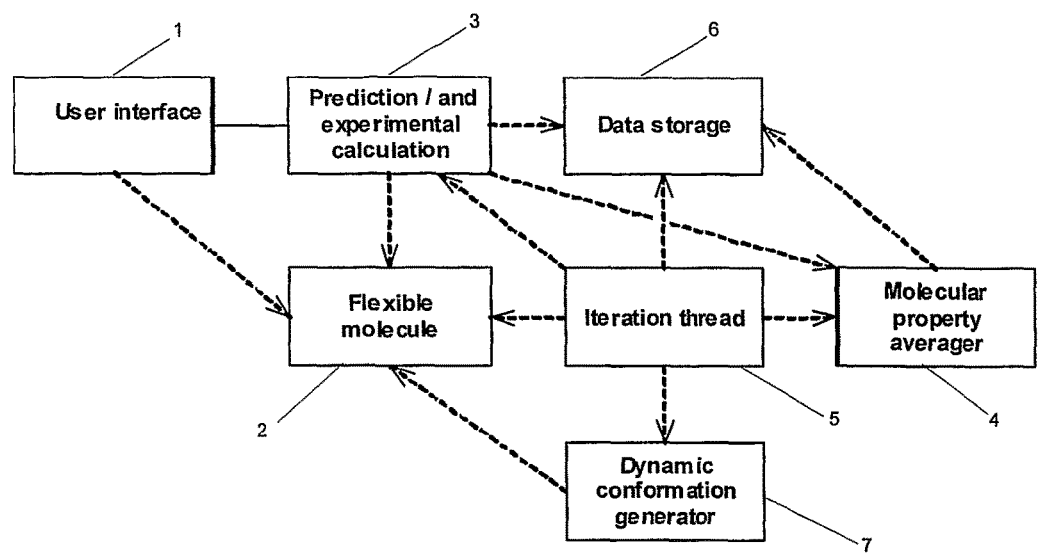
FIG. 5 is a schematic illustration of components used to implement an embodiment of the present invention.
Figure 6:
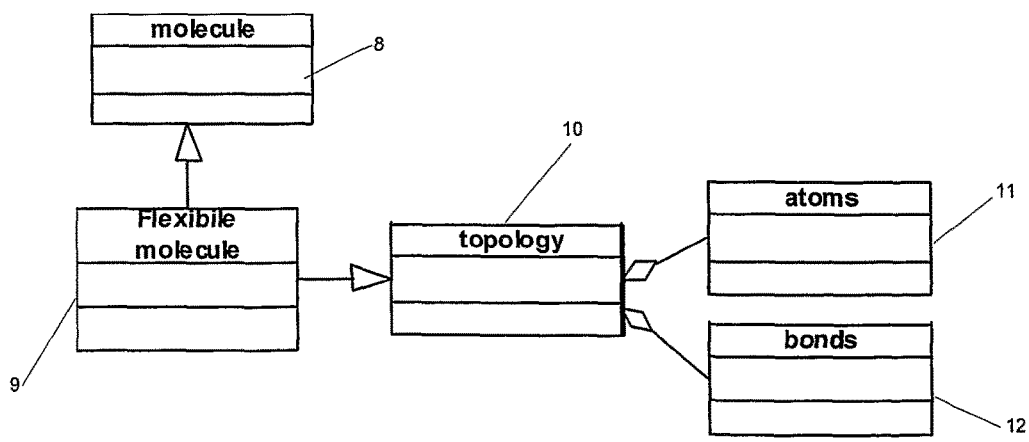
FIG. 6 is a UML diagram showing classes used to represent a flexible molecule.
Figure 7:
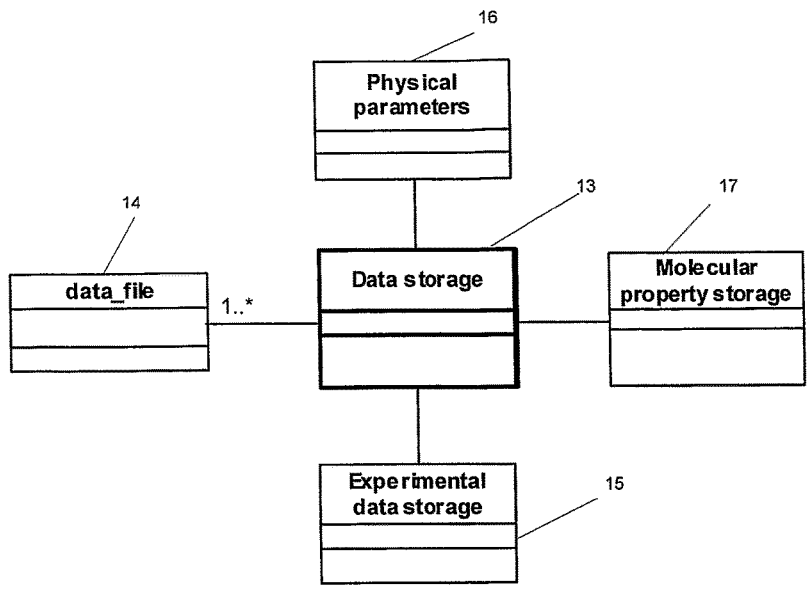
FIG. 7 is a UML diagram showing classes used to store data.
Figure 8:
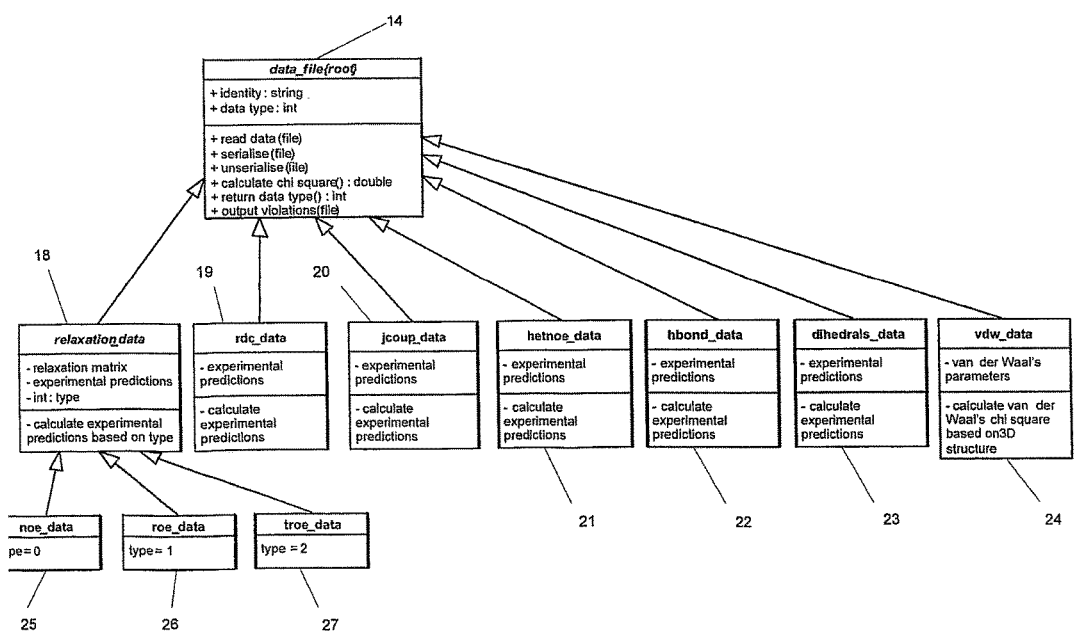
FIG. 8 is a UML diagram showing classes used to represent data files.
Figure 12:
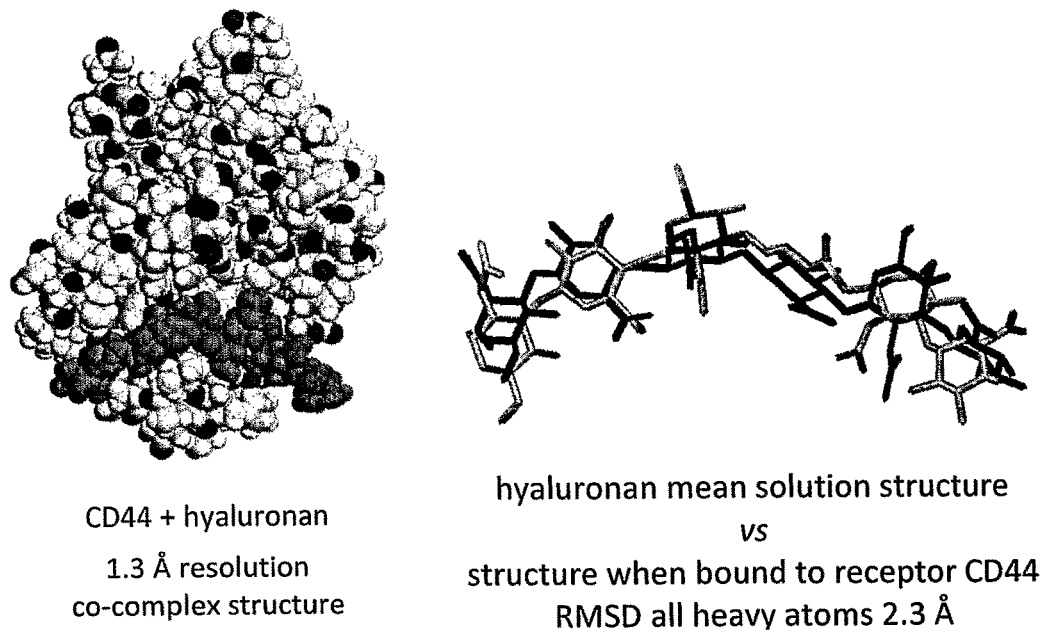
Figure 13:
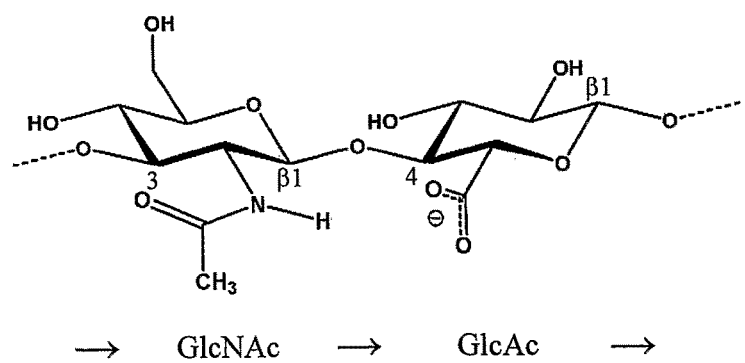
Figure 14:
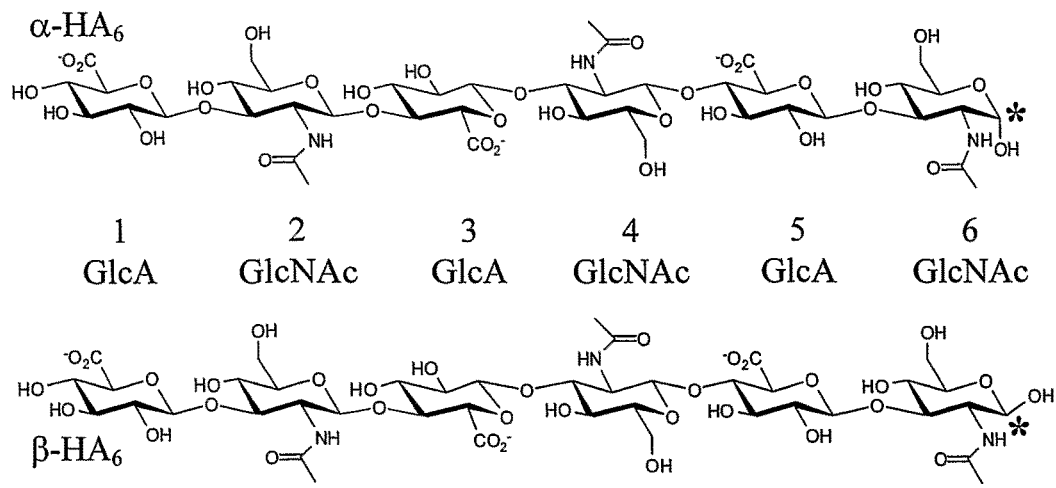
Figure 15:
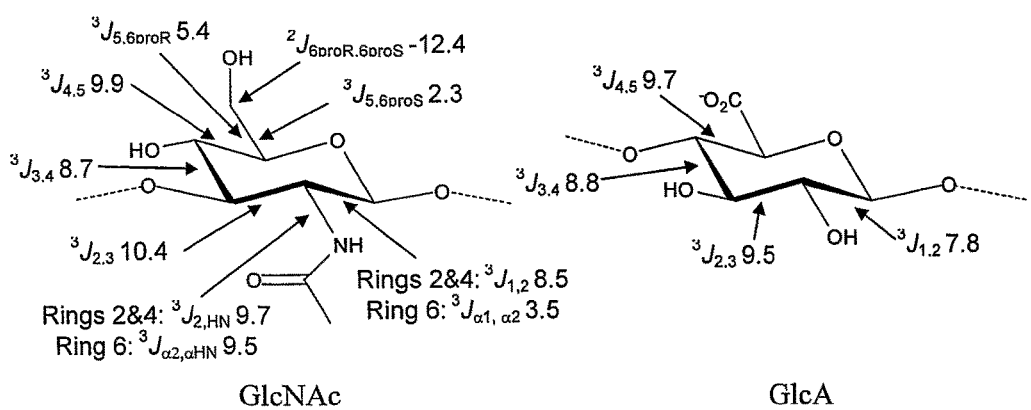
Figure 16:
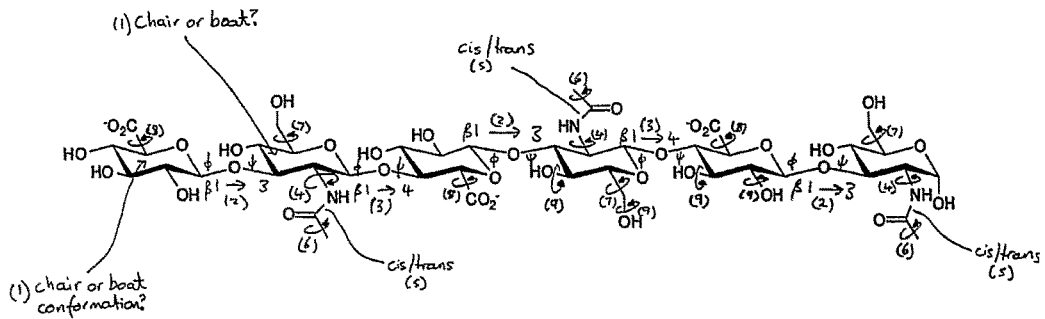
Figure 17:
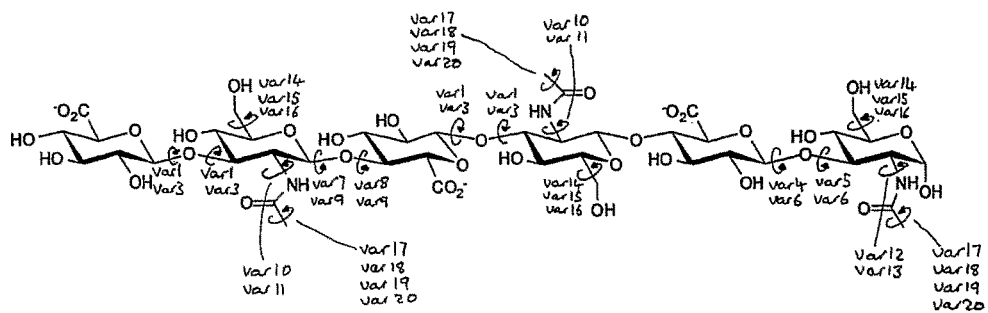
Figure 18:
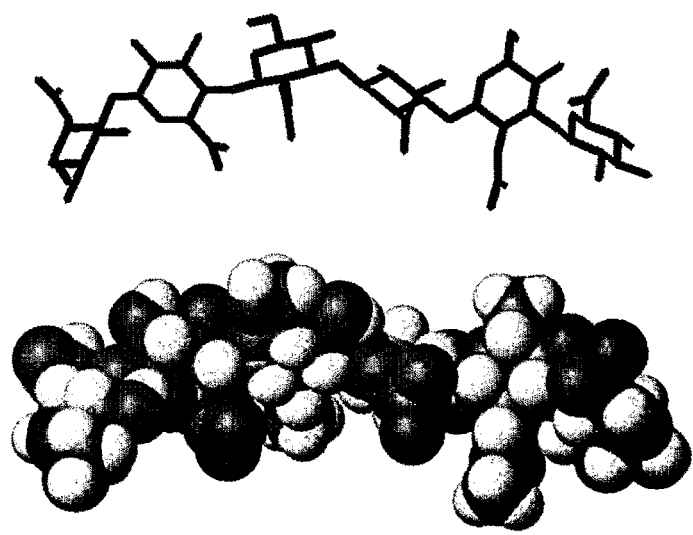
Figure 19:
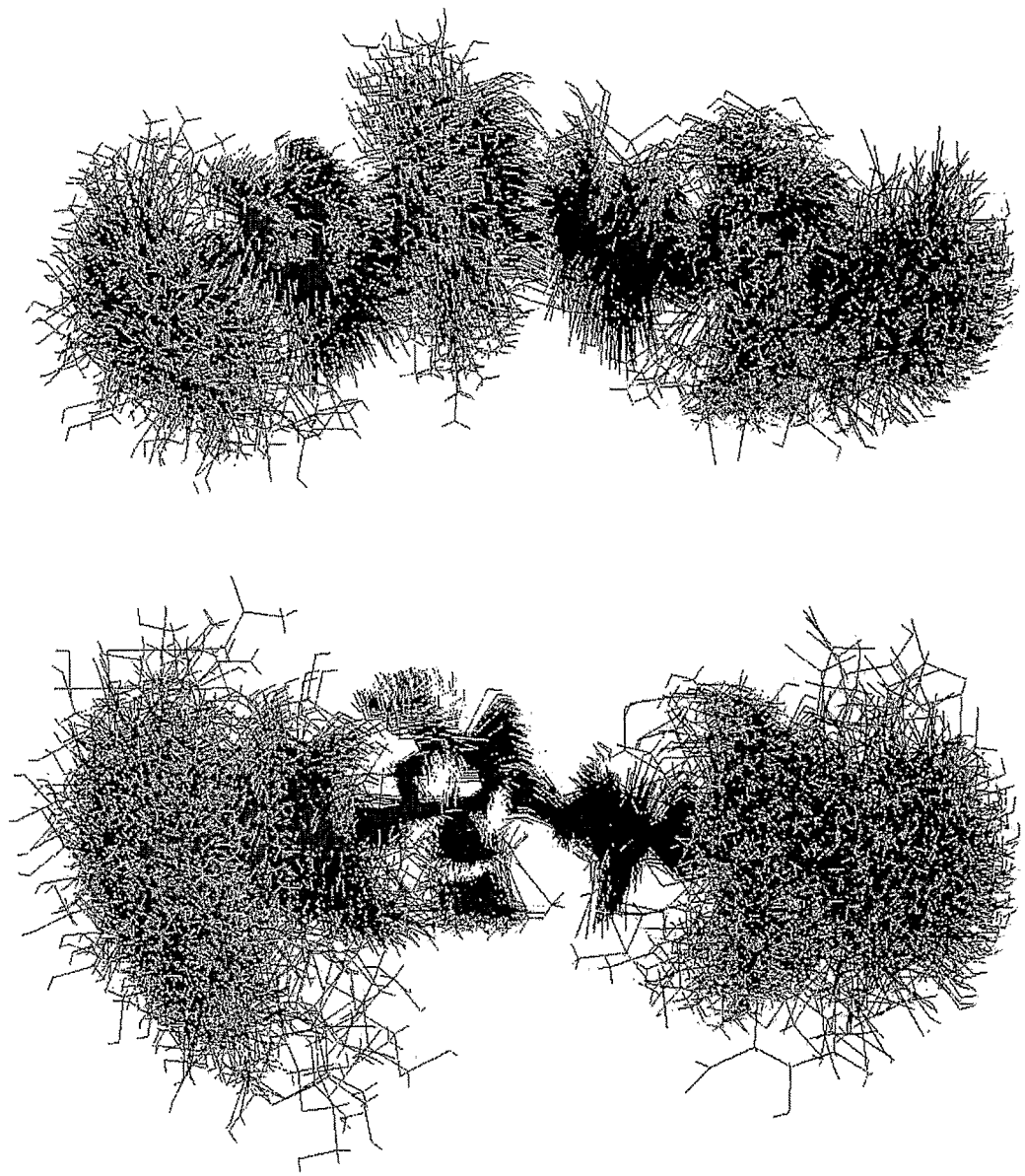
Figure 20:
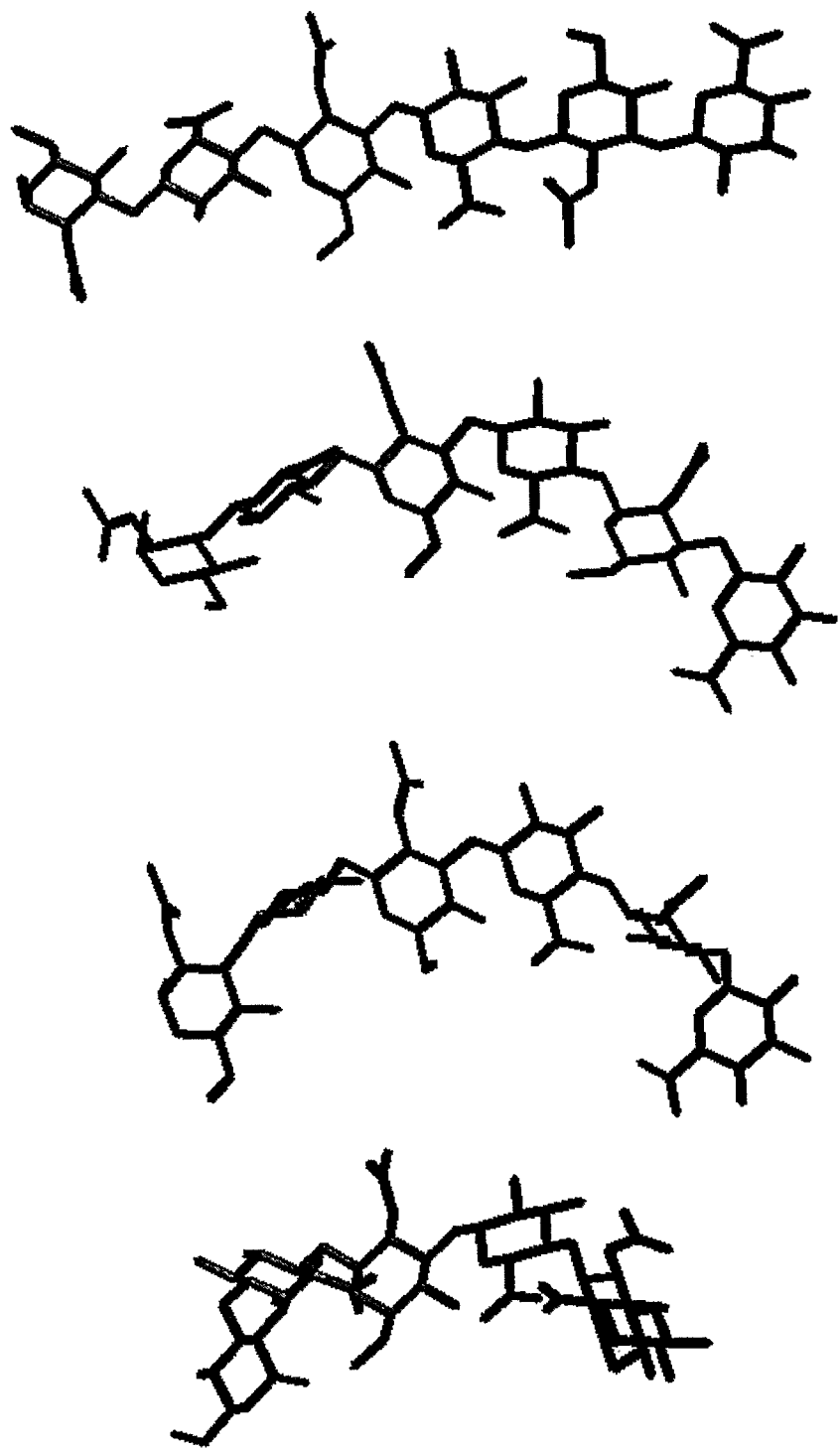
Figure 21:
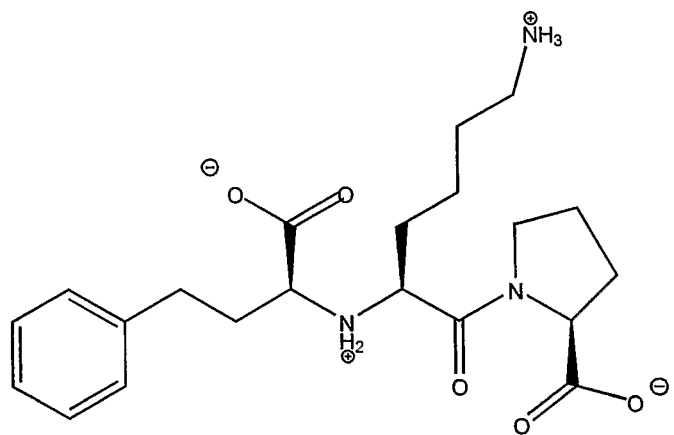
Figure 22:
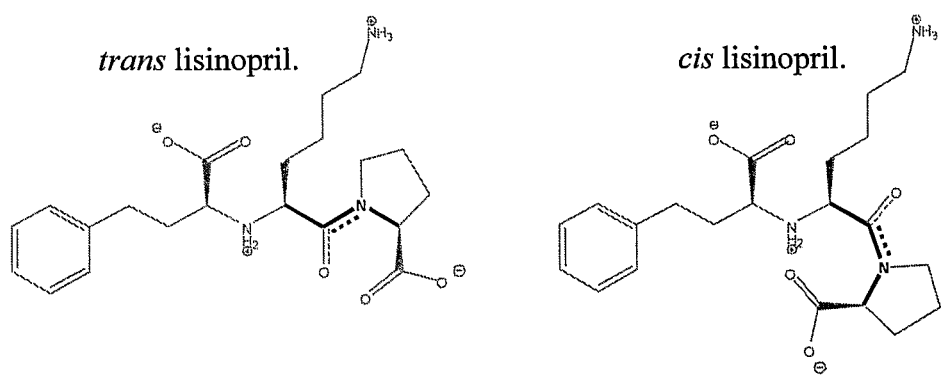
Figure 23:
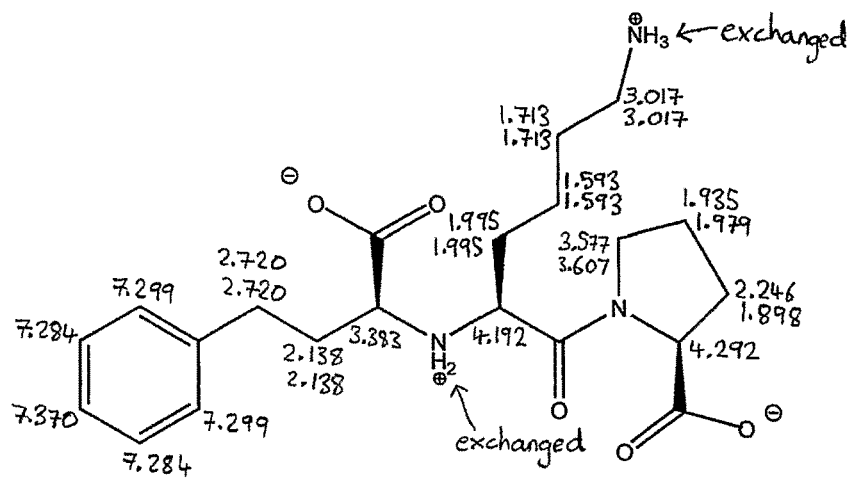
Figure 24:
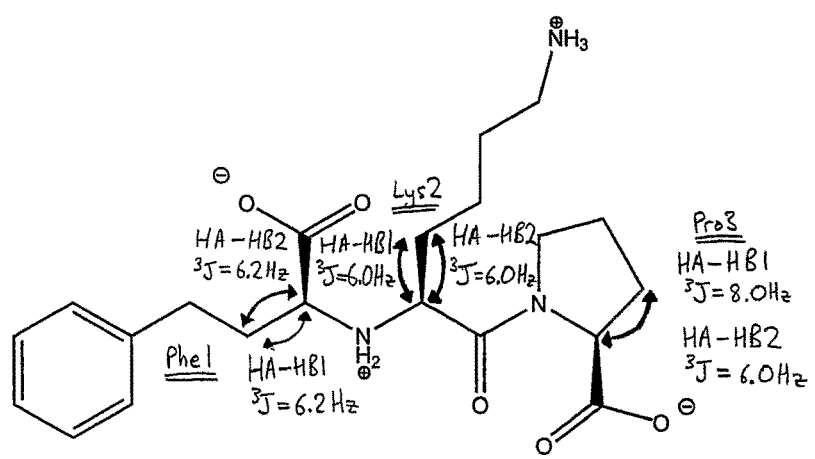
Figure 25:
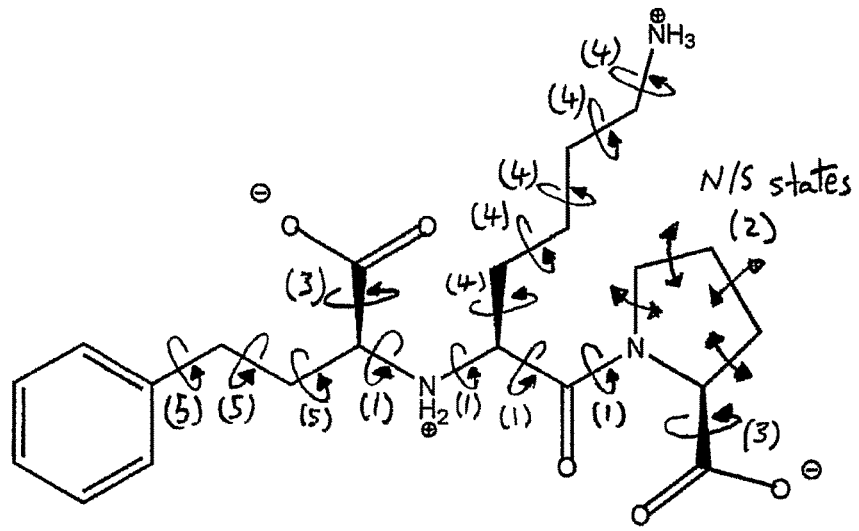
Figure 26:
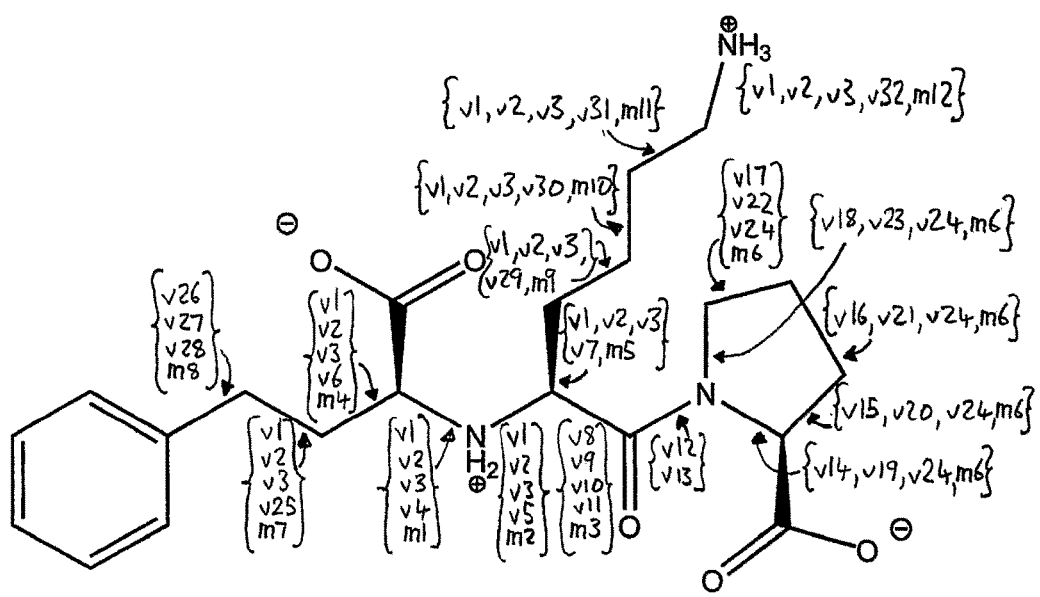
Figure 29:
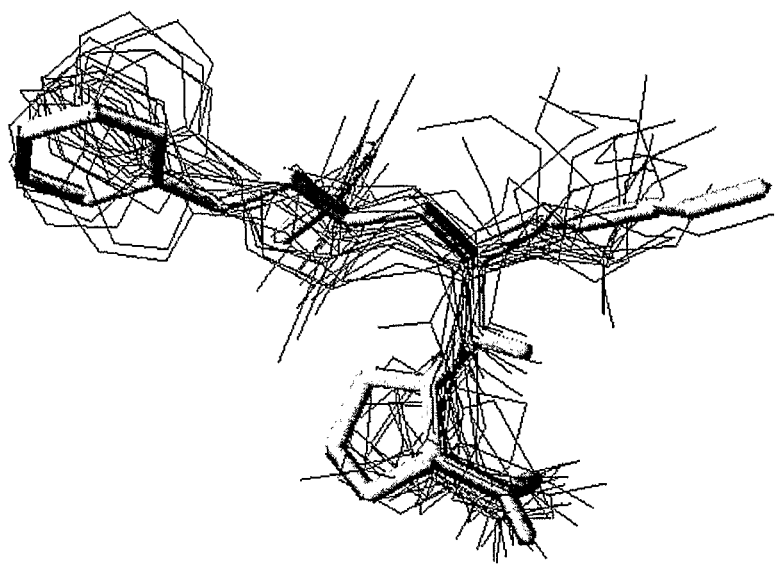
Figure 31:
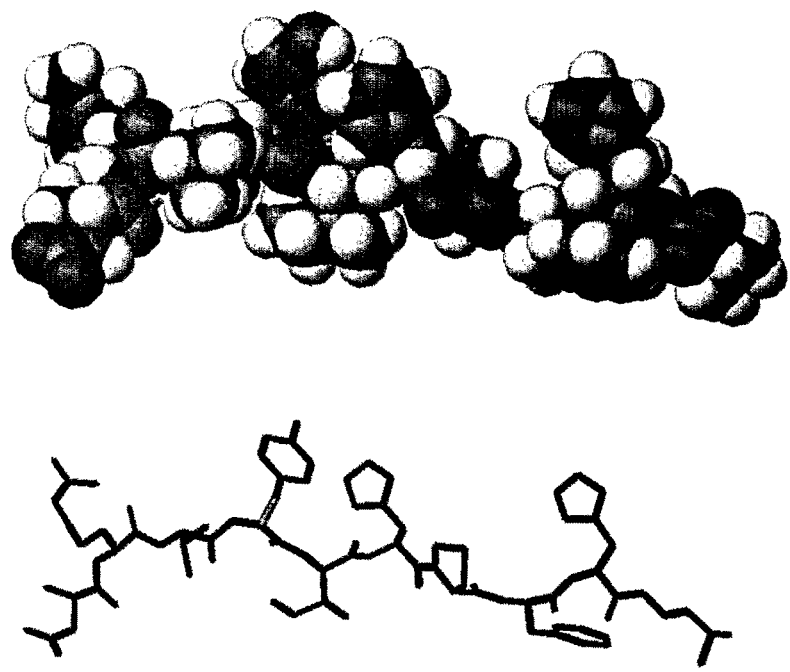
Figure 32:
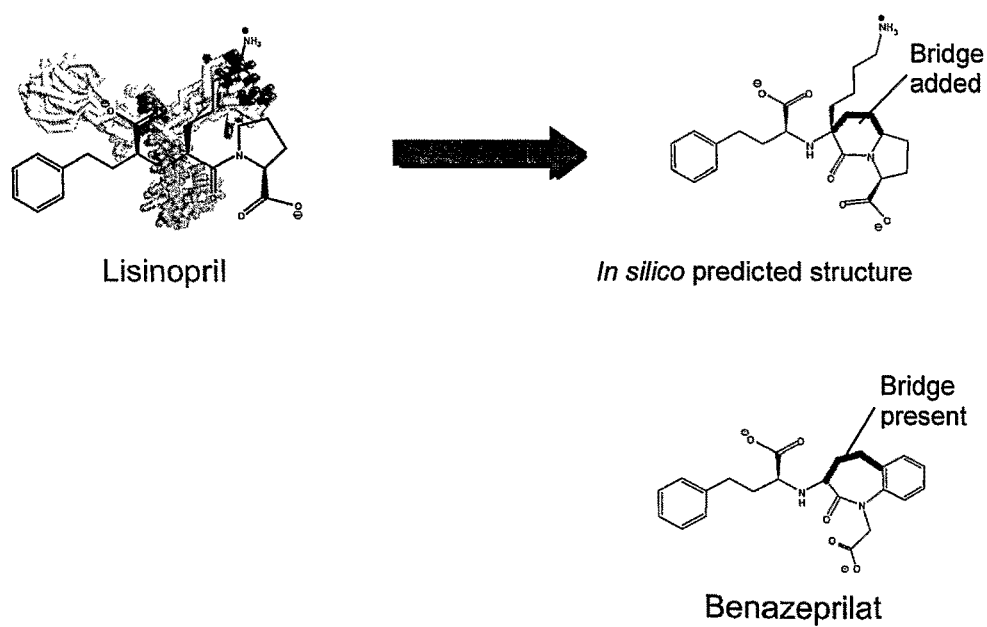

FIG. 9. Proton-resonance scaling factors for the simple case where all multiplet components are resolved. This occurs when the scalar-couplings ($J_1$, $J_2$, . . . ) are large compared to line-widths and they are sufficiently dissimilar;

FIG. 10. Proton-resonance scaling factors for the case where not all multiplet components are resolved, but overlaps are perfect due to chemical similarity. This can happen when the scalar-couplings ($J_1$, $J_2$, . . . ) are large compared to line-widths and have the same value, J;

FIG. 11. Calculation of the broadening factor (b) that has to be applied to components of a proton-resonance multiplet that overlap in order to interpret the height of that resonance quantitatively, using a set of combined scaling-factors;

FIG. 12. Use of structure determination in docking studies (see Examples for details below). The co-complex structure shown above is taken from the protein databank (code 2JCQ) [31];

FIG. 13. The repeated disaccharide unit of hyaluronan, which comprises N-acetyl-D-glucosamine (GlcNAc) and D-glucuronic acid (GlcA). These residues are connected by alternating [3]-6 and 131-4 glycosidic linkages (indicated);

FIG. 14. Hyaluronan hexasaccharide (HA$_6$) exists in aqueous solution as a mixture of α- and β-stereoisomer forms due to the presence of a hemiacetal group in the terminal GlcNAc ring (ring 6). The chemical-bonding difference between these two forms is indicated with an asterix. GlcA=D-glucuronic acid; GlcNAc=N-acetyl-D-glucosamine; numbers refer to ring number designations;

FIG. 15. Two- and three-bond homonuclear scalar coupling constants in GlcNAc (left) and GlcA (right) residues in HA oligosaccharides. The proton names (e.g., HN, H-6proS, H2) and value of the coupling (in Hz) for each coupled pair of protons are indicated. Ring hydrogen atoms have been omitted from the chemical structure for the sake of clarity;

FIG. 16. Conformationally-flexible bonds and chemistries within α-HA$_6$;

FIG. 17. Relationship of each variable in the dynamic model file to the rotatable bonds in α-HA$_6$;

FIG. 18. Mean 3D-solution structure of α-HA$_6$. (Top) stick representation with hydrogen atoms omitted. (Bottom) space-filling representation. Ring 6 is at the left in both views;

FIG. 19. 3D-solution structure of α-HA$_6$, showing the best ensemble of 250 structures that are collectively consistent with all the experimental data. (Top) Best-fit dynamic ensemble. (Bottom) Best-fit dynamic ensemble overlaid on the central two rings. Ring 6 is at the left in both views;

FIG. 20. Individual structures selected from the dynamic ensemble of 250 structures. These represent possible momentary solution conformations of α-HA$_6$. Hydrogen atoms have been omitted;

FIG. 21. Chemical structure of lisinopril, showing its ionization state at pH 6.0;

FIG. 22. Lisinopril exists in aqueous solution as a mixture of trans and cis stereoisomer forms due to the presence of the proline amide bond. The difference between these two forms is indicated in black;

FIG. 23. Proton chemical shifts for trans lisinopril in 100% D$_2$O at pH*6.0, 278K;

FIG. 24. $^3J_{HH}$ coupling constants measured in trans lisinopril;

FIG. 25. Conformationally-flexible bonds and chemistries within lisinopril;

FIG. 26. Relationship of each variable (v) and probability mode (m) in the dynamic model file to the chemical structure of trans lisinopril;

FIG. 27. Mean 3D-solution structure of lisinopril. (Top) Stick representation and (Bottom) space-filling representation;

FIG. 28. Dynamic 3D-solution structure of trans lisinopril, showing 20 random structures from the best ensemble of 250 structures;

FIG. 29. Correspondence of the dynamic solution structure of trans lisinopril (thin blue lines; overlay of 20 random structures from the best ensemble of 250 structures in the best ensemble) to the structure of trans lisinopril when bound to ACE (thick yellow lines) [41]. It is clear that the ensemble of structures for the unbound solution conformation of lisinopril provides a good starting point for predicting a likely enzyme-bound conformation;

FIG. 30. Two views of the 3D dynamic solution structure of trans AngiotensinI, showing 10 structures from the best dynamic ensemble of structures. Each residue is labelled. The two views are rotated approximately 90° relative to each other and only the heavy atoms are shown;

FIG. 31. Two views of the 3D dynamic solution structure of trans AngiotensinI, showing the mean dynamic structure in spacefilling (top) and sticks (bottom) representations. Hydrogen atoms have been omitted from the sticks representation. Both views are in an identical orientation, with Asp1 on the left; and FIG. 32. Structure of Lisinopril (left), derivative developed in silico designed to remove undesirable degree of freedom by inclusion of briding group (shown in bold) (top right), and next-generation ACE-inhibitor, Benazeprilat (bottom right).

EXAMPLE 1

Hyaluronan Hexasaccharide

Hyaluronan (HA) is a carbohydrate composed of a repeated disaccharide of N-acetyl-D-glucosamine (GlcNAc) and D-glucuronic acid (GlcA) (see FIG. 13). Amidst many other functions, HA provides structural integrity and organisation to vertebrate extracellular matrices. The polysaccharide form of HA, which has thousands of disaccharide repeats, is involved in both physiological (e.g., cervical ripening, tooth development) and disease processes (e.g., endometrial cancer, atherosclerosis). Oligosaccharides of HA, which have only a few disaccharide repeats, have distinct activities under other conditions (e.g., inducing dendritic cell maturation). HA is consequently commercially important in the biotechnology and cosmetics sectors.

Oligosaccharides of hyaluronan are easier to study than the polymer, since they can be purified to a homogenous preparation of defined length and do not form extremely viscous solutions as the polymer does [33]. The hexasaccharide of HA (HA$_6$, FIG. 14), which comprises only three repeated disaccharides of HA, has been shown to be a length of HA long enough to have the local structural characteristics of the polymer that is still being amenable to structural analysis by NMR [34, 35]. In this worked example, we demonstrate how the dynamic 3D-solution structure of HA$_6$ was determined from experimental NMR data using the methodology described in this patent.

Chemical Shift Assignment and Measurement of Homonuclear Scalar Coupling Constants Due to the presence of a 'reducing terminus' in HA$_6$ (i.e., a hemiacetal group), the terminal ring of HA$_6$ (ring 6) actually exists in solution as an inseparable mixture of α- and β-stereoisomers (FIG. 14); these two forms have near-identical chemical shifts [34]. We have previously assigned all $^1H$, $^{15}N$ and $^{13}C$ chemical shifts within both the α- and β-forms of HA$_6$ and determined the mole abundance ratio of these two forms to be 60% α and 40% β [35]. Since α-HA$_6$ was more abundant in the mixture, and had considerably better resolution than β-HA$_6$, it was decided at this stage to determine the dynamic 3D-structure of α-HA$_6$ rather than β-HA$_6$.

$^2J_{HH}$ and $^3J_{HH}$ coupling constants have been measured in GlcA and GlcNAc rings in a variety of HA oligosaccharides, giving consensus values for each coupling constant in these residue types (FIG. 15) [35].

Analysis of Spectral Lineshapes

Four different NOESY and T-ROESY datasets were used to provide structural restraints for α-HA$_6$. These were a 2D-[$^1H$, $^1H$]-NOESY dataset, a 2D-[$^1H$, $^1H$]-T-ROESY dataset, a 3D [$^1H$, $^{15}N$]-NOESY-HSQC dataset and a 3D-[$^1H$, $^{15}N$]-FT-ROESY-HSQC dataset; full details of the acquisition parameters for each dataset are given below. Scaling factor sets were determined for each of these datasets as follows. The $^2J_{HH}$ and $^3J_{HH}$ scalar couplings of all protons within α-HA$_6$, which are required for the broadening adjustment formula, were taken from FIG. 15.

The 2D-[$^1$H, $^1$H]-NOESY dataset was recorded with sufficient data points in the acquisition dimension to resolve proton multiplet splitting, but with small enough number of data points in the indirect dimension to prevent these multiplets from being resolved (i.e., simplifying the analysis of proton multiplets to just the acquisition dimension, as described above). The value of λ (this line-width of resonances in Hz, see above) for this dataset was determined by measurement of NOESY cross-peaks to amide and GlcA H1 protons, which all manifest as simple doublets (each doublet component therefore giving a true measure for λ). Values of 4.83, 4.75, 5.28 and 5.21 Hz were measured from the separate resonances in each doublet, giving an average value for λ of 4.8 Hz. This value for λ, the scalar coupling constants (FIG. 15) and the broadening adjustment formula were used to determine scaling-factor sets for each proton in α-HA$_6$ in this 2D-[$^1$H, $^1$H]-NOESY dataset as follows:

GlcA rings 1,3 & 5, H1 proton: since this proton has only one $^3$J$_{HH}$ coupling-constant of 7.8 Hz, which is bigger than λ, it manifests in the acquisition dimension of this 2D-NOESY spectrum as a simple doublet (i.e., as FIG. 9, one scalar-coupling). The scaling factor set for each component in the doublet is therefore 2, i.e. $f_i$={2, 2}.

GlcA rings 1,3 & 5, H2 proton: this proton has two $^3$J$_{HH}$ coupling-constants of 9.5 Hz and 7.8 Hz, which results in a basic appearance of a triplet for this proton (i.e., as FIG. 10, two scalar-couplings), i.e. an initial scaling factor set of $f_i$={4, 2, 4}. However, since the two coupling constants are not identical, the two middle multiplet components do not exactly overlap and the central peak of the 'triplet' is broadened. The separation Δν between these middle components is (9.5−7.8)=1.7 Hz, which is considerably less than λ, and the broadening on this component is determined by the broadening adjustment formula as (4.8/(4.8−1,7/2))=1.2. This broadening adjustment is multiplied by the overlap-adjustment factor (i.e., 2), to give the combined scaling factor (see above) for the central peak in the resonance multiplet as 2.4. The scaling factor set for each component in the triplet of this proton is therefore $f_i$={4, 2.4, 4}.

GlcA rings 1,3 & 5, H3 proton: similarly to GlcA H2 protons, this proton has two $^3$J$_{HH}$ coupling-constants of different values, namely of 9.5 Hz and 8.8 Hz. Following the same process for GlcA H2, it can be seen that the basic triplet appearance with initial scaling factors pattern $f_i$={4, 2, 4} also needs to be corrected for the broadening on the central peak caused by the non-identity of the two coupling constants. The difference Δν in Hz between the couplings (1.3 Hz) gives an broadening adjustment factor of 1.1, resulting in a corrected scaling-factor set of $f_i$={4, 2.2, 4}.

GlcA rings 1,3 & 5, H4 proton: this proton has two $^3$J$_{HH}$ coupling-constants of values 9.7 and 8.8 Hz. Following the same reasoning as for GlcA H2 and H3 protons leads to the scaling factor set of $f_i$={4, 2.2, 4}.

GlcA rings 1,3 & 5, H5 proton: this proton has only one $^3$J$_{HH}$ coupling-constant of 7.8 Hz, which is bigger than λ. It is therefore a simple doublet (i.e., as FIG. 9, one scalar-coupling) with a scaling-factor set of $f_i$={2, 2}.

GlcNAc rings 2 & 4, H1 proton: This proton has only one $^3$J$_{HH}$ coupling-constant of 8.5 Hz, which is bigger than λ. (i.e., as FIG. 9, one scalar-coupling) with a scaling-factor set of $f_i$={2, 2}.

GlcNAc rings 2 & 4, H2 proton: this proton has three $^3$J$_{HH}$ coupling-constants in H$_2$O of 10.4 Hz, 9.7 Hz and 8.5 Hz, which results in a basic appearance of a quartet (i.e., as FIG. 10, three scalar-couplings) for this proton, i.e. an initial scaling factor set of $f_i$={8, 2.7, 2.7, 8}. While the two exterior multiplet components are clearly resolved and retain the initial scaling factors of 8, the inner pair of components in the quartet are somewhat broadened by the non-equality of the 3 coupling constants. Analysis of broadending adjustments in this case is quite involved but, by treating the overlap as two successive pairs of overlapping multiplet components, the broadening formula indicates the central resonances are to be further scaled by a factor of 1.4. The corrected scaling factor set is therefore $f_i$={8, 3.8, 3.8, 8}.

GlcNAc rings 2&4, H3 proton: has two $^3$J$_{HH}$ coupling-constants of values of 10.4 Hz and 8.7 Hz (therefore appears as FIG. 10, two scalar-couplings) giving an initial scaling factor set of $f_i$={4, 2, 4}. Application of the broadening formula to the central resonance as before results in the corrected scaling-factor set of $f_i$={4, 2.4, 4}.

GlcNAc rings 2&4, H4 proton: has two $^3$J$_{HH}$ coupling constants of values of 9.9 Hz and 8.7 Hz. The correct scaling factor accounting for the broadening on the central resonance is therefore $f_i$={4, 2.4, 4}.

GlcNAc rings 2&4, H5 proton: has four different $^3$J$_{HH}$ coupling-constants, which results in multiple overlaps and makes the resonance appear as a broad plateau with 4 resonances (most like FIG. 9, two scalar-couplings). The scaling factor for this proton was calculated to be $f_i$={2.8, 2.8, 2.8, 2.8} from consideration of the overlapping multiplet components, see FIG. 11.

GlcNAc rings 2&4, H6proS proton: has one $^2$J$_{HH}$ and one $^3$J$_{HH}$ coupling-constant, of values of −12.3 Hz and 2.3 Hz, and therefore manifests as a doublet of broadened resonances (i.e., most like FIG. 9, one scalar-coupling in appearance), giving an initial scaling factor set of $f_i$={2, 2}. The broadening on each resonance is caused by the small 2.3 Hz coupling, which results in a broadening adjustment for each scaling factor of 1.3. The correct scaling factor set for this proton is therefore $f_i$={2.6, 2.6}.

GlcNAc rings 2&4, H6proR proton: has one $^2$J$_{HH}$ and one $^3$J$_{HH}$ coupling-constant, of values of −12.3 Hz and 5.4 Hz, and manifests as a four clearly-resolved resonances due to the frequency differences between them and λ (i.e., looks most like FIG. 9, two scalar-couplings). The scaling factor set for this proton is therefore $f_i$={4, 4, 4, 4}.

GlcNAc rings 2&4, HN proton: This proton has only one $^3$J$_{HH}$ coupling-constant of 9.7 Hz, which is bigger than λ. It is therefore a simple doublet (i.e., most like FIG. 9, one scalar-coupling) with scaling factor set of $f_i$={2, 2}.

In the case of GlcNAc ring 6, the different coupling constant between protons H1 and H2 (see FIG. 15) compared to GlcNAc rings 2&4 results in slightly different scaling factor sets for H1 and H2 protons compared to GlcNAc rings 4 and 6. Moreover, all scaling factors are multiplied by the mole abundance 1/r (r=0.6) scaling ratio of 1.7 to compensate for the α-anomer only being at 60% mole abundance.

GlcNAc ring 6, H1 proton: This proton has only one $^3$J$_{HH}$ coupling-constant of 3.5 Hz, which is smaller than λ. It therefore manifests in the spectrum as a broadened singlet (i.e., most like FIG. 9, one scalar-coupling), with a broadening adjustment 1.6. Its scaling factor set is therefore $f_i$={1.6} and, after mole abundance scaling, $f_i$={2.7}.

GlcNAc ring 6, H2 proton: this proton has three $^3$J$_{HH}$ coupling constants in H$_2$O of 10.4, 9.7 and 3.5 Hz, which results in a basic appearance of a triplet for this proton (i.e., most like FIG. 10, two scalar-couplings) with multiple broadenings, giving an initial scaling factor set of $f_i$={4, 2, 4}. The outer two resonances are broadened by the 3.5 Hz coupling, given a broadening adjustment of 1.6 in both cases. The inner resonance is broadened principally by the 3.5 Hz coupling with a broadening adjustment of 1.6, but the 0.7 Hz difference between the two large couplings also contributes with an additional broadening adjustment of 1.1, giving a net of 1.7. The scaling factor for the central resonance is therefore 3.4. The scaling factor set is therefore $f_i=\{6.2-3.4-6.2\}$ and after mole abundance scaling, $f_i=\{10.5, 5.8, 10.5\}$.

GlcNAc ring 6, H2, H3, H4, H5, H6proS, H6proR protons: Since these protons have the same coupling constants as GlcNAc rings 2&4, they have the same scaling factor sets as in GlcNAc rings 2&4, but each scaling factor in each scaling factor set is multiplied by the mole abundance scaling ratio of 1.7.

In summary, the scaling factor sets for proton resonance multiplets in the 2D [$^1$H, $^1$H]-NOESY dataset were as follows:

| GlcA rings 1, 3 5 | | GlcNAc rings 2, 4 | | GlcNAc ring 6 | |
|---|---|---|---|---|---|
| H1 | {2, 2} | H1 | {2, 2} | H1 | {2.7} |
| H2 | {4, 2.4, 4} | H2 | {8, 3.8, 3.8, 8} | H2 | {10.5, 5.8, 10.5} |
| H3 | {4, 2.2, 4} | H3 | {4, 2.5, 4} | H3 | {6.8, 4.3, 6.8} |
| H4 | {4, 2.2, 4} | H4 | {4, 2.3, 4} | H4 | {6.8, 3.9, 6.8} |
| H5 | {2, 2} | H5 | {2.8, 2.8. 2.8, 2.8} | H5 | {4.8, 4.8. 4.8, 4.8} |
| | | H6proS | {2.6, 2.6} | H6proS | {4.4, 4.4} |
| | | H6proR | {4, 4, 4, 4} | H6proR | {6.8, 6.8, 6.8, 6.8} |
| | | HN | {2, 2} | HN | {3.4, 3.4} |

The 2D [$^1$H, $^1$H]-T-ROESY dataset was recorded with sufficient data points in the acquisition dimension to resolve proton multiplet splitting, but with small enough number of data points in the indirect dimension to prevent these multiplets from being resolved. The spectral line-width ($\lambda$) of this dataset was determined to be 6.5 Hz in an manner analogous to that for the 2D [$^1$H, $^1$H]-NOESY dataset described above. Following a process similar to that described above, the scaling factor sets for this 2D-T-ROESY spectrum were calculated to be as follows:

| GlcA rings 1, 3 5 | | GlcNAc rings 2, 4 | | GlcNAc ring 6 | |
|---|---|---|---|---|---|
| H1 | {2, 2} | H1 | {2, 2} | H1 | {2.7} |
| H2 | {4, 2.3, 4} | H2 | {6.0, 4, 4} | H2 | {6.0, 6.0} |
| H3 | {4, 2.1, 4} | H3 | {4, 2.3, 4} | H3 | {6.8, 4.1, 6.8} |
| H4 | {4, 2.2, 4} | H4 | {4, 2.2, 4} | H4 | {6.8, 3.7, 6.8} |
| H5 | {2, 2} | H5 | {2.4, 2.4. 2.4, 2.4} | H5 | {4.1, 4.1. 4.1, 4.1} |
| | | H6proS | {2.3, 2.3} | H6proS | {3.9, 3.9} |
| | | H6proR | {3.4, 3.4} | H6proR | {5.8, 5.8} |
| | | HN | exchanged | HN | exchanged |

The first notable difference between the scaling factor sets for this spectrum and for the 2D-NOESY described above is that the amide protons have no scaling factors—this arises because the spectrum was recorded on a 100% D$_2$O $\alpha$-HA$_6$ sample, and therefore the amide protons completely exchange with solvent deuterons and become NMR-inactive. The second notable difference is that the GlcNAc H2 proton on rings 2 and 4 only have two $^3J_{HH}$ scalar-coupling constants present (the amide proton has exchanged), resulting in a initial triplet scaling-factor set (i.e., most like FIG. 10, two scalar-couplings), rather than the quartet seen for H$_2$O samples.

The 3D [$^1$H, $^{15}$N]-NOESY-HSQC dataset was recorded with sufficient data points in the acquisition dimension to resolve proton multiplet splitting, but with small enough number of data points in the indirect dimension to prevent these multiplets from being resolved. Scaling factor sets need only be determined for the amide proton in this dataset, since it does not contain peaks from any other proton in $\alpha$-HA$_6$. Since each amide proton is coupled to a ring H2 proton with scalar-couplings of ~9.5 Hz (see FIG. 15) and value of $\lambda$ of this dataset was 6 Hz, each NOE manifests as a simple doublet of resonances in the spectrum, i.e. initial scaling factors sets of $f_i=\{2, 2\}$. In the case of the amide proton in ring 6, each scaling factor in the initial scaling-factor set must be multiplied by the mole abundance scaling (=1.7), i.e., the scaling factor set for ring 6 is $f_i=\{3.3, 3.3\}$. The scaling factor sets for rings 2 and 4 are not adjusted by mole abundance ratios, and therefore remain as $f_i=\{2, 2\}$.

The 3D [$^1$H, $^{15}$N]-T-ROESY-HSQC dataset was acquired with very similar parameters to the 3D [$^1$H, $^{15}$N]-NOESY-HSQC and therefore had the same scaling factors sets.

Measurement and Quantitation of NMR Spectra

Five different kinds of NMR data in seven different experimental NMR datasets were used in the determination of the dynamic solution structure of $\alpha$-HA$_6$. These restraints were used by the optimisation algorithm to find the best values for the 13 unknown variables (see above). The five kinds of NMR data used were:

1) NOESY relaxation data: two experimental datasets, 1) [$^1$H, $^{15}$N]-NOESY-HSQC, 2) [$^1$H, $^1$H]-2D-NOESY
2) T-ROESY relaxation data: two experimental datasets, 1) [$^1$H, $^{15}$N]-T-ROESY-HSQC, 2) [$^1$H, $^1$H]-2D-NOESY
3) conformation-dependent scalar couplings: one experimental dataset
4) residual dipolar couplings (RDCs): one experimental dataset
5) order parameters (calculated from [$^1$H, $^{15}$N]-heteronuclear-NOE and T$_1$-measurements): one experimental dataset.

The pertinent acquisition parameters for each of these different NMR datasets, and the number of structural restraints measured from them, were as follows (all datasets were acquired at 298K).

The 2D [$^1$H, $^1$H]-NOESY spectrum was recorded on a sample of 5 mM HA$_6$ (95% H$_2$O, pH 6.0, 0.3 mM DSS) at 900 MHz with a NOE mixing time of 400 ms and sweep widths of 10800 Hz in both dimensions. Using the scaling factor sets described above, true peak-heights for each NOE peak were determined, resulting in 82 NOE structural restraints. Errors on each NOE restraint were using the initial m value of 0.4 for a 2D-NOESY spectrum. 94 noNOE structural restraints were also measured from this spectrum, following the methodology described above. These NOE and noNOE structural restraints were contained in the dataset file given in Appendix A.

The 3D [$^1$H, $^{15}$N]-NOESY-HSQC spectrum was recorded on a sample of 12 mM $^{15}$N-labelled HA$_6$ (95% H$_2$O) at 600 MHz (NOE mixing time 400 ms, sweep width of 7200 Hz for both proton dimensions, 140 Hz for $^{15}$N dimension, $^{15}$N offset at 122.5 ppm), as described previously [8, 36]. Using the scaling factor sets detailed above, the true peak-height for one mole abundance for each NOE cross-peak and diagonal-peak was determined. The m value for the 3D [$^1$H, $^{15}$N]-NOESY-HSQC spectrum was set to 0.4, enabling the errors on the true peak heights to be calculated as described above. 19 NOE restraints were measured from this spectrum, which are given in the dataset file in Appendix A.

The 2D [$^1$H, $^1$H]-T-ROESY spectrum was recorded on a sample of 20 mM HA$_6$ (100% D$_2$O, pH 6.0, 0.3 mM DSS) at 600 MHz with a NOE mixing time of 400 ms and sweep widths of 7200 Hz in both dimensions. Using the scaling-factor sets, described above, 62 ROE structural restraints were measured from this spectrum. Errors on each ROE restraint were determined as described above, using the initial m value of 0.5 for a 2D [$^1$H, $^1$H]-T-ROESY spectrum. 63 noROE structural restraints were also measured from this spectrum. These ROE and noROE structural restraints were contained in the dataset file given in Appendix A.

The 3D [$^1$H, $^{15}$N]-T-ROESY-HSQC spectrum was recorded on a sample of 12 mM $^{15}$N-labelled HA$_6$ (95% H$_2$O) at 600 MHz (ROE mixing time 400 ms, sweep width of 7200 Hz for both proton dimensions, 140 Hz for $^{15}$N dimension, $^{15}$N offset at 122.5 ppm). Errors on each ROE restraint were determined with the formula as described above, using the initial m value of 0.2 for a 3D [$^1$H, $^{15}$N]-T-ROESY-HSQC spectrum. 18 ROE structural restraints were measured from this spectrum, as listed in the dataset file given in Appendix A.

Conformation-dependent scalar coupling constants for the acetamideo sidechain groups ($^3J_{2,HN}$) in α-HA$_6$ have been measured previously (see FIG. 15) [35]. As noted above, the coupling constant for ring 6 was observed to have a slightly different value to that of rings 2 and 4. The best Karplus equation for relating these coupling constants to the dihedral angle in the molecule is given by quantum mechanical calculations, as described previously [37]. The combined error in measurement of the coupling (~0.3 Hz) and predictive accuracy of these Karplus relations (~0.3 Hz) is ~0.5 Hz. The three scalar coupling constants were contained in the dataset file given in Appendix A.

Residual dipolar coupling data for α-HA$_6$ has not been previously reported and was therefore measured de novo for this work following the methods using high-resolution 1D NMR-spectra and natural abundance [$^1$H, $^{13}$C]-HSQC/[$^1$H, $^{15}$N]-HSQC spectra described above. A [$^1$H, $^{13}$C]-HSQC spectrum (without $^{13}$C-broadband decoupling during acquisition) was recorded at natural abundance in the absence of alignment media (as we have described previously [35]) on a 20 mM sample of HA$_6$ in 50% D$_2$O for the measurement of the one-bond C—H and overlapped H—H coupling constants. A second [$^1$H, $^{13}$C]-HSQC spectrum was recorded at natural abundance with identical acquisition parameters on a sample containing alignment media (5 mM sample of HA$_6$ in 50% D$_2$O, with alignment phage present at 3 mg/ml). 31 non-overlapped RDCs (numbers 1 to 31 in the list in Appendix A) and 27 overlapped RDCs were measured from the [$^1$H, $^{13}$C]-HSQC spectra (numbers 101 to 127 in the list in Appendix A). Three more non-overlapped RDCs (numbers 131 to 132 in the list in Appendix A) were obtained on the same samples from [$^1$H, $^{15}$N]-HSQC spectra recorded at natural abundance. Three additional non-overlapped RDCs were measured from high-resolution 1D NMR spectra (numbers 128 to 130 in the list in Appendix A). The standard error on each RDC structural restraint was determined to be 0.35 Hz using the methodology described above. These RDCs (65 in total) were contained in the dataset file given in Appendix A.

Order parameters and their errors for the three acetamido N—H groups in α-HA$_6$ have been measured previously [22]. The three order parameters were contained in the dataset file given in Appendix A.

Molecule Specification

The experimental datasets described above were acquired in two different solvents, namely H$_2$O and D$_2$O. The solvent mask (see above) for each of these was determined as follows:

1) H$_2$O solvent mask: all hydroxyl protons in α-HA$_6$ exchange very rapidly with solvent protons, so these protons were all defined as NMR-inactive (exc*HO*). The amide protons exchange sufficiently slowly to be observable, i.e., are NMR-active [34]. All other protons were defined as active (add*H*).

2) D$_2$O solvent mask: all hydroxyl (exc*HO*) and amide protons (exc*H$_2$N) in α-HA$_6$ completely exchange with solvent deuterons, so these protons were all defined as NMR-inactive. All other protons were defined as active (add*H*).

The actual file used to specify these two solvent masks was as follows:

```
remark Solvent masks for alpha-HA6
conditions:

solvents 2
endsection
solvent:

name h2o
add * H*
exc * HO*
endsection
solvent:

name d2o
add * H*
exc * HO*
exc * H2N
endsection
```

The locations of various atoms within α-HA$_6$ relative to the rest of the molecular structure could not be specified from the experimental data available (namely the two oxygen atoms in each carboxylate group and all the hydroxyl protons). While these atoms were retained in the molecule for the sake of visual reality, it was necessary that their (arbitrarily defined) internal coordinates should not affect the structure calculations by adverse van der Waals interactions. These atoms were therefore set to be van der Waals inactive by the following van der Waals mask:

```
remark Van der Waals mask for alpha-HA6
configuration:

vdw.cutoff 6.0
vdw.coupling 1e-4
endsection
nonbonded:

vdw * H* 0.016 0.60
vdw * C* 0.100 1.91
vdw * N* 0.170 1.92
vdw * O* 0.210 1.66
remark exclude all hydroxyl protons
exc * HO*
remark exclude the oxygen atoms in the carboxylate groups
exc * O6A
exc * O6B
endsection
```

Experimental Data Input

The value of $\tau_c$ was set to 0.4 ms for all rounds of structure calculations, having been experimentally determined as described previously [22]. The various experimental datasets described above were recorded on NMR samples containing different H$_2$O/D$_2$O solvent mixtures (see above), and therefore the adjusted solvent viscosities for each dataset were calculated using equations (22) and (23). The seven experimental dataset files used in the structure calculations are given in Appendix A.

Dynamic Model

The pertinent conformationally-flexible bonds and chemistries within $\alpha$-HA$_6$ were identified, using the methodology described above, as being (see FIG. 16):

1) each of the six carbohydrate rings could exist in a variety of conformations, for example chair, boat or skew-boat conformation.
2) the three $\beta1\rightarrow3$ glycosidic linkages, i.e. the linkages between rings 1&2, 3&4 and 5&6. Each chemical bond on either side of the linkage oxygen atom has an undefined dihedral angle, designated phi ($\varphi$) and psi ($\phi$) respectively.
3) the two $\beta1\rightarrow4$ glycosidic linkages, i.e. the linkages between rings 2&3 and 3&4. Each chemical bond on either side of the linkage oxygen atom has an undefined dihedral angle, designated phi ($\varphi$) and psi ($\phi$) respectively.
4) the three acetamido sidechain groups can rotate with respect to their GlcNAc rings (rings 2, 4 and 6) about each N(nitrogen)-C2(ring) bond.
5) the three acetamido sidechain groups (rings 2, 4 and 6) can exist in either cis or trans conformations at the amide N(nitrogen)-C(carbonyl) bond.
6) the three methyl groups on the acetamido sidechain groups (rings 2, 4 and 6) can rotate with respect to their acetamido sidechains about the C(methyl)-C(carbonyl) bond.
7) the three hydroxymethyl sidechain groups can rotate with respect to their GlcNAc rings (rings 2, 4 and 6) about the C6(hydroxymethyl)-C5(ring) bond.
8) The three carboxylate groups can rotate with respect to their GlcA rings (rings 1, 3 and 5) about the C(carboxylate)-C5(ring) bond.
9) all the hydroxyl groups in all the GlcNAc and GlcA rings can rotate about their respective O(oxygen)-C(carbon) bonds.

To create a realistic dynamic model of the molecule upon which to compare against the observed experimental data, degrees of freedom were modelled as follows:

1) the large values for the $^3J_{HH}$ coupling constants in both GlcA and GlcNAc rings indicate that the rings adopt a $^4C_1$ chair conformation in aqueous solution, and do not appreciably interconvert with other forms [36]. Each carbohydrate ring was therefore modelled in a rigid $^4C_1$ chair conformation.
2) the two $\beta1\rightarrow3$ glycosidic linkages between rings 1&2 and 3&4 have been shown by the analysis of chemical shifts and NOE patterns to adopt virtually identical (though unknown) conformations in aqueous solution, without any experimental evidence for the presence of multiple stable, interchanging conformations [8, 34, 36]. These two $\beta1\rightarrow3$ linkages were therefore represented with the same variables, which were a single unimodal conformation probability distribution for each of the phi ($\varphi$) and psi ($\phi$) angles (i.e., two mean values, $\mu_\varphi$, and $\mu_\phi$, for linkages between 1&2 and 3&4) and, since these two dihedral angles are directly coupled together dynamically, they were given the same standard-deviation angle of local libration ($\sigma$). The $\beta1\rightarrow3$ glycosidic linkage between rings 5&6 (the 'alpha' linkage) has been shown by the analysis of chemical shifts, NOE patterns and molecular dynamics simulations to be likely to be adopting a different conformation in solution from the other two $\beta1\rightarrow3$ linkages [8, 34, 36]. This linkage was therefore modelled in the same way as the other $\beta1\rightarrow6$ linkages (i.e., two mean values, $\mu_\varphi$ & $\mu_\phi$ having the same standard deviation angle of local libration $\sigma$), but had variables independent of the other two $\beta1\rightarrow3$ linkages.
3) The two $\beta1\rightarrow4$ glycosidic linkages have been shown by the analysis of chemical shifts and NOE patterns to adopt virtually identical (though unknown) conformations in aqueous solution, without any experimental evidence for the presence of multiple stable, interchanging conformations [8, 34, 36]. The two $\beta1\rightarrow4$ linkages were therefore represented with the same variables, namely a single unimodal conformation probability distribution for each of the phi ($\varphi$) and psi ($\phi$) angles (i.e., $\mu_\varphi$ and $\mu_\phi$, for linkages between 2&3 and 4&5) with the same standard deviation angle of local libration ($\sigma$).
4) All the acetamido sidechain groups in rings 2 and 4 have been shown to be adopting an approximately trans conformation with respect to the ring (i.e., HN—N—C2-H2 dihedral=180°, although the amide group in ring 6 has been shown to be different to the other two by a small but unknown amount [8, 34, 36]. There is no experimental evidence from either assignment spectra or NOE restraints for the presence of multiple conformations for any amide group [8, 35]. The acetamido sidechains were therefore all modelled with unimodal conformation probability distributions. Since the acetamido sidechains in rings 2 and 4 are indistinguishable in solution, the same variables were used for both of them ($\mu_{HN}$, $\sigma_{HN}$ in residues 2 & 4), whereas the acetamido sidechain in ring 6 was modelled with independent variables ($\|_{HN}$, $\sigma_{HN}$ for residue 6).
5) The amide bonds in the three acetamido sidechain groups were set to be in the trans conformations, since this is the expected geometry for this chemical group in the absence of other forces, and is the state found in monosaccharide GlcNAc [38].
6) Methyl groups rotate freely around the C—C bond, with the 3 staggered rotamer positions being slightly favoured over semi-eclipsed states. This motion was modelled by a trimodal conformation model, in which the dihedral angle was given three values (0°, 120° and 240°, corresponding to the 3 staggered rotamer positions) with an equal probability of being in each conformation. In addition, the local libration was set to a fixed value of 30° for each conformation.
7) The three hydroxymethyl sidechain groups have been shown to be adopting indistinguishable conformations from each other in aqueous solution by comparison of chemical shifts and $^3J_{5,6proS}$ and $^3J_{5,6proR}$ couplings constants [35]. According to the relation of Hasnoot et al. [15], the values observed for these two couplings (see FIG. 15) indicate that each hydroxymethyl group is rapidly interchanging between two conformers (termed gg and gt) in a 50:50% ratio. This motion was therefore modelled with a bimodal conformational model, in which the dihedral angle was given the two appropriate values for gg and gt with an equal probability of being in each conformation, and a fixed local libration of 15° for each conformation (i.e., an appropriate value based upon our experience of other systems since there was insufficient experimental data to determine this value more precisely).
8) There was no experimental data available to restrain the conformations of the three carboxylate groups (the oxygen atoms are NMR-inactive), so the positions of the two oxygen atoms in each group could not be determined with respect to the rest of the molecule. The carboxlate groups were therefore all given the same arbitrary value and, in order to prevent them from influencing the structure calculation by steric clashes that may have arisen because of a poor choice of the arbitrary value, they were set to not contribute to any van der Waals repulsions (see above). Fortunately, rotations of the carboxylate groups do not affect the overall shape or dynamic motions of $\alpha$-HA$_6$. In addition, since all experiments were performed at pH 6.0, the carboxylate groups were modelled in the unprotonated state [36].

9) Similarly, there was no experimental data available to restrain the conformations of any of the hydrogen atoms in the hydroxyl groups (they exchange with solvent water very rapidly), so the positions of the hydrogen atoms in each hydroxyl group could not be determined with respect to the rest of the molecule. The hydroxyl protons were therefore given arbitrary values and made van der Waals inactive to prevent them from influencing the structure calculation by unfortunate steric clashes that may have arisen due to a poor choice of the arbitrary value.

The specific implementation of these considerations was achieved using the following dynamic-model file:

```
remark Dynamic model of alpha-HA6
variables:

remark b1-3 linkages rings 1-2 & 3-4 means
var 1 rand 0 360 jump 180
var 2 rand 0 360 jump 180
remark b1-3 linkages rings 1-2 & 3-4 Gaussain spread
var 3 fix 18 jump 10.0 start 0.3
remark b1-3 linkage rings 5-6 mean
var 4 rand 0 360 jump 180
var 5 rand 0 360 jump 180
remark b1-3 linkage rings 5-6 Gaussian spread
var 6 fix 18 jump 10.0 start 0.3
remark b1-4 linkages rings 2-3 & 4-5 means
var 7 rand 0 360 jump 180
var 8 rand 0 360 jump 180
remark b1-4 linkages rings 2-3 & 4-5 Gaussian spread
var 9 fix 18 jump 10.0 start 0.3
remark amides rings 2&4 mean
var 10 fix 119.5 jump 2.0 start 0.3
remark amides rings 2&4 Gaussian spread
var 11 fix 24 jump 10.0 start 0.3
remark amide ring 6 mean
var 12 fix 119.5 jump 2.0 start 0.3
remark amide ring 6 Gaussian spread
var 13 fix 24 jump 10.0 start 0.3
remark hydroxymethyls rings 2&4&6 mean
var 14 fix −60 jump 0.0 start 0.0
var 15 fix 60 jump 0.0 start 0.0
remark hydroxymethyl rings 2&4&6 Gaussian spread
var 16 fix 15 jump 0.0 start 0.0
remark methyl groups rings 2&4&6 means
var 17 fix −120 jump 0.0 start 0.0
var 18 fix 120 jump 0.0 start 0.0
var 19 fix 0 jump 0.0 start 0.0
remark methyl Gaussian rings 2&4&6 spread
var 20 fix 30 jump 0.0 start 0.0
endsection
probabilities:

remark hydroxymethyl groups rings 2&4&6 bimodal distribution
mode 1 2 0.5 0.0
remark methyl groups rings 2&4&6 trimodal distribution
mode 2 3 0.33 0.66 0.0
endsection
dynamics:

remark b1-3 linkages rings 1-2 & 3-4
gyrate 41 1 3
gyrate 42 2 3
gyrate 93 1 3
gyrate 94 2 3
remark b1-3 linkage rings 5-6
gyrate 146 4 6
gyrate 147 5 6
remark b1-4 linkages rings 2-3 & 4-5
gyrate 70 7 9
gyrate 71 8 9
gyrate 122 7 9
gyrate 123 8 9
remark amides rings 2&4
gyrate 31 10 11
gyrate 83 10 11
remark amide ring 6
gyrate 136 12 13
remark hydroxymethyls rings 2&4&6
multigyrate 48 1 14 16 15 16
multigyrate 100 1 14 16 15 16
multigyrate 153 1 14 16 15 16
remark methyl groups rings 2&4&6
multigyrate 35 2 17 20 18 20 19 20
multigyrate 87 2 17 20 18 20 19 20
multigyrate 140 2 17 20 18 20 19 20
endsection
```

In the variables section of this file, 20 variables are defined (var 1 to var 20) and which of these variable were used for each rotatable bond in $\alpha$-HA$_6$ is shown in FIG. 17. Two variables (var 4 and var 5) are assigned to the $\beta 1 \rightarrow 6$ linkages between rings 5 and 6 (remark b1-3 linkages ring 5-6 mean) for the mean values of the $\phi$ and $\varphi$ dihedral angles, respectively, and one variable (var 6) is assigned to their common Gaussian spread (remark b1-3 linkage rings 5-6 Gaussian spread). These $\phi$ and $\varphi$ mean dihedral angles are both given a random value between 0° and 360° (rand 0 360) at the start (start 0.0) of the iterative optimisation, while the Gaussian spread is assigned a specific (and reasonable) value of 20° (fix 20) at the start of the optimisation, which is varied at each step of the iteration by a random amount up to 10° (jump 10.0) from the start of the optimisation (start 0.0). The other two $\beta 1 \rightarrow 6$ linkages are similarly specified (var 1, var 2 and var 3) and, because they are given the same variables, they are modelled as being dynamically and conformationally identical to each other. The unimodal distributions for the $\phi$ and $\varphi$ bonds in the two $\beta 1 \rightarrow 4$ linkages are similarly specified by variables 7 to 9. The unimodal distributions for the acetamido sidechains C2-N2 bond are similarly specified by variables 9 and 10 (sidechains in rings 2 and 4) and 11 and 12 (sidechain in ring 6). The hydroxymethyl groups all have the same bimodal angular distribution. The two mean dihedral angles of for this bimodal distribution are specified with var 14 and var 15, which are both fixed (jump 0.0) from the start (start 0.0) of the optimisation, and they both have the same Gaussian spread (var 16) of 15° (fix 15.0) that does not vary throughout the optimisation (jump 0.0). The methyl groups all have the same trimodal angular distribution. The three mean dihedral angles for this trimodal distribution are specified with var 17, var 18 and var 19, which are all fixed (jump 0.0) from the start (start 0.0) of the optimisation, and they all have the same Gaussian spread (var 20) of 30° (fix 30.0) that does not vary throughout the optimisation (jump 0.0). These variables are mapped to particular dihedral angles within the molecule using the probabilities, gyrations and multigyrations (as described above).

In this manner, all the flexible parts of the $\alpha$-HA$_6$ molecule and their behaviour are defined for the computer, according to the analysis of the nine degrees of freedom given above. Since variables 14 to 20 have a predefined fixed value, there are therefore 13 distinct unknown molecular variables to determine in order to solve the solution structure of $\alpha$-HA$_6$.

Structure Calculations

Each round of structures calculations for $\alpha$-HA$_6$ comprised 40 runs. Statistics were performed on the lowest 10 $\chi^2_{total}$ runs. Each individual run had 10,000 iteration steps and the dynamic ensemble was composed of 100 structures. The seven experimental dataset files (see Appendix A) were brought in progressively in successive rounds of structure calculations, as described below.

The initial 3D-model of the HA hexasaccharide was constructed based on knowledge of standard bond distances, angles and chemistries for the parts of the molecule that were in a fixed geometrical relationship (as described above). In the initial rounds of structure calculations (rounds 1 through 30), four dataset files were used to determine a rough solution conformation for $\alpha$-HA$_6$. These were:

1) the order parameters dataset file (3 structural restraints)
2) the scalar couplings dataset file (3 structural restraints)
3) the $^{15}$N-NOESY-HSQC dataset file (19 structural restraints)
4) the 2D-NOESY dataset file (82 NOE structural restraints).

The structural restraints in the order parameters, scalar couplings and $^{15}$N-NOESY-HSQC dataset files were relatively few and easily generated and therefore very unlikely to contain any mistakes and could all be included right from the start of the structure-determination process. In contrast, the large 2D-NOESY dataset file was expected to contain many mistakes, and therefore only the most certain NOE structural restraints were used in the first round of calculations (~60 restraints), and no 'noNOE' structural restraints were used. After 30 rounds of structure calculations, the erroneous NOE structural restraints in the 2D-NOESY dataset had been corrected, and all NOE structural restraints had been included. The top 10 of the 40 runs in this round all gave similar values for the 10 unknown variables, as shown in the statistics below:

run, as well as the mean value and standard deviation (StDev) for these $\chi^2_{total}$ values. Above this line, the $\chi^2_{total}$, mean and standard deviation values are given for each individual dataset file that was used in this round of calculations, i.e., the $^{15}$N-NOESY-HSQC(NOE-HSQC), 2D-NOESY (2D-NOESY), scalar coupling (JCOUP) and order parameters (ORDER). The $\chi^2_{total}$, mean and standard deviation values are also given for the van der Waals (VDW) term in each run. Following the TotChi line are the results for the 10 variables var 1 to var 10 specified in the dynamic model file. After this round of calculations, therefore, the $\beta1\rightarrow3$ linkages between rings 1&2 and 3&4 were found to have $\phi$ and $\varphi$ angles of $-83.4\pm8.9°$ (var 1) and $-119.3\pm5.2°$ (var 2), respectively, with a Gaussian spread of $20.9\pm5.5°$ (var 3). The $\beta1\rightarrow3$ linkage between rings 5&6 was found to have $\phi$ and $\varphi$ angles of $-58.4\pm25.7°$ (var 4) and $-129.7\pm5.2°$ (var 5), respectively, with a Gaussian spread of $16.7\pm3.5°$ (var 6). The $\beta1\rightarrow4$ linkage was found to have $\phi$ and $\varphi$ angles of $-91.9\pm8.8°$ (var 7) and $-129.3\pm16.5°$ (var 8), with a Gaussian spread of $18.9\pm3.0°$ (var 9). The acetamido groups in rings 2 & 4 had a mean value of $119.1\pm1.3$ (var 10) with a Gaussian spread of $32.3\pm1.6°$ (var 11), whilst that in ring 6 had a mean value of $119.1\pm1.0°$ (var 12) with a Gaussian spread of $26.4\pm2.6°$ (var 13).

In order to see if any one dataset file was unduly biasing the emerging structure, the $\chi^2_{dataset}$/restraint (Chi/Res) for each dataset and $\chi^2_{total}$/restraint was calculated:

| Dataset | Restraints | Tot Chi | Chi/Res | Viol(>10) | Percent |
|---|---|---|---|---|---|
| TOTAL | 107 | 142.3 | 1.3 | 0 | 0 |
| 2D-NOESY | 82 | 107.9 | 1.3 | 0 | 0 |
| JCOUP | 3 | 2.6 | 0.9 | 0 | 0 |
| 15N-NOESY-HSQC | 19 | 29.6 | 1.6 | 0 | 0 |
| ORDER | 3 | 2.2 | 0.7 | 0 | 0 |

In this case, it can be seen that the Chi/Res values are similar for each dataset (from 0.9 to 1.6), indicating that no one dataset file is dominating the others. Since the errors for Round30 statistics:

| Parameter | Mean | StDev | \multicolumn{10}{c|}{Ranked run no.} | | | | | | | | | |
|---|---|---|---|---|---|---|---|---|---|---|---|---|
| | | | 22 | 27 | 24 | 10 | 12 | 11 | 5 | 15 | 9 | 26 |
| 15N-NOE | 108.3 | 4.3 | 98.6 | 103.2 | 106.8 | 110.5 | 111.0 | 112.5 | 107.5 | 112.1 | 108.2 | 112.4 |
| 2D-NOE | 29.6 | 1.6 | 31.1 | 28.6 | 28.2 | 29.1 | 27.3 | 28.8 | 33.2 | 28.9 | 30.9 | 29.6 |
| JCOUP | 2.6 | 0.9 | 2.2 | 2.7 | 2.2 | 2.3 | 1.6 | 2.9 | 3.5 | 4.4 | 3.6 | 1.1 |
| ORDER | 2.2 | 1.5 | 2.0 | 2.2 | 1.5 | 1.1 | 2.5 | 0.2 | 2.0 | 0.4 | 4.5 | 5.3 |
| VDW | 1.3 | 0.9 | 2.5 | 1.9 | 2.6 | 0.5 | 1.7 | 1.7 | 0.2 | 1.0 | 0.5 | 0.3 |
| TotChi | 143.9 | 3.8 | 136.5 | 138.6 | 141.2 | 143.5 | 144.1 | 146.0 | 146.5 | 146.7 | 147.6 | 148.7 |
| 1-3_phi | −83.4 | 8.9 | −95.2 | −74.3 | −88.5 | −76.4 | −92.8 | −96.2 | −75.7 | −73.2 | −74.8 | −87.1 |
| 1-3_psi | −119.3 | 5.2 | −115.3 | −122.9 | −112.0 | −123.6 | −114.5 | −121.6 | −124.7 | −112.1 | −119.8 | −126.8 |
| 1-3_dyn | 20.9 | 5.5 | 18.8 | 24.4 | 11.5 | 25.1 | 16.3 | 23.2 | 25.9 | 12.4 | 27.5 | 23.9 |
| a1-3_phi | −58.4 | 25.7 | −71.6 | −61.1 | −84.3 | −57.0 | −87.2 | −58.4 | 0.3 | −31.6 | −49.0 | −83.9 |
| a1-3_psi | −129.7 | 5.2 | −131.2 | −129.8 | −122.9 | −126.8 | −127.5 | −133.9 | −135.8 | −133.9 | −135.6 | −119.4 |
| a1-3_dyn | 16.7 | 3.5 | 17.2 | 15.1 | 15.8 | 17.1 | 18.7 | 20.5 | 17.1 | 22.1 | 14.7 | 8.4 |
| 1-4_phi | −91.9 | 8.8 | −97.4 | −110.2 | −89.0 | −91.2 | −93.9 | −77.8 | −88.4 | −93.6 | −79.8 | |
| 1-4_psi | −129.3 | 16.5 | −150.5 | −140.2 | −121.3 | −108.2 | −117.0 | −113.1 | −153.9 | −148.0 | −112.6 | −127.8 |
| 1-4_dyn | 18.9 | 3.0 | 18.5 | 17.3 | 24.0 | 16.6 | 21.4 | 15.5 | 20.2 | 23.2 | 15.2 | 17.2 |
| HN | 119.1 | 1.3 | 120.3 | 117.3 | 116.7 | 119.1 | 119.0 | 121.4 | 120.1 | 119.7 | 118.3 | 118.8 |
| HN_dyn | 32.3 | 1.6 | 33.7 | 34.3 | 31.4 | 32.0 | 35.4 | 30.2 | 30.5 | 31.8 | 31.8 | 32.3 |
| HN_a | 119.1 | 1.0 | 120.1 | 119.4 | 118.9 | 117.2 | 117.9 | 120.5 | 120.3 | 119.2 | 119.1 | 118.4 |
| HN_a_dy | 26.4 | 2.6 | 30.0 | 30.5 | 30.0 | 24.8 | 24.4 | 25.3 | 25.4 | 25.0 | 23.0 | 25.9 |

In this table, the output data from the top ten best $\chi^2_{total}$ are shown, where run number 22 is the best and run number 26 is the 10$^{th}$ best. TotChi line gives the $\chi^2_{total}$ value for each the order parameters and scalar coupling data can be determined directly, while the errors for the NOESY dataset files depend upon the imprecisely known value m, of the value of m for the 2D-NOESY dataset (0.4) and $^{15}$N-NOESY-HSQC dataset (0.4) can be seen to be suitable. None of the 107 structural restraints used in this round of calculations were violators.

In the next ten rounds of structure calculations, the noNOE structural restraints from the 2D-NOESY spectrum were included. The results from the round of structure calculations where all noNOEs were included without any being violators, or any of the structural restraints in the other dataset files being violators, were as follows:

(−50.4±7.7°, −127.4±3.5°) with a Gaussian spread of 15.7±2.8° and while the β1→4 linkages prefers a (φ, φ) conformation of (−82.0±10.6°, −131.4±15.1°) with a Gaussian spread of 18.7±5.1°. The amide groups are not much different to Round 30. The Chi/Res value for the noNOE restraints (2 D-NOESY (no)) is 0.5, which is considerably less than that of the other datasets. This was important since noNOE structural restraints actually represent the lack of observed data, and therefore have less confidence than Round40 statistics:

| Parameter | Mean | StDev | \multicolumn{10}{c}{Ranked run no.} |
|---|---|---|---|---|---|---|---|---|---|---|---|---|
| | | | 30 | 40 | 35 | 9 | 37 | 14 | 19 | 39 | 38 | 5 |
| 15N-NOE | 27.6 | 1.1 | 28.1 | 28.0 | 27.1 | 27.7 | 26.6 | 29.0 | 26.5 | 29.7 | 27.0 | 26.4 |
| 2D-NOE | 163.7 | 2.5 | 160.5 | 161.3 | 162.6 | 164.6 | 162.2 | 163.2 | 166.8 | 164.1 | 169.3 | 162.8 |
| JCOUP | 2.9 | 2.5 | 0.8 | 0.9 | 2.3 | 0.0 | 4.4 | 4.2 | 3.5 | 0.5 | 3.7 | 8.8 |
| ORDER | 1.9 | 1.2 | 0.8 | 2.0 | 0.9 | 1.8 | 1.7 | 1.5 | 1.3 | 4.3 | 0.5 | 3.8 |
| VDW | 0.5 | 0.3 | 0.8 | 0.4 | 1.0 | 0.1 | 0.5 | 0.3 | 0.6 | 0.6 | 0.8 | 0.3 |
| TotChi | 196.6 | 3.6 | 190.9 | 192.7 | 193.9 | 194.3 | 195.3 | 198.2 | 198.5 | 199.2 | 201.3 | 202.0 |
| 1-3_phi | −62.7 | 8.2 | −67.6 | −64.3 | −74.0 | −58.0 | −67.3 | −60.7 | −54.6 | −44.3 | −68.9 | −67.4 |
| 1-3_psi | −112.2 | 4.1 | −117.3 | −109.7 | −111.6 | −120.2 | −109.5 | −115.6 | −106.5 | −112.1 | −108.3 | −110.9 |
| 1-3_dyn | 20.0 | 4.7 | 19.1 | 21.6 | 17.6 | 26.3 | 19.0 | 26.1 | 20.5 | 24.2 | 9.9 | 16.0 |
| a1-3_phi | −50.4 | 7.7 | −57.7 | −48.4 | −64.2 | −40.0 | −52.0 | −53.5 | −40.2 | −48.2 | −42.5 | −57.3 |
| a1-3_psi | −127.4 | 3.5 | −124.5 | −131.6 | −125.9 | −127.5 | −129.0 | −128.7 | −122.5 | −134.5 | −124.3 | −125.9 |
| a1-3_dyn | 15.7 | 2.8 | 10.2 | 20.4 | 13.8 | 17.0 | 15.1 | 15.0 | 19.0 | 15.6 | 13.5 | 17.6 |
| 1-4_phi | −82.0 | 10.6 | −79.3 | −70.5 | −87.5 | −72.2 | −92.7 | −105.4 | −84.9 | −80.5 | −68.8 | −78.2 |
| 1-4_psi | −131.4 | 15.1 | −135.6 | −156.8 | −138.7 | −130.6 | −115.2 | −117.3 | −122.3 | −150.5 | −107.3 | −139.4 |
| 1-4_dyn | 18.7 | 5.1 | 22.0 | 13.8 | 20.0 | 9.0 | 17.2 | 14.7 | 18.9 | 19.2 | 28.2 | 23.7 |
| HN | 119.0 | 0.9 | 117.2 | 118.8 | 119.4 | 118.3 | 120.2 | 119.6 | 120.3 | 119.4 | 118.4 | 118.9 |
| HN_dyn | 31.5 | 1.9 | 31.1 | 32.0 | 28.8 | 30.7 | 34.1 | 30.1 | 35.1 | 32.4 | 29.4 | 31.0 |
| HN_a | 119.5 | 0.6 | 118.0 | 119.7 | 120.1 | 119.3 | 119.3 | 119.9 | 119.1 | 120.3 | 119.2 | 119.8 |
| HN_a_dy | 25.8 | 3.2 | 28.0 | 29.1 | 28.1 | 31.2 | 23.3 | 24.4 | 24.3 | 25.6 | 24.7 | 19.2 |

| Dataset | Restraints | Tot Chi | Chi/Res | Viol (>10) | Percent |
|---|---|---|---|---|---|
| TOTAL | 204 | 196.7 | 1.0 | 0 | 0 |
| 2D-NOESY | 85 | 116.7 | 1.4 | 0 | 0 |
| 2D-NOESY (no) | 94 | 47.4 | 0.5 | 0 | 0 |
| JCOUP | 3 | 2.9 | 1.0 | 0 | 0 |
| 15N-NOESY-HSQC | 19 | 27.8 | 1.5 | 0 | 0 |
| ORDER | 3 | 1.9 | 0.6 | 0 | 0 |

As can be seen from these results, the new values for the glycosidic linkage variables are different to those determined in the earlier rounds (which had less data), although they are basically similar. With these structural restraint data, the 131-6 linkages between rings 1 &2 and rings 3&4 prefers a (φ, φ) conformation of (−62.7±8.2°, −112.0±4.1°) with a Gaussian spread of 20.0±4.7°, the β1→3 linkage between rings 5&6 prefers a (φ, φ) conformation of directly observed structural restraints, and should therefore not be dominating the structure calculations.

Over the next 30 rounds of calculations, the RDC data was included, again first as a base dataset (~45 restraints) and then the remaining ~20. The results from the round of structure calculations where all RDCs were included without any being violators, or any of the structural restraints in the other dataset files being violators, were as follows:

Round70 statistics:

| Parameter | Mean | StDev | \multicolumn{10}{c}{Ranked run no.} |
|---|---|---|---|---|---|---|---|---|---|---|---|---|
| | | | 22 | 27 | 16 | 15 | 35 | 24 | 30 | 25 | 1 | 36 |
| RDC | 71.8 | 3.3 | 69.1 | 68.7 | 71.9 | 79.0 | 68.9 | 71.4 | 76.2 | 71.9 | 68.2 | 72.7 |
| 15N-NOE | 26.4 | 1.4 | 28.0 | 24.6 | 26.3 | 27.7 | 25.3 | 23.9 | 28.2 | 26.1 | 26.7 | 26.9 |
| 2D-NOE | 176.3 | 3.8 | 177.2 | 181.2 | 171.8 | 174.9 | 175.6 | 183.2 | 177.1 | 171.0 | 172.5 | 178.9 |
| JCOUP | 4.4 | 3.6 | 0.6 | 1.9 | 4.8 | 0.2 | 6.4 | 2.7 | 2.7 | 9.9 | 11.5 | 3.5 |
| ORDER | 4.6 | 2.7 | 1.5 | 2.2 | 5.0 | 2.2 | 6.6 | 3.9 | 1.1 | 8.4 | 8.9 | 6.4 |
| VDW | 1.8 | 0.7 | 1.5 | 1.5 | 2.7 | 1.6 | 3.0 | 2.3 | 2.2 | 0.5 | 1.6 | 1.1 |
| TotChi | 285.3 | 3.8 | 277.8 | 280.1 | 282.5 | 285.5 | 285.8 | 287.3 | 287.5 | 287.8 | 289.4 | 289.6 |
| 1-3_phi | −70.4 | 8.3 | −76.1 | −73.3 | −69.1 | −55.5 | −78.8 | −82.7 | −71.9 | −69.2 | −56.2 | −71.6 |
| 1-3_psi | −114.4 | 4.3 | −107.6 | −116.1 | −110.4 | −115.4 | −110.2 | −110.9 | −119.0 | −122.3 | −115.5 | −116.0 |
| 1-3_dyn | 21.0 | 4.1 | 13.9 | 22.4 | 23.4 | 24.8 | 14.8 | 17.3 | 19.6 | 25.3 | 24.4 | 24.1 |
| a1-3_phi | −20.3 | 9.1 | −17.0 | −25.6 | −12.7 | −8.5 | −31.6 | −35.2 | −5.1 | −22.8 | −23.3 | −20.8 |

-continued

| Round70 statistics: | | | | | | | | | | | |
|---|---|---|---|---|---|---|---|---|---|---|---|
| a1-3_psi | −120.5 | 3.8 | −126.6 | −113.4 | −126.7 | −120.8 | −119.8 | −118.7 | −122.1 | −118.3 | −119.6 | −118.7 |
| a1-3_dyn | 16.7 | 3.4 | 17.0 | 14.5 | 22.1 | 10.8 | 12.7 | 18.4 | 18.3 | 17.0 | 14.9 | 21.4 |
| 1-4_phi | −59.4 | 4.2 | −53.9 | −59.5 | −53.4 | −60.5 | −60.4 | −56.2 | −63.2 | −67.6 | −56.6 | −62.9 |
| 1-4_psi | −152.3 | 8.5 | −150.7 | −148.7 | −155.5 | −167.1 | −141.4 | −150.8 | −166.3 | −141.8 | −145.5 | −155.0 |
| 1-4_dyn | 19.2 | 4.9 | 15.8 | 16.8 | 19.5 | 9.2 | 27.9 | 21.8 | 16.1 | 18.6 | 23.0 | 23.0 |
| HN | 119.7 | 1.1 | 121.1 | 119.1 | 118.0 | 118.1 | 118.8 | 119.5 | 120.6 | 120.6 | 120.0 | 121.3 |
| HN_dyn | 30.7 | 3.5 | 36.3 | 34.2 | 29.3 | 33.8 | 27.2 | 30.3 | 33.9 | 28.5 | 24.8 | 29.0 |
| HN_a | 119.3 | 0.9 | 120.8 | 118.7 | 118.8 | 120.6 | 120.0 | 119.3 | 119.0 | 119.0 | 117.6 | 118.9 |
| HN_a_dy | 26.7 | 4.9 | 31.1 | 27.5 | 25.8 | 37.0 | 22.4 | 30.3 | 25.9 | 19.6 | 21.2 | 25.9 |

| Dataset | Restraints | Tot Chi | Chi/Res | Viol (>10) | Percent |
|---|---|---|---|---|---|
| TOTAL | 269 | 283.5 | 1.1 | 0 | 0 |
| 2D-NOESY | 85 | 129.6 | 1.5 | 0 | 0 |
| 2D-NOESY (no) | 94 | 47.1 | 0.5 | 0 | 0 |
| JCOUP | 3 | 4.4 | 1.5 | 0 | 0 |
| 15N-NOESY-HSQC | 19 | 26.2 | 1.4 | 0 | 0 |
| ORDER | 3 | 4.6 | 1.5 | 0 | 0 |
| RDC | 65 | 71.6 | 1.1 | 0 | 0 |

As can be seen from these results, the new values for the glycosidic linkage variables are only slightly different to those determined in round40. With these structural restraint data, the β1→3 linkages between rings 1 & 2 and 3 & 4 prefers a (ϕ, φ) conformation of (−70.4±8.3°, −114.4±4.3°) with a Gaussian spread of 21.0±4.1°, the β1→3 linkage between rings 5 & 6 prefers a (ϕ, φ) conformation of (−20.3±9.1°, −120.5±16.7°) with a Gaussian spread of 16.7±3.4° and the β1→4 linkage prefers a (ϕ, φ) conformation of (−59.4±4.2°, −152.3±8.5°) with a Gaussian spread of 19.2±4.9°. The amide groups are again very similar to previous rounds of calculations.

Over the next 5 rounds of calculations, the [$^1$H, $^{15}$N]-T-ROESY-HSQC data was included as an entire block, since the structural restrains had high confidence of not having mistakes. Inclusion of this dataset revealed a few mistakes in the other dataset files, however. The results from the round of structure calculations where all the $^{15}$N-filtered-ROEs were included without any being violators, or any of the structural restraints in the other dataset files being violators, were as follows:

| Round75 statistics: | | | | | | | | | | | |
|---|---|---|---|---|---|---|---|---|---|---|---|
| | | | Ranked run no. | | | | | | | | |
| Parameter | Mean | StDev | 7 | 4 | 17 | 14 | 3 | 40 | 5 | 24 | 16 | 9 |
| RDC | 76.1 | 2.9 | 70.9 | 80.5 | 77.7 | 73.5 | 80.0 | 74.6 | 77.6 | 76.1 | 76.9 | 73.5 |
| 15N-NOE | 30.1 | 0.7 | 29.7 | 29.8 | 30.1 | 29.7 | 28.5 | 31.0 | 31.3 | 30.4 | 30.3 | 30.4 |
| 2D-NOE | 179.2 | 4.6 | 176.4 | 171.2 | 173.9 | 176.3 | 180.4 | 185.8 | 180.7 | 182.2 | 186.1 | 179.1 |
| 15N-ROE | 20.2 | 2.9 | 17.8 | 22.2 | 21.7 | 22.5 | 20.2 | 18.8 | 19.2 | 18.0 | 15.2 | 26.2 |
| JCOUP | 3.6 | 1.8 | 6.7 | 0.6 | 1.1 | 4.3 | 2.4 | 2.5 | 5.4 | 4.0 | 5.2 | 3.3 |
| ORDER | 3.0 | 1.7 | 3.7 | 4.7 | 5.4 | 3.7 | 0.9 | 0.6 | 1.8 | 5.0 | 1.9 | 2.9 |
| VDW | 1.4 | 0.8 | 2.3 | 1.8 | 1.2 | 1.2 | 0.8 | 0.4 | 0.2 | 1.6 | 2.2 | 2.6 |
| TotChi | 313.7 | 3.4 | 307.6 | 310.9 | 311.1 | 311.2 | 313.3 | 313.6 | 316.3 | 317.4 | 317.8 | 317.9 |
| 1-3_phi | −70.7 | 5.6 | −79.6 | −80.2 | −70.7 | −74.3 | −64.1 | −63.8 | −71.6 | −70.1 | −65.8 | −66.8 |
| 1-3_psi | −122.9 | 3.7 | −122.9 | −120.3 | −121.9 | −124.0 | −120.4 | −127.1 | −123.8 | −129.7 | −123.8 | −115.5 |
| 1-3_dyn | 21.5 | 3.9 | 13.2 | 19.8 | 22.1 | 22.8 | 24.3 | 22.6 | 24.2 | 28.3 | 18.1 | 19.9 |
| a1-3_phi | −16.6 | 4.1 | −20.4 | −23.8 | −13.2 | −17.6 | −17.5 | −12.0 | −22.0 | −11.9 | −12.2 | −15.4 |
| a1-3_psi | −121.7 | 2.6 | −119.9 | −122.1 | −120.9 | −121.1 | −117.3 | −124.5 | −124.4 | −118.9 | −121.5 | −126.3 |
| a1-3_dyn | 18.1 | 2.1 | 20.6 | 14.5 | 15.0 | 16.4 | 18.3 | 19.6 | 17.6 | 17.8 | 20.9 | 20.1 |
| 1-4_phi | −63.6 | 7.0 | −61.4 | −66.1 | −67.3 | −65.3 | −77.1 | −54.8 | −56.1 | −71.9 | −55.8 | −59.9 |
| 1-4_psi | −147.0 | 8.8 | −139.0 | −148.4 | −158.8 | −143.4 | −155.4 | −141.6 | −127.8 | −150.7 | −149.9 | −154.8 |
| 1-4_dyn | 19.9 | 3.2 | 22.6 | 19.6 | 17.2 | 21.8 | 14.2 | 15.8 | 21.3 | 19.0 | 22.4 | 25.2 |
| HN | 119.6 | 0.9 | 118.2 | 119.6 | 119.5 | 120.2 | 120.2 | 121.7 | 119.5 | 118.6 | 119.3 | 119.3 |
| HN_dyn | 30.5 | 2.2 | 32.8 | 32.1 | 30.8 | 28.3 | 33.6 | 29.9 | 26.1 | 31.5 | 28.4 | 31.1 |
| HN_a | 119.7 | 0.7 | 118.3 | 119.7 | 119.2 | 120.5 | 119.5 | 119.1 | 120.3 | 120.2 | 119.3 | 120.4 |
| HN_a_dy | 25.8 | 2.9 | 19.2 | 28.6 | 30.1 | 27.9 | 23.5 | 26.1 | 26.4 | 24.5 | 25.1 | 26.3 |

| Dataset | Restraints | Tot Chi | Chi/Res | Viol (>10) | Percent |
|---|---|---|---|---|---|
| TOTAL | 287 | 312.3 | 1.1 | 0 | 0 |
| 2D-NOESY | 85 | 126.7 | 1.5 | 0 | 0 |
| 2D-NOESY (no) | 94 | 52.4 | 0.6 | 0 | 0 |
| JCOUP | 3 | 3.6 | 1.2 | 0 | 0 |
| 15N-NOESY-HSQC | 19 | 30.2 | 1.6 | 0 | 0 |
| ORDER | 3 | 3.1 | 1.0 | 0 | 0 |

| | | Round75 statistics: | | | |
|---|---|---|---|---|---|
| RDC | 65 | 76.1 | 1.2 | 0 | 0 |
| 15N-ROESY-HSQC | 18 | 20.1 | 1.1 | 0 | 0 |

As can be seen from these results, the new values for the glycosidic linkage variables are very similar to those determined in round70. With these structural restraint data, the β1→3 linkages between rings 1&2 and 3&4 prefer a (ϕ, φ) conformation of (−70.7±5.6°, −122.9±3.7°) with a Gaussian spread of 21.5±3.9°, the β1→3 linkage between rings 5&6 prefers a (ϕ, φ) conformation of (−16.6±4.1°, −121.7±2.6°) with a Gaussian spread of 18.1±2.1° and the β1→4 linkages prefer a (ϕ, φ) conformation of (−63.6±7.0°, −147.0±8.8°) with a Gaussian spread of 19.9±3.2°. The amide groups are again very similar to previous rounds of calculations.

Over the next 35 rounds of calculations, the 2D-T-ROESY data was included (there were artefacts in some parts of this spectrum, requiring a lot of rounds of calculations to weed out the anomalous data points), again first as a base dataset (~40 restraints) of ROE structural restraints and then the remaining ~20. The results from the round of structure calculations where all ROEs from this dataset were included without any being violators, or any of the structural restraints in the other dataset files being violators, were as follows:

As can be seen from these results, the new values for the glycosidic linkage variables are barely different to those determined in round75. With these structural restraint data, the β1→3 linkages between rings 1&2 and 3&4 prefer a (ϕ, φ) conformation of (−68.8±10.1°, −120.6±3.7°) with a Gaussian spread of 20.6±4.5°, the β1→3 linkage between rings 5&6 prefers a (ϕ, φ) conformation of (−21.9±8.5°, −118.4±3.6°) with a Gaussian spread of 17.8±3.7° and the β1→4 linkages prefer a (ϕ, φ) conformation of (−60.4±5.7°, −146.9±12.9°) with a Gaussian spread of 21.7±2.4°. The amide groups are again very similar to previous rounds of calculations.

Over the next 15 rounds of calculations, the noROEs in the 2D-T-ROESY dataset were included. The results from the round of structure calculations where all noROEs were included without any being violators, or any of the structural restraints in the other dataset files being violators, were as follows:

| | | | Round110 statistics: | | | | | | | | |
|---|---|---|---|---|---|---|---|---|---|---|---|
| | | | | | | Ranked run no. | | | | | |
| Parameter | Mean | StDev | 40 | 2 | 14 | 20 | 36 | 15 | 13 | 6 | 9 | 30 |
| RDC | 73.3 | 3.1 | 75.2 | 76.1 | 68.8 | 76.8 | 69.8 | 76.0 | 69.7 | 74.5 | 69.7 | 76.1 |
| 15N-NOE | 28.9 | 1.2 | 28.9 | 31.3 | 28.2 | 30.3 | 27.4 | 29.6 | 27.1 | 29.4 | 28.1 | 28.4 |
| 2D-NOE | 180.8 | 4.3 | 178.8 | 176.1 | 187.9 | 176.0 | 179.4 | 175.1 | 187.1 | 181.7 | 183.4 | 182.8 |
| 15N-ROE | 20.7 | 3.3 | 17.2 | 16.9 | 20.0 | 22.7 | 28.2 | 21.9 | 19.3 | 19.5 | 23.3 | 17.9 |
| 2D-ROE | 80.2 | 1.7 | 77.6 | 81.3 | 81.0 | 77.4 | 82.4 | 79.8 | 80.9 | 79.3 | 79.7 | 82.5 |
| JCOUP | 4.6 | 2.1 | 3.5 | 1.1 | 6.6 | 7.2 | 0.5 | 5.7 | 5.9 | 5.0 | 4.5 | 5.7 |
| ORDER | 3.0 | 1.9 | 2.9 | 7.3 | 0.7 | 1.8 | 5.4 | 2.9 | 2.2 | 4.1 | 1.8 | 1.3 |
| VDW | 1.9 | 1.3 | 1.7 | 1.4 | 0.2 | 1.6 | 0.8 | 3.1 | 2.2 | 1.3 | 5.2 | 1.2 |
| TotChi | 393.3 | 2.8 | 385.7 | 391.4 | 393.5 | 393.6 | 393.8 | 394.1 | 394.4 | 394.8 | 395.7 | 395.9 |
| 1-3_phi | −68.8 | 10.1 | −65.6 | −68.8 | −89.3 | −53.7 | −78.5 | −74.9 | −67.6 | −55.2 | −70.8 | −63.2 |
| 1-3_psi | −120.6 | 3.7 | −120.5 | −126.2 | −118.4 | −116.2 | −117.8 | −118.0 | −121.4 | −124.6 | −116.4 | −126.3 |
| 1-3_dyn | 20.6 | 4.5 | 25.2 | 26.2 | 18.5 | 24.3 | 11.9 | 18.0 | 18.0 | 24.1 | 16.0 | 23.6 |
| a1-3_phi | −21.9 | 8.5 | −18.1 | −18.6 | −38.9 | −12.4 | −25.4 | −20.9 | −23.3 | −9.3 | −18.7 | −33.5 |
| a1-3_psi | −118.4 | 3.6 | −112.4 | −121.3 | −121.4 | −125.0 | −116.2 | −115.1 | −117.3 | −121.9 | −116.2 | −117.6 |
| a1-3_dyn | 17.8 | 3.7 | 16.5 | 14.2 | 23.6 | 18.0 | 15.3 | 12.5 | 20.4 | 22.8 | 14.4 | 20.2 |
| 1-4_phi | −60.4 | 5.7 | −63.1 | −60.5 | −54.8 | −54.1 | −60.6 | −64.7 | −63.0 | −73.1 | −53.5 | −56.9 |
| 1-4_psi | −146.9 | 12.9 | −157.5 | −142.2 | −120.5 | −150.5 | −148.7 | −147.6 | −155.4 | −158.8 | −160.6 | −126.8 |
| 1-4_dyn | 21.7 | 2.4 | 19.9 | 22.0 | 19.4 | 20.8 | 20.4 | 22.5 | 22.2 | 20.9 | 28.1 | 20.4 |
| HN | 119.9 | 0.7 | 120.1 | 118.8 | 120.8 | 121.1 | 118.8 | 120.1 | 119.4 | 119.6 | 120.0 | 120.0 |
| HN_dyn | 29.7 | 2.4 | 28.4 | 28.2 | 33.6 | 28.2 | 33.7 | 32.5 | 29.1 | 27.3 | 27.0 | 28.7 |
| HN_a | 119.3 | 0.9 | 120.3 | 119.7 | 118.5 | 119.7 | 118.0 | 120.2 | 119.8 | 118.3 | 118.4 | 120.4 |
| HN_a_dy | 25.0 | 2.3 | 22.9 | 27.6 | 24.7 | 25.2 | 29.3 | 22.4 | 21.5 | 24.8 | 26.5 | 24.6 |

| Dataset | Restraints | Tot Chi | Chi/Res | Viol (>10) | Percent |
|---|---|---|---|---|---|
| TOTAL | 349 | 391.6 | 1.1 | 0 | 0 |
| 2D-NOESY | 85 | 130.6 | 1.5 | 0 | 0 |
| 2D-NOESY (no) | 94 | 50.3 | 0.5 | 0 | 0 |
| JCOUP | 3 | 4.6 | 1.5 | 0 | 0 |
| 2D-ROESY | 62 | 80.0 | 1.3 | 0 | 0 |
| 15N-NOESY-HSQC | 19 | 29.1 | 1.5 | 0 | 0 |
| ORDER | 3 | 3.1 | 1.0 | 0 | 0 |
| RDC | 65 | 73.3 | 1.1 | 0 | 0 |
| 15N-ROESY-HSQC | 18 | 20.7 | 1.1 | 0 | 0 |

Round125 statistics:

| Parameter | Mean | StDev | \multicolumn{10}{c}{Ranked run no.} |
|---|---|---|---|---|---|---|---|---|---|---|---|---|
| | | | 14 | 16 | 36 | 28 | 13 | 7 | 33 | 24 | 12 | 40 |
| RDC | 75.6 | 5.1 | 81.7 | 69.3 | 72.3 | 75.7 | 75.5 | 81.1 | 70.0 | 84.9 | 70.5 | 74.7 |
| 15N-NOE | 29.6 | 1.1 | 29.1 | 28.1 | 27.9 | 31.5 | 29.8 | 30.5 | 29.0 | 30.6 | 29.1 | 29.9 |
| 2D-NOE | 180.6 | 4.2 | 174.2 | 179.7 | 176.0 | 181.1 | 178.4 | 185.7 | 181.7 | 177.8 | 182.9 | 188.9 |
| 15N-ROE | 19.1 | 2.6 | 18.9 | 20.2 | 25.1 | 17.6 | 16.5 | 19.9 | 15.2 | 21.0 | 19.0 | 17.0 |
| 2D-ROE | 85.8 | 2.4 | 81.8 | 83.0 | 84.0 | 85.8 | 89.1 | 84.9 | 86.5 | 86.2 | 86.9 | 89.7 |
| JCOUP | 3.5 | 4.1 | 0.9 | 4.0 | 2.3 | 1.6 | 5.9 | 0.2 | 14.3 | 0.3 | 5.3 | 0.4 |
| ORDER | 5.2 | 2.9 | 2.3 | 6.6 | 5.8 | 6.0 | 7.4 | 0.9 | 6.5 | 1.4 | 10.7 | 4.0 |
| VDW | 1.0 | 0.6 | 0.5 | 0.9 | 1.0 | 1.4 | 0.5 | 1.1 | 1.2 | 2.4 | 0.3 | 0.6 |
| TotChi | 400.3 | 5.8 | 389.4 | 391.8 | 394.4 | 400.7 | 403.2 | 404.5 | 404.6 | 404.6 | 404.7 | 405.1 |
| 1-3_phi | −71.6 | 7.6 | −69.0 | −70.1 | −63.1 | −70.5 | −72.8 | −91.3 | −74.5 | −62.2 | −72.1 | −70.0 |
| 1-3_psi | −124.3 | 6.1 | −137.6 | −117.6 | −131.6 | −126.7 | −120.4 | −123.9 | −124.1 | −117.8 | −118.7 | −124.8 |
| 1-3_dyn | 21.5 | 6.0 | 32.4 | 15.5 | 31.3 | 26.4 | 16.2 | 21.6 | 19.8 | 17.4 | 18.5 | 15.8 |
| a1-3_phi | −20.4 | 9.3 | −9.9 | −20.4 | −15.4 | −11.2 | −27.8 | −38.5 | −33.3 | −15.3 | −19.4 | −12.6 |
| a1-3_psi | −123.1 | 2.9 | −123.8 | −125.6 | −116.2 | −123.5 | −122.6 | −124.9 | −120.7 | −125.7 | −126.3 | −121.6 |
| a1-3_dyn | 17.3 | 3.0 | 19.0 | 22.9 | 15.5 | 16.0 | 14.4 | 13.8 | 20.7 | 13.9 | 20.3 | 16.7 |
| 1-4_phi | −58.0 | 6.1 | −71.0 | −48.6 | −61.5 | −62.3 | −61.8 | −58.6 | −54.8 | −55.8 | −52.2 | −54.0 |
| 1-4_psi | −142.1 | 14.5 | −164.3 | −144.5 | −151.5 | −158.0 | −131.8 | −121.5 | −129.9 | −155.9 | −122.2 | −141.0 |
| 1-4_dyn | 18.9 | 6.6 | 3.8 | 22.9 | 10.6 | 19.0 | 22.3 | 17.6 | 26.2 | 22.4 | 25.6 | 18.7 |
| HN | 119.6 | 0.9 | 117.5 | 119.6 | 118.6 | 121.0 | 120.4 | 120.3 | 120.0 | 119.8 | 119.2 | 119.5 |
| HN_dyn | 30.9 | 2.3 | 32.3 | 32.1 | 32.4 | 29.0 | 28.5 | 34.1 | 27.6 | 31.8 | 27.9 | 33.3 |
| HN_a | 119.2 | 0.8 | 118.6 | 119.1 | 118.9 | 119.6 | 119.6 | 119.7 | 120.1 | 117.4 | 120.0 | 119.1 |
| HN_a_dy | 26.1 | 3.9 | 28.6 | 23.2 | 25.3 | 31.3 | 22.5 | 26.1 | 17.6 | 30.0 | 26.5 | 29.4 |

| Dataset | Restraints | Tot Chi | Chi/Res | Viol (>10) | Percent |
|---|---|---|---|---|---|
| TOTAL | 412 | 399.2 | 1.0 | 0 | 0 |
| 2D-NOESY | 85 | 128.7 | 1.5 | 0 | 0 |
| 2D-NOESY (no) | 94 | 51.8 | 0.6 | 0 | 0 |
| JCOUP | 3 | 3.6 | 1.2 | 0 | 0 |
| 2D-ROESY | 62 | 82.3 | 1.3 | 0 | 0 |
| 2D-ROESY (no) | 63 | 3.6 | 0.1 | 0 | 0 |
| 15N-NOESY-HSQC | 19 | 29.4 | 1.5 | 0 | 0 |
| ORDER | 3 | 5.1 | 1.7 | 0 | 0 |
| RDC | 65 | 75.6 | 1.2 | 0 | 0 |
| 15N-ROESY-HSQC | 18 | 19.1 | 1.1 | 0 | 0 |

As can be seen from these results, the values for each of the 10 variables, in particular the glycosidic linkage variables and their Gaussian spreads, have not significantly changed since before the inclusion of any 2D-T-ROESY data (either ROEs or noROEs), that is since round75. Since the inclusion of this large body of data (154 structural restraints) did not alter the values for these 10 variables, the dynamic structure was deemed to be solved, and there was no need for further experimental data.

Structure Refinement

The dynamic 3D-solution structure of α-HA$_6$ was refined using a dynamic-model file (shown below), in which the starting values for the 13 variables were taken from the results of round125 (see above). This allowed the optimisation algorithm to explore this specific $\chi^2_{total}$ minimum quite effectively, searching for the best possible values of the 13 variables. The ensemble size was increased to 250, 15,000 iteration steps were performed for each run and 100 runs were performed. All seven NMR datasets used in round125 were used in the structure refinement.

```
remark Dynamic model file for minimisation of alpha-HA6
variables:
remark b1-3 linkages rings 1-2 & 3-4 means
var 1 fix −70 jump 10.0 start 0.02
var 2 fix −125 jump 10.0 start 0.02
remark b1-3 linkages rings 1-2 & 3-4 Gaussain spread
var 3 fix 22 jump 10.0 start 0.3
```

-continued

```
remark b1-3 linkage rings 5-6 mean
var 4 fix −20 jump 10.0 start 0.02
var 5 fix −125 jump 10.0 start 0.02
remark b1-3 linkage rings 5-6 Gaussian spread
var 6 fix 18 jump 10.0 start 0.3
remark b1-4 linkages rings 2-3 & 4-5 means
var 7 fix −60 jump 10.0 start 0.02
var 8 fix −140 jump 10.0 start 0.02
remark b1-4 linkages rings 2-3 & 4-5 Gaussian spread
var 9 fix 19 jump 10.0 start 0.3
remark amides rings 2&4 mean
var 10 fix 120 jump 5.0 start 0.3
remark amides rings 2&4 Gaussian spread
var 11 fix 30 jump 10.0 start 0.3
remark amide ring 6 mean
var 12 fix 120 jump 5.0 start 0.3
remark amide ring 6 Gaussian spread
var 13 fix 25 jump 10.0 start 0.3
remark hydroxymethyls rings 2&4&6 mean
var 14 fix −60 jump 0.0 start 0.0
var 15 fix 60 jump 0.0 start 0.0
remark hydroxymethyl rings 2&4&6 Gaussian spread
var 16 fix 15 jump 0.0 start 0.0
remark methyl groups rings 2&4&6 means
var 17 fix −120 jump 0.0 start 0.0
var 18 fix 120 jump 0.0 start 0.0
var 19 fix 0 jump 0.0 start 0.0
remark methyl Gaussian rings 2&4&6 spread
var 20 fix 30 jump 0.0 start 0.0
endsection
```

-continued

```
probabilities:

remark hydroxymethyl groups rings 2&4&6 bimodal distribution
mode 1 2 0.5 0.0
remark methyl groups rings 2&4&6 trimodal distribution
mode 2 3 0.33 0.66 0.0
endsection
dynamics:

remark b1-3 linkages rings 1-2 & 3-4
gyrate 41 1 3
gyrate 42 2 3
gyrate 93 1 3
gyrate 94 2 3
remark b1-3 linkage rings 5-6
gyrate 146 4 6
```

-continued

```
multigyrate 48 1 14 16 15 16
multigyrate 100 1 14 16 15 16
multigyrate 153 1 14 16 15 16
remark methyl groups rings 2&4&6
multigyrate 35 2 17 20 18 20 19 20
multigyrate 87 2 17 20 18 20 19 20
multigyrate 140 2 17 20 18 20 19 20
endsection
```

The 20 runs with lowest total $\chi^2_{total}$ value out of 100 runs in total for this minimisation round were taken for statistical analysis. The values for the best 5 runs are shown here for the sake of brevity, although the mean (Mean) and standard deviation (stDev) values are those calculated from the best 20:

Refinement round statistics:

| Parameter | Mean | StDev | \multicolumn{5}{c}{Ranked run no.} |
| --- | --- | --- | --- | --- | --- | --- | --- |
| | | | 11 | 5 | 73 | 53 | 98 |
| RDC | 71.4 | 2.2 | 69.7 | 72.9 | 68.5 | 69.5 | 68.0 ... |
| 15N-NOE | 29.4 | 1.0 | 29.4 | 29.7 | 29.4 | 29.4 | 29.2 ... |
| 2D-NOE | 178.1 | 2.6 | 176.5 | 179.0 | 174.2 | 176.3 | 178.6 ... |
| 15N-ROE | 19.0 | 2.4 | 18.4 | 16.5 | 23.3 | 18.1 | 19.1 ... |
| 2D-ROE | 84.1 | 1.5 | 81.9 | 82.6 | 81.9 | 84.2 | 84.8 ... |
| JCOUP | 2.7 | 1.1 | 2.2 | 2.1 | 5.5 | 2.7 | 5.1 ... |
| ORDER | 1.7 | 1.2 | 3.3 | 0.5 | 1.5 | 5.0 | 0.2 ... |
| VDW | 1.1 | 0.4 | 2.0 | 1.8 | 1.1 | 0.8 | 1.4 ... |
| TotChi | 387.6 | 1.6 | 383.5 | 385.1 | 385.4 | 386.1 | 386.5 ... |
| 1-3_phi | −69.7 | 4.1 | −73.8 | −66.5 | −65.6 | −72.4 | −77.8 ... |
| 1-3_psi | −122.3 | 1.9 | −122.5 | −120.2 | −119.9 | −123.6 | −121.4 ... |
| 1-3_dyn | 23.5 | 2.2 | 22.7 | 25.0 | 25.0 | 22.9 | 22.4 ... |
| a1-3_phi | −20.4 | 2.6 | −18.6 | −17.4 | −17.0 | −20.6 | −24.3 ... |
| a1-3_psi | −121.8 | 2.3 | −120.1 | −121.1 | −121.2 | −119.8 | −121.4 ... |
| a1-3_dyn | 17.5 | 1.1 | 16.1 | 17.6 | 15.9 | 16.9 | 19.3 ... |
| 1-4_phi | −60.6 | 2.4 | −60.6 | −58.1 | −60.6 | −60.7 | −63.6 ... |
| 1-4_psi | −142.2 | 4.7 | −146.5 | −149.2 | −150.5 | −144.5 | −138.2 ... |
| 1-4_dyn | 19.4 | 1.3 | 20.3 | 17.3 | 19.0 | 18.9 | 20.9 ... |
| HN | 120.4 | 0.8 | 121.7 | 120.5 | 122.2 | 120.1 | 120.0 ... |
| HN_dyn | 29.8 | 1.4 | 31.3 | 30.5 | 26.9 | 30.4 | 29.0 ... |
| HN_a | 119.6 | 1.0 | 118.5 | 118.8 | 116.9 | 119.8 | 120.1 ... |
| HN_a_dy | 25.8 | 1.0 | 25.7 | 26.7 | 24.6 | 25.6 | 24.4 ... |

| Dataset | Restraints | Tot Chi | Chi/Res | Viol (>10) | Percent |
| --- | --- | --- | --- | --- | --- |
| TOTAL | 412 | 386.9 | 0.9 | 0 | 0 |
| 2D-NOESY | 85 | 29.2 | .5 | 0 | 0 |
| 2D-NOESY(no) | 94 | 49.3 | 0.5 | 0 | 0 |
| JCOUP | 3 | 2.8 | 0.9 | 0 | 0 |
| 2D-ROESY | 62 | 80.8 | 1.3 | 0 | 0 |
| 2D-ROESY (no) | 63 | 3.3 | 0.1 | 0 | 0 |
| 15N-NOESY-HSQC | 19 | 29.4 | 1.5 | 0 | 0 |
| ORDER | 3 | 1.7 | 0.6 | 0 | 0 |
| RDC | 65 | 71.3 | 1.1 | 0 | 0 |
| 15N-ROESY-HSQC | 18 | 19.1 | 1.1 | 0 | 0 |

-continued

```
gyrate 147 5 6
remark b1-4 linkages rings 2-3 & 4-5
gyrate 70 7 9
gyrate 71 8 9
gyrate 122 7 9
gyrate 123 8 9
remark amides rings 2&4
gyrate 31 10 11
gyrate 83 10 11
remark amide ring 6
gyrate 136 12 13
remark hydroxymethyls rings 2&4&6
```

No structural restraint has an $\chi^2_{restraint}$ value greater than 10.0 with these values for the variables, demonstrating the quality of the structure. The final list of all 412 structural restraints with their individual $\chi^2$ restraint values is given in Appendix A. Therefore, using the optimisation algorithm, the best fit values for the 13 variables describing the dynamic solution structure of α-HA$_6$ have been determined. Since there are 412 structural restraints, this represents an average of 31.7 structural restraints per degree of freedom defined. The best fit values are: the β1→3 linkages between rings 1&2 and 3&4 have ϕ and φ angles of −69.7±4.1° (var 1) and −122.3±1.9° (var 2), respectively, with a Gaussian spread of libration of 23.5±2.2° (var 3); the β1→3 linkage between rings 5&6 has ϕ and φ angles of −20.4±2.6° (var 4)

and −121.8±2.3° (var 5), respectively, with a Gaussian spread of libration of 17.5±1.1° (var 6); the β1→4 linkages have φ and φ angles of −60.4±2.4° (var 7) and −142.2±4.7° (var 8), with a Gaussian spread of libration of 19.4±1.3° (var 9). The acetamido groups in rings 2 & 4 have a mean dihedral angle value of 120.4±0.8° (var 10) (i.e., HN and H2 are exactly trans to each other, sine the dihedral is defined on the heavy atoms) with a gaussian spread of 29.8±1.4° (var 11). The acetamido group in ring 6 has a mean value of 119.6±1.0° (var 12) with a gaussian spread of 25.8±1.0° (var 13). The coordinates for the mean solution structure for α-HA$_6$, generated according to these variables, is given in Appendix A. Several visual representations of the mean structure and dynamic ensemble of structures are given in FIGS. 18-20.

APPENDIX A

Hyaluronan Hexasaccharide

Starting 3D-Coordinates for a Hyaluronan Hexasaccharide as a PDB

This is the protein databank (PDB) file format. Column 2 is the atoms number, column 3 the atom type, column 5 the residue number and columns 6-8 are the (x,y,z) Cartesian coordinates of each atomic nucleus.

| ATOM | 1 | C1 | BGLA | 1 | 8.160 | 3.740 | −6.827 | 0.00 | 0.00 | MOLG |
|---|---|---|---|---|---|---|---|---|---|---|
| ATOM | 2 | H1 | BGLA | 1 | 8.574 | 3.399 | −5.860 | 0.00 | 0.00 | MOLG |
| ATOM | 3 | C5 | BGLA | 1 | 9.716 | 5.669 | −6.880 | 0.00 | 0.00 | MOLG |
| ATOM | 4 | H5 | BGLA | 1 | 10.140 | 5.318 | −5.935 | 0.00 | 0.00 | MOLG |
| ATOM | 5 | O5 | BGLA | 1 | 8.279 | 5.214 | −6.937 | 0.00 | 0.00 | MOLG |
| ATOM | 6 | C2 | BGLA | 1 | 8.929 | 3.076 | −7.999 | 0.00 | 0.00 | MOLG |
| ATOM | 7 | H2 | BGLA | 1 | 8.489 | 3.373 | −8.954 | 0.00 | 0.00 | MOLG |
| ATOM | 8 | O2 | BGLA | 1 | 8.794 | 1.631 | −7.841 | 0.00 | 0.00 | MOLG |
| ATOM | 9 | HO2 | BGLA | 1 | 7.851 | 1.418 | −7.765 | 0.00 | 0.00 | MOLG |
| ATOM | 10 | C3 | BGLA | 1 | 10.428 | 3.481 | −7.940 | 0.00 | 0.00 | MOLG |
| ATOM | 11 | H3 | BGLA | 1 | 10.887 | 3.139 | −7.008 | 0.00 | 0.00 | MOLG |
| ATOM | 12 | O3 | BGLA | 1 | 11.173 | 2.937 | −9.072 | 0.00 | 0.00 | MOLG |
| ATOM | 13 | HO3 | BGLA | 1 | 11.990 | 3.449 | −9.107 | 0.00 | 0.00 | MOLG |
| ATOM | 14 | C4 | BGLA | 1 | 10.493 | 5.025 | −8.053 | 0.00 | 0.00 | MOLG |
| ATOM | 15 | H4 | BGLA | 1 | 10.078 | 5.364 | −9.006 | 0.00 | 0.00 | MOLG |
| ATOM | 16 | O4 | BGLA | 1 | 11.889 | 5.426 | −7.973 | 0.00 | 0.00 | MOLG |
| ATOM | 17 | HO4 | BGLA | 1 | 11.893 | 6.325 | −7.577 | 0.00 | 0.00 | MOLG |
| ATOM | 18 | C6 | BGLA | 1 | 9.950 | 7.231 | −6.916 | 0.00 | 0.00 | MOLG |
| ATOM | 19 | O6A | BGLA | 1 | 9.481 | 8.033 | −8.095 | 0.00 | 0.00 | MOLG |
| ATOM | 20 | O6B | BGLA | 1 | 10.641 | 7.914 | −5.772 | 0.00 | 0.00 | MOLG |
| ATOM | 21 | C1 | BNAG | 2 | 4.120 | 2.919 | −4.124 | 0.00 | 0.00 | MOLG |
| ATOM | 22 | H1 | BNAG | 2 | 4.797 | 3.132 | −3.275 | 0.00 | 0.00 | MOLG |
| ATOM | 23 | C5 | BNAG | 2 | 4.228 | 5.292 | −4.758 | 0.00 | 0.00 | MOLG |
| ATOM | 24 | H5 | BNAG | 2 | 4.879 | 5.486 | −3.900 | 0.00 | 0.00 | MOLG |
| ATOM | 25 | O5 | BNAG | 2 | 3.336 | 4.141 | −4.431 | 0.00 | 0.00 | MOLG |
| ATOM | 26 | C2 | BNAG | 2 | 4.990 | 2.530 | −5.355 | 0.00 | 0.00 | MOLG |
| ATOM | 27 | H2 | BNAG | 2 | 4.333 | 2.345 | −6.209 | 0.00 | 0.00 | MOLG |
| ATOM | 28 | N2 | BNAG | 2 | 5.726 | 1.286 | −5.066 | 0.00 | 0.00 | MOLG |
| ATOM | 29 | H2N | BNAG | 2 | 6.406 | 1.341 | −4.312 | 0.00 | 0.00 | MOLG |
| ATOM | 30 | C2N | BNAG | 2 | 5.542 | 0.115 | −5.720 | 0.00 | 0.00 | MOLG |
| ATOM | 31 | O2N | BNAG | 2 | 4.736 | 0.008 | −6.632 | 0.00 | 0.00 | MOLG |
| ATOM | 32 | CME | BNAG | 2 | 6.403 | −1.077 | −5.257 | 0.00 | 0.00 | MOLG |
| ATOM | 33 | H1M | BNAG | 2 | 7.443 | −0.757 | −5.132 | 0.00 | 0.00 | MOLG |
| ATOM | 34 | H2M | BNAG | 2 | 6.040 | −1.469 | −4.299 | 0.00 | 0.00 | MOLG |
| ATOM | 35 | H3M | BNAG | 2 | 6.363 | −1.870 | −6.011 | 0.00 | 0.00 | MOLG |
| ATOM | 36 | C3 | BNAG | 2 | 5.953 | 3.700 | −5.681 | 0.00 | 0.00 | MOLG |
| ATOM | 37 | H3 | BNAG | 2 | 6.614 | 3.890 | −4.830 | 0.00 | 0.00 | MOLG |
| ATOM | 38 | O3 | BNAG | 2 | 6.739 | 3.377 | −6.907 | 0.00 | 0.00 | MOLG |
| ATOM | 39 | C4 | BNAG | 2 | 5.096 | 4.945 | −5.992 | 0.00 | 0.00 | MOLG |
| ATOM | 40 | H4 | BNAG | 2 | 4.464 | 4.764 | −6.867 | 0.00 | 0.00 | MOLG |
| ATOM | 41 | O4 | BNAG | 2 | 5.958 | 6.074 | −6.259 | 0.00 | 0.00 | MOLG |
| ATOM | 42 | HO4 | BNAG | 2 | 6.796 | 5.770 | −6.649 | 0.00 | 0.00 | MOLG |
| ATOM | 43 | C6 | BNAG | 2 | 3.343 | 6.533 | −4.986 | 0.00 | 0.00 | MOLG |
| ATOM | 44 | H61 | BNAG | 2 | 2.970 | 6.923 | −4.037 | 0.00 | 0.00 | MOLG |
| ATOM | 45 | H62 | BNAG | 2 | 3.922 | 7.320 | −5.475 | 0.00 | 0.00 | MOLG |
| ATOM | 46 | O6 | BNAG | 2 | 2.217 | 6.195 | −5.822 | 0.00 | 0.00 | MOLG |
| ATOM | 47 | HO6 | BNAG | 2 | 2.533 | 5.645 | −6.548 | 0.00 | 0.00 | MOLG |
| ATOM | 48 | C1 | BGLA | 3 | 0.677 | 1.330 | −0.317 | 0.00 | 0.00 | MOLG |
| ATOM | 49 | H1 | BGLA | 3 | 0.071 | 0.554 | −0.821 | 0.00 | 0.00 | MOLG |
| ATOM | 50 | C5 | BGLA | 3 | 2.698 | 0.706 | −1.617 | 0.00 | 0.00 | MOLG |
| ATOM | 51 | H5 | BGLA | 3 | 2.093 | −0.039 | −2.143 | 0.00 | 0.00 | MOLG |
| ATOM | 52 | O5 | BGLA | 3 | 2.100 | 0.907 | −0.248 | 0.00 | 0.00 | MOLG |
| ATOM | 53 | C2 | BGLA | 3 | 0.592 | 2.672 | −1.095 | 0.00 | 0.00 | MOLG |
| ATOM | 54 | H2 | BGLA | 3 | 1.148 | 3.449 | −0.563 | 0.00 | 0.00 | MOLG |
| ATOM | 55 | O2 | BGLA | 3 | −0.812 | 3.055 | −1.158 | 0.00 | 0.00 | MOLG |
| ATOM | 56 | HO2 | BGLA | 3 | −1.156 | 3.107 | −0.252 | 0.00 | 0.00 | MOLG |
| ATOM | 57 | C3 | BGLA | 3 | 1.153 | 2.490 | −2.530 | 0.00 | 0.00 | MOLG |
| ATOM | 58 | H3 | BGLA | 3 | 0.572 | 1.750 | −3.087 | 0.00 | 0.00 | MOLG |
| ATOM | 59 | O3 | BGLA | 3 | 1.176 | 3.746 | −3.280 | 0.00 | 0.00 | MOLG |
| ATOM | 60 | HO3 | BGLA | 3 | 1.783 | 3.612 | −4.019 | 0.00 | 0.00 | MOLG |
| ATOM | 61 | C4 | BGLA | 3 | 2.619 | 2.037 | −2.390 | 0.00 | 0.00 | MOLG |

-continued

| | | | | | | | | | | |
|---|---|---|---|---|---|---|---|---|---|---|
| ATOM | 62 | H4 | BGLA | 3 | 3.175 | 2.801 | −1.837 | 0.00 | 0.00 | MOLG |
| ATOM | 63 | O4 | BGLA | 3 | 3.182 | 1.845 | −3.755 | 0.00 | 0.00 | MOLG |
| ATOM | 64 | C6 | BGLA | 3 | 4.189 | 0.180 | −1.617 | 0.00 | 0.00 | MOLG |
| ATOM | 65 | O6A | BGLA | 3 | 4.515 | −1.152 | −2.225 | 0.00 | 0.00 | MOLG |
| ATOM | 66 | O6B | BGLA | 3 | 5.278 | 1.013 | −1.007 | 0.00 | 0.00 | MOLG |
| ATOM | 67 | C1 | BNAG | 4 | −2.161 | −0.903 | 2.896 | 0.00 | 0.00 | MOLG |
| ATOM | 68 | H1 | BNAG | 4 | −1.887 | −1.813 | 2.329 | 0.00 | 0.00 | MOLG |
| ATOM | 69 | C5 | BNAG | 4 | 0.054 | −0.923 | 3.969 | 0.00 | 0.00 | MOLG |
| ATOM | 70 | H5 | BNAG | 4 | 0.310 | −1.831 | 3.414 | 0.00 | 0.00 | MOLG |
| ATOM | 71 | O5 | BNAG | 4 | −1.423 | −0.891 | 4.183 | 0.00 | 0.00 | MOLG |
| ATOM | 72 | C2 | BNAG | 4 | −1.762 | 0.344 | 2.054 | 0.00 | 0.00 | MOLG |
| ATOM | 73 | H2 | BNAG | 4 | −2.012 | 1.248 | 2.616 | 0.00 | 0.00 | MOLG |
| ATOM | 74 | N2 | BNAG | 4 | −2.542 | 0.358 | 0.803 | 0.00 | 0.00 | MOLG |
| ATOM | 75 | H2N | BNAG | 4 | −2.303 | −0.362 | 0.125 | 0.00 | 0.00 | MOLG |
| ATOM | 76 | C2N | BNAG | 4 | −3.530 | 1.240 | 0.516 | 0.00 | 0.00 | MOLG |
| ATOM | 77 | O2N | BNAG | 4 | −3.843 | 2.131 | 1.290 | 0.00 | 0.00 | MOLG |
| ATOM | 78 | CME | BNAG | 4 | −4.241 | 1.060 | −0.840 | 0.00 | 0.00 | MOLG |
| ATOM | 79 | H1M | BNAG | 4 | −5.007 | 0.280 | −0.756 | 0.00 | 0.00 | MOLG |
| ATOM | 80 | H2M | BNAG | 4 | −4.725 | 1.992 | −1.153 | 0.00 | 0.00 | MOLG |
| ATOM | 81 | H3M | BNAG | 4 | −3.510 | 0.760 | −1.597 | 0.00 | 0.00 | MOLG |
| ATOM | 82 | C3 | BNAG | 4 | −0.235 | 0.306 | 1.779 | 0.00 | 0.00 | MOLG |
| ATOM | 83 | H3 | BNAG | 4 | 0.025 | −0.592 | 1.208 | 0.00 | 0.00 | MOLG |
| ATOM | 84 | O3 | BNAG | 4 | 0.179 | 1.539 | 1.050 | 0.00 | 0.00 | MOLG |
| ATOM | 85 | C4 | BNAG | 4 | 0.483 | 0.317 | 3.146 | 0.00 | 0.00 | MOLG |
| ATOM | 86 | H4 | BNAG | 4 | 0.244 | 1.235 | 3.690 | 0.00 | 0.00 | MOLG |
| ATOM | 87 | O4 | BNAG | 4 | 1.914 | 0.255 | 2.940 | 0.00 | 0.00 | MOLG |
| ATOM | 88 | HO4 | BNAG | 4 | 2.132 | 0.692 | 2.098 | 0.00 | 0.00 | MOLG |
| ATOM | 89 | C6 | BNAG | 4 | 0.757 | −0.974 | 5.342 | 0.00 | 0.00 | MOLG |
| ATOM | 90 | H61 | BNAG | 4 | 0.406 | −1.833 | 5.919 | 0.00 | 0.00 | MOLG |
| ATOM | 91 | H62 | BNAG | 4 | 1.836 | −1.073 | 5.210 | 0.00 | 0.00 | MOLG |
| ATOM | 92 | O6 | BNAG | 4 | 0.485 | 0.219 | 6.106 | 0.00 | 0.00 | MOLG |
| ATOM | 93 | HO6 | BNAG | 4 | 0.916 | 0.151 | 6.960 | 0.00 | 0.00 | MOLG |
| ATOM | 94 | C1 | BGLA | 5 | −6.107 | −3.901 | 4.931 | 0.00 | 0.00 | MOLG |
| ATOM | 95 | H1 | BGLA | 5 | −6.799 | −3.126 | 5.312 | 0.00 | 0.00 | MOLG |
| ATOM | 96 | C5 | BGLA | 5 | −5.501 | −2.467 | 3.001 | 0.00 | 0.00 | MOLG |
| ATOM | 97 | H5 | BGLA | 5 | −6.166 | −1.696 | 3.402 | 0.00 | 0.00 | MOLG |
| ATOM | 98 | O5 | BGLA | 5 | −6.021 | −3.810 | 3.453 | 0.00 | 0.00 | MOLG |
| ATOM | 99 | C2 | BGLA | 5 | −4.696 | −3.693 | 5.532 | 0.00 | 0.00 | MOLG |
| ATOM | 100 | H2 | BGLA | 5 | −4.020 | −4.481 | 5.188 | 0.00 | 0.00 | MOLG |
| ATOM | 101 | O2 | BGLA | 5 | −4.776 | −3.743 | 6.989 | 0.00 | 0.00 | MOLG |
| ATOM | 102 | HO2 | BGLA | 5 | −3.931 | −3.393 | 7.298 | 0.00 | 0.00 | MOLG |
| ATOM | 103 | C3 | BGLA | 5 | −4.149 | −2.303 | 5.131 | 0.00 | 0.00 | MOLG |
| ATOM | 104 | H3 | BGLA | 5 | −4.795 | −1.505 | 5.511 | 0.00 | 0.00 | MOLG |
| ATOM | 105 | O3 | BGLA | 5 | −2.803 | −2.127 | 5.671 | 0.00 | 0.00 | MOLG |
| ATOM | 106 | HO3 | BGLA | 5 | −2.318 | −1.516 | 5.095 | 0.00 | 0.00 | MOLG |
| ATOM | 107 | C4 | BGLA | 5 | −4.091 | −2.259 | 3.593 | 0.00 | 0.00 | MOLG |
| ATOM | 108 | H4 | BGLA | 5 | −3.425 | −3.050 | 3.232 | 0.00 | 0.00 | MOLG |
| ATOM | 109 | O4 | BGLA | 5 | −3.602 | −0.916 | 3.196 | 0.00 | 0.00 | MOLG |
| ATOM | 110 | C6 | BGLA | 5 | −5.446 | −2.274 | 1.435 | 0.00 | 0.00 | MOLG |
| ATOM | 111 | O6A | BGLA | 5 | −6.232 | −1.175 | 0.786 | 0.00 | 0.00 | MOLG |
| ATOM | 112 | O6B | BGLA | 5 | −4.607 | −3.192 | 0.595 | 0.00 | 0.00 | MOLG |
| ATOM | 113 | C1 | ANAG | 6 | −9.771 | −5.639 | 7.394 | 0.00 | 0.00 | MOLG |
| ATOM | 114 | H1 | ANAG | 6 | −9.902 | −5.840 | 8.472 | 0.00 | 0.00 | MOLG |
| ATOM | 115 | O1 | ANAG | 6 | −10.531 | −4.478 | 7.072 | 0.00 | 0.00 | MOLG |
| ATOM | 116 | HO1 | ANAG | 6 | −11.413 | −4.826 | 6.920 | 0.00 | 0.00 | MOLG |
| ATOM | 117 | C5 | ANAG | 6 | −10.162 | −6.634 | 5.164 | 0.00 | 0.00 | MOLG |
| ATOM | 118 | H5 | ANAG | 6 | −10.663 | −5.719 | 4.836 | 0.00 | 0.00 | MOLG |
| ATOM | 119 | O5 | ANAG | 6 | −10.333 | −6.791 | 6.655 | 0.00 | 0.00 | MOLG |
| ATOM | 120 | C2 | ANAG | 6 | −8.249 | −5.521 | 7.079 | 0.00 | 0.00 | MOLG |
| ATOM | 121 | H2 | ANAG | 6 | −7.758 | −6.450 | 7.380 | 0.00 | 0.00 | MOLG |
| ATOM | 122 | N2 | ANAG | 6 | −7.560 | −4.441 | 7.822 | 0.00 | 0.00 | MOLG |
| ATOM | 123 | H2N | ANAG | 6 | −8.004 | −3.534 | 7.767 | 0.00 | 0.00 | MOLG |
| ATOM | 124 | C2N | ANAG | 6 | −6.412 | −4.597 | 8.534 | 0.00 | 0.00 | MOLG |
| ATOM | 125 | O2N | ANAG | 6 | −5.842 | −5.671 | 8.624 | 0.00 | 0.00 | MOLG |
| ATOM | 126 | CME | ANAG | 6 | −5.874 | −3.328 | 9.223 | 0.00 | 0.00 | MOLG |
| ATOM | 127 | H1M | ANAG | 6 | −6.237 | −2.437 | 8.698 | 0.00 | 0.00 | MOLG |
| ATOM | 128 | H2M | ANAG | 6 | −6.216 | −3.298 | 10.264 | 0.00 | 0.00 | MOLG |
| ATOM | 129 | H3M | ANAG | 6 | −4.778 | −3.325 | 9.210 | 0.00 | 0.00 | MOLG |
| ATOM | 130 | C3 | ANAG | 6 | −8.046 | −5.311 | 5.562 | 0.00 | 0.00 | MOLG |
| ATOM | 131 | H3 | ANAG | 6 | −8.544 | −4.389 | 5.249 | 0.00 | 0.00 | MOLG |
| ATOM | 132 | O3 | ANAG | 6 | −6.591 | −5.245 | 5.283 | 0.00 | 0.00 | MOLG |
| ATOM | 133 | C4 | ANAG | 6 | −8.649 | −6.529 | 4.836 | 0.00 | 0.00 | MOLG |
| ATOM | 134 | H4 | ANAG | 6 | −8.132 | −7.442 | 5.141 | 0.00 | 0.00 | MOLG |
| ATOM | 135 | O4 | ANAG | 6 | −8.479 | −6.353 | 3.408 | 0.00 | 0.00 | MOLG |
| ATOM | 136 | HO4 | ANAG | 6 | −7.576 | −6.045 | 3.230 | 0.00 | 0.00 | MOLG |
| ATOM | 137 | C6 | ANAG | 6 | −10.826 | −7.824 | 4.440 | 0.00 | 0.00 | MOLG |
| ATOM | 138 | H61 | ANAG | 6 | −11.860 | −7.946 | 4.769 | 0.00 | 0.00 | MOLG |

| ATOM | 139 | H62 | ANAG | 6 | −10.833 | −7.653 | 3.361 | 0.00 | 0.00 | MOLG |
|---|---|---|---|---|---|---|---|---|---|---|
| ATOM | 140 | O6  | ANAG | 6 | −10.122 | −9.053 | 4.721 | 0.00 | 0.00 | MOLG |
| ATOM | 141 | HO6 | ANAG | 6 | −10.547 | −9.771 | 4.246 | 0.00 | 0.00 | MOLG |
| END  |     |     |      |   |         |        |       |      |      |      |

Internal Coordinate Table for a Hyaluronan Hexasaccharide

The first column specifies the internal coordinate number, the next eight columns represent the atoms definitions. The next five column specify a distance (ij), angle (ijk), dihedral (ijkl), angle (jkl) and distance (kl). An asterisk in column 7 means that the atoms are in a fixed geometry with respect to other atoms (usually specifying fixed geometry due to hybridisation, e.g., $sp^2$, $sp^3$) and the angles are used in a slightly different manner, but these angles are not subject to variation during optimisation.

| 1 | 2 | O3 | 1 | C1 | 1 | O5 | 1 | C5 | 1.46881 | 108.618 | −179.317 | 111.931 | 1.50839 |
|---|---|---|---|---|---|---|---|---|---|---|---|---|---|
| 2 | 2 | O3 | 1 | O5 | 1 | *C1 | 1 | C2 | 1.46881 | 108.618 | 119.308 | 109.25 | 1.55108 |
| 3 | 2 | O3 | 1 | O5 | 1 | *C1 | 1 | H1 | 1.46881 | 108.618 | −119.795 | 109.959 | 1.10579 |
| 4 | 1 | C4 | 1 | C5 | 1 | O5 | 1 | C1 | 1.54738 | 108.916 | 60.0395 | 111.931 | 1.48288 |
| 5 | 1 | C4 | 1 | O5 | 1 | *C5 | 1 | C6 | 1.54738 | 108.916 | 122.915 | 116.007 | 1.57984 |
| 6 | 1 | C4 | 1 | O5 | 1 | *C5 | 1 | H5 | 1.54738 | 108.916 | −118.201 | 107.77 | 1.09362 |
| 7 | 1 | O5 | 1 | C1 | 1 | C2 | 1 | O2 | 1.48288 | 109.25 | 179.474 | 107.224 | 1.45987 |
| 8 | 1 | O2 | 1 | C1 | 1 | *C2 | 1 | C3 | 1.45987 | 107.224 | −119.538 | 109.756 | 1.55387 |
| 9 | 1 | O2 | 1 | C1 | 1 | *C2 | 1 | H2 | 1.45987 | 107.224 | 118.538 | 110.146 | 1.09263 |
| 10 | 1 | C1 | 1 | C2 | 1 | O2 | 1 | HO2 | 1.55108 | 107.224 | 53.3625 | 108.41 | 0.969739 |
| 11 | 1 | C1 | 1 | C2 | 1 | C3 | 1 | O3 | 1.55108 | 109.756 | −176.756 | 111.447 | 1.46027 |
| 12 | 1 | O3 | 1 | C2 | 1 | *C3 | 1 | C4 | 1.46027 | 111.447 | 116.898 | 107.302 | 1.54949 |
| 13 | 1 | O3 | 1 | C2 | 1 | *C3 | 1 | H3 | 1.46027 | 111.447 | −121.927 | 110.836 | 1.09374 |
| 14 | 1 | C2 | 1 | C3 | 1 | O3 | 1 | HO3 | 1.55387 | 111.447 | 162.78 | 105.215 | 0.96481 |
| 15 | 1 | O5 | 1 | C5 | 1 | C4 | 1 | C3 | 1.50839 | 108.916 | −59.823 | 109.777 | 1.54949 |
| 16 | 1 | C3 | 1 | C5 | 1 | *C4 | 1 | O4 | 1.54949 | 109.777 | −118.244 | 108.994 | 1.45465 |
| 17 | 1 | C3 | 1 | C5 | 1 | *C4 | 1 | H4 | 1.54949 | 109.777 | 122.251 | 109.945 | 1.09332 |
| 18 | 1 | C2 | 1 | C3 | 1 | C4 | 1 | C5 | 1.55387 | 107.302 | 60.1054 | 109.777 | 1.54738 |
| 19 | 1 | C5 | 1 | C4 | 1 | O4 | 1 | HO4 | 1.54738 | 108.994 | −31.4217 | 106.162 | 0.982361 |
| 20 | 1 | O5 | 1 | C5 | 1 | C6 | 1 | O6A | 1.50839 | 116.007 | −60.3259 | 119.992 | 1.50107 |
| 21 | 1 | O6A | 1 | C5 | 1 | *C6 | 1 | O6B | 1.50107 | 119.992 | 179.997 | 120.049 | 1.5009 |
| 22 | 3 | O4 | 2 | C1 | 2 | O5 | 2 | C5 | 1.47292 | 108.411 | 177.566 | 111.385 | 1.49245 |
| 23 | 3 | O4 | 2 | O5 | 2 | *C1 | 2 | C2 | 1.47292 | 108.411 | 122.382 | 109.72 | 1.55679 |
| 24 | 3 | O4 | 2 | O5 | 2 | *C1 | 2 | H1 | 1.47292 | 108.411 | −119.339 | 108.871 | 1.10657 |
| 25 | 2 | C4 | 2 | C5 | 2 | O5 | 2 | C1 | 1.54809 | 109.688 | 59.9715 | 111.385 | 1.48398 |
| 26 | 2 | C4 | 2 | O5 | 2 | *C5 | 2 | C6 | 1.54809 | 109.688 | 123.117 | 108.072 | 1.5412 |
| 27 | 2 | C4 | 2 | O5 | 2 | *C5 | 2 | H5 | 1.54809 | 109.688 | −119.495 | 108.692 | 1.09435 |
| 28 | 2 | O5 | 2 | C1 | 2 | C2 | 2 | N2 | 1.48398 | 109.72 | −177.748 | 109.566 | 1.47403 |
| 29 | 2 | N2 | 2 | C1 | 2 | *C2 | 2 | C3 | 1.47403 | 109.566 | −122.352 | 108.959 | 1.55001 |
| 30 | 2 | N2 | 2 | C1 | 2 | *C2 | 2 | H2 | 1.47403 | 109.566 | 118.034 | 108.913 | 1.09325 |
| 31 | 2 | C1 | 2 | C2 | 2 | N2 | 2 | C2N | 1.55679 | 109.566 | 115.346 | 124.57 | 1.35381 |
| 32 | 2 | C2N | 2 | C2 | 2 | *N2 | 2 | H2N | 1.35381 | 124.57 | −179.409 | 115.699 | 1.01683 |
| 33 | 2 | C2 | 2 | N2 | 2 | C2N | 2 | CME | 1.47403 | 124.57 | −179.405 | 116.603 | 1.54161 |
| 34 | 2 | CME | 2 | N2 | 2 | *C2N | 2 | O2N | 1.54161 | 116.603 | −179.909 | 121.735 | 1.22181 |
| 35 | 2 | N2 | 2 | C2N | 2 | CME | 2 | H1M | 1.35381 | 116.603 | −45.6045 | 109.797 | 1.09527 |
| 36 | 2 | H1M | 2 | C2N | 2 | *CME | 2 | H2M | 1.09527 | 109.797 | 119.908 | 110.72 | 1.0969 |
| 37 | 2 | H1M | 2 | C2N | 2 | *CME | 2 | H3M | 1.09527 | 109.797 | −119.549 | 109.437 | 1.09497 |
| 38 | 2 | C1 | 2 | C2 | 2 | C3 | 2 | O3 | 1.55679 | 108.959 | −176.706 | 109.681 | 1.49171 |
| 39 | 2 | O3 | 2 | C2 | 2 | *C3 | 2 | C4 | 1.49171 | 109.681 | 116.853 | 107.839 | 1.54311 |
| 40 | 2 | O3 | 2 | C2 | 2 | *C3 | 2 | H3 | 1.49171 | 109.681 | −122.4 | 110.049 | 1.09418 |
| 41 | 1 | O5 | 1 | C1 | 2 | O3 | 2 | C3 | 1.48288 | 108.618 | −73.6356 | 114.298 | 1.49171 |
| 42 | 2 | C2 | 2 | C3 | 2 | O3 | 1 | C1 | 1.55001 | 109.681 | −137.983 | 114.298 | 1.46881 |
| 43 | 2 | O5 | 2 | C5 | 2 | C4 | 2 | C3 | 1.49245 | 109.688 | −59.8491 | 109.365 | 1.54311 |
| 44 | 2 | C3 | 2 | C5 | 2 | *C4 | 2 | O4 | 1.54311 | 109.365 | −119.185 | 107.852 | 1.44533 |
| 45 | 2 | C3 | 2 | C5 | 2 | *C4 | 2 | H4 | 1.54311 | 109.365 | 121.728 | 110.523 | 1.09445 |
| 46 | 2 | O3 | 2 | C3 | 2 | C4 | 2 | C5 | 1.49171 | 107.559 | 178.271 | 109.365 | 1.54809 |
| 47 | 2 | C5 | 2 | C4 | 2 | O4 | 2 | HO4 | 1.54809 | 107.852 | 149.107 | 110.099 | 0.973016 |
| 48 | 2 | O5 | 2 | C5 | 2 | C6 | 2 | O6 | 1.49245 | 108.072 | −45.3199 | 110.199 | 1.44257 |
| 49 | 2 | O6 | 2 | C5 | 2 | *C6 | 2 | H61 | 1.44257 | 110.199 | 120.363 | 110.809 | 1.09171 |
| 50 | 2 | O6 | 2 | C5 | 2 | *C6 | 2 | H62 | 1.44257 | 110.199 | −120.01 | 109.994 | 1.09258 |
| 51 | 2 | C5 | 2 | C6 | 2 | O6 | 2 | HO6 | 1.5412 | 110.199 | −43.6484 | 108.315 | 0.964071 |
| 52 | 4 | O3 | 3 | C1 | 3 | O5 | 3 | C5 | 1.46982 | 108.767 | −178.507 | 112.064 | 1.50737 |
| 53 | 4 | O3 | 3 | O5 | 3 | *C1 | 3 | C2 | 1.46982 | 108.767 | 118.502 | 108.754 | 1.55354 |
| 54 | 4 | O3 | 3 | O5 | 3 | *C1 | 3 | H1 | 1.46982 | 108.767 | −120.379 | 110.247 | 1.10609 |
| 55 | 3 | C4 | 3 | C5 | 3 | O5 | 3 | C1 | 1.54121 | 108.664 | 60.0468 | 112.064 | 1.48614 |
| 56 | 3 | C4 | 3 | O5 | 3 | *C5 | 3 | C6 | 1.54121 | 108.664 | 123.074 | 114.739 | 1.58106 |
| 57 | 3 | C4 | 3 | O5 | 3 | *C5 | 3 | H5 | 1.54121 | 108.664 | −117.561 | 107.937 | 1.09441 |
| 58 | 3 | O5 | 3 | C1 | 3 | C2 | 3 | O2 | 1.48614 | 108.754 | 179.466 | 107.549 | 1.45667 |
| 59 | 3 | O2 | 3 | C1 | 3 | *C2 | 3 | C3 | 1.45667 | 107.549 | −119.597 | 110.004 | 1.55147 |
| 60 | 3 | O2 | 3 | C1 | 3 | *C2 | 3 | H2 | 1.45667 | 107.549 | 118.502 | 110.019 | 1.09357 |
| 61 | 3 | C1 | 3 | C2 | 3 | O2 | 3 | HO2 | 1.55354 | 107.549 | 56.6882 | 108.382 | 0.970503 |
| 62 | 3 | C1 | 3 | C2 | 3 | C3 | 3 | O3 | 1.55354 | 110.004 | −176.337 | 112.279 | 1.46307 |
| 63 | 3 | O3 | 3 | C2 | 3 | *C3 | 3 | C4 | 1.46307 | 112.279 | 116.579 | 107.127 | 1.54077 |

| | | | | | | | | | | | |
|---|---|---|---|---|---|---|---|---|---|---|---|
| 64 | 3 | O3 | 3 | C2 | 3 | *C3 | 3 | H3 | 1.46307 | 112.279 | −122.498 | 111.005 | 1.09335 |
| 65 | 3 | C2 | 3 | C3 | 3 | O3 | 3 | HO3 | 1.55147 | 112.279 | 162.001 | 106.442 | 0.965674 |
| 66 | 3 | O5 | 3 | C5 | 3 | C4 | 3 | O4 | 1.50737 | 108.664 | −178.871 | 109.211 | 1.48898 |
| 67 | 3 | O4 | 3 | C5 | 3 | *C4 | 3 | C3 | 1.48898 | 109.211 | 118.986 | 110.38 | 1.54077 |
| 68 | 3 | O4 | 3 | C5 | 3 | *C4 | 3 | H4 | 1.48898 | 109.211 | −121.536 | 108.861 | 1.09482 |
| 69 | 3 | C2 | 3 | C3 | 3 | C4 | 3 | O4 | 1.55147 | 107.127 | 179.621 | 108.323 | 1.48898 |
| 70 | 2 | O5 | 2 | C1 | 3 | O4 | 3 | C4 | 1.48398 | 108.411 | −74.4818 | 112.113 | 1.48898 |
| 71 | 3 | C5 | 3 | C4 | 3 | O4 | 2 | C1 | 1.54121 | 109.211 | −133.198 | 112.113 | 1.47292 |
| 72 | 3 | O5 | 3 | C5 | 3 | C6 | 3 | O6A | 1.50737 | 114.739 | 117.52 | 120.024 | 1.50005 |
| 73 | 3 | O6A | 3 | C5 | 3 | *C6 | 3 | O6B | 1.50005 | 120.024 | −179.926 | 119.979 | 1.50064 |
| 74 | 5 | O4 | 4 | C1 | 4 | O5 | 4 | C5 | 1.47195 | 108.074 | 178.115 | 111.57 | 1.49277 |
| 75 | 5 | O4 | 4 | O5 | 4 | *C1 | 4 | C2 | 1.47195 | 108.074 | 121.821 | 109.587 | 1.55665 |
| 76 | 5 | O4 | 4 | O5 | 4 | *C1 | 4 | H1 | 1.47195 | 108.074 | −119.431 | 109.144 | 1.10665 |
| 77 | 4 | C4 | 4 | C5 | 4 | O5 | 4 | C1 | 1.54886 | 109.455 | 59.9473 | 111.57 | 1.48363 |
| 78 | 4 | C4 | 4 | O5 | 4 | *C5 | 4 | C6 | 1.54886 | 109.455 | 122.618 | 108.897 | 1.54335 |
| 79 | 4 | C4 | 4 | O5 | 4 | *C5 | 4 | H5 | 1.54886 | 109.455 | −119.319 | 108.777 | 1.09454 |
| 80 | 4 | O5 | 4 | C1 | 4 | C2 | 4 | N2 | 1.48363 | 109.587 | −177.533 | 109.328 | 1.47431 |
| 81 | 4 | N2 | 4 | C1 | 4 | *C2 | 4 | C3 | 1.47431 | 109.328 | −122.516 | 109.172 | 1.55203 |
| 82 | 4 | N2 | 4 | C1 | 4 | *C2 | 4 | H2 | 1.47431 | 109.328 | 117.728 | 109.007 | 1.09342 |
| 83 | 4 | C1 | 4 | C2 | 4 | N2 | 4 | C2N | 1.55665 | 109.328 | 109.611 | 124.862 | 1.35515 |
| 84 | 4 | C2N | 4 | C2 | 4 | *N2 | 4 | H2N | 1.35515 | 124.862 | −179.66 | 115.75 | 1.01745 |
| 85 | 4 | C2 | 4 | N2 | 4 | C2N | 4 | CME | 1.47431 | 124.862 | −178.74 | 116.522 | 1.54164 |
| 86 | 4 | CME | 4 | N2 | 4 | *C2N | 4 | O2N | 1.54164 | 116.522 | 179.951 | 121.842 | 1.22103 |
| 87 | 4 | N2 | 4 | C2N | 4 | CME | 4 | H1M | 1.35515 | 116.522 | 81.7555 | 109.747 | 1.09645 |
| 88 | 4 | H1M | 4 | C2N | 4 | *CME | 4 | H2M | 1.09645 | 109.747 | 119.901 | 110.832 | 1.09583 |
| 89 | 4 | H1M | 4 | C2N | 4 | *CME | 4 | H3M | 1.09645 | 109.747 | −119.49 | 109.415 | 1.09426 |
| 90 | 4 | C1 | 4 | C2 | 4 | C3 | 4 | O3 | 1.55665 | 109.172 | −176.309 | 109.851 | 1.49102 |
| 91 | 4 | O3 | 4 | C2 | 4 | *C3 | 4 | C4 | 1.49102 | 109.851 | 116.469 | 107.485 | 1.54413 |
| 92 | 4 | O3 | 4 | C2 | 4 | *C3 | 4 | H3 | 1.49102 | 109.851 | −122.334 | 110.239 | 1.09547 |
| 93 | 3 | O5 | 3 | C1 | 4 | O3 | 4 | C3 | 1.48614 | 108.767 | −81.1834 | 115.545 | 1.49102 |
| 94 | 4 | C2 | 4 | C3 | 4 | O3 | 3 | C1 | 1.55203 | 109.851 | −114.743 | 115.545 | 1.46982 |
| 95 | 4 | O5 | 4 | C5 | 4 | C4 | 4 | C3 | 1.49277 | 109.455 | −59.9379 | 109.628 | 1.54413 |
| 96 | 4 | C3 | 4 | C5 | 4 | *C4 | 4 | O4 | 1.54413 | 109.628 | −119.443 | 108.375 | 1.44708 |
| 97 | 4 | C3 | 4 | C5 | 4 | *C4 | 4 | H4 | 1.54413 | 109.628 | 121.491 | 110.317 | 1.09352 |
| 98 | 4 | O3 | 4 | C3 | 4 | C4 | 4 | C5 | 1.49102 | 107.328 | 178.203 | 109.628 | 1.54886 |
| 99 | 4 | C5 | 4 | C4 | 4 | O4 | 4 | HO4 | 1.54886 | 108.375 | 150.177 | 108.989 | 0.973374 |
| 100 | 4 | O5 | 4 | C5 | 4 | C6 | 4 | O6 | 1.49277 | 108.897 | −63.3575 | 110.974 | 1.44254 |
| 101 | 4 | O6 | 4 | C5 | 4 | *C6 | 4 | H61 | 1.44254 | 110.974 | 119.813 | 110.452 | 1.09271 |
| 102 | 4 | O6 | 4 | C5 | 4 | *C6 | 4 | H62 | 1.44254 | 110.974 | −120.841 | 110.223 | 1.09154 |
| 103 | 4 | C5 | 4 | C6 | 4 | O6 | 4 | HO6 | 1.54335 | 110.974 | 178.675 | 109.162 | 0.95901 |
| 104 | 6 | O3 | 5 | C1 | 5 | O5 | 5 | C5 | 1.47122 | 108.272 | −178.739 | 111.897 | 1.50942 |
| 105 | 6 | O3 | 5 | O5 | 5 | *C1 | 5 | C2 | 1.47122 | 108.272 | 118.759 | 109.016 | 1.5477 |
| 106 | 6 | O3 | 5 | O5 | 5 | *C1 | 5 | H1 | 1.47122 | 108.272 | −120.742 | 109.655 | 1.10664 |
| 107 | 5 | C4 | 5 | C5 | 5 | O5 | 5 | C1 | 1.54332 | 108.65 | 59.9488 | 111.897 | 1.48329 |
| 108 | 5 | C4 | 5 | O5 | 5 | *C5 | 5 | C6 | 1.54332 | 108.65 | 122.757 | 114.695 | 1.57881 |
| 109 | 5 | C4 | 5 | O5 | 5 | *C5 | 5 | H5 | 1.54332 | 108.65 | −117.633 | 107.927 | 1.09429 |
| 110 | 5 | O5 | 5 | C1 | 5 | C2 | 5 | O2 | 1.48329 | 109.016 | 178.406 | 109.448 | 1.46005 |
| 111 | 5 | O2 | 5 | C1 | 5 | *C2 | 5 | C3 | 1.46005 | 109.448 | −118.516 | 110.031 | 1.54664 |
| 112 | 5 | O2 | 5 | C1 | 5 | *C2 | 5 | H2 | 1.46005 | 109.448 | 119.638 | 110.152 | 1.09373 |
| 113 | 5 | C1 | 5 | C2 | 5 | O2 | 5 | HO2 | 1.5477 | 109.448 | −166.271 | 105.013 | 0.965405 |
| 114 | 5 | C1 | 5 | C2 | 5 | C3 | 5 | O3 | 1.5477 | 110.031 | −178.488 | 109.772 | 1.46092 |
| 115 | 5 | O3 | 5 | C2 | 5 | *C3 | 5 | C4 | 1.46092 | 109.772 | 118.736 | 107.337 | 1.53972 |
| 116 | 5 | O3 | 5 | C2 | 5 | *C3 | 5 | H3 | 1.46092 | 109.772 | −120.641 | 110.88 | 1.09477 |
| 117 | 5 | C2 | 5 | C3 | 5 | O3 | 5 | HO3 | 1.54664 | 109.772 | 152.259 | 108.491 | 0.969702 |
| 118 | 5 | O5 | 5 | C5 | 5 | C4 | 5 | O4 | 1.50942 | 108.65 | −177.676 | 108.695 | 1.48337 |
| 119 | 5 | O4 | 5 | C5 | 5 | *C4 | 5 | C3 | 1.48337 | 108.695 | 117.91 | 110.175 | 1.53972 |
| 120 | 5 | O4 | 5 | C5 | 5 | *C4 | 5 | H4 | 1.48337 | 108.695 | −121.851 | 109.377 | 1.09524 |
| 121 | 5 | C2 | 5 | C3 | 5 | C4 | 5 | O4 | 1.54664 | 107.337 | 178.496 | 107.796 | 1.48337 |
| 122 | 4 | O5 | 4 | C1 | 5 | O4 | 5 | C4 | 1.48363 | 108.074 | −78.1341 | 112.66 | 1.48337 |
| 123 | 5 | C5 | 5 | C4 | 5 | O4 | 4 | C1 | 1.54332 | 108.695 | −142.547 | 112.66 | 1.47195 |
| 124 | 5 | O5 | 5 | C5 | 5 | C6 | 5 | O6A | 1.50942 | 114.695 | 119.91 | 120.055 | 1.49893 |
| 125 | 5 | O6A | 5 | C5 | 5 | *C6 | 5 | O6B | 1.49893 | 120.055 | −179.956 | 119.992 | 1.50075 |
| 126 | 6 | O5 | 6 | C1 | 6 | O1 | 6 | HO1 | 1.47955 | 108.604 | 31.8202 | 103.324 | 0.960277 |
| 127 | 6 | O5 | 6 | O1 | 6 | *C1 | 6 | C2 | 1.47955 | 108.604 | 122.28 | 114.429 | 1.55873 |
| 128 | 6 | O5 | 6 | O1 | 6 | *C1 | 6 | H1 | 1.47955 | 108.604 | −116.193 | 107.8 | 1.10438 |
| 129 | 6 | O1 | 6 | C1 | 6 | O5 | 6 | C5 | 1.4245 | 108.604 | 65.4749 | 111.683 | 1.50896 |
| 130 | 6 | C4 | 6 | C5 | 6 | O5 | 6 | C1 | 1.5517 | 109.05 | 60.0827 | 111.683 | 1.47955 |
| 131 | 6 | C4 | 6 | O5 | 6 | *C5 | 6 | C6 | 1.5517 | 109.05 | 122.744 | 109.548 | 1.5431 |
| 132 | 6 | C4 | 6 | O5 | 6 | *C5 | 6 | H5 | 1.5517 | 109.05 | −119.188 | 109.361 | 1.09353 |
| 133 | 6 | O5 | 6 | C1 | 6 | C2 | 6 | N2 | 1.47955 | 109.202 | −176.931 | 114.086 | 1.48094 |
| 134 | 6 | N2 | 6 | C1 | 6 | *C2 | 6 | C3 | 1.48094 | 114.086 | −123.144 | 109.697 | 1.54486 |
| 135 | 6 | N2 | 6 | C1 | 6 | *C2 | 6 | H2 | 1.48094 | 114.086 | 117.734 | 108.58 | 1.09303 |
| 136 | 6 | C1 | 6 | C2 | 6 | N2 | 6 | C2N | 1.55873 | 114.086 | 129.507 | 124.876 | 1.35985 |
| 137 | 6 | C2N | 6 | C2 | 6 | *N2 | 6 | H2N | 1.35985 | 124.876 | 179.625 | 114.992 | 1.01134 |
| 138 | 6 | C2 | 6 | N2 | 6 | C2N | 6 | CME | 1.48094 | 124.876 | 179.809 | 115.746 | 1.54095 |
| 139 | 6 | CME | 6 | N2 | 6 | *C2N | 6 | O2N | 1.54095 | 115.746 | 179.986 | 122.302 | 1.21921 |
| 140 | 6 | N2 | 6 | C2N | 6 | CME | 6 | H1M | 1.35985 | 115.746 | −24.4507 | 109.856 | 1.09603 |
| 141 | 6 | H1M | 6 | C2N | 6 | *CME | 6 | H2M | 1.09603 | 109.856 | 120.123 | 109.77 | 1.09615 |
| 142 | 6 | H1M | 6 | C2N | 6 | *CME | 6 | H3M | 1.09603 | 109.856 | −119.969 | 110.247 | 1.09608 |

-continued

| | | | | | | | | | | |
|---|---|---|---|---|---|---|---|---|---|---|
| 143 | 6 | C1 | 6 | C2 | 6 | C3 | 6 | O3 | 1.55873 | 109.697 | −178.228 | 108.646 | 1.48298 |
| 144 | 6 | O3 | 6 | C2 | 6 | *C3 | 6 | C4 | 1.48298 | 108.646 | 118.275 | 107.686 | 1.54085 |
| 145 | 6 | O3 | 6 | C2 | 6 | *C3 | 6 | H3 | 1.48298 | 108.646 | −121.232 | 109.621 | 1.09364 |
| 146 | 5 | O5 | 5 | C1 | 6 | O3 | 6 | C3 | 1.48329 | 108.272 | −97.8928 | 114.107 | 1.48298 |
| 147 | 6 | C2 | 6 | C3 | 6 | O3 | 5 | C1 | 1.54486 | 108.646 | −108.314 | 114.107 | 1.47122 |
| 148 | 6 | O5 | 6 | C5 | 6 | C4 | 6 | C3 | 1.50896 | 109.05 | −59.759 | 109.601 | 1.54085 |
| 149 | 6 | C3 | 6 | C5 | 6 | *C4 | 6 | O4 | 1.54085 | 109.601 | −119.186 | 109.328 | 1.44881 |
| 150 | 6 | C3 | 6 | C5 | 6 | *C4 | 6 | H4 | 1.54085 | 109.601 | 121.346 | 110.231 | 1.09265 |
| 151 | 6 | O3 | 6 | C3 | 6 | C4 | 6 | C5 | 1.48298 | 109.299 | 177.998 | 109.601 | 1.5517 |
| 152 | 6 | C5 | 6 | C4 | 6 | O4 | 6 | HO4 | 1.5517 | 109.328 | 164.466 | 109.177 | 0.970545 |
| 153 | 6 | O5 | 6 | C5 | 6 | C6 | 6 | O6 | 1.50896 | 109.548 | −66.9804 | 110.81 | 1.44396 |
| 154 | 6 | O6 | 6 | C5 | 6 | *C6 | 6 | H61 | 1.44396 | 110.81 | 119.674 | 110.626 | 1.09192 |
| 155 | 6 | O6 | 6 | C5 | 6 | *C6 | 6 | H62 | 1.44396 | 110.81 | −120.96 | 110.209 | 1.09249 |
| 156 | 6 | C5 | 6 | C6 | 6 | O6 | 6 | HO6 | 1.5431 | 110.81 | −178.992 | 108.93 | 0.960091 |

[$^1$H-$^1$H]-NOESY Dataset for a Hyaluronan Hexasaccharide remark 2D-NOESY data for alpha-HA6 configuration:

field 900
solvent h2o
temp 298
visc 0.88
ident 2D-NOESY
mix_time 400 ms
endsection data:

| remark | NOE no. | ring | | ring | donor | ring | | ring | acc | int | error | code |
|---|---|---|---|---|---|---|---|---|---|---|---|---|
| asgn | 1 | a | | 6 | H1M | a | | 6 | H2N | 4.75 | 1.90 | 0 |
| ovlp | 1 | a | | 6 | H2M | a | | 6 | H2N | 4.75 | 1.90 | 0 |
| ovlp | 1 | a | | 6 | H3M | a | | 6 | H2N | 4.75 | 1.90 | 0 |
| asgn | 2 | a | | 6 | H1 | a | | 6 | H2N | 1.37 | 0.55 | 0 |
| asgn | 3 | a | | 6 | H2N | a | | 6 | H2N | 110.02 | 44.01 | 0 |
| asgn | 4 | a | | 6 | H3 | a | | 6 | H2N | 2.10 | 0.84 | 0 |
| asgn | 5 | a | | 6 | H4 | a | | 6 | H2N | 0.09 | 0.05 | 0 |
| asgn | 6 | a' | | 5 | H1 | a | | 6 | H2N | 2.57 | 1.03 | 0 |
| asgn | 7 | a' | | 5 | H2 | a | | 6 | H2N | 0.09 | 0.05 | 0 |
| asgn | 8 | a' | | 5 | H3 | a | | 6 | H2N | 0.14 | 0.07 | 0 |
| asgn | 9 | a' | | 5 | H5 | a | | 6 | H2N | 0.31 | 0.13 | 0 |
| asgn | 10 | a | | 6 | H1 | a | | 6 | H1 | 421.59 | 168.63 | 0 |
| asgn | 11 | a | | 6 | H3 | a | | 6 | H1 | 1.41 | 0.56 | 0 |
| asgn | 12 | a | | 6 | H4 | a | | 6 | H1 | 0.69 | 0.28 | 0 |
| asgn | 13 | a | | 6 | H5 | a | | 6 | H1 | 0.72 | 0.29 | 0 |
| asgn | 14 | a | | 6 | H1 | a | | 6 | H2 | 12.46 | 5.02 | 0 |
| asgn | 15 | a | | 6 | H2 | a | | 6 | H2 | 303.23 | 122.37 | 0 |
| asgn | 16 | a | | 6 | H4 | a | | 6 | H2 | 3.19 | 1.30 | 0 |
| asgn | 17 | a' | | 5 | H1 | a | | 6 | H2 | 1.56 | 0.64 | 0 |
| asgn | 301 | a | | 6 | H1M | a | | 6 | H1M | 1284.96 | 513.98 | 6 |
| ovlp | 301 | a | | 6 | H2M | a | | 6 | H1M | 1284.96 | 513.98 | 6 |
| ovlp | 301 | a | | 6 | H3M | a | | 6 | H1M | 1284.96 | 513.98 | 6 |
| ovlp | 301 | a | | 6 | H1M | a | | 6 | H2M | 1284.96 | 513.98 | 6 |
| ovlp | 301 | a | | 6 | H2M | a | | 6 | H2M | 1284.96 | 513.98 | 6 |
| ovlp | 301 | a | | 6 | H3M | a | | 6 | H2M | 1284.96 | 513.98 | 6 |
| ovlp | 301 | a | | 6 | H1M | a | | 6 | H3M | 1284.96 | 513.98 | 6 |
| ovlp | 301 | a | | 6 | H2M | a | | 6 | H3M | 1284.96 | 513.98 | 6 |
| ovlp | 301 | a | | 6 | H3M | a | | 6 | H3M | 1284.96 | 513.98 | 6 |
| asgn | 18 | a' | | 5 | H1 | a' | | 5 | H1 | 283.02 | 113.22 | 0 |
| asgn | 19 | a' | | 5 | H3 | a' | | 5 | H1 | 6.48 | 2.59 | 0 |
| asgn | 20 | a' | | 5 | H4 | a' | | 5 | H1 | 2.00 | 0.80 | 0 |
| asgn | 21 | a' | | 5 | H5 | a' | | 5 | H1 | 21.03 | 8.41 | 0 |
| asgn | 22 | a | | 6 | H2 | a' | | 5 | H1 | 0.85 | 0.34 | 0 |
| asgn | 23 | a | | 6 | H3 | a' | | 5 | H1 | 10.22 | 4.09 | 0 |
| asgn | 24 | a | | 6 | H1M | a' | | 5 | H1 | 0.66 | 0.27 | 0 |
| ovlp | 24 | a | | 6 | H2M | a' | | 5 | H1 | 0.66 | 0.27 | 0 |
| ovlp | 24 | a | | 6 | H3M | a' | | 5 | H1 | 0.66 | 0.27 | 0 |
| asgn | 25 | a' | | 5 | H2 | a' | | 5 | H2 | 272.87 | 109.21 | 0 |
| asgn | 26 | a' | | 5 | H4 | a' | | 5 | H2 | 10.10 | 4.04 | 0 |
| asgn | 27 | a | | 6 | H3 | a' | | 5 | H2 | 1.32 | 0.53 | 0 |
| asgn | 28 | g | | 4 | H1 | a' | | 5 | H2 | 1.20 | 0.48 | 0 |
| asgn | 29 | f' | | 3 | H1 | f' | | 3 | H1 | 311.90 | 124.76 | 0 |

| | | | | | | | | | |
|---|---|---|---|---|---|---|---|---|---|
| remark 2D-NOESY data for alpha-HA6 | | | | | | | | | |
| asgn | 30 | f' | 3 | H3 | f' | 3 | H1 | 9.81 | 3.92 | 0 |
| asgn | 31 | g | 4 | H1M | f' | 3 | H1 | 1.09 | 0.44 | 0 |
| ovlp | 31 | g | 4 | H2M | f' | 3 | H1 | 1.09 | 0.44 | 0 |
| ovlp | 31 | g | 4 | H3M | f' | 3 | H1 | 1.09 | 0.44 | 0 |
| asgn | 32 | g | 4 | H2 | f' | 3 | H1 | 0.91 | 0.37 | 0 |
| asgn | 33 | g | 4 | H3 | f' | 3 | H1 | 25.86 | 10.34 | 0 |
| ovlp | 33 | f' | 3 | H5 | f' | 3 | H1 | 25.86 | 10.34 | 0 |
| asgn | 34 | f' | 3 | H1 | g | 4 | H4 | 0.80 | 0.32 | 0 |
| asgn | 35 | f' | 3 | H2 | f' | 3 | H2 | 268.44 | 107.59 | 0 |
| asgn | 36 | f' | 3 | H4 | f' | 3 | H2 | 8.79 | 3.52 | 0 |
| asgn | 37 | w | 2 | H1 | f' | 3 | H2 | 0.91 | 0.37 | 0 |
| asgn | 38 | g | 4 | H1M | g | 4 | H2N | 9.42 | 3.77 | 0 |
| ovlp | 38 | g | 4 | H2M | g | 4 | H2N | 9.42 | 3.77 | 0 |
| ovlp | 38 | g | 4 | H3M | g | 4 | H2N | 9.42 | 3.77 | 0 |
| asgn | 39 | g | 4 | H1 | g | 4 | H2N | 3.70 | 1.48 | 0 |
| asgn | 40 | g | 4 | H2N | g | 4 | H2N | 185.95 | 74.38 | 0 |
| asgn | 41 | g | 4 | H3 | g | 4 | H2N | 5.84 | 2.34 | 0 |
| ovlp | 41 | a' | 5 | H5 | g | 4 | H2N | 5.84 | 2.34 | 0 |
| ovlp | 41 | f' | 3 | H5 | g | 4 | H2N | 5.84 | 2.34 | 0 |
| asgn | 42 | g | 4 | H4 | g | 4 | H2N | 0.22 | 0.09 | 0 |
| asgn | 43 | g | 4 | H5 | g | 4 | H2N | 0.40 | 0.16 | 0 |
| asgn | 44 | f' | 3 | H1 | g | 4 | H2N | 4.86 | 1.94 | 0 |
| asgn | 45 | f' | 3 | H2 | g | 4 | H2H | 0.19 | 0.08 | 0 |
| asgn | 46 | f' | 3 | H3 | g | 4 | H2N | 0.33 | 0.13 | 0 |
| asgn | 47 | g | 4 | H1 | g | 4 | H1 | 218.09 | 87.24 | 0 |
| asgn | 48 | g | 4 | H2N | g | 4 | H1 | 4.71 | 1.88 | 0 |
| asgn | 49 | g | 4 | H3 | g | 4 | H1 | 12.75 | 5.10 | 0 |
| ovlp | 49 | a' | 5 | H5 | g | 4 | H1 | 12.75 | 5.10 | 0 |
| asgn | 50 | g | 4 | H5 | g | 4 | H1 | 9.57 | 3.83 | 0 |
| asgn | 51 | a' | 5 | H4 | g | 4 | H1 | 17.14 | 6.85 | 0 |
| asgn | 52 | a' | 5 | H2 | g | 4 | H1 | 0.71 | 0.28 | 0 |
| asgn | 53 | g | 4 | H1M | g | 4 | H1 | 0.37 | 0.15 | 0 |
| ovlp | 53 | g | 4 | H2M | g | 4 | H1 | 0.37 | 0.15 | 0 |
| ovlp | 53 | g | 4 | H3M | g | 4 | H1 | 0.37 | 0.15 | 0 |
| asgn | 54 | g | 4 | H1 | a' | 5 | H3 | 0.71 | 0.28 | 0 |
| asgn | 55 | g | 4 | H1M | f' | 3 | H3 | 0.91 | 0.37 | 0 |
| ovlp | 55 | g | 4 | H2M | f' | 3 | H3 | 0.91 | 0.37 | 0 |
| ovlp | 55 | g | 4 | H3M | f' | 3 | H3 | 0.91 | 0.37 | 0 |
| asgn | 56 | g | 4 | H1M | g | 4 | H2 | 1.03 | 0.41 | 0 |
| ovlp | 56 | g | 4 | H2M | g | 4 | H2 | 1.03 | 0.41 | 0 |
| ovlp | 56 | g | 4 | H3M | g | 4 | H2 | 1.03 | 0.41 | 0 |
| asgn | 302 | g | 4 | H1M | g | 4 | H1M | 1206.25 | 482.50 | 6 |
| ovlp | 302 | g | 4 | H2M | g | 4 | H1M | 1206.25 | 482.50 | 6 |
| ovlp | 302 | g | 4 | H3M | g | 4 | H1M | 1206.25 | 482.50 | 6 |
| ovlp | 302 | g | 4 | H1M | g | 4 | H2M | 1206.25 | 482.50 | 6 |
| ovlp | 302 | g | 4 | H2M | g | 4 | H2M | 1206.25 | 482.50 | 6 |
| ovlp | 302 | g | 4 | H3M | g | 4 | H2M | 1206.25 | 482.50 | 6 |
| ovlp | 302 | g | 4 | H1M | g | 4 | H3M | 1206.25 | 482.50 | 6 |
| ovlp | 302 | g | 4 | H2M | g | 4 | H3M | 1206.25 | 482.50 | 6 |
| ovlp | 302 | g | 4 | H3M | g | 4 | H3M | 1206.25 | 482.50 | 6 |
| asgn | 57 | w | 2 | H1M | w | 2 | H2N | 8.91 | 3.56 | 0 |
| ovlp | 57 | w | 2 | H2M | w | 2 | H2N | 8.91 | 3.56 | 0 |
| ovlp | 57 | w | 2 | H3M | w | 2 | H2N | 8.91 | 3.56 | 0 |
| asgn | 58 | w | 2 | H1 | w | 2 | H2N | 3.73 | 1.49 | 0 |
| asgn | 59 | w | 2 | H2N | w | 2 | H2N | 249.70 | 99.88 | 0 |
| asgn | 60 | w | 2 | H3 | w | 2 | H2N | 6.44 | 2.58 | 0 |
| ovlp | 60 | w' | 1 | H5 | w | 2 | H2N | 6.44 | 2.58 | 0 |
| ovlp | 60 | f' | 3 | H5 | w | 2 | H2N | 6.44 | 2.58 | 0 |
| asgn | 61 | w | 2 | H4 | w | 2 | H2N | 0.21 | 0.09 | 0 |
| asgn | 62 | w | 2 | H5 | w | 2 | H2N | 0.45 | 0.18 | 0 |
| asgn | 63 | w' | 1 | H1 | w | 2 | H2N | 5.94 | 2.38 | 0 |
| asgn | 64 | w' | 1 | H2 | w | 2 | H2N | 0.20 | 0.08 | 0 |
| asgn | 65 | w' | 1 | H3 | w | 2 | H2N | 0.34 | 0.14 | 0 |
| asgn | 66 | w | 2 | H1 | w | 2 | H1 | 259.20 | 103.68 | 0 |
| asgn | 67 | w | 2 | H3 | w | 2 | H1 | 13.51 | 5.40 | 0 |
| ovlp | 67 | f' | 3 | H5 | w | 2 | H1 | 13.51 | 5.40 | 0 |
| asgn | 68 | w | 2 | H5 | w | 2 | H1 | 11.58 | 4.63 | 0 |
| asgn | 69 | f' | 3 | H4 | w | 2 | H1 | 15.61 | 6.24 | 0 |
| asgn | 70 | f' | 3 | H2 | w | 2 | H1 | 0.51 | 0.20 | 0 |
| asgn | 71 | w | 2 | H1M | w | 2 | H1 | 0.27 | 0.11 | 0 |
| ovlp | 71 | w | 2 | H2M | w | 2 | H1 | 0.27 | 0.11 | 0 |
| ovlp | 71 | w | 2 | H3M | w | 2 | H1 | 0.27 | 0.11 | 0 |
| asgn | 72 | w | 2 | H1M | w | 2 | H2 | 1.04 | 0.42 | 0 |
| ovlp | 72 | w | 2 | H2M | w | 2 | H2 | 1.04 | 0.42 | 0 |
| ovlp | 72 | w | 2 | H3M | w | 2 | H2 | 1.04 | 0.42 | 0 |
| asgn | 303 | w | 2 | H1M | w | 2 | H1M | 1476.08 | 590.43 | 6 |
| ovlp | 303 | w | 2 | H2M | w | 2 | H1M | 1476.08 | 590.43 | 6 |

| | | | | | | | | | | |
|---|---|---|---|---|---|---|---|---|---|---|
| remark 2D-NOESY data for alpha-HA6 | | | | | | | | | | |
| ovlp | 303 | w | 2 | H3M | w | 2 | H1M | 1476.08 | 590.43 | 6 |
| ovlp | 303 | w | 2 | H1M | w | 2 | H2M | 1476.08 | 590.43 | 6 |
| ovlp | 303 | w | 2 | H2M | w | 2 | H2M | 1476.08 | 590.43 | 6 |
| ovlp | 303 | w | 2 | H3M | w | 2 | H2M | 1476.08 | 590.43 | 6 |
| ovlp | 303 | w | 2 | H1M | w | 2 | H3M | 1476.08 | 590.43 | 6 |
| ovlp | 303 | w | 2 | H2M | w | 2 | H3M | 1476.08 | 590.43 | 6 |
| ovlp | 303 | w | 2 | H3M | w | 2 | H3M | 1476.08 | 590.43 | 6 |
| asgn | 73 | w | 2 | H1M | w' | 1 | H3 | 0.57 | 0.23 | 0 |
| ovlp | 73 | w | 2 | H2M | w' | 1 | H3 | 0.57 | 0.23 | 0 |
| ovlp | 73 | w | 2 | H3M | w' | 1 | H3 | 0.57 | 0.23 | 0 |
| asgn | 74 | w' | 1 | H1 | w' | 1 | H1 | 311.90 | 124.76 | 0 |
| asgn | 75 | w' | 1 | H3 | w' | 1 | H1 | 8.22 | 3.29 | 0 |
| asgn | 76 | w | 2 | H1M | w' | 1 | H1 | 1.09 | 0.44 | 0 |
| ovlp | 76 | w | 2 | H2M | w' | 1 | H1 | 1.09 | 0.44 | 0 |
| ovlp | 76 | w | 2 | H3M | w' | 1 | H1 | 1.09 | 0.44 | 0 |
| asgn | 77 | w | 2 | H2 | w' | 1 | H1 | 0.91 | 0.37 | 0 |
| asgn | 78 | w | 2 | H3 | w' | 1 | H1 | 25.86 | 10.34 | 0 |
| ovlp | 78 | w' | 1 | H5 | w' | 1 | H1 | 25.86 | 10.34 | 0 |
| asgn | 79 | w' | 1 | H1 | w | 2 | H4 | 0.32 | 0.13 | 0 |
| asgn | 80 | w | 2 | H1 | f' | 3 | H3 | 0.71 | 0.28 | 0 |
| asgn | 81 | w' | 1 | H2 | w' | 1 | H2 | 265.54 | 106.31 | 0 |
| asgn | 82 | w' | 1 | H5 | w' | 1 | H2 | 1.33 | 0.56 | 0 |
| asgn | 83 | a' | 5 | H3 | g | 4 | H1 | 0.35 | 0.14 | 0 |
| asgn | 84 | a | 6 | H1M | a | 6 | H1 | 0.40 | 0.16 | 0 |
| ovlp | 84 | a | 6 | H2M | a | 6 | H1 | 0.40 | 0.16 | 0 |
| ovlp | 84 | a | 6 | H3M | a | 6 | H1 | 0.40 | 0.16 | 0 |
| asgn | 85 | a | 6 | H1M | a | 6 | H2 | 0.40 | 0.17 | 0 |
| ovlp | 85 | a | 6 | H2M | a | 6 | H2 | 0.40 | 0.17 | 0 |
| ovlp | 85 | a | 6 | H3M | a | 6 | H2 | 0.40 | 0.17 | 0 |
| remark | noNOEs | | | | | | | | | |
| asgn | 101 | a' | 5 | H2 | a | 6 | H1 | 0.00 | 0.14 | 0 |
| asgn | 102 | a' | 5 | H3 | a | 6 | H1 | 0.00 | 0.03 | 0 |
| asgn | 103 | a' | 5 | H4 | a | 6 | H1 | 0.00 | 0.23 | 0 |
| asgn | 104 | a | 6 | H61 | a | 6 | H1 | 0.00 | 0.35 | 0 |
| asgn | 105 | a' | 5 | H1 | a | 6 | H1 | 0.00 | 0.05 | 0 |
| asgn | 106 | a | 6 | H61 | a | 6 | H2 | 0.00 | 0.12 | 0 |
| asgn | 107 | a | 6 | H62 | a | 6 | H2 | 0.00 | 0.11 | 0 |
| asgn | 108 | a | 6 | H5 | a | 6 | H2 | 0.00 | 0.38 | 0 |
| asgn | 109 | a' | 5 | H5 | a | 6 | H2 | 0.00 | 0.08 | 0 |
| asgn | 110 | a' | 5 | H3 | a | 6 | H2 | 0.00 | 0.14 | 0 |
| asgn | 111 | a' | 5 | H2 | a | 6 | H2 | 0.00 | 0.06 | 0 |
| asgn | 112 | a | 6 | H61 | a | 6 | H2N | 0.00 | 0.02 | 0 |
| asgn | 113 | a | 6 | H62 | a | 6 | H2N | 0.00 | 0.02 | 0 |
| asgn | 114 | a | 6 | H5 | a | 6 | H2N | 0.00 | 0.15 | 0 |
| asgn | 115 | a' | 5 | H4 | a | 6 | H2N | 0.00 | 0.02 | 0 |
| asgn | 116 | g | 4 | H1M | a' | 5 | H1 | 0.00 | 0.12 | 0 |
| ovlp | 116 | g | 4 | H2M | a' | 5 | H1 | 0.00 | 0.12 | 0 |
| ovlp | 116 | g | 4 | H3M | a' | 5 | H1 | 0.00 | 0.12 | 0 |
| asgn | 117 | a | 6 | H4 | a' | 5 | H1 | 0.00 | 0.14 | 0 |
| asgn | 118 | a | 6 | H5 | a' | 5 | H1 | 0.00 | 0.23 | 0 |
| asgn | 119 | a | 6 | H61 | a' | 5 | H1 | 0.00 | 0.09 | 0 |
| asgn | 120 | a | 6 | H62 | a' | 5 | H1 | 0.00 | 0.09 | 0 |
| asgn | 121 | g | 4 | H2N | a' | 5 | H1 | 0.00 | 0.04 | 0 |
| asgn | 122 | g | 4 | H2 | a' | 5 | H1 | 0.00 | 0.14 | 0 |
| asgn | 123 | g | 4 | H4 | a' | 5 | H1 | 0.00 | 0.14 | 0 |
| asgn | 124 | g | 4 | H5 | a' | 5 | H1 | 0.00 | 0.13 | 0 |
| asgn | 125 | g | 4 | H61 | a' | 5 | H1 | 0.00 | 0.30 | 0 |
| asgn | 126 | g | 4 | H1M | a' | 5 | H2 | 0.00 | 0.10 | 0 |
| ovlp | 126 | g | 4 | H2M | a' | 5 | H2 | 0.00 | 0.10 | 0 |
| ovlp | 126 | g | 4 | H3M | a' | 5 | H2 | 0.00 | 0.10 | 0 |
| asgn | 127 | a | 6 | H61 | a' | 5 | H2 | 0.00 | 0.29 | 0 |
| asgn | 128 | a | 6 | H62 | a' | 5 | H2 | 0.00 | 0.22 | 0 |
| asgn | 129 | g | 4 | H62 | a' | 5 | H2 | 0.00 | 0.22 | 0 |
| asgn | 130 | a | 6 | H2 | a' | 5 | H2 | 0.00 | 0.12 | 0 |
| asgn | 131 | a | 6 | H4 | a' | 5 | H2 | 0.00 | 0.20 | 0 |
| asgn | 132 | a | 6 | H1M | a' | 5 | H2 | 0.00 | 0.10 | 0 |
| ovlp | 132 | a | 6 | H2M | a' | 5 | H2 | 0.00 | 0.10 | 0 |
| ovlp | 132 | a | 6 | H3M | a' | 5 | H2 | 0.00 | 0.10 | 0 |
| asgn | 133 | w | 2 | H1M | f' | 3 | H1 | 0.00 | 0.91 | 0 |
| ovlp | 133 | w | 2 | H2M | f' | 3 | H1 | 0.00 | 0.91 | 0 |
| ovlp | 133 | w | 2 | H3M | f' | 3 | H1 | 0.00 | 0.91 | 0 |
| asgn | 134 | g | 4 | H4 | f' | 3 | H1 | 0.00 | 0.27 | 0 |
| asgn | 135 | g | 4 | H5 | f' | 3 | H1 | 0.00 | 1.17 | 0 |
| asgn | 136 | g | 4 | H61 | f' | 3 | H1 | 0.00 | 0.16 | 0 |
| asgn | 137 | g | 4 | H62 | f' | 3 | H1 | 0.00 | 0.27 | 0 |
| asgn | 138 | w | 2 | H5 | f' | 3 | H1 | 0.00 | 1.17 | 0 |
| asgn | 139 | w | 2 | H61 | f' | 3 | H1 | 0.00 | 0.16 | 0 | remark 2D-NOESY data for alpha-HA6

| | | | | | | | | | |
|---|---|---|---|---|---|---|---|---|---|
| asgn | 140 | w | 2 | H62 | f' | 3 | H1 | 0.00 | 0.27 | 0 |
| asgn | 141 | w | 2 | H1M | f' | 3 | H1 | 0.00 | 0.91 | 0 |
| ovlp | 141 | w | 2 | H2M | f' | 3 | H1 | 0.00 | 0.91 | 0 |
| ovlp | 141 | w | 2 | H3M | f' | 3 | H1 | 0.00 | 0.91 | 0 |
| asgn | 142 | g | 4 | H1M | f' | 3 | H2 | 0.00 | 0.06 | 0 |
| ovlp | 142 | g | 4 | H2M | f' | 3 | H2 | 0.00 | 0.06 | 0 |
| ovlp | 142 | g | 4 | H3M | f' | 3 | H2 | 0.00 | 0.06 | 0 |
| asgn | 143 | w | 2 | H61 | f' | 3 | H2 | 0.00 | 0.09 | 0 |
| asgn | 144 | w | 2 | H62 | f' | 3 | H2 | 0.00 | 0.04 | 0 |
| asgn | 145 | g | 4 | H61 | f' | 3 | H2 | 0.00 | 0.09 | 0 |
| asgn | 146 | g | 4 | H62 | f' | 3 | H2 | 0.00 | 0.04 | 0 |
| asgn | 147 | g | 4 | H1 | f' | 3 | H2 | 0.00 | 0.26 | 0 |
| asgn | 148 | g | 4 | H1M | f' | 3 | H4 | 0.00 | 0.09 | 0 |
| ovlp | 148 | g | 4 | H2M | f' | 3 | H4 | 0.00 | 0.09 | 0 |
| ovlp | 148 | g | 4 | H3M | f' | 3 | H4 | 0.00 | 0.09 | 0 |
| asgn | 149 | w | 2 | H1M | f' | 3 | H4 | 0.00 | 0.11 | 0 |
| ovlp | 149 | w | 2 | H2M | f' | 3 | H4 | 0.00 | 0.11 | 0 |
| ovlp | 149 | w | 2 | H3M | f' | 3 | H4 | 0.00 | 0.11 | 0 |
| asgn | 150 | g | 4 | H4 | g | 4 | H1 | 0.00 | 0.43 | 0 |
| asgn | 151 | g | 4 | H61 | g | 4 | H1 | 0.00 | 0.26 | 0 |
| asgn | 152 | f' | 3 | H1 | g | 4 | H1 | 0.00 | 0.53 | 0 |
| asgn | 153 | f' | 3 | H2 | g | 4 | H1 | 0.00 | 0.31 | 0 |
| asgn | 154 | f' | 3 | H3 | g | 4 | H1 | 0.00 | 0.13 | 0 |
| asgn | 155 | f' | 3 | H4 | g | 4 | H1 | 0.00 | 3.40 | 0 |
| asgn | 156 | g | 4 | H62 | g | 4 | H1 | 0.00 | 0.17 | 0 |
| asgn | 157 | g | 4 | H61 | g | 4 | H2N | 0.00 | 0.05 | 0 |
| asgn | 158 | g | 4 | H62 | g | 4 | H2N | 0.00 | 0.04 | 0 |
| asgn | 159 | a' | 5 | H1 | g | 4 | H2N | 0.00 | 0.43 | 0 |
| asgn | 160 | f' | 3 | H4 | g | 4 | H2N | 0.00 | 0.20 | 0 |
| asgn | 161 | a' | 5 | H2 | g | 4 | H2N | 0.00 | 0.04 | 0 |
| asgn | 162 | a' | 5 | H3 | g | 4 | H2N | 0.00 | 0.17 | 0 |
| asgn | 163 | g | 4 | H1M | g | 4 | H4 | 0.00 | 0.03 | 0 |
| ovlp | 163 | g | 4 | H2M | g | 4 | H4 | 0.00 | 0.03 | 0 |
| ovlp | 163 | g | 4 | H3H | g | 4 | H4 | 0.00 | 0.03 | 0 |
| asgn | 164 | g | 4 | H1M | g | 4 | H5 | 0.00 | 0.06 | 0 |
| ovlp | 164 | g | 4 | H2M | g | 4 | H5 | 0.00 | 0.06 | 0 |
| ovlp | 164 | g | 4 | H3M | g | 4 | H5 | 0.00 | 0.06 | 0 |
| asgn | 165 | g | 4 | H1M | g | 4 | H61 | 0.00 | 0.02 | 0 |
| ovlp | 165 | g | 4 | H2M | g | 4 | H61 | 0.00 | 0.02 | 0 |
| ovlp | 165 | g | 4 | H3M | g | 4 | H61 | 0.00 | 0.02 | 0 |
| asgn | 166 | g | 4 | H1M | g | 4 | H62 | 0.00 | 0.04 | 0 |
| ovlp | 166 | g | 4 | H2M | g | 4 | H62 | 0.00 | 0.04 | 0 |
| ovlp | 166 | g | 4 | H3M | g | 4 | H62 | 0.00 | 0.04 | 0 |
| asgn | 167 | w' | 1 | H1 | w | 2 | H1 | 0.00 | 0.54 | 0 |
| asgn | 168 | w' | 1 | H2 | w | 2 | H1 | 0.00 | 0.06 | 0 |
| asgn | 169 | w' | 1 | H3 | w | 2 | H1 | 0.00 | 7.41 | 0 |
| asgn | 170 | w' | 1 | H4 | w | 2 | H1 | 0.00 | 7.41 | 0 |
| asgn | 171 | w | 2 | H4 | w | 2 | H1 | 0.00 | 0.37 | 0 |
| asgn | 172 | w | 2 | H61 | w | 2 | H1 | 0.00 | 0.31 | 0 |
| asgn | 173 | w | 2 | H62 | w | 2 | H1 | 0.00 | 0.16 | 0 |
| asgn | 174 | f' | 3 | H3 | w | 2 | H1 | 0.00 | 0.16 | 0 |
| asgn | 175 | w | 2 | H61 | w | 2 | H2N | 0.00 | 0.07 | 0 |
| asgn | 176 | w | 2 | H62 | w | 2 | H2N | 0.00 | 0.04 | 0 |
| asgn | 177 | f' | 3 | H3 | w | 2 | H2N | 0.00 | 0.04 | 0 |
| asgn | 178 | w' | 1 | H4 | w | 2 | H2N | 0.00 | 0.10 | 0 |
| asgn | 179 | f' | 3 | H2 | w | 2 | H2N | 0.00 | 0.04 | 0 |
| asgn | 180 | w | 2 | H1M | w | 2 | H3 | 0.00 | 0.24 | 0 |
| ovlp | 180 | w | 2 | H2M | w | 2 | H3 | 0.00 | 0.24 | 0 |
| ovlp | 180 | w | 2 | H3M | w | 2 | H3 | 0.00 | 0.24 | 0 |
| asgn | 181 | w | 2 | H1M | w | 2 | H4 | 0.00 | 0.08 | 0 |
| ovlp | 181 | w | 2 | H2M | w | 2 | H4 | 0.00 | 0.08 | 0 |
| ovlp | 181 | w | 2 | H3M | w | 2 | H4 | 0.00 | 0.08 | 0 |
| asgn | 182 | w | 2 | H1M | w | 2 | H5 | 0.00 | 0.04 | 0 |
| ovlp | 182 | w | 2 | H2M | w | 2 | H5 | 0.00 | 0.04 | 0 |
| ovlp | 182 | w | 2 | H3M | w | 2 | H5 | 0.00 | 0.04 | 0 |
| asgn | 183 | w | 2 | H1M | w | 2 | H61 | 0.00 | 0.02 | 0 |
| ovlp | 183 | w | 2 | H2M | w | 2 | H61 | 0.00 | 0.02 | 0 |
| ovlp | 183 | w | 2 | H3M | w | 2 | H61 | 0.00 | 0.02 | 0 |
| asgn | 184 | w | 2 | H1M | w | 2 | H62 | 0.00 | 0.04 | 0 |
| ovlp | 184 | w | 2 | H2M | w | 2 | H62 | 0.00 | 0.04 | 0 |
| ovlp | 184 | w | 2 | H3M | w | 2 | H62 | 0.00 | 0.04 | 0 |
| asgn | 185 | w' | 1 | H4 | w' | 1 | H1 | 0.00 | 2.83 | 0 |
| asgn | 186 | w | 2 | H4 | w' | 1 | H1 | 0.00 | 0.31 | 0 |
| asgn | 187 | w | 2 | H5 | w' | 1 | H1 | 0.00 | 0.69 | 0 |
| asgn | 188 | w | 2 | H61 | w' | 1 | H1 | 0.00 | 0.10 | 0 |
| asgn | 189 | w | 2 | H62 | w' | 1 | H1 | 0.00 | 0.07 | 0 |
| asgn | 190 | w | 2 | H1M | w' | 1 | H2 | 0.00 | 0.64 | 0 |

-continued

| | | | | | | | | | |
|---|---|---|---|---|---|---|---|---|---|
| | remark 2D-NOESY data for alpha-HA6 | | | | | | | | |
| ovlp | 190 | w | 2 | H2M | w' | 1 | H2 | 0.00 | 0.64 | 0 |
| ovlp | 190 | w | 2 | H3M | w' | 1 | H2 | 0.00 | 0.64 | 0 |
| asgn | 191 | w | 2 | H62 | w' | 1 | H2 | 0.00 | 0.05 | 0 |
| asgn | 192 | w | 2 | H4 | w' | 1 | H2 | 0.00 | 0.34 | 0 |
| asgn | 193 | w | 2 | H1 | w' | 1 | H2 | 0.00 | 0.04 | 0 |
| asgn | 194 | w | 2 | H1M | w' | 1 | H2 | 0.00 | 0.08 | 0 |
| ovlp | 194 | w | 2 | H2M | w' | 1 | H2 | 0.00 | 0.08 | 0 |
| ovlp | 194 | w | 2 | H3M | w' | 1 | H2 | 0.00 | 0.08 | 0 |
| endsection | | | | | | | | | | |

[$^1$H-$^{15}$N]-NOESY-HSQC Dataset for a Hyaluronan Hexasaccharide remark 15N-NOESY-HSQC data for alpha-HA6
configuration:

field   750
solvent   h2o
ident   15N-NOESY-HSQC
temp   298
visc   0.88
mix_time   400 ms
endsection
data:

| asgn | 1 | a | 6 | H1M | a | 6 | H2N | 48.8 | 19.6 | 0 |
|---|---|---|---|---|---|---|---|---|---|---|
| ovlp | 1 | a | 6 | H2M | a | 6 | H2N | 48.8 | 19.6 | 0 |
| ovlp | 1 | a | 6 | H3M | a | 6 | H2N | 48.8 | 19.6 | 0 |
| asgn | 2 | a | 6 | H3 | a | 6 | H2N | 34.2 | 13.7 | 0 |
| asgn | 3 | a | 6 | H2 | a | 6 | H2N | 12.6 | 5.1 | 0 |
| asgn | 4 | a' | 5 | H1 | a | 6 | H2N | 58.7 | 23.5 | 0 |
| asgn | 5 | a | 6 | H1 | a | 6 | H2N | 22.4 | 9.0 | 0 |
| asgn | 6 | a | 6 | H2N | a | 6 | H2N | 1918.9 | 767.6 | 0 |
| asgn | 7 | a' | 5 | H5 | a | 6 | H2N | 7.9 | 3.3 | 0 |
| asgn | 8 | w | 2 | H1M | w | 2 | H2N | 93.9 | 37.6 | 0 |

-continued

| ovlp | 8 | w | 2 | H2M | w | 2 | H2N | 93.9 | 37.6 | 0 |
|---|---|---|---|---|---|---|---|---|---|---|
| ovlp | 8 | w | 2 | H3M | w | 2 | H2N | 93.9 | 37.6 | 0 |
| asgn | 9 | w | 2 | H3 | w | 2 | H2N | 126.8 | 50.7 | 0 |
| ovlp | 9 | w' | 1 | H5 | w | 2 | H2N | 126.8 | 50.7 | 0 |
| ovlp | 9 | f | 3 | H5 | w | 2 | H2N | 126.8 | 50.7 | 0 |
| asgn | 10 | w | 2 | H2 | w | 2 | H2N | 30.2 | 12.1 | 0 |
| asgn | 11 | w' | 1 | H1 | w | 2 | H2N | 109.6 | 43.8 | 0 |
| asgn | 12 | w | 2 | H1 | w | 2 | H2N | 74.8 | 29.9 | 0 |
| asgn | 13 | w | 2 | H2N | w | 2 | H2N | 3575.4 | 1430.2 | 0 |
| asgn | 14 | g | 4 | H1M | g | 4 | H2N | 120.9 | 48.4 | 0 |
| ovlp | 14 | g | 4 | H2M | g | 4 | H2N | 120.9 | 48.4 | 0 |
| ovlp | 14 | g | 4 | H3M | g | 4 | H2N | 120.9 | 48.4 | 0 |
| asgn | 15 | g | 4 | H3 | g | 4 | H2N | 118.5 | 47.4 | 0 |
| ovlp | 15 | a' | 5 | H5 | g | 4 | H2N | 118.5 | 47.4 | 0 |
| ovlp | 15 | f | 3 | H5 | g | 4 | H2N | 118.5 | 47.4 | 0 |
| asgn | 16 | g | 4 | H2 | g | 4 | H2N | 35.4 | 14.2 | 0 |
| asgn | 17 | f | 3 | H1 | g | 4 | H2N | 105.0 | 42.0 | 0 |
| asgn | 18 | g | 4 | H1 | g | 4 | H2N | 89.6 | 35.9 | 0 |
| asgn | 19 | g | 4 | H2N | g | 4 | H2N | 2955.4 | 1182.3 | 0 |
| endsection | | | | | | | | | | |

[$^1$H-$^1$H]-T-ROESY Dataset for a Hyaluronan Hexasaccharide remark 2D-T-ROESY data for alpha-HA6
configuration:

field   600
solvent   d2o
ident   2D-TROESY
temp   298
visc   1.08
mix_time 400 ms
endsection
data:

| asgn | 1 | a | 6 | H1 | a | 6 | H1 | 2404.98 | 1202.49 | 0 |
|---|---|---|---|---|---|---|---|---|---|---|
| asgn | 2 | a | 6 | H1 | a | 6 | H2 | −87.92 | 44.04 | 0 |
| asgn | 3 | a | 6 | H1 | a | 6 | H3 | −10.51 | 5.38 | 0 |
| asgn | 4 | a | 6 | H1 | a | 6 | H4 | −2.06 | 1.12 | 0 |
| asgn | 5 | a | 6 | H1 | a | 6 | H5 | −4.60 | 2.31 | 0 |
| asgn | 6 | a | 6 | H2 | a | 6 | H1 | −91.54 | 46.02 | 0 |
| asgn | 7 | a | 6 | H2 | a | 6 | H2 | 1994.95 | 1001.93 | 0 |
| asgn | 8 | a | 6 | H2 | a | 6 | H4 | −37.45 | 19.18 | 0 |
| asgn | 9 | a | 6 | H2 | a' | 5 | H1 | −12.85 | 6.45 | 0 |
| asgn | 10 | a | 6 | H3 | a' | 5 | H1 | −36.87 | 18.44 | 0 |
| asgn | 11 | a | 6 | H4 | a | 6 | H2 | −35.65 | 17.84 | 0 |
| asgn | 12 | a | 6 | H1M | a | 6 | H1 | −1.78 | 0.91 | 0 |
| ovlp | 12 | a | 6 | H2M | a | 6 | H1 | −1.78 | 0.91 | 0 |
| ovlp | 12 | a | 6 | H3M | a | 6 | H1 | −1.78 | 0.91 | 0 |
| asgn | 13 | a | 6 | H1M | a | 6 | H2 | −4.89 | 2.48 | 0 |
| ovlp | 13 | a | 6 | H2M | a | 6 | H2 | −4.89 | 2.48 | 0 |
| ovlp | 13 | a | 6 | H3M | a | 6 | H2 | −4.89 | 2.48 | 0 |
| asgn | 14 | a | 6 | H1M | a | 6 | H3 | −2.53 | 1.32 | 0 |
| ovlp | 14 | a | 6 | H2M | a | 6 | H3 | −2.53 | 1.32 | 0 |
| ovlp | 14 | a | 6 | H3M | a | 6 | H3 | −2.53 | 1.32 | 0 |
| asgn | 15 | a | 6 | H1M | a' | 5 | H1 | −3.88 | 1.95 | 0 |
| ovlp | 15 | a | 6 | H2M | a' | 5 | H1 | −3.88 | 1.95 | 0 |
| ovlp | 15 | a | 6 | H3M | a' | 5 | H1 | −3.88 | 1.95 | 0 |

-continued

| | | | | | | | | | | |
|---|---|---|---|---|---|---|---|---|---|---|
| asgn | 16 | a' | 5 | H1 | a | 6 | H2 | −5.55 | 2.79 | 0 |
| asgn | 17 | a' | 5 | H1 | a | 6 | H3 | −56.88 | 28.48 | 0 |
| asgn | 18 | a' | 5 | H1 | a | 6 | H4 | −6.00 | 3.03 | 0 |
| asgn | 19 | a' | 5 | H1 | a' | 5 | H1 | 573.02 | 286.71 | 0 |
| asgn | 20 | a' | 5 | H1 | a' | 5 | H3 | −34.08 | 17.04 | 0 |
| asgn | 21 | a' | 5 | H1 | a' | 5 | H4 | −18.12 | 9.88 | 0 |
| asgn | 22 | a' | 5 | H1 | a' | 5 | H5 | −24.25 | 12.97 | 0 |
| asgn | 23 | a' | 5 | H2 | a | 6 | H3 | −5.63 | 2.84 | 0 |
| asgn | 24 | a' | 5 | H2 | a' | 5 | H2 | 642.51 | 326.60 | 0 |
| asgn | 25 | a' | 5 | H3 | a' | 5 | H1 | −19.80 | 9.90 | 0 |
| asgn | 26 | a' | 5 | H4 | a' | 5 | H1 | −17.16 | 8.59 | 0 |
| asgn | 27 | a' | 5 | H4 | a' | 5 | H2 | −27.04 | 13.53 | 0 |
| asgn | 28 | a' | 5 | H5 | a' | 5 | H1 | −43.88 | 21.95 | 0 |
| asgn | 29 | f' | 3 | H1 | f' | 3 | H1 | 624.53 | 312.27 | 0 |
| asgn | 30 | f' | 3 | H2 | f' | 3 | H2 | 516.19 | 269.50 | 0 |
| asgn | 31 | f' | 3 | H3 | f' | 3 | H1 | −21.99 | 11.00 | 0 |
| asgn | 32 | f' | 3 | H4 | f' | 3 | H2 | −24.69 | 13.33 | 0 |
| asgn | 33 | g | 4 | H1M | f' | 3 | H3 | −7.80 | 3.92 | 0 |
| ovlp | 33 | g | 4 | H2M | f' | 3 | H3 | −7.80 | 3.92 | 0 |
| ovlp | 33 | g | 4 | H3M | f' | 3 | H3 | −7.80 | 3.92 | 0 |
| asgn | 34 | w | 2 | H4 | w' | 1 | H1 | −3.07 | 1.54 | 0 |
| asgn | 35 | w | 2 | H1M | w' | 1 | H2 | −4.04 | 2.04 | 0 |
| ovlp | 35 | w | 2 | H2M | w' | 1 | H2 | −4.04 | 2.04 | 0 |
| ovlp | 35 | w | 2 | H3M | w' | 1 | H2 | −4.04 | 2.04 | 0 |
| asgn | 36 | w | 2 | H1M | w' | 1 | H3 | −3.75 | 1.89 | 0 |
| ovlp | 36 | w | 2 | H2M | w' | 1 | H3 | −3.75 | 1.89 | 0 |
| ovlp | 36 | w | 2 | H3M | w' | 1 | H3 | −3.75 | 1.89 | 0 |
| asgn | 37 | w' | 1 | H1 | w | 2 | H4 | −4.45 | 2.23 | 0 |
| asgn | 38 | w' | 1 | H1 | w' | 1 | H1 | 624.53 | 312.27 | 0 |
| asgn | 39 | w' | 1 | H1 | w' | 1 | H3 | −31.07 | 15.54 | 0 |
| asgn | 40 | w' | 1 | H2 | w' | 1 | H2 | 666.60 | 333.91 | 0 |
| asgn | 41 | w' | 1 | H3 | w' | 1 | H1 | −28.71 | 14.36 | 0 |
| asgn | 42 | g | 4 | H1 | g | 4 | H1 | 1507.50 | 754.78 | 0 |
| ovlp | 42 | w | 2 | H1 | w | 2 | H1 | 1507.50 | 754.78 | 0 |
| asgn | 43 | g | 4 | H1 | g | 4 | H5 | −84.68 | 42.69 | 0 |
| ovlp | 43 | w | 2 | H1 | w | 2 | H5 | −84.68 | 42.69 | 0 |
| asgn | 44 | g | 4 | H5 | g | 4 | H1 | −73.73 | 37.22 | 0 |
| ovlp | 44 | w | 2 | H5 | w | 2 | H1 | −73.73 | 37.22 | 0 |
| asgn | 45 | g | 4 | H2 | f' | 3 | H1 | −10.58 | 5.29 | 0 |
| ovlp | 45 | w | 2 | H2 | w' | 1 | H1 | −10.58 | 5.29 | 0 |
| asgn | 46 | f' | 3 | H1 | g | 4 | H2 | −9.46 | 4.73 | 0 |
| ovlp | 46 | w' | 1 | H1 | w | 2 | H2 | −9.46 | 4.73 | 0 |
| asgn | 47 | f' | 3 | H3 | w | 2 | H1 | −4.07 | 2.26 | 0 |
| asgn | 48 | a' | 5 | H3 | g | 4 | H1 | −6.92 | 3.85 | 0 |
| asgn | 49 | g | 4 | H1 | a' | 5 | H3 | −2.86 | 1.58 | 0 |
| asgn | 50 | f' | 3 | H1 | f' | 3 | H3 | −38.94 | 19.48 | 0 |
| asgn | 51 | f' | 3 | H4 | w | 2 | H1 | −46.75 | 23.38 | 0 |
| asgn | 52 | a' | 5 | H4 | g | 4 | H1 | −79.48 | 39.74 | 0 |
| asgn | 53 | w | 2 | H1 | f' | 3 | H4 | −26.68 | 13.53 | 0 |
| asgn | 54 | g | 4 | H1 | a' | 5 | H4 | −26.68 | 13.53 | 0 |
| asgn | 55 | g | 4 | H1 | g | 4 | H3 | −14.33 | 8.23 | 0 |
| ovlp | 55 | g | 4 | H1 | f' | 3 | H3 | −14.33 | 8.23 | 0 |
| ovlp | 55 | g | 4 | H1 | a' | 5 | H5 | −14.33 | 8.23 | 0 |
| asgn | 56 | w | 2 | H1 | w | 2 | H3 | −14.33 | 8.23 | 0 |
| ovlp | 56 | w | 2 | H1 | w' | 1 | H3 | −14.33 | 8.23 | 0 |
| ovlp | 56 | w | 2 | H1 | f' | 3 | H5 | −14.33 | 8.23 | 0 |
| asgn | 57 | g | 4 | H1M | f' | 3 | H1 | −4.72 | 2.36 | 0 |
| ovlp | 57 | g | 4 | H2M | f' | 3 | H1 | −4.72 | 2.36 | 0 |
| ovlp | 57 | g | 4 | H3M | f' | 3 | H1 | −4.72 | 2.36 | 0 |
| asgn | 58 | w | 2 | H1M | w' | 1 | H1 | −4.72 | 2.36 | 0 |
| ovlp | 58 | w | 2 | H2M | w' | 1 | H1 | −4.72 | 2.36 | 0 |
| ovlp | 58 | w | 2 | H3M | w' | 1 | H1 | −4.72 | 2.36 | 0 |
| asgn | 59 | g | 4 | H1M | g | 4 | H1 | −1.29 | 0.65 | 0 |
| ovlp | 59 | g | 4 | H2M | g | 4 | H1 | −1.29 | 0.65 | 0 |
| ovlp | 59 | g | 4 | H3M | g | 4 | H1 | −1.29 | 0.65 | 0 |
| asgn | 60 | w | 2 | H1M | w | 2 | H1 | −1.29 | 0.65 | 0 |
| ovlp | 60 | w | 2 | H2M | w | 2 | H1 | −1.29 | 0.65 | 0 |
| ovlp | 60 | w | 2 | H3M | w | 2 | H1 | −1.29 | 0.65 | 0 |
| asgn | 61 | g | 4 | H1M | g | 4 | H2 | −4.24 | 2.13 | 0 |
| ovlp | 61 | g | 4 | H2M | g | 4 | H2 | −4.24 | 2.13 | 0 |
| ovlp | 61 | g | 4 | H3M | g | 4 | H2 | −4.24 | 2.13 | 0 |
| asgn | 62 | w | 2 | H1M | w | 2 | H2 | −4.24 | 2.13 | 0 |
| ovlp | 62 | w | 2 | H2M | w | 2 | H2 | −4.24 | 2.13 | 0 |
| ovlp | 62 | w | 2 | H3M | w | 2 | H2 | −4.24 | 2.13 | 0 |
| remark | noROES | | | | | | | | | |
| asgn | 101 | g | 4 | H1M | a | 6 | H1 | 0.00 | 0.59 | 0 |
| ovlp | 101 | g | 4 | H2M | a | 6 | H1 | 0.00 | 0.59 | 0 |
| ovlp | 101 | g | 4 | H3M | a | 6 | H1 | 0.00 | 0.59 | 0 |
| asgn | 102 | a' | 5 | H2 | a | 6 | H1 | 0.00 | 0.57 | 0 |

-continued

| | | | | | | | | | |
|---|---|---|---|---|---|---|---|---|---|
| asgn | 103 | a' | 5 | H3 | a | 6 | H1 | 0.00 | 0.74 | 0 |
| asgn | 104 | a' | 5 | H4 | a | 6 | H1 | 0.00 | 1.10 | 0 |
| asgn | 105 | a | 6 | H61 | a | 6 | H1 | 0.00 | 0.92 | 0 |
| asgn | 106 | a' | 5 | H1 | a | 6 | H1 | 0.00 | 0.80 | 0 |
| asgn | 107 | a | 6 | H61 | a | 6 | H2 | 0.00 | 2.46 | 0 |
| asgn | 108 | a | 6 | H62 | a | 6 | H2 | 0.00 | 1.83 | 0 |
| asgn | 109 | a | 6 | H5 | a | 6 | H2 | 0.00 | 6.56 | 0 |
| asgn | 110 | a' | 5 | H5 | a | 6 | H2 | 0.00 | 3.79 | 0 |
| asgn | 111 | a' | 5 | H3 | a | 6 | H2 | 0.00 | 4.19 | 0 |
| asgn | 112 | a' | 5 | H2 | a | 6 | H2 | 0.00 | 1.01 | 0 |
| asgn | 113 | g | 4 | H1M | a' | 5 | H1 | 0.00 | 2.05 | 0 |
| ovlp | 113 | g | 4 | H2M | a' | 5 | H1 | 0.00 | 2.05 | 0 |
| ovlp | 113 | g | 4 | H3M | a' | 5 | H1 | 0.00 | 2.05 | 0 |
| asgn | 114 | a | 6 | H4 | a' | 5 | H1 | 0.00 | 0.55 | 0 |
| asgn | 115 | a | 6 | H5 | a' | 5 | H1 | 0.00 | 1.67 | 0 |
| asgn | 116 | a | 6 | H61 | a' | 5 | H1 | 0.00 | 1.52 | 0 |
| asgn | 117 | a | 6 | H62 | a' | 5 | H1 | 0.00 | 1.67 | 0 |
| asgn | 118 | g | 4 | H2 | a' | 5 | H1 | 0.00 | 1.67 | 0 |
| asgn | 119 | g | 4 | H3 | a' | 5 | H1 | 0.00 | 7.90 | 0 |
| asgn | 120 | g | 4 | H4 | a' | 5 | H1 | 0.00 | 0.79 | 0 |
| asgn | 121 | g | 4 | H5 | a' | 5 | H1 | 0.00 | 0.68 | 0 |
| asgn | 122 | g | 4 | H61 | a' | 5 | H1 | 0.00 | 1.89 | 0 |
| asgn | 123 | w | 2 | H1M | a' | 5 | H1 | 0.00 | 2.05 | 0 |
| ovlp | 123 | w | 2 | H2M | a' | 5 | H1 | 0.00 | 2.05 | 0 |
| ovlp | 123 | w | 2 | H3M | a' | 5 | H1 | 0.00 | 2.05 | 0 |
| asgn | 124 | a | 6 | H61 | a' | 5 | H2 | 0.00 | 1.19 | 0 |
| asgn | 125 | a | 6 | H62 | a' | 5 | H2 | 0.00 | 1.69 | 0 |
| asgn | 126 | g | 4 | H62 | a' | 5 | H2 | 0.00 | 0.54 | 0 |
| asgn | 127 | a | 6 | H1 | a' | 5 | H2 | 0.00 | 0.32 | 0 |
| asgn | 128 | a | 6 | H2 | a' | 5 | H2 | 0.00 | 1.31 | 0 |
| asgn | 129 | a | 6 | H4 | a' | 5 | H2 | 0.00 | 3.91 | 0 |
| asgn | 130 | a | 6 | H1M | a' | 5 | H2 | 0.00 | 3.55 | 0 |
| ovlp | 130 | a | 6 | H2M | a' | 5 | H2 | 0.00 | 3.55 | 0 |
| ovlp | 130 | a | 6 | H3M | a' | 5 | H2 | 0.00 | 3.55 | 0 |
| asgn | 131 | w | 2 | H1M | f' | 3 | H1 | 0.00 | 4.08 | 0 |
| ovlp | 131 | w | 2 | H2M | f' | 3 | H1 | 0.00 | 4.08 | 0 |
| ovlp | 131 | w | 2 | H3M | f' | 3 | H1 | 0.00 | 4.08 | 0 |
| asgn | 132 | g | 4 | H4 | f' | 3 | H1 | 0.00 | 3.40 | 0 |
| asgn | 133 | g | 4 | H5 | f' | 3 | H1 | 0.00 | 0.95 | 0 |
| asgn | 134 | g | 4 | H61 | f' | 3 | H1 | 0.00 | 2.72 | 0 |
| asgn | 135 | g | 4 | H62 | f' | 3 | H1 | 0.00 | 1.72 | 0 |
| asgn | 136 | w | 2 | H4 | f' | 3 | H1 | 0.00 | 0.96 | 0 |
| asgn | 137 | w | 2 | H5 | f' | 3 | H1 | 0.00 | 0.95 | 0 |
| asgn | 138 | w | 2 | H61 | f' | 3 | H1 | 0.00 | 2.72 | 0 |
| asgn | 139 | w | 2 | H62 | f' | 3 | H1 | 0.00 | 1.72 | 0 |
| asgn | 140 | w | 2 | H1M | f' | 3 | H2 | 0.00 | 2.19 | 0 |
| ovlp | 140 | w | 2 | H2M | f' | 3 | H2 | 0.00 | 2.19 | 0 |
| ovlp | 140 | w | 2 | H3M | f' | 3 | H2 | 0.00 | 2.19 | 0 |
| asgn | 141 | w | 2 | H62 | f' | 3 | H2 | 0.00 | 0.88 | 0 |
| asgn | 142 | g | 4 | H62 | f' | 3 | H2 | 0.00 | 0.88 | 0 |
| asgn | 143 | g | 4 | H1 | f' | 3 | H2 | 0.00 | 1.05 | 0 |
| asgn | 144 | g | 4 | H1M | f' | 3 | H4 | 0.00 | 1.92 | 0 |
| ovlp | 144 | g | 4 | H2M | f' | 3 | H4 | 0.00 | 1.92 | 0 |
| ovlp | 144 | g | 4 | H3M | f' | 3 | H4 | 0.00 | 1.92 | 0 |
| asgn | 145 | g | 4 | H62 | g | 4 | H1 | 0.00 | 1.21 | 0 |
| asgn | 146 | f' | 3 | H1 | g | 4 | H1 | 0.00 | 5.64 | 0 |
| asgn | 147 | f' | 3 | H2 | g | 4 | H1 | 0.00 | 0.18 | 0 |
| asgn | 148 | a' | 5 | H3 | g | 4 | H1 | 0.00 | 0.83 | 0 |
| asgn | 149 | g | 4 | H1M | g | 4 | H4 | 0.00 | 1.39 | 0 |
| ovlp | 149 | g | 4 | H2M | g | 4 | H4 | 0.00 | 1.39 | 0 |
| ovlp | 149 | g | 4 | H3M | g | 4 | H4 | 0.00 | 1.39 | 0 |
| asgn | 150 | g | 4 | H1M | g | 4 | H61 | 0.00 | 1.28 | 0 |
| ovlp | 150 | g | 4 | H2M | g | 4 | H61 | 0.00 | 1.28 | 0 |
| ovlp | 150 | g | 4 | H3M | g | 4 | H61 | 0.00 | 1.28 | 0 |
| asgn | 151 | g | 4 | H1M | g | 4 | H62 | 0.00 | 1.47 | 0 |
| ovlp | 151 | g | 4 | H2M | g | 4 | H62 | 0.00 | 1.47 | 0 |
| ovlp | 151 | g | 4 | H3M | g | 4 | H62 | 0.00 | 1.47 | 0 |
| asgn | 152 | w' | 1 | H1 | w | 2 | H1 | 0.00 | 5.64 | 0 |
| asgn | 153 | w' | 1 | H2 | w | 2 | H1 | 0.00 | 0.18 | 0 |
| asgn | 154 | w | 2 | H62 | w | 2 | H1 | 0.00 | 0.83 | 0 |
| asgn | 155 | w | 2 | H1M | w | 2 | H4 | 0.00 | 1.44 | 0 |
| ovlp | 155 | w | 2 | H2M | w | 2 | H4 | 0.00 | 1.44 | 0 |
| ovlp | 155 | w | 2 | H3M | w | 2 | H4 | 0.00 | 1.44 | 0 |
| asgn | 156 | w | 2 | H1M | w | 2 | H5 | 0.00 | 1.60 | 0 |
| ovlp | 156 | w | 2 | H2M | w | 2 | H5 | 0.00 | 1.60 | 0 |
| ovlp | 156 | w | 2 | H3M | w | 2 | H5 | 0.00 | 1.60 | 0 |
| asgn | 157 | w | 2 | H1M | w | 2 | H61 | 0.00 | 1.28 | 0 |
| ovlp | 157 | w | 2 | H2M | w | 2 | H61 | 0.00 | 1.28 | 0 |
| ovlp | 157 | w | 2 | H3M | w | 2 | H61 | 0.00 | 1.28 | 0 |

-continued

| | | | | | | | | | |
|---|---|---|---|---|---|---|---|---|---|
| asgn | 158 | w | 2 | H1M | w | 2 | H62 | 0.00 | 1.47 | 0 |
| ovlp | 158 | w | 2 | H2M | w | 2 | H62 | 0.00 | 1.47 | 0 |
| ovlp | 158 | w | 2 | H3M | w | 2 | H62 | 0.00 | 1.47 | 0 |
| asgn | 159 | w | 2 | H61 | w' | 1 | H1 | 0.00 | 2.72 | 0 |
| asgn | 160 | w | 2 | H62 | w' | 1 | H1 | 0.00 | 1.72 | 0 |
| asgn | 161 | w | 2 | H62 | w' | 1 | H2 | 0.00 | 0.59 | 0 |
| asgn | 162 | w | 2 | H4 | w' | 1 | H2 | 0.00 | 1.97 | 0 |
| asgn | 163 | w | 2 | H1 | w' | 1 | H2 | 0.00 | 0.63 | 0 |
| endsection | | | | | | | | | | |

[$^1$H-$^{15}$N]-T-ROESY-HSQC Dataset for a Hyaluronan Hexasaccharide

```
remark 15N-T-ROESY-HSQC data for alpha-HA6
configuration:

field    600
solvent  h2o
temp     298
visc     0.88
ident    15N-TROESY-HSQC
mix_time 400 ms
endsection
data:

asgn   1   a    6  H1M  a    6  H2N   -17.0   3.4   0
ovlp   1   a    6  H2M  a    6  H2N   -17.0   3.4   0
ovlp   1   a    6  H3M  a    6  H2N   -17.0   3.4   0
asgn   2   a    6  H3   a    6  H2N   -13.1   2.6   0
asgn   3   a    6  H2   a    6  H2N    -8.9   1.8   0
asgn   4   a'   5  H1   a    6  H2N    -9.5   1.9   0
asgn   5   a    6  H1   a    6  H2N    -5.1   1.0   0
asgn   6   a    6  H2N  a    6  H2N   332.3  66.5   0
asgn   7   w    2  H1M  w    2  H2N   -22.9   4.6   0
ovlp   7   w    2  H2M  w    2  H2N   -22.9   4.6   0
ovlp   7   w    2  H3M  w    2  H2N   -22.9   4.6   0
asgn   8   w    2  H3   w    2  H2N   -16.3   3.3   0
ovlp   8   w'   1  H5   w    2  H2N   -16.3   3.3   0
ovlp   8   f    3  H5   w    2  H2N   -16.3   3.3   0
asgn   9   w    2  H2   w    2  H2N   -12.5   2.5   0
asgn  10   w'   1  H1   w    2  H2N   -13.1   2.6   0
asgn  11   w    2  H1   w    2  H2N   -18.7   3.7   0
asgn  12   w    2  H2N  w    2  H2N   437.9  87.6   0
asgn  13   g    4  H1M  g    4  H2N   -18.2   3.6   0
ovlp  13   g    4  H2M  g    4  H2N   -18.2   3.6   0
ovlp  13   g    4  H3M  g    4  H2N   -18.2   3.6   0
asgn  14   g    4  H3   g    4  H2N   -13.8   2.8   0
ovlp  14   f    3  H5   g    4  H2N   -13.8   2.8   0
ovlp  14   a'   5  H5   g    4  H2N   -13.8   2.8   0
asgn  15   g    4  H2   g    4  H2N   -10.7   2.1   0
asgn  16   f    3  H1   g    4  H2N   -12.3   2.5   0
asgn  17   g    4  H1   g    4  H2N   -15.3   3.1   0
asgn  18   g    4  H2N  g    4  H2N   348.4  69.7   0
endsection
```

Scalar-Coupling Dataset for a Hyaluronan Hexasaccharide

```
remark Conformation-dependent scalar couplings
configuration:

field    900
solvent  h2o
ident    JCOUP
endsection
data:

remark atoms karplus c1 c2 c3 phase experimental error
coup   1   2  H2   2  C2   2  N2   2  H2N   9.45  -2.08  0.63  0  9.67  0.5  0
coup   2   4  H2   4  C2   4  N2   4  H2N   9.45  -2.08  0.63  0  9.75  0.5  0
coup   3   6  H2   6  C2   6  N2   6  H2N   9.81  -1.51  0.62  0  9.38  0.5  0
endsection
```

Residual Dipolar Coupling Dataset for a Hyaluronan Hexasaccharide

```
remark Residual dipolar couplings for alpha-HA6
configuration:

field    900
solvent  h2o
ident    RDC
endsection
data:

asgn   1   a    6  C1   a    6  H1    -5.85  0.35  0
asgn   2   a    6  C2   a    6  H2     0.69  0.35  0
asgn   3   a    6  C3   a    6  H3    -1.06  0.35  0
asgn   4   a    6  C5   a    6  H5    -1.23  0.35  0
asgn   5   a    6  C6   a    6  H61   -1.32  0.35  0
asgn   6   a    6  C6   a    6  H62   -0.83  0.35  0
asgn   7   a    6  CME  a    6  H1M   -1.11  0.35  0
ovlp   7   a    6  CME  a    6  H2M   -1.11  0.35  0
ovlp   7   a    6  CME  a    6  H3M   -1.11  0.35  0
asgn   8   a'   5  C1   a'   5  H1     4.37  0.35  0
asgn   9   a'   5  C2   a'   5  H2     5.33  0.35  0
asgn  10   a'   5  C3   a'   5  H3     5.20  0.35  0
asgn  11   a'   5  C4   a'   5  H4     3.96  0.35  0
asgn  12   g    4  C1   g    4  H1     4.12  0.35  0
asgn  13   g    4  C2   g    4  H2     5.40  0.35  0
asgn  14   g    4  C3   g    4  H3     4.38  0.35  0
asgn  15   g    4  C4   g    4  H4     5.38  0.35  0
asgn  16   g    4  CME  g    4  H1M   -1.61  0.35  0
ovlp  16   g    4  CME  g    4  H2M   -1.61  0.35  0
ovlp  16   g    4  CME  g    4  H3M   -1.61  0.35  0
asgn  17   f    3  C1   f    3  H1     3.14  0.35  0
asgn  18   f    3  C2   f    3  H2     4.61  0.35  0
asgn  19   f    3  C3   f    3  H3     4.61  0.35  0
asgn  20   f    3  C4   f    3  H4     2.58  0.35  0
asgn  21   f    3  C5   f    3  H5     3.63  0.35  0
asgn  22   w    2  C1   w    2  H1     4.63  0.35  0
asgn  23   w    2  C2   w    2  H2     5.18  0.35  0
asgn  24   w    2  C3   w    2  H3     4.95  0.35  0
asgn  25   w    2  C4   w    2  H4     5.34  0.35  0
asgn  26   w    2  CME  w    2  H1M   -1.83  0.35  0
ovlp  26   w    2  CME  w    2  H2M   -1.83  0.35  0
ovlp  26   w    2  CME  w    2  H3M   -1.83  0.35  0
asgn  27   w'   1  C1   w'   1  H1     1.42  0.35  0
asgn  28   w'   1  C2   w'   1  H2     2.60  0.35  0
asgn  29   w'   1  C3   w'   1  H3     2.43  0.35  0
```

-continued

| | | | | | | | | | |
|---|---|---|---|---|---|---|---|---|---|
| asgn | 30 | w' | 1 | C4 | w' | 1 | H4 | 1.13 | 0.35 | 0 |
| asgn | 31 | w' | 1 | C5 | w' | 1 | H5 | 2.10 | 0.35 | 0 |
| asgn | 101 | a | 6 | H2 | a | 6 | H1 | 0.10 | 0.35 | 0 |
| ovlp | 101 | a | 6 | H2 | a | 6 | H3 | 0.10 | 0.35 | 0 |
| asgn | 102 | a | 6 | H3 | a | 6 | H2 | −1.01 | 0.35 | 0 |
| ovlp | 102 | a | 6 | H3 | a | 6 | H4 | −1.01 | 0.35 | 0 |
| asgn | 103 | a | 6 | H4 | a | 6 | H3 | 3.12 | 0.35 | 0 |
| ovlp | 103 | a | 6 | H4 | a | 6 | H5 | 3.12 | 0.35 | 0 |
| asgn | 104 | a | 6 | H5 | a | 6 | H4 | 6.45 | 0.35 | 0 |
| ovlp | 104 | a | 6 | H5 | a | 6 | H61 | 6.45 | 0.35 | 0 |
| ovlp | 104 | a | 6 | H5 | a | 6 | H62 | 6.45 | 0.35 | 0 |
| asgn | 105 | a | 6 | H62 | a | 6 | H61 | −3.23 | 0.35 | 0 |
| ovlp | 105 | a | 6 | H62 | a | 6 | H5 | −3.23 | 0.35 | 0 |
| asgn | 106 | a' | 5 | H1 | a' | 5 | H2 | 0.78 | 0.35 | 0 |
| asgn | 107 | a' | 5 | H2 | a' | 5 | H1 | 1.09 | 0.35 | 0 |
| ovlp | 107 | a' | 5 | H2 | a' | 5 | H3 | 1.09 | 0.35 | 0 |
| asgn | 108 | a' | 5 | H3 | a' | 5 | H2 | 1.27 | 0.35 | 0 |
| ovlp | 108 | a' | 5 | H3 | a' | 5 | H4 | 1.27 | 0.35 | 0 |
| asgn | 109 | a' | 5 | H4 | a' | 5 | H3 | 1.40 | 0.35 | 0 |
| ovlp | 109 | a' | 5 | H4 | a' | 5 | H5 | 1.40 | 0.35 | 0 |
| asgn | 110 | g | 4 | H1 | g | 4 | H2 | −0.36 | 0.35 | 0 |
| asgn | 111 | g | 4 | H2 | g | 4 | H1 | 2.28 | 0.35 | 0 |
| ovlp | 111 | g | 4 | H2 | g | 4 | H3 | 2.28 | 0.35 | 0 |
| asgn | 112 | g | 4 | H3 | g | 4 | H2 | 1.37 | 0.35 | 0 |
| ovlp | 112 | g | 4 | H3 | g | 4 | H4 | 1.37 | 0.35 | 0 |
| asgn | 113 | g | 4 | H4 | g | 4 | H3 | 1.61 | 0.35 | 0 |
| ovlp | 113 | g | 4 | H4 | g | 4 | H5 | 1.61 | 0.35 | 0 |
| asgn | 114 | g | 4 | H62 | g | 4 | H5 | −3.35 | 0.35 | 0 |
| ovlp | 114 | g | 4 | H62 | g | 4 | H61 | −3.35 | 0.35 | 0 |
| asgn | 115 | f | 3 | H1 | f | 3 | H2 | −0.19 | 0.35 | 0 |
| asgn | 116 | f | 3 | H2 | f | 3 | H1 | 1.01 | 0.35 | 0 |
| ovlp | 116 | f | 3 | H2 | f | 3 | H3 | 1.01 | 0.35 | 0 |
| asgn | 117 | f | 3 | H3 | f | 3 | H2 | 1.33 | 0.35 | 0 |
| ovlp | 117 | f | 3 | H3 | f | 3 | H4 | 1.33 | 0.35 | 0 |
| asgn | 118 | f | 3 | H4 | f | 3 | H3 | 0.35 | 0.35 | 0 |
| ovlp | 118 | f | 3 | H4 | f | 3 | H5 | 0.35 | 0.35 | 0 |
| asgn | 119 | f | 3 | H5 | f | 3 | H4 | −0.02 | 0.35 | 0 |
| asgn | 120 | w | 2 | H1 | w | 2 | H2 | 0.55 | 0.35 | 0 |
| asgn | 121 | w | 2 | H2 | w | 2 | H1 | 2.52 | 0.35 | 0 |
| ovlp | 121 | w | 2 | H2 | w | 2 | H3 | 2.52 | 0.35 | 0 |
| asgn | 122 | w | 2 | H3 | w | 2 | H2 | 1.19 | 0.35 | 0 |
| ovlp | 122 | w | 2 | H3 | w | 2 | H4 | 1.19 | 0.35 | 0 |
| asgn | 123 | w' | 1 | H1 | w' | 1 | H2 | 0.17 | 0.35 | 0 |
| asgn | 124 | w' | 1 | H2 | w' | 1 | H1 | −0.37 | 0.35 | 0 |
| ovlp | 124 | w' | 1 | H2 | w' | 1 | H3 | −0.37 | 0.35 | 0 |
| asgn | 125 | w' | 1 | H3 | w' | 1 | H2 | 0.59 | 0.35 | 0 |
| ovlp | 125 | w' | 1 | H3 | w' | 1 | H4 | 0.59 | 0.35 | 0 |
| asgn | 126 | w' | 1 | H4 | w' | 1 | H3 | −0.37 | 0.35 | 0 |
| ovlp | 126 | w' | 1 | H4 | w' | 1 | H5 | −0.37 | 0.35 | 0 |
| asgn | 127 | w' | 1 | H5 | w' | 1 | H4 | −0.15 | 0.35 | 0 |
| asgn | 128 | a | 6 | H2N | a | 6 | H2 | 0.10 | 0.35 | 0 |
| asgn | 129 | a | 6 | H1 | a | 6 | H2 | 0.90 | 0.35 | 0 |
| asgn | 130 | a' | 5 | H1 | a' | 5 | H2 | 1.06 | 0.35 | 0 |
| asgn | 131 | a | 6 | H2N | a | 6 | N2 | 0.82 | 0.35 | 0 |
| asgn | 132 | w | 2 | H2N | w | 2 | N2 | −1.30 | 0.35 | 0 |
| asgn | 133 | g | 4 | H2N | g | 4 | N2 | −1.83 | 0.35 | 0 |
| endsection | | | | | | | | | | |

Order Parameter Dataset for a Hyaluronan Hexasaccharide

```
remark Order parameters for amide groups
configuration:

solvent  h2o
ident    ORDER
endsection
data:

hnoe    1    w    2    H2N    w    2    N2    0.44    0.01    0
hnoe    2    g    4    H2N    g    4    N2    0.57    0.01    0
hnoe    3    a    6    H2N    a    6    N2    0.51    0.02    0
endsection
```

Final $\chi^2_{restraint}$ Values for Each Structural Restraint after Structure Refinement In this file the fields for each line are as follows: the first number is the structural restraint number (e.g., 123), this is followed by six letters or numbers defining the atoms involved in the structural restraint (e.g. w 2 H1M a' 5 H1), the next two values define the structural restraint measurement and its error (e.g. 0.00 2.00), the next two three values gives the predicted value of this structural restraint from the dynamic ensemble(e.g. −0.00), the $\chi^2_{restraint}$ value for this structural restraint (e.g. 0.00) and the standard deviation for the $\chi^2_{restraint}$ value (e.g. 0.00). The next value is the flag value (e.g. 0), while the next value gives the number of overlaps the restraint had (e.g. +2). The final field gives the name of the dataset file the structural restraint is found in (e.g. 2D-ROESY). The structural restraints are sorted from lowest to highest $\chi^2_{restraint}$ value in this file (i.e., restraint 123 in the 2D-T-ROESY dataset to restraint 104 in the RDC dataset).

| | | | | | | | | | | | | | |
|---|---|---|---|---|---|---|---|---|---|---|---|---|---|
| 123 | w | 2 | H1M | a' | 5 | H1 | 0.00 | 2.00 | −0.00 | 0.00 | 0.00 | 0 | +2 2D-ROESY |
| 170 | w' | 1 | H4 | w | 2 | H1 | 0.00 | 7.40 | 0.01 | 0.00 | 0.00 | 0 | +0 2D-NOESY |
| 119 | g | 4 | H3 | a' | 5 | H1 | 0.00 | 7.90 | −0.01 | 0.00 | 0.00 | 0 | +0 2D-NOESY |
| 155 | f | 3 | H4 | g | 4 | H1 | 0.00 | 3.40 | 0.01 | 0.00 | 0.00 | 0 | +0 2D-NOESY |
| 169 | w' | 1 | H3 | w | 2 | H1 | 0.00 | 7.40 | 0.02 | 0.00 | 0.00 | 0 | +0 2D-NOESY |
| 150 | g | 4 | H1M | g | 4 | H61 | 0.00 | 1.30 | −0.00 | 0.00 | 0.00 | 0 | +2 2D-ROESY |
| 157 | w | 2 | H1M | w | 2 | H61 | 0.00 | 1.30 | −0.00 | 0.00 | 0.00 | 0 | +2 2D-ROESY |
| 151 | g | 4 | H1M | g | 4 | H62 | 0.00 | 1.50 | −0.01 | 0.00 | 0.00 | 0 | +2 2D-ROESY |
| 158 | w | 2 | H1M | w | 2 | H62 | 0.00 | 1.50 | −0.01 | 0.00 | 0.00 | 0 | +2 2D-ROESY |
| 131 | w | 2 | H1M | f | 3 | H1 | 0.00 | 4.10 | −0.02 | 0.00 | 0.00 | 0 | +2 2D-ROESY |
| 138 | w | 2 | H61 | f | 3 | H1 | 0.00 | 2.70 | −0.02 | 0.00 | 0.00 | 0 | +0 2D-ROESY |
| 101 | g | 4 | H1M | a | 6 | H1 | 0.00 | 0.59 | −0.00 | 0.00 | 0.00 | 0 | +2 2D-ROESY |
| 139 | w | 2 | H62 | f | 3 | H1 | 0.00 | 1.70 | −0.01 | 0.00 | 0.00 | 0 | +0 2D-ROESY |
| 140 | w | 2 | H1M | f | 3 | H2 | 0.00 | 2.20 | −0.02 | 0.00 | 0.00 | 0 | +2 2D-ROESY |
| 122 | g | 4 | H61 | a' | 5 | H1 | 0.00 | 1.90 | −0.02 | 0.00 | 0.00 | 0 | +0 2D-ROESY |
| 138 | w | 2 | H5 | f | 3 | H1 | 0.00 | 1.20 | 0.01 | 0.00 | 0.00 | 0 | +0 2D-NOESY |
| 113 | g | 4 | H1M | a' | 5 | H1 | 0.00 | 2.00 | −0.02 | 0.00 | 0.00 | 0 | +2 2D-ROESY |
| 146 | f | 3 | H1 | g | 4 | H1 | 0.00 | 5.60 | 0.03 | 0.00 | 0.00 | 0 | +0 2D-ROESY |
| 134 | g | 4 | H61 | f | 3 | H1 | 0.00 | 2.70 | −0.03 | 0.00 | 0.00 | 0 | +0 2D-ROESY |
| 145 | g | 4 | H62 | g | 4 | H1 | 0.00 | 1.20 | −0.01 | 0.00 | 0.00 | 0 | +0 2D-ROESY |
| 115 | a | 6 | H5 | a' | 5 | H1 | 0.00 | 1.70 | −0.02 | 0.00 | 0.00 | 0 | +0 2D-ROESY |
| 144 | g | 4 | H1M | f | 3 | H4 | 0.00 | 1.90 | −0.01 | 0.00 | 0.00 | 0 | +2 2D-ROESY |
| 111 | a' | 5 | H3 | a | 6 | H2 | 0.00 | 4.20 | −0.06 | 0.00 | 0.00 | 0 | +0 2D-ROESY |
| 116 | a | 6 | H61 | a' | 5 | H1 | 0.00 | 1.50 | −0.02 | 0.00 | 0.00 | 0 | +0 2D-ROESY |
| 133 | w | 2 | H1M | f | 3 | H1 | 0.00 | 0.91 | 0.01 | 0.00 | 0.00 | 0 | +2 2D-NOESY |
| 141 | w | 2 | H1M | f | 3 | H1 | 0.00 | 0.91 | 0.01 | 0.00 | 0.00 | 0 | +2 2D-NOESY |

-continued

| | | | | | | | | | | | | |
|---|---|---|---|---|---|---|---|---|---|---|---|---|
| 117 | a | 6 | H62 | a' | 5 | H1 | 0.00 | 1.70 | −0.03 | 0.00 | 0.00 | 0 | +0 | 2D-ROESY |
| 39 | w' | 1 | H1 | w' | 1 | H3 | −31.00 | 16.00 | −31.00 | 0.00 | 0.00 | 0 | +0 | 2D-ROESY |
| 152 | w' | 1 | H1 | w | 2 | H1 | 0.00 | 5.60 | 0.06 | 0.00 | 0.00 | 0 | +0 | 2D-ROESY |
| 159 | w | 2 | H61 | w' | 1 | H1 | 0.00 | 2.70 | −0.05 | 0.00 | 0.00 | 0 | +0 | 2D-ROESY |
| 156 | w | 2 | H1M | w | 2 | H5 | 0.00 | 1.60 | −0.03 | 0.00 | 0.00 | 0 | +2 | 2D-ROESY |
| 136 | w | 2 | H4 | f' | 3 | H1 | 0.00 | 0.96 | −0.02 | 0.00 | 0.00 | 0 | +0 | 2D-ROESY |
| 154 | w | 2 | H62 | w | 2 | H1 | 0.00 | 0.83 | −0.01 | 0.00 | 0.00 | 0 | +0 | 2D-ROESY |
| 135 | g | 4 | H62 | f' | 3 | H1 | 0.00 | 1.70 | −0.03 | 0.00 | 0.00 | 0 | +0 | 2D-ROESY |
| 130 | a | 6 | H1M | a' | 5 | H2 | 0.00 | 3.50 | −0.07 | 0.00 | 0.00 | 0 | +2 | 2D-ROESY |
| 104 | a' | 5 | H4 | a | 6 | H1 | 0.00 | 1.10 | −0.02 | 0.00 | 0.00 | 0 | +0 | 2D-ROESY |
| 120 | g | 4 | H4 | a' | 5 | H1 | 0.00 | 0.79 | −0.02 | 0.00 | 0.00 | 0 | +0 | 2D-ROESY |
| 110 | a' | 5 | H5 | a | 6 | H2 | 0.00 | 3.80 | −0.09 | 0.00 | 0.00 | 0 | +0 | 2D-ROESY |
| 140 | w | 2 | H62 | f' | 3 | H1 | 0.00 | 0.27 | 0.01 | 0.00 | 0.00 | 0 | +0 | 2D-ROESY |
| 103 | a' | 5 | H3 | a | 6 | H1 | 0.00 | 0.74 | −0.02 | 0.00 | 0.00 | 0 | +0 | 2D-ROESY |
| 103 | a' | 5 | H4 | a | 6 | H1 | 0.00 | 0.23 | 0.01 | 0.00 | 0.00 | 0 | +0 | 2D-NOESY |
| 125 | g | 4 | H61 | a' | 5 | H1 | 0.00 | 0.30 | 0.01 | 0.00 | 0.00 | 0 | +0 | 2D-NOESY |
| 137 | w | 2 | H5 | f' | 3 | H1 | 0.00 | 0.95 | −0.03 | 0.00 | 0.00 | 0 | +0 | 2D-ROESY |
| 118 | g | 4 | H2 | a' | 5 | H1 | 0.00 | 1.70 | −0.05 | 0.00 | 0.00 | 0 | +0 | 2D-ROESY |
| 159 | a' | 5 | H1 | g | 4 | H2N | 0.00 | 0.43 | 0.01 | 0.00 | 0.00 | 0 | +0 | 2D-NOESY |
| 160 | w | 2 | H62 | w' | 1 | H1 | 0.00 | 1.70 | −0.05 | 0.00 | 0.00 | 0 | +0 | 2D-ROESY |
| 117 | f' | 3 | H3 | f' | 3 | H2 | 1.30 | 0.35 | 1.30 | 0.00 | 0.00 | 0 | +1 | RDC |
| 107 | a | 6 | H61 | a | 6 | H2 | 0.00 | 2.50 | −0.09 | 0.00 | 0.00 | 0 | +0 | 2D-ROESY |
| 11 | a | 6 | H4 | a | 6 | H2 | −36.00 | 18.00 | −35.00 | 0.00 | 0.00 | 0 | +0 | 2D-ROESY |
| 155 | w | 2 | H1M | w | 2 | H4 | 0.00 | 1.40 | −0.06 | 0.00 | 0.00 | 0 | +2 | 2D-ROESY |
| 142 | g | 4 | H62 | f' | 3 | H2 | 0.00 | 0.88 | −0.03 | 0.00 | 0.00 | 0 | +0 | 2D-ROESY |
| 121 | g | 4 | H5 | a' | 5 | H1 | 0.00 | 0.68 | −0.03 | 0.00 | 0.00 | 0 | +0 | 2D-ROESY |
| 149 | g | 4 | H1M | g | 4 | H4 | 0.00 | 1.40 | −0.06 | 0.00 | 0.00 | 0 | +2 | 2D-ROESY |
| 123 | g | 4 | H4 | a' | 5 | H1 | 0.00 | 0.14 | 0.01 | 0.00 | 0.00 | 0 | +0 | 2D-NOESY |
| 139 | w | 2 | H61 | f' | 3 | H1 | 0.00 | 0.16 | 0.01 | 0.00 | 0.00 | 0 | +0 | 2D-NOESY |
| 125 | a | 6 | H62 | a' | 5 | H2 | 0.00 | 1.70 | −0.09 | 0.00 | 0.00 | 0 | +0 | 2D-ROESY |
| 143 | g | 4 | H1 | f' | 3 | H2 | 0.00 | 1.10 | −0.06 | 0.00 | 0.00 | 0 | +0 | 2D-ROESY |
| 161 | w | 2 | H62 | w' | 1 | H2 | 0.00 | 0.59 | −0.03 | 0.00 | 0.00 | 0 | +0 | 2D-ROESY |
| 124 | a | 6 | H61 | a' | 5 | H2 | 0.00 | 1.20 | −0.07 | 0.00 | 0.00 | 0 | +0 | 2D-ROESY |
| 120 | w | 2 | H1 | w | 2 | H2 | 0.55 | 0.35 | 0.58 | 0.00 | 0.00 | 0 | +0 | RDC |
| 38 | g | 4 | H1M | g | 4 | H2N | 9.40 | 3.80 | 9.30 | 0.00 | 0.00 | 0 | +2 | 2D-NOESY |
| 153 | f' | 3 | H2 | g | 4 | H1 | 0.00 | 0.31 | 0.02 | 0.00 | 0.00 | 0 | +0 | 2D-NOESY |
| 108 | a | 6 | H62 | a | 6 | H2 | 0.00 | 1.80 | −0.13 | 0.01 | 0.00 | 0 | +0 | 2D-ROESY |
| 137 | g | 4 | H62 | f' | 3 | H1 | 0.00 | 0.27 | 0.02 | 0.01 | 0.00 | 0 | +0 | 2D-ROESY |
| 147 | g | 4 | H1 | f' | 3 | H2 | 0.00 | 0.26 | 0.02 | 0.01 | 0.00 | 0 | +0 | 2D-NOESY |
| 124 | g | 4 | H5 | a' | 5 | H1 | 0.00 | 0.13 | 0.01 | 0.01 | 0.00 | 0 | +0 | 2D-NOESY |
| 29 | f' | 3 | H1 | f' | 3 | H1 | 620.00 | 310.00 | 600.00 | 0.01 | 0.00 | 0 | +0 | 2D-ROESY |
| 102 | a' | 5 | H2 | a | 6 | H1 | 0.00 | 0.57 | −0.05 | 0.01 | 0.00 | 0 | +0 | 2D-ROESY |
| 31 | f' | 3 | H3 | f' | 3 | H1 | −22.00 | 11.00 | −23.00 | 0.01 | 0.00 | 0 | +0 | 2D-ROESY |
| 163 | w | 2 | H1 | w' | 1 | H2 | 0.00 | 0.63 | −0.06 | 0.01 | 0.00 | 0 | +0 | 2D-ROESY |
| 127 | a | 6 | H61 | a' | 5 | H2 | 0.00 | 0.29 | 0.03 | 0.01 | 0.00 | 0 | +0 | 2D-NOESY |
| 40 | g | 4 | H2N | g | 4 | H2N | 190.00 | 74.00 | 190.00 | 0.01 | 0.00 | 0 | +0 | 2D-NOESY |
| 122 | w | 2 | H3 | w | 2 | H2 | 1.20 | 0.35 | 1.10 | 0.01 | 0.00 | 0 | +1 | RDC |
| 101 | a' | 5 | H2 | a | 6 | H1 | 0.00 | 0.14 | 0.01 | 0.01 | 0.00 | 0 | +0 | 2D-NOESY |
| 127 | w' | 1 | H5 | w' | 1 | H4 | −0.15 | 0.35 | −0.11 | 0.01 | 0.01 | 0 | +0 | RDC |
| 126 | g | 4 | H1M | a' | 5 | H2 | 0.00 | 0.10 | 0.01 | 0.01 | 0.00 | 0 | +2 | 2D-NOESY |
| 57 | w | 2 | H1M | w | 2 | H2N | 8.90 | 3.60 | 9.20 | 0.01 | 0.01 | 0 | +2 | 2D-NOESY |
| 160 | f' | 3 | H4 | g | 4 | H2N | 0.00 | 0.20 | 0.02 | 0.01 | 0.00 | 0 | +0 | 2D-NOESY |
| 145 | g | 4 | H61 | f' | 3 | H2 | 0.00 | 0.09 | 0.01 | 0.01 | 0.00 | 0 | +0 | 2D-NOESY |
| 154 | f' | 3 | H3 | g | 4 | H1 | 0.00 | 0.13 | 0.02 | 0.02 | 0.00 | 0 | +0 | 2D-NOESY |
| 141 | w | 2 | H62 | f' | 3 | H2 | 0.00 | 0.88 | −0.11 | 0.02 | 0.01 | 0 | +0 | 2D-ROESY |
| 116 | g | 4 | H1M | a' | 5 | H1 | 0.00 | 0.12 | 0.01 | 0.02 | 0.01 | 0 | +2 | 2D-NOESY |
| 136 | g | 4 | H61 | f' | 3 | H1 | 0.00 | 0.16 | 0.02 | 0.02 | 0.01 | 0 | +0 | 2D-NOESY |
| 8 | a | 6 | H2 | a | 6 | H4 | −37.00 | 19.00 | −35.00 | 0.02 | 0.01 | 0 | +0 | 2D-ROESY |
| 119 | a | 6 | H61 | a' | 5 | H1 | 0.00 | 0.09 | 0.01 | 0.02 | 0.01 | 0 | +0 | 2D-NOESY |
| 122 | g | 4 | H2 | a' | 5 | H1 | 0.00 | 0.14 | 0.02 | 0.02 | 0.01 | 0 | +0 | 2D-NOESY |
| 11 | a' | 5 | C4 | a' | 5 | H4 | 4.00 | 0.35 | 4.10 | 0.02 | 0.04 | 0 | +0 | RDC |
| 120 | a | 6 | H62 | a' | 5 | H1 | 0.00 | 0.09 | 0.01 | 0.02 | 0.01 | 0 | +0 | 2D-NOESY |
| 128 | a | 6 | H62 | a' | 5 | H2 | 0.00 | 0.22 | 0.03 | 0.02 | 0.01 | 0 | +0 | 2D-NOESY |
| 107 | a' | 5 | H2 | a' | 5 | H1 | 1.10 | 0.35 | 0.94 | 0.03 | 0.01 | 0 | +1 | RDC |
| 135 | g | 4 | H5 | f' | 3 | H1 | 0.00 | 1.20 | 0.19 | 0.03 | 0.01 | 0 | +0 | 2D-NOESY |
| 110 | a' | 5 | H3 | a | 6 | H2 | 0.00 | 0.14 | 0.02 | 0.03 | 0.01 | 0 | +0 | 2D-NOESY |
| 127 | a | 6 | H1 | a' | 5 | H2 | 0.00 | 0.32 | −0.05 | 0.03 | 0.01 | 0 | +0 | 2D-ROESY |
| 14 | g | 4 | C3 | g | 4 | H3 | 4.40 | 0.35 | 4.50 | 0.03 | 0.03 | 0 | +0 | RDC |
| 116 | f' | 3 | H2 | f' | 3 | H1 | 1.00 | 0.35 | 0.84 | 0.03 | 0.02 | 0 | +1 | RDC |
| 185 | w' | 1 | H4 | w' | 1 | H1 | 0.00 | 2.80 | 0.48 | 0.03 | 0.01 | 0 | +0 | 2D-ROESY |
| 41 | w' | 1 | H3 | w' | 1 | H1 | −29.00 | 14.00 | −31.00 | 0.03 | 0.02 | 0 | +0 | 2D-ROESY |
| 1 | a | 6 | H1M | a | 6 | H2N | −17.00 | 3.40 | −17.00 | 0.03 | 0.03 | 0 | +2 | 15N-ROESY-HSQC |
| 71 | w | 2 | H1M | w | 2 | H1 | 0.27 | 0.11 | 0.29 | 0.03 | 0.02 | 0 | +2 | 2D-NOESY |
| 166 | g | 4 | H1M | g | 4 | H62 | 0.04 | 0.01 | 0.04 | 0.04 | 0.02 | 0 | +2 | 2D-NOESY |
| 190 | w | 2 | H1M | w' | 1 | H2 | 0.00 | 0.64 | 0.12 | 0.04 | 0.02 | 0 | +2 | 2D-NOESY |
| 126 | g | 4 | H62 | a' | 5 | H2 | 0.00 | 0.54 | −0.10 | 0.04 | 0.03 | 0 | +0 | 2D-ROESY |
| 184 | w | 2 | H1M | w | 2 | H62 | 0.00 | 0.04 | 0.01 | 0.04 | 0.02 | 0 | +2 | 2D-NOESY |
| 22 | w | 2 | C1 | w | 2 | H1 | 4.60 | 0.35 | 4.50 | 0.04 | 0.05 | 0 | +0 | RDC |
| 129 | g | 4 | H62 | a' | 5 | H2 | 0.00 | 0.22 | 0.04 | 0.04 | 0.03 | 0 | +0 | 2D-NOESY |

-continued

| | | | | | | | | | | | | |
|---|---|---|---|---|---|---|---|---|---|---|---|---|
| 132 | g | 4 | H4 | f | 3 | H1 | 0.00 | 3.40 | -0.66 | 0.04 | 0.03 | 0 | +0 | 2D-ROESY |
| 108 | a' | 5 | H3 | a' | 5 | H2 | 1.30 | 0.35 | 1.10 | 0.04 | 0.03 | 0 | +1 | RDC |
| 125 | w' | 1 | H3 | w' | 1 | H2 | 0.59 | 0.35 | 0.80 | 0.04 | 0.03 | 0 | +1 | RDC |
| 129 | a | 6 | H1 | a | 6 | H2 | 0.90 | 0.35 | 0.76 | 0.04 | 0.04 | 0 | +0 | RDC |
| 132 | w | 2 | H2N | w | 2 | N2 | -1.30 | 0.35 | -1.20 | 0.04 | 0.06 | 0 | +0 | RDC |
| 102 | a' | 5 | H3 | a | 6 | H1 | 0.00 | 0.03 | 0.01 | 0.04 | 0.04 | 0 | +0 | 2D-NOESY |
| 106 | a' | 5 | H1 | a | 6 | H1 | 0.00 | 0.80 | -0.17 | 0.05 | 0.04 | 0 | +0 | 2D-ROESY |
| 7 | a' | 5 | H2 | a | 6 | H2N | 0.09 | 0.05 | 0.08 | 0.05 | 0.06 | 0 | +0 | 2D-NOESY |
| 85 | a | 6 | H1M | a | 6 | H2 | 0.40 | 0.17 | 0.44 | 0.05 | 0.06 | 0 | +2 | 2D-ROESY |
| 109 | a | 6 | H5 | a | 6 | H2 | 0.00 | 6.60 | -1.60 | 0.06 | 0.07 | 0 | +0 | 2D-ROESY |
| 178 | w' | 1 | H4 | w | 2 | H2N | 0.00 | 0.10 | 0.02 | 0.06 | 0.07 | 0 | +0 | 2D-NOESY |
| 188 | w | 2 | H61 | w' | 1 | H1 | 0.00 | 0.10 | 0.03 | 0.06 | 0.08 | 0 | +0 | 2D-NOESY |
| 133 | g | 4 | H5 | f | 3 | H1 | 0.00 | 0.95 | 0.23 | 0.06 | 0.09 | 0 | +0 | 2D-ROESY |
| 12 | g | 4 | C1 | g | 4 | H1 | 4.10 | 0.35 | 4.40 | 0.07 | 0.12 | 0 | +0 | RDC |
| 191 | w | 2 | H62 | w' | 1 | H2 | 0.00 | 0.05 | 0.01 | 0.07 | 0.09 | 0 | +0 | 2D-NOESY |
| 81 | w' | 1 | H2 | w' | 1 | H2 | 270.00 | 110.00 | 240.00 | 0.07 | 0.09 | 0 | +0 | 2D-NOESY |
| 58 | w | 2 | H1 | w | 2 | H2N | 3.70 | 1.50 | 4.10 | 0.07 | 0.13 | 0 | +0 | 2D-NOESY |
| 105 | a | 6 | H61 | a | 6 | H1 | 0.00 | 0.92 | -0.24 | 0.07 | 0.09 | 0 | +0 | 2D-ROESY |
| 104 | a | 6 | H61 | a | 6 | H1 | 0.00 | 0.35 | 0.09 | 0.07 | 0.09 | 0 | +0 | 2D-NOESY |
| 112 | g | 4 | H3 | g | 4 | H2 | 1.40 | 0.35 | 1.10 | 0.07 | 0.11 | 0 | +1 | RDC |
| 128 | a | 6 | H2 | a' | 5 | H2 | 0.00 | 1.30 | -0.36 | 0.07 | 0.10 | 0 | +0 | 2D-ROESY |
| 39 | g | 4 | H1 | g | 4 | H2N | 3.70 | 1.50 | 4.10 | 0.07 | 0.14 | 0 | +0 | 2D-NOESY |
| 51 | f | 3 | H4 | w | 2 | H1 | -47.00 | 23.00 | -41.00 | 0.08 | 0.17 | 0 | +0 | 2D-ROESY |
| 113 | g | 4 | H4 | g | 4 | H3 | 1.60 | 0.35 | 1.30 | 0.08 | 0.11 | 0 | +1 | RDC |
| 162 | a' | 5 | H3 | g | 4 | H2N | 0.00 | 0.17 | 0.05 | 0.08 | 0.12 | 0 | +0 | 2D-NOESY |
| 47 | g | 4 | H1 | g | 4 | H1 | 220.00 | 87.00 | 190.00 | 0.08 | 0.13 | 0 | +0 | 2D-ROESY |
| 15 | a | 6 | H1M | a' | 5 | H1 | -3.90 | 1.90 | -3.40 | 0.08 | 0.25 | 0 | +2 | 2D-ROESY |
| 31 | g | 4 | H1M | f | 3 | H1 | 1.10 | 0.44 | 1.00 | 0.08 | 0.28 | 0 | +2 | 2D-NOESY |
| 21 | f | 3 | C5 | f | 3 | H5 | 3.60 | 0.35 | 3.80 | 0.09 | 0.36 | 0 | +0 | RDC |
| 101 | a | 6 | H2 | a | 6 | H1 | 0.10 | 0.35 | -0.06 | 0.09 | 0.15 | 0 | +1 | RDC |
| 19 | a' | 5 | H1 | a' | 5 | H1 | 570.00 | 290.00 | 660.00 | 0.09 | 0.16 | 0 | +0 | 2D-ROESY |
| 8 | w | 2 | H1M | w | 2 | H2N | 94.00 | 38.00 | 82.00 | 0.09 | 0.16 | 0 | +2 | 15N-NOESY-HSQC |
| 119 | f | 3 | H5 | f | 3 | H4 | -0.02 | 0.35 | 0.11 | 0.09 | 0.21 | 0 | +0 | RDC |
| 128 | a | 6 | H2N | a | 6 | H2 | 0.10 | 0.35 | 0.31 | 0.10 | 0.20 | 0 | +0 | RDC |
| 121 | g | 4 | H2N | a' | 5 | H1 | 0.00 | 0.04 | 0.01 | 0.10 | 0.18 | 0 | +0 | 2D-NOESY |
| 35 | f | 3 | H2 | f | 3 | H2 | 270.00 | 110.00 | 240.00 | 0.10 | 0.20 | 0 | +0 | 2D-NOESY |
| 175 | w | 2 | H61 | w | 2 | H2N | 0.00 | 0.07 | 0.02 | 0.10 | 0.18 | 0 | +0 | 2D-NOESY |
| 147 | f | 3 | H2 | g | 4 | H1 | 0.00 | 0.18 | -0.06 | 0.10 | 0.19 | 0 | +0 | 2D-ROESY |
| 24 | w | 2 | C3 | w | 2 | H3 | 5.00 | 0.35 | 4.60 | 0.10 | 0.29 | 0 | +0 | RDC |
| 153 | w' | 1 | H2 | w | 2 | H1 | 0.00 | 0.18 | -0.06 | 0.10 | 0.20 | 0 | +0 | 2D-ROESY |
| 146 | g | 4 | H62 | f | 3 | H2 | 0.00 | 0.04 | 0.01 | 0.11 | 0.23 | 0 | +0 | 2D-NOESY |
| 48 | g | 4 | H2N | g | 4 | H1 | 4.70 | 1.90 | 4.10 | 0.11 | 0.26 | 0 | +0 | 2D-NOESY |
| 61 | w | 2 | H4 | w | 2 | H2N | 0.21 | 0.09 | 0.18 | 0.12 | 0.28 | 0 | +0 | 2D-NOESY |
| 187 | w | 2 | H5 | w' | 1 | H1 | 0.00 | 0.69 | 0.24 | 0.12 | 0.28 | 0 | +0 | 2D-NOESY |
| 112 | a' | 5 | H2 | a | 6 | H2 | 0.00 | 1.00 | -0.36 | 0.12 | 0.29 | 0 | +0 | 2D-ROESY |
| 183 | w | 2 | H1M | w | 2 | H61 | 0.00 | 0.02 | 0.01 | 0.12 | 0.26 | 0 | +2 | 2D-NOESY |
| 165 | g | 4 | H1M | g | 4 | H61 | 0.00 | 0.02 | 0.01 | 0.12 | 0.26 | 0 | +2 | 2D-NOESY |
| 25 | a' | 5 | H2 | a' | 5 | H2 | 270.00 | 110.00 | 230.00 | 0.13 | 0.32 | 0 | +0 | 2D-NOESY |
| 31 | w' | 1 | C5 | w' | 1 | H5 | 2.10 | 0.35 | 1.90 | 0.13 | 1.30 | 0 | +0 | RDC |
| 1 | a | 6 | C1 | a | 6 | H1 | -5.80 | 0.35 | -5.90 | 0.13 | 0.66 | 0 | +0 | RDC |
| 74 | w' | 1 | H1 | w' | 1 | H1 | 310.00 | 120.00 | 270.00 | 0.13 | 0.32 | 0 | +0 | 2D-ROESY |
| 118 | a | 6 | H5 | a' | 5 | H1 | 0.00 | 0.23 | 0.08 | 0.13 | 0.31 | 0 | +0 | 2D-NOESY |
| 44 | g | 4 | H5 | g | 4 | H1 | -74.00 | 37.00 | -60.00 | 0.13 | 0.31 | 0 | +1 | 2D-ROESY |
| 24 | a' | 5 | H2 | a' | 5 | H2 | 640.00 | 330.00 | 760.00 | 0.14 | 0.36 | 0 | +0 | 2D-ROESY |
| 40 | w' | 1 | H2 | w' | 1 | H2 | 670.00 | 330.00 | 790.00 | 0.14 | 0.37 | 0 | +0 | 2D-ROESY |
| 102 | a | 6 | H3 | a | 6 | H2 | -1.00 | 0.35 | -0.70 | 0.14 | 0.39 | 0 | +1 | RDC |
| 168 | w' | 1 | H2 | w | 2 | H1 | 0.00 | 0.06 | 0.02 | 0.14 | 0.35 | 0 | +0 | 2D-NOESY |
| 148 | g | 4 | H1M | f | 3 | H4 | 0.00 | 0.09 | 0.03 | 0.15 | 0.48 | 0 | +2 | 2D-NOESY |
| 189 | w | 2 | H62 | w' | 1 | H1 | 0.00 | 0.07 | 0.03 | 0.15 | 0.42 | 0 | +0 | 2D-NOESY |
| 29 | w' | 1 | C3 | w' | 1 | H3 | 2.40 | 0.35 | 2.20 | 0.15 | 1.20 | 0 | +0 | RDC |
| 118 | f | 3 | H4 | f | 3 | H3 | 0.35 | 0.35 | 0.66 | 0.15 | 0.49 | 0 | +1 | RDC |
| 76 | w | 2 | H1M | w' | 1 | H1 | 1.10 | 0.44 | 1.20 | 0.17 | 1.60 | 0 | +2 | 2D-NOESY |
| 6 | a' | 5 | H1 | a | 6 | H2N | 2.60 | 1.00 | 2.70 | 0.17 | 2.90 | 0 | +0 | 2D-NOESY |
| 3 | a | 6 | H2 | a | 6 | H2N | -8.90 | 1.80 | -8.10 | 0.19 | 0.88 | 0 | +0 | 15N-ROESY-HSQC |
| 157 | g | 4 | H61 | g | 4 | H2N | 0.00 | 0.05 | 0.02 | 0.19 | 0.68 | 0 | +0 | 2D-NOESY |
| 162 | w | 2 | H4 | w' | 1 | H2 | 0.00 | 2.00 | -0.85 | 0.19 | 0.73 | 0 | +0 | 2D-NOESY |
| 105 | a | 6 | H62 | a | 6 | H61 | -3.20 | 0.35 | -2.90 | 0.19 | 1.80 | 0 | +1 | RDC |
| 42 | g | 4 | H4 | g | 4 | H2N | 0.22 | 0.09 | 0.18 | 0.20 | 0.78 | 0 | +0 | 2D-NOESY |
| 129 | a | 6 | H4 | a' | 5 | H2 | 0.00 | 3.90 | -1.80 | 0.21 | 0.84 | 0 | +0 | 2D-ROESY |
| 28 | a' | 5 | H5 | a' | 5 | H1 | -44.00 | 22.00 | -34.00 | 0.21 | 0.85 | 0 | +0 | 2D-ROESY |
| 109 | a' | 5 | H5 | a | 6 | H2 | 0.00 | 0.08 | 0.04 | 0.22 | 0.92 | 0 | +0 | 2D-NOESY |
| 192 | w | 2 | H4 | w' | 1 | H2 | 0.00 | 0.34 | 0.16 | 0.22 | 0.94 | 0 | +0 | 2D-NOESY |
| 2 | a | 6 | H3 | a | 6 | H2N | 34.00 | 14.00 | 41.00 | 0.23 | 1.00 | 0 | +0 | 15N-NOESY-HSQC |
| 17 | g | 4 | H1 | g | 4 | H2N | -15.00 | 3.10 | -14.00 | 0.23 | 1.30 | 0 | +0 | 15N-ROESY-HSQC |
| 5 | a | 6 | C6 | a | 6 | H61 | -1.30 | 0.35 | -1.50 | 0.23 | 2.00 | 0 | +0 | RDC |
| 13 | a | 6 | H5 | a | 6 | H1 | 0.72 | 0.29 | 0.58 | 0.23 | 1.00 | 0 | +0 | 2D-NOESY |
| 42 | g | 4 | H1 | g | 4 | H1 | 1500.00 | 750.00 | 1100.00 | 0.24 | 1.10 | 0 | +1 | 2D-ROESY |
| 20 | a' | 5 | H1 | a' | 5 | H3 | -34.00 | 17.00 | -26.00 | 0.24 | 1.10 | 0 | +0 | 2D-ROESY |
| 23 | w | 2 | C2 | w | 2 | H2 | 5.20 | 0.35 | 4.70 | 0.24 | 1.40 | 0 | +0 | RDC |

-continued

| | | | | | | | | | | | | |
|---|---|---|---|---|---|---|---|---|---|---|---|---|
| 27 | a' | 5 | H4 | a' | 5 | H2 | −27.00 | 14.00 | −34.00 | 0.24 | 1.10 | 0 | +0 2D-ROESY |
| 44 | f | 3 | H1 | g | 4 | H2N | 4.90 | 1.90 | 4.00 | 0.25 | 2.20 | 0 | +0 2D-NOESY |
| 12 | w | 2 | H2N | w | 2 | H2N | 440.00 | 88.00 | 400.00 | 0.25 | 1.40 | 0 | +0 15N-ROESY-HSQC |
| 123 | w' | 1 | H1 | w' | 1 | H2 | 0.17 | 0.35 | −0.08 | 0.25 | 1.30 | 0 | +0 RDC |
| 17 | f | 3 | C1 | f | 3 | H1 | 3.10 | 0.35 | 3.50 | 0.25 | 1.90 | 0 | +0 RDC |
| 2 | 3J | 4 | H2 | 3J | 4 | H2N | 9.80 | 0.50 | 9.90 | 0.25 | 3.70 | 1 | +0 JCOUP |
| 2 | a | 6 | H1 | a | 6 | H2N | 1.40 | 0.55 | 1.60 | 0.26 | 1.50 | 0 | +0 2D-NOESY |
| 53 | g | 4 | H1M | g | 4 | H1 | 0.37 | 0.15 | 0.29 | 0.26 | 1.30 | 0 | +2 2D-NOESY |
| 79 | w' | 1 | H1 | w | 2 | H4 | 0.32 | 0.13 | 0.26 | 0.26 | 1.40 | 0 | +0 2D-NOESY |
| 132 | a | 6 | H1M | a' | 5 | H2 | 0.00 | 0.10 | 0.05 | 0.26 | 1.30 | 0 | +2 2D-NOESY |
| 152 | f | 3 | H1 | g | 4 | H1 | 0.00 | 0.53 | 0.27 | 0.26 | 1.30 | 0 | +0 2D-NOESY |
| 161 | a' | 5 | H2 | g | 4 | H2N | 0.00 | 0.04 | 0.02 | 0.28 | 1.50 | 0 | +0 2D-NOESY |
| 179 | f | 3 | H2 | w | 2 | H2N | 0.00 | 0.04 | 0.02 | 0.28 | 1.70 | 0 | +0 2D-NOESY |
| 14 | g | 4 | H3 | g | 4 | H2N | −14.00 | 2.80 | −12.00 | 0.30 | 2.10 | 0 | +2 15N-ROESY-HSQC |
| 158 | g | 4 | H62 | g | 4 | H2N | 0.00 | 0.04 | 0.02 | 0.30 | 1.80 | 0 | +0 2D-NOESY |
| 126 | w' | 1 | H4 | w' | 1 | H3 | −0.37 | 0.35 | 0.06 | 0.30 | 1.80 | 0 | +1 RDC |
| 193 | w | 2 | H1 | w' | 1 | H2 | 0.00 | 0.04 | 0.02 | 0.30 | 1.80 | 0 | +0 2D-NOESY |
| 176 | w | 2 | H62 | w | 2 | H2N | 0.00 | 0.04 | 0.02 | 0.31 | 1.80 | 0 | +0 2D-NOESY |
| 59 | w | 2 | H2N | w | 2 | H2N | 250.00 | 100.00 | 190.00 | 0.31 | 1.90 | 0 | +0 2D-NOESY |
| 6 | a | 6 | H2N | a | 6 | H2N | 1900.00 | 770.00 | 2400.00 | 0.31 | 1.90 | 0 | +0 15N-NOESY-HSQC |
| 43 | g | 4 | H1 | g | 4 | H5 | −85.00 | 43.00 | −60.00 | 0.32 | 2.00 | 0 | +1 2D-ROESY |
| 27 | w' | 1 | C1 | w' | 1 | H1 | 1.40 | 0.35 | 1.80 | 0.33 | 2.90 | 0 | +0 RDC |
| 109 | a' | 5 | H4 | a' | 5 | H3 | 1.40 | 0.35 | 0.88 | 0.33 | 2.10 | 0 | +1 RDC |
| 25 | a' | 5 | H3 | a' | 5 | H1 | −20.00 | 9.90 | −26.00 | 0.36 | 2.50 | 0 | +0 2D-ROESY |
| 181 | w | 2 | H1M | w | 2 | H4 | 0.00 | 0.08 | 0.05 | 0.36 | 2.40 | 0 | +2 2D-NOESY |
| 18 | g | 4 | H2N | g | 4 | H2N | 350.00 | 70.00 | 390.00 | 0.37 | 3.20 | 0 | +0 15N-ROESY-HSQC |
| 25 | w | 2 | C4 | w | 2 | H4 | 5.30 | 0.35 | 4.70 | 0.37 | 3.00 | 0 | +0 RDC |
| 15 | g | 4 | C4 | g | 4 | H4 | 5.40 | 0.35 | 4.70 | 0.37 | 2.90 | 0 | +0 RDC |
| 19 | a' | 5 | H3 | a' | 5 | H1 | 6.50 | 2.60 | 4.90 | 0.38 | 2.80 | 0 | +0 2D-NOESY |
| 13 | g | 4 | H1M | g | 4 | H2N | −18.00 | 3.60 | −16.00 | 0.38 | 3.10 | 0 | +2 15N-ROESY-HSQC |
| 8 | a' | 5 | C1 | a' | 5 | H1 | 4.40 | 0.35 | 3.80 | 0.38 | 3.20 | 0 | +0 RDC |
| 19 | g | 4 | H2N | g | 4 | H2N | 3000.00 | 1200.00 | 2200.00 | 0.38 | 2.80 | 0 | +0 15N-NOESY-HSQC |
| 167 | w' | 1 | H1 | w | 2 | H1 | 0.00 | 0.54 | 0.33 | 0.38 | 2.70 | 0 | +0 2D-NOESY |
| 164 | g | 4 | H1M | g | 4 | H5 | 0.00 | 0.06 | 0.04 | 0.39 | 2.90 | 0 | +2 2D-NOESY |
| 149 | w | 2 | H1M | f | 3 | H4 | 0.00 | 0.11 | 0.07 | 0.40 | 3.20 | 0 | +2 2D-NOESY |
| 18 | a' | 5 | H1 | a' | 5 | H1 | 280.00 | 110.00 | 210.00 | 0.40 | 3.10 | 0 | +0 2D-NOESY |
| 115 | f | 3 | H1 | f | 3 | H2 | −0.19 | 0.35 | 0.07 | 0.41 | 3.30 | 0 | +0 RDC |
| 66 | w | 2 | H1 | w | 2 | H1 | 260.00 | 100.00 | 190.00 | 0.42 | 3.50 | 0 | +0 2D-NOESY |
| 5 | a | 6 | H1 | a | 6 | H5 | −4.60 | 2.30 | −3.10 | 0.43 | 3.50 | 0 | +0 2D-ROESY |
| 8 | a' | 5 | H3 | a | 6 | H2N | 0.14 | 0.07 | 0.09 | 0.44 | 4.00 | 0 | +0 2D-NOESY |
| 19 | f | 3 | C3 | f | 3 | H3 | 4.60 | 0.35 | 4.10 | 0.46 | 5.50 | 0 | +0 RDC |
| 5 | a | 6 | H1 | a | 6 | H2N | 22.00 | 9.00 | 16.00 | 0.47 | 4.20 | 0 | +0 15N-NOESY-HSQC |
| 28 | w' | 1 | C2 | w' | 1 | H2 | 2.60 | 0.35 | 2.10 | 0.47 | 6.40 | 0 | +0 RDC |
| 13 | g | 4 | C2 | g | 4 | H2 | 5.40 | 0.35 | 4.60 | 0.48 | 4.80 | 0 | +0 RDC |
| 106 | a' | 5 | H1 | a' | 5 | H2 | 0.78 | 0.35 | 0.38 | 0.49 | 4.90 | 0 | +0 RDC |
| 36 | f | 3 | H4 | f | 3 | H2 | 8.80 | 3.50 | 6.30 | 0.49 | 4.70 | 0 | +0 2D-NOESY |
| 15 | a | 6 | H2 | a | 6 | H2 | 300.00 | 120.00 | 220.00 | 0.49 | 4.70 | 0 | +0 2D-NOESY |
| 130 | a | 6 | H2 | a' | 5 | H2 | 0.00 | 0.12 | 0.09 | 0.50 | 4.90 | 0 | +0 2D-NOESY |
| 1 | 3J | 2 | H2 | 3J | 2 | H2N | 9.70 | 0.50 | 9.90 | 0.52 | 12.00 | 1 | +0 JCOUP |
| 10 | w | 2 | H2 | w | 2 | H2N | 30.00 | 12.00 | 22.00 | 0.52 | 5.20 | 0 | +0 15N-NOESY-HSQC |
| 2 | g | 4 | H2N | g | 4 | N2 | 0.57 | 0.01 | 0.57 | 0.52 | 15.00 | 0 | +0 ORDER |
| 16 | f | 3 | H1 | g | 4 | H2N | −12.00 | 2.50 | −13.00 | 0.53 | 10.00 | 0 | +0 15N-ROESY-HSQC |
| 83 | a' | 5 | H3 | g | 4 | H1 | 0.35 | 0.14 | 0.25 | 0.55 | 6.70 | 0 | +0 2D-NOESY |
| 58 | w | 2 | H1M | w' | 1 | H1 | −4.70 | 2.40 | −3.00 | 0.55 | 6.70 | 0 | +2 2D-ROESY |
| 22 | a' | 5 | H1 | a' | 5 | H5 | −24.00 | 13.00 | −34.00 | 0.55 | 5.80 | 0 | +0 2D-ROESY |
| 32 | f | 3 | H4 | f | 3 | H2 | −25.00 | 13.00 | −35.00 | 0.57 | 6.20 | 0 | +0 2D-ROESY |
| 172 | w | 2 | H61 | w | 2 | H1 | 0.00 | 0.31 | 0.24 | 0.58 | 6.30 | 0 | +0 2D-NOESY |
| 4 | a' | 5 | H1 | a | 6 | H2N | −9.50 | 1.90 | −9.80 | 0.58 | 30.00 | 0 | +0 15N-ROESY-HSQC |
| 3 | a | 6 | H2N | a | 6 | N2 | 0.51 | 0.02 | 0.50 | 0.58 | 18.00 | 0 | +0 ORDER |
| 63 | w' | 1 | H1 | w | 2 | H2N | 5.90 | 2.40 | 4.20 | 0.59 | 7.90 | 0 | +0 2D-NOESY |
| 1 | w | 2 | H2N | w | 2 | N2 | 0.44 | 0.01 | 0.44 | 0.59 | 27.00 | 0 | +0 ORDER |
| 14 | g | 4 | H1M | g | 4 | H2N | 120.00 | 48.00 | 83.00 | 0.60 | 6.90 | 0 | +2 15N-NOESY-HSQC |
| 134 | g | 4 | H4 | f | 3 | H1 | 0.00 | 0.27 | 0.21 | 0.61 | 7.20 | 0 | +0 2D-NOESY |
| 41 | g | 4 | H3 | g | 4 | H2N | 5.80 | 2.30 | 4.00 | 0.63 | 7.60 | 0 | +2 2D-NOESY |
| 55 | g | 4 | H1M | f | 3 | H3 | 0.91 | 0.37 | 0.81 | 0.64 | 20.00 | 0 | +2 2D-NOESY |
| 84 | a | 6 | H1M | a | 6 | H1 | 0.40 | 0.16 | 0.27 | 0.64 | 7.90 | 0 | +2 2D-NOESY |
| 9 | a' | 5 | H5 | a | 6 | H2N | 0.31 | 0.13 | 0.40 | 0.65 | 16.00 | 0 | +0 2D-NOESY |
| 50 | f | 3 | H1 | f | 3 | H3 | −39.00 | 19.00 | −23.00 | 0.67 | 8.60 | 0 | +0 2D-NOESY |
| 186 | w | 2 | H4 | w' | 1 | H1 | 0.00 | 0.31 | 0.26 | 0.68 | 8.80 | 0 | +0 2D-NOESY |
| 106 | a | 6 | H61 | a | 6 | H2 | 0.00 | 0.12 | 0.10 | 0.68 | 8.70 | 0 | +0 2D-NOESY |
| 43 | g | 4 | H5 | g | 4 | H2N | 0.40 | 0.16 | 0.27 | 0.69 | 9.10 | 0 | +0 2D-NOESY |
| 75 | w' | 1 | H3 | w' | 1 | H1 | 8.20 | 3.30 | 5.40 | 0.74 | 10.00 | 0 | +0 2D-NOESY |
| 143 | w | 2 | H61 | f | 3 | H2 | 0.00 | 0.09 | 0.08 | 0.75 | 11.00 | 0 | +0 2D-NOESY |
| 18 | f | 3 | C2 | f | 3 | H2 | 4.60 | 0.35 | 4.00 | 0.76 | 14.00 | 0 | +0 RDC |
| 151 | g | 4 | H61 | g | 4 | H1 | 0.00 | 0.26 | 0.23 | 0.78 | 12.00 | 0 | +0 2D-NOESY |
| 133 | g | 4 | H2N | g | 4 | N2 | −1.80 | 0.35 | −1.20 | 0.79 | 13.00 | 0 | +0 RDC |
| 124 | w' | 1 | H2 | w' | 1 | H1 | −0.37 | 0.35 | 0.55 | 0.80 | 12.00 | 0 | +1 RDC |
| 114 | g | 4 | H62 | g | 4 | H5 | −3.40 | 0.35 | −2.30 | 0.81 | 16.00 | 0 | +1 RDC |
| 29 | f | 3 | H1 | f | 3 | H1 | 310.00 | 120.00 | 200.00 | 0.84 | 13.00 | 0 | +0 2D-NOESY |

-continued

| | | | | | | | | | | | | | |
|---|---|---|---|---|---|---|---|---|---|---|---|---|---|
| 23 | a' | 5 | H2 | a | 6 | H3 | −5.60 | 2.80 | −3.10 | 0.84 | 14.00 | 0 | +0 2D-ROESY |
| 50 | g | 4 | H5 | g | 4 | H1 | 9.60 | 3.80 | 6.10 | 0.84 | 14.00 | 0 | +0 2D-NOESY |
| 2 | a | 6 | H3 | a | 6 | H2N | −13.00 | 2.60 | −15.00 | 0.85 | 15.00 | 0 | +0 15N-ROESY-HSQC |
| 13 | w | 2 | H2N | w | 2 | H2N | 3600.00 | 1400.00 | 2200.00 | 0.86 | 14.00 | 0 | +0 15N-NOESY-HSQC |
| 30 | f | 3 | H2 | f | 3 | H2 | 520.00 | 270.00 | 770.00 | 0.87 | 14.00 | 0 | +0 2D-NOESY |
| 60 | w | 2 | H3 | w | 2 | H2N | 6.40 | 2.60 | 4.00 | 0.88 | 15.00 | 0 | +2 2D-NOESY |
| 182 | w | 2 | H1M | w | 2 | H5 | 0.00 | 0.04 | 0.04 | 0.89 | 15.00 | 0 | +2 2D-NOESY |
| 54 | g | 4 | H1 | a' | 5 | H4 | −27.00 | 14.00 | −40.00 | 0.92 | 18.00 | 0 | +0 2D-ROESY |
| 12 | a | 6 | H4 | a | 6 | H1 | 0.69 | 0.28 | 0.42 | 0.95 | 17.00 | 0 | +0 2D-NOESY |
| 16 | g | 4 | H2 | g | 4 | H2N | 35.00 | 14.00 | 21.00 | 0.96 | 18.00 | 0 | +0 15N-NOESY-HSQC |
| 62 | w | 2 | H5 | w | 2 | H2N | 0.45 | 0.18 | 0.27 | 0.97 | 18.00 | 0 | +0 2D-NOESY |
| 112 | a | 6 | H61 | a | 6 | H2N | 0.00 | 0.02 | 0.02 | 0.98 | 18.00 | 0 | +0 2D-NOESY |
| 150 | g | 4 | H4 | g | 4 | H1 | 0.00 | 0.43 | 0.43 | 0.98 | 18.00 | 0 | +0 2D-NOESY |
| 26 | a' | 5 | H4 | a' | 5 | H2 | 10.00 | 4.00 | 6.10 | 0.98 | 18.00 | 0 | +0 2D-NOESY |
| 78 | w | 2 | H3 | w' | 1 | H1 | 26.00 | 10.00 | 16.00 | 0.98 | 19.00 | 0 | +1 2D-NOESY |
| 148 | a' | 5 | H3 | g | 4 | H1 | 0.00 | 0.83 | −0.82 | 0.98 | 19.00 | 0 | +0 2D-ROESY |
| 131 | a | 6 | H2N | a | 6 | N2 | 0.82 | 0.35 | 0.20 | 1.00 | 22.00 | 0 | +0 RDC |
| 117 | a | 6 | H4 | a' | 5 | H1 | 0.00 | 0.14 | 0.14 | 1.00 | 20.00 | 0 | +0 2D-NOESY |
| 52 | a' | 5 | H4 | g | 4 | H1 | −79.00 | 40.00 | −40.00 | 1.00 | 20.00 | 0 | +0 2D-ROESY |
| 113 | a | 6 | H62 | a | 6 | H2N | 0.00 | 0.02 | 0.02 | 1.10 | 23.00 | 0 | +0 2D-NOESY |
| 5 | a | 6 | H1 | a | 6 | H2N | −5.10 | 1.00 | −6.10 | 1.10 | 26.00 | 0 | +0 15N-ROESY-HSQC |
| 4 | a | 6 | H1 | a | 6 | H4 | −2.10 | 1.10 | −0.90 | 1.10 | 23.00 | 0 | +0 2D-ROESY |
| 156 | g | 4 | H62 | g | 4 | H1 | 0.00 | 0.17 | 0.18 | 1.10 | 22.00 | 0 | +0 2D-NOESY |
| 53 | w | 2 | H1 | f | 3 | H4 | −27.00 | 14.00 | −41.00 | 1.10 | 27.00 | 0 | +0 2D-ROESY |
| 114 | a | 6 | H4 | a' | 5 | H1 | 0.00 | 0.55 | −0.57 | 1.10 | 22.00 | 0 | +0 2D-ROESY |
| 57 | g | 4 | H1M | f | 3 | H1 | −4.70 | 2.40 | −2.20 | 1.20 | 27.00 | 0 | +2 2D-ROESY |
| 36 | w | 2 | H1M | w' | 1 | H3 | −3.80 | 1.90 | −1.80 | 1.20 | 31.00 | 0 | +2 2D-ROESY |
| 10 | a' | 5 | C3 | a' | 5 | H3 | 5.20 | 0.35 | 4.10 | 1.20 | 27.00 | 0 | +0 RDC |
| 30 | w' | 1 | C4 | w' | 1 | H4 | 1.10 | 0.35 | 1.90 | 1.20 | 32.00 | 0 | +0 RDC |
| 10 | a | 6 | H1 | a | 6 | H1 | 420.00 | 170.00 | 240.00 | 1.20 | 27.00 | 0 | +0 2D-NOESY |
| 177 | f | 3 | H3 | w | 2 | H2N | 0.00 | 0.04 | 0.05 | 1.30 | 33.00 | 0 | +0 2D-NOESY |
| 144 | w | 2 | H62 | f | 3 | H2 | 0.00 | 0.04 | 0.05 | 1.30 | 36.00 | 0 | +0 2D-NOESY |
| 2 | a | 6 | H1 | a | 6 | H2 | −88.00 | 44.00 | −38.00 | 1.30 | 32.00 | 0 | +0 2D-ROESY |
| 173 | w | 2 | H62 | w | 2 | H1 | 0.00 | 0.16 | 0.18 | 1.30 | 30.00 | 0 | +0 2D-NOESY |
| 68 | w | 2 | H5 | w | 2 | H1 | 12.00 | 4.60 | 6.20 | 1.30 | 34.00 | 0 | +0 2D-NOESY |
| 171 | w | 2 | H4 | w | 2 | H1 | 0.00 | 0.37 | 0.43 | 1.30 | 34.00 | 0 | +0 2D-NOESY |
| 14 | a | 6 | H1 | a | 6 | H2 | 12.00 | 5.00 | 6.40 | 1.40 | 40.00 | 0 | +0 2D-ROESY |
| 108 | a | 6 | H5 | a | 6 | H2 | 0.00 | 0.38 | 0.44 | 1.40 | 35.00 | 0 | +0 2D-NOESY |
| 130 | a' | 5 | H1 | a' | 5 | H2 | 1.10 | 0.35 | 0.38 | 1.40 | 38.00 | 0 | +0 RDC |
| 6 | a | 6 | H2 | a | 6 | H1 | −92.00 | 46.00 | −38.00 | 1.40 | 37.00 | 0 | +0 2D-ROESY |
| 73 | w | 2 | H1M | w' | 1 | H3 | 0.57 | 0.23 | 0.76 | 1.40 | 92.00 | 0 | +2 2D-NOESY |
| 46 | f | 3 | H1 | g | 4 | H2 | −9.50 | 4.70 | −3.90 | 1.40 | 39.00 | 0 | +1 2D-ROESY |
| 12 | a | 6 | H1 | w | 2 | H2N | 75.00 | 30.00 | 40.00 | 1.40 | 36.00 | 0 | +0 15N-NOESY-HSQC |
| 38 | w' | 1 | H1 | w' | 1 | H1 | 620.00 | 310.00 | 990.00 | 1.40 | 36.00 | 0 | +0 2D-NOESY |
| 105 | a' | 5 | H1 | a | 6 | H1 | 0.00 | 0.05 | 0.06 | 1.40 | 38.00 | 0 | +0 2D-NOESY |
| 180 | w | 2 | H1M | w | 2 | H3 | 0.00 | 0.24 | 0.29 | 1.50 | 41.00 | 0 | +2 2D-NOESY |
| 77 | w | 2 | H2 | w' | 1 | H1 | 0.91 | 0.37 | 0.46 | 1.50 | 43.00 | 0 | +0 2D-NOESY |
| 70 | f | 3 | H2 | w | 2 | H1 | 0.51 | 0.20 | 0.27 | 1.50 | 43.00 | 0 | +0 2D-NOESY |
| 7 | a' | 5 | H5 | a | 6 | H2N | 7.90 | 3.30 | 3.90 | 1.50 | 46.00 | 0 | +0 15N-NOESY-HSQC |
| 9 | a' | 5 | C2 | a' | 5 | H2 | 5.30 | 0.35 | 4.10 | 1.60 | 53.00 | 0 | +0 RDC |
| 8 | w | 2 | H3 | w | 2 | H2N | −16.00 | 3.30 | −12.00 | 1.60 | 47.00 | 0 | +2 15N-ROESY-HSQC |
| 45 | f | 3 | H2 | g | 4 | H2N | 0.19 | 0.08 | 0.09 | 1.60 | 48.00 | 0 | +0 2D-NOESY |
| 45 | g | 4 | H2 | f | 3 | H1 | −11.00 | 5.30 | −3.90 | 1.60 | 50.00 | 0 | +1 2D-ROESY |
| 69 | f | 3 | H4 | w | 2 | H1 | 16.00 | 6.20 | 7.80 | 1.60 | 47.00 | 0 | +0 2D-NOESY |
| 11 | w | 2 | H1 | w | 2 | H2N | −19.00 | 3.70 | −14.00 | 1.70 | 58.00 | 0 | +0 15N-ROESY-HSQC |
| 64 | w' | 1 | H2 | w | 2 | H2N | 0.20 | 0.08 | 0.10 | 1.70 | 57.00 | 0 | +0 2D-NOESY |
| 7 | a | 6 | H2 | a | 6 | H2 | 2000.00 | 1000.00 | 690.00 | 1.70 | 55.00 | 0 | +0 2D-ROESY |
| 33 | g | 4 | H3 | f | 3 | H1 | 26.00 | 10.00 | 12.00 | 1.70 | 55.00 | 0 | +1 2D-NOESY |
| 1 | a | 6 | H1 | a | 6 | H1 | 2400.00 | 1200.00 | 820.00 | 1.70 | 56.00 | 0 | +0 2D-NOESY |
| 49 | g | 4 | H1 | a' | 5 | H3 | −2.90 | 1.60 | −0.82 | 1.70 | 54.00 | 0 | +0 2D-ROESY |
| 12 | a | 6 | H1M | a | 6 | H1 | −1.80 | 0.91 | −0.60 | 1.70 | 55.00 | 0 | +2 2D-ROESY |
| 10 | w' | 1 | H1 | w | 2 | H2N | −13.00 | 2.60 | −16.00 | 1.70 | 82.00 | 0 | +0 15N-ROESY-HSQC |
| 15 | g | 4 | H2 | g | 4 | H2N | −11.00 | 2.10 | −7.90 | 1.70 | 59.00 | 0 | +0 15N-ROESY-HSQC |
| 110 | g | 4 | H1 | g | 4 | H2 | −0.36 | 0.35 | 0.54 | 1.80 | 61.00 | 0 | +0 RDC |
| 32 | g | 4 | H2 | f | 3 | H1 | 0.91 | 0.37 | 0.42 | 1.80 | 63.00 | 0 | +0 2D-NOESY |
| 59 | g | 4 | H1M | g | 4 | H1 | −1.30 | 0.65 | −0.42 | 1.80 | 60.00 | 0 | +2 2D-ROESY |
| 60 | w | 2 | H1M | w | 2 | H1 | −1.30 | 0.65 | −0.41 | 1.80 | 63.00 | 0 | +2 2D-ROESY |
| 65 | w' | 1 | H3 | w | 2 | H2N | 0.34 | 0.14 | 0.15 | 1.80 | 68.00 | 0 | +0 2D-NOESY |
| 4 | a' | 5 | H1 | a | 6 | H2N | 59.00 | 24.00 | 27.00 | 1.90 | 71.00 | 0 | +0 15N-NOESY-HSQC |
| 30 | f | 3 | H3 | f | 3 | H1 | 9.80 | 3.90 | 4.50 | 1.90 | 66.00 | 0 | +0 2D-NOESY |
| 134 | a | 6 | H2N | a | 6 | N2 | 1.10 | 0.35 | 0.20 | 1.90 | 76.00 | 0 | +0 RDC |
| 10 | a | 6 | H3 | a' | 5 | H1 | −37.00 | 18.00 | −12.00 | 1.90 | 67.00 | 0 | +0 2D-ROESY |
| 18 | g | 4 | H1 | g | 4 | H2N | 90.00 | 36.00 | 40.00 | 1.90 | 70.00 | 0 | +0 15N-NOESY-HSQC |
| 51 | a' | 5 | H4 | g | 4 | H1 | 17.00 | 6.80 | 7.50 | 2.00 | 74.00 | 0 | +0 2D-NOESY |
| 6 | a | 6 | H2N | a | 6 | H2N | 330.00 | 66.00 | 430.00 | 2.00 | 77.00 | 0 | +0 15N-ROESY-HSQC |
| 114 | a | 6 | H5 | a | 6 | H2N | 0.00 | 0.15 | 0.21 | 2.00 | 74.00 | 0 | +0 2D-NOESY |
| 111 | a' | 5 | H2 | a | 6 | H2 | 0.00 | 0.06 | 0.09 | 2.00 | 78.00 | 0 | +0 2D-NOESY |
| 3 | 3J | 6 | H2 | 3J | 6 | H2N | 9.40 | 0.50 | 10.00 | 2.00 | 82.00 | 1 | +0 JCOUP |
| 55 | g | 4 | H1 | g | 4 | H3 | −14.00 | 8.20 | −26.00 | 2.00 | 74.00 | 0 | +2 2D-ROESY |

-continued

| | | | | | | | | | | | | | |
|---|---|---|---|---|---|---|---|---|---|---|---|---|---|
| 3 | a | 6 | C3 | a | 6 | H3 | −1.10 | 0.35 | −0.31 | 2.00 | 88.00 | 0 | +0 RDC |
| 34 | w | 2 | H4 | w' | 1 | H1 | −3.10 | 1.50 | −0.89 | 2.00 | 76.00 | 0 | +0 2D-ROESY |
| 46 | f | 3 | H3 | g | 4 | H2N | 0.33 | 0.13 | 0.14 | 2.10 | 82.00 | 0 | +0 2D-NOESY |
| 56 | w | 2 | H1 | w | 2 | H3 | −14.00 | 8.20 | −26.00 | 2.10 | 89.00 | 0 | +2 2D-ROESY |
| 47 | f | 3 | H3 | w | 2 | H1 | −4.10 | 2.30 | −0.78 | 2.10 | 85.00 | 0 | +0 2D-ROESY |
| 3 | a | 6 | H1 | a | 6 | H3 | −11.00 | 5.40 | −2.70 | 2.10 | 84.00 | 0 | +0 2D-ROESY |
| 27 | a | 6 | H3 | a' | 5 | H2 | 1.30 | 0.53 | 0.56 | 2.10 | 83.00 | 0 | +0 2D-NOESY |
| 72 | w | 2 | H1M | w | 2 | H2 | 1.00 | 0.42 | 0.42 | 2.20 | 88.00 | 0 | +2 2D-NOESY |
| 56 | g | 4 | H1M | g | 4 | H2 | 1.00 | 0.41 | 0.42 | 2.20 | 91.00 | 0 | +2 2D-NOESY |
| 16 | a' | 5 | H1 | a | 6 | H2 | −5.50 | 2.80 | −1.40 | 2.20 | 95.00 | 0 | +0 2D-ROESY |
| 67 | w | 2 | H3 | w | 2 | H1 | 14.00 | 5.40 | 5.40 | 2.20 | 95.00 | 0 | +1 2D-NOESY |
| 194 | w | 2 | H1M | w' | 1 | H2 | 0.00 | 0.08 | 0.12 | 2.20 | 98.00 | 0 | +2 2D-NOESY |
| 49 | g | 4 | H3 | g | 4 | H1 | 13.00 | 5.10 | 5.20 | 2.20 | 89.00 | 0 | +1 2D-NOESY |
| 62 | w | 2 | H1M | w | 2 | H2 | −4.20 | 2.10 | −0.99 | 2.30 | 100.00 | 0 | +2 2D-ROESY |
| 7 | w | 2 | H1M | w | 2 | H2N | −23.00 | 4.60 | −16.00 | 2.30 | 100.00 | 0 | +2 15N-ROESY-HSQC |
| 11 | a | 6 | H3 | a | 6 | H1 | 1.40 | 0.56 | 0.56 | 2.30 | 100.00 | 0 | +0 2D-NOESY |
| 33 | g | 4 | H1M | f | 3 | H3 | −7.80 | 3.90 | −1.90 | 2.30 | 110.00 | 0 | +2 2D-NOESY |
| 61 | g | 4 | H1M | g | 4 | H2 | −4.20 | 2.10 | −0.99 | 2.30 | 100.00 | 0 | +2 2D-ROESY |
| 11 | w' | 1 | H1 | w | 2 | H2N | 110.00 | 44.00 | 41.00 | 2.40 | 110.00 | 0 | +0 15N-NOESY-HSQC |
| 174 | f | 3 | H3 | w | 2 | H1 | 0.00 | 0.16 | 0.25 | 2.40 | 110.00 | 0 | +0 2D-NOESY |
| 82 | w' | 1 | H5 | w' | 1 | H2 | 1.30 | 0.56 | 0.47 | 2.40 | 110.00 | 0 | +0 2D-NOESY |
| 107 | a | 6 | H62 | a | 6 | H2 | 0.00 | 0.11 | 0.17 | 2.40 | 110.00 | 0 | +0 2D-NOESY |
| 4 | a | 6 | C5 | a | 6 | H5 | −1.20 | 0.35 | −0.42 | 2.40 | 120.00 | 0 | +0 RDC |
| 48 | a' | 5 | H3 | g | 4 | H1 | −6.90 | 3.90 | −0.82 | 2.50 | 120.00 | 0 | +0 2D-ROESY |
| 17 | a' | 5 | H1 | a | 6 | H3 | −57.00 | 28.00 | −12.00 | 2.50 | 120.00 | 0 | +0 2D-ROESY |
| 37 | w' | 1 | H1 | w | 2 | H4 | −4.50 | 2.20 | −0.89 | 2.50 | 120.00 | 0 | +0 2D-ROESY |
| 13 | a | 6 | H1M | a | 6 | H2 | −4.90 | 2.50 | −0.95 | 2.50 | 120.00 | 0 | +2 2D-ROESY |
| 14 | a | 6 | H1M | a | 6 | H3 | −2.50 | 1.30 | −0.46 | 2.50 | 120.00 | 0 | +2 2D-ROESY |
| 163 | g | 4 | H1M | g | 4 | H4 | 0.00 | 0.03 | 0.05 | 2.50 | 120.00 | 0 | +2 2D-NOESY |
| 17 | f | 3 | H1 | g | 4 | H2N | 100.00 | 42.00 | 39.00 | 2.50 | 120.00 | 0 | +0 15N-NOESY-HSQC |
| 52 | a' | 5 | H2 | g | 4 | H1 | 0.71 | 0.28 | 0.25 | 2.70 | 140.00 | 0 | +0 2D-NOESY |
| 22 | a | 6 | H2 | a' | 5 | H1 | 0.85 | 0.34 | 0.30 | 2.70 | 130.00 | 0 | +0 2D-NOESY |
| 54 | g | 4 | H1 | a' | 5 | H3 | 0.71 | 0.28 | 0.25 | 2.70 | 140.00 | 0 | +0 2D-NOESY |
| 131 | a | 6 | H4 | a' | 5 | H2 | 0.00 | 0.20 | 0.33 | 2.70 | 140.00 | 0 | +0 2D-NOESY |
| 80 | w | 2 | H1 | f | 3 | H3 | 0.71 | 0.28 | 0.25 | 2.80 | 150.00 | 0 | +0 2D-NOESY |
| 15 | g | 4 | H3 | g | 4 | H2N | 120.00 | 47.00 | 38.00 | 2.90 | 160.00 | 0 | +2 15N-NOESY-HSQC |
| 21 | a' | 5 | H1 | a' | 5 | H4 | −18.00 | 9.90 | −1.30 | 2.90 | 160.00 | 0 | +0 2D-ROESY |
| 9 | w | 2 | H3 | w | 2 | H2N | 130.00 | 51.00 | 39.00 | 3.00 | 170.00 | 0 | +2 15N-NOESY-HSQC |
| 111 | g | 4 | H2 | g | 4 | H1 | 2.30 | 0.35 | 0.84 | 3.00 | 170.00 | 0 | +1 RDC |
| 37 | w | 2 | H1 | f | 3 | H2 | 0.91 | 0.37 | 0.27 | 3.00 | 170.00 | 0 | +0 2D-NOESY |
| 2 | a | 6 | C2 | a | 6 | H2 | 0.69 | 0.35 | −0.26 | 3.10 | 210.00 | 0 | +0 RDC |
| 20 | f | 3 | C4 | f | 3 | H4 | 2.60 | 0.35 | 4.10 | 3.10 | 180.00 | 0 | +0 RDC |
| 21 | a' | 5 | H5 | a' | 5 | H1 | 21.00 | 8.40 | 6.30 | 3.10 | 180.00 | 0 | +0 2D-NOESY |
| 26 | w | 2 | CME | w | 2 | H1M | −1.80 | 0.35 | −3.70 | 3.20 | 200.00 | 0 | +2 RDC |
| 142 | g | 4 | H1M | f | 3 | H2 | 0.00 | 0.06 | 0.11 | 3.20 | 200.00 | 0 | +2 2D-NOESY |
| 18 | a' | 5 | H1 | a | 6 | H4 | −6.00 | 3.00 | −0.57 | 3.20 | 190.00 | 0 | +0 2D-ROESY |
| 9 | a | 6 | H2 | a' | 5 | H1 | −13.00 | 6.50 | −1.40 | 3.20 | 190.00 | 0 | +0 2D-NOESY |
| 121 | w | 2 | H2 | w | 2 | H1 | 2.50 | 0.35 | 0.92 | 3.20 | 190.00 | 0 | +1 RDC |
| 9 | w | 2 | H2 | w | 2 | H2N | −12.00 | 2.50 | −8.00 | 3.30 | 210.00 | 0 | +0 15N-ROESY-HSQC |
| 34 | f | 3 | H1 | g | 4 | H4 | 0.80 | 0.32 | 0.21 | 3.40 | 220.00 | 0 | +0 2D-NOESY |
| 26 | a' | 5 | H4 | a' | 5 | H1 | −17.00 | 8.60 | −1.30 | 3.40 | 220.00 | 0 | +0 2D-NOESY |
| 115 | a' | 5 | H4 | a | 6 | H2N | 0.00 | 0.02 | 0.04 | 3.50 | 250.00 | 0 | +0 2D-NOESY |
| 35 | w | 2 | H1M | w' | 1 | H2 | −4.00 | 2.00 | −0.24 | 3.50 | 230.00 | 0 | +2 2D-ROESY |
| 3 | a | 6 | H2 | a | 6 | H2N | 13.00 | 5.10 | 22.00 | 3.60 | 240.00 | 0 | +0 15N-NOESY-HSQC |
| 17 | a' | 5 | H1 | a | 6 | H2 | 1.60 | 0.64 | 0.30 | 3.90 | 290.00 | 0 | +0 2D-NOESY |
| 20 | a' | 5 | H4 | a' | 5 | H1 | 2.00 | 0.80 | 0.43 | 3.90 | 280.00 | 0 | +0 2D-NOESY |
| 1 | a | 6 | H1M | a | 6 | H2N | 49.00 | 20.00 | 88.00 | 3.90 | 290.00 | 0 | +2 15N-NOESY-HSQC |
| 28 | g | 4 | H1 | a' | 5 | H2 | 1.20 | 0.48 | 0.25 | 3.90 | 290.00 | 0 | +0 2D-NOESY |
| 7 | a | 6 | CME | a | 6 | H1M | −1.10 | 0.35 | −3.30 | 3.90 | 290.00 | 0 | +2 RDC |
| 23 | a | 6 | H3 | a' | 5 | H1 | 10.00 | 4.10 | 2.10 | 3.90 | 300.00 | 0 | +0 2D-NOESY |
| 5 | a | 6 | H4 | a | 6 | H2N | 0.09 | 0.05 | 0.19 | 4.20 | 340.00 | 0 | +0 2D-NOESY |
| 3 | a | 6 | H2N | a | 6 | H2N | 110.00 | 44.00 | 200.00 | 4.40 | 360.00 | 0 | +0 2D-NOESY |
| 103 | a | 6 | H4 | a | 6 | H3 | 3.10 | 0.35 | 0.80 | 4.90 | 450.00 | 0 | +1 RDC |
| 16 | a | 6 | H4 | a | 6 | H2 | 3.20 | 1.30 | 6.30 | 5.70 | 630.00 | 0 | +0 2D-NOESY |
| 4 | a | 6 | H3 | a | 6 | H2N | 2.10 | 0.84 | 4.10 | 5.90 | 670.00 | 0 | +0 2D-NOESY |
| 16 | g | 4 | CME | g | 4 | H1M | −1.60 | 0.35 | −4.20 | 6.00 | 700.00 | 0 | +2 RDC |
| 6 | a | 6 | C6 | a | 6 | H62 | −0.83 | 0.35 | −2.20 | 6.00 | 760.00 | 0 | +0 RDC |
| 1 | a | 6 | H1M | a | 6 | H2N | 4.80 | 1.90 | 9.80 | 7.00 | 940.00 | 0 | +2 2D-NOESY |
| 24 | a | 6 | H1M | a' | 5 | H1 | 0.66 | 0.27 | 1.40 | 8.40 | 1500.00 | 0 | +2 2D-NOESY |
| 104 | a | 6 | H5 | a | 6 | H4 | 6.50 | 0.35 | 2.10 | 10.00 | 2000.00 | 0 | +2 RDC |

PDB Coordinate for the Final Optimized Mean Structure

| ATOM | 1 | C1 | BGLA | 1 | 7.691 | 2.111 | −7.763 | 0.00 | 0.00 | MOLG |
|---|---|---|---|---|---|---|---|---|---|---|
| ATOM | 2 | H1 | BGLA | 1 | 8.059 | 1.588 | −6.861 | 0.00 | 0.00 | MOLG |
| ATOM | 3 | C5 | BGLA | 1 | 9.670 | 3.603 | −7.779 | 0.00 | 0.00 | MOLG |

-continued

| | | | | | | | | | |
|---|---|---|---|---|---|---|---|---|---|
| ATOM | 4 | H5 | BGLA | 1 | 10.044 | 3.071 | −6.900 | 0.00 | 0.00 | MOLG |
| ATOM | 5 | O5 | BGLA | 1 | 8.164 | 3.516 | −7.763 | 0.00 | 0.00 | MOLG |
| ATOM | 6 | C2 | BGLA | 1 | 8.207 | 1.397 | −9.039 | 0.00 | 0.00 | MOLG |
| ATOM | 7 | H2 | BGLA | 1 | 7.802 | 1.883 | −9.931 | 0.00 | 0.00 | MOLG |
| ATOM | 8 | O2 | BGLA | 1 | 7.727 | 0.020 | −8.989 | 0.00 | 0.00 | MOLG |
| ATOM | 9 | HO2 | BGLA | 1 | 6.766 | 0.035 | −8.859 | 0.00 | 0.00 | MOLG |
| ATOM | 10 | C3 | BGLA | 1 | 9.760 | 1.421 | −9.062 | 0.00 | 0.00 | MOLG |
| ATOM | 11 | H3 | BGLA | 1 | 10.170 | 0.891 | −8.199 | 0.00 | 0.00 | MOLG |
| ATOM | 12 | O3 | BGLA | 1 | 10.285 | 0.826 | −10.288 | 0.00 | 0.00 | MOLG |
| ATOM | 13 | HO3 | BGLA | 1 | 11.200 | 1.126 | −10.344 | 0.00 | 0.00 | MOLG |
| ATOM | 14 | C4 | BGLA | 1 | 10.199 | 2.907 | −9.055 | 0.00 | 0.00 | MOLG |
| ATOM | 15 | H4 | BGLA | 1 | 9.830 | 3.427 | −9.944 | 0.00 | 0.00 | MOLG |
| ATOM | 16 | O4 | BGLA | 1 | 11.653 | 2.950 | −9.050 | 0.00 | 0.00 | MOLG |
| ATOM | 17 | HO4 | BGLA | 1 | 11.900 | 3.778 | −8.585 | 0.00 | 0.00 | MOLG |
| ATOM | 18 | C6 | BGLA | 1 | 10.281 | 5.059 | −7.707 | 0.00 | 0.00 | MOLG |
| ATOM | 19 | O6A | BGLA | 1 | 9.961 | 6.060 | −8.777 | 0.00 | 0.00 | MOLG |
| ATOM | 20 | O6B | BGLA | 1 | 11.179 | 5.440 | −6.568 | 0.00 | 0.00 | MOLG |
| ATOM | 21 | C1 | BNAG | 2 | 3.985 | 2.018 | −4.633 | 0.00 | 0.00 | MOLG |
| ATOM | 22 | H1 | BNAG | 2 | 4.770 | 2.300 | −3.906 | 0.00 | 0.00 | MOLG |
| ATOM | 23 | C5 | BNAG | 2 | 4.039 | 4.308 | −5.526 | 0.00 | 0.00 | MOLG |
| ATOM | 24 | H5 | BNAG | 2 | 4.800 | 4.573 | −4.786 | 0.00 | 0.00 | MOLG |
| ATOM | 25 | O5 | BNAG | 2 | 3.182 | 3.221 | −4.965 | 0.00 | 0.00 | MOLG |
| ATOM | 26 | C2 | BNAG | 2 | 4.680 | 1.479 | −5.917 | 0.00 | 0.00 | MOLG |
| ATOM | 27 | H2 | BNAG | 2 | 3.914 | 1.224 | −6.654 | 0.00 | 0.00 | MOLG |
| ATOM | 28 | N2 | BNAG | 2 | 5.432 | 0.253 | −5.593 | 0.00 | 0.00 | MOLG |
| ATOM | 29 | H2N | BNAG | 2 | 6.154 | 0.353 | −4.885 | 0.00 | 0.00 | MOLG |
| ATOM | 30 | C2N | BNAG | 2 | 5.210 | −0.956 | −6.161 | 0.00 | 0.00 | MOLG |
| ATOM | 31 | O2N | BNAG | 2 | 4.352 | −1.117 | −7.016 | 0.00 | 0.00 | MOLG |
| ATOM | 32 | CME | BNAG | 2 | 6.096 | −2.120 | −5.674 | 0.00 | 0.00 | MOLG |
| ATOM | 33 | H1M | BNAG | 2 | 6.665 | −2.531 | −6.516 | 0.00 | 0.00 | MOLG |
| ATOM | 34 | H2M | BNAG | 2 | 6.804 | −1.776 | −4.910 | 0.00 | 0.00 | MOLG |
| ATOM | 35 | H3M | BNAG | 2 | 5.464 | −2.908 | −5.253 | 0.00 | 0.00 | MOLG |
| ATOM | 36 | C3 | BNAG | 2 | 5.607 | 2.582 | −6.488 | 0.00 | 0.00 | MOLG |
| ATOM | 37 | H3 | BNAG | 2 | 6.377 | 2.843 | −5.755 | 0.00 | 0.00 | MOLG |
| ATOM | 38 | O3 | BNAG | 2 | 6.222 | 2.111 | −7.763 | 0.00 | 0.00 | MOLG |
| ATOM | 39 | C4 | BNAG | 2 | 4.733 | 3.810 | −6.818 | 0.00 | 0.00 | MOLG |
| ATOM | 40 | H4 | BNAG | 2 | 3.990 | 3.555 | −7.579 | 0.00 | 0.00 | MOLG |
| ATOM | 41 | O4 | BNAG | 2 | 5.567 | 4.882 | −7.313 | 0.00 | 0.00 | MOLG |
| ATOM | 42 | HO4 | BNAG | 2 | 6.342 | 4.516 | −7.773 | 0.00 | 0.00 | MOLG |
| ATOM | 43 | C6 | BNAG | 2 | 3.148 | 5.542 | −5.770 | 0.00 | 0.00 | MOLG |
| ATOM | 44 | H61 | BNAG | 2 | 2.698 | 5.885 | −4.837 | 0.00 | 0.00 | MOLG |
| ATOM | 45 | H62 | BNAG | 2 | 3.745 | 6.358 | −6.183 | 0.00 | 0.00 | MOLG |
| ATOM | 46 | O6 | BNAG | 2 | 2.094 | 5.219 | −6.701 | 0.00 | 0.00 | MOLG |
| ATOM | 47 | HO6 | BNAG | 2 | 2.474 | 4.705 | −7.423 | 0.00 | 0.00 | MOLG |
| ATOM | 48 | C1 | BGLA | 3 | 0.306 | 1.365 | −0.794 | 0.00 | 0.00 | MOLG |
| ATOM | 49 | H1 | BGLA | 3 | −0.326 | 0.548 | −1.190 | 0.00 | 0.00 | MOLG |
| ATOM | 50 | C5 | BGLA | 3 | 2.356 | 0.358 | −1.767 | 0.00 | 0.00 | MOLG |
| ATOM | 51 | H5 | BGLA | 3 | 1.730 | −0.433 | −2.191 | 0.00 | 0.00 | MOLG |
| ATOM | 52 | O5 | BGLA | 3 | 1.679 | 0.867 | −0.520 | 0.00 | 0.00 | MOLG |
| ATOM | 53 | C2 | BGLA | 3 | 0.392 | 2.529 | −1.819 | 0.00 | 0.00 | MOLG |
| ATOM | 54 | H2 | BGLA | 3 | 0.971 | 3.355 | −1.399 | 0.00 | 0.00 | MOLG |
| ATOM | 55 | O2 | BGLA | 3 | −0.967 | 2.987 | −2.078 | 0.00 | 0.00 | MOLG |
| ATOM | 56 | HO2 | BGLA | 3 | −1.370 | 3.241 | −1.232 | 0.00 | 0.00 | MOLG |
| ATOM | 57 | C3 | BGLA | 3 | 1.038 | 2.028 | −3.138 | 0.00 | 0.00 | MOLG |
| ATOM | 58 | H3 | BGLA | 3 | 0.438 | 1.234 | −3.591 | 0.00 | 0.00 | MOLG |
| ATOM | 59 | O3 | BGLA | 3 | 1.222 | 3.105 | −4.109 | 0.00 | 0.00 | MOLG |
| ATOM | 60 | HO3 | BGLA | 3 | 1.868 | 2.786 | −4.752 | 0.00 | 0.00 | MOLG |
| ATOM | 61 | C4 | BGLA | 3 | 2.447 | 1.511 | −2.784 | 0.00 | 0.00 | MOLG |
| ATOM | 62 | H4 | BGLA | 3 | 3.024 | 2.330 | −2.341 | 0.00 | 0.00 | MOLG |
| ATOM | 63 | O4 | BGLA | 3 | 3.089 | 1.015 | −4.032 | 0.00 | 0.00 | MOLG |
| ATOM | 64 | C6 | BGLA | 3 | 3.793 | −0.260 | −1.534 | 0.00 | 0.00 | MOLG |
| ATOM | 65 | O6A | BGLA | 3 | 4.048 | −1.705 | −1.844 | 0.00 | 0.00 | MOLG |
| ATOM | 66 | O6B | BGLA | 3 | 4.902 | 0.600 | −1.002 | 0.00 | 0.00 | MOLG |
| ATOM | 67 | C1 | BNAG | 4 | −2.406 | −0.099 | 2.989 | 0.00 | 0.00 | MOLG |
| ATOM | 68 | H1 | BNAG | 4 | −2.142 | −1.113 | 2.632 | 0.00 | 0.00 | MOLG |
| ATOM | 69 | C5 | BNAG | 4 | −0.124 | 0.167 | 3.874 | 0.00 | 0.00 | MOLG |
| ATOM | 70 | H5 | BNAG | 4 | 0.123 | −0.842 | 3.529 | 0.00 | 0.00 | MOLG |
| ATOM | 71 | O5 | BNAG | 4 | −1.584 | 0.226 | 4.180 | 0.00 | 0.00 | MOLG |
| ATOM | 72 | C2 | BNAG | 4 | −2.103 | 0.920 | 1.852 | 0.00 | 0.00 | MOLG |
| ATOM | 73 | H2 | BNAG | 4 | −2.342 | 1.927 | 2.204 | 0.00 | 0.00 | MOLG |
| ATOM | 74 | N2 | BNAG | 4 | −2.964 | 0.628 | 0.691 | 0.00 | 0.00 | MOLG |
| ATOM | 75 | H2N | BNAG | 4 | −2.865 | −0.301 | 0.290 | 0.00 | 0.00 | MOLG |
| ATOM | 76 | C2N | BNAG | 4 | −3.856 | 1.494 | 0.152 | 0.00 | 0.00 | MOLG |
| ATOM | 77 | O2N | BNAG | 4 | −4.000 | 2.626 | 0.587 | 0.00 | 0.00 | MOLG |
| ATOM | 78 | CME | BNAG | 4 | −4.681 | 0.977 | −1.043 | 0.00 | 0.00 | MOLG |
| ATOM | 79 | H1M | BNAG | 4 | −4.493 | 1.604 | −1.922 | 0.00 | 0.00 | MOLG |
| ATOM | 80 | H2M | BNAG | 4 | −4.410 | −0.056 | −1.287 | 0.00 | 0.00 | MOLG |
| ATOM | 81 | H3M | BNAG | 4 | −5.747 | 1.023 | −0.796 | 0.00 | 0.00 | MOLG |
| ATOM | 82 | C3 | BNAG | 4 | −0.597 | 0.841 | 1.484 | 0.00 | 0.00 | MOLG |

| | | | | | | | | | |
|---|---|---|---|---|---|---|---|---|---|
| ATOM | 83 | H3 | BNAG | 4 | −0.348 | −0.162 | 1.121 | 0.00 | 0.00 | MOLG |
| ATOM | 84 | O3 | BNAG | 4 | −0.271 | 1.874 | 0.459 | 0.00 | 0.00 | MOLG |
| ATOM | 85 | C4 | BNAG | 4 | 0.211 | 1.184 | 2.755 | 0.00 | 0.00 | MOLG |
| ATOM | 86 | H4 | BNAG | 4 | −0.020 | 2.201 | 3.085 | 0.00 | 0.00 | MOLG |
| ATOM | 87 | O4 | BNAG | 4 | 1.625 | 1.096 | 2.466 | 0.00 | 0.00 | MOLG |
| ATOM | 88 | HO4 | BNAG | 4 | 1.773 | 1.326 | 1.532 | 0.00 | 0.00 | MOLG |
| ATOM | 89 | C6 | BNAG | 4 | 0.670 | 0.451 | 5.166 | 0.00 | 0.00 | MOLG |
| ATOM | 90 | H61 | BNAG | 4 | 0.430 | −0.290 | 5.932 | 0.00 | 0.00 | MOLG |
| ATOM | 91 | H62 | BNAG | 4 | 1.743 | 0.397 | 4.969 | 0.00 | 0.00 | MOLG |
| ATOM | 92 | O6 | BNAG | 4 | 0.353 | 1.756 | 5.691 | 0.00 | 0.00 | MOLG |
| ATOM | 93 | HO6 | BNAG | 4 | 0.844 | 1.897 | 6.502 | 0.00 | 0.00 | MOLG |
| ATOM | 94 | C1 | BGLA | 5 | −5.910 | −1.910 | 6.615 | 0.00 | 0.00 | MOLG |
| ATOM | 95 | H1 | BGLA | 5 | −6.670 | −1.107 | 6.607 | 0.00 | 0.00 | MOLG |
| ATOM | 96 | C5 | BGLA | 5 | −5.539 | −1.635 | 4.179 | 0.00 | 0.00 | MOLG |
| ATOM | 97 | H5 | BGLA | 5 | −6.272 | −0.822 | 4.188 | 0.00 | 0.00 | MOLG |
| ATOM | 98 | O5 | BGLA | 5 | −5.887 | −2.588 | 5.296 | 0.00 | 0.00 | MOLG |
| ATOM | 99 | C2 | BGLA | 5 | −4.510 | −1.312 | 6.898 | 0.00 | 0.00 | MOLG |
| ATOM | 100 | H2 | BGLA | 5 | −3.762 | −2.109 | 6.944 | 0.00 | 0.00 | MOLG |
| ATOM | 101 | O2 | BGLA | 5 | −4.531 | −0.610 | 8.177 | 0.00 | 0.00 | MOLG |
| ATOM | 102 | HO2 | BGLA | 5 | −3.722 | −0.085 | 8.188 | 0.00 | 0.00 | MOLG |
| ATOM | 103 | C3 | BGLA | 5 | −4.139 | −0.290 | 5.798 | 0.00 | 0.00 | MOLG |
| ATOM | 104 | H3 | BGLA | 5 | −4.857 | 0.536 | 5.774 | 0.00 | 0.00 | MOLG |
| ATOM | 105 | O3 | BGLA | 5 | −2.803 | 0.244 | 6.051 | 0.00 | 0.00 | MOLG |
| ATOM | 106 | HO3 | BGLA | 5 | −2.411 | 0.507 | 5.203 | 0.00 | 0.00 | MOLG |
| ATOM | 107 | C4 | BGLA | 5 | −4.141 | −1.042 | 4.454 | 0.00 | 0.00 | MOLG |
| ATOM | 108 | H4 | BGLA | 5 | −3.404 | −1.851 | 4.489 | 0.00 | 0.00 | MOLG |
| ATOM | 109 | O4 | BGLA | 5 | −3.822 | −0.062 | 3.386 | 0.00 | 0.00 | MOLG |
| ATOM | 110 | C6 | BGLA | 5 | −5.563 | −2.274 | 2.735 | 0.00 | 0.00 | MOLG |
| ATOM | 111 | O6A | BGLA | 5 | −6.491 | −1.732 | 1.689 | 0.00 | 0.00 | MOLG |
| ATOM | 112 | O6B | BGLA | 5 | −4.656 | −3.424 | 2.409 | 0.00 | 0.00 | MOLG |
| ATOM | 113 | C1 | ANAG | 6 | −8.943 | −5.604 | 7.325 | 0.00 | 0.00 | MOLG |
| ATOM | 114 | H1 | ANAG | 6 | −9.890 | −5.743 | 7.876 | 0.00 | 0.00 | MOLG |
| ATOM | 115 | O1 | ANAG | 6 | −9.245 | −5.610 | 5.933 | 0.00 | 0.00 | MOLG |
| ATOM | 116 | HO1 | ANAG | 6 | −9.258 | −6.545 | 5.713 | 0.00 | 0.00 | MOLG |
| ATOM | 117 | C5 | ANAG | 6 | −6.734 | −6.650 | 6.952 | 0.00 | 0.00 | MOLG |
| ATOM | 118 | H5 | ANAG | 6 | −6.876 | −6.578 | 5.870 | 0.00 | 0.00 | MOLG |
| ATOM | 119 | O5 | ANAG | 6 | −8.078 | −6.766 | 7.626 | 0.00 | 0.00 | MOLG |
| ATOM | 120 | C2 | ANAG | 6 | −8.247 | −4.303 | 7.828 | 0.00 | 0.00 | MOLG |
| ATOM | 121 | H2 | ANAG | 6 | −8.080 | −4.392 | 8.905 | 0.00 | 0.00 | MOLG |
| ATOM | 122 | N2 | ANAG | 6 | −9.055 | −3.075 | 7.645 | 0.00 | 0.00 | MOLG |
| ATOM | 123 | H2N | ANAG | 6 | −9.292 | −2.859 | 6.686 | 0.00 | 0.00 | MOLG |
| ATOM | 124 | C2N | ANAG | 6 | −9.469 | −2.259 | 8.650 | 0.00 | 0.00 | MOLG |
| ATOM | 125 | O2N | ANAG | 6 | −9.203 | −2.480 | 9.821 | 0.00 | 0.00 | MOLG |
| ATOM | 126 | CME | ANAG | 6 | −10.298 | −1.034 | 8.221 | 0.00 | 0.00 | MOLG |
| ATOM | 127 | H1M | ANAG | 6 | −9.788 | −0.114 | 8.530 | 0.00 | 0.00 | MOLG |
| ATOM | 128 | H2M | ANAG | 6 | −10.418 | −1.031 | 7.131 | 0.00 | 0.00 | MOLG |
| ATOM | 129 | H3M | ANAG | 6 | −11.289 | −1.063 | 8.686 | 0.00 | 0.00 | MOLG |
| ATOM | 130 | C3 | ANAG | 6 | −6.886 | −4.132 | 7.117 | 0.00 | 0.00 | MOLG |
| ATOM | 131 | H3 | ANAG | 6 | −7.043 | −4.055 | 6.037 | 0.00 | 0.00 | MOLG |
| ATOM | 132 | O3 | ANAG | 6 | −6.226 | −2.913 | 7.643 | 0.00 | 0.00 | MOLG |
| ATOM | 133 | C4 | ANAG | 6 | −6.025 | −5.365 | 7.455 | 0.00 | 0.00 | MOLG |
| ATOM | 134 | H4 | ANAG | 6 | −5.858 | −5.422 | 8.534 | 0.00 | 0.00 | MOLG |
| ATOM | 135 | O4 | ANAG | 6 | −4.743 | −5.234 | 6.793 | 0.00 | 0.00 | MOLG |
| ATOM | 136 | HO4 | ANAG | 6 | −4.413 | −4.328 | 6.912 | 0.00 | 0.00 | MOLG |
| ATOM | 137 | C6 | ANAG | 6 | −5.900 | −7.917 | 7.239 | 0.00 | 0.00 | MOLG |
| ATOM | 138 | H61 | ANAG | 6 | −6.412 | −8.806 | 6.866 | 0.00 | 0.00 | MOLG |
| ATOM | 139 | H62 | ANAG | 6 | −4.930 | −7.851 | 6.742 | 0.00 | 0.00 | MOLG |
| ATOM | 140 | O6 | ANAG | 6 | −5.695 | −8.084 | 8.659 | 0.00 | 0.00 | MOLG |
| ATOM | 141 | HO6 | ANAG | 6 | −5.162 | −8.869 | 8.806 | 0.00 | 0.00 | MOLG |
| END | | | | | | | | | | |

EXAMPLE 2

Lisinopril

Lisinopril is a hydrophilic organic drug molecule (see FIG. 21) used to treat hypertension, congestive heart failure, heart attacks and is also used to prevent renal and retinal complications of diabetes. Lisinopril is an inhibitor of angiotensin converting enzyme (ACE), which catalyses the conversion of AngiotensinI to AngiotensinII (a potent vasoconstrictor) and is involved in the inactivation of bradykinin (a potent vasodilator). Historically, lisinopril was the third ACE inhibitor developed (after captopril and enalapril) and was introduced into therapy in the early 1990s. Lisinopril was developed by Merck & Co. and is marketed worldwide as Prinivil® and by AstraZeneca as Zestril®. In Australia it is marketed by AlphaPharm as Lisodur®. In this worked example, we demonstrate how the dynamic 3D-solution structure of lisinopril was determined from experimental NMR data using the methodology described in this application.

Chemical Shift Assignment and Measurement of Homonuclear Scalar-Coupling Constants Lisinopril is a peptidomimetic molecule, having a similar chemical structure to the tripeptide $NH_3$-Phe-Lys-Pro-COO. The atoms and residues in lisinopril were therefore given names based on nomenclature for this peptide (see Appendix B); the extra saturated carbon in the phenylalanine sidechain is designated CG. Since all NMR data on lisinopril was recorded at pH 6.0, the ionization state of the amine groups (i.e., the backbone secondary amine and the Lys3 sidechain primary amine) and carboxylate groups (in residues Phe1 and Pro3) can be immediately defined from the typical $pK_a$ values of these groups as shown in FIG. 21. Partial conjugation of the lone pair of electrons from the proline residue's nitrogen atom with the adjacent carbonyl double-bond results in the presence of both cis and trans stereoisomers of lisinopril in solution (FIG. 22).

The $^1H$ and $^{13}C$ chemical shifts of both stereoisomers of lisinopril at 278 K were assigned using [$^1H$-$^1H$]-COSY, [$^1H$-$^1H$]-TOCSY and natural-abundance [$^1H$-$^{13}C$]-HSQC spectra recorded at 600 MHz on a 20 mM NMR sample (100% $D_2O$, pH*6.0, 0.3 mM DSS) of lisinopril. By integration of peak volumes for resonances that were distinct for the cis and trans forms, the mole abundance ratio was determined to be 80% trans:20% cis. Since trans-lisinopril was more abundant in the mixture, it was decided at this stage to determine the dynamic 3D-structure of trans lisinopril. The proton chemical shifts for trans lisinopril are given in FIG. 23.

With the exception of the HA protons in trans lisinopril, most protons had complex spectral lineshapes due the large number of scalar-couplings present (as many as five $^2J_{HH}/^3J_{HH}$ scalar coupling in the lysine sidechain) and strong-coupling. This complexity prevented the measurement of many scalar-couplings. However, the six $^3J_{HH}$ coupling constants shown in FIG. 23 were measured.

Analysis of Spectral Lineshapes

A 2D [$^1H$, $^1H$]-T-ROESY dataset was used to provide structural restraints for trans lisinopril. This dataset was recorded with sufficient data points in the acquisition dimension to resolve proton multiplet splittings but few enough data points in the indirect dimension to prevent these splittings being resolved (i.e., simplying the analysis of proton multiplets to just the acquisition dimension). The value of λ (1.8 Hz) for this dataset was determined by measurement resonances from ROEs to the Pro3 HA proton. The scaling factor sets for each proton in trans lisinopril in this 2D [$^1H$, $^1H$]-T-ROESY dataset were determined as follows:

Pro3, HA proton: This proton has two $^3J_{HH}$ coupling constants of 6.0 and 8.0 Hz (see FIG. 24), and manifests in the spectrum as a simple doublet of doublets (i.e., as in FIG. 9, two scalar couplings). It therefore has an initial scaling factor set of $f_i=\{4, 4, 4, 4\}$. Each scaling factor is multipled by the mole abundance scaling ratio (=1/0.8) of 1.25 to give the corrected scaling factor set of $f_i=\{5, 5, 5, 5\}$.

Phe 1, HA proton: This proton would be expected to manifest in the spectrum as an ideal triplet (i.e. as shown in FIG. 10, two scalar couplings). However, chemical exchange at the secondary amine group adjacent to this proton results in a further broadening of this proton's multiplet resonances, making this multiplet appear as a broad singlet (i.e., most like FIG. 9, no scalar couplings). The scaling factor set for this proton was therefore estimated by comparing it with that of the Pro3 HA diagonal peak in the spectrum. Using the scaling factor set for Pro3 HA, i.e., f={5, 5, 5, 5}, the true peak-height for the Pro3 HA diagonal peak was determined. Since the Phe1 HA protons would be expected to give a similar true peak-height as the Pro3 HA diagonal in this spectrum, the scaling factor could be estimated as the value required to scale the observed singlet Phe1 HA diagonal peak height to the same value as the true peak height for the Pro3 HA diagonal peak. This gave an estimated scaling factor set of $f_i=\{4.5\}$.

Lys2, HA proton: This proton experienced a similar broadening to that observed for the Phe1 HA proton. It was treated in the same manner, giving an estimated scaling factor set of $f_i=\{4.1\}$.

All other protons: Had very complex lineshapes and suffered from strong-coupling. Their initial scaling-factor sets were determined using the rules for strongly-coupled protons (see above). Each scaling factor was then multiplied by the mole abundance ratio. In summary, the scaling factor sets for proton resonance multiplets in the 2D [$^1H$, $^1H$]-NOESY dataset were as follows:

| | | |
|---|---|---|
| Phe1 | HA | {4.5} |
| | HB1 | {31.8, 17.8, 7.8, 5.6, 5.1, 7.8, 17.1, 40.0} |
| | HB2 | {31.8, 17.8, 7.8, 5.6, 5.1, 7.8, 17.1, 40.0} |
| | HG1 | {30.1, 22.1, 12.6, 9.1, 7.4, 8.3, 8.5, 11.4, 23.4, 36.5} |
| | HG2 | {30.1, 22.1, 12.6, 9.1, 7.4, 8.3, 8.5, 11.4, 23.4, 36.5} |
| | HZ1 | {2.1, 3.0} |
| | HZ2 | {2.1, 3.0} |
| | HH | {6.4, 2.6, 3.9} |
| Lys2 | HA | {4.1} |
| | HB1 | {6.6, 4.0, 4.0, 6.6} |
| | HB2 | {6.6, 4.0, 4.0, 6.6} |
| | HG1 | {41.6, 17.5, 13.6, 7.6, 5.8, 6.0, 10.4, 24.3, 42.8, 90.4} |
| | HG2 | {41.6, 17.5, 13.6, 7.6, 5.8, 6.0, 10.4, 24.3, 42.8, 90.4} |
| | HD1 | {13.4, 5.4, 3.9, 5.0, 12.6} |
| | HD2 | {13.4, 5.4, 3.9, 5.0, 12.6} |
| | HE1 | {5.0, 2.5, 5.0} |
| | HE2 | {5.0, 2.5, 5.0} |
| Pro3 | HA | {5, 5, 5, 5} |
| | HB1 | {26.5, 7.0, 4.8, 5.6, 67.5, 12.4} |
| | HB2 | {5.6, 5.6, 5.6, 7.5} |
| | HG1 | {22.4, 15.0, 11.0, 9.8, 10.9, 11.4, 10.3, 11.3, 12.9, 19.6} |
| | HG2 | {22.4, 15.0, 11.0, 9.8, 10.9, 11.4, 10.3, 11.3, 12.9, 19.6} |
| | HD1 | {16.1, 9.8, 7.3, 5.3, 7.9, 8.1, 17.0} |
| | HD2 | {16.1, 9.8, 7.3, 5.3, 7.9, 8.1, 17.0} |

Measurement and Quantitation of NMR Spectra

Two different kinds of NMR data in seven different experimental NMR datasets were used in the determination of the dynamic solution structure of trans lisinopril:
1) T-ROESY relaxation data: one experimental dataset, 2D [$^1H$-$^1H$]-T-ROESY
2) Conformation-dependent scalar couplings: one experimental dataset The pertinent acquisition parameters for each of these different NMR datasets (and the number of structural restraints measured from them) were as follows. The 2D [$^1H$, $^1H$]-T-ROESY spectrum was recorded on a sample of 20 mM lisinopril (100% $D_2O$, pH*6.0, 0.3 mM DSS) at 600 MHz and 278 K with an ROE mixing time of 400 ms and sweep widths of 7200 Hz in both dimensions. Using the scaling-factor sets described above, 67 ROE structural restraints were measured from this spectrum. Errors on each ROE restraint were determined as described above, using the initial m value of 0.5 for a 2D [$^1H$, $^1H$]-T-ROESY spectrum (39 noROE structural restraints were also inferred from their absence in this spectrum). These ROE and noROE structural restraints are detailed in the dataset file given in Appendix B.

Since the proline ring is in an equilibrium between two known conformations, the two scalar coupling constants to the HA proton in this ring (see FIG. 24) do not help to define the ring's geometry any more precisely; these scalar coupling constants were therefore not used as structural restraints. The remaining four scalar coupling-constants shown in FIG. 24 could be used as structural restraints in structure calculations to help define unknown bond geometries. The best Karplus equation for relating these coupling-constants to the dihedral angle in the molecule is that typically used for $\chi^1$ sidechain geometries in proteins and peptides [39]. The combined error in measurement of the coupling (~0.3 Hz) and predictive accuracy of these Karplus relations (~0.3 Hz) is ~0.5 Hz. The four scalar coupling-constant measurements are listed in the relevant dataset file (see Appendix B).

Molecule Specification

The experimental datasets described above were both acquired in $D_2O$. In $D_2O$, all the amine protons in lisinopril exchange very rapidly with solvent deuterons. These protons were therefore defined as NMR-inactive (exc 1 HN*, exc 2 HZ*). All other protons were defined as active (add*H*). The file used to specify this solvent mask was as follows:

```
remark Solvent mask for lisinopril
conditions:

solvents 1
endsection
solvent:

name d2o
add    *    H*
exc    1    HN*
exc    2    HZ*
endsection
```

The locations of the two oxygen atoms in each carboxylate group in lisinopril relative to the rest of the molecular structure could not be specified from the experimental data. These atoms were therefore set to be van der Waals inactive, as detailed in the following van der Waals input file:

```
remark Van der Waals mask for lisinopril
configuration:

vdw.cutoff 6.0
vdw.coupling 1e-4
endsection
nonbonded:

vdw * H* 0.016 0.60
vdw * C* 0.100 1.91
vdw * N* 0.170 1.82
vdw * O* 0.210 1.66
remark exclude the oxygen atoms in the carboxylate groups
exc 1 O*
exc 3 O*
endsection
```

Experimental Data Input

The value of $\tau_c$ has not been precisely measured experimentally for trans lisinopril. However, a 2D-[$^1$H, $^1$H]-NOESY spectrum recorded on the sample of 20 mM $HA_6$ (100% $D_2O$, pH 6.0, 0.3 mM DSS) at 600 MHz and 278 K (i.e., identical sample conditions to that used for the 2D [$^1$H, $^1$H]-T-ROESY) showed weak positive NOEs. The formula for the threshold value of $\tau_c$ at which NOEs become positive (see above) therefore indicates that under these conditions, trans lisinopril has a $\tau_c$ value less than 0.3 ns; the value was therefore initially set to 0.1 ns. After a few rounds of structure calculations (see above methodology), $\tau_c$ was found to prefer a value of 0.2 ns; the adjusted solvent viscosity of 100% $D_2O$ at 278 K for the 2D [$^1$H, $^1$H]-T-ROESY dataset was determined to be 1.94, using equations (22) and (23). The two experimental dataset files used in the structure calculations are given in Appendix B.

Dynamic Model

The pertinent conformationally-flexible bonds and chemistries within lisinopril were identified, using the methodology described above (see FIG. 25):

1) Four single bonds comprising the backbone of the molecule, namely, $N^{F1}$-$CA^{F1}$, $N^{F1}$-$CA^{K2}$, $CA^{K2}$-$C^{K2}$, $C^{K2}$-$N^{P3}$.
2) Proline rings adopt two major conformations in solution, termed N and S states (also termed UP and DOWN conformations, or C3'-endo and C3'-exo conformations) [15]. In the case of a trans proline ring, these are found in an ~50:50 ratio [40].
3) The carboxylate group in residue Phe1 can rotate about the $CA^{F1}$-$C^{F1}$ single bond. Similarly, the carboxylate group in residue Pro3 can rotate about the $CA^{P3}$-$C^{P3}$ single bond.
4) The five single bonds in the lysine sidechain can rotate ($CA^{K2}$-$CB^{K2}$, $CB^{K2}$-$CG^{K2}$, $CG^{K2}$-$CD^{K2}$, $CD^{K2}$-$CE^{K2}$, $CE^{K2}$-$NZ^{K2}$).
5) The three single bonds in the phenylalanine sidechain can rotate ($CA^{F1}$-$CB^{F1}$, $CB^{F1}$-$CG^{F1}$, $CG^{F1}$-$CD^{F1}$).

To create a realistic dynamic model of the molecule that could be used to optimise against the observed experimental data, the following degrees of freedom were modelled in the dynamic model file (see below):

1) The $N^{F1}$-$CA^{F1}$ and $N^{F1}$-$CA^{K2}$ bonds are between $sp^3$-hybridised atoms and therefore require a trimodal model. The three rotamer states (gt, tg, gg) were specified with variables 1, 2 and 3 (which remain fixed throughout the iterative optimisation) and each bond was given its own Gaussian spread value (var 4 and var 5, respectively), which was allowed to vary throughout the optimisation. The relative populations of the three rotamer states for each bond were allowed to vary throughout the optimisation, with probabilities mode 1 and mode 2, respectively. The $CA^{K2}$-$C^{K2}$ bond is between an $sp^3$-hybridised atom ($CA^{K2}$) and an $sp^2$ hybridised atom ($C^{K2}$) and therefore requires a bimodal model. This was modelled with two mean values (var 8 and 10) that were allowed to vary throughout the optimisation, and two different Gaussian spread values (var 9 and 11). The relative proportion of these two conformations was allowed to vary with probability mode 3. Since only the trans form of lisinopril is being modelled, the $C^{K2}$-$N^{P3}$ bond is represented with a fixed unimodal model, taking the mean dihedral angle appropriate for a trans geometry, i.e. 180°. The Gaussian spread on this bond was set to a small value and given a small jump size, reflecting the fact that peptide bonds are fairly rigid.
2) The two major conformations of the proline ring have well-defined geometries [15]. Each bond in the ring was therefore given a bimodal model of two fixed mean values and a Gaussian spread of zero. The ring was alternated between the two states using probability mode 6, which was set to a fixed value of 0.5, reflecting the 50:50 ratio of these conformations seen in solution.
3) There are no structural restraints involving the carboxylate oxygen atoms of either carboxylate group and therefore precise dihedral angle values for bonds $CA^{F1}$-$C^{F1}$ and $CA^{P3}$-$C^{P3}$ cannot be determined from these datasets. To prevent their initial arbitrary positions influencing the iterative optimisation, the carboxylate atoms were set to be van der Waals inactive (see above).
4) The $CA^{K2}$-$CB^{K2}$, $CB^{K2}$-$CG^{K2}$, $CG^{K2}$-$CD^{K2}$, $CD^{K2}$-$CE^{K2}$, $CE^{K2}$-$NZ^{K2}$ bonds are all between $sp^3$-hybridised atoms and therefore require a trimodal model. Since the HB1 and HB2 protons have the same chemical shift (see FIG. 23), they require a symmetric trimodal model (var 1, var 2, var 3, var 7, mode 5 4), i.e., where the probability values for tg and gt rotamers are always equal and the single remaining degree of probability freedom is allowed to vary. By the same reasoning, the $CB^{K2}$-$CG^{K2}$, $CG^{K2}$-$CD^{K2}$ and $CD^{K2}$-$CE^{K2}$ bonds were also given a symmetric trimodal model (modes 9, 10 and 11) with probability values that were allowed to vary and each had their own Gaussian spread (var 29-31). The $CE^{K2}$-$NZ^{K2}$ bond was modelled in the same manner as a methyl group (see for hyaluronan hexassaccharide in Appendix A).

5) The $CA^{F1}$-$CB^{F1}$ and $CB^{F1}$-$CG^{F1}$ bonds are between $sp^3$-hybridised atoms and therefore require a trimodal model. Since the HB protons have the same chemical shifts (see FIG. 23), a symmetric trimodal model was used for the $CA^{F1}$-$CB^{F1}$ bond (var 1, var 2, var 3, var 6, mode 4 4) in which the probability value was allowed to vary. Similarly, since the HG protons have the same chemical shifts (see FIG. 23), a symmetric trimodal model was used for the $CB^{F1}$-$CG^{F1}$ bond (var 1, var 2, var 3, var 6, mode 7 4) in which the probability value was allowed to vary. The $CG^{F1}$-$CD^{F1}$ bond is between an $sp^3$-hybridised atom ($CG^{F1}$) and an $sp^2$-hybridised atom ($CD^{F1}$) and therefore requires a bimodal model. The two dihedral angle conformations shown in the dynamic model file (var 26, var 27) were chosen since they model both forms of the symmetric conformation predominantly observed for this bond in a wide range of small molecule crystal structures. A single Gaussian value was given to the bond due to this symmetry (var 28).

The specific implementation of these considerations was achieved using the dynamic model file given below. The relationship of each variable and probability mode to the chemical structure is given in FIG. 26.

```
remark Dynamic model of lisinopril
variables:

remark generic trimodal staggered conformation mean angles
var 1 fix 60 jump 0.0 start 0.02     # mean 1
var 2 fix 300 jump 0.0 start 0.02    # mean 2
var 3 fix 180 jump 0.0 start 0.02    # mean 3
remark backbone Gaussian spreads
var 4 fix 20 jump 5.0 start 0.02     # remark F1CA-K2N bond
var 5 fix 20 jump 5.0 start 0.02     # remark K2N-K2CA bond
var 6 fix 20 jump 5.0 start 0.02     # remark F1CA-F1CB bond
var 7 fix 20 jump 5.0 start 0.02     # remark K2CA-K2CB bond
remark K2CA-K2CO bond bimodal model
var 8 fix 300 jump 20.0 start 0.02   # remark mean 1
var 9 fix 20 jump 5.0 start 0.02     # remark Gaussian spread 1
var 10 fix 120 jump 20.0 start 0.02  # remark mean 2
var 11 fix 20 jump 5.0 start 0.02    # remark Gaussian spread 2
remark proline amide bond set to trans conformation
var 12 fix 180 jump 0.0 start 0.02   # remark mean set to trans
var 13 fix 4 jump 2.0 start 0.02     # remark Gaussian spread
remark proline ring bimodal flip between N and S states
remark parameters for N state = gamma exo = UP
var 14 fix -48.82 jump 0.0 start 0.0   # remark dihedral no. 49 mean 1
var 15 fix -46.58 jump 0.0 start 0.0   # remark dihedral no. 54 mean 1
var 16 fix 58.07 jump 0.0 start 0.0    # remark dihedral no. 57 mean 1
var 17 fix -157.04 jump 0.0 start 0.0  # remark dihedral no. 60 mean 1
var 18 fix -48.96 jump 0.0 start 0.0   # remark dihedral no. 63 mean 1
remark parameters for S state = gamma endo = DOWN
var 19 fix -74.71 jump 0.0 start 0.0   # remark dihedral no. 49 mean 2
var 20 fix 45.29 jump 0.0 start 0.0    # remark dihedral no. 54 mean 2
var 21 fix -56.00 jump 0.0 start 0.0   # remark dihedral no. 57 mean 2
var 22 fix 157.82 jump 0.0 start 0.0   # remark dihedral no. 60 mean 2
var 23 fix 46.64 jump 0.0 start 0.0    # remark dihedral no. 63 mean 2
remark proline ring bimodal flip Gaussian spread for both states
var 24 fix 0.0 jump 0.0 start 0.0
remark 'phenylalanine' sidechain
var 25 fix 20 jump 5.0 start 0.02    # remark F1CB-F1CG Gaussian spread
remark F1CG-F1CD bimodal model and Gaussian spread
var 26 fix 90 jump 0.0 start 0.02    # remark mean 1
var 27 fix 270 jump 0.0 start 0.02   # remark mean 2
var 28 fix 20 jump 5.0 start 0.02    # remark Gaussian
remark lysine sidechain Gaussian spreads
var 29 fix 20 jump 5.0 start 0.02    # remark CB-CG Gaussian spread
var 30 fix 20 jump 5.0 start 0.02    # remark CG-CD Gaussian spread
var 31 fix 20 jump 5.0 start 0.02    # remark CD-CE Gaussian spread
var 32 fix 20 jump 0.0 start 0.02    # remark CE-CZ Gaussian spread
endsection
probabilities:

mode 1 3 0.33 0.66 0.1      # remark F1 CA-N bond
mode 2 3 0.33 0.66 0.1      # remark F1 N-CA K2 bond
mode 3 2 0.05 0.1           # remark K2 CA-C bond
mode 4 4 0.33 0.66 0.1      # remark F1 CA-CB bond
mode 5 4 0.33 0.66 0.1      # remark K2 CA-CB bond
mode 6 2 0.5 0.0            # remark proline ring flip
mode 7 4 0.33 0.66 0.1      # remark F1 CB-CG bond
mode 8 2 0.5 0.0            # remark F1CG-CD bond
mode 9 4 0.33 0.66 0.1      # remark K2 CB-CG bond
mode 10 4 0.33 0.66 0.1     # remark K2 CG-CD bond
mode 11 4 0.33 0.66 0.1     # remark K2 CD-CE bond
mode 12 3 0.33 0.66 0.0     # remark K2 CE-CZ bond
endsection
dynamics:

remark backbone
multigyrate 1 1 1 4 2 4 3 4      # remark F1 CA-N bond
multigyrate 27 2 1 5 2 5 3 5     # remark F1 N-CA K2 bond
multigyrate 30 3 8 9 10 11       # remark K2 CA-C bond
gyrate 47 12 13                  # remark P3 amide bond
remark 'phenylalanine' sidechain
multigyrate 8 4 1 6 2 6 3 6      # remark F1 CA-CB bond
multigyrate 11 7 1 25 2 25 3 25  # remark F1 CB-CG bond
multigyrate 14 8 26 28 27 28     # remark F1 CG-CD bond
remark lysine sidechain
multigyrate 32 5 1 7 2 7 3 7     # remark K2 CA-CB bond
multigyrate 35 9 1 29 2 29 3 29  # remark K2 CB-CG bond
multigyrate 38 10 1 30 2 30 3 30 # remark K2 CG-CD bond
multigyrate 46 11 1 31 2 31 3 31 # remark K2 CD-CE bond
multigyrate 41 12 1 32 2 32 3 32 # remark K2 CE-CZ bond
remark proline ring flip
multigyrate 49 6 14 24 19 24
multigyrate 54 6 15 24 20 24
multigyrate 57 6 16 24 21 24
multigyrate 60 6 17 24 22 24
multigyrate 63 6 18 24 23 24
endsection
```

In this manner, all the flexible parts of the trans lisinopril molecule and their behaviour are defined as required for the computer implementation of the ensemble generation algorithm. In this model, there are 13 unknown Gaussian spreads, 2 unknown mean dihedral angle values and 11 probability values to determine in order to solve the solution structure of trans lisinopril.

Structure Calculations

Each round of structure calculations for trans lisinopril comprised 100 runs; a larger number than that used for $\alpha$-$HA_6$ (40) was chosen because of the greater number of degrees of freedom being modelled. Statistics were performed on the lowest 25 $\chi^2_{total}$ runs. Each individual run had 10,000 iteration steps and the dynamic ensemble was composed of 250 structures; a larger number than that used for $\alpha$-$HA_6$ (40) was chosen because of the greater number of bi- and trimodal models used in the dynamic model file. The scalar-coupling dataset file (see Appendix B) had low experimental errors and was used from the first round of structure calculations. The base dataset (37 structural restraints) for the 2D [$^1$H, $^1$H]-T-ROESY dataset was established over the first 8 rounds of structure calculations, after which point the structures loosely converged to preferred (and structurally plausible) values for each unknown parameter. The primary and secondary statistics tables for the top 25 of the 100 runs in this round are shown below (only the first 10 ranked run numbers are given):

| | | | \multicolumn{10}{c|}{Round8 statistics:} |
|---|---|---|---|---|---|---|---|---|---|---|---|
| | | | \multicolumn{10}{c|}{Ranked run no.} |
| Parameter | Mean | StDev | 8 | 32 | 51 | 64 | 29 | 16 | 57 | 91 | 38 | 92 |
|---|---|---|---|---|---|---|---|---|---|---|---|
| T-ROESY | 24.07 | 3.36 | 17.55 | 17.63 | 21.32 | 20.78 | 22.91 | 21.87 | 23.35 | 23.63 | 23.26 | 19.92 |
| JCOUP | 3.01 | 1.65 | 3.57 | 1.30 | 1.56 | 1.73 | 1.11 | 1.17 | 2.22 | 2.49 | 3.25 | 7.86 |
| VDW | 1.74 | 0.75 | 1.44 | 3.72 | 1.14 | 1.88 | 1.23 | 3.38 | 1.29 | 1.66 | 1.50 | 1.18 |
| TotChi | 28.81 | 3.57 | 22.56 | 22.64 | 24.02 | 24.38 | 25.26 | 26.43 | 26.86 | 27.78 | 28.01 | 28.96 |
| | | | | | | Variables 1-32: | | | | | | |
| sp3-1 | 60.00 | 0.00 | 60.00 | 60.00 | 60.00 | 60.00 | 60.00 | 60.00 | 60.00 | 60.00 | 60.00 | 60.00 |
| sp3-2 | 300.00 | 0.00 | 300.00 | 300.00 | 300.00 | 300.00 | 300.00 | 300.00 | 300.00 | 300.00 | 300.00 | 300.00 |
| sp3-3 | 180.00 | 0.00 | 180.00 | 180.00 | 180.00 | 180.00 | 180.00 | 180.00 | 180.00 | 180.00 | 180.00 | 180.00 |
| F1phi-g | 14.40 | 5.83 | 20.00 | 9.57 | 11.91 | 12.21 | 22.64 | 7.70 | 12.51 | 14.81 | 16.70 | 10.64 |
| K2phi-g | 10.81 | 6.14 | 1.18 | 15.77 | 7.47 | 10.04 | 8.35 | 2.86 | 0.95 | 4.02 | 13.58 | 10.05 |
| F1chi-g | 23.80 | 12.33 | 23.28 | 34.80 | 25.69 | 41.83 | 20.52 | 15.93 | 17.20 | 6.56 | 8.87 | 17.50 |
| K1chi-g | 21.74 | 10.83 | 35.10 | 13.19 | 17.84 | 3.96 | 20.72 | 28.29 | 28.57 | 16.06 | 26.60 | 41.88 |
| Kpsi1 | −36.49 | 18.89 | −40.71 | −7.52 | −3.73 | −10.86 | −26.74 | −36.26 | −62.44 | −52.87 | −26.05 | −29.25 |
| Kpsi1-g | 19.92 | 10.25 | 12.87 | 16.80 | 39.80 | 26.73 | 13.66 | 1.26 | 14.61 | 23.77 | 18.42 | 36.77 |
| Kpsi2 | 113.76 | 9.65 | 117.51 | 125.54 | 112.61 | 121.31 | 109.99 | 122.88 | 104.11 | 111.54 | 117.01 | 130.96 |
| Kpsi2-g | 17.07 | 8.78 | 28.04 | 23.73 | 23.94 | 21.49 | 22.61 | 20.03 | 16.81 | 21.27 | 16.90 | 3.50 |
| Ptrans | 180.00 | 0.00 | 180.00 | 180.00 | 180.00 | 180.00 | 180.00 | 180.00 | 180.00 | 180.00 | 180.00 | 180.00 |
| Ptrans-g | 5.14 | 3.31 | 3.63 | 8.83 | 10.83 | 2.91 | 0.36 | 3.16 | 1.99 | 6.85 | 1.41 | 5.06 |
| P-ring | −48.82 | 0.00 | −48.82 | −48.82 | −48.82 | −48.82 | −48.82 | −48.82 | −48.82 | −48.82 | −48.82 | −48.82 |
| P-ring | −46.58 | 0.00 | −46.58 | −46.58 | −46.58 | −46.58 | −46.58 | −46.58 | −46.58 | −46.58 | −46.58 | −46.58 |
| P-ring | 58.07 | 0.00 | 58.07 | 58.07 | 58.07 | 58.07 | 58.07 | 58.07 | 58.07 | 58.07 | 58.07 | 58.07 |
| P-ring | −157.04 | 0.00 | −157.04 | −157.04 | −157.04 | −157.04 | −157.04 | −157.04 | −157.04 | −157.04 | −157.04 | −157.04 |
| P-ring | −48.96 | 0.00 | −48.96 | −48.96 | −48.96 | −48.96 | −48.96 | −48.96 | −48.96 | −48.96 | −48.96 | −48.96 |
| P-ring | −74.71 | 0.00 | −74.71 | −74.71 | −74.71 | −74.71 | −74.71 | −74.71 | −74.71 | −74.71 | −74.71 | −74.71 |
| P-ring | 45.29 | 0.00 | 45.29 | 45.29 | 45.29 | 45.29 | 45.29 | 45.29 | 45.29 | 45.29 | 45.29 | 45.29 |
| P-ring | −56.00 | 0.00 | −56.00 | −56.00 | −56.00 | −56.00 | −56.00 | −56.00 | −56.00 | −56.00 | −56.00 | −56.00 |
| P-ring | 157.82 | 0.00 | 157.82 | 157.82 | 157.82 | 157.82 | 157.82 | 157.82 | 157.82 | 157.82 | 157.82 | 157.82 |
| P-ring | 46.64 | 0.00 | 46.64 | 46.64 | 46.64 | 46.64 | 46.64 | 46.64 | 46.64 | 46.64 | 46.64 | 46.64 |
| P-ring-g | 0.00 | 0.00 | 0.00 | 0.00 | 0.00 | 0.00 | 0.00 | 0.00 | 0.00 | 0.00 | 0.00 | 0.00 |
| F1chi2-g | 15.21 | 5.10 | 12.50 | 14.54 | 14.67 | 13.74 | 13.61 | 18.75 | 19.90 | 16.31 | 1.12 | 23.36 |
| F1chi3 | 90.00 | 0.00 | 90.00 | 90.00 | 90.00 | 90.00 | 90.00 | 90.00 | 90.00 | 90.00 | 90.00 | 90.00 |
| F1chi3 | 270.00 | 0.00 | 270.00 | 270.00 | 270.00 | 270.00 | 270.00 | 270.00 | 270.00 | 270.00 | 270.00 | 270.00 |
| F1chi3-g | 29.88 | 6.24 | 39.65 | 24.31 | 35.28 | 29.60 | 32.05 | 28.21 | 38.67 | 30.91 | 20.82 | 31.22 |
| K2chi2-g | 21.26 | 10.23 | 22.83 | 40.01 | 3.68 | 34.80 | 17.56 | 25.36 | 20.55 | 23.83 | 31.25 | 12.04 |
| K2chi3-g | 19.91 | 8.42 | 20.93 | 22.39 | 6.45 | 21.23 | 9.33 | 13.88 | 19.35 | 27.45 | 22.29 | 20.91 |
| K2chi4-g | 17.22 | 9.27 | 12.82 | 27.17 | 25.59 | 12.17 | 20.26 | 18.75 | 24.30 | 24.30 | 7.10 | 10.17 |
| K2chi5-g | 20.00 | 0.00 | 20.00 | 20.00 | 20.00 | 20.00 | 20.00 | 20.00 | 20.00 | 20.00 | 20.00 | 20.00 |
| | | | | | | Probabilities: | | | | | | |
| Fphi1 | 0.01 | 0.01 | 0.00 | 0.00 | 0.02 | 0.00 | 0.01 | 0.00 | 0.00 | 0.00 | 0.01 | 0.00 |
| Fphi1 | 0.95 | 0.02 | 0.94 | 0.96 | 0.97 | 0.95 | 0.95 | 0.95 | 0.99 | 0.92 | 0.93 | 0.94 |
| Kphi1 | 0.01 | 0.01 | 0.00 | 0.01 | 0.00 | 0.00 | 0.00 | 0.01 | 0.00 | 0.01 | 0.01 | 0.01 |
| Kphi1 | 0.96 | 0.05 | 0.99 | 0.98 | 0.99 | 1.00 | 0.91 | 0.96 | 0.96 | 0.88 | 1.00 | 0.95 |
| Kpsi | 0.08 | 0.07 | 0.00 | 0.00 | 0.01 | 0.00 | 0.00 | 0.13 | 0.09 | 0.05 | 0.03 | 0.07 |
| Fchi1 | 0.33 | 0.05 | 0.29 | 0.29 | 0.38 | 0.32 | 0.35 | 0.34 | 0.28 | 0.36 | 0.30 | 0.35 |
| Fchi1 | 0.67 | 0.11 | 0.57 | 0.58 | 0.76 | 0.63 | 0.70 | 0.68 | 0.55 | 0.72 | 0.61 | 0.70 |
| Kchi1 | 0.34 | 0.02 | 0.35 | 0.33 | 0.34 | 0.34 | 0.34 | 0.31 | 0.33 | 0.31 | 0.31 | 0.37 |
| Kchi1 | 0.69 | 0.05 | 0.69 | 0.67 | 0.67 | 0.68 | 0.69 | 0.63 | 0.66 | 0.63 | 0.63 | 0.74 |
| Pflip | 0.50 | 0.00 | 0.50 | 0.50 | 0.50 | 0.50 | 0.50 | 0.50 | 0.50 | 0.50 | 0.50 | 0.50 |
| Fchi2 | 0.00 | 0.00 | 0.00 | 0.00 | 0.00 | 0.00 | 0.00 | 0.00 | 0.00 | 0.00 | 0.00 | 0.00 |
| Fchi2 | 0.00 | 0.00 | 0.00 | 0.00 | 0.00 | 0.00 | 0.00 | 0.00 | 0.00 | 0.00 | 0.00 | 0.00 |
| Fchi3 | 0.50 | 0.00 | 0.50 | 0.50 | 0.50 | 0.50 | 0.50 | 0.50 | 0.50 | 0.50 | 0.50 | 0.50 |
| Kchi2 | 0.41 | 0.04 | 0.44 | 0.46 | 0.40 | 0.50 | 0.40 | 0.47 | 0.43 | 0.41 | 0.47 | 0.39 |
| Kchi2 | 0.82 | 0.09 | 0.88 | 0.92 | 0.80 | 1.00 | 0.81 | 0.93 | 0.86 | 0.82 | 0.94 | 0.79 |
| Kchi3 | 0.43 | 0.05 | 0.49 | 0.41 | 0.45 | 0.45 | 0.50 | 0.48 | 0.43 | 0.39 | 0.45 | 0.43 |
| Kchi3 | 0.86 | 0.10 | 0.97 | 0.82 | 0.89 | 0.89 | 0.99 | 0.95 | 0.87 | 0.79 | 0.90 | 0.87 |
| Kchi4 | 0.16 | 0.15 | 0.00 | 0.00 | 0.00 | 0.00 | 0.00 | 0.39 | 0.17 | 0.08 | 0.18 | 0.23 |
| Kchi4 | 0.32 | 0.31 | 0.00 | 0.00 | 0.00 | 0.00 | 0.00 | 0.79 | 0.34 | 0.16 | 0.36 | 0.46 |
| Kchi5 | 0.33 | 0.00 | 0.33 | 0.33 | 0.33 | 0.33 | 0.33 | 0.33 | 0.33 | 0.33 | 0.33 | 0.33 |
| Kchi5 | 0.66 | 0.00 | 0.66 | 0.66 | 0.66 | 0.66 | 0.66 | 0.66 | 0.66 | 0.66 | 0.66 | 0.66 |

| Dataset | Restraints | Tot Chi | Chi/Res | Viol (>10) | Percent |
|---|---|---|---|---|---|
| TOTAL | 42 | 27.1 | 0.6 | 0 | 0 |
| JCOUP | 4 | 3.0 | 0.8 | 0 | 0 |
| 2D-T-ROESY | 37 | 24.1 | 0.7 | 0 | 0 |

In this case, it can be seen that the Chi/Res values are similar for the two datasets, indicating that the 2D-T-ROESY does not particularly dominate the scalar-coupling dataset (JCOUP), i.e., the m value of 0.4 is suitable.

In the next 29 rounds of structure calculations, more ROE structural restraints and many noROE structure restraints were included. The results from the round of structure calculations, where the 2D [$^1$H, $^1$H]-T-ROESY dataset had been completely analysed, were as follows:

| | | | \multicolumn{5}{c|}{Round37 statistics:} | |
|---|---|---|---|---|---|---|---|---|
| | | | \multicolumn{5}{c|}{Ranked run no.} | |
| Parameter | Mean | StDev | 41 | 98 | 86 | 29 | 94 | |
| T-ROESY | 161.6 | 3.50 | 156.19 | 154.83 | 154.78 | 155.06 | 157.52 | ... |
| JCOUP | 3.0 | 1.04 | 1.30 | 2.65 | 4.63 | 3.76 | 2.99 | ... |
| VDW | 2.1 | 0.92 | 0.33 | 1.23 | 0.95 | 2.94 | 1.66 | ... |
| TotChi | 166.7 | 4.35 | 157.82 | 158.71 | 160.36 | 161.76 | 162.17 | ... |
| | | | \multicolumn{5}{c|}{Variables 1-32:} | |
| sp3-1 | 60.00 | 0.00 | 60.00 | 60.00 | 60.00 | 60.00 | 60.00 | ... |
| sp3-2 | 300.00 | 0.00 | 300.00 | 300.00 | 300.00 | 300.00 | 300.00 | ... |
| sp3-3 | 180.00 | 0.00 | 180.00 | 180.00 | 180.00 | 180.00 | 180.00 | ... |
| F1phi-g | 14.75 | 3.32 | 14.35 | 12.87 | 18.03 | 13.38 | 16.16 | ... |
| K2phi-g | 9.14 | 4.87 | 2.31 | 3.48 | 11.46 | 7.23 | 10.41 | ... |
| F1chi-g | 22.56 | 6.30 | 20.51 | 23.87 | 15.22 | 18.25 | 26.70 | ... |
| F1chi-g | 18.29 | 7.96 | 21.38 | 18.13 | 6.21 | 17.12 | 20.40 | ... |
| Kpsi1 | −40.16 | 17.70 | −39.79 | −37.90 | −21.28 | −1.03 | −46.05 | ... |
| Kpsi1-g | 17.68 | 9.12 | 32.62 | 8.91 | 22.82 | 20.11 | 26.41 | ... |
| Kpsi2 | 115.23 | 5.78 | 113.36 | 110.31 | 107.36 | 119.39 | 117.51 | ... |
| Kpsi2-g | 20.08 | 7.20 | 21.62 | 2.32 | 22.33 | 23.71 | 30.12 | ... |
| Ptrans | 180.00 | 0.00 | 180.00 | 180.00 | 180.00 | 180.00 | 180.00 | ... |
| Ptrans-g | 6.03 | 3.26 | 6.54 | 8.73 | 2.86 | 4.33 | 5.93 | ... |
| P-ring | −48.82 | 0.00 | −48.82 | −48.82 | −48.82 | −48.82 | −48.82 | ... |
| P-ring | −46.58 | 0.00 | −46.58 | −46.58 | −46.58 | −46.58 | −46.58 | ... |
| P-ring | 58.07 | 0.00 | 58.07 | 58.07 | 58.07 | 58.07 | 58.07 | ... |
| P-ring | −157.04 | 0.00 | −157.04 | −157.04 | −157.04 | −157.04 | −157.04 | ... |
| P-ring | −48.96 | 0.00 | −48.96 | −48.96 | −48.96 | −48.96 | −48.96 | ... |
| P-ring | −74.71 | 0.00 | −74.71 | −74.71 | −74.71 | −74.71 | −74.71 | ... |
| P-ring | 45.29 | 0.00 | 45.29 | 45.29 | 45.29 | 45.29 | 45.29 | ... |
| P-ring | −56.00 | 0.00 | −56.00 | −56.00 | −56.00 | −56.00 | −56.00 | ... |
| P-ring | 157.82 | 0.00 | 157.82 | 157.82 | 157.82 | 157.82 | 157.82 | ... |
| P-ring | 46.64 | 0.00 | 46.64 | 46.64 | 46.64 | 46.64 | 46.64 | ... |
| P-ring-g | 0.00 | 0.00 | 0.00 | 0.00 | 0.00 | 0.00 | 0.00 | ... |
| F1chi2-g | 12.88 | 3.45 | 14.63 | 13.65 | 17.19 | 5.57 | 9.88 | ... |
| F1chi3 | 90.00 | 0.00 | 90.00 | 90.00 | 90.00 | 90.00 | 90.00 | ... |
| F1chi3 | 270.00 | 0.00 | 270.00 | 270.00 | 270.00 | 270.00 | 270.00 | ... |
| F1chi3-g | 30.55 | 5.92 | 29.41 | 37.53 | 30.43 | 34.58 | 23.76 | ... |
| K2chi2-g | 21.55 | 5.45 | 14.20 | 19.68 | 24.80 | 31.48 | 23.98 | ... |
| K2chi3-g | 24.39 | 7.71 | 11.39 | 26.76 | 22.78 | 13.10 | 32.87 | ... |
| K2chi4-g | 18.93 | 6.00 | 13.19 | 14.93 | 23.30 | 23.13 | 11.30 | ... |
| K2chi5-g | 20.00 | 0.00 | 20.00 | 20.00 | 20.00 | 20.00 | 20.00 | ... |
| | | | \multicolumn{5}{c|}{Probabilities:} | |
| Fphi1 | 0.00 | 0.00 | 0.00 | 0.00 | 0.01 | 0.01 | 0.00 | ... |
| Fphi1 | 0.95 | 0.02 | 0.97 | 0.96 | 0.95 | 0.94 | 0.97 | ... |
| Kphi1 | 0.00 | 0.01 | 0.00 | 0.01 | 0.00 | 0.00 | 0.00 | ... |
| Kphi1 | 0.96 | 0.04 | 0.89 | 1.00 | 1.00 | 0.92 | 0.88 | ... |
| Kpsi | 0.08 | 0.09 | 0.04 | 0.23 | 0.01 | 0.02 | 0.03 | ... |
| Fchi1 | 0.34 | 0.02 | 0.31 | 0.36 | 0.33 | 0.30 | 0.31 | ... |
| Fchi1 | 0.68 | 0.05 | 0.62 | 0.72 | 0.66 | 0.60 | 0.63 | ... |
| Kchi1 | 0.34 | 0.02 | 0.36 | 0.37 | 0.34 | 0.36 | 0.35 | ... |
| Kchi1 | 0.68 | 0.04 | 0.72 | 0.75 | 0.67 | 0.73 | 0.70 | ... |
| Pflip | 0.50 | 0.00 | 0.50 | 0.50 | 0.50 | 0.50 | 0.50 | ... |
| Fchi2 | 0.00 | 0.00 | 0.00 | 0.00 | 0.00 | 0.00 | 0.00 | ... |
| Fchi2 | 0.00 | 0.00 | 0.00 | 0.00 | 0.00 | 0.00 | 0.00 | ... |
| Fchi3 | 0.50 | 0.00 | 0.50 | 0.50 | 0.50 | 0.50 | 0.50 | ... |
| Kchi2 | 0.41 | 0.04 | 0.41 | 0.37 | 0.48 | 0.45 | 0.41 | ... |
| Kchi2 | 0.83 | 0.08 | 0.82 | 0.75 | 0.97 | 0.91 | 0.81 | ... |
| Kchi3 | 0.47 | 0.03 | 0.48 | 0.45 | 0.41 | 0.49 | 0.48 | ... |
| Kchi3 | 0.93 | 0.07 | 0.96 | 0.91 | 0.81 | 0.97 | 0.95 | ... |
| Kchi4 | 0.12 | 0.12 | 0.13 | 0.00 | 0.16 | 0.00 | 0.34 | ... |
| Kchi4 | 0.25 | 0.25 | 0.27 | 0.00 | 0.33 | 0.00 | 0.68 | ... |
| Kchi5 | 0.33 | 0.00 | 0.33 | 0.33 | 0.33 | 0.33 | 0.33 | ... |
| Kchi5 | 0.66 | 0.00 | 0.66 | 0.66 | 0.66 | 0.66 | 0.66 | ... |

-continued

| Round37 statistics: | | | | |
|---|---|---|---|---|
| Dataset | Restraints | Tot Chi | Chi/Res | Viol (>10) | Percent |
| TOTAL | 110 | 164.6 | 1.5 | 0 | 0 |
| JCOUP | 4 | 3.0 | 0.8 | 0 | 0 |
| 2D-T-ROESY | 67 | 122.5 | 1.8 | 0 | 0 |
| 2D-ROE (no) | 39 | 39.1 | 1.0 | 0 | 0 |

As can be seen from these results, the values for each of the parameters, in particular the backbone bonds' mean values, Gaussian spreads and probability values, are similar to the results from round8. No structural restraint has an $\chi^2_{restraint}$ value greater than 10.0. Since the inclusion of the additional data (68 structural restraints) relative to round8 did not alter appreciably alter the optimised dynamic structure, the dynamic structure has been solved to a first approximation. By inclusion of other kinds of NMR datasets a more complete view of the dynamic structure of this molecule would easily be obtained (as described above for the hyaluronan hexasaccharide).

The coordinates for the mean dynamic solution structure for trans lisinopril, generated according to these values, is given in Appendix B. Several visual representations of the mean dynamic structure and dynamic ensemble of structures are given in FIGS. 27-29.

APPENDIX B

Lisinopril

Starting PDB 3D-Coordinates for Lisinopril

| ATOM | 1 | N | PHE | 1 | 41.892 | 33.386 | 47.518 | 1.00 | 14.83 | N |
|---|---|---|---|---|---|---|---|---|---|---|
| ATOM | 2 | C | PHE | 1 | 42.413 | 35.599 | 48.383 | 1.00 | 13.57 | C |
| ATOM | 3 | CA | PHE | 1 | 41.287 | 34.591 | 48.121 | 1.00 | 14.83 | C |
| ATOM | 4 | CB | PHE | 1 | 40.573 | 34.333 | 49.466 | 1.00 | 12.04 | C |
| ATOM | 5 | CG | PHE | 1 | 39.958 | 35.712 | 49.908 | 1.00 | 13.87 | C |
| ATOM | 6 | CD | PHE | 1 | 39.145 | 35.742 | 51.173 | 1.00 | 15.99 | C |
| ATOM | 7 | CE1 | PHE | 1 | 38.817 | 36.998 | 51.671 | 1.00 | 16.62 | C |
| ATOM | 8 | CZ1 | PHE | 1 | 38.060 | 37.122 | 52.827 | 1.00 | 18.46 | C |
| ATOM | 9 | CZ2 | PHE | 1 | 37.952 | 34.724 | 52.998 | 1.00 | 17.75 | C |
| ATOM | 10 | CE2 | PHE | 1 | 38.710 | 34.598 | 51.839 | 1.00 | 14.59 | C |
| ATOM | 11 | CH | PHE | 1 | 37.626 | 35.983 | 53.493 | 1.00 | 18.68 | C |
| ATOM | 12 | O1 | PHE | 1 | 43.578 | 35.177 | 48.743 | 1.00 | 15.16 | O |
| ATOM | 13 | O2 | PHE | 1 | 42.213 | 36.867 | 48.241 | 1.00 | 13.89 | O |
| ATOM | 14 | HN1 | PHE | 1 | 42.639 | 33.070 | 48.151 | 1.00 | 15.26 | H |
| ATOM | 15 | HN2 | PHE | 1 | 41.187 | 32.646 | 47.426 | 1.00 | 15.26 | H |
| ATOM | 16 | HA | PHE | 1 | 40.522 | 35.003 | 47.465 | 1.00 | 15.26 | H |
| ATOM | 17 | HB1 | PHE | 1 | 39.765 | 33.604 | 49.315 | 1.00 | 15.26 | H |
| ATOM | 18 | HB2 | PHE | 1 | 41.280 | 33.954 | 50.217 | 1.00 | 15.26 | H |
| ATOM | 19 | HG1 | PHE | 1 | 40.729 | 36.481 | 50.019 | 1.00 | 15.26 | H |
| ATOM | 20 | HG2 | PHE | 1 | 39.298 | 36.063 | 49.103 | 1.00 | 15.26 | H |
| ATOM | 21 | HE1 | PHE | 1 | 39.147 | 37.868 | 51.160 | 1.00 | 15.26 | H |
| ATOM | 22 | HE2 | PHE | 1 | 38.945 | 33.635 | 51.475 | 1.00 | 15.26 | H |
| ATOM | 23 | HZ1 | PHE | 1 | 37.813 | 38.085 | 53.200 | 1.00 | 15.26 | H |
| ATOM | 24 | HZ2 | PHE | 1 | 37.618 | 33.858 | 53.507 | 1.00 | 15.26 | H |
| ATOM | 25 | HH | PHE | 1 | 37.047 | 36.074 | 54.375 | 1.00 | 15.26 | H |
| ATOM | 26 | NZ | LYS | 2 | 43.457 | 27.603 | 44.528 | 1.00 | 21.85 | N |
| ATOM | 27 | C | LYS | 2 | 41.351 | 34.015 | 45.039 | 1.00 | 13.99 | C |
| ATOM | 28 | CA | LYS | 2 | 42.481 | 33.694 | 46.117 | 1.00 | 12.80 | C |
| ATOM | 29 | CB | LYS | 2 | 43.308 | 32.421 | 45.667 | 1.00 | 14.69 | C |
| ATOM | 30 | CG | LYS | 2 | 42.490 | 31.102 | 45.569 | 1.00 | 16.12 | C |
| ATOM | 31 | CD | LYS | 2 | 43.411 | 29.976 | 45.107 | 1.00 | 17.50 | C |
| ATOM | 32 | CE | LYS | 2 | 42.590 | 28.689 | 44.990 | 1.00 | 20.10 | C |
| ATOM | 33 | O | LYS | 2 | 40.868 | 33.083 | 44.393 | 1.00 | 13.04 | O |
| ATOM | 34 | HA | LYS | 2 | 43.163 | 34.547 | 46.194 | 1.00 | 15.26 | H |
| ATOM | 35 | HB1 | LYS | 2 | 43.752 | 32.630 | 44.684 | 1.00 | 15.26 | H |
| ATOM | 36 | HB2 | LYS | 2 | 44.111 | 32.257 | 46.399 | 1.00 | 15.26 | H |
| ATOM | 37 | HG1 | LYS | 2 | 42.063 | 30.855 | 46.551 | 1.00 | 15.26 | H |
| ATOM | 38 | HG2 | LYS | 2 | 41.687 | 31.208 | 44.841 | 1.00 | 15.26 | H |
| ATOM | 39 | HD1 | LYS | 2 | 43.833 | 30.230 | 44.124 | 1.00 | 15.26 | H |
| ATOM | 40 | HD2 | LYS | 2 | 44.224 | 29.837 | 45.831 | 1.00 | 15.26 | H |
| ATOM | 41 | HE1 | LYS | 2 | 41.777 | 28.841 | 44.265 | 1.00 | 15.26 | H |
| ATOM | 42 | HE2 | LYS | 2 | 42.165 | 28.434 | 45.970 | 1.00 | 15.26 | H |
| ATOM | 43 | HZ1 | LYS | 2 | 42.907 | 26.737 | 44.446 | 1.00 | 15.26 | H |
| ATOM | 44 | HZ2 | LYS | 2 | 44.221 | 27.464 | 45.203 | 1.00 | 15.26 | H |
| ATOM | 45 | HZ3 | LYS | 2 | 43.850 | 27.849 | 43.609 | 1.00 | 15.26 | H |
| ATOM | 46 | N | PRO | 3 | 40.930 | 35.339 | 44.618 | 1.00 | 13.77 | N |
| ATOM | 47 | C | PRO | 3 | 40.142 | 34.777 | 42.294 | 1.00 | 13.82 | C |
| ATOM | 48 | CA | PRO | 3 | 39.936 | 35.545 | 43.566 | 1.00 | 14.91 | C |
| ATOM | 49 | CB | PRO | 3 | 40.139 | 37.060 | 43.316 | 1.00 | 14.97 | C |
| ATOM | 50 | CG | PRO | 3 | 40.147 | 37.501 | 44.731 | 1.00 | 16.22 | C |
| ATOM | 51 | CD | PRO | 3 | 41.336 | 36.609 | 45.160 | 1.00 | 12.52 | C |
| ATOM | 52 | O1 | PRO | 3 | 39.211 | 34.122 | 41.809 | 1.00 | 13.99 | O |

-continued

| ATOM | 53 | O2  | PRO | 3 | 41.287 | 34.807 | 41.704 | 1.00 | 11.94 | O |
| ATOM | 54 | HA  | PRO | 3 | 38.938 | 35.354 | 43.983 | 1.00 | 15.26 | H |
| ATOM | 55 | HB1 | PRO | 3 | 41.132 | 37.258 | 42.891 | 1.00 | 15.26 | H |
| ATOM | 56 | HB2 | PRO | 3 | 39.356 | 37.495 | 42.680 | 1.00 | 15.26 | H |
| ATOM | 57 | HG1 | PRO | 3 | 40.335 | 38.572 | 44.882 | 1.00 | 15.26 | H |
| ATOM | 58 | HG2 | PRO | 3 | 39.211 | 37.191 | 45.222 | 1.00 | 15.26 | H |
| ATOM | 59 | HD1 | PRO | 3 | 41.502 | 36.613 | 46.212 | 1.00 | 15.26 | H |
| ATOM | 60 | HD2 | PRO | 3 | 42.247 | 36.931 | 44.638 | 1.00 | 15.26 | H |
| END |

Internal Coordinate Table for Lisinopril

| 1 | 2 | CA | 1 | N | 1 | CA | 1 | C | 1.55099 | 111.214 | −49.413 | 107.805 | 1.53412 |
|---|---|---|---|---|---|---|---|---|---|---|---|---|---|
| 2 | 2 | CA | 1 | CA | 1 | *N | 1 | HN1 | 1.55099 | 111.214 | 120.217 | 107.302 | 1.02879 |
| 3 | 2 | CA | 1 | CA | 1 | *N | 1 | HN2 | 1.55099 | 111.214 | −120.767 | 110.12 | 1.02612 |
| 4 | 1 | C | 1 | N | 1 | *CA | 1 | CB | 1.53412 | 107.805 | −119.227 | 114.091 | 1.54493 |
| 5 | 1 | C | 1 | N | 1 | *CA | 1 | HA | 1.53412 | 107.805 | 122.427 | 110.539 | 1.08884 |
| 6 | 1 | O1 | 1 | C | 1 | CA | 1 | N | 1.29014 | 119.706 | −35.4021 | 107.805 | 1.47667 |
| 7 | 1 | O1 | 1 | CA | 1 | *C | 1 | O2 | 1.29014 | 119.706 | 179.56 | 120.836 | 1.29128 |
| 8 | 1 | N | 1 | CA | 1 | CB | 1 | CG | 1.47667 | 114.091 | 71.909 | 106.213 | 1.57305 |
| 9 | 1 | CG | 1 | CA | 1 | *CB | 1 | HB1 | 1.57305 | 106.213 | 118.006 | 109.355 | 1.09863 |
| 10 | 1 | CG | 1 | CA | 1 | *CB | 1 | HB2 | 1.57305 | 106.213 | −120.897 | 110.782 | 1.09899 |
| 11 | 1 | CA | 1 | CB | 1 | CG | 1 | CD | 1.54493 | 106.213 | 150.504 | 117.7 | 1.50383 |
| 12 | 1 | CD | 1 | CB | 1 | *CG | 1 | HG1 | 1.50383 | 117.7 | 123.412 | 111.66 | 1.09469 |
| 13 | 1 | CD | 1 | CB | 1 | *CG | 1 | HG2 | 1.50383 | 117.7 | −120.624 | 107.976 | 1.09833 |
| 14 | 1 | CB | 1 | CG | 1 | CD | 1 | CE1 | 1.57305 | 117.7 | 137.931 | 116.563 | 1.3902 |
| 15 | 1 | CE1 | 1 | CG | 1 | *CD | 1 | CE2 | 1.3902 | 116.563 | 179.409 | 123.672 | 1.39382 |
| 16 | 1 | CG | 1 | CD | 1 | CE1 | 1 | CZ1 | 1.50383 | 116.563 | 179.433 | 120.574 | 1.38722 |
| 17 | 1 | CZ1 | 1 | CD | 1 | *CE1 | 1 | HE1 | 1.38722 | 120.574 | −179.819 | 119.613 | 1.06262 |
| 18 | 1 | CD | 1 | CE1 | 1 | CZ1 | 1 | CH | 1.3902 | 120.574 | 0.0518447 | 119.748 | 1.38847 |
| 19 | 1 | CH | 1 | CE1 | 1 | *CZ1 | 1 | HZ1 | 1.38847 | 119.748 | 179.964 | 120.06 | 1.06167 |
| 20 | 1 | CG | 1 | CD | 1 | CE2 | 1 | CZ2 | 1.50383 | 123.672 | −179.446 | 119.613 | 1.39098 |
| 21 | 1 | CZ2 | 1 | CD | 1 | *CE2 | 1 | HE2 | 1.39098 | 119.613 | 179.811 | 120.943 | 1.05583 |
| 22 | 1 | CH | 1 | CZ2 | 1 | CE2 | 1 | CD | 1.39169 | 120.368 | 0.060035 | 119.613 | 1.39382 |
| 23 | 1 | CH | 1 | CE2 | 1 | *CZ2 | 1 | HZ2 | 1.39169 | 120.368 | 179.872 | 119.904 | 1.05835 |
| 24 | 1 | CE1 | 1 | CZ1 | 1 | CH | 1 | CZ2 | 1.38722 | 119.748 | −0.0465081 | 119.934 | 1.39169 |
| 25 | 1 | CZ2 | 1 | CZ1 | 1 | *CH | 1 | HH | 1.39169 | 119.934 | −179.91 | 119.974 | 1.05939 |
| 26 | 1 | CE2 | 1 | CZ2 | 1 | CH | 1 | CZ1 | 1.39098 | 120.368 | −0.00939496 | 119.934 | 1.38847 |
| 27 | 1 | CA | 1 | N | 2 | CA | 2 | C | 1.47667 | 111.214 | −58.9079 | 112.423 | 1.59418 |
| 28 | 2 | C | 1 | N | 2 | *CA | 2 | CB | 1.59418 | 112.423 | −120.806 | 107.173 | 1.58435 |
| 29 | 2 | C | 1 | N | 2 | *CA | 2 | HA | 1.59418 | 112.423 | 121.63 | 109.154 | 1.0942 |
| 30 | 3 | N | 2 | C | 2 | CA | 1 | N | 1.45189 | 125.802 | 115.244 | 112.423 | 1.55099 |
| 31 | 1 | N | 2 | CA | 2 | *C | 2 | O | 1.45189 | 125.802 | 172.215 | 118.71 | 1.23239 |
| 32 | 1 | N | 2 | CA | 2 | CB | 2 | CG | 1.55099 | 107.173 | 58.1242 | 115.134 | 1.55469 |
| 33 | 2 | CG | 2 | CA | 2 | *CB | 2 | HB1 | 1.55469 | 115.134 | 121.594 | 108.176 | 1.09909 |
| 34 | 2 | CG | 2 | CA | 2 | *CB | 2 | HB2 | 1.55469 | 115.134 | −120.232 | 108.175 | 1.09877 |
| 35 | 2 | CA | 2 | CB | 2 | CG | 2 | CD | 1.58435 | 115.134 | 38.7557 | 109.135 | 1.52637 |
| 36 | 2 | CD | 2 | CB | 2 | *CG | 2 | HG1 | 1.52637 | 109.135 | 120.428 | 109.785 | 1.09942 |
| 37 | 2 | CD | 2 | CB | 2 | *CG | 2 | HG2 | 1.52637 | 109.135 | −118.93 | 110.322 | 1.08936 |
| 38 | 2 | CB | 2 | CG | 2 | CD | 2 | CE | 1.55469 | 109.135 | −172.096 | 108.605 | 1.53124 |
| 39 | 2 | CE | 2 | CG | 2 | *CD | 2 | HD1 | 1.53124 | 108.605 | 119.326 | 109.365 | 1.09947 |
| 40 | 2 | CE | 2 | CG | 2 | *CD | 2 | HD2 | 1.53124 | 108.605 | −120.336 | 109.916 | 1.09738 |
| 41 | 2 | HZ1 | 2 | NZ | 2 | CE | 2 | CD | 1.02865 | 109.459 | 63.4589 | 109.228 | 1.53124 |
| 42 | 2 | HZ1 | 2 | CE | 2 | *NZ | 2 | HZ2 | 1.02865 | 109.459 | −120.167 | 109.431 | 1.02873 |
| 43 | 2 | HZ1 | 2 | CE | 2 | *NZ | 2 | HZ3 | 1.02865 | 109.459 | 119.886 | 109.27 | 1.03014 |
| 44 | 2 | CD | 2 | NZ | 2 | *CE | 2 | HE1 | 1.53124 | 109.228 | 119.698 | 109.437 | 1.09938 |
| 45 | 2 | CD | 2 | NZ | 2 | *CE | 2 | HE2 | 1.53124 | 109.228 | −120.062 | 109.777 | 1.0988 |
| 46 | 2 | CG | 2 | CD | 2 | CE | 2 | NZ | 1.52637 | 108.605 | 104.867 | 109.228 | 1.46455 |
| 47 | 2 | CA | 2 | C | 3 | N | 3 | CA | 1.59418 | 125.802 | −165.648 | 122.302 | 1.46212 |
| 48 | 3 | CA | 2 | C | 3 | *N | 3 | CD | 1.46212 | 122.302 | 177.147 | 127.858 | 1.43897 |
| 49 | 3 | C | 3 | N | 3 | CA | 3 | C | 1.45189 | 122.302 | −48.7512 | 116.415 | 1.50051 |
| 50 | 3 | C | 3 | N | 3 | *CA | 3 | CB | 1.50051 | 116.415 | −118.387 | 99.5022 | 1.54892 |
| 51 | 3 | C | 3 | N | 3 | *CA | 3 | HA | 1.50051 | 116.415 | 126.034 | 108.65 | 1.09811 |
| 52 | 3 | O1 | 3 | C | 3 | CA | 3 | N | 1.23681 | 120.011 | 129.838 | 116.415 | 1.46212 |
| 53 | 3 | O1 | 3 | CA | 3 | *C | 3 | O2 | 1.23681 | 120.011 | 179.538 | 119.877 | 1.28844 |
| 54 | 3 | N | 3 | CA | 3 | CB | 3 | CG | 1.46212 | 99.5022 | −46.5389 | 97.8978 | 1.48153 |
| 55 | 3 | CG | 3 | CA | 3 | *CB | 3 | HB1 | 1.48153 | 97.8978 | 112.881 | 110.888 | 1.09815 |
| 56 | 3 | CG | 3 | CA | 3 | *CB | 3 | HB2 | 1.48153 | 97.8978 | −122.661 | 112.769 | 1.09818 |
| 57 | 3 | CA | 3 | CB | 3 | CG | 3 | CD | 1.54892 | 97.8978 | 58.0691 | 95.6158 | 1.54739 |
| 58 | 3 | CD | 3 | CB | 3 | *CG | 3 | HG1 | 1.54739 | 95.6158 | 118.701 | 114.975 | 1.09786 |
| 59 | 3 | CD | 3 | CB | 3 | *CG | 3 | HG2 | 1.54739 | 95.6158 | −115.301 | 109.706 | 1.10133 |
| 60 | 2 | C | 3 | N | 3 | CD | 3 | CG | 1.45189 | 127.858 | −157.073 | 100.77 | 1.54739 |
| 61 | 3 | CG | 3 | N | 3 | *CD | 3 | HD1 | 1.54739 | 100.77 | 121.749 | 114.771 | 1.06576 |
| 62 | 3 | CG | 3 | N | 3 | *CD | 3 | HD2 | 1.54739 | 100.77 | −115.09 | 108.34 | 1.09734 |
| 63 | 3 | CB | 3 | CG | 3 | CD | 3 | N | 1.48153 | 95.6158 | −49.0119 | 100.77 | 1.43897 |

[¹H-¹H]-T-ROESY Dataset for Lisinopril

| | remark 2D-T-ROESY data for TRANS lisinopril | | | | | | | | |
|---|---|---|---|---|---|---|---|---|---|
| configuration: | | | | | | | | | | field 600
solvent d2o
temp 278
visc 1.94
ident 2D-T-ROESY
mix_time 400 ms
endsection

| | | | | | data: | | | | |
|---|---|---|---|---|---|---|---|---|---|
| remark | ROE no. | ring | ring | donor | ring | ring | acc | int | error | code |

| remark | ROE no. | ring | | donor | ring | | acc | int | error | code |
|---|---|---|---|---|---|---|---|---|---|---|
| asgn | 1 | F | 1 | HA | K | 2 | HD1 | −2.01 | 0.88 | 0 |
| ovlp | 1 | F | 1 | HA | K | 2 | HD2 | −2.01 | 0.88 | 0 |
| asgn | 2 | F | 1 | HG1 | K | 2 | HD1 | −2.37 | 1.44 | 0 |
| ovlp | 2 | F | 1 | HG2 | K | 2 | HD1 | −2.37 | 1.44 | 0 |
| ovlp | 2 | F | 1 | HG2 | K | 2 | HD2 | −2.37 | 1.44 | 0 |
| ovlp | 2 | F | 1 | HG1 | K | 2 | HD2 | −2.37 | 1.44 | 0 |
| asgn | 3 | K | 2 | HD1 | P | 3 | HA | −1.42 | 0.79 | 0 |
| ovlp | 3 | K | 2 | HD2 | P | 3 | HA | −1.42 | 0.79 | 0 |
| asgn | 4 | F | 1 | HE1 | F | 1 | HA | −12.13 | 6.06 | 0 |
| ovlp | 4 | F | 1 | HZ2 | F | 1 | HA | −12.13 | 6.06 | 0 |
| ovlp | 4 | F | 1 | HE2 | F | 1 | HA | −12.13 | 6.06 | 0 |
| ovlp | 4 | F | 1 | HZ1 | F | 1 | HA | −12.13 | 6.06 | 0 |
| asgn | 5 | F | 1 | HH | F | 1 | HA | −1.97 | 0.99 | 0 |
| asgn | 6 | K | 2 | HA | F | 1 | HA | −24.12 | 12.06 | 0 |
| asgn | 7 | K | 2 | HB1 | F | 1 | HA | −5.08 | 2.54 | 0 |
| ovlp | 7 | K | 2 | HB2 | F | 1 | HA | −5.08 | 2.54 | 0 |
| asgn | 8 | K | 2 | HD1 | F | 1 | HA | −2.03 | 1.01 | 0 |
| ovlp | 8 | K | 2 | HD2 | F | 1 | HA | −2.03 | 1.01 | 0 |
| asgn | 9 | P | 3 | HA | F | 1 | HA | −13.05 | 6.53 | 0 |
| asgn | 10 | P | 3 | HB1 | F | 1 | HA | −3.18 | 1.59 | 0 |
| asgn | 11 | P | 3 | HA | F | 1 | HB1 | −2.16 | 1.08 | 0 |
| ovlp | 11 | P | 3 | HA | F | 1 | HB2 | −2.16 | 1.08 | 0 |
| asgn | 12 | F | 1 | HG1 | F | 1 | HG1 | 3027.97 | 1513.98 | 0 |
| ovlp | 12 | F | 1 | HG1 | F | 1 | HG1 | 3027.97 | 1513.98 | 0 |
| ovlp | 12 | F | 1 | HG2 | F | 1 | HG1 | 3027.97 | 1513.98 | 0 |
| ovlp | 12 | F | 1 | HG2 | F | 1 | HG2 | 3027.97 | 1513.98 | 0 |
| asgn | 13 | F | 1 | HE1 | F | 1 | HG1 | −164.49 | 82.25 | 0 |
| ovlp | 13 | F | 1 | HZ2 | F | 1 | HG2 | −164.49 | 82.25 | 0 |
| ovlp | 13 | F | 1 | HE2 | F | 1 | HG1 | −164.49 | 82.25 | 0 |
| ovlp | 13 | F | 1 | HZ1 | F | 1 | HG2 | −164.49 | 82.25 | 0 |
| ovlp | 13 | F | 1 | HE1 | F | 1 | HG2 | −164.49 | 82.25 | 0 |
| ovlp | 13 | F | 1 | HE2 | F | 1 | HG2 | −164.49 | 82.25 | 0 |
| ovlp | 13 | F | 1 | HZ2 | F | 1 | HG1 | −164.49 | 82.25 | 0 |
| ovlp | 13 | F | 1 | HZ1 | F | 1 | HG1 | −164.49 | 82.25 | 0 |
| asgn | 14 | F | 1 | HG1 | K | 2 | HG1 | −2.86 | 0.88 | 0 |
| ovlp | 14 | F | 1 | HG2 | K | 2 | HG1 | −2.86 | 0.88 | 0 |
| ovlp | 14 | F | 1 | HG1 | K | 2 | HG2 | −2.86 | 0.88 | 0 |
| ovlp | 14 | F | 1 | HG2 | K | 2 | HG2 | −2.86 | 0.88 | 0 |
| asgn | 15 | K | 2 | HD1 | F | 1 | HG1 | −3.99 | 2.00 | 0 |
| ovlp | 15 | K | 2 | HD1 | F | 1 | HG2 | −3.99 | 2.00 | 0 |
| ovlp | 15 | K | 2 | HD2 | F | 1 | HG1 | −3.99 | 2.00 | 0 |
| ovlp | 15 | K | 2 | HD2 | F | 1 | HG2 | −3.99 | 2.00 | 0 |
| asgn | 16 | P | 3 | HA | F | 1 | HG1 | −4.93 | 2.47 | 0 |
| ovlp | 16 | P | 3 | HA | F | 1 | HG2 | −4.93 | 2.47 | 0 |
| asgn | 17 | P | 3 | HB2 | F | 1 | HG1 | −6.58 | 3.29 | 0 |
| ovlp | 17 | P | 3 | HB2 | F | 1 | HG2 | −6.58 | 3.29 | 0 |
| asgn | 18 | F | 1 | HE1 | F | 1 | HE1 | 13344.29 | 6672.15 | 0 |
| ovlp | 18 | F | 1 | HE2 | F | 1 | HE1 | 13344.29 | 6672.15 | 0 |
| ovlp | 18 | F | 1 | HZ2 | F | 1 | HE1 | 13344.29 | 6672.15 | 0 |
| ovlp | 18 | F | 1 | HZ1 | F | 1 | HZ2 | 13344.29 | 6672.15 | 0 |
| ovlp | 18 | F | 1 | HE2 | F | 1 | HZ1 | 13344.29 | 6672.15 | 0 |
| ovlp | 18 | F | 1 | HE2 | F | 1 | HE2 | 13344.29 | 6672.15 | 0 |
| ovlp | 18 | F | 1 | HZ2 | F | 1 | HZ2 | 13344.29 | 6672.15 | 0 |
| ovlp | 18 | F | 1 | HE2 | F | 1 | HZ2 | 13344.29 | 6672.15 | 0 |
| ovlp | 18 | F | 1 | HZ1 | F | 1 | HZ1 | 13344.29 | 6672.15 | 0 |
| ovlp | 18 | F | 1 | HE1 | F | 1 | HE2 | 13344.29 | 6672.15 | 0 |
| ovlp | 18 | F | 1 | HE1 | F | 1 | HZ2 | 13344.29 | 6672.15 | 0 |
| ovlp | 18 | F | 1 | HZ1 | F | 1 | HE1 | 13344.29 | 6672.15 | 0 |
| ovlp | 18 | F | 1 | HZ1 | F | 1 | HE2 | 13344.29 | 6672.15 | 0 |
| ovlp | 18 | F | 1 | HZ2 | F | 1 | HE2 | 13344.29 | 6672.15 | 0 |
| ovlp | 18 | F | 1 | HZ2 | F | 1 | HZ1 | 13344.29 | 6672.15 | 0 |
| ovlp | 18 | F | 1 | HE1 | F | 1 | HZ1 | 13344.29 | 6672.15 | 0 |
| asgn | 19 | F | 1 | HA | F | 1 | HE1 | −10.76 | 5.38 | 0 |

-continued

| | | | | | | | | | |
|---|---|---|---|---|---|---|---|---|---|
| | remark 2D-T-ROESY data for TRANS lisinopril | | | | | | | | |
| ovlp | 19 | F | 1 | HA | F | 1 | HE2 | −10.76 | 5.38 | 0 |
| ovlp | 19 | F | 1 | HA | F | 1 | HZ2 | −10.76 | 5.38 | 0 |
| ovlp | 19 | F | 1 | HA | F | 1 | HZ1 | −10.76 | 5.38 | 0 |
| asgn | 20 | F | 1 | HG1 | F | 1 | HE1 | −104.88 | 52.44 | 0 |
| ovlp | 20 | F | 1 | HG2 | F | 1 | HE2 | −104.88 | 52.44 | 0 |
| ovlp | 20 | F | 1 | HG2 | F | 1 | HZ2 | −104.88 | 52.44 | 0 |
| ovlp | 20 | F | 1 | HG2 | F | 1 | HZ1 | −104.88 | 52.44 | 0 |
| ovlp | 20 | F | 1 | HG1 | F | 1 | HE2 | −104.88 | 52.44 | 0 |
| ovlp | 20 | F | 1 | HG2 | F | 1 | HE1 | −104.88 | 52.44 | 0 |
| ovlp | 20 | F | 1 | HG2 | F | 1 | HZ2 | −104.88 | 52.44 | 0 |
| asgn | 21 | P | 3 | HA | F | 1 | HE1 | −12.55 | 6.27 | 0 |
| ovlp | 21 | P | 3 | HA | F | 1 | HZ1 | −12.55 | 6.27 | 0 |
| ovlp | 21 | P | 3 | HA | F | 1 | HE2 | −12.55 | 6.27 | 0 |
| ovlp | 21 | P | 3 | HA | F | 1 | HZ2 | −12.55 | 6.27 | 0 |
| asgn | 22 | P | 3 | HD1 | F | 1 | HE1 | −6.16 | 3.08 | 0 |
| ovlp | 22 | P | 3 | HD2 | F | 1 | HZ1 | −6.16 | 3.08 | 0 |
| ovlp | 22 | P | 3 | HD2 | F | 1 | HE1 | −6.16 | 3.08 | 0 |
| ovlp | 22 | P | 3 | HD2 | F | 1 | HZ1 | −6.16 | 3.08 | 0 |
| ovlp | 22 | P | 3 | HD2 | F | 1 | HE2 | −6.16 | 3.08 | 0 |
| ovlp | 22 | P | 3 | HD2 | F | 1 | HZ2 | −6.16 | 3.08 | 0 |
| ovlp | 22 | P | 3 | HD2 | F | 1 | HE2 | −6.16 | 3.08 | 0 |
| asgn | 23 | F | 1 | HH | F | 1 | HH | 12824.54 | 6412.27 | 0 |
| asgn | 24 | P | 3 | HA | F | 1 | HH | −19.16 | 9.58 | 0 |
| asgn | 25 | K | 2 | HG1 | K | 2 | HA | −6.62 | 3.31 | 0 |
| ovlp | 25 | K | 2 | HG2 | K | 2 | HA | −6.62 | 3.31 | 0 |
| asgn | 26 | F | 1 | HA | K | 2 | HA | −10.36 | 5.18 | 0 |
| asgn | 27 | F | 1 | HB1 | K | 2 | HA | −1.29 | 0.64 | 0 |
| ovlp | 27 | F | 1 | HB2 | K | 2 | HA | −1.29 | 0.64 | 0 |
| asgn | 28 | P | 3 | HD1 | K | 2 | HA | −48.23 | 24.11 | 0 |
| ovlp | 28 | P | 3 | HD2 | K | 2 | HA | −48.23 | 24.11 | 0 |
| asgn | 29 | K | 2 | HB1 | K | 2 | HB1 | 980.97 | 490.49 | 0 |
| ovlp | 29 | K | 2 | HB2 | K | 2 | HB1 | 980.97 | 490.49 | 0 |
| ovlp | 29 | K | 2 | HB1 | K | 2 | HB2 | 980.97 | 490.49 | 0 |
| ovlp | 29 | K | 2 | HB2 | K | 2 | HB2 | 980.97 | 490.49 | 0 |
| asgn | 30 | F | 1 | HA | K | 2 | HB1 | −3.12 | 1.56 | 0 |
| ovlp | 30 | F | 1 | HA | K | 2 | HB2 | −3.12 | 1.56 | 0 |
| asgn | 31 | F | 1 | HE1 | K | 2 | HB1 | −0.65 | 0.32 | 0 |
| ovlp | 31 | F | 1 | HE2 | K | 2 | HB1 | −0.65 | 0.32 | 0 |
| ovlp | 31 | F | 1 | HE1 | K | 2 | HB2 | −0.65 | 0.32 | 0 |
| ovlp | 31 | F | 1 | HE2 | K | 2 | HB2 | −0.65 | 0.32 | 0 |
| ovlp | 31 | F | 1 | HZ1 | K | 2 | HB1 | −0.65 | 0.32 | 0 |
| ovlp | 31 | F | 1 | HZ2 | K | 2 | HB1 | −0.65 | 0.32 | 0 |
| ovlp | 31 | F | 1 | HZ1 | K | 2 | HB2 | −0.65 | 0.32 | 0 |
| ovlp | 31 | F | 1 | HZ2 | K | 2 | HB2 | −0.65 | 0.32 | 0 |
| asgn | 32 | P | 3 | HA | K | 2 | HB1 | −24.34 | 12.17 | 0 |
| ovlp | 32 | P | 3 | HA | K | 2 | HB2 | −24.34 | 12.17 | 0 |
| asgn | 33 | P | 3 | HD1 | K | 2 | HB1 | −84.00 | 42.00 | 0 |
| ovlp | 33 | P | 3 | HD2 | K | 2 | HB1 | −84.00 | 42.00 | 0 |
| ovlp | 33 | P | 3 | HD1 | K | 2 | HB2 | −84.00 | 42.00 | 0 |
| ovlp | 33 | P | 3 | HD2 | K | 2 | HB2 | −84.00 | 42.00 | 0 |
| asgn | 34 | K | 2 | HG1 | K | 2 | HG1 | 767.20 | 383.60 | 0 |
| ovlp | 34 | K | 2 | HG1 | K | 2 | HG2 | 767.20 | 383.60 | 0 |
| ovlp | 34 | K | 2 | HG2 | K | 2 | HG1 | 767.20 | 383.60 | 0 |
| ovlp | 34 | K | 2 | HG2 | K | 2 | HG2 | 767.20 | 383.60 | 0 |
| asgn | 35 | K | 2 | HA | K | 2 | HG1 | −13.62 | 6.81 | 0 |
| ovlp | 35 | K | 2 | HA | K | 2 | HG2 | −13.62 | 6.81 | 0 |
| asgn | 36 | K | 2 | HE1 | K | 2 | HG1 | −170.41 | 85.21 | 0 |
| ovlp | 36 | K | 2 | HE2 | K | 2 | HG1 | −170.41 | 85.21 | 0 |
| ovlp | 36 | K | 2 | HE1 | K | 2 | HG2 | −170.41 | 85.21 | 0 |
| ovlp | 36 | K | 2 | HE2 | K | 2 | HG2 | −170.41 | 85.21 | 0 |
| asgn | 37 | F | 1 | HE1 | K | 2 | HG1 | −0.49 | 0.24 | 0 |
| ovlp | 37 | F | 1 | HE1 | K | 2 | HG2 | −0.49 | 0.24 | 0 |
| ovlp | 37 | F | 1 | HZ1 | K | 2 | HG2 | −0.49 | 0.24 | 0 |
| ovlp | 37 | F | 1 | HZ2 | K | 2 | HG1 | −0.49 | 0.24 | 0 |
| ovlp | 37 | F | 1 | HZ1 | K | 2 | HG1 | −0.49 | 0.24 | 0 |
| ovlp | 37 | F | 1 | HE2 | K | 2 | HG1 | −0.49 | 0.24 | 0 |
| ovlp | 37 | F | 1 | HE2 | K | 2 | HG2 | −0.49 | 0.24 | 0 |
| ovlp | 37 | F | 1 | HZ2 | K | 2 | HG2 | −0.49 | 0.24 | 0 |
| asgn | 38 | P | 3 | HA | K | 2 | HG1 | −3.66 | 1.83 | 0 |
| ovlp | 38 | P | 3 | HA | K | 2 | HG2 | −3.66 | 1.83 | 0 |
| asgn | 39 | P | 3 | HD1 | K | 2 | HG1 | −27.73 | 13.86 | 0 |
| ovlp | 39 | P | 3 | HD2 | K | 2 | HG2 | −27.73 | 13.86 | 0 |
| ovlp | 39 | P | 3 | HD2 | K | 2 | HG1 | −27.73 | 13.86 | 0 |
| ovlp | 39 | P | 3 | HD1 | K | 2 | HG2 | −27.73 | 13.86 | 0 |
| asgn | 40 | K | 2 | HD1 | K | 2 | HD1 | 1112.30 | 556.15 | 0 |

-continued

| | | | | | | | | | |
|---|---|---|---|---|---|---|---|---|---|
| | remark 2D-T-ROESY data for TRANS lisinopril |
| ovlp | 40 | K | 2 | HD2 | K | 2 | HD1 | 1112.30 | 556.15 | 0 |
| ovlp | 40 | K | 2 | HD2 | K | 2 | HD2 | 1112.30 | 556.15 | 0 |
| ovlp | 40 | K | 2 | HD1 | K | 2 | HD2 | 1112.30 | 556.15 | 0 |
| asgn | 41 | F | 1 | HE1 | K | 2 | HD1 | −0.81 | 0.40 | 0 |
| asgn | 41 | F | 1 | HE2 | K | 2 | HD1 | −0.81 | 0.40 | 0 |
| asgn | 41 | F | 1 | HZ1 | K | 2 | HD1 | −0.81 | 0.40 | 0 |
| asgn | 41 | F | 1 | HZ2 | K | 2 | HD1 | −0.81 | 0.40 | 0 |
| asgn | 41 | F | 1 | HE1 | K | 2 | HD2 | −0.81 | 0.40 | 0 |
| asgn | 41 | F | 1 | HE2 | K | 2 | HD2 | −0.81 | 0.40 | 0 |
| asgn | 41 | F | 1 | HZ1 | K | 2 | HD2 | −0.81 | 0.40 | 0 |
| asgn | 41 | F | 1 | HZ2 | K | 2 | HD2 | −0.81 | 0.40 | 0 |
| asgn | 42 | F | 1 | HH | K | 2 | HD1 | −0.51 | 0.25 | 0 |
| ovlp | 42 | F | 1 | HE2 | K | 2 | HD2 | −0.81 | 0.40 | 0 |
| ovlp | 42 | F | 1 | HZ1 | K | 2 | HD1 | −0.81 | 0.40 | 0 |
| ovlp | 42 | F | 1 | HH | K | 2 | HD2 | −0.51 | 0.25 | 0 |
| ovlp | 42 | F | 1 | HZ1 | K | 2 | HD1 | −0.81 | 0.40 | 0 |
| ovlp | 42 | F | 1 | HE1 | K | 2 | HD2 | −0.81 | 0.40 | 0 |
| ovlp | 42 | F | 1 | HZ2 | K | 2 | HD2 | −0.81 | 0.40 | 0 |
| ovlp | 42 | F | 1 | HZ2 | K | 2 | HD2 | −0.81 | 0.40 | 0 |
| ovlp | 42 | F | 1 | HE2 | K | 2 | HD1 | −0.81 | 0.40 | 0 |
| asgn | 43 | P | 3 | HA | K | 2 | HD1 | −3.00 | 1.50 | 0 |
| ovlp | 43 | P | 3 | HA | K | 2 | HD2 | −3.00 | 1.50 | 0 |
| asgn | 44 | P | 3 | HD1 | K | 2 | HD1 | −21.06 | 10.53 | 0 |
| ovlp | 44 | P | 3 | HD2 | K | 2 | HD1 | −21.06 | 10.53 | 0 |
| ovlp | 44 | P | 3 | HD1 | K | 2 | HD2 | −21.06 | 10.53 | 0 |
| ovlp | 44 | P | 3 | HD2 | K | 2 | HD2 | −21.06 | 10.53 | 0 |
| asgn | 45 | K | 2 | HE1 | K | 2 | HE1 | 10977.13 | 5488.57 | 0 |
| ovlp | 45 | K | 2 | HE2 | K | 2 | HE1 | 10977.13 | 5488.57 | 0 |
| ovlp | 45 | K | 2 | HE1 | K | 2 | HE2 | 10977.13 | 5488.57 | 0 |
| ovlp | 45 | K | 2 | HE2 | K | 2 | HE2 | 10977.13 | 5488.57 | 0 |
| asgn | 46 | P | 3 | HA | P | 3 | HA | 4186.68 | 2093.34 | 0 |
| asgn | 47 | P | 3 | HD1 | P | 3 | HA | −16.65 | 8.33 | 0 |
| ovlp | 47 | P | 3 | HD2 | P | 3 | HA | −16.65 | 8.33 | 0 |
| asgn | 48 | F | 1 | HA | P | 3 | HA | −11.50 | 5.75 | 0 |
| asgn | 49 | F | 1 | HE1 | P | 3 | HA | −11.26 | 5.63 | 0 |
| ovlp | 49 | F | 1 | HE2 | P | 3 | HA | −11.26 | 5.63 | 0 |
| ovlp | 49 | F | 1 | HZ1 | P | 3 | HA | −11.26 | 5.63 | 0 |
| ovlp | 49 | F | 1 | HZ2 | P | 3 | HA | −11.26 | 5.63 | 0 |
| asgn | 50 | F | 1 | HH | P | 3 | HA | −6.54 | 3.27 | 0 |
| asgn | 51 | P | 3 | HB1 | P | 3 | HB1 | 2659.43 | 1329.72 | 0 |
| asgn | 52 | P | 3 | HA | P | 3 | HB1 | −201.63 | 100.82 | 0 |
| asgn | 53 | P | 3 | HD1 | P | 3 | HB1 | −32.47 | 16.24 | 0 |
| ovlp | 53 | P | 3 | HD2 | P | 3 | HB1 | −32.47 | 16.24 | 0 |
| asgn | 54 | F | 1 | HE1 | P | 3 | HB1 | −4.25 | 2.13 | 0 |
| ovlp | 54 | F | 1 | HE2 | P | 3 | HB1 | −4.25 | 2.13 | 0 |
| ovlp | 54 | F | 1 | HZ1 | P | 3 | HB1 | −4.25 | 2.13 | 0 |
| ovlp | 54 | F | 1 | HZ2 | P | 3 | HB1 | −4.25 | 2.13 | 0 |
| asgn | 55 | F | 1 | HH | P | 3 | HB1 | −3.21 | 1.60 | 0 |
| asgn | 56 | P | 3 | HD1 | P | 3 | HB2 | −42.69 | 21.34 | 0 |
| ovlp | 56 | P | 3 | HD2 | P | 3 | HB2 | −42.69 | 21.34 | 0 |
| asgn | 57 | K | 2 | HE1 | P | 3 | HG1 | −32.35 | 16.18 | 0 |
| ovlp | 57 | K | 2 | HE2 | P | 3 | HG2 | −32.35 | 16.18 | 0 |
| ovlp | 57 | K | 2 | HE1 | P | 3 | HG2 | −32.35 | 16.18 | 0 |
| ovlp | 57 | K | 2 | HE2 | P | 3 | HG1 | −32.35 | 16.18 | 0 |
| asgn | 58 | P | 3 | HD1 | P | 3 | HD1 | 2988.43 | 1494.21 | 0 |
| ovlp | 58 | P | 3 | HD2 | P | 3 | HD2 | 2988.43 | 1494.21 | 0 |
| ovlp | 58 | P | 3 | HD2 | P | 3 | HD1 | 2988.43 | 1494.21 | 0 |
| ovlp | 58 | P | 3 | HD1 | P | 3 | HD2 | 2988.43 | 1494.21 | 0 |
| asgn | 59 | P | 3 | HA | P | 3 | HD1 | −16.06 | 8.03 | 0 |
| ovlp | 59 | P | 3 | HA | P | 3 | HD2 | −16.06 | 8.03 | 0 |
| asgn | 60 | F | 1 | HE1 | P | 3 | HD1 | 8.77 | 4.39 | 0 |
| ovlp | 60 | F | 1 | HE1 | P | 3 | HD2 | 8.77 | 4.39 | 0 |
| ovlp | 60 | F | 1 | HE2 | P | 3 | HD1 | 8.77 | 4.39 | 0 |
| ovlp | 60 | F | 1 | HZ1 | P | 3 | HD2 | 8.77 | 4.39 | 0 |
| ovlp | 60 | F | 1 | HZ2 | P | 3 | HD2 | 8.77 | 4.39 | 0 |
| ovlp | 60 | F | 1 | HE2 | P | 3 | HD2 | 8.77 | 4.39 | 0 |
| ovlp | 60 | F | 1 | HZ1 | P | 3 | HD1 | 8.77 | 4.39 | 0 |
| ovlp | 60 | F | 1 | HZ2 | P | 3 | HD1 | 8.77 | 4.39 | 0 |
| asgn | 61 | F | 1 | HH | P | 3 | HD1 | 4.62 | 2.31 | 0 |
| ovlp | 61 | F | 1 | HH | P | 3 | HD2 | 4.62 | 2.31 | 0 |
| asgn | 62 | K | 2 | HA | P | 3 | HD1 | −100.32 | 50.16 | 0 |
| ovlp | 62 | K | 2 | HA | P | 3 | HD2 | −100.32 | 50.16 | 0 |
| asgn | 63 | K | 2 | HB1 | P | 3 | HD1 | −145.35 | 72.67 | 0 |
| ovlp | 63 | K | 2 | HB2 | P | 3 | HD1 | −145.35 | 72.67 | 0 |
| ovlp | 63 | K | 2 | HB1 | P | 3 | HD2 | −145.35 | 72.67 | 0 |
| ovlp | 63 | K | 2 | HB2 | P | 3 | HD2 | −145.35 | 72.67 | 0 |
| asgn | 64 | K | 2 | HG1 | P | 3 | HD1 | −26.97 | 13.49 | 0 |

-continued

| | | | | | | | | | | |
|---|---|---|---|---|---|---|---|---|---|---|
| \multicolumn{11}{|c|}{remark 2D-T-ROESY data for TRANS lisinopril} |

| | | | | | | | | | | |
|---|---|---|---|---|---|---|---|---|---|---|
| ovlp | 64 | K | 2 | HG2 | P | 3 | HD2 | −26.97 | 13.49 | 0 |
| ovlp | 64 | K | 2 | HG1 | P | 3 | HD2 | −26.97 | 13.49 | 0 |
| ovlp | 64 | K | 2 | HG2 | P | 3 | HD1 | −26.97 | 13.49 | 0 |
| asgn | 65 | K | 2 | HD1 | P | 3 | HD1 | −26.95 | 13.48 | 0 |
| ovlp | 65 | K | 2 | HD2 | P | 3 | HD1 | −26.95 | 13.48 | 0 |
| ovlp | 65 | K | 2 | HD1 | P | 3 | HD2 | −26.95 | 13.48 | 0 |
| ovlp | 65 | K | 2 | HD2 | P | 3 | HD2 | −26.95 | 13.48 | 0 |
| asgn | 66 | K | 2 | HE1 | P | 3 | HD1 | −13.04 | 6.52 | 0 |
| ovlp | 66 | K | 2 | HE1 | P | 3 | HD2 | −13.04 | 6.52 | 0 |
| ovlp | 66 | K | 2 | HE2 | P | 3 | HD2 | −13.04 | 6.52 | 0 |
| ovlp | 66 | K | 2 | HE2 | P | 3 | HD1 | −13.04 | 6.52 | 0 |
| asgn | 67 | K | 2 | HA | F | 1 | HB1 | −2.66 | 1.79 | 0 |
| ovlp | 67 | K | 2 | HA | F | 1 | HB2 | −2.66 | 1.79 | 0 |
| remark | noROEs | | | | | | | | | |
| asgn | 101 | P | 3 | HB2 | F | 1 | HB1 | 0.00 | 0.41 | 0 |
| ovlp | 101 | P | 3 | HB2 | F | 1 | HB2 | 0.00 | 0.41 | 0 |
| asgn | 102 | K | 2 | HG1 | F | 1 | HB1 | 0.00 | 0.41 | 0 |
| ovlp | 102 | K | 2 | HG1 | F | 1 | HB2 | 0.00 | 0.41 | 0 |
| ovlp | 102 | K | 2 | HG2 | F | 1 | HB2 | 0.00 | 0.41 | 0 |
| ovlp | 102 | K | 2 | HG2 | F | 1 | HB1 | 0.00 | 0.41 | 0 |
| asgn | 103 | K | 2 | HB1 | F | 1 | HG1 | 0.00 | 0.58 | 0 |
| ovlp | 103 | K | 2 | HB2 | F | 1 | HG1 | 0.00 | 0.58 | 0 |
| ovlp | 103 | K | 2 | HB1 | F | 1 | HG2 | 0.00 | 0.58 | 0 |
| ovlp | 103 | K | 2 | HB2 | F | 1 | HG2 | 0.00 | 0.58 | 0 |
| asgn | 104 | K | 2 | HB1 | F | 1 | HE1 | 0.00 | 3.08 | 0 |
| ovlp | 104 | K | 2 | HB2 | F | 1 | HE1 | 0.00 | 3.08 | 0 |
| ovlp | 104 | K | 2 | HB2 | F | 1 | HE2 | 0.00 | 3.08 | 0 |
| ovlp | 104 | K | 2 | HB2 | F | 1 | HZ1 | 0.00 | 3.08 | 0 |
| ovlp | 104 | K | 2 | HB1 | F | 1 | HZ2 | 0.00 | 3.08 | 0 |
| ovlp | 104 | K | 2 | HB1 | F | 1 | HZ1 | 0.00 | 3.08 | 0 |
| ovlp | 104 | K | 2 | HB1 | F | 1 | HE2 | 0.00 | 3.08 | 0 |
| ovlp | 104 | K | 2 | HB2 | F | 1 | HZ2 | 0.00 | 3.08 | 0 |
| asgn | 105 | K | 2 | HA | F | 1 | HH | 0.00 | 0.21 | 0 |
| asgn | 106 | K | 2 | HE1 | F | 1 | HH | 0.00 | 0.21 | 0 |
| ovlp | 106 | K | 2 | HE2 | F | 1 | HH | 0.00 | 0.21 | 0 |
| asgn | 107 | P | 3 | HB1 | F | 1 | HH | 0.00 | 0.21 | 0 |
| asgn | 108 | K | 2 | HB1 | F | 1 | HH | 0.00 | 0.21 | 0 |
| ovlp | 108 | K | 2 | HB2 | F | 1 | HH | 0.00 | 0.21 | 0 |
| asgn | 109 | K | 2 | HG1 | F | 1 | HH | 0.00 | 0.21 | 0 |
| ovlp | 109 | K | 2 | HG2 | F | 1 | HH | 0.00 | 0.21 | 0 |
| asgn | 110 | K | 2 | HD1 | F | 1 | HH | 0.00 | 0.21 | 0 |
| ovlp | 110 | K | 2 | HD2 | F | 1 | HH | 0.00 | 0.21 | 0 |
| asgn | 111 | F | 1 | HE1 | K | 2 | HA | 0.00 | 0.33 | 0 |
| ovlp | 111 | F | 1 | HZ1 | K | 2 | HA | 0.00 | 0.33 | 0 |
| ovlp | 111 | F | 1 | HE2 | K | 2 | HA | 0.00 | 0.33 | 0 |
| ovlp | 111 | F | 1 | HZ2 | K | 2 | HA | 0.00 | 0.33 | 0 |
| asgn | 112 | F | 1 | HH | K | 2 | HA | 0.00 | 0.33 | 0 |
| asgn | 113 | P | 3 | HB1 | K | 2 | HA | 0.00 | 0.33 | 0 |
| asgn | 114 | P | 3 | HB2 | K | 2 | HA | 0.00 | 0.33 | 0 |
| asgn | 115 | P | 3 | HG1 | K | 2 | HA | 0.00 | 0.33 | 0 |
| ovlp | 115 | P | 3 | HG2 | K | 2 | HA | 0.00 | 0.33 | 0 |
| asgn | 116 | F | 1 | HH | K | 2 | HG1 | 0.00 | 0.46 | 0 |
| ovlp | 116 | F | 1 | HH | K | 2 | HG2 | 0.00 | 0.46 | 0 |
| asgn | 117 | P | 3 | HB1 | K | 2 | HG1 | 0.00 | 0.46 | 0 |
| ovlp | 117 | P | 3 | HB1 | K | 2 | HG2 | 0.00 | 0.46 | 0 |
| asgn | 118 | F | 1 | HB1 | K | 2 | HG1 | 0.00 | 0.46 | 0 |
| ovlp | 118 | F | 1 | HB1 | K | 2 | HG2 | 0.00 | 0.46 | 0 |
| ovlp | 118 | F | 1 | HB2 | K | 2 | HG1 | 0.00 | 0.46 | 0 |
| ovlp | 118 | F | 1 | HB2 | K | 2 | HG2 | 0.00 | 0.46 | 0 |
| asgn | 119 | P | 3 | HB2 | K | 2 | HG1 | 0.00 | 0.46 | 0 |
| ovlp | 119 | P | 3 | HB2 | K | 2 | HG2 | 0.00 | 0.46 | 0 |
| asgn | 120 | P | 3 | HB1 | K | 2 | HD1 | 0.00 | 0.31 | 0 |
| ovlp | 120 | P | 3 | HB1 | K | 2 | HD2 | 0.00 | 0.31 | 0 |
| asgn | 121 | F | 1 | HH | K | 2 | HE1 | 0.00 | 0.20 | 0 |
| ovlp | 121 | F | 1 | HH | K | 2 | HE2 | 0.00 | 0.20 | 0 |
| asgn | 122 | P | 3 | HB2 | K | 2 | HE1 | 0.00 | 0.20 | 0 |
| ovlp | 122 | P | 3 | HB2 | K | 2 | HE2 | 0.00 | 0.20 | 0 |
| asgn | 123 | F | 1 | HB1 | P | 3 | HA | 0.00 | 1.81 | 0 |
| ovlp | 123 | F | 1 | HB2 | P | 3 | HA | 0.00 | 1.81 | 0 |
| asgn | 124 | K | 2 | HA | P | 3 | HB1 | 0.00 | 0.38 | 0 |
| asgn | 124 | F | 1 | HA | P | 3 | HB1 | 0.00 | 0.38 | 0 |
| asgn | 125 | K | 2 | HE1 | P | 3 | HB1 | 0.00 | 0.38 | 0 |
| ovlp | 125 | K | 2 | HE2 | P | 3 | HB1 | 0.00 | 0.38 | 0 |
| asgn | 126 | F | 1 | HB1 | P | 3 | HB1 | 0.00 | 0.38 | 0 |
| ovlp | 126 | F | 1 | HB2 | P | 3 | HB1 | 0.00 | 0.38 | 0 |
| asgn | 127 | K | 2 | HB1 | P | 3 | HB1 | 0.00 | 0.38 | 0 |
| ovlp | 127 | K | 2 | HB2 | P | 3 | HB1 | 0.00 | 0.38 | 0 |

| | | | | remark 2D-T-ROESY data for TRANS lisinopril | | | | | |
|---|---|---|---|---|---|---|---|---|---|
| asgn | 128 | K | 2 | HD1 | P | 3 | HB1 | 0.00 | 0.38 | 0 |
| ovlp | 128 | K | 2 | HD2 | P | 3 | HB1 | 0.00 | 0.38 | 0 |
| asgn | 129 | K | 2 | HG1 | P | 3 | HB1 | 0.00 | 0.38 | 0 |
| ovlp | 129 | K | 2 | HG2 | P | 3 | HB1 | 0.00 | 0.38 | 0 |
| asgn | 130 | K | 2 | HA | P | 3 | HB2 | 0.00 | 0.45 | 0 |
| asgn | 130 | F | 1 | HA | P | 3 | HB2 | 0.00 | 0.45 | 0 |
| asgn | 131 | K | 2 | HE1 | P | 3 | HB2 | 0.00 | 0.45 | 0 |
| ovlp | 131 | K | 2 | HE2 | P | 3 | HB2 | 0.00 | 0.45 | 0 |
| asgn | 132 | F | 1 | HG1 | P | 3 | HB2 | 0.00 | 0.45 | 0 |
| ovlp | 132 | F | 1 | HG2 | P | 3 | HB2 | 0.00 | 0.45 | 0 |
| asgn | 133 | F | 1 | HB1 | P | 3 | HB2 | 0.00 | 0.45 | 0 |
| ovlp | 133 | F | 1 | HB2 | P | 3 | HB2 | 0.00 | 0.45 | 0 |
| asgn | 134 | K | 2 | HD1 | P | 3 | HB2 | 0.00 | 0.45 | 0 |
| ovlp | 134 | K | 2 | HD2 | P | 3 | HB2 | 0.00 | 0.45 | 0 |
| asgn | 135 | K | 2 | HG1 | P | 3 | HB2 | 0.00 | 0.45 | 0 |
| ovlp | 135 | K | 2 | HG2 | P | 3 | HB2 | 0.00 | 0.45 | 0 |
| asgn | 136 | K | 2 | HA | P | 3 | HG1 | 0.00 | 0.77 | 0 |
| ovlp | 136 | K | 2 | HA | P | 3 | HG2 | 0.00 | 0.77 | 0 |
| asgn | 137 | F | 1 | HG1 | P | 3 | HG1 | 0.00 | 0.77 | 0 |
| ovlp | 137 | F | 1 | HG2 | P | 3 | HG1 | 0.00 | 0.77 | 0 |
| ovlp | 137 | F | 1 | HG1 | P | 3 | HG2 | 0.00 | 0.77 | 0 |
| ovlp | 137 | F | 1 | HG2 | P | 3 | HG2 | 0.00 | 0.77 | 0 |
| asgn | 138 | F | 1 | HB1 | P | 3 | HG1 | 0.00 | 0.77 | 0 |
| ovlp | 138 | F | 1 | HB2 | P | 3 | HG1 | 0.00 | 0.77 | 0 |
| ovlp | 138 | F | 1 | HB2 | P | 3 | HG2 | 0.00 | 0.77 | 0 |
| ovlp | 138 | F | 1 | HB1 | P | 3 | HG2 | 0.00 | 0.77 | 0 |
| asgn | 139 | P | 3 | HB1 | F | 1 | HG1 | 0.00 | 0.58 | 0 |
| ovlp | 139 | P | 3 | HB1 | F | 1 | HG2 | 0.00 | 0.58 | 0 |
| endsection | | | | | | | | | | |

Scalar-Coupling Dataset for Lisinopril

| remark Conformation-dependent scalar couplings |
|---|
| configuration: |

```
field       600
solvent     d2o
ident       JCOUP
endsection
data:

remark atoms karplus c1 c2 c3 phase experimental error
coup   1   2 HA   2 CA   2 CB   2 HB1   7.23  -1.37  2.22   0   6.0  0.5   0
coup   2   2 HA   2 CA   2 CB   2 HB2   7.23  -1.37  2.22   0   6.0  0.5   0
coup   3   1 HB1  1 CB   1 CA   1 HA    7.23  -1.37  2.22   0   6.2  0.5   0
coup   4   1 HB2  1 CB   1 CA   1 HA    7.23  -1.37  2.22   0   6.2  0.5   0
endsection
```

$\chi^2_{restraint}$ Values for the Best Optimised Dynamic Structure of Lisinopril

| 104 | K | 2 | HB1 | F | 1 | HE1 | 0.00 | 3.10 | −0.49 | 0.03 | 0.02 | 0 | +7 | 2D-T-ROESY |
|---|---|---|---|---|---|---|---|---|---|---|---|---|---|---|
| 130 | K | 2 | HA | P | 3 | HB2 | 0.00 | 0.45 | 0.05 | 0.03 | 0.04 | 0 | +0 | 2D-T-ROESY |
| 136 | K | 2 | HA | P | 3 | HG1 | 0.00 | 0.77 | 0.09 | 0.05 | 0.26 | 0 | +1 | 2D-T-ROESY |
| 114 | P | 3 | HB2 | K | 2 | HA | 0.00 | 0.33 | 0.05 | 0.06 | 0.14 | 0 | +0 | 2D-T-ROESY |
| 112 | F | 1 | HH | K | 2 | HA | 0.00 | 0.33 | 0.09 | 0.07 | 0.09 | 0 | +0 | 2D-T-ROESY |
| 116 | F | 1 | HH | K | 2 | HG1 | 0.00 | 0.46 | 0.12 | 0.07 | 0.09 | 0 | +1 | 2D-T-ROESY |
| 107 | P | 3 | HB1 | F | 1 | HH | 0.00 | 0.21 | 0.05 | 0.08 | 0.36 | 0 | +0 | 2D-T-ROESY |
| 131 | K | 2 | HE1 | P | 3 | HB2 | 0.00 | 0.45 | 0.01 | 0.10 | 0.72 | 0 | +1 | 2D-T-ROESY |
| 126 | F | 1 | HB1 | P | 3 | HB1 | 0.00 | 0.38 | 0.01 | 0.10 | 1.40 | 0 | +1 | 2D-T-ROESY |
| 105 | K | 2 | HA | F | 1 | HH | 0.00 | 0.21 | 0.09 | 0.16 | 0.53 | 0 | +0 | 2D-T-ROESY |
| 13 | F | 1 | HE1 | F | 1 | HG1 | −160.00 | 82.00 | −190.00 | 0.18 | 2.00 | 0 | +7 | 2D-T-ROESY |
| 29 | K | 2 | HB1 | K | 2 | HB1 | 980.00 | 490.00 | 1100.00 | 0.19 | 2.80 | 0 | +3 | 2D-T-ROESY |
| 18 | F | 1 | HE1 | F | 1 | HE1 | 13000.00 | 6700.00 | 11000.00 | 0.20 | 1.20 | 0 | +15 | 2D-T-ROESY |
| 15 | K | 2 | HD1 | F | 1 | HG1 | −4.00 | 2.00 | −3.50 | 0.20 | 2.10 | 0 | +3 | 2D-T-ROESY |
| 106 | K | 2 | HE1 | F | 1 | HH | 0.00 | 0.21 | 0.10 | 0.22 | 1.10 | 0 | +1 | 2D-T-ROESY |
| 127 | K | 2 | HB1 | P | 3 | HB1 | 0.00 | 0.38 | −0.10 | 0.24 | 3.00 | 0 | +1 | 2D-T-ROESY |
| 134 | K | 2 | HD1 | P | 3 | HB2 | 0.00 | 0.45 | −0.05 | 0.24 | 11.00 | 0 | +1 | 2D-T-ROESY |
| 6 | K | 2 | HA | F | 1 | HA | −24.00 | 12.00 | −19.00 | 0.24 | 1.60 | 0 | +0 | 2D-T-ROESY |
| 46 | P | 3 | HA | P | 3 | HA | 4200.00 | 2100.00 | 3200.00 | 0.25 | 1.90 | 0 | +0 | 2D-T-ROESY |

-continued

| 121 | F | 1 | HH | K | 2 | HE1 | 0.00 | 0.20 | 0.10 | 0.25 | 1.30 | 0 | +1 | 2D-T-ROESY |
|---|---|---|---|---|---|---|---|---|---|---|---|---|---|---|
| 133 | F | 1 | HB1 | P | 3 | HB2 | 0.00 | 0.45 | −0.05 | 0.26 | 3.20 | 0 | +1 | 2D-T-ROESY |
| 115 | P | 3 | HG1 | K | 2 | HA | 0.00 | 0.33 | 0.09 | 0.29 | 7.90 | 0 | +1 | 2D-T-ROESY |
| 1 | 3J | 2 | HA | 3J | 2 | HB1 | 6.00 | 0.50 | 6.00 | 0.29 | 3.70 | 0 | +0 | JCOUP |
| 3 | K | 2 | HD1 | P | 3 | HA | −1.40 | 0.79 | −1.70 | 0.31 | 4.30 | 0 | +1 | 2D-T-ROESY |
| 101 | P | 3 | HB2 | F | 1 | HB1 | 0.00 | 0.41 | −0.05 | 0.31 | 4.50 | 0 | +1 | 2D-T-ROESY |
| 108 | K | 2 | HB1 | F | 1 | HH | 0.00 | 0.21 | 0.12 | 0.31 | 2.00 | 0 | +1 | 2D-T-ROESY |
| 132 | F | 1 | HG1 | P | 3 | HB2 | 0.00 | 0.45 | −0.21 | 0.32 | 3.30 | 0 | +1 | 2D-T-ROESY |
| 109 | K | 2 | HG1 | F | 1 | HH | 0.00 | 0.21 | 0.12 | 0.32 | 2.10 | 0 | +1 | 2D-T-ROESY |
| 28 | P | 3 | HD1 | K | 2 | HA | −48.00 | 24.00 | −36.00 | 0.33 | 4.00 | 0 | +1 | 2D-T-ROESY |
| 40 | K | 2 | HD1 | K | 2 | HD1 | 1100.00 | 560.00 | 1400.00 | 0.33 | 5.10 | 0 | +3 | 2D-T-ROESY |
| 48 | F | 1 | HA | P | 3 | HA | −12.00 | 5.80 | −8.50 | 0.36 | 4.60 | 0 | +0 | 2D-T-ROESY |
| 64 | K | 2 | HG1 | P | 3 | HG1 | −27.00 | 13.00 | −23.00 | 0.36 | 6.80 | 0 | +3 | 2D-T-ROESY |
| 65 | K | 2 | HD1 | P | 3 | HD1 | −27.00 | 13.00 | −23.00 | 0.36 | 5.10 | 0 | +3 | 2D-T-ROESY |
| 8 | K | 2 | HD1 | F | 1 | HA | −2.00 | 1.00 | −1.80 | 0.36 | 7.40 | 0 | +1 | 2D-T-ROESY |
| 110 | K | 2 | HD1 | F | 1 | HH | 0.00 | 0.21 | 0.13 | 0.37 | 2.80 | 0 | +1 | 2D-T-ROESY |
| 39 | P | 3 | HD1 | K | 2 | HG1 | −28.00 | 14.00 | −23.00 | 0.38 | 7.10 | 0 | +3 | 2D-T-ROESY |
| 42 | F | 1 | HH | K | 2 | HD1 | −0.51 | 0.25 | −0.40 | 0.39 | 6.70 | 0 | +8 | 2D-T-ROESY |
| 37 | F | 1 | HE1 | K | 2 | HG1 | −0.49 | 0.24 | −0.60 | 0.44 | 8.60 | 0 | +7 | 2D-T-ROESY |
| 35 | K | 2 | HA | K | 2 | HG1 | −14.00 | 6.80 | −9.60 | 0.44 | 7.00 | 0 | +1 | 2D-T-ROESY |
| 49 | F | 1 | HE1 | P | 3 | HA | −11.00 | 5.60 | −9.40 | 0.44 | 11.00 | 0 | +3 | 2D-T-ROESY |
| 67 | K | 2 | HA | F | 1 | HB1 | −2.70 | 1.80 | −1.50 | 0.45 | 5.50 | 0 | +1 | 2D-T-ROESY |
| 31 | F | 1 | HE1 | K | 2 | HB1 | −0.65 | 0.32 | −0.49 | 0.47 | 6.60 | 0 | +7 | 2D-T-ROESY |
| 1 | F | 1 | HA | K | 2 | HD1 | −2.00 | 0.88 | −1.80 | 0.47 | 13.00 | 0 | +1 | 2D-T-ROESY |
| 11 | P | 3 | HA | F | 1 | HB1 | −2.20 | 1.10 | −2.00 | 0.48 | 11.00 | 0 | +1 | 2D-T-ROESY |
| 44 | P | 3 | HD1 | K | 2 | HD1 | −21.00 | 11.00 | −23.00 | 0.49 | 12.00 | 0 | +3 | 2D-T-ROESY |
| 21 | P | 3 | HA | F | 1 | HE1 | −13.00 | 6.30 | −9.40 | 0.52 | 14.00 | 0 | +3 | 2D-T-ROESY |
| 122 | P | 3 | HB2 | K | 2 | HE1 | 0.00 | 0.20 | 0.01 | 0.52 | 19.00 | 0 | +1 | 2D-T-ROESY |
| 7 | K | 2 | HB1 | F | 1 | HA | −5.10 | 2.50 | −3.60 | 0.55 | 12.00 | 0 | +1 | 2D-T-ROESY |
| 9 | P | 3 | HA | F | 1 | HA | −13.00 | 6.50 | −8.50 | 0.55 | 8.60 | 0 | +0 | 2D-T-ROESY |
| 27 | F | 1 | HB1 | K | 2 | HA | −1.30 | 0.64 | −1.50 | 0.56 | 23.00 | 0 | +1 | 2D-T-ROESY |
| 119 | P | 3 | HB2 | K | 2 | HG1 | 0.00 | 0.46 | 0.17 | 0.56 | 16.00 | 0 | +1 | 2D-T-ROESY |
| 23 | F | 1 | HH | F | 1 | HH | 13000.00 | 6400.00 | 8100.00 | 0.57 | 7.30 | 0 | +0 | 2D-T-ROESY |
| 135 | K | 2 | HG1 | P | 3 | HB2 | 0.00 | 0.45 | 0.17 | 0.59 | 18.00 | 0 | +1 | 2D-T-ROESY |
| 102 | P | 3 | HB1 | F | 1 | HG1 | 0.00 | 0.58 | 0.15 | 0.60 | 100.00 | 0 | +1 | 2D-T-ROESY |
| 30 | F | 1 | HA | K | 2 | HB1 | −3.10 | 1.60 | −3.60 | 0.62 | 16.00 | 0 | +1 | 2D-T-ROESY |
| 2 | 3J | 2 | HA | 3J | 2 | HB2 | 6.00 | 0.50 | 5.80 | 0.65 | 20.00 | 0 | +0 | JCOUP |
| 138 | F | 1 | HB1 | P | 3 | HG1 | 0.00 | 0.77 | −0.45 | 0.66 | 18.00 | 0 | +3 | 2D-T-ROESY |
| 59 | P | 3 | HA | P | 3 | HD1 | −16.00 | 8.00 | −9.00 | 0.79 | 13.00 | 0 | +1 | 2D-T-ROESY |
| 43 | P | 3 | HA | K | 2 | HD1 | −3.00 | 1.50 | −1.70 | 0.80 | 15.00 | 0 | +1 | 2D-T-ROESY |
| 2 | F | 1 | HG1 | K | 2 | HD1 | −2.40 | 1.40 | −3.50 | 0.82 | 25.00 | 0 | +3 | 2D-T-ROESY |
| 47 | P | 3 | HD1 | P | 3 | HA | −17.00 | 8.30 | −9.00 | 0.86 | 15.00 | 0 | +1 | 2D-T-ROESY |
| 14 | F | 1 | HG1 | K | 2 | HG1 | −2.90 | 0.88 | −2.10 | 0.88 | 40.00 | 0 | +3 | 2D-T-ROESY |
| 4 | 3J | 1 | HB2 | 3J | 1 | HA | 6.20 | 0.50 | 6.00 | 1.00 | 45.00 | 0 | +0 | JCOUP |
| 56 | P | 3 | HD1 | P | 3 | HB2 | −43.00 | 21.00 | −22.00 | 1.00 | 22.00 | 0 | +1 | 2D-T-ROESY |
| 3 | 3J | 1 | HB1 | 3J | 1 | HA | 6.20 | 0.50 | 5.70 | 1.10 | 37.00 | 0 | +0 | JCOUP |
| 51 | P | 3 | HB1 | P | 3 | HB1 | 2700.00 | 1300.00 | 1200.00 | 1.20 | 27.00 | 0 | +0 | 2D-T-ROESY |
| 25 | K | 2 | HG1 | K | 2 | HA | −6.60 | 3.30 | −9.60 | 1.20 | 46.00 | 0 | +1 | 2D-T-ROESY |
| 12 | F | 1 | HG1 | F | 1 | HG1 | 3000.00 | 1500.00 | 1300.00 | 1.30 | 36.00 | 0 | +3 | 2D-T-ROESY |
| 123 | F | 1 | HB1 | P | 3 | HA | 0.00 | 1.80 | −2.00 | 1.30 | 50.00 | 0 | +1 | 2D-T-ROESY |
| 53 | P | 3 | HD1 | P | 3 | HB1 | −32.00 | 16.00 | −50.00 | 1.40 | 77.00 | 0 | +1 | 2D-T-ROESY |
| 117 | P | 3 | HB1 | K | 2 | HG1 | 0.00 | 0.46 | 0.19 | 1.40 | 100.00 | 0 | +1 | 2D-T-ROESY |
| 41 | F | 1 | HE1 | K | 2 | HD1 | −0.81 | 0.40 | −0.34 | 1.60 | 67.00 | 0 | +7 | 2D-T-ROESY |
| 62 | K | 2 | HA | P | 3 | HD1 | −100.00 | 50.00 | −36.00 | 1.70 | 55.00 | 0 | +1 | 2D-T-ROESY |
| 111 | F | 1 | HE1 | K | 2 | HA | 0.00 | 0.33 | −0.14 | 1.90 | 320.00 | 0 | +3 | 2D-T-ROESY |
| 58 | P | 3 | HD1 | P | 3 | HD1 | 3000.00 | 1500.00 | 940.00 | 1.90 | 68.00 | 0 | +3 | 2D-T-ROESY |
| 129 | K | 2 | HG1 | P | 3 | HB1 | 0.00 | 0.38 | 0.19 | 2.00 | 220.00 | 0 | +1 | 2D-T-ROESY |
| 128 | K | 2 | HD1 | P | 3 | HB1 | 0.00 | 0.38 | 0.28 | 2.10 | 270.00 | 0 | +1 | 2D-T-ROESY |
| 124 | K | 2 | HA | P | 3 | HB1 | 0.00 | 0.38 | 0.54 | 2.10 | 100.00 | 0 | +0 | 2D-T-ROESY |
| 38 | P | 3 | HA | K | 2 | HG1 | −3.70 | 1.80 | −0.95 | 2.20 | 97.00 | 0 | +1 | 2D-T-ROESY |
| 34 | K | 2 | HG1 | K | 2 | HG1 | 770.00 | 380.00 | 1300.00 | 2.20 | 120.00 | 0 | +3 | 2D-T-ROESY |
| 16 | P | 3 | HA | F | 1 | HG1 | −4.90 | 2.50 | −1.30 | 2.30 | 110.00 | 0 | +1 | 2D-T-ROESY |
| 118 | F | 1 | HB1 | K | 2 | HG1 | 0.00 | 0.46 | −0.58 | 2.40 | 150.00 | 0 | +3 | 2D-T-ROESY |
| 26 | F | 1 | HA | K | 2 | HA | −10.00 | 5.20 | −19.00 | 2.70 | 170.00 | 0 | +0 | 2D-T-ROESY |
| 20 | F | 1 | HG1 | F | 1 | HE1 | −100.00 | 52.00 | −190.00 | 2.70 | 200.00 | 0 | +7 | 2D-T-ROESY |
| 36 | K | 2 | HE1 | K | 2 | HG1 | −170.00 | 85.00 | −29.00 | 2.80 | 150.00 | 0 | +3 | 2D-T-ROESY |
| 113 | P | 3 | HB1 | K | 2 | HA | 0.00 | 0.33 | 0.54 | 2.80 | 180.00 | 0 | +0 | 2D-T-ROESY |
| 139 | K | 2 | HG1 | F | 1 | HG1 | 0.00 | 0.41 | −0.58 | 3.00 | 240.00 | 0 | +3 | 2D-T-ROESY |
| 52 | P | 3 | HA | P | 3 | HB1 | −200.00 | 100.00 | −27.00 | 3.00 | 170.00 | 0 | +0 | 2D-T-ROESY |
| 103 | P | 3 | HB1 | F | 1 | HG1 | 0.00 | 0.58 | −0.96 | 3.10 | 270.00 | 0 | +3 | 2D-T-ROESY |
| 120 | P | 3 | HB1 | K | 2 | HD1 | 0.00 | 0.31 | 0.28 | 3.20 | 600.00 | 0 | +1 | 2D-T-ROESY |
| 125 | K | 2 | HE1 | P | 3 | HB1 | 0.00 | 0.38 | 0.35 | 3.30 | 560.00 | 0 | +1 | 2D-T-ROESY |
| 33 | P | 3 | HD1 | K | 2 | HD1 | −84.00 | 42.00 | −5.90 | 3.50 | 240.00 | 0 | +3 | 2D-T-ROESY |
| 45 | K | 2 | HE1 | K | 2 | HE1 | 11000.00 | 5500.00 | 710.00 | 3.50 | 230.00 | 0 | +3 | 2D-T-ROESY |
| 17 | P | 3 | HB2 | F | 1 | HG1 | −6.60 | 3.30 | −0.21 | 3.70 | 270.00 | 0 | +1 | 2D-T-ROESY |
| 32 | P | 3 | HA | K | 2 | HB1 | −24.00 | 12.00 | −1.00 | 3.70 | 260.00 | 0 | +1 | 2D-T-ROESY |
| 137 | F | 1 | HG1 | P | 3 | HG1 | 0.00 | 0.77 | −0.92 | 3.70 | 2400.00 | 0 | +3 | 2D-T-ROESY |
| 63 | K | 2 | HB1 | P | 3 | HD1 | −150.00 | 73.00 | −5.90 | 3.70 | 260.00 | 0 | +3 | 2D-T-ROESY |
| 61 | F | 1 | HH | P | 3 | HD1 | 4.60 | 2.30 | 0.12 | 3.80 | 270.00 | 0 | +1 | 2D-T-ROESY |

-continued

| | | | | | | | | | | | | | |
|---|---|---|---|---|---|---|---|---|---|---|---|---|---|
| 19 | F | 1 | HA | F | 1 | HE1 | −11.00 | 5.40 | −0.18 | 3.90 | 290.00 | 0 | +3 | 2D-T-ROESY |
| 4 | F | 1 | HE1 | F | 1 | HA | −12.00 | 6.10 | −0.18 | 3.90 | 290.00 | 0 | +3 | 2D-T-ROESY |
| 57 | K | 2 | HE1 | P | 3 | HG1 | −32.00 | 16.00 | −0.16 | 4.00 | 300.00 | 0 | +3 | 2D-T-ROESY |
| 55 | F | 1 | HH | P | 3 | HB1 | −3.20 | 1.60 | 0.05 | 4.10 | 330.00 | 0 | +0 | 2D-T-ROESY |
| 22 | P | 3 | HD1 | F | 1 | HE1 | −6.20 | 3.10 | −0.22 | 4.10 | 370.00 | 0 | +7 | 2D-T-ROESY |
| 24 | P | 3 | HA | F | 1 | HH | −19.00 | 9.60 | 0.53 | 4.20 | 340.00 | 0 | +7 | 2D-T-ROESY |
| 54 | F | 1 | HE1 | P | 3 | HB1 | −4.20 | 2.10 | 0.11 | 4.20 | 350.00 | 0 | +3 | 2D-T-ROESY |
| 50 | F | 1 | HH | P | 3 | HA | −6.50 | 3.30 | 0.53 | 4.70 | 450.00 | 0 | +0 | 2D-T-ROESY |
| 60 | F | 1 | HE1 | P | 3 | HD1 | 8.80 | 4.40 | −0.97 | 5.50 | 1100.00 | 0 | +7 | 2D-T-ROESY |
| 66 | K | 2 | HE1 | P | 3 | HD1 | −13.00 | 6.50 | −16.00 | 5.50 | 2300.00 | 0 | +3 | 2D-T-ROESY |
| 10 | P | 3 | HB1 | F | 1 | HA | −3.20 | 1.60 | 0.33 | 5.60 | 1000.00 | 0 | +0 | 2D-T-ROESY |
| 5 | F | 1 | HH | F | 1 | HA | −2.00 | 0.99 | 0.44 | 5.90 | 670.00 | 0 | +0 | 2D-T-ROESY |

PDB Coordinates for the Best Mean Optimised Dynamic Structure of Lisinopril

| | | | | | | | | | |
|---|---|---|---|---|---|---|---|---|---|
| ATOM | 1 | N | PHE | 1 | 0.066 | 0.786 | 1.247 | 1.00 | 0.00 | MOLG |
| ATOM | 2 | C | PHE | 1 | −1.730 | 0.523 | −0.373 | 1.00 | 0.00 | MOLG |
| ATOM | 3 | CA | PHE | 1 | −1.353 | 0.399 | 1.109 | 1.00 | 0.00 | MOLG |
| ATOM | 4 | CB | PHE | 1 | −2.329 | 1.285 | 1.912 | 1.00 | 0.00 | MOLG |
| ATOM | 5 | CG | PHE | 1 | −3.769 | 0.715 | 1.634 | 1.00 | 0.00 | MOLG |
| ATOM | 6 | CD | PHE | 1 | −4.933 | 1.397 | 2.300 | 1.00 | 0.00 | MOLG |
| ATOM | 7 | CE1 | PHE | 1 | −5.526 | 2.440 | 1.599 | 1.00 | 0.00 | MOLG |
| ATOM | 8 | CZ1 | PHE | 1 | −6.612 | 3.119 | 2.130 | 1.00 | 0.00 | MOLG |
| ATOM | 9 | CZ2 | PHE | 1 | −6.520 | 1.712 | 4.080 | 1.00 | 0.00 | MOLG |
| ATOM | 10 | CE2 | PHE | 1 | −5.433 | 1.030 | 3.548 | 1.00 | 0.00 | MOLG |
| ATOM | 11 | CH | PHE | 1 | −7.112 | 2.755 | 3.374 | 1.00 | 0.00 | MOLG |
| ATOM | 12 | O1 | PHE | 1 | −1.216 | 1.467 | −1.086 | 1.00 | 0.00 | MOLG |
| ATOM | 13 | O2 | PHE | 1 | −2.551 | −0.310 | −0.919 | 1.00 | 0.00 | MOLG |
| ATOM | 14 | HN1 | PHE | 1 | 0.150 | 1.760 | 0.923 | 1.00 | 0.00 | MOLG |
| ATOM | 15 | HN2 | PHE | 1 | 0.354 | 0.727 | 2.230 | 1.00 | 0.00 | MOLG |
| ATOM | 16 | HA | PHE | 1 | −1.510 | −0.612 | 1.481 | 1.00 | 0.00 | MOLG |
| ATOM | 17 | HB1 | PHE | 1 | −2.102 | 1.198 | 2.984 | 1.00 | 0.00 | MOLG |
| ATOM | 18 | HB2 | PHE | 1 | −2.251 | 2.335 | 1.600 | 1.00 | 0.00 | MOLG |
| ATOM | 19 | HG1 | PHE | 1 | −3.996 | 0.695 | 0.563 | 1.00 | 0.00 | MOLG |
| ATOM | 20 | HG2 | PHE | 1 | −3.789 | −0.333 | 1.964 | 1.00 | 0.00 | MOLG |
| ATOM | 21 | HE1 | PHE | 1 | −5.145 | 2.716 | 0.647 | 1.00 | 0.00 | MOLG |
| ATOM | 22 | HE2 | PHE | 1 | −4.998 | 0.238 | 4.095 | 1.00 | 0.00 | MOLG |
| ATOM | 23 | HZ1 | PHE | 1 | −7.060 | 3.915 | 1.587 | 1.00 | 0.00 | MOLG |
| ATOM | 24 | HZ2 | PHE | 1 | −6.905 | 1.436 | 5.027 | 1.00 | 0.00 | MOLG |
| ATOM | 25 | HH | PHE | 1 | −7.941 | 3.271 | 3.783 | 1.00 | 0.00 | MOLG |
| ATOM | 26 | NZ | LYS | 2 | 6.665 | 0.555 | 1.257 | 1.00 | 0.00 | MOLG |
| ATOM | 27 | C | LYS | 2 | 0.875 | −1.664 | 0.831 | 1.00 | 0.00 | MOLG |
| ATOM | 28 | CA | LYS | 2 | 0.985 | −0.133 | 0.401 | 1.00 | 0.00 | MOLG |
| ATOM | 29 | CB | LYS | 2 | 2.470 | 0.377 | 0.601 | 1.00 | 0.00 | MOLG |
| ATOM | 30 | CG | LYS | 2 | 2.982 | 0.361 | 2.069 | 1.00 | 0.00 | MOLG |
| ATOM | 31 | CD | LYS | 2 | 4.404 | 0.915 | 2.108 | 1.00 | 0.00 | MOLG |
| ATOM | 32 | CE | LYS | 2 | 5.297 | 0.034 | 1.230 | 1.00 | 0.00 | MOLG |
| ATOM | 33 | O | LYS | 2 | 1.499 | −2.046 | 1.824 | 1.00 | 0.00 | MOLG |
| ATOM | 34 | HA | LYS | 2 | 0.718 | −0.033 | −0.656 | 1.00 | 0.00 | MOLG |
| ATOM | 35 | HB1 | LYS | 2 | 3.135 | −0.253 | −0.007 | 1.00 | 0.00 | MOLG |
| ATOM | 36 | HB2 | LYS | 2 | 2.528 | 1.415 | 0.243 | 1.00 | 0.00 | MOLG |
| ATOM | 37 | HG1 | LYS | 2 | 2.326 | 0.975 | 2.700 | 1.00 | 0.00 | MOLG |
| ATOM | 38 | HG2 | LYS | 2 | 3.002 | −0.660 | 2.452 | 1.00 | 0.00 | MOLG |
| ATOM | 39 | HD1 | LYS | 2 | 4.406 | 1.942 | 1.716 | 1.00 | 0.00 | MOLG |
| ATOM | 40 | HD2 | LYS | 2 | 4.778 | 0.915 | 3.141 | 1.00 | 0.00 | MOLG |
| ATOM | 41 | HE1 | LYS | 2 | 4.920 | 0.051 | 0.196 | 1.00 | 0.00 | MOLG |
| ATOM | 42 | HE2 | LYS | 2 | 5.283 | −0.996 | 1.609 | 1.00 | 0.00 | MOLG |
| ATOM | 43 | HZ1 | LYS | 2 | 6.673 | 1.520 | 0.898 | 1.00 | 0.00 | MOLG |
| ATOM | 44 | HZ2 | LYS | 2 | 7.269 | −0.037 | 0.670 | 1.00 | 0.00 | MOLG |
| ATOM | 45 | HZ3 | LYS | 2 | 7.014 | 0.545 | 2.226 | 1.00 | 0.00 | MOLG |
| ATOM | 46 | N | PRO | 3 | 0.226 | −2.717 | 0.070 | 1.00 | 0.00 | MOLG |
| ATOM | 47 | C | PRO | 3 | 1.442 | −4.890 | 0.439 | 1.00 | 0.00 | MOLG |
| ATOM | 48 | CA | PRO | 3 | 0.171 | −4.100 | 0.540 | 1.00 | 0.00 | MOLG |
| ATOM | 49 | CB | PRO | 3 | −0.888 | −4.661 | −0.441 | 1.00 | 0.00 | MOLG |
| ATOM | 50 | CG | PRO | 3 | −0.349 | −4.064 | −1.687 | 1.00 | 0.00 | MOLG |
| ATOM | 51 | CD | PRO | 3 | −0.490 | −2.596 | −1.172 | 1.00 | 0.00 | MOLG |
| ATOM | 52 | O1 | PRO | 3 | 1.864 | −5.514 | 1.421 | 1.00 | 0.00 | MOLG |
| ATOM | 53 | O2 | PRO | 3 | 2.089 | −4.924 | −0.675 | 1.00 | 0.00 | MOLG |
| ATOM | 54 | HA | PRO | 3 | −0.216 | −4.107 | 1.568 | 1.00 | 0.00 | MOLG |
| ATOM | 55 | HB1 | PRO | 3 | −0.807 | −5.753 | −0.524 | 1.00 | 0.00 | MOLG |
| ATOM | 56 | HB2 | PRO | 3 | −1.913 | −4.371 | −0.172 | 1.00 | 0.00 | MOLG |
| ATOM | 57 | HG1 | PRO | 3 | 0.681 | −4.353 | −1.931 | 1.00 | 0.00 | MOLG |
| ATOM | 58 | HG2 | PRO | 3 | −1.030 | −4.277 | −2.526 | 1.00 | 0.00 | MOLG |

-continued

| ATOM | 59 | HD1 | PRO | 3 | −1.498 | −2.266 | −1.076 | 1.00 | 0.00 | MOLG |
|---|---|---|---|---|---|---|---|---|---|---|
| ATOM | 60 | HD2 | PRO | 3 | 0.065 | −1.908 | −1.824 | 1.00 | 0.00 | MOLG |
| END | | | | | | | | | | |

EXAMPLE 3

AngiotensinI

AngiotensinI is a natural decapeptide that causes blood vessels to constrict and drives blood pressure up. It is a decapeptide hormone (sequence DRVYIHPFHL) and a powerful dipsogen. It is derived from the precursor molecule angiotensinogen, a serum globulin produced in the liver, and plays an important role in the renin-angiotensin system. Angiotensin-converting enzyme (ACE) cleaves the two C-terminal residues from AngiotensinI to create AngiotensinII, which mediates these biological processes. In this worked example, we demonstrate how the dynamic 3D-solution structure of AngiotensinI was determined from experimental NMR data using the methodology according to the present invention.

Chemical Shift Assignment and Measurement of Homonuclear Scalar-Coupling Constants The atoms and residues in AngiotensinI were given names according to XPLOR format (see Appendix C). All the NMR data on AngiotensinI was recorded at pH 6.0, which, in combination with the typical $pK_a$ values, dictates the ionization state of most of the titratable groups in the molecule, namely: backbone N-terminal amine group, +ve; Asp1 sidechain, −ve; Arg2 sidechain, +ve; backbone C-terminal carboxylate, −ve. The two hisitidine sidechains (His6, His9) were given a +ve charge, consistent with their expected $pK_a$ value (6.5), although further experimental data should be collected to determine if this is indeed the case. Partial conjugation of the lone pair of electrons from the proline residue's nitrogen atom with the adjacent carbonyl double-bond results in the presence of both cis and trans stereoisomers of AngiotensinI in solution.

The $^1$H and $^{13}$C chemical shifts of both stereoisomers of AngiotensinI at 300 K were assigned using [$^1$H-$^1$H]-COSY, [$^1$H-$^1$H]-TOCSY and natural-abundance [$^1$H-$^{13}$C]-HSQC spectra recorded at 600 MHz on a 5 mM NMR sample (5% D$_2$O, pH 6.0, 0.3 mM DSS) of AngiotensinI. By integration of peak volumes for resonances that were distinct for the cis and trans forms, the mole abundance ratio was determined to be 80% trans:20% cis. Since trans-AngiotensinI is more abundant in the mixture, it was decided at this stage to determine the dynamic 3D-structure of trans AngiotensinI. The measured proton chemical shifts for AngiotensinI are given in Table 2 below.

TABLE 2

Chemical shifts for AngiotensinI

| | | Shift (ppm)[a] | |
|---|---|---|---|
| Residue | Atom | trans | cis |
| D1 | HA | 4.251 | 4.251 |
| | *HB1*[b] | *2.824* | *2.824* |
| | *HB2* | *2.679* | *2.679* |
| R2 | HA | 4.347 | 4.347 |
| | HB*[c] | 1.737 | 1.737 |
| | HG* | 1.519 | 1.519 |
| | HD* | 3.148 | 3.148 |

TABLE 2-continued

Chemical shifts for AngiotensinI

| | | Shift (ppm)[a] | |
|---|---|---|---|
| Residue | Atom | trans | cis |
| | HE | 7.115 | 7.115 |
| V3 | HN | 8.234 | 8.234 |
| | HA | 4.084 | 4.084 |
| | HB | 1.969 | 1.969 |
| | *HG1\** | *0.912* | *0.896* |
| | *HH2\** | *0.866* | *0.851* |
| Y4 | HN | 8.499 | 8.476 |
| | HA | 4.593 | 4.593 |
| | HB* | 2.921 | ? |
| | HD* | 7.087 | 7.087 |
| | HE* | 6.759 | 6.759 |
| I5 | HN | 8.028 | 8.112 |
| | HA | 4.065 | 4.124 |
| | HB | 1.710 | 1.710 |
| | *HG11* | *1.378* | *1.378* |
| | *HG12* | *1.091* | *1.091* |
| | HG2* | 0.791 | 0.869 |
| | HD1* | 0.797 | 0.865 |
| H6 | HN | 8.371 | 8.148 |
| | HA | 4.746 | 4.746 |
| | *HB1* | *3.200* | *3.046* |
| | *HB2* | *3.200* | *2.973* |
| | HD2 | 7.304 | 7.163 |
| | HE1 | 8.501 | 8.501 |
| P7 | HA | 4.301 | 4.082 |
| | *HB1* | *2.276* | *2.130* |
| | *HB2* | *1.942* | *2.058* |
| | HG* | 1.960 | 1.824 |
| | *HD1* | *3.763* | *3.568* |
| | *HD2* | *3.423* | *3.396* |
| F8 | HN | 8.386 | 8.630 |
| | HA | 4.590 | 4.481 |
| | HB* | 3.050 | 3.125 |
| | HD* | 7.208 | 7.169 |
| | HE* | 7.323 | 7.276 |
| | HZ | 7.278 | 7.278 |
| H9 | HN | 8.050 | 7.869 |
| | HA | 4.579 | 4.534 |
| | HB* | 3.168 | 3.154 |
| | HD2 | 7.155 | 7.155 |
| | HE1 | 8.331 | 8.331 |
| L10 | HN | 8.052 | 8.084 |
| | HA | 4.141 | 4.091 |
| | HB* | 1.584 | 1.556 |
| | HG | 1.578 | 1.578 |
| | HD1* | 0.925 | 0.925 |
| | HD2* | 0.894 | 0.871 |

[a]All $^1$H chemical shifts were determined at 300 K, pH 6.0 in 5% D$_2$O/90% H$_2$O, relative to internal DSS.
[b]Chemical shifts in italics denote atoms that could not been stereospecifically assigned without reference to the local 3D structure.
[c]Atoms with an asterisk denote degenerate chemical shitfts (e.g. HB* indicates that HB1 and HB2 have identical values).

Chemical shifts were also measured at 278K and 310 K and seen not to vary significantly (or, in the case of the amide protons, only vary linearly, see below), i.e., indicating that the conformation of the molecule is not noticeably perturbed over this temperature range.

With the exception of the HA and HN protons in trans AngiotensinI, most protons had complex spectral lineshapes due the large number of scalar-couplings present (as many as five $^2J_{HH}/^3J_{HH}$ scalar coupling in the arginine sidechain) and strong-coupling. This complexity prevented the measurement of most scalar-couplings in the sidechains. However, $^3J_{HH}$ coupling constants were measured for various sidechain protons, as shown in the scalar-coupling restraint lists (see Appendix C).

Analysis of Spectral Lineshapes

A 2D [$^1$H, $^1$H]-NOESY dataset was used to provide structural restraints for trans AngiotensinI. The value of λ (1.8 Hz) for this dataset was determined by measurement of resonances from NOEs to the Ile5 HN proton. All HN protons had simple doublet scaling factor sets (i.e. $f_i$={2, 2}). Various aromatic ring protons had either no, one or two $^3J$ scalar-couplings, and did not suffer from strong-coupling, and therefore also had ideal singlet (e.g. His6 HE1), doublet (e.g. Tyr4 HD*) or triplet lineshapes (e.g Phe8 HZ), respectively. Several HA protons (e.g. His6 HA) had basic quadruplet lineshapes because they had three $^3J$ scalar couplings; in these cases the broadening formula was applied as described above. All other protons had complex lineshapes and suffered from strong-coupling—their scaling-factor sets were determined using the rules for strongly-coupled protons (see above).

To summarise, the scaling factor sets for each proton in trans AngiotensinI in this 2D [$^1$H, $^1$H]-NOESY dataset were as follows:

| | | |
|---|---|---|
| Asp1 | HN | {2, 2} |
| | HA | {4, 4, 4, 4} |
| | HB1 | {4, 4, 4, 4} |
| | HB2 | {4, 4, 4, 4} |
| Arg2 | HN | {2, 2} |
| | HA | {4, 2, 4} |
| | HB* | {6.0, 3.0, 3.0, 6.0} |
| | HG* | {15.0, 10.2, 7.7, 7.5, 9.1, 8.2, 6.8, 8.3, 13.5} |
| | HD* | {2} [estimated] |
| | HE | {2, 2} |
| Val3 | HN | {2, 2} |
| | HA | {4, 2.2 4} |
| | HB | {16.4, 6.1, 3.7, 3.6, 6.1, 16.4} |
| | HG1* | {2, 2} |
| | HG2* | {2, 2} |
| Tyr4 | HN | {2, 2} |
| | HA | {8.0, 2.7, 2.7, 8.0} |
| | HB* | {2, 2} |
| | HD* | {2, 2} |
| | HE* | {2, 2} |
| Ile5 | HN | {2, 2} |
| | HA | {4, 2.2, 4} |
| | HB | {6.3, 3.4, 3.4, 6.3} |
| | HG11 | {6.4, 3.3, 3.3, 5.6, 18.2} |
| | HG12 | {15.7, 6.9, 4.4, 4.3, 4.9, 9.2, 47.7} |
| | HG2* | {2, 2} |
| | HD1* | {4, 2, 4} |
| His6 | HN | {2, 2} |
| | HA | {8.0, 2.7, 2.7, 8.0} |
| | HB1 | {4, 4, 4, 4} |
| | HB2 | {4, 4, 4, 4} |
| | HD2 | {1} |
| | HE1 | {1} |
| Pro7 | HA | {4, 2.5, 4} |
| | HB1 | {15.8, 5.4, 4.0, 4.0, 5.4, 15.8} |
| | HB2 | {—} [shape too broadened and complex for analysis] |
| | HG* | {12.6, 6.7, 4.9, 4.8, 6.4, 8.5, 11.6} |
| | HD1 | {6.1, 3.0, 3.0, 6.1} |
| | HD2 | {6.1, 3.0, 3.0, 6.1} |
| Phe8 | HN | {2, 2} |
| | HA | {8.0, 2.7, 2.7, 8.0} |
| | HB* | {15.0, 11.2, 6.2, 5.5, 5.5, 6.2, 11.2, 15.0} |
| | HD* | {2, 2} |
| | HE* | {2, 2} |
| | HZ | {4, 2, 4} |
| His9 | HN | {2, 2} |
| | HA | {9.6, 2.8, 2.7, 5.9} |
| | HB* | {15.5, 13.2, 6.1, 5.3, 5.3, 6.1, 13.2, 15.5} |
| | HD2 | {1} |
| | HE1 | {1} |
| Leu10 | HN | {2, 2} |
| | HA | {8.0, 2.7, 2.7, 8.0} |
| | HB* | {2.0} [estimated] |
| | HG | {2.0} [estimated] |
| | HD1* | {2, 2} |
| | HD2* | {2, 2} |

Measurement and Quantitation of NMR Spectra

All NMR spectra were recorded on a sample of 5 mM AngiotensinI (5% D$_2$O, pH 6.0, 0.3 mM DSS) at 600 MHz. Four different kinds of NMR data in six different experimental NMR datasets were used in the determination of the dynamic solution structure of trans AngiotensinI:

1) NOESY relaxation data: one experimental dataset, a 2D [$^1$H-$^1$H]-NOESY
2) Conformation-dependent scalar couplings: three experimental datasets
3) Dihedral angle restraints: one experimental dataset
4) Hydrogen bond restraints: one experimental dataset The pertinent acquisition parameters for each of these different NMR datasets (and the number of structural restraints measured from them) were as follows:

1) The 2D [$^1$H, $^1$H]-NOESY spectrum was recorded at 278 K with an NOE mixing time of 700 ms and sweep widths of 7200 Hz in both dimensions. Using the scaling-factor sets described above, 343 NOE and 382 noNOE structural restraints were measured from this spectrum. Errors on each NOE restraint were determined as described above, using the initial m value of 0.4 for a 2D [$^1$H, $^1$H]-NOESY spectrum. The header for this file is given in Appendix C, while the NOE and noNOE structural restraints are detailed implicitly in the $\chi^2_{restraint}$ file in Appendix C for the sake of brevity.

2) A total of 61 conformation-dependent scalar couplings were measured for HN protons, HA protons and the Ile5 CA-CB-CG1-CD1 dihedral angle from 1D, $^{15}$N-HSQC and $^{13}$C-HSQC spectra at 278K, 298K and 310K. These were organised into a separate scalar-coupling restraint file for each temperature, which are all given in Appendix C.

3) Dihedral angle restraints were generated using the chemical shifts shown in Table 2 and the program TALOS [42]. These predicted phi and psi backbone angles with their (doubled) error values were used in the dihedral angle restraints file given in Appendix C, which contained a total of 16 restraints.

4) The presence and absence of hydrogen bonds for amide groups in AngiotensinI were determined from amide proton chemical shift temperature coefficients. Temperature coefficients more negative than −4.6 ppb/K indicate the absence of any significant hydrogen bonding interactions involving the amide proton [44]. Values for temperature coefficients for amide protons for AngiotensinI were measured as described in Blundell and Almond (2007) [43]. Values were: Val3 (−8.9 ppb/K), Tyr4 (−9.4 ppb/K), Ile5 (−6.4 ppb/K), His6 (−8.9 ppb/K), Phe8 (−9.1 ppb/K) and Leu10 (−8.2 ppb/K) and all were therefore found to be more negative than −4.6 ppb/K, indicating that they make no significant hydrogen bonds (i.e., <~10-20% of the time) in aqueous solution. Accordingly, 5 hydrogen bond restraints were included in the structure calculations in the file given in Appendix C.

Molecule Specification

All experimental datasets were acquired in H$_2$O. In H$_2$O, the N-terminal primary amine, Arg2 guanidino sidechain protons, Tyr4 hydroxyl proton, and both histidine sidechain amine protons in both His6 and His9 are in fast exchange.

All these protons were therefore defined as NMR-inactive in the solvent mask file as follows:

```
remark Solvent mask for AngiotensinI
conditions:

solvents 1
endsection
solvent:

name h2o
add * H*
exc 1 HN*
exc 2 HH*
exc 4 HH
exc 6 HD1
exc 6 HE2
exc 9 HD1
exc 9 HE2
endsection
```

The locations of the two oxygen atoms in the carboxylate groups in AngiotensinI (i.e., Asp1 sidechain & C-terminus), the Arg2 guanidino group and Tyr4 hydroxyl proton relative to the rest of the molecular structure could not be specified from the experimental data. These atoms were therefore set to be van der Waals inactive, as detailed in the following van der Waals input file:

```
remark Van der Waals mask for AngiotensinI
configuration:

vdw.cutoff 6.0
vdw.coupling 1e-4
endsection
nonbonded:

remark: include all atoms
vdw * H* 0.016 0.60
vdw * C* 0.100 1.91
vdw * N* 0.170 1.82
vdw * O* 0.210 1.66
remark: then exclude these atoms
exc 1 OD*
exc 2 HH*
exc 2 NH1
exc 2 NH2
exc 2 CZ
exc 2 NE
exc 2 HE
exc 4 HH
exc 10 OE*
endsection
```

Experimental Data Input

The value of $\tau_c$ has not been precisely measured experimentally for trans AngiotensinI. Therefore, a value of 0.4 ns for $\tau_c$ was used as an estimate. After a few rounds of structure calculations, it was apparent that the molecule was adopting a highly-extended shape and that a symmetric top anisotropic model was likely to be more appropriate. By repeated rounds of calculation for a constant set of 2D-NOESY data, this was indeed found to be the case, with a considerably better fit to the experimental data being achieved with this anisotropic model. The best fit to the experimental data (i.e. lowest $\chi^2_{total}$) was found with a perpendicular $\tau_c$ value of 1.2 and a parallel $\tau_c$ value of 0.5 ns. All the experimental data files used in the structure calculations are detailed in Appendix C.

Dynamic Model

The pertinent conformationally-flexible bonds and chemistries within AngiotensinI were identified, using the methodology described above:

1) Phi ($\varphi$, $N^i$-$CA^i$), psi ($\varphi$, $CA^i$-$C^i$) and omega ($\omega$, $C^i$-$N^{i+1}$) single bonds for each residue, comprising the backbone of the molecule.
2) Two single bonds in the Asp1 sidechain can rotate (CA-CB, CB-CG).
3) Four single bonds in the Arg2 sidechain can rotate (CA-CB, CB-CG, CG-CD, CD-NE).
4) Three single bonds in the Val3 sidechain can rotate (CA-CB, CB-CG1, CB-CG2).
5) Three single bonds in the Tyr4 sidechain can rotate (CA-CB, CB-CG, OH-HH).
6) Four single bonds in the Ile5 sidechain can rotate (CA-CB, CB-CG1, CG1-CD1, CB-CG2).
7) Two single bonds in the His6 sidechain can rotate (CA-CB, CB-CG).
8) The Pro7 ring adopts two major conformations in solution, as described above for lisinopril.
9) Two single bonds in the Phe8 sidechain can rotate (CA-CB, CB-CG).
10) Two single bonds in the His9 sidechain can rotate (CA-CB, CB-CG).
11) Four single bonds in the Leu10 sidechain can rotate (CA-CB, CB-CG, CG-CD1, CG-CD2).

To create a realistic dynamic model of the molecule that could be used to optimise against the observed experimental data, the above degrees of freedom were modelled in the dynamic model file as follows:

1) The majority of backbone phi and psi bonds are between $sp^2$- and $sp^3$-hybridised atoms and therefore take a bimodal model in the first instance. All the backbone omega bonds were represented with a fixed unimodal model, taking the mean dihedral angle appropriate for a trans geometry, i.e. 180°. The N-terminal amine bond (Asp1 N-CA) is between two $sp^3$-hybridised atoms and therefore takes a trimodal model to represent the rotation of the amine group.
2) The CA-CB bond (also called chi1, $\chi1$) in the Asp1 sidechain is between $sp^3$-hybridised atoms and therefore takes a trimodal model. The three rotamer states (gt, tg, gg) were specified with three different variables (var 11, 12, 13) and given the same Gaussian spread (var 14) on each rotamer position. The initial partition used to seed the three rotamer states was estimated from the difference in $^3J$ coupling constants between the HA and HB1/HB2 protons. The CB-CG bond (also called chit, $\chi2$) in the Asp1 sidechain is $sp^2$- and $sp^3$-hybridised atoms and therefore takes a bimodal model.
3) The CA-CB, CB-CG and CG-CD bonds ($\chi1$, $\chi2$, $\chi3$) in the Arg2 sidechain are between $sp^3$-hybridised atoms and therefore take trimodal models. For each bond, the three rotamer states (gt, tg, gg) were specified with three different variables and given the same Gaussian spread on each rotamer position. The CD-NE bond ($\chi4$) in the Arg2 sidechain is between $sp^2$- and $sp^3$-hybridised atoms and therefore takes a bimodal model.
4) The CA-CB bond (also called chi 1, $\chi1$) in the Val3 sidechain is between $sp^3$-hybridised atoms and therefore takes a trimodal model. The three rotamer states (gt, tg, gg) were specified with three different variables and given the same Gaussian spread on each rotamer position. The initial partition used to seed the three rotamer states was estimated from the $^3J$ coupling constants between the HA and HB protons. The two methyl groups are connected by bonds CB-CG1 and CB-CG2, which are between two $sp^3$-hybridised atoms. These were both given a trimodal model to represent the rotation of the methyl groups.
5) The CA-CB bond ($\chi1$) in the Tyr sidechain is between $sp^3$-hybridised atoms and therefore takes a trimodal model.

The CB-CG bond ($\chi 2$) is between sp²- and sp³-hybridised atoms and therefore takes a bimodal model. The OH-HH bond takes a unimodal model.

6) All the bonds within the Ile5 sidechain are between sp³-hybridised atoms and therefore take trimodal models. The initial partitions used to seed the three rotamer states for the CA-CB and CB-CG1 bonds were estimated from the HA-HB, HB-HG12 and HB-HG13 ³J coupling constants.

7) The CA-CB bond ($\chi 1$) in the His6 sidechain is between sp³-hybridised atoms and therefore takes a trimodal model. The CB-CG bond ($\chi 2$) is between sp²- and sp³-hybridised atoms and therefore takes a bimodal model.

8) The two conformations for the Proline ring were represented in an identical fashion to that used for lisinopril above.

9) The CA-CB bond ($\chi 1$) in the Phe8 sidechain is between sp³-hybridised atoms and therefore takes a trimodal model. The CB-CG bond ($\chi 2$) is between sp²- and sp³-hybridised atoms and therefore takes a bimodal model.

10) The CA-CB bond ($\chi 1$) in the His9 sidechain is between sp³-hybridised atoms and therefore takes a trimodal model. The CB-CG bond ($\chi 2$) is between sp²- and sp³-hybridised atoms and therefore takes a bimodal model.

11) All the bonds within the Leu10 sidechain are between sp³-hybridised atoms and therefore take trimodal models.

The specific implementation of these considerations was achieved with the dynamic model file given below (see Appendix C for the associated internal coordinates table).

```
remark Dynamic model of AngiotensinI
variables:

remark D1
remark D1 phi (N-terminus)
var 1 fix 60 jump 0.0 start 0.0
var 2 fix 300 jump 0.0 start 0.0
var 3 fix 180 jump 0.0 start 0.0
var 4 fix 20 jump 0.0 start 0.0
remark D1 psi
var 5 rand 0 360 jump 180.0 start 0.0
var 6 fix 15 jump 5.0 start 0.0
var 7 rand 0 360 jump 180.0 start 0.0
var 8 fix 15 jump 5.0 start 0.0
remark D1 omega
var 9 fix 180 jump 0.0 start 0.0
var 10 fix 0.0 jump 0.0 start 0.0
remark D1 chi1
var 11 fix 60 jump 0.0 start 0.0
var 12 fix 300 jump 0.0 start 0.0
var 13 fix 180 jump 0.0 start 0.0
var 14 fix 20 jump 5.0 start 0.0
remark D1 chi2
var 15 rand 0 360 jump 180.0 start 0.0
var 16 rand 0 360 jump 180.0 start 0.0
var 17 fix 20 jump 0.0 start 0.0
remark R2
remark R2 phi
var 18 rand 0 360 jump 180.0 start 0.0
var 19 fix 15 jump 5.0 start 0.0
var 20 rand 0 360 jump 180.0 start 0.0
var 21 fix 15 jump 5.0 start 0.0
remark R2 psi
var 22 rand 0 360 jump 180.0 start 0.0
var 23 fix 15 jump 5.0 start 0.0
var 24 rand 0 360 jump 180.0 start 0.0
var 25 fix 15 jump 5.0 start 0.0
remark R2 omega
var 26 fix 180 jump 0.0 start 0.0
var 27 fix 0.0 jump 0.0 start 0.0
remark R2 chi1
var 28 fix 60 jump 0.0 start 0.0
var 29 fix 300 jump 0.0 start 0.0
var 30 fix 180 jump 0.0 start 0.0
var 31 fix 20 jump 5.0 start 0.0
remark R2 chi2
var 32 fix 60 jump 0.0 start 0.0
var 33 fix 300 jump 0.0 start 0.0
var 34 fix 180 jump 0.0 start 0.0
var 35 fix 20 jump 5.0 start 0.0
remark R2 chi3
var 36 fix 60 jump 0.0 start 0.0
var 37 fix 300 jump 0.0 start 0.0
var 38 fix 180 jump 0.0 start 0.0
var 39 fix 20 jump 5.0 start 0.0
remark R2 chi4
var 40 rand 0 360 jump 180.0 start 0.0
var 41 rand 0 360 jump 180.0 start 0.0
var 42 fix 20 jump 5.0 start 0.0
remark V3
remark V3 phi
var 43 rand 0 360 jump 180.0 start 0.0
var 44 fix 15 jump 5.0 start 0.0
var 45 rand 0 360 jump 180.0 start 0.0
var 46 fix 15 jump 5.0 start 0.0
remark V3 psi
var 47 rand 0 360 jump 180.0 start 0.0
var 48 fix 15 jump 5.0 start 0.0
var 49 rand 0 360 jump 180.0 start 0.0
var 50 fix 15 jump 5.0 start 0.0
remark V3 omega
var 51 fix 180 jump 0.0 start 0.0
var 52 fix 0.0 jump 0.0 start 0.0
remark V3 chi1
var 53 fix 60 jump 0.0 start 0.0
var 54 fix 300 jump 0.0 start 0.0
var 55 fix 180 jump 0.0 start 0.0
var 56 fix 20 jump 5.0 start 0.0
remark V3 chi2 methyl CG2
var 57 fix 60 jump 0.0 start 0.0
var 58 fix 300 jump 0.0 start 0.0
var 59 fix 180 jump 0.0 start 0.0
var 60 fix 20 jump 0.0 start 0.0
remark V3 chi3 methyl CG1
var 61 fix 60 jump 0.0 start 0.0
var 62 fix 300 jump 0.0 start 0.0
var 63 fix 180 jump 0.0 start 0.0
var 64 fix 20 jump 0.0 start 0.0
remark Y4
remark Y4 phi
var 65 rand 0 360 jump 180.0 start 0.0
var 66 fix 15 jump 5.0 start 0.0
var 67 rand 0 360 jump 180.0 start 0.0
var 68 fix 15 jump 5.0 start 0.0
remark Y4 psi
var 69 rand 0 360 jump 180.0 start 0.0
var 70 fix 15 jump 5.0 start 0.0
var 71 rand 0 360 jump 180.0 start 0.0
var 72 fix 15 jump 5.0 start 0.0
remark Y4 omega
var 73 fix 180 jump 0.0 start 0.0
var 74 fix 0.0 jump 0.0 start 0.0
remark Y4 chi1
var 75 fix 60 jump 0.0 start 0.0
var 76 fix 300 jump 0.0 start 0.0
var 77 fix 180 jump 0.0 start 0.0
var 78 fix 20 jump 5.0 start 0.0
remark Y4 chi2
var 79 rand 0 360 jump 180.0 start 0.0
var 80 rand 0 360 jump 180.0 start 0.0
var 81 fix 20 jump 5.0 start 0.0
remark Y4 chi3 hydroxyl
var 82 rand 0 360 jump 180.0 start 0.0
var 83 fix 20 jump 0.0 start 0.0
remark I5
remark I5 phi
var 84 rand 0 360 jump 180.0 start 0.0
var 85 fix 15 jump 5.0 start 0.0
var 86 rand 0 360 jump 180.0 start 0.0
var 87 fix 15 jump 5.0 start 0.0
remark I5 psi
var 88 rand 0 360 jump 180.0 start 0.0
var 89 fix 15 jump 5.0 start 0.0
var 90 rand 0 360 jump 180.0 start 0.0
```

```
var 91 fix 15 jump 5.0 start 0.0
remark I5 omega
var 92 fix 180 jump 0.0 start 0.0
var 93 fix 0.0 jump 0.0 start 0.0
remark I5 chi1
var 94 fix 60 jump 0.0 start 0.0
var 95 fix 300 jump 0.0 start 0.0
var 96 fix 180 jump 0.0 start 0.0
var 97 fix 20 jump 5.0 start 0.0
remark I5 chi2
var 98 fix 60 jump 0.0 start 0.0
var 99 fix 300 jump 0.0 start 0.0
var 100 fix 180 jump 0.0 start 0.0
var 101 fix 20 jump 5.0 start 0.0
remark I5 chi3 methyl CD1
var 102 fix 60 jump 0.0 start 0.0
var 103 fix 300 jump 0.0 start 0.0
var 104 fix 180 jump 0.0 start 0.0
var 105 fix 20 jump 0.0 start 0.0
remark I5 chi4 methyl CG2
var 106 fix 60 jump 0.0 start 0.0
var 107 fix 300 jump 0.0 start 0.0
var 108 fix 180 jump 0.0 start 0.0
var 109 fix 20 jump 0.0 start 0.0
remark H6
remark H6 phi
var 110 rand 0 360 jump 180.0 start 0.0
var 111 fix 15 jump 5.0 start 0.0
var 112 rand 0 360 jump 180.0 start 0.0
var 113 fix 15 jump 5.0 start 0.0
remark H6 psi
var 114 rand 0 360 jump 180.0 start 0.0
var 115 fix 15 jump 5.0 start 0.0
var 116 rand 0 360 jump 180.0 start 0.0
var 117 fix 15 jump 5.0 start 0.0
remark H6 omega TRANS PROLINE
var 118 fix 0 jump 0.0 start 0.0
var 119 fix 0.0 jump 0.0 start 0.0
remark H6 chi1
var 120 fix 60 jump 0.0 start 0.0
var 121 fix 300 jump 0.0 start 0.0
var 122 fix 180 jump 0.0 start 0.0
var 123 fix 20 jump 0.0 start 0.0
remark H6 chi2
var 124 rand 0 360 jump 180.0 start 0.0
var 125 rand 0 360 jump 180.0 start 0.0
var 126 fix 20 jump 5.0 start 0.0
remark P7
remark P7 psi
var 127 rand 0 360 jump 180.0 start 0.0
var 128 fix 15 jump 5.0 start 0.0
var 129 rand 0 360 jump 180.0 start 0.0
var 130 fix 15 jump 5.0 start 0.0
remark P7 omega
var 131 fix 180 jump 0.0 start 0.0
var 132 fix 0.0 jump 0.0 start 0.0
remark P7 ring flip
remark N state = gamma exo = UP
var 133 fix −167.15 jump 0.0 start 0.0
var 134 fix −54.52 jump 0.0 start 0.0
var 135 fix 58.07 jump 0.0 start 0.0
var 136 fix −48.96 jump 0.0 start 0.0
var 137 fix −157.04 jump 0.0 start 0.0
remark S state = gamma endo = DOWN
var 138 fix 167.46 jump 0.0 start 0.0
var 139 fix 45.29 jump 0.0 start 0.0
var 140 fix −55.99 jump 0.0 start 0.0
var 141 fix 46.66 jump 0.0 start 0.0
var 142 fix 157.82 jump 0.0 start 0.0
remark dynamics
var 143 fix 0.0 jump 0.0 start 0.0
remark F8
remark F8 phi
var 144 rand 0 360 jump 180.0 start 0.0
var 145 fix 15 jump 5.0 start 0.0
var 146 rand 0 360 jump 180.0 start 0.0
var 147 fix 15 jump 5.0 start 0.0
remark F8 psi
var 148 rand 0 360 jump 180.0 start 0.0
var 149 fix 15 jump 5.0 start 0.0
var 150 rand 0 360 jump 180.0 start 0.0
var 151 fix 15 jump 5.0 start 0.0
remark F8 omega
var 152 fix 180 jump 0.0 start 0.0
var 153 fix 0.0 jump 0.0 start 0.0
remark F8 chi1
var 154 fix 60 jump 0.0 start 0.0
var 155 fix 300 jump 0.0 start 0.0
var 156 fix 180 jump 0.0 start 0.0
var 157 fix 20 jump 5.0 start 0.0
remark F8 chi2
var 158 rand 0 360 jump 180.0 start 0.0
var 159 rand 0 360 jump 180.0 start 0.0
var 160 fix 20 jump 5.0 start 0.0
remark H9
remark H9 phi
var 161 rand 0 360 jump 180.0 start 0.0
var 162 fix 15 jump 5.0 start 0.0
var 163 rand 0 360 jump 180.0 start 0.0
var 164 fix 15 jump 5.0 start 0.0
remark H9 psi
var 165 rand 0 360 jump 180.0 start 0.0
var 166 fix 15 jump 5.0 start 0.0
var 167 rand 0 360 jump 180.0 start 0.0
var 168 fix 15 jump 5.0 start 0.0
remark H9 omega
var 169 fix 180 jump 0.0 start 0.0
var 170 fix 0.0 jump 0.0 start 0.0
remark H9 chi1
var 171 fix 60 jump 0.0 start 0.0
var 172 fix 300 jump 0.0 start 0.0
var 173 fix 180 jump 0.0 start 0.0
var 174 fix 20 jump 5.0 start 0.0
remark H9 chi2
var 175 rand 0 360 jump 180.0 start 0.0
var 176 rand 0 360 jump 180.0 start 0.0
var 177 fix 20 jump 5.0 start 0.0
remark L10
remark L10 phi
var 178 rand 0 360 jump 180.0 start 0.0
var 179 fix 15 jump 5.0 start 0.0
var 180 rand 0 360 jump 180.0 start 0.0
var 181 fix 15 jump 5.0 start 0.0
remark L10 psi (C-terminus)
var 182 rand 0 360 jump 180.0 start 0.0
var 183 rand 0 360 jump 180.0 start 0.0
var 184 fix 15 jump 0.0 start 0.0
remark L10 chi1
var 185 fix 60 jump 0.0 start 0.0
var 186 fix 300 jump 0.0 start 0.0
var 187 fix 180 jump 0.0 start 0.0
var 188 fix 20 jump 5.0 start 0.0
remark L10 chi2
var 189 fix 60 jump 0.0 start 0.0
var 190 fix 300 jump 0.0 start 0.0
var 191 fix 180 jump 0.0 start 0.0
var 192 fix 20 jump 5.0 start 0.0
remark L10 chi3 methyl CD1
var 193 fix 60 jump 0.0 start 0.0
var 194 fix 300 jump 0.0 start 0.0
var 195 fix 180 jump 0.0 start 0.0
var 196 fix 20 jump 0.0 start 0.0
remark L10 chi4 methyl CD2
var 197 fix 60 jump 0.0 start 0.0
var 198 fix 300 jump 0.0 start 0.0
var 199 fix 180 jump 0.0 start 0.0
var 200 fix 20 jump 0.0 start 0.0
endsection
probabilities:

remark D1
remark D1 phi (N-terminus)
mode 1 3 0.33 0.66 0.0
remark D1 psi
mode 2 2 0.5 0.1
remark D1 chi1
mode 3 3 0.09 0.29 0.05
remark D1 chi2
```

```
mode 4 2 0.5 0.1
remark R2
remark R2 phi
mode 5 2 0.5 0.1
remark R2 psi
mode 6 2 0.5 0.1
remark R2 chi1
mode 7 3 0.33 0.66 0.0
remark R2 chi2
mode 8 3 0.33 0.66 0.1
remark R2 chi3
mode 9 3 0.33 0.66 0.1
remark R2 chi4
mode 10 2 0.5 0.1
remark V3
remark V3 phi
mode 11 2 0.5 0.1
remark V3 psi
mode 12 2 0.5 0.1
remark V3 chi1
mode 13 3 0.15 0.30 0.05
remark V3 chi2 methyl CG2
mode 14 3 0.33 0.66 0.0
remark V4 chi3 methyl CG1
mode 15 3 0.33 0.66 0.0
remark Y4
remark Y4 phi
mode 16 2 0.5 0.1
remark Y4 psi
mode 17 2 0.5 0.1
remark Y4 chi1
mode 18 3 0.33 0.66 0.0
remark Y4 chi2
mode 19 2 0.5 0.0
remark I5
remark I5 phi
mode 20 2 0.5 0.1
remark I5 psi
mode 21 2 0.5 0.1
remark I5 chi1
mode 22 3 0.10 0.20 0.05
remark I5 chi2
mode 23 3 0.33 0.89 0.05
remark I5 chi3 methyl CD1
mode 24 3 0.33 0.66 0.0
remark I5 chi4 methyl CG2
mode 25 3 0.33 0.66 0.0
remark H6
remark H6 phi
mode 26 2 0.5 0.1
remark H6 psi
mode 27 2 0.5 0.1
remark H6 chi1
mode 28 3 0.13 0.81 0.05
remark H6 chi2
mode 29 2 0.5 0.1
remark P7
remark P7 psi
mode 30 2 0.5 0.1
remark P7 ring
mode 31 2 0.5 0.0
remark F8
remark F8 phi
mode 32 2 0.5 0.1
remark F8 psi
mode 33 2 0.5 0.1
remark F8 chi1
mode 34 3 0.33 0.66 0.1
remark F8 chi2
mode 35 2 0.5 0.0
remark H9
remark H9 phi
mode 36 2 0.5 0.1
remark H9 psi
mode 37 2 0.5 0.1
remark H9 chi1
mode 38 3 0.33 0.66 0.1
remark H9 chi2
mode 39 2 0.5 0.1
remark L10
remark L10 phi
mode 40 2 0.5 0.1
remark L10 psi (C-terminus)
mode 41 2 0.5 0.1
remark L10 chi1
mode 42 3 0.33 0.66 0.1
remark L10 chi2
mode 43 4 0.33 0.1
remark L10 chi3 methyl CD1
mode 44 3 0.33 0.66 0.0
remark L10 chi4 methyl CD2
mode 45 3 0.33 0.66 0.0
endsection
dynamics:

remark D1
remark D1 phi (N-terminus)
multigyrate 1 1 1 4 2 4 3 4
remark D1 psi
multigyrate 11 2 5 6 7 6
remark D1 omega
gyrate 13 9 10
remark D1 chi1
multigyrate 6 3 11 14 12 14 13 14
remark D1 chi2
multigyrate 9 4 15 17 16 17
remark R2
remark R2 phi
multigyrate 15 5 18 19 20 19
remark R2 psi
multigyrate 35 6 22 23 24 23
remark R2 omega
gyrate 37 26 27
remark R2 chi1
multigyrate 18 7 28 31 29 31 30 31
remark R2 chi2
multigyrate 21 8 32 35 33 35 34 35
remark R2 chi3
multigyrate 24 9 36 39 37 39 38 39
remark R2 chi4
multigyrate 27 10 40 42 41 42
remark V3
remark V3 phi
multigyrate 39 11 43 44 45 43
remark V3 psi
multigyrate 51 12 47 48 49 48
remark V3 omega
gyrate 53 51 52
remark V3 chi1
multigyrate 42 13 53 56 54 56 55 56
remark V3 chi2 methyl CG2
multigyrate 45 14 57 60 58 60 59 60
remark V3 chi3 methyl CG1
multigyrate 48 15 61 64 62 64 63 64
remark Y4
remark Y4 phi
multigyrate 55 16 65 66 67 66
remark Y4 psi
multigyrate 75 17 69 70 71 70
remark Y4 omega
gyrate 77 73 74
remark Y4 chi1
multigyrate 58 18 75 78 76 78 77 78
remark Y4 chi2
multigyrate 61 19 79 81 80 81
remark Y4 chi3 hydroxyl
gyrate 69 82 83
remark I5
remark I5 phi
multigyrate 79 20 84 85 86 85
remark I5 psi
multigyrate 94 21 88 89 90 89
remark I5 omega
gyrate 96 92 93
remark I5 chi1
multigyrate 82 22 94 97 95 97 96 97
remark I5 chi2
multigyrate 88 23 98 101 99 101 100 101
```

-continued

```
remark I5 chi3 methyl CD1
multigyrate 91 24 102 105 103 105 104 105
remark I5 chi4 methyl CG2
multigyrate 85 25 106 109 107 109 108 109
remark H6
remark H6 phi
multigyrate 98 26 110 111 112 111
remark H6 psi
multigyrate 115 27 114 115 116 115
remark H6 omega
gyrate 117 118 119
remark H6 chi1
multigyrate 101 28 120 123 121 123 122 123
remark H6 chi2
multigyrate 104 29 124 126 125 126
remark P7
remark P7 psi
multigyrate 132 30 127 128 129 128
remark P7 omega
gyrate 134 131 132
remark P7 ring flip
multigyrate 122 31 133 143 138 143
multigyrate 125 31 134 143 139 143
multigyrate 131 31 135 143 140 143
multigyrate 128 31 136 143 141 143
multigyrate 119 31 137 143 142 143
remark F8
remark F8 phi
multigyrate 136 32 144 145 146 145
remark F8 psi
multigyrate 155 33 148 149 150 149
remark F8 omega
gyrate 157 152 153
remark F8 chi1
multigyrate 139 34 154 157 155 157 156 157
remark F8 chi2
multigyrate 142 35 158 160 159 160
remark H9
remark H9 phi
multigyrate 159 36 161 162 163 162
remark H9 psi
multigyrate 176 37 165 166 167 166
remark H9 omega
gyrate 178 169 170
remark H9 chi1
multigyrate 162 38 171 174 172 174 173 174
remark H9 chi2
multigyrate 165 39 175 177 176 177
remark L10
remark L10 phi
multigyrate 180 40 178 179 180 179
remark L10 psi (C-terminus)
multigyrate 195 41 182 184 183 184
remark L10 chi1
multigyrate 183 42 185 188 186 188 187 188
remark L10 chi2
multigyrate 186 43 189 192 190 192 191 192
remark L10 chi3 methyl CD1
multigyrate 189 44 193 196 194 196 195 196
remark L10 chi4 methyl CD2
multigyrate 192 45 197 200 198 200 199 200
endsection
```

In this manner, all the flexible parts of the trans AngiotensinI molecule and their behaviour were fully defined as required for the computer implementation of the ensemble-generation algorithm according to the present invention.

Structure Calculations

Each round of structure calculations for trans AngiotensinI comprised 480 runs; a larger number than that used for lisinopril (100) was chosen because of the greater number of degrees of freedom being modelled. Statistics were performed on the lowest 15 $\chi^2_{total}$ runs. Each individual run had 5,000 iteration steps initially and the dynamic ensemble was composed of 200 structures; a larger number than that used for $\alpha$-HA$_6$ (40) was chosen because of the greater number of bi- and trimodal models used in the dynamic model file.

One of the challenges presented by this peptide arose from the large number of initially stereochemically ambiguous protons. While the chemical shifts of all protons at stereogenic centres within the molecule had been assigned, the identity of which proton was proR and which was proS could not be determined simply from the assignment spectra collected. Therefore, while unique and specific structural restraints (including both scalar coupling and NOE data) to stereospecifically ambiguous protons could be resolved, they could not be included in the structural calculations until this ambiguity had been solved. Some of these stereocentres could be readily determined by consideration of local NOEs and scalar coupling constants without the more detailed 3D knowledge gained from structure calculations:

1) Val3 HG1*/HG2*: the coupling constant between HA and HB indicated that HA and HB protons had a strong preference to be trans to each other, which meant that one methyl group was on average closer to protons within Tyr4 while the other was on average closer to Arg2. Comparison of NOE intensities between protons in Tyr4 and Arg2 to both Val3 methyl groups therefore allowed the two methyl groups to be easily stereospecifically assigned.

2) Pro7 HD1/HD2: Comparison of NOE intensities between the Pro7 HA proton and both HD protons, which are both at a fixed distance from Pro7 HA, allowed the two HD protons to be immediately stereospecifically assigned.

The scalar-coupling, dihedral angle and hydrogen bond restraint files (see Appendix C) had high confidence and were used almost in their entirety from the first round of structure calculations. A base dataset (167 NOE and 44 noNOE structural restraints) for the 2D [$^1$H, $^1$H]-NOESY dataset was established over the first 30 rounds of structure calculations, after which point the structures loosely converged to preferred regions of the Ramachandran plot for all residues. The secondary statistics table at this point was as follows:

| Dataset | Restraints | Tot Chi | Chi/Res | Viol(>10) | Percent |
|---|---|---|---|---|---|
| TOTAL | 283 | 479.4 | 1.7 | 1 | 0 |
| JCOUP | 21 | 6.2 | 0.8 | 0 | 0 |
| 2D-NOESY | 167 | 380.6 | 2.3 | 1 | 1 |
| 2D-NOE (no) | 44 | 11.6 | 0.3 | 0 | 0 |
| J5DEGC | 20 | 22.8 | 1.1 | 0 | 0 |
| HBOND | 5 | 2.8 | 0.6 | 0 | 0 |
| TDIHEDRALS | 16 | 39.5 | 2.5 | 0 | 0 |
| J15DEGC | 9 | 6.1 | 0.7 | 0 | 0 |

In this case, it can be seen that the Chi/Res values are similar for the datasets, indicating that no one datasat is particularly dominating the results from the structure calculations. Indeed, the higher values observed for the 2D-NOESY dataset were understood to be due to the sub-optimal value for the correlation time, and the relatively crude searching of conformational space afforded by the small number of iteration steps (5,000). At this point, it was clear that the peptide was adopting a grossly-extended conformation and therefore an anisotropic model would be more suitable. Screening a range of values for both perpendicular and parallel correlation times for a symmetric top model for AngiotensinI showed that values of 1.2 ns (perpendicular) and 0.5 ns (parallel) gave considerably better $\chi^2_{dataset}$ scores for the 2D-NOESY data than the original symmetric model with correlation time 0.4 ns, and these were used throughout the remaining rounds of calculations. In addition, 10,000 iterative steps were used to allow the structure to be optimised more effectively.

Over the next 30 rounds of structure calculations, more NOE structural restraints (total 277) and many noNOE (total 225) structure restraints were included following the iterative method of weeding out incorrectly analysed and artefactual data described above. At this point, excellent convergence of the structures was being achieved, and the secondary statistics table was as follows:

| Dataset | Restraints | Tot Chi | Chi/Res | Viol(>10) | Percent |
|---|---|---|---|---|---|
| TOTAL | 557 | 937.3 | 1.7 | 0 | 0 |
| JCOUP | 24 | 31.6 | 1.3 | 0 | 0 |
| 2D-NOESY | 270 | 753.4 | 2.8 | 0 | 0 |
| 2D-NOE (no) | 208 | 71.5 | 0.3 | 0 | 0 |
| J5DEGC | 24 | 30.5 | 1.3 | 0 | 0 |
| HBOND | 5 | 3.0 | 0.6 | 0 | 0 |
| TDIHEDRALS | 17 | 35.3 | 2.1 | 0 | 0 |
| J15DEGC | 9 | 12.0 | 1.3 | 0 | 0 |

During this process, as the structures became more resolved, it became possible to stereospecifically assign the remaining sterochemically ambiguous protons as follows:
1) Pro7 HB1/HB2: Comparison of NOE intensities between protons in Phe8 and Ile5 to both Pro7 HB protons allowed the two HB protons to be easily stereospecifically assigned, because the structures were showing that one face of the proline ring faces Phe8 while the other faces Ile5.
2) Asp1 HB1/HB2, Ile5 HG11/HG12, His6 HB1/HB2, Leu10 HD1*/HD2*: these protons were stereospecifically assigned by running rounds of calculations for all 32 possible combinations with the same data and comparing the $\chi^2_{total}$ scores. Considerable differences in $\chi^2_{total}$ between these rounds gave a very high confidence for the stereospecific assignment of the Ile5 HG1* and His6 HB* protons, and a good confidence for the stereospecific assignment of the Asp1 HB* and Leu10 HD* protons.

Over the next 15 rounds of structure calculations, the remaining NOE and noNOE restraints were included until the 2D [$^1$H, $^1$H]-NOESY dataset had been completely analysed. At this point, the secondary statistics table was as follows:

| Dataset | Restraints | Tot Chi | Chi/Res | Viol(>10) | Percent |
|---|---|---|---|---|---|
| TOTAL | 807 | 1417.2 | 1.8 | 5 | 1 |
| JCOUP | 26 | 46.6 | 1.8 | 0 | 0 |
| 2D-NOESY | 343 | 1120.1 | 3.3 | 4 | 1 |
| 2D-NOE (no) | 382 | 150.0 | 0.4 | 1 | 0 |
| J5DEGC | 26 | 39.3 | 1.5 | 0 | 0 |
| HBOND | 5 | 1.4 | 0.3 | 0 | 0 |
| TDIHEDRALS | 16 | 43.9 | 2.7 | 0 | 0 |
| J15DEGC | 9 | 15.9 | 1.8 | 0 | 0 |

Since the inclusion of the additional data in these 15 rounds (250 structural restraints) relative to the previous rounds did not appreciably alter the optimised dynamic structure, the dynamic structure was deemed to have been solved to a first approximation.

Structure Refinement

The dynamic 3D-solution structure of AngiotensinI was refined using a dynamic-model file, in which the starting values for the variables were taken from the results of the last round above. This allowed the optimisation algorithm to explore this specific $\chi^2_{total}$ minimum quite effectively. The ensemble size was increased and more iteration steps were performed. The secondary statistics table after structure refinement was as follows:

| Dataset | Restraints | Tot Chi | Chi/Res | Viol(>10) | Percent |
|---|---|---|---|---|---|
| TOTAL | 807 | 1110.3 | 1.4 | 3 | 1 |
| JCOUP | 26 | 33.4 | 1.3 | 0 | 0 |
| 2D-NOESY | 343 | 885.7 | 2.6 | 3 | 1 |
| 2D-NOE (no) | 382 | 115.3 | 0.3 | 0 | 0 |
| J5DEGC | 26 | 43.5 | 1.7 | 0 | 0 |
| HBOND | 5 | 0.8 | 0.2 | 0 | 0 |
| TDIHEDRALS | 16 | 21.8 | 1.4 | 0 | 0 |
| J15DEGC | 9 | 9.8 | 1.1 | 0 | 0 |

Only 3 structural restraints have a $\chi^2_{restraint}$ value greater than 10.0, which all relate to the Leu10 sidechain. This indicates that the calculated structure for this sidechain is somewhat inconsistent with the experimental data here for some reason. It is most likely that this inconsistency is due to the poor scaling factors for the Leu10 HB* and HG protons, which had to be estimated because of line broadening caused by strong coupling between Leu10 HB* and HG. Further experimental data is required to determine the structure of the Leu10 sidechain more precisely. The final list of all 807 structural restraints with their individual $\chi^2$ restraint values is given in Appendix C. Several visual representations of the mean dynamic structure and dynamic ensemble of structures for AngiotensinI are given in FIGS. 30-31.

APPENDIX C

AngiotensinI

Starting PDB 3D-coordinates for AngiotensinI

| ATOM | 1 | N | ASP | 1 | −16.312 | −2.194 | 1.677 | 1.00 | 0.00 | N |
|---|---|---|---|---|---|---|---|---|---|---|
| ATOM | 2 | HN1 | ASP | 1 | −16.934 | −2.998 | 1.894 | 1.00 | 0.00 | H |
| ATOM | 3 | HN2 | ASP | 1 | −16.799 | −1.541 | 1.031 | 1.00 | 0.00 | H |
| ATOM | 4 | HN3 | ASP | 1 | −16.069 | −1.695 | 2.557 | 1.00 | 0.00 | H |
| ATOM | 5 | CA | ASP | 1 | −15.069 | −2.690 | 1.033 | 1.00 | 0.00 | C |
| ATOM | 6 | HA | ASP | 1 | −14.603 | −3.350 | 1.750 | 1.00 | 0.00 | H |
| ATOM | 7 | CB | ASP | 1 | −15.425 | −3.464 | −0.273 | 1.00 | 0.00 | C |
| ATOM | 8 | HB1 | ASP | 1 | −16.219 | −4.211 | −0.050 | 1.00 | 0.00 | H |
| ATOM | 9 | HB2 | ASP | 1 | −15.825 | −2.761 | −1.034 | 1.00 | 0.00 | H |
| ATOM | 10 | CG | ASP | 1 | −14.222 | −4.223 | −0.848 | 1.00 | 0.00 | C |
| ATOM | 11 | OD1 | ASP | 1 | −13.815 | −3.908 | −1.998 | 1.00 | 0.00 | O |
| ATOM | 12 | OD2 | ASP | 1 | −13.697 | −5.123 | −0.139 | 1.00 | 0.00 | O |
| ATOM | 13 | C | ASP | 1 | −14.144 | −1.537 | 0.747 | 1.00 | 0.00 | C |
| ATOM | 14 | O | ASP | 1 | −14.577 | −0.405 | 0.530 | 1.00 | 0.00 | O |
| ATOM | 15 | N | ARG | 2 | −12.824 | −1.825 | 0.742 | 1.00 | 0.00 | N |

| | | | | | | | | | |
|---|---|---|---|---|---|---|---|---|---|
| ATOM | 16 | HN | ARG | 2 | −12.495 | −2.746 | 0.935 | 1.00 | 0.00 | H |
| ATOM | 17 | CA | ARG | 2 | −11.806 | −0.864 | 0.421 | 1.00 | 0.00 | C |
| ATOM | 18 | HA | ARG | 2 | −12.201 | −0.128 | −0.266 | 1.00 | 0.00 | H |
| ATOM | 19 | CB | ARG | 2 | −11.197 | −0.179 | 1.672 | 1.00 | 0.00 | C |
| ATOM | 20 | HB1 | ARG | 2 | −12.022 | 0.318 | 2.230 | 1.00 | 0.00 | H |
| ATOM | 21 | HB2 | ARG | 2 | −10.760 | −0.950 | 2.343 | 1.00 | 0.00 | H |
| ATOM | 22 | CG | ARG | 2 | −10.127 | 0.885 | 1.365 | 1.00 | 0.00 | C |
| ATOM | 23 | HG1 | ARG | 2 | −9.291 | 0.407 | 0.808 | 1.00 | 0.00 | H |
| ATOM | 24 | HG2 | ARG | 2 | −10.578 | 1.663 | 0.711 | 1.00 | 0.00 | H |
| ATOM | 25 | CD | ARG | 2 | −9.554 | 1.544 | 2.628 | 1.00 | 0.00 | C |
| ATOM | 26 | HD1 | ARG | 2 | −10.349 | 2.078 | 3.191 | 1.00 | 0.00 | H |
| ATOM | 27 | HD2 | ARG | 2 | −9.079 | 0.777 | 3.276 | 1.00 | 0.00 | H |
| ATOM | 28 | NE | ARG | 2 | −8.513 | 2.542 | 2.212 | 1.00 | 0.00 | N |
| ATOM | 29 | HE | ARG | 2 | −8.434 | 2.774 | 1.242 | 1.00 | 0.00 | H |
| ATOM | 30 | CZ | ARG | 2 | −7.656 | 3.133 | 3.101 | 1.00 | 0.00 | C |
| ATOM | 31 | NH2 | ARG | 2 | −6.723 | 4.019 | 2.644 | 1.00 | 0.00 | N |
| ATOM | 32 | HH22 | ARG | 2 | −6.091 | 4.455 | 3.286 | 1.00 | 0.00 | H |
| ATOM | 33 | HH21 | ARG | 2 | −6.668 | 4.228 | 1.668 | 1.00 | 0.00 | H |
| ATOM | 34 | NH1 | ARG | 2 | −7.720 | 2.850 | 4.434 | 1.00 | 0.00 | N |
| ATOM | 35 | HH12 | ARG | 2 | −7.086 | 3.291 | 5.069 | 1.00 | 0.00 | H |
| ATOM | 36 | HH11 | ARG | 2 | −8.401 | 2.202 | 4.775 | 1.00 | 0.00 | H |
| ATOM | 37 | C | ARG | 2 | −10.744 | −1.658 | −0.273 | 1.00 | 0.00 | C |
| ATOM | 38 | O | ARG | 2 | −10.421 | −2.772 | 0.139 | 1.00 | 0.00 | O |
| ATOM | 39 | N | VAL | 3 | −10.180 | −1.082 | −1.359 | 1.00 | 0.00 | N |
| ATOM | 40 | HN | VAL | 3 | −10.487 | −0.192 | −1.686 | 1.00 | 0.00 | H |
| ATOM | 41 | CA | VAL | 3 | −9.067 | −1.644 | −2.079 | 1.00 | 0.00 | C |
| ATOM | 42 | HA | VAL | 3 | −8.700 | −2.528 | −1.576 | 1.00 | 0.00 | H |
| ATOM | 43 | CB | VAL | 3 | −9.372 | −1.965 | −3.538 | 1.00 | 0.00 | C |
| ATOM | 44 | HB | VAL | 3 | −9.686 | −1.043 | −4.076 | 1.00 | 0.00 | H |
| ATOM | 45 | CG2 | VAL | 3 | −8.115 | −2.538 | −4.231 | 1.00 | 0.00 | C |
| ATOM | 46 | HG21 | VAL | 3 | −8.359 | −2.834 | −5.273 | 1.00 | 0.00 | H |
| ATOM | 47 | HG22 | VAL | 3 | −7.300 | −1.785 | −4.269 | 1.00 | 0.00 | M |
| ATOM | 48 | HG23 | VAL | 3 | −7.749 | −3.433 | −3.686 | 1.00 | 0.00 | H |
| ATOM | 49 | CG1 | VAL | 3 | −10.544 | −2.969 | −3.590 | 1.00 | 0.00 | C |
| ATOM | 50 | HG11 | VAL | 3 | −10.749 | −3.259 | −4.643 | 1.00 | 0.00 | H |
| ATOM | 51 | HG12 | VAL | 3 | −10.294 | −3.885 | −3.014 | 1.00 | 0.00 | H |
| ATOM | 52 | HG13 | VAL | 3 | −11.469 | −2.523 | −3.169 | 1.00 | 0.00 | H |
| ATOM | 53 | C | VAL | 3 | −8.034 | −0.562 | −1.986 | 1.00 | 0.00 | C |
| ATOM | 54 | O | VAL | 3 | −8.273 | 0.575 | −2.392 | 1.00 | 0.00 | O |
| ATOM | 55 | N | TYR | 4 | −6.863 | −0.903 | −1.406 | 1.00 | 0.00 | N |
| ATOM | 56 | HN | TYR | 4 | −6.685 | −1.831 | −1.089 | 1.00 | 0.00 | H |
| ATOM | 57 | CA | TYR | 4 | −5.815 | 0.048 | −1.164 | 1.00 | 0.00 | C |
| ATOM | 58 | HA | TYR | 4 | −5.763 | 0.736 | −1.998 | 1.00 | 0.00 | H |
| ATOM | 59 | CB | TYR | 4 | −6.017 | 0.809 | 0.183 | 1.00 | 0.00 | C |
| ATOM | 60 | HB1 | TYR | 4 | −6.994 | 1.336 | 0.154 | 1.00 | 0.00 | H |
| ATOM | 61 | HB2 | TYR | 4 | −6.040 | 0.089 | 1.029 | 1.00 | 0.00 | H |
| ATOM | 62 | CG | TYR | 4 | −4.958 | 1.853 | 0.447 | 1.00 | 0.00 | C |
| ATOM | 63 | CD1 | TYR | 4 | −4.835 | 2.977 | −0.388 | 1.00 | 0.00 | C |
| ATOM | 64 | HD1 | TYR | 4 | −5.522 | 3.113 | −1.211 | 1.00 | 0.00 | H |
| ATOM | 65 | CE1 | TYR | 4 | −3.817 | 3.915 | −0.176 | 1.00 | 0.00 | C |
| ATOM | 66 | HE1 | TYR | 4 | −3.730 | 4.767 | −0.834 | 1.00 | 0.00 | M |
| ATOM | 67 | CZ | TYR | 4 | −2.910 | 3.739 | 0.879 | 1.00 | 0.00 | C |
| ATOM | 68 | OH | TYR | 4 | −1.869 | 4.672 | 1.084 | 1.00 | 0.00 | O |
| ATOM | 69 | HH | TYR | 4 | −1.354 | 4.380 | 1.840 | 1.00 | 0.00 | H |
| ATOM | 70 | CD2 | TYR | 4 | −4.051 | 1.694 | 1.510 | 1.00 | 0.00 | C |
| ATOM | 71 | HD2 | TYR | 4 | −4.128 | 0.832 | 2.156 | 1.00 | 0.00 | H |
| ATOM | 72 | CE2 | TYR | 4 | −3.032 | 2.629 | 1.726 | 1.00 | 0.00 | C |
| ATOM | 73 | HE2 | TYR | 4 | −2.338 | 2.485 | 2.541 | 1.00 | 0.00 | H |
| ATOM | 74 | C | TYR | 4 | −4.547 | −0.756 | −1.126 | 1.00 | 0.00 | C |
| ATOM | 75 | O | TYR | 4 | −4.547 | −1.935 | −0.774 | 1.00 | 0.00 | O |
| ATOM | 76 | N | ILE | 5 | −3.427 | −0.097 | −1.491 | 1.00 | 0.00 | N |
| ATOM | 77 | HN | ILE | 5 | −3.468 | 0.847 | −1.809 | 1.00 | 0.00 | N |
| ATOM | 78 | CA | ILE | 5 | −2.103 | −0.633 | −1.357 | 1.00 | 0.00 | C |
| ATOM | 79 | HA | ILE | 5 | −2.086 | −1.305 | −0.509 | 1.00 | 0.00 | H |
| ATOM | 80 | CB | ILE | 5 | −1.593 | −1.374 | −2.597 | 1.00 | 0.00 | C |
| ATOM | 81 | HB | ILE | 5 | −2.292 | −2.227 | −2.768 | 1.00 | 0.00 | H |
| ATOM | 82 | CG2 | ILE | 5 | −1.658 | −0.481 | −3.859 | 1.00 | 0.00 | C |
| ATOM | 83 | HG21 | ILE | 5 | −1.408 | −1.075 | −4.763 | 1.00 | 0.00 | H |
| ATOM | 84 | HG22 | ILE | 5 | −2.676 | −0.064 | −4.001 | 1.00 | 0.00 | H |
| ATOM | 85 | HG23 | ILE | 5 | −0.934 | 0.357 | −3.787 | 1.00 | 0.00 | H |
| ATOM | 86 | CG1 | ILE | 5 | −0.191 | −1.988 | −2.352 | 1.00 | 0.00 | C |
| ATOM | 87 | HG11 | ILE | 5 | 0.558 | −1.172 | −2.260 | 1.00 | 0.00 | H |
| ATOM | 88 | HG12 | ILE | 5 | −0.213 | −2.539 | −1.386 | 1.00 | 0.00 | H |
| ATOM | 89 | CD1 | ILE | 5 | 0.263 | −2.955 | −3.450 | 1.00 | 0.00 | C |
| ATOM | 90 | HD1 | ILE | 5 | 1.241 | −3.407 | −3.180 | 1.00 | 0.00 | H |
| ATOM | 91 | HD2 | ILE | 5 | −0.479 | −3.772 | −3.576 | 1.00 | 0.00 | H |
| ATOM | 92 | HD3 | ILE | 5 | 0.379 | −2.426 | −4.419 | 1.00 | 0.00 | H |
| ATOM | 93 | C | ILE | 5 | −1.270 | 0.569 | −1.010 | 1.00 | 0.00 | C |
| ATOM | 94 | O | ILE | 5 | −1.438 | 1.646 | −1.582 | 1.00 | 0.00 | O |

| | | | | | | | | | |
|---|---|---|---|---|---|---|---|---|---|
| ATOM | 95 | N | HIS | 6 | −0.369 | 0.410 | −0.013 | 1.00 | 0.00 | N |
| ATOM | 96 | HN | HIS | 6 | −0.259 | −0.465 | 0.452 | 1.00 | 0.00 | H |
| ATOM | 97 | CA | HIS | 6 | 0.496 | 1.464 | 0.447 | 1.00 | 0.00 | C |
| ATOM | 98 | HA | HIS | 6 | 0.019 | 2.414 | 0.257 | 1.00 | 0.00 | H |
| ATOM | 99 | CB | HIS | 6 | 0.790 | 1.352 | 1.963 | 1.00 | 0.00 | C |
| ATOM | 100 | HB1 | HIS | 6 | −0.176 | 1.341 | 2.513 | 1.00 | 0.00 | H |
| ATOM | 101 | HB2 | HIS | 6 | 1.305 | 0.390 | 2.177 | 1.00 | 0.00 | H |
| ATOM | 102 | CD2 | HIS | 6 | 2.918 | 2.493 | 2.907 | 1.00 | 0.00 | C |
| ATOM | 103 | HD2 | HIS | 6 | 3.646 | 1.691 | 2.944 | 1.00 | 0.00 | H |
| ATOM | 104 | CG | HIS | 6 | 1.625 | 2.479 | 2.509 | 1.00 | 0.00 | C |
| ATOM | 105 | NE2 | HIS | 6 | 3.213 | 3.778 | 3.275 | 1.00 | 0.00 | N |
| ATOM | 106 | HE2 | HIS | 6 | 4.098 | 4.103 | 3.610 | 1.00 | 0.00 | H |
| ATOM | 107 | ND1 | HIS | 6 | 1.149 | 3.756 | 2.640 | 1.00 | 0.00 | N |
| ATOM | 108 | HD1 | HIS | 6 | 0.225 | 4.064 | 2.408 | 1.00 | 0.00 | H |
| ATOM | 109 | CE1 | HIS | 6 | 2.128 | 4.521 | 3.104 | 1.00 | 0.00 | C |
| ATOM | 110 | HE1 | HIS | 6 | 2.054 | 5.569 | 3.308 | 1.00 | 0.00 | H |
| ATOM | 111 | C | HIS | 6 | 1.794 | 1.313 | −0.312 | 1.00 | 0.00 | C |
| ATOM | 112 | O | HIS | 6 | 2.284 | 0.187 | −0.390 | 1.00 | 0.00 | O |
| ATOM | 113 | N | PRO | 7 | 2.402 | 2.351 | −0.889 | 1.00 | 0.00 | N |
| ATOM | 114 | CD | PRO | 7 | 1.819 | 3.685 | −1.040 | 1.00 | 0.00 | C |
| ATOM | 115 | HD1 | PRO | 7 | 0.970 | 3.620 | −1.755 | 1.00 | 0.00 | H |
| ATOM | 116 | HD2 | PRO | 7 | 1.472 | 4.084 | −0.064 | 1.00 | 0.00 | H |
| ATOM | 117 | CA | PRO | 7 | 3.666 | 2.228 | −1.594 | 1.00 | 0.00 | C |
| ATOM | 118 | HA | PRO | 7 | 3.654 | 1.355 | −2.233 | 1.00 | 0.00 | H |
| ATOM | 119 | CB | PRO | 7 | 3.793 | 3.536 | −2.391 | 1.00 | 0.00 | C |
| ATOM | 120 | HB1 | PRO | 7 | 3.336 | 3.386 | −3.394 | 1.00 | 0.00 | H |
| ATOM | 121 | HB2 | PRO | 7 | 4.840 | 3.873 | −2.521 | 1.00 | 0.00 | H |
| ATOM | 122 | CG | PRO | 7 | 2.943 | 4.549 | −1.616 | 1.00 | 0.00 | H |
| ATOM | 123 | HG1 | PRO | 7 | 2.565 | 5.367 | −2.260 | 1.00 | 0.00 | C |
| ATOM | 124 | HG2 | PRO | 7 | 3.544 | 4.976 | −0.783 | 1.00 | 0.00 | H |
| ATOM | 125 | C | PRO | 7 | 4.782 | 2.094 | −0.587 | 1.00 | 0.00 | C |
| ATOM | 126 | O | PRO | 7 | 4.741 | 2.757 | 0.449 | 1.00 | 0.00 | O |
| ATOM | 127 | N | PHE | 8 | 5.765 | 1.214 | −0.872 | 1.00 | 0.00 | N |
| ATOM | 128 | HN | PHE | 8 | 5.773 | 0.693 | −1.722 | 1.00 | 0.00 | H |
| ATOM | 129 | CA | PHE | 8 | 6.845 | 0.944 | 0.036 | 1.00 | 0.00 | C |
| ATOM | 130 | HA | PHE | 8 | 7.085 | 1.848 | 0.581 | 1.00 | 0.00 | H |
| ATOM | 131 | CB | PHE | 8 | 6.508 | −0.225 | 1.009 | 1.00 | 0.00 | C |
| ATOM | 132 | HB1 | PHE | 8 | 5.586 | 0.029 | 1.575 | 1.00 | 0.00 | H |
| ATOM | 133 | HB2 | PHE | 8 | 6.316 | −1.158 | 0.437 | 1.00 | 0.00 | H |
| ATOM | 134 | CG | PHE | 8 | 7.597 | −0.479 | 2.025 | 1.00 | 0.00 | C |
| ATOM | 135 | CD1 | PHE | 8 | 7.892 | 0.477 | 3.012 | 1.00 | 0.00 | C |
| ATOM | 136 | HD1 | PHE | 8 | 7.327 | 1.397 | 3.056 | 1.00 | 0.00 | H |
| ATOM | 137 | CE1 | PHE | 8 | 8.917 | 0.250 | 3.939 | 1.00 | 0.00 | C |
| ATOM | 138 | HE1 | PHE | 8 | 9.138 | 0.992 | 4.692 | 1.00 | 0.00 | H |
| ATOM | 139 | CZ | PHE | 8 | 9.658 | −0.937 | 3.888 | 1.00 | 0.00 | C |
| ATOM | 140 | HZ | PHE | 8 | 10.450 | −1.111 | 4.601 | 1.00 | 0.00 | H |
| ATOM | 141 | CD2 | PHE | 8 | 8.347 | −1.669 | 1.985 | 1.00 | 0.00 | C |
| ATOM | 142 | HD2 | PHE | 8 | 8.139 | −2.410 | 1.227 | 1.00 | 0.00 | H |
| ATOM | 143 | CE2 | PHE | 8 | 9.372 | −1.898 | 2.911 | 1.00 | 0.00 | C |
| ATOM | 144 | HE2 | PHE | 8 | 9.944 | −2.813 | 2.868 | 1.00 | 0.00 | H |
| ATOM | 145 | C | PHE | 8 | 8.017 | 0.579 | −0.828 | 1.00 | 0.00 | C |
| ATOM | 146 | O | PHE | 8 | 7.865 | −0.085 | −1.853 | 1.00 | 0.00 | O |
| ATOM | 147 | N | HIS | 9 | 9.223 | 1.012 | −0.398 | 1.00 | 0.00 | N |
| ATOM | 148 | HN | HIS | 9 | 9.302 | 1.585 | 0.414 | 1.00 | 0.00 | H |
| ATOM | 149 | CA | HIS | 9 | 10.475 | 0.603 | −0.973 | 1.00 | 0.00 | C |
| ATOM | 150 | HA | HIS | 9 | 10.315 | −0.163 | −1.720 | 1.00 | 0.00 | H |
| ATOM | 151 | CB | HIS | 9 | 11.287 | 1.773 | −1.578 | 1.00 | 0.00 | C |
| ATOM | 152 | HB1 | HIS | 9 | 10.697 | 2.229 | −2.403 | 1.00 | 0.00 | H |
| ATOM | 153 | HB2 | HIS | 9 | 11.443 | 2.557 | −0.805 | 1.00 | 0.00 | H |
| ATOM | 154 | CD2 | HIS | 9 | 13.876 | 1.667 | −1.688 | 1.00 | 0.00 | C |
| ATOM | 155 | HD2 | HIS | 9 | 14.194 | 2.300 | −0.869 | 1.00 | 0.00 | H |
| ATOM | 156 | CG | HIS | 9 | 12.630 | 1.363 | −2.123 | 1.00 | 0.00 | C |
| ATOM | 157 | NE2 | HIS | 9 | 14.758 | 0.995 | −2.491 | 1.00 | 0.00 | N |
| ATOM | 158 | HE2 | HIS | 9 | 15.756 | 1.019 | −2.413 | 1.00 | 0.00 | H |
| ATOM | 159 | ND1 | HIS | 9 | 12.771 | 0.507 | −3.182 | 1.00 | 0.00 | N |
| ATOM | 160 | HD1 | HIS | 9 | 12.024 | 0.091 | −3.702 | 1.00 | 0.00 | H |
| ATOM | 161 | CE1 | HIS | 9 | 14.066 | 0.303 | −3.385 | 1.00 | 0.00 | C |
| ATOM | 162 | HE1 | HIS | 9 | 14.485 | −0.323 | −4.146 | 1.00 | 0.00 | H |
| ATOM | 163 | C | HIS | 9 | 11.244 | 0.015 | 0.171 | 1.00 | 0.00 | C |
| ATOM | 164 | O | HIS | 9 | 11.283 | 0.586 | 1.260 | 1.00 | 0.00 | O |
| ATOM | 165 | N | LEU | 10 | 11.869 | −1.160 | −0.066 | 1.00 | 0.00 | N |
| ATOM | 166 | HN | LEU | 10 | 11.815 | −1.605 | −0.957 | 1.00 | 0.00 | H |
| ATOM | 167 | CA | LEU | 10 | 12.662 | −1.850 | 0.920 | 1.00 | 0.00 | C |
| ATOM | 168 | HA | LEU | 10 | 12.303 | −1.587 | 1.906 | 1.00 | 0.00 | H |
| ATOM | 169 | CB | LEU | 10 | 12.568 | −3.389 | 0.756 | 1.00 | 0.00 | C |
| ATOM | 170 | HB1 | LEU | 10 | 11.493 | −3.621 | 0.576 | 1.00 | 0.00 | H |
| ATOM | 171 | HB2 | LEU | 10 | 13.124 | −3.720 | −0.146 | 1.00 | 0.00 | H |
| ATOM | 172 | CG | LEU | 10 | 13.003 | −4.231 | 1.984 | 1.00 | 0.00 | C |
| ATOM | 173 | HG | LEU | 10 | 12.496 | −3.798 | 2.877 | 1.00 | 0.00 | H |

-continued

| | | | | | | | | | | |
|---|---|---|---|---|---|---|---|---|---|---|
| ATOM | 174 | CD1 | LEU | 10 | 12.499 | −5.681 | 1.845 | 1.00 | 0.00 | C |
| ATOM | 175 | HD11 | LEU | 10 | 12.757 | −6.267 | 2.752 | 1.00 | 0.00 | H |
| ATOM | 176 | HD12 | LEU | 10 | 11.396 | −5.696 | 1.717 | 1.00 | 0.00 | H |
| ATOM | 177 | HD13 | LEU | 10 | 12.966 | −6.168 | 0.963 | 1.00 | 0.00 | H |
| ATOM | 178 | CD2 | LEU | 10 | 14.520 | −4.216 | 2.260 | 1.00 | 0.00 | C |
| ATOM | 179 | HD21 | LEU | 10 | 14.758 | −4.891 | 3.109 | 1.00 | 0.00 | H |
| ATOM | 180 | HD22 | LEU | 10 | 15.078 | −4.564 | 1.365 | 1.00 | 0.00 | H |
| ATOM | 181 | HD23 | LEU | 10 | 14.866 | −3.197 | 2.526 | 1.00 | 0.00 | H |
| ATOM | 182 | C | LEU | 10 | 14.104 | −1.354 | 0.736 | 1.00 | 0.00 | C |
| ATOM | 183 | OE1 | LEU | 10 | 14.697 | −1.629 | −0.341 | 1.00 | 0.00 | O |
| ATOM | 184 | OE2 | LEU | 10 | 14.621 | −0.684 | 1.669 | 1.00 | 0.00 | O |
| END | | | | | | | | | | |

Internal Coordinate Table for AngiotensinI

| | | | | | | | | | | | | | |
|---|---|---|---|---|---|---|---|---|---|---|---|---|---|
| 1 | 1 | HN1 | 1 | N | 1 | CA | 1 | CB | 1.03942 | 109.453 | 58.9129 | 109.747 | 1.55931 |
| 2 | 1 | HN1 | 1 | CA | 1 | *N | 1 | HN2 | 1.03942 | 109.453 | −120.095 | 109.412 | 1.03966 |
| 3 | 1 | HN1 | 1 | CA | 1 | *N | 1 | HN3 | 1.03942 | 109.453 | 119.982 | 109.357 | 1.04041 |
| 4 | 1 | CB | 1 | N | 1 | *CA | 1 | C | 1.55931 | 109.747 | 122.578 | 109.926 | 1.5056 |
| 5 | 1 | CB | 1 | N | 1 | *CA | 1 | HA | 1.55931 | 109.747 | −119.466 | 106.098 | 1.08021 |
| 6 | 1 | N | 1 | CA | 1 | CB | 1 | CG | 1.48519 | 109.747 | −169.346 | 112.361 | 1.53425 |
| 7 | 1 | CG | 1 | CA | 1 | *CB | 1 | HB1 | 1.53425 | 112.361 | 119.292 | 109.165 | 1.11273 |
| 8 | 1 | CG | 1 | CA | 1 | *CB | 1 | HB2 | 1.53425 | 112.361 | −122.649 | 109.995 | 1.11055 |
| 9 | 1 | CA | 1 | CB | 1 | CG | 1 | OD1 | 1.55931 | 112.361 | −118.346 | 118.144 | 1.25991 |
| 10 | 1 | OD1 | 1 | CB | 1 | *CG | 1 | OD2 | 1.25991 | 118.144 | 179.802 | 117.974 | 1.26028 |
| 11 | 1 | N | 1 | CA | 1 | C | 2 | N | 1.48519 | 109.926 | 151.281 | 115.958 | 1.35106 |
| 12 | 2 | N | 1 | CA | 1 | *C | 1 | O | 1.35106 | 115.958 | 179.877 | 121.432 | 1.23126 |
| 13 | 1 | CA | 1 | C | 2 | N | 2 | CA | 1.5056 | 115.958 | 176.706 | 123.414 | 1.43628 |
| 14 | 2 | CA | 1 | C | 2 | *N | 2 | HN | 1.43628 | 123.414 | −177.835 | 121.243 | 0.996861 |
| 15 | 1 | C | 2 | N | 2 | CA | 2 | CB | 1.35106 | 123.414 | 95.2178 | 113.178 | 1.55084 |
| 16 | 2 | CB | 2 | N | 2 | *CA | 2 | C | 1.55084 | 113.178 | 118.81 | 104.573 | 1.49663 |
| 17 | 2 | CB | 2 | N | 2 | *CA | 2 | HA | 1.55084 | 113.178 | −124.378 | 109.782 | 1.08152 |
| 18 | 2 | N | 2 | CA | 2 | CB | 2 | CG | 1.43628 | 113.178 | −178.484 | 114.66 | 1.53988 |
| 19 | 2 | CG | 2 | CA | 2 | *CB | 2 | HB1 | 1.53988 | 114.66 | 120.313 | 108.092 | 1.1131 |
| 20 | 2 | CG | 2 | CA | 2 | *CB | 2 | HB2 | 1.53988 | 114.66 | −122.984 | 109.569 | 1.1116 |
| 21 | 2 | CA | 2 | CB | 2 | CG | 2 | CD | 1.55084 | 114.66 | 179.723 | 113.07 | 1.53551 |
| 22 | 2 | CD | 2 | CB | 2 | *CG | 2 | HG1 | 1.53551 | 113.07 | 120.623 | 108.972 | 1.11249 |
| 23 | 2 | CD | 2 | CB | 2 | *CG | 2 | HG2 | 1.53551 | 113.07 | −121.823 | 108.595 | 1.11194 |
| 24 | 2 | CB | 2 | CG | 2 | CD | 2 | NE | 1.53988 | 113.07 | 179.157 | 108.434 | 1.50091 |
| 25 | 2 | NE | 2 | CG | 2 | *CD | 2 | HD1 | 1.50091 | 108.434 | 119 | 110.861 | 1.11092 |
| 26 | 2 | NE | 2 | CG | 2 | *CD | 2 | HD2 | 1.50091 | 108.434 | −119.052 | 110.064 | 1.11077 |
| 27 | 2 | CG | 2 | CD | 2 | NE | 2 | CZ | 1.53551 | 108.434 | −168.57 | 122.77 | 1.36896 |
| 28 | 2 | CZ | 2 | CD | 2 | *NE | 2 | HE | 1.36896 | 122.77 | 179.059 | 118.534 | 1.00048 |
| 29 | 2 | CD | 2 | NE | 2 | CZ | 2 | NH2 | 1.50091 | 122.77 | 179.135 | 119.377 | 1.36541 |
| 30 | 2 | NH2 | 2 | NE | 2 | *CZ | 2 | NH1 | 1.36541 | 119.377 | −179.978 | 121.039 | 1.36421 |
| 31 | 2 | NE | 2 | CZ | 2 | NH2 | 2 | HH22 | 1.36896 | 119.377 | −179.893 | 119.965 | 1.00084 |
| 32 | 2 | HH22 | 2 | CZ | 2 | *NH2 | 2 | HH21 | 1.00084 | 119.965 | 179.655 | 120.003 | 0.999641 |
| 33 | 2 | NE | 2 | CZ | 2 | NH1 | 2 | HH12 | 1.36896 | 121.039 | 179.996 | 119.956 | 0.999831 |
| 34 | 2 | HH12 | 2 | CZ | 2 | *NH1 | 2 | HH11 | 0.999831 | 119.956 | 179.984 | 119.973 | 0.999973 |
| 35 | 2 | N | 2 | CA | 2 | C | 3 | N | 1.43628 | 104.573 | 138.359 | 116.251 | 1.3525 |
| 36 | 3 | N | 2 | CA | 2 | *C | 2 | O | 1.3525 | 116.251 | −179.862 | 120.74 | 1.23088 |
| 37 | 2 | CA | 2 | C | 3 | N | 3 | CA | 1.49663 | 116.251 | 174.351 | 123.894 | 1.4398 |
| 38 | 3 | CA | 2 | C | 3 | *N | 3 | HN | 1.4398 | 123.894 | −176.413 | 121.018 | 0.996633 |
| 39 | 2 | C | 3 | N | 3 | CA | 3 | CB | 1.3525 | 123.894 | 119.093 | 113.958 | 1.52471 |
| 40 | 3 | CB | 3 | N | 3 | *CA | 3 | C | 1.52471 | 113.958 | 119.468 | 102.707 | 1.49882 |
| 41 | 3 | CB | 3 | N | 3 | *CA | 3 | HA | 1.52471 | 113.958 | −124.297 | 110.418 | 1.08127 |
| 42 | 3 | N | 3 | CA | 3 | CB | 3 | CG2 | 1.4398 | 113.958 | 179.011 | 110.147 | 1.54552 |
| 43 | 3 | CG2 | 3 | CA | 3 | *CB | 3 | CG1 | 1.54552 | 110.147 | 122.039 | 108.72 | 1.54412 |
| 44 | 3 | CG2 | 3 | CA | 3 | *CB | 3 | HB | 1.54552 | 110.147 | −119.849 | 110.161 | 1.11271 |
| 45 | 3 | CA | 3 | CB | 3 | CG2 | 3 | HG21 | 1.52471 | 110.147 | 176.212 | 109.931 | 1.11037 |
| 46 | 3 | HG21 | 3 | CB | 3 | *CG2 | 3 | HG22 | 1.11037 | 109.931 | 119.598 | 111.157 | 1.11026 |
| 47 | 3 | HG21 | 3 | CB | 3 | *CG2 | 3 | HG23 | 1.11037 | 109.931 | −119.679 | 110.302 | 1.10996 |
| 48 | 3 | CA | 3 | CB | 3 | CG1 | 3 | HG11 | 1.52471 | 108.72 | −177.029 | 109.975 | 1.11128 |
| 49 | 3 | HG11 | 3 | CB | 3 | *CG1 | 3 | HG12 | 1.11128 | 109.975 | 119.705 | 110.363 | 1.11055 |
| 50 | 3 | HG11 | 3 | CB | 3 | *CG1 | 3 | HG13 | 1.11128 | 109.975 | −119.575 | 111.01 | 1.10986 |
| 51 | 3 | N | 3 | CA | 3 | C | 4 | N | 1.4398 | 102.707 | 121.471 | 116.229 | 1.35053 |
| 52 | 4 | N | 3 | CA | 3 | *C | 3 | O | 1.35053 | 116.229 | −178.282 | 120.838 | 1.23074 |
| 53 | 3 | CA | 3 | C | 4 | N | 4 | CA | 1.49882 | 116.229 | −175.637 | 122.552 | 1.43571 |
| 54 | 4 | CA | 3 | C | 4 | *N | 4 | HN | 1.43571 | 122.552 | 177.834 | 121.772 | 0.996673 |
| 55 | 3 | C | 4 | N | 4 | CA | 4 | CB | 1.35053 | 122.552 | 85.1621 | 111.968 | 1.56024 |
| 56 | 4 | CB | 4 | N | 4 | *CA | 4 | C | 1.56024 | 111.968 | 120.078 | 105.423 | 1.50189 |
| 57 | 4 | CB | 4 | N | 4 | *CA | 4 | HA | 1.56024 | 111.968 | −123.467 | 109.04 | 1.08241 |
| 58 | 4 | N | 4 | CA | 4 | CB | 4 | CG | 1.43571 | 111.968 | −177.97 | 113.408 | 1.51034 |
| 59 | 4 | CG | 4 | CA | 4 | *CB | 4 | HB1 | 1.51034 | 113.408 | 119.045 | 108.835 | 1.11045 |
| 60 | 4 | CG | 4 | CA | 4 | *CB | 4 | HB2 | 1.51034 | 113.408 | −122.736 | 110.118 | 1.11115 |
| 61 | 4 | CA | 4 | CB | 4 | CG | 4 | CD1 | 1.56024 | 113.408 | 64.7325 | 120.682 | 1.40561 |

-continued

| | | | | | | | | | | | |
|---|---|---|---|---|---|---|---|---|---|---|---|
| 62 | 4 | CD1 | 4 | CB | 4 | *CG | 4 | CD2 | 1.40561 | 120.682 | −178.013 | 120.409 | 1.40638 |
| 63 | 4 | CB | 4 | CG | 4 | CD1 | 4 | CE1 | 1.51034 | 120.682 | −177.278 | 120.617 | 1.4004 |
| 64 | 4 | CE1 | 4 | CG | 4 | *CD1 | 4 | HD1 | 1.4004 | 120.617 | 179.069 | 119.83 | 1.08065 |
| 65 | 4 | CG | 4 | CD1 | 4 | CE1 | 4 | CZ | 1.40561 | 120.617 | −0.13183 | 119.999 | 1.40237 |
| 66 | 4 | CZ | 4 | CD1 | 4 | *CE1 | 4 | HE1 | 1.40237 | 119.999 | 179.432 | 119.652 | 1.08002 |
| 67 | 4 | CD1 | 4 | CE1 | 4 | CZ | 4 | OH | 1.4004 | 119.999 | 179.028 | 120.186 | 1.41287 |
| 68 | 4 | OH | 4 | CE1 | 4 | *CZ | 4 | CE2 | 1.41287 | 120.186 | −179.553 | 119.85 | 1.40157 |
| 69 | 4 | CE1 | 4 | CZ | 4 | OH | 4 | HH | 1.40237 | 120.186 | −179.5 | 107.975 | 0.960221 |
| 70 | 4 | CB | 4 | CG | 4 | CD2 | 4 | CE2 | 1.51034 | 120.409 | 177.294 | 120.705 | 1.39973 |
| 71 | 4 | CE2 | 4 | CG | 4 | *CD2 | 4 | HD2 | 1.39973 | 120.705 | −178.803 | 119.761 | 1.07995 |
| 72 | 4 | CE1 | 4 | CZ | 4 | CE2 | 4 | CD2 | 1.40237 | 119.85 | 0.53599 | 119.943 | 1.39973 |
| 73 | 4 | CD2 | 4 | CZ | 4 | *CE2 | 4 | HE2 | 1.39973 | 119.943 | 179.45 | 120.375 | 1.08009 |
| 74 | 4 | CG | 4 | CD2 | 4 | CE2 | 4 | CZ | 1.40638 | 120.705 | 0.109096 | 119.943 | 1.40157 |
| 75 | 4 | N | 4 | CA | 4 | C | 5 | N | 1.43571 | 105.423 | 152.145 | 115.616 | 1.34978 |
| 76 | 5 | N | 4 | CA | 4 | *C | 4 | O | 1.34978 | 115.616 | 179.545 | 121.345 | 1.23042 |
| 77 | 4 | CA | 4 | C | 5 | N | 5 | CA | 1.50189 | 115.616 | 171.62 | 123.925 | 1.43465 |
| 78 | 5 | CA | 4 | C | 5 | *N | 5 | HN | 1.43465 | 123.925 | −174.775 | 120.959 | 0.996966 |
| 79 | 4 | C | 5 | N | 5 | CA | 5 | CB | 1.34978 | 123.925 | 92.1859 | 114.353 | 1.53192 |
| 80 | 5 | CB | 5 | N | 5 | *CA | 5 | C | 1.53192 | 114.353 | 123.264 | 103.547 | 1.50303 |
| 81 | 5 | CB | 5 | N | 5 | *CA | 5 | HA | 1.53192 | 114.353 | −122.243 | 108.645 | 1.08212 |
| 82 | 5 | N | 5 | CA | 5 | CB | 5 | CG2 | 1.43465 | 114.353 | 55.3434 | 111.533 | 1.54736 |
| 83 | 5 | CG2 | 5 | CA | 5 | *CB | 5 | CG1 | 1.54736 | 111.533 | 127.679 | 111.394 | 1.55004 |
| 84 | 5 | CG2 | 5 | CA | 5 | *CB | 5 | HB | 1.54736 | 111.533 | −116.263 | 106.572 | 1.116 |
| 85 | 5 | CA | 5 | CB | 5 | CG2 | 5 | HG21 | 1.53192 | 111.533 | −172.804 | 110.235 | 1.1102 |
| 86 | 5 | HG21 | 5 | CB | 5 | *CG2 | 5 | HG22 | 1.1102 | 110.235 | 119.273 | 111.095 | 1.10922 |
| 87 | 5 | HG21 | 5 | CB | 5 | *CG2 | 5 | HG23 | 1.1102 | 110.235 | −119.576 | 110.822 | 1.10978 |
| 88 | 5 | CA | 5 | CB | 5 | CG1 | 5 | CD1 | 1.53192 | 111.394 | 169.263 | 113.879 | 1.53193 |
| 89 | 5 | CD1 | 5 | CB | 5 | *CG1 | 5 | HG11 | 1.53193 | 113.879 | 122.02 | 109.378 | 1.11145 |
| 90 | 5 | CD1 | 5 | CB | 5 | *CG1 | 5 | HG12 | 1.53193 | 113.879 | −120.732 | 108.397 | 1.11231 |
| 91 | 5 | CB | 5 | CG1 | 5 | CD1 | 5 | HD1 | 1.55004 | 113.879 | −176.308 | 110.096 | 1.11072 |
| 92 | 5 | HD1 | 5 | CG1 | 5 | *CD1 | 5 | HD2 | 1.11072 | 110.096 | 119.669 | 110.341 | 1.11082 |
| 93 | 5 | HD1 | 5 | CG1 | 5 | *CD1 | 5 | HD3 | 1.11072 | 110.096 | −119.814 | 110.843 | 1.11007 |
| 94 | 5 | N | 5 | CA | 5 | C | 6 | N | 1.43465 | 103.547 | 135.689 | 116.433 | 1.35318 |
| 95 | 6 | N | 5 | CA | 5 | *C | 5 | O | 1.35318 | 116.433 | −177.818 | 121.115 | 1.23099 |
| 96 | 5 | CA | 5 | C | 6 | N | 6 | CA | 1.50303 | 116.433 | −179.461 | 123.347 | 1.43901 |
| 97 | 6 | CA | 5 | C | 6 | *N | 6 | HN | 1.43901 | 123.347 | −179.584 | 121.348 | 0.99697 |
| 98 | 5 | C | 6 | N | 6 | CA | 6 | CB | 1.35318 | 123.347 | 147.132 | 111.972 | 1.5483 |
| 99 | 6 | CB | 6 | N | 6 | *CA | 6 | C | 1.5483 | 111.972 | 118.699 | 106.414 | 1.51119 |
| 100 | 6 | CB | 6 | N | 6 | *CA | 6 | HA | 1.5483 | 111.972 | −120.12 | 108.82 | 1.07987 |
| 101 | 6 | N | 6 | CA | 6 | CB | 6 | CG | 1.43901 | 111.972 | −176.564 | 113.977 | 1.50515 |
| 102 | 6 | CG | 6 | CA | 6 | *CB | 6 | HB1 | 1.50515 | 113.977 | 120.559 | 108.672 | 1.11166 |
| 103 | 6 | CG | 6 | CA | 6 | *CB | 6 | HB2 | 1.50515 | 113.977 | −122.256 | 109.814 | 1.11196 |
| 104 | 6 | CA | 6 | CB | 6 | CG | 6 | CD2 | 1.5483 | 113.977 | −107.221 | 130.139 | 1.35294 |
| 105 | 6 | CD2 | 6 | CB | 6 | *CG | 6 | ND1 | 1.35294 | 130.139 | 177.51 | 122.699 | 1.36911 |
| 106 | 6 | NE2 | 6 | CD2 | 6 | CG | 6 | CB | 1.36882 | 107.144 | 177.798 | 130.139 | 1.50515 |
| 107 | 6 | NE2 | 6 | CG | 6 | *CD2 | 6 | HD2 | 1.36882 | 107.144 | −179.227 | 130.117 | 1.08377 |
| 108 | 6 | CG | 6 | CD2 | 6 | NE2 | 6 | CE1 | 1.35294 | 107.144 | −0.0103181 | 108.36 | 1.32609 |
| 109 | 6 | CE1 | 6 | CD2 | 6 | *NE2 | 6 | HE2 | 1.32609 | 108.36 | −179.618 | 125.844 | 1.00054 |
| 110 | 6 | CB | 6 | CG | 6 | ND1 | 6 | CE1 | 1.50515 | 122.699 | −177.981 | 108.351 | 1.32626 |
| 111 | 6 | CE1 | 6 | CG | 6 | *ND1 | 6 | HD1 | 1.32626 | 108.351 | 178.888 | 125.846 | 1.00123 |
| 112 | 6 | CD2 | 6 | NE2 | 6 | CE1 | 6 | ND1 | 1.36882 | 108.36 | 0.027564 | 109.02 | 1.32626 |
| 113 | 6 | ND1 | 6 | NE2 | 6 | *CE1 | 6 | HE1 | 1.32626 | 109.02 | 179.971 | 125.496 | 1.07023 |
| 114 | 6 | CG | 6 | ND1 | 6 | CE1 | 6 | NE2 | 1.36911 | 108.351 | −0.0339579 | 109.02 | 1.32609 |
| 115 | 6 | N | 6 | CA | 6 | C | 7 | N | 1.43901 | 106.414 | 133.108 | 122.066 | 1.33418 |
| 116 | 7 | N | 6 | CA | 6 | *C | 6 | O | 1.33418 | 122.066 | −179.778 | 117.731 | 1.23047 |
| 117 | 6 | CA | 6 | C | 7 | N | 7 | CD | 1.51119 | 122.066 | −9.65365 | 124.903 | 1.46364 |
| 118 | 7 | CD | 6 | C | 7 | *N | 7 | CA | 1.46364 | 124.903 | −171.884 | 122.724 | 1.45253 |
| 119 | 6 | C | 7 | N | 7 | CD | 7 | CG | 1.33418 | 124.903 | 174.1 | 105.121 | 1.53024 |
| 120 | 7 | CG | 7 | N | 7 | *CD | 7 | HD1 | 1.53024 | 105.121 | 118.338 | 108.494 | 1.11187 |
| 121 | 7 | CG | 7 | N | 7 | *CD | 7 | HD2 | 1.53024 | 105.121 | −120.135 | 111.187 | 1.11004 |
| 122 | 6 | C | 7 | N | 7 | CA | 7 | CB | 1.33418 | 122.724 | 165.431 | 104.568 | 1.53695 |
| 123 | 7 | CB | 7 | N | 7 | *CA | 7 | C | 1.53695 | 104.568 | 118.955 | 109.097 | 1.50913 |
| 124 | 7 | CB | 7 | N | 7 | *CA | 7 | HA | 1.53695 | 104.568 | −121.029 | 110.202 | 1.08194 |
| 125 | 7 | N | 7 | CA | 7 | CB | 7 | CG | 1.45253 | 104.568 | 25.0499 | 104.74 | 1.53274 |
| 126 | 7 | CG | 7 | CA | 7 | *CB | 7 | HB1 | 1.53274 | 104.74 | −115.758 | 108.594 | 1.11237 |
| 127 | 7 | CG | 7 | CA | 7 | *CB | 7 | HB2 | 1.53274 | 104.74 | 123.04 | 113.449 | 1.10755 |
| 128 | 7 | N | 7 | CD | 7 | CG | 7 | CB | 1.46364 | 105.121 | 28.1237 | 102.974 | 1.53274 |
| 129 | 7 | CB | 7 | CD | 7 | *CG | 7 | HG1 | 1.53274 | 102.974 | 121.498 | 112.655 | 1.10758 |
| 130 | 7 | CB | 7 | CD | 7 | *CG | 7 | HG2 | 1.53274 | 102.974 | −116.291 | 109.372 | 1.11239 |
| 131 | 7 | CA | 7 | CB | 7 | CG | 7 | CD | 1.53695 | 104.74 | −32.6465 | 102.974 | 1.53024 |
| 132 | 7 | N | 7 | CA | 7 | C | 8 | N | 1.45253 | 109.097 | 139.786 | 117.1 | 1.34978 |
| 133 | 8 | N | 7 | CA | 7 | *C | 7 | O | 1.34978 | 117.1 | −178.478 | 119.291 | 1.23067 |
| 134 | 7 | CA | 7 | C | 8 | N | 8 | CA | 1.50913 | 117.1 | −176.689 | 122.451 | 1.43658 |
| 135 | 8 | CA | 7 | C | 8 | *N | 8 | HN | 1.43658 | 122.451 | 178.507 | 121.773 | 0.996998 |
| 136 | 7 | C | 8 | N | 8 | CA | 8 | CB | 1.34978 | 122.451 | 89.9685 | 111.912 | 1.55784 |
| 137 | 8 | CB | 8 | N | 8 | *CA | 8 | C | 1.55784 | 111.912 | 119.961 | 105.597 | 1.5011 |
| 138 | 8 | CB | 8 | N | 8 | *CA | 8 | HA | 1.55784 | 111.912 | −123.405 | 109.144 | 1.08252 |
| 139 | 8 | N | 8 | CA | 8 | CB | 8 | CG | 1.43658 | 111.912 | −176.81 | 112.97 | 1.51086 |
| 140 | 8 | CG | 8 | CA | 8 | *CB | 8 | HB1 | 1.51086 | 112.97 | 118.941 | 109.031 | 1.11129 |

-continued

| | | | | | | | | | | |
|---|---|---|---|---|---|---|---|---|---|---|
| 141 | 8 CG | 8 CA | 8 *CB | 8 HB2 | 1.51086 | 112.97 | −122.534 | 110.24 | 1.1111 |
| 142 | 8 CA | 8 CB | 8 CG | 8 CD1 | 1.55784 | 112.97 | 66.5034 | 120.611 | 1.40539 |
| 143 | 8 CD1 | 8 CB | 8 *CG | 8 CD2 | 1.40539 | 120.611 | −178.998 | 120.478 | 1.4072 |
| 144 | 8 CB | 8 CG | 8 CD1 | 8 CE1 | 1.51086 | 120.611 | −178.907 | 120.545 | 1.40053 |
| 145 | 8 CE1 | 8 CG | 8 *CD1 | 8 HD1 | 1.40053 | 120.545 | 179.791 | 119.869 | 1.08054 |
| 146 | 8 CG | 8 CD1 | 8 CE1 | 8 CZ | 1.40539 | 120.545 | −0.00451033 | 120.039 | 1.40023 |
| 147 | 8 CZ | 8 CD1 | 8 *CE1 | 8 HE1 | 1.40023 | 120.039 | 179.83 | 119.993 | 1.08001 |
| 148 | 8 CD1 | 8 CE1 | 8 CZ | 8 CE2 | 1.40053 | 120.039 | −0.111613 | 119.949 | 1.39995 |
| 149 | 8 CE2 | 8 CE1 | 8 *CZ | 8 HZ | 1.39995 | 119.949 | 179.95 | 120.047 | 1.07977 |
| 150 | 8 CB | 8 CG | 8 CD2 | 8 CE2 | 1.51086 | 120.478 | 178.92 | 120.642 | 1.40019 |
| 151 | 8 CE2 | 8 CG | 8 *CD2 | 8 HD2 | 1.40019 | 120.642 | −179.341 | 119.829 | 1.08024 |
| 152 | 8 CE1 | 8 CZ | 8 CE2 | 8 CD2 | 1.40023 | 119.949 | 0.123335 | 119.922 | 1.40019 |
| 153 | 8 CD2 | 8 CZ | 8 *CE2 | 8 HE2 | 1.40019 | 119.922 | 179.705 | 120.079 | 1.07993 |
| 154 | 8 CG | 8 CD2 | 8 CE2 | 8 CZ | 1.4072 | 120.642 | −0.0193345 | 119.922 | 1.39995 |
| 155 | 8 N | 8 CA | 8 C | 9 N | 1.43658 | 105.597 | 143.236 | 115.826 | 1.3516 |
| 156 | 9 N | 8 CA | 8 *C | 8 O | 1.3516 | 115.826 | 179.342 | 120.94 | 1.2307 |
| 157 | 8 CA | 8 C | 9 N | 9 CA | 1.5011 | 115.826 | 170.499 | 123.977 | 1.43715 |
| 158 | 9 CA | 8 C | 9 *N | 9 HN | 1.43715 | 123.977 | −174.139 | 120.928 | 0.996952 |
| 159 | 8 C | 9 N | 9 CA | 9 CB | 1.3516 | 123.977 | 118.543 | 113.479 | 1.54734 |
| 160 | 9 CB | 9 N | 9 *CA | 9 C | 1.54734 | 113.479 | 118.75 | 104.671 | 1.49861 |
| 161 | 9 CB | 9 N | 9 *CA | 9 HA | 1.54734 | 113.479 | −124.111 | 110.422 | 1.08183 |
| 162 | 9 N | 9 CA | 9 CB | 9 CG | 1.43715 | 113.479 | 177.199 | 113.8 | 1.50625 |
| 163 | 9 CG | 9 CA | 9 *CB | 9 HB1 | 1.50625 | 113.8 | 120.99 | 108.766 | 1.11205 |
| 164 | 9 CG | 9 CA | 9 *CB | 9 HB2 | 1.50625 | 113.8 | −121.739 | 109.568 | 1.11199 |
| 165 | 9 CA | 9 CB | 9 CG | 9 CD2 | 1.54734 | 113.8 | −112.438 | 130.016 | 1.35431 |
| 166 | 9 CD2 | 9 CB | 9 *CG | 9 ND1 | 1.35431 | 130.016 | 176.612 | 122.815 | 1.36898 |
| 167 | 9 NE2 | 9 CD2 | 9 CG | 9 CB | 1.36906 | 107.106 | 177.205 | 130.016 | 1.50625 |
| 168 | 9 NE2 | 9 CG | 9 *CD2 | 9 HD2 | 1.36906 | 107.106 | −179.46 | 130.116 | 1.08285 |
| 169 | 9 CG | 9 CD2 | 9 NE2 | 9 CE1 | 1.35431 | 107.106 | −0.0763064 | 108.392 | 1.32551 |
| 170 | 9 CE1 | 9 CD2 | 9 *NE2 | 9 HE2 | 1.32551 | 108.392 | −179.729 | 125.778 | 1.00133 |
| 171 | 9 CB | 9 CG | 9 ND1 | 9 CE1 | 1.50625 | 122.815 | −177.513 | 108.365 | 1.32659 |
| 172 | 9 CE1 | 9 CG | 9 *ND1 | 9 HD1 | 1.32659 | 108.365 | 178.824 | 125.804 | 1.00073 |
| 173 | 9 CD2 | 9 NE2 | 9 CE1 | 9 ND1 | 1.36906 | 108.392 | −0.065808 | 109.035 | 1.32659 |
| 174 | 9 ND1 | 9 NE2 | 9 *CE1 | 9 HE1 | 1.32659 | 109.035 | −179.774 | 125.469 | 1.07077 |
| 175 | 9 CG | 9 ND1 | 9 CE1 | 9 NE2 | 1.36898 | 108.365 | 0.181656 | 109.035 | 1.32551 |
| 176 | 9 N | 9 CA | 9 C | 10 N | 1.43715 | 104.671 | 134.529 | 116.388 | 1.35182 |
| 177 | 10 N | 9 CA | 9 *C | 9 O | 1.35182 | 116.388 | −179.594 | 120.657 | 1.23024 |
| 178 | 9 CA | 9 C | 10 N | 10 CA | 1.49861 | 116.388 | 179.245 | 123.407 | 1.44123 |
| 179 | 10 CA | 9 C | 10 *N | 10 HN | 1.44123 | 123.407 | −179.309 | 121.291 | 0.997408 |
| 180 | 9 C | 10 N | 10 CA | 10 CB | 1.35182 | 123.407 | 146.897 | 111.683 | 1.55057 |
| 181 | 10 CB | 10 N | 10 *CA | 10 C | 1.55057 | 111.683 | 121.658 | 106.26 | 1.53598 |
| 182 | 10 CB | 10 N | 10 *CA | 10 HA | 1.55057 | 111.683 | −119.853 | 108.94 | 1.08178 |
| 183 | 10 N | 10 CA | 10 CB | 10 CG | 1.44123 | 111.683 | −161.882 | 115.978 | 1.55118 |
| 184 | 10 CG | 10 CA | 10 *CB | 10 HB1 | 1.55118 | 115.978 | 118.31 | 106.391 | 1.11438 |
| 185 | 10 CG | 10 CA | 10 *CB | 10 HB2 | 1.55118 | 115.978 | −126.021 | 110.581 | 1.11009 |
| 186 | 10 CA | 10 CB | 10 CG | 10 CD1 | 1.55057 | 115.978 | 164.138 | 110.337 | 1.54138 |
| 187 | 10 CD1 | 10 CB | 10 *CG | 10 CD2 | 1.54138 | 110.337 | 125.024 | 114.35 | 1.54198 |
| 188 | 10 CD1 | 10 CB | 10 *CG | 10 HG | 1.54138 | 110.337 | −115.943 | 107.21 | 1.11444 |
| 189 | 10 CB | 10 CG | 10 CD1 | 10 HD11 | 1.55118 | 110.337 | −176.558 | 110.296 | 1.11023 |
| 190 | 10 HD11 | 10 CG | 10 *CD1 | 10 HD12 | 1.11023 | 110.296 | 119.913 | 110.357 | 1.1105 |
| 191 | 10 HD11 | 10 CG | 10 *CD1 | 10 HD13 | 1.11023 | 110.296 | −120.002 | 110.284 | 1.11049 |
| 192 | 10 CB | 10 CG | 10 CD2 | 10 HD21 | 1.55118 | 114.35 | −176.316 | 109.986 | 1.11044 |
| 193 | 10 HD21 | 10 CG | 10 *CD2 | 10 HD22 | 1.11044 | 109.986 | 119.691 | 110.303 | 1.11063 |
| 194 | 10 HD21 | 10 CG | 10 *CD2 | 10 HD23 | 1.11044 | 109.986 | −119.439 | 111.037 | 1.10853 |
| 195 | 10 N | 10 CA | 10 C | 10 OE1 | 1.44123 | 106.26 | −65.2432 | 118.282 | 1.25984 |
| 196 | 10 OE1 | 10 CA | 10 *C | 10 OE2 | 1.25984 | 118.282 | 179.375 | 117.928 | 1.25963 |

Structural Restraint Files for AngiotensinI 1) 2D-NOESY restraints file: [for the sake of brevity, only the header is given here. The data for all 343 NOE and 383 noNOE restraints is given implicitly in the $\chi^2_{restraint}$ values file below]

| remark | 2D NOESY |
|---|---|
| remark | TRANS angiotensin1 | configuration:

| field | 600 |
|---|---|
| solvent | h2o |
| temp | 278 |
| visc | 1.54 |
| ident | 2D-NOESY |
| mix_time | 700 ms |
| endsection | |

2) Scalar coupling restraints files:

remark conformation-dependent scalar couplings for angtensinI, 5 deg C.
remark TRANS angiotensinI
configuration:

field    600

-continued

```
solvent      h2o
temp         278
visc         1.54
ident        J5DEGC
endsection
data:

coup    1   3 HA    3 CA    3 N     3 HN    7.9   -1.05  0.65  0   8.06   0.4   0
coup    2   4 HA    4 CA    4 N     4 HN    7.9   -1.05  0.65  0   7.64   0.4   0
coup    3   5 HA    5 CA    5 N     5 HN    7.9   -1.05  0.65  0   8.62   0.4   0
coup    4   6 HA    6 CA    6 N     6 HN    7.9   -1.05  0.65  0   6.37   0.4   0
coup    5   8 HA    8 CA    8 N     8 HN    7.9   -1.05  0.65  0   6.55   0.4   0
coup    6   9 HA    9 CA    9 N     9 HN    7.9   -1.05  0.65  0   7.41   0.4   0
coup    7  10 HA   10 CA   10 N    10 HN    7.9   -1.05  0.65  0   7.25   0.4   0
coup    8   3 HA    3 CA    3 N     3 HN    7.9   -1.05  0.65  0   7.94   0.4   0
coup    9   4 HA    4 CA    4 N     4 HN    7.9   -1.05  0.65  0   7.47   0.4   0
coup   10  10 HA   10 CA   10 N    10 HN    7.9   -1.05  0.65  0   7.24   0.4   0
coup   11   3 HA    3 CA    3 N     3 HN    7.9   -1.05  0.65  0   7.84   0.4   0
coup   12   4 HA    4 CA    4 N     4 HN    7.9   -1.05  0.65  0   7.43   0.4   0
coup   13  10 HA   10 CA   10 N    10 HN    7.9   -1.05  0.65  0   7.22   0.4   0
coup   14   1 HA    1 CA    1 CB    1 HB1   7.23  -1.37  2.22  0   5.32   0.5   0
coup   15   1 HA    1 CA    1 CB    1 HB2   7.23  -1.37  2.22  0   8.26   0.5   0
coup   16   1 HA    1 CA    1 CB    1 HB1   7.23  -1.37  2.22  0   4.99   0.5   0
coup   17   1 HA    1 CA    1 CB    1 HB2   7.23  -1.37  2.22  0   8.66   0.5   0
coup   18   2 HA    2 CA    2 CB    2 HB1   7.23  -1.37  2.22  0   6.85   0.5   0
coup   19   2 HA    2 CA    2 CB    2 HB2   7.23  -1.37  2.22  0   6.85   0.5   0
coup   20   3 HA    3 CA    3 CB    3 HB    7.23  -1.37  2.22  0   8.29   0.5   0
coup   21   5 HA    5 CA    5 CB    5 HB    7.23  -1.37  2.22  0   9.23   0.5   0
coup   22   6 HA    6 CA    6 CB    6 HB1   7.23  -1.37  2.22  0  19.51   1.5   0
ovlp   22   6 HA    6 CA    6 CB    6 HB2   7.23  -1.37  2.22  0  19.51   1.5   0
ovlp   22   6 HA    6 CA    6 N     6 HN    7.9   -1.05  0.65  0  19.51   1.5   0
coup   23   6 HA    6 CA    6 CB    6 HB1   7.23  -1.37  2.22  0   4.73   0.5   0
coup   23   6 HA    6 CA    6 CB    6 HB2   7.23  -1.37  2.22  0   8.13   0.5   0
coup   24   9 HA    9 CA    9 CB    9 HB1   7.23  -1.37  2.22  0  19.2    1.5   0
ovlp   24   9 HA    9 CA    9 CB    9 HB2   7.23  -1.37  2.22  0  19.2    1.5   0
ovlp   24   9 HA    9 CA    9 N     9 HN    7.9   -1.05  0.65  0  19.2    1.5   0
coup   25  10 HA   10 CA   10 CB   10 HB1   7.23  -1.37  2.22  0  20.9    1.5   0
ovlp   25  10 HA   10 CA   10 CB   10 HB2   7.23  -1.37  2.22  0  20.9    1.5   0
ovlp   25  10 HA   10 CA   10 N    10 HN    7.9   -1.05  0.65  0  20.9    1.5   0
endsection
remark conformation-dependent scalar couplings for angtensinI, 15 deg C.
remark TRANS angiotensinI
configuration:

field        600
solvent      h2o
temp         288
visc         1.54
ident        J15DEGC
endsection
data:

coup    1   3 HA    3 CA    3 N     3 HN    7.9   -1.05  0.65  0   8.12   0.4   0
coup    2   4 HA    4 CA    4 N     4 HN    7.9   -1.05  0.65  0   7.73   0.4   0
coup    3   5 HA    5 CA    5 N     5 HN    7.9   -1.05  0.65  0   8.58   0.4   0
coup    4   6 HA    6 CA    6 N     6 HN    7.9   -1.05  0.65  0   6.43   0.4   0
coup    5   8 HA    8 CA    8 N     8 HN    7.9   -1.05  0.65  0   6.63   0.4   0
coup    6   9 HA    9 CA    9 N     9 HN    7.9   -1.05  0.65  0   7.19   0.4   0
coup    7  10 HA   10 CA   10 N    10 HN    7.9   -1.05  0.65  0   7.36   0.4   0
coup    8   3 HA    3 CA    3 N     3 HN    7.9   -1.05  0.65  0   7.94   0.3   0
coup    9   5 HA    5 CA    5 N     5 HN    7.9   -1.05  0.65  0   8.52   0.3   0
endsection
remark conformation-dependent scalar couplings for angtensinI, 25° C.
remark TRANS angiotensinI
configuration:

field        600
solvent      h2o
temp         298
visc         0.88
ident        JCOUP
endsection
data:

coup    1   3 HA    3 CA    3 N     3 HN    7.9   -1.05  0.65  0   8.21   0.4   0
coup    2   4 HA    4 CA    4 N     4 HN    7.9   -1.05  0.65  0   7.96   0.4   0
coup    3   5 HA    5 CA    5 N     5 HN    7.9   -1.05  0.65  0   8.54   0.4   0
coup    4   6 HA    6 CA    6 N     6 HN    7.9   -1.05  0.65  0   6.04   0.4   0
coup    5   8 HA    8 CA    8 N     8 HN    7.9   -1.05  0.65  0   6.73   0.4   0
```

-continued

| | | | | | | | | | | | | | | |
|---|---|---|---|---|---|---|---|---|---|---|---|---|---|---|
| coup | 7 | 10 HA | 10 CA | 10 N | 10 HN | 7.9 | −1.05 | 0.65 | 0 | 7.61 | 0.4 | 0 | | |
| coup | 8 | 3 HA | 3 CA | 3 N | 3 HN | 7.9 | −1.05 | 0.65 | 0 | 7.90 | 0.4 | 0 | | |
| coup | 9 | 4 HA | 4 CA | 4 N | 4 HN | 7.9 | −1.05 | 0.65 | 0 | 7.45 | 0.4 | 0 | | |
| coup | 10 | 5 HA | 5 CA | 5 N | 5 HN | 7.9 | −1.05 | 0.65 | 0 | 8.31 | 0.4 | 0 | | |
| coup | 11 | 1 HA | 1 CA | 1 CB | 1 HB1 | 7.23 | −1.37 | 2.22 | 0 | 12.85 | 1.0 | 0 | | |
| ovlp | 11 | 1 HA | 1 CA | 1 CB | 1 HB2 | 7.23 | −1.37 | 2.22 | 0 | 12.85 | 1.0 | 0 | | |
| coup | 12 | 1 HA | 1 CA | 1 CB | 1 HB1 | 7.23 | −1.37 | 2.22 | 0 | 4.46 | 0.5 | 0 | | |
| coup | 13 | 1 HA | 1 CA | 1 CB | 1 HB2 | 7.23 | −1.37 | 2.22 | 0 | 8.38 | 0.5 | 0 | | |
| coup | 14 | 2 HA | 2 CA | 2 CB | 2 HB1 | 7.23 | −1.37 | 2.22 | 0 | 6.91 | 0.5 | 0 | | |
| coup | 15 | 2 HA | 2 CA | 2 CB | 2 HB2 | 7.23 | −1.37 | 2.22 | 0 | 6.91 | 0.5 | 0 | | |
| coup | 16 | 3 HA | 3 CA | 3 CB | 3 HB | 7.23 | −1.37 | 2.22 | 0 | 7.79 | 0.5 | 0 | | |
| coup | 17 | 5 HA | 5 CA | 5 CB | 5 HB | 7.23 | −1.37 | 2.22 | 0 | 7.89 | 0.5 | 0 | | |
| coup | 18 | 6 HA | 6 CA | 6 CB | 6 HB1 | 7.23 | −1.37 | 2.22 | 0 | 4.93 | 0.5 | 0 | | |
| coup | 19 | 6 HA | 6 CA | 6 CB | 6 HB2 | 7.23 | −1.37 | 2.22 | 0 | 8.34 | 0.5 | 0 | | |
| coup | 21 | 3 HA | 3 CA | 3 N | 3 HN | 7.9 | −1.05 | 0.65 | 0 | 7.97 | 0.5 | 0 | | |
| coup | 23 | 5 HA | 5 CA | 5 N | 5 HN | 7.9 | −1.05 | 0.65 | 0 | 8.34 | 0.5 | 0 | | |
| coup | 24 | 8 HA | 8 CA | 8 N | 8 HN | 7.9 | −1.05 | 0.65 | 0 | 6.49 | 0.5 | 0 | | |
| coup | 25 | 10 HA | 10 CA | 10 N | 10 HN | 7.9 | −1.05 | 0.65 | 0 | 7.10 | 0.5 | 0 | | |
| coup | 30 | 3 HA | 3 CA | 3 N | 3 HN | 7.9 | −1.05 | 0.65 | 0 | 8.04 | 0.4 | 0 | | |
| coup | 31 | 5 HA | 5 CA | 5 N | 5 HN | 7.9 | −1.05 | 0.65 | 0 | 8.33 | 0.4 | 0 | | |
| coup | 32 | 5 HG11 | 5 CG1 | 5 CB | 5 HB | 12.0 | −1.0 | 2.0 | 0 | 5.8 | 1.0 | 0 | | |
| coup | 33 | 5 HG12 | 5 CG1 | 5 CB | 5 HB | 12.0 | −1.0 | 2.0 | 0 | 8.0 | 0.6 | 0 | | |
| endsection | | | | | | | | | | | | | | |

3) Dihedral restraints file:

remark Angiotensin1, dihedral angle restraints
remark given twice the error value from TALOS
configuration:

| | |
|---|---|
| field | 600 |
| solvent | h2o |
| temp | 298 |
| visc | 0.88 |
| ident | TDIHEDRALS |
| endsection | |
| data: | | remark dihedral_no dihedral_atom_identifiers (x8) angle error code
remark phi

| | | | | | | | | | | | |
|---|---|---|---|---|---|---|---|---|---|---|---|
| dihe | 1 | 1 C | 2 N | 2 CA | 2 C | −85 | 26 | 0 |
| dihe | 2 | 2 C | 3 N | 3 CA | 3 C | −100 | 34 | 0 |
| dihe | 3 | 3 C | 4 N | 4 CA | 4 C | −120 | 60 | 0 |
| dihe | 4 | 4 C | 5 N | 5 CA | 5 C | −100 | 24 | 0 |
| dihe | 5 | 5 C | 6 N | 6 CA | 6 C | −93 | 46 | 0 |
| dihe | 6 | 6 C | 7 N | 7 CA | 7 C | −71 | 16 | 0 |
| dihe | 7 | 7 C | 8 N | 8 CA | 8 C | −113 | 52 | 0 |
| dihe | 8 | 8 C | 9 N | 9 CA | 9 C | −103 | 42 | 0 | remark psi

| | | | | | | | | | |
|---|---|---|---|---|---|---|---|---|---|
| dihe | 9 | 2 N | 2 CA | 2 C | 3 N | 138 | 36 | 0 |
| dihe | 10 | 3 N | 3 CA | 3 C | 4 N | 130 | 36 | 0 |
| dihe | 11 | 4 N | 4 CA | 4 C | 5 N | 120 | 14 | 0 |
| dihe | 12 | 5 N | 5 CA | 5 C | 6 N | 121 | 18 | 0 |
| dihe | 13 | 6 N | 6 CA | 6 C | 7 N | 122 | 16 | 0 |
| dihe | 14 | 7 N | 7 CA | 7 C | 8 N | 146 | 28 | 0 |
| dihe | 15 | 8 N | 8 CA | 8 C | 9 N | 129 | 36 | 0 | remark omega

| | | | | | | | | | |
|---|---|---|---|---|---|---|---|---|---|
| dihe | 17 | 3 CA | 3 C | 4 N | 4 CA | 180 | 20 | 0 |
| endsection | | | | | | | | | |

4) Hydrogen bond restraints file:

remark hydrogen bond restraints file for AngiotensinI
configuration:

| | |
|---|---|
| solvent | h2o |
| ident | HBOND |
| endsection | |
| data: | | remark atomsx3 d1 range d2 range ang percent perc_error start code

| | | | | | | | |
|---|---|---|---|---|---|---|---|
| | 2 | 3 N | 3 HN | 1 O | 2.9 0.4 2.0 0.5 110 0 10 0.0 0 | | |
| hcomb | 2 | 3 N | 3 HN | 1 OD1 | | | |
| hcomb | 2 | 3 N | 3 HN | 1 OD2 | | | |
| hcomb | 2 | 3 N | 3 HN | 2 O | | | |
| hcomb | 2 | 3 N | 3 HN | 4 O | | | |
| hcomb | 2 | 3 N | 3 HN | 4 OH | | | |
| hcomb | 2 | 3 N | 3 HN | 5 O | | | |
| hcomb | 2 | 3 N | 3 HN | 6 O | | | |
| hcomb | 2 | 3 N | 3 HN | 6 ND1 | | | |
| hcomb | 2 | 3 N | 3 HN | 6 NE2 | | | |
| hcomb | 2 | 3 N | 3 HN | 7 O | | | |
| hcomb | 2 | 3 N | 3 HN | 8 O | | | |
| hcomb | 2 | 3 N | 3 HN | 9 O | | | |
| hcomb | 2 | 3 N | 3 HN | 9 ND1 | | | |
| hcomb | 2 | 3 N | 3 HN | 9 NE2 | | | |
| hcomb | 2 | 3 N | 3 HN | 10 OE1 | | | |
| hcomb | 2 | 3 N | 3 HN | 10 OE1 | | | |
| hbond | 3 | 4 N | 4 HN | 1 O | 2.9 0.4 2.0 0.5 110 0 10 0.0 0 | | |
| hcomb | 3 | 4 N | 4 HN | 1 OD1 | | | |
| hcomb | 3 | 4 N | 4 HN | 1 OD2 | | | |
| hcomb | 3 | 4 N | 4 HN | 2 O | | | |
| hcomb | 3 | 4 N | 4 HN | 3 O | | | |

-continued

| | | | | | | | |
|---|---|---|---|---|---|---|---|
| hcomb | 3 | 4 | N | 4 | HN | 4 | OH |
| hcomb | 3 | 4 | N | 4 | HN | 5 | O |
| hcomb | 3 | 4 | N | 4 | HN | 6 | O |
| hcomb | 3 | 4 | N | 4 | HN | 6 | ND1 |
| hcomb | 3 | 4 | N | 4 | HN | 6 | NE2 |
| hcomb | 3 | 4 | N | 4 | HN | 7 | O |
| hcomb | 3 | 4 | N | 4 | HN | 8 | O |
| hcomb | 3 | 4 | N | 4 | HN | 9 | O |
| hcomb | 3 | 4 | N | 4 | HN | 9 | ND1 |
| hcomb | 3 | 4 | N | 4 | HN | 9 | NE2 |
| hcomb | 3 | 4 | N | 4 | HN | 10 | OE1 |
| hcomb | 3 | 4 | N | 4 | HN | 10 | OE1 |
| hbond | 4 | 6 | N | 6 | HN | 1 | O   2.9 0.4 2.0 0.5 110 0 10 0.0 0 |
| hcomb | 4 | 6 | N | 6 | HN | 1 | OD1 |
| hcomb | 4 | 6 | N | 6 | HN | 1 | OD2 |
| hcomb | 4 | 6 | N | 6 | HN | 2 | O |
| hcomb | 4 | 6 | N | 6 | HN | 3 | O |
| hcomb | 4 | 6 | N | 6 | HN | 4 | O |
| hcomb | 4 | 6 | N | 6 | HN | 4 | OH |
| hcomb | 4 | 6 | N | 6 | HN | 5 | O |
| hcomb | 4 | 6 | N | 6 | HN | 6 | ND1 |
| hcomb | 4 | 6 | N | 6 | HN | 6 | NE2 |
| hcomb | 4 | 6 | N | 6 | HN | 7 | O |
| hcomb | 4 | 6 | N | 6 | HN | 8 | O |
| hcomb | 4 | 6 | N | 6 | HN | 9 | O |
| hcomb | 4 | 6 | N | 6 | HN | 9 | ND1 |
| hcomb | 4 | 6 | N | 6 | HN | 9 | NE2 |
| hcomb | 4 | 6 | N | 6 | HN | 10 | OE1 |
| hcomb | 4 | 6 | N | 6 | HN | 10 | OE1 |
| hbond | 5 | 8 | N | 8 | HN | 1 | O   2.9 0.4 2.0 0.5 110 0 10 0.0 0 |
| hcomb | 5 | 8 | N | 8 | HN | 1 | OD1 |
| hcomb | 5 | 8 | N | 8 | HN | 1 | OD2 |
| hcomb | 5 | 8 | N | 8 | HN | 2 | O |
| hcomb | 5 | 8 | N | 8 | HN | 3 | O |
| hcomb | 5 | 8 | N | 8 | HN | 4 | O |
| hcomb | 5 | 8 | N | 8 | HN | 4 | OH |
| hcomb | 5 | 8 | N | 8 | HN | 5 | O |
| hcomb | 5 | 8 | N | 8 | HN | 6 | O |
| hcomb | 5 | 8 | N | 8 | HN | 6 | ND1 |
| hcomb | 5 | 8 | N | 8 | HN | 6 | NE2 |
| hcomb | 5 | 8 | N | 8 | HN | 7 | O |
| hcomb | 5 | 8 | N | 8 | HN | 9 | O |
| hcomb | 5 | 8 | N | 8 | HN | 9 | ND1 |
| hcomb | 5 | 8 | N | 8 | HN | 9 | NE2 |
| hcomb | 5 | 8 | N | 8 | HN | 10 | OE1 |
| hcomb | 5 | 8 | N | 8 | HN | 10 | OE1 |
| hbond | 6 | 10 | N | 10 | HN | 1 | O   2.9 0.4 2.0 0.5 110 0 20 0.0 0 |
| hcomb | 6 | 10 | N | 10 | HN | 1 | OD1 |
| hcomb | 6 | 10 | N | 10 | HN | 1 | OD2 |
| hcomb | 6 | 10 | N | 10 | HN | 2 | O |
| hcomb | 6 | 10 | N | 10 | HN | 3 | O |
| hcomb | 6 | 10 | N | 10 | HN | 4 | O |
| hcomb | 6 | 10 | N | 10 | HN | 4 | OH |
| hcomb | 6 | 10 | N | 10 | HN | 5 | O |
| hcomb | 6 | 10 | N | 10 | HN | 6 | O |
| hcomb | 6 | 10 | N | 10 | HN | 6 | ND1 |
| hcomb | 6 | 10 | N | 10 | HN | 6 | NE2 |
| hcomb | 6 | 10 | N | 10 | HN | 7 | O |
| hcomb | 6 | 10 | N | 10 | HN | 8 | O |
| hcomb | 6 | 10 | N | 10 | HN | 9 | O |
| hcomb | 6 | 10 | N | 10 | HN | 9 | ND1 |
| hcomb | 6 | 10 | N | 10 | HN | 9 | NE2 |
| endsection | | | | | | | |

$\chi^2_{restraint}$ Values for the Best Optimised Dynamic Structure of AngiotensinI

| 5 | 8 | | N | 8 | HN | 1 | O | 0.00 | 10.00 | 0.00 | 0.00 | 0.0 | 0 | 16 | HBOND |
|---|---|---|---|---|---|---|---|---|---|---|---|---|---|---|---|
| 17 | 3D | | 3 | CA | 3D | 4 | CA | 180.00 | 20.00 | 180.00 | 0.00 | 0.0 | 0 | 0 | TDIHEDRALS |
| 1147 | D1 | | 1 | HB1 | L10 | 10 | HD11 | 0.00 | 94.00 | 0.00 | 0.00 | 0.0 | 0 | 2 | 2D-NOESY |
| 1148 | D1 | | 1 | HB1 | L10 | 10 | HD21 | 0.00 | 77.00 | 0.00 | 0.00 | 0.0 | 0 | 2 | 2D-NOESY |
| 540 | H9 | | 9 | HA | D1 | 1 | HB1 | 0.00 | 99.00 | 0.01 | 0.00 | 0.0 | 5 | 0 | 2D-NOESY |
| 541 | H9 | | 9 | HD2 | D1 | 1 | HB1 | 0.00 | 76.00 | 0.00 | 0.00 | 0.0 | 0 | 0 | 2D-NOESY |
| 521 | H9 | | 9 | HB2 | D1 | 1 | HA | 0.00 | 81.00 | 0.01 | 0.00 | 0.0 | 5 | 0 | 2D-NOESY |
| 567 | H9 | | 9 | HD2 | D1 | 1 | HB2 | 0.00 | 53.00 | 0.00 | 0.00 | 0.0 | 0 | 0 | 2D-NOESY |
| 545 | L10 | | 10 | HN | D1 | 1 | HB1 | 0.00 | 18.00 | 0.00 | 0.00 | 0.0 | 5 | 0 | 2D-NOESY |

-continued

| | | | | | | | | | | | | |
|---|---|---|---|---|---|---|---|---|---|---|---|---|
| 1057 | D1 | 1 | HB2 | H9 | 9 | HD2 | 0.00 | 40.00 | 0.00 | 0.00 | 0.0 | 0 | 0 | 2D-NOESY |
| 570 | L10 | 10 | HA | D1 | 1 | HB2 | 0.00 | 22.00 | 0.00 | 0.00 | 0.0 | 5 | 0 | 2D-NOESY |
| 1056 | D1 | 1 | HB1 | H9 | 9 | HD2 | 0.00 | 33.00 | 0.00 | 0.00 | 0.0 | 0 | 0 | 2D-NOESY |
| 1050 | R2 | 2 | HB1 | H9 | 9 | HA | 0.00 | 66.00 | 0.01 | 0.00 | 0.0 | 5 | 1 | 2D-NOESY |
| 566 | H9 | 9 | HA | D1 | 1 | HB2 | 0.00 | 29.00 | 0.01 | 0.00 | 0.0 | 5 | 0 | 2D-NOESY |
| 1052 | R2 | 2 | HB1 | H9 | 9 | HB2 | 0.00 | 31.00 | 0.01 | 0.00 | 0.0 | 5 | 1 | 2D-NOESY |
| 522 | H9 | 9 | HD2 | D1 | 1 | HA | 0.00 | 48.00 | 0.01 | 0.00 | 0.0 | 0 | 0 | 2D-NOESY |
| 641 | L10 | 10 | HA | R2 | 2 | HG1 | 0.00 | 21.00 | 0.01 | 0.00 | 0.0 | 2 | 1 | 2D-NOESY |
| 1108 | R2 | 2 | HA | H9 | 9 | HN | 0.00 | 7.50 | 0.00 | 0.00 | 0.0 | 1 | 0 | 2D-NOESY |
| 721 | L10 | 10 | HB1 | V3 | 3 | HN | 0.00 | 2.70 | 0.00 | 0.00 | 0.0 | 1 | 2 | 2D-NOESY |
| 1128 | D1 | 1 | HB2 | L10 | 10 | HB1 | 0.00 | 17.00 | 0.00 | 0.00 | 0.0 | 5 | 2 | 2D-NOESY |
| 717 | H9 | 9 | HA | V3 | 3 | HN | 0.00 | 4.10 | 0.00 | 0.00 | 0.0 | 1 | 0 | 2D-NOESY |
| 830 | L10 | 10 | HA | I5 | 5 | HG12 | 0.00 | 420.00 | 0.11 | 0.00 | 0.0 | 5 | 0 | 2D-NOESY |
| 523 | L10 | 10 | HB1 | D1 | 1 | HA | 0.00 | 36.00 | 0.01 | 0.00 | 0.0 | 5 | 2 | 2D-NOESY |
| 543 | L10 | 10 | HA | D1 | 1 | HB1 | 0.00 | 11.00 | 0.00 | 0.00 | 0.0 | 5 | 0 | 2D-NOESY |
| 568 | H9 | 9 | HE1 | D1 | 1 | HB2 | 0.00 | 21.00 | 0.01 | 0.00 | 0.0 | 0 | 0 | 2D-NOESY |
| 1129 | R2 | 2 | HA | L10 | 10 | HB1 | 0.00 | 25.00 | 0.01 | 0.00 | 0.0 | 0 | 2 | 2D-NOESY |
| 1119 | R2 | 2 | HG1 | L10 | 10 | HA | 0.00 | 14.00 | 0.01 | 0.00 | 0.0 | 2 | 1 | 2D-NOESY |
| 1049 | D1 | 1 | HA | H9 | 9 | HA | 0.00 | 31.00 | 0.01 | 0.00 | 0.0 | 5 | 0 | 2D-NOESY |
| 544 | L10 | 10 | HB1 | D1 | 1 | HB1 | 0.00 | 11.00 | 0.00 | 0.00 | 0.0 | 5 | 2 | 2D-NOESY |
| 542 | H9 | 9 | HE1 | D1 | 1 | HB1 | 0.00 | 17.00 | 0.01 | 0.00 | 0.0 | 0 | 0 | 2D-NOESY |
| 572 | L10 | 10 | HN | D1 | 1 | HB2 | 0.00 | 4.40 | 0.00 | 0.00 | 0.0 | 5 | 0 | 2D-NOESY |
| 642 | L10 | 10 | HN | R2 | 2 | HG1 | 0.00 | 9.30 | 0.00 | 0.00 | 0.0 | 2 | 1 | 2D-NOESY |
| 1105 | D1 | 1 | HA | H9 | 9 | HN | 0.00 | 3.70 | 0.00 | 0.00 | 0.0 | 1 | 0 | 2D-NOESY |
| 1015 | D1 | 1 | HA | F8 | 8 | HN | 0.00 | 21.00 | 0.01 | 0.00 | 0.0 | 1 | 0 | 2D-NOESY |
| 686 | L10 | 10 | HB1 | V3 | 3 | HG21 | 0.00 | 81.00 | 0.04 | 0.00 | 0.0 | 5 | 8 | 2D-NOESY |
| 561 | F8 | 8 | HA | D1 | 1 | HB2 | 0.00 | 29.00 | 0.01 | 0.00 | 0.0 | 5 | 0 | 2D-NOESY |
| 1055 | D1 | 1 | HA | H9 | 9 | HD2 | 0.00 | 22.00 | 0.01 | 0.00 | 0.0 | 0 | 0 | 2D-NOESY |
| 569 | H9 | 9 | HN | D1 | 1 | HB2 | 0.00 | 14.00 | 0.01 | 0.00 | 0.0 | 5 | 0 | 2D-NOESY |
| 718 | H9 | 9 | HB1 | V3 | 3 | HN | 0.00 | 2.50 | 0.00 | 0.00 | 0.0 | 1 | 1 | 2D-NOESY |
| 639 | H9 | 9 | HE1 | R2 | 2 | HG1 | 0.00 | 52.00 | 0.02 | 0.00 | 0.0 | 0 | 1 | 2D-NOESY |
| 1109 | R2 | 2 | HG1 | H9 | 9 | HN | 0.00 | 3.80 | 0.00 | 0.00 | 0.0 | 1 | 1 | 2D-NOESY |
| 571 | L10 | 10 | HB1 | D1 | 1 | HB2 | 0.00 | 8.80 | 0.00 | 0.00 | 0.0 | 5 | 2 | 2D-NOESY |
| 640 | H9 | 9 | HN | R2 | 2 | HG1 | 0.00 | 34.00 | 0.02 | 0.00 | 0.0 | 2 | 1 | 2D-NOESY |
| 713 | F8 | 8 | HD1 | V3 | 3 | HN | 0.00 | 16.00 | 0.01 | 0.00 | 0.0 | 0 | 1 | 2D-NOESY |
| 1120 | V3 | 3 | HN | L10 | 10 | HA | 0.00 | 15.00 | 0.01 | 0.00 | 0.0 | 5 | 0 | 2D-NOESY |
| 519 | F8 | 8 | HB1 | D1 | 1 | HA | 0.00 | 91.00 | 0.05 | 0.00 | 0.0 | 5 | 1 | 2D-NOESY |
| 536 | F8 | 8 | HD1 | D1 | 1 | HB1 | 0.00 | 76.00 | 0.04 | 0.00 | 0.0 | 0 | 1 | 2D-NOESY |
| 537 | F8 | 8 | HE2 | D1 | 1 | HB1 | 0.00 | 60.00 | 0.03 | 0.00 | 0.0 | 0 | 0 | 2D-NOESY |
| 1059 | R2 | 2 | HG1 | H9 | 9 | HD2 | 0.00 | 21.00 | 0.01 | 0.00 | 0.0 | 0 | 1 | 2D-NOESY |
| 1130 | V3 | 3 | HB | L10 | 10 | HB1 | 0.00 | 23.00 | 0.02 | 0.00 | 0.0 | 0 | 2 | 2D-NOESY |
| 562 | F8 | 8 | HD1 | D1 | 1 | HB2 | 0.00 | 63.00 | 0.04 | 0.00 | 0.0 | 0 | 1 | 2D-NOESY |
| 716 | F8 | 8 | HZ | V3 | 3 | HN | 0.00 | 9.80 | 0.01 | 0.00 | 0.0 | 0 | 0 | 2D-NOESY |
| 637 | H9 | 9 | HA | R2 | 2 | HG1 | 0.00 | 19.00 | 0.01 | 0.00 | 0.0 | 2 | 1 | 2D-NOESY |
| 708 | P7 | 7 | HB2 | V3 | 3 | HN | 0.00 | 11.00 | 0.01 | 0.00 | 0.0 | 1 | 0 | 2D-NOESY |
| 812 | L10 | 10 | HA | I5 | 5 | HG11 | 0.00 | 140.00 | 0.10 | 0.00 | 0.0 | 5 | 0 | 2D-NOESY |
| 539 | F8 | 8 | HZ | D1 | 1 | HB1 | 0.00 | 60.00 | 0.04 | 0.00 | 0.0 | 0 | 0 | 2D-NOESY |
| 711 | F8 | 8 | HA | V3 | 3 | HN | 0.00 | 4.10 | 0.00 | 0.00 | 0.0 | 1 | 0 | 2D-NOESY |
| 1131 | V3 | 3 | HN | L10 | 10 | HB1 | 0.00 | 15.00 | 0.01 | 0.00 | 0.0 | 0 | 2 | 2D-NOESY |
| 1016 | D1 | 1 | HB1 | F8 | 8 | HN | 0.00 | 5.30 | 0.00 | 0.00 | 0.0 | 1 | 0 | 2D-NOESY |
| 988 | D1 | 1 | HB1 | F8 | 8 | HD1 | 0.00 | 48.00 | 0.04 | 0.00 | 0.0 | 0 | 1 | 2D-NOESY |
| 1017 | D1 | 1 | HB2 | F8 | 8 | HN | 0.00 | 4.30 | 0.00 | 0.00 | 0.0 | 1 | 0 | 2D-NOESY |
| 538 | F8 | 8 | HN | D1 | 1 | HB1 | 0.00 | 19.00 | 0.02 | 0.00 | 0.0 | 5 | 0 | 2D-NOESY |
| 1062 | V3 | 3 | HN | H9 | 9 | HD2 | 0.00 | 19.00 | 0.02 | 0.00 | 0.0 | 0 | 0 | 2D-NOESY |
| 1136 | I5 | 5 | HG12 | L10 | 10 | HB1 | 0.00 | 85.00 | 0.10 | 0.00 | 0.0 | 0 | 2 | 2D-NOESY |
| 565 | F8 | 8 | HZ | D1 | 1 | HB2 | 0.00 | 42.00 | 0.04 | 0.00 | 0.0 | 0 | 0 | 2D-NOESY |
| 813 | L10 | 10 | HB1 | I5 | 5 | HG11 | 0.00 | 78.00 | 0.09 | 0.00 | 0.0 | 5 | 2 | 2D-NOESY |
| 563 | F8 | 8 | HE1 | D1 | 1 | HB2 | 0.00 | 60.00 | 0.06 | 0.00 | 0.0 | 0 | 1 | 2D-NOESY |
| 564 | F8 | 8 | HN | D1 | 1 | HB1 | 0.00 | 15.00 | 0.02 | 0.00 | 0.0 | 5 | 0 | 2D-NOESY |
| 973 | D1 | 1 | HB2 | F8 | 8 | HA | 0.00 | 10.00 | 0.01 | 0.00 | 0.0 | 5 | 0 | 2D-NOESY |
| 1001 | D1 | 1 | HB1 | F8 | 8 | HE1 | 0.00 | 52.00 | 0.07 | 0.00 | 0.0 | 0 | 1 | 2D-NOESY |
| 968 | D1 | 1 | HB2 | P7 | 7 | HD2 | 0.00 | 42.00 | 0.06 | 0.00 | 0.0 | 5 | 0 | 2D-NOESY |
| 714 | F8 | 8 | HE1 | V3 | 3 | HN | 0.00 | 9.80 | 0.01 | 0.00 | 0.0 | 0 | 1 | 2D-NOESY |
| 956 | D1 | 1 | HB1 | P7 | 7 | HD1 | 0.00 | 53.00 | 0.07 | 0.00 | 0.0 | 5 | 0 | 2D-NOESY |
| 638 | H9 | 9 | HD2 | R2 | 2 | HG1 | 0.00 | 9.60 | 0.01 | 0.00 | 0.0 | 0 | 1 | 2D-NOESY |
| 560 | P7 | 7 | HD2 | D1 | 1 | HB2 | 0.00 | 40.00 | 0.06 | 0.00 | 0.0 | 5 | 0 | 2D-NOESY |
| 1058 | R2 | 2 | HB1 | H9 | 9 | HD2 | 0.00 | 8.00 | 0.01 | 0.00 | 0.0 | 0 | 1 | 2D-NOESY |
| 923 | D1 | 1 | HB1 | P7 | 7 | HB1 | 0.00 | 21.00 | 0.03 | 0.00 | 0.0 | 5 | 0 | 2D-NOESY |
| 648 | L10 | 10 | HB1 | V3 | 3 | HA | 0.00 | 8.60 | 0.02 | 0.00 | 0.0 | 5 | 2 | 2D-NOESY |
| 687 | L10 | 10 | HN | V3 | 3 | HG21 | 0.00 | 16.00 | 0.03 | 0.00 | 0.0 | 5 | 2 | 2D-NOESY |
| 679 | F8 | 8 | HB1 | V3 | 3 | HG21 | 0.00 | 36.00 | 0.06 | 0.00 | 0.0 | 5 | 0 | 2D-NOESY |
| 712 | F8 | 8 | HB1 | V3 | 3 | HG21 | 0.00 | 2.70 | 0.00 | 0.00 | 0.0 | 1 | 1 | 2D-NOESY |
| 632 | F8 | 8 | HB1 | V3 | 3 | HN | 0.00 | 23.00 | 0.04 | 0.00 | 0.0 | 2 | 3 | 2D-NOESY |
| 985 | R2 | 2 | HB1 | F8 | 8 | HB1 | 0.00 | 22.00 | 0.04 | 0.00 | 0.0 | 5 | 3 | 2D-NOESY |
| 974 | R2 | 2 | HB1 | F8 | 8 | HA | 0.00 | 16.00 | 0.03 | 0.00 | 0.0 | 5 | 1 | 2D-NOESY |
| 978 | V3 | 3 | HN | F8 | 8 | HA | 0.00 | 32.00 | 0.07 | 0.00 | 0.0 | 5 | 0 | 2D-NOESY |
| 990 | R2 | 2 | HG1 | F8 | 8 | HD1 | 0.00 | 32.00 | 0.07 | 0.00 | 0.0 | 0 | 3 | 2D-NOESY |
| 636 | F8 | 8 | HZ | R2 | 2 | HG1 | 0.00 | 19.00 | 0.04 | 0.00 | 0.0 | 0 | 1 | 2D-NOESY |
| 520 | F8 | 8 | HE1 | D1 | 1 | HA | 0.00 | 48.00 | 0.11 | 0.00 | 0.0 | 0 | 1 | 2D-NOESY |

-continued

| | | | | | | | | | | | | |
|---|---|---|---|---|---|---|---|---|---|---|---|---|
| 986 | R2 | 2 | HG1 | F8 | 8 | HB1 | 0.00 | 18.00 | 0.04 | 0.00 | 0.0 | 2 | 3 2D-NOESY |
| 513 | H6 | 6 | HB1 | D1 | 1 | HA | 0.00 | 81.00 | 0.20 | 0.00 | 0.0 | 5 | 0 2D-NOESY |
| 1000 | D1 | 1 | HA | F8 | 8 | HE1 | 0.00 | 47.00 | 0.11 | 0.00 | 0.0 | 0 | 1 2D-NOESY |
| 1110 | V3 | 3 | HG11 | H9 | 9 | HN | 0.00 | 4.10 | 0.01 | 0.00 | 0.0 | 0 | 2 2D-NOESY |
| 1135 | Y4 | 4 | HN | L10 | 10 | HB1 | 0.00 | 8.60 | 0.02 | 0.00 | 0.0 | 5 | 2 2D-NOESY |
| 987 | D1 | 1 | HA | F8 | 8 | HD1 | 0.00 | 31.00 | 0.08 | 0.00 | 0.0 | 0 | 1 2D-NOESY |
| 957 | D1 | 1 | HB2 | P7 | 7 | HD1 | 0.00 | 30.00 | 0.07 | 0.00 | 0.0 | 5 | 0 2D-NOESY |
| 831 | L10 | 10 | HB1 | I5 | 5 | HG12 | 0.00 | 31.00 | 0.10 | 0.00 | 0.0 | 5 | 2 2D-NOESY |
| 684 | H9 | 9 | HB2 | V3 | 3 | HG21 | 0.00 | 16.00 | 0.05 | 0.00 | 0.0 | 5 | 2 2D-NOESY |
| 535 | P7 | 7 | HG1 | D1 | 1 | HB1 | 0.00 | 23.00 | 0.07 | 0.00 | 0.0 | 5 | 1 2D-NOESY |
| 1063 | Y4 | 4 | HN | H9 | 9 | HD2 | 0.00 | 23.00 | 0.06 | 0.00 | 0.0 | 0 | 0 2D-NOESY |
| 683 | H9 | 9 | HB1 | V3 | 3 | HG21 | 0.00 | 19.00 | 0.05 | 0.00 | 0.0 | 5 | 2 2D-NOESY |
| 922 | D1 | 1 | HB2 | P7 | 7 | HA | 0.00 | 22.00 | 0.07 | 0.00 | 0.0 | 5 | 0 2D-NOESY |
| 1018 | R2 | 2 | HG1 | F8 | 8 | HN | 0.00 | 4.60 | 0.02 | 0.00 | 0.0 | 1 | 1 2D-NOESY |
| 627 | P7 | 7 | HB1 | R2 | 2 | HG1 | 0.00 | 40.00 | 0.16 | 0.00 | 0.0 | 2 | 1 2D-NOESY |
| 516 | P7 | 7 | HB1 | D1 | 1 | HA | 0.00 | 16.00 | 0.07 | 0.00 | 0.0 | 5 | 0 2D-NOESY |
| 532 | H6 | 6 | HA | D1 | 1 | HB1 | 0.00 | 25.00 | 0.11 | 0.00 | 0.0 | 5 | 0 2D-NOESY |
| 1060 | V3 | 3 | HA | H9 | 9 | HD2 | 0.00 | 9.10 | 0.03 | 0.00 | 0.0 | 0 | 0 2D-NOESY |
| 705 | H6 | 6 | HE1 | V3 | 3 | HN | 0.00 | 21.00 | 0.07 | 0.00 | 0.0 | 1 | 0 2D-NOESY |
| 619 | I5 | 5 | HG12 | R2 | 2 | HG1 | 0.00 | 270.00 | 1.30 | 0.00 | 0.0 | 2 | 1 2D-NOESY |
| 873 | D1 | 1 | HB1 | H6 | 6 | HA | 0.00 | 22.00 | 0.11 | 0.00 | 0.0 | 5 | 0 2D-NOESY |
| 631 | F8 | 8 | HA | R2 | 2 | HG1 | 0.00 | 6.90 | 0.04 | 0.00 | 0.0 | 2 | 1 2D-NOESY |
| 1061 | V3 | 3 | HG21 | H9 | 9 | HD2 | 0.00 | 21.00 | 0.09 | 0.00 | 0.0 | 0 | 2 2D-NOESY |
| 533 | H6 | 6 | HE1 | D1 | 1 | HB1 | 0.00 | 23.00 | 0.11 | 0.00 | 0.0 | 4 | 0 2D-NOESY |
| 855 | L10 | 10 | HN | I5 | 5 | HD1 | 0.00 | 38.00 | 0.20 | 0.00 | 0.0 | 5 | 2 2D-NOESY |
| 926 | V3 | 3 | HG11 | P7 | 7 | HB1 | 0.00 | 180.00 | 0.93 | 0.00 | 0.0 | 5 | 2 2D-NOESY |
| 1121 | Y4 | 4 | HD1 | L10 | 10 | HA | 0.00 | 24.00 | 0.11 | 0.00 | 0.0 | 5 | 1 2D-NOESY |
| 647 | F8 | 8 | HZ | V3 | 3 | HA | 0.00 | 23.00 | 0.13 | 0.00 | 0.0 | 0 | 0 2D-NOESY |
| 685 | H9 | 9 | HD2 | V3 | 3 | HG21 | 0.00 | 19.00 | 0.09 | 0.00 | 0.0 | 0 | 2 2D-NOESY |
| 810 | H9 | 9 | HB1 | I5 | 5 | HG11 | 0.00 | 14.00 | 0.08 | 0.00 | 0.0 | 5 | 0 2D-NOESY |
| 815 | L10 | 10 | HN | I5 | 5 | HG11 | 0.00 | 8.30 | 0.05 | 0.00 | 0.0 | 5 | 0 2D-NOESY |
| 557 | H6 | 6 | HD2 | D1 | 1 | HB2 | 0.00 | 53.00 | 0.27 | 0.00 | 0.0 | 0 | 0 2D-NOESY |
| 727 | L10 | 10 | HB1 | Y4 | 4 | HB1 | 0.00 | 14.00 | 0.09 | 0.00 | 0.0 | 5 | 5 2D-NOESY |
| 556 | H6 | 6 | HA | D1 | 1 | HB2 | 0.00 | 16.00 | 0.10 | 0.00 | 0.0 | 5 | 0 2D-NOESY |
| 1003 | V3 | 3 | HA | F8 | 8 | HE1 | 0.00 | 70.00 | 0.35 | 0.00 | 0.0 | 0 | 1 2D-NOESY |
| 1132 | Y4 | 4 | HB1 | L10 | 10 | HB1 | 0.00 | 14.00 | 0.09 | 0.00 | 0.0 | 5 | 5 2D-NOESY |
| 1002 | R2 | 2 | HG1 | F8 | 8 | HE1 | 0.00 | 21.00 | 0.11 | 0.00 | 0.0 | 0 | 3 2D-NOESY |
| 635 | F8 | 8 | HN | R2 | 2 | HG1 | 0.00 | 11.00 | 0.07 | 0.00 | 0.0 | 2 | 1 2D-NOESY |
| 927 | V3 | 3 | HG21 | P7 | 7 | HB1 | 0.00 | 180.00 | 1.20 | 0.00 | 0.0 | 5 | 2 2D-NOESY |
| 633 | F8 | 8 | HD1 | R2 | 2 | HG1 | 0.00 | 10.00 | 0.07 | 0.00 | 0.0 | 0 | 3 2D-NOESY |
| 1123 | I5 | 5 | HG11 | L10 | 10 | HA | 0.00 | 15.00 | 0.10 | 0.00 | 0.0 | 5 | 0 2D-NOESY |
| 1122 | I5 | 5 | HB | L10 | 10 | HA | 0.00 | 18.00 | 0.13 | 0.00 | 0.0 | 5 | 0 2D-NOESY |
| 833 | L10 | 10 | HN | I5 | 5 | HG12 | 0.00 | 7.50 | 0.06 | 0.00 | 0.0 | 5 | 0 2D-NOESY |
| 872 | D1 | 1 | HA | H6 | 6 | HA | 0.00 | 42.00 | 0.30 | 0.00 | 0.0 | 5 | 0 2D-NOESY |
| 518 | P7 | 7 | HG1 | D1 | 1 | HA | 0.00 | 23.00 | 0.17 | 0.00 | 0.0 | 5 | 1 2D-NOESY |
| 558 | H6 | 6 | HE1 | D1 | 1 | HB2 | 0.00 | 15.00 | 0.10 | 0.00 | 0.0 | 4 | 0 2D-NOESY |
| 634 | F8 | 8 | HE1 | R2 | 2 | HG1 | 0.00 | 19.00 | 0.11 | 0.00 | 0.0 | 0 | 3 2D-NOESY |
| 994 | V3 | 3 | HN | F8 | 8 | HD1 | 0.00 | 22.00 | 0.18 | 0.00 | 0.0 | 0 | 1 2D-NOESY |
| 975 | R2 | 2 | HG1 | F8 | 8 | HA | 0.00 | 4.30 | 0.04 | 0.00 | 0.0 | 2 | 1 2D-NOESY |
| 844 | L10 | 10 | HN | I5 | 5 | HG21 | 0.00 | 30.00 | 0.25 | 0.00 | 0.0 | 5 | 2 2D-NOESY |
| 991 | V3 | 3 | HA | F8 | 8 | HD1 | 0.00 | 22.00 | 0.19 | 0.00 | 0.0 | 0 | 1 2D-NOESY |
| 739 | L10 | 10 | HA | Y4 | 4 | HE1 | 0.00 | 25.00 | 0.21 | 0.00 | 0.0 | 5 | 1 2D-NOESY |
| 897 | D1 | 1 | HB2 | H6 | 6 | HD2 | 0.00 | 38.00 | 0.27 | 0.00 | 0.0 | 4 | 0 2D-NOESY |
| 989 | R2 | 2 | HB1 | F8 | 8 | HD1 | 0.00 | 7.00 | 0.07 | 0.00 | 0.0 | 0 | 3 2D-NOESY |
| 827 | F8 | 8 | HA | I5 | 5 | HG12 | 0.00 | 110.00 | 1.10 | 0.00 | 0.0 | 5 | 0 2D-NOESY |
| 1053 | I5 | 5 | HG12 | H9 | 9 | HB1 | 0.00 | 16.00 | 0.17 | 0.00 | 0.0 | 5 | 1 2D-NOESY |
| 1066 | I5 | 5 | HG11 | H9 | 9 | HD2 | 0.00 | 21.00 | 0.21 | 0.00 | 0.0 | 0 | 0 2D-NOESY |
| 829 | H9 | 9 | HB1 | I5 | 5 | HG12 | 0.00 | 15.00 | 0.17 | 0.00 | 0.0 | 5 | 1 2D-NOESY |
| 976 | V3 | 3 | HG11 | F8 | 8 | HA | 0.00 | 19.00 | 0.22 | 0.00 | 0.0 | 5 | 2 2D-NOESY |
| 732 | L10 | 10 | HB1 | Y4 | 4 | HD1 | 0.00 | 20.00 | 0.20 | 0.00 | 0.0 | 5 | 5 2D-NOESY |
| 816 | D1 | 1 | HB1 | I5 | 5 | HG12 | 0.00 | 75.00 | 0.79 | 0.00 | 0.0 | 5 | 0 2D-NOESY |
| 821 | V3 | 3 | HG11 | I5 | 5 | HG12 | 0.00 | 2900.00 | 33.00 | 0.00 | 0.0 | 5 | 2 2D-NOESY |
| 1125 | H6 | 6 | HN | L10 | 10 | HA | 0.00 | 17.00 | 0.20 | 0.00 | 0.0 | 5 | 0 2D-NOESY |
| 3 | 4 | | N 4 | | | HN 1 O | 0.00 | 10.00 | 0.03 | 0.00 | 0.0 | 0 | 16 HBOND |
| 707 | P7 | 7 | HB1 | V3 | 3 | HN | 0.00 | 0.95 | 0.01 | 0.00 | 0.0 | 1 | 0 2D-NOESY |
| 1124 | I5 | 5 | HG12 | L10 | 10 | HA | 0.00 | 8.60 | 0.11 | 0.00 | 0.0 | 5 | 0 2D-NOESY |
| 835 | D1 | 1 | HB1 | I5 | 5 | HG21 | 0.00 | 86.00 | 0.99 | 0.00 | 0.0 | 5 | 2 2D-NOESY |
| 924 | R2 | 2 | HD1 | P7 | 7 | HB1 | 0.00 | 47.00 | 0.34 | 0.00 | 0.0 | 2 | 1 2D-NOESY |
| 798 | R2 | 2 | HG1 | I5 | 5 | HG11 | 0.00 | 110.00 | 1.50 | 0.00 | 0.0 | 2 | 1 2D-NOESY |
| 667 | P7 | 7 | HB2 | V3 | 3 | HG11 | 0.00 | 48.00 | 0.60 | 0.00 | 0.0 | 5 | 2 2D-NOESY |
| 1004 | V3 | 3 | HG21 | F8 | 8 | HE1 | 0.00 | 120.00 | 1.50 | 0.00 | 0.0 | 0 | 5 2D-NOESY |
| 822 | V3 | 3 | HG21 | I5 | 5 | HG12 | 0.00 | 2900.00 | 39.00 | 0.00 | 0.0 | 5 | 2 2D-NOESY |
| 517 | P7 | 7 | HD2 | D1 | 1 | HA | 0.00 | 12.00 | 0.17 | 0.00 | 0.0 | 5 | 0 2D-NOESY |
| 887 | L10 | 10 | HA | H6 | 6 | HA | 0.00 | 22.00 | 0.32 | 0.00 | 0.0 | 5 | 0 2D-NOESY |
| 874 | D1 | 1 | HB2 | H6 | 6 | HA | 0.00 | 6.70 | 0.10 | 0.00 | 0.0 | 5 | 0 2D-NOESY |
| 527 | Y4 | 4 | HA | D1 | 1 | HB1 | 0.00 | 84.00 | 1.20 | 0.00 | 0.0 | 5 | 0 2D-NOESY |
| 925 | R2 | 2 | HG1 | P7 | 7 | HB1 | 0.00 | 11.00 | 0.16 | 0.00 | 0.0 | 2 | 1 2D-NOESY |
| 702 | H6 | 6 | HB1 | V3 | 3 | HN | 0.00 | 3.00 | 0.05 | 0.00 | 0.0 | 1 | 0 2D-NOESY |
| 928 | V3 | 3 | HN | P7 | 7 | HB1 | 0.00 | 17.00 | 0.27 | 0.00 | 0.0 | 5 | 0 2D-NOESY |

-continued

| | | | | | | | | | | | | |
|---|---|---|---|---|---|---|---|---|---|---|---|---|
| 514 | H | 6 | HD2 | D1 | 1 | HA | 0.00 | 48.00 | 0.82 | 0.00 | 0.0 | 4 | 0 | 2D-NOESY |
| 1152 | P7 | 7 | HB2 | L10 | 10 | HD21 | 0.00 | 180.00 | 3.30 | 0.00 | 0.0 | 0 | 2 | 2D-NOESY |
| 1067 | I5 | 5 | HG12 | H9 | 9 | HD2 | 0.00 | 12.00 | 0.21 | 0.00 | 0.0 | 0 | 0 | 2D-NOESY |
| 811 | H9 | 9 | HD2 | I5 | 5 | HG11 | 0.00 | 12.00 | 0.21 | 0.00 | 0.0 | 0 | 0 | 2D-NOESY |
| 515 | H6 | 6 | HE1 | D1 | 1 | HA | 0.00 | 20.00 | 0.36 | 0.00 | 0.0 | 4 | 0 | 2D-NOESY |
| 741 | L10 | 10 | HN | Y4 | 4 | HE1 | 0.00 | 26.00 | 0.44 | 0.00 | 0.0 | 5 | 1 | 2D-NOESY |
| 534 | H6 | 6 | HN | D1 | 1 | HB1 | 0.00 | 19.00 | 0.40 | 0.00 | 0.0 | 5 | 0 | 2D-NOESY |
| 820 | R2 | 2 | HG1 | I5 | 5 | HG12 | 0.00 | 60.00 | 1.30 | 0.00 | 0.0 | 2 | 1 | 2D-NOESY |
| 703 | H6 | 6 | HB2 | V3 | 3 | HN | 0.00 | 2.70 | 0.06 | 0.00 | 0.0 | 1 | 0 | 2D-NOESY |
| 1133 | Y4 | 4 | HD1 | L10 | 10 | HB1 | 0.00 | 9.90 | 0.20 | 0.00 | 0.0 | 5 | 5 | 2D-NOESY |
| 806 | F8 | 8 | HA | I5 | 5 | HG11 | 0.00 | 45.00 | 1.00 | 0.00 | 0.0 | 5 | 0 | 2D-NOESY |
| 802 | H6 | 6 | HE1 | I5 | 5 | HG11 | 0.00 | 120.00 | 2.70 | 0.00 | 0.0 | 4 | 0 | 2D-NOESY |
| 901 | L10 | 10 | HN | H6 | 6 | HD2 | 0.00 | 34.00 | 0.69 | 0.00 | 0.0 | 4 | 0 | 2D-NOESY |
| 559 | H6 | 6 | HN | D1 | 1 | HB2 | 0.00 | 15.00 | 0.35 | 0.00 | 0.0 | 5 | 0 | 2D-NOESY |
| 704 | H6 | 6 | HD2 | V3 | 3 | HN | 0.00 | 11.00 | 0.25 | 0.00 | 0.0 | 1 | 0 | 2D-NOESY |
| 995 | Y4 | 4 | HN | F8 | 8 | HD1 | 0.00 | 16.00 | 0.33 | 0.00 | 0.0 | 0 | 1 | 2D-NOESY |
| 903 | D1 | 1 | HB1 | H6 | 6 | HE1 | 0.00 | 4.90 | 0.11 | 0.00 | 0.0 | 4 | 0 | 2D-NOESY |
| 646 | P7 | 7 | HB2 | V3 | 3 | HA | 0.00 | 9.10 | 0.23 | 0.00 | 0.0 | 5 | 0 | 2D-NOESY |
| 837 | R2 | 2 | HG1 | I5 | 5 | HG21 | 0.00 | 76.00 | 1.90 | 0.00 | 0.0 | 2 | 5 | 2D-NOESY |
| 755 | R2 | 2 | HG1 | I5 | 5 | HA | 0.00 | 55.00 | 1.40 | 0.00 | 0.0 | 2 | 1 | 2D-NOESY |
| 528 | I5 | 5 | HA | D1 | 1 | HB1 | 0.00 | 23.00 | 0.58 | 0.00 | 0.0 | 5 | 0 | 2D-NOESY |
| 676 | P7 | 7 | HB2 | V3 | 3 | HG21 | 0.00 | 31.00 | 0.79 | 0.00 | 0.0 | 5 | 2 | 2D-NOESY |
| 618 | I5 | 5 | HA | R2 | 2 | HG1 | 0.00 | 54.00 | 1.40 | 0.00 | 0.0 | 2 | 1 | 2D-NOESY |
| 794 | D1 | 1 | HB1 | I5 | 5 | HG11 | 0.00 | 32.00 | 0.85 | 0.00 | 0.0 | 5 | 0 | 2D-NOESY |
| 875 | R2 | 2 | HA | H6 | 6 | HA | 0.00 | 37.00 | 1.00 | 0.00 | 0.0 | 5 | 0 | 2D-NOESY |
| 630 | P7 | 7 | HG1 | R2 | 2 | HG1 | 0.00 | 31.00 | 0.78 | 0.00 | 0.0 | 2 | 3 | 2D-NOESY |
| 740 | L10 | 10 | HB1 | Y4 | 4 | HE1 | 0.00 | 21.00 | 0.49 | 0.00 | 0.0 | 5 | 5 | 2D-NOESY |
| 846 | D1 | 1 | HB1 | I5 | 5 | HD1 | 0.00 | 100.00 | 3.00 | 0.00 | 0.0 | 5 | 2 | 2D-NOESY |
| 840 | H6 | 6 | HE1 | I5 | 5 | HG21 | 0.00 | 330.00 | 10.00 | 0.00 | 0.0 | 4 | 2 | 2D-NOESY |
| 1111 | H6 | 6 | HD2 | H9 | 9 | HN | 0.00 | 22.00 | 0.60 | 0.00 | 0.0 | 1 | 0 | 2D-NOESY |
| 666 | P7 | 7 | HB1 | V3 | 3 | HG11 | 0.00 | 31.00 | 0.93 | 0.00 | 0.0 | 5 | 2 | 2D-NOESY |
| 1151 | P7 | 7 | HB2 | L10 | 10 | HD11 | 0.00 | 110.00 | 3.50 | 0.00 | 0.0 | 0 | 2 | 2D-NOESY |
| 955 | D1 | 1 | HA | P7 | 7 | HD1 | 0.00 | 6.50 | 0.21 | 0.00 | 0.0 | 5 | 0 | 2D-NOESY |
| 890 | L10 | 10 | HD21 | H6 | 6 | HA | 0.00 | 21.00 | 0.64 | 0.00 | 0.0 | 0 | 2 | 2D-NOESY |
| 552 | I5 | 5 | HA | D1 | 1 | HB2 | 0.00 | 15.00 | 0.51 | 0.00 | 0.0 | 5 | 0 | 2D-NOESY |
| 817 | D1 | 1 | HB2 | I5 | 5 | HG12 | 0.00 | 23.00 | 0.71 | 0.00 | 0.0 | 5 | 0 | 2D-NOESY |
| 645 | P7 | 7 | HB1 | V3 | 3 | HA | 0.00 | 9.60 | 0.34 | 0.00 | 0.0 | 5 | 0 | 2D-NOESY |
| 710 | P7 | 7 | HD2 | V3 | 3 | HN | 0.00 | 1.30 | 0.04 | 0.00 | 0.0 | 1 | 0 | 2D-NOESY |
| 554 | I5 | 5 | HG12 | D1 | 1 | HB2 | 0.00 | 22.00 | 0.71 | 0.00 | 0.0 | 5 | 0 | 2D-NOESY |
| 889 | L10 | 10 | HD11 | H6 | 6 | HA | 0.00 | 21.00 | 0.69 | 0.00 | 0.0 | 0 | 2 | 2D-NOESY |
| 966 | L10 | 10 | HA | P7 | 7 | HD1 | 0.00 | 13.00 | 0.46 | 0.00 | 0.0 | 5 | 0 | 2D-NOESY |
| 851 | H6 | 6 | HE1 | I5 | 5 | HD1 | 0.00 | 330.00 | 12.00 | 0.00 | 0.0 | 4 | 2 | 2D-NOESY |
| 735 | D1 | 1 | HB2 | Y4 | 4 | HE1 | 0.00 | 46.00 | 1.20 | 0.00 | 0.0 | 5 | 1 | 2D-NOESY |
| 854 | H9 | 9 | HE1 | I5 | 5 | HD1 | 0.00 | 38.00 | 1.20 | 0.00 | 0.0 | 0 | 2 | 2D-NOESY |
| 1065 | I5 | 5 | HB | H9 | 9 | HD2 | 0.00 | 8.00 | 0.29 | 0.00 | 0.0 | 0 | 0 | 2D-NOESY |
| 549 | Y4 | 4 | HD1 | D1 | 1 | HB2 | 0.00 | 72.00 | 2.00 | 0.00 | 0.0 | 5 | 1 | 2D-NOESY |
| 896 | D1 | 1 | HA | H6 | 6 | HD2 | 0.00 | 21.00 | 0.82 | 0.00 | 0.0 | 4 | 0 | 2D-NOESY |
| 701 | H6 | 6 | HA | V3 | 3 | HN | 0.00 | 2.00 | 0.08 | 0.00 | 0.0 | 1 | 0 | 2D-NOESY |
| 680 | F8 | 8 | HD1 | V3 | 3 | HG21 | 0.00 | 19.00 | 0.77 | 0.00 | 0.0 | 0 | 5 | 2D-NOESY |
| 891 | L10 | 10 | HN | H6 | 6 | HA | 0.00 | 13.00 | 0.56 | 0.00 | 0.0 | 5 | 0 | 2D-NOESY |
| 555 | I5 | 5 | HN | D1 | 1 | HB2 | 0.00 | 14.00 | 0.59 | 0.00 | 0.0 | 5 | 0 | 2D-NOESY |
| 977 | V3 | 3 | HG21 | F8 | 8 | HA | 0.00 | 6.70 | 0.30 | 0.00 | 0.0 | 5 | 2 | 2D-NOESY |
| 529 | I5 | 5 | HB | D1 | 1 | HB1 | 0.00 | 15.00 | 0.66 | 0.00 | 0.0 | 5 | 0 | 2D-NOESY |
| 550 | Y4 | 4 | HE1 | D1 | 1 | HB2 | 0.00 | 36.00 | 1.20 | 0.00 | 0.0 | 5 | 1 | 2D-NOESY |
| 893 | R2 | 2 | HG1 | H6 | 6 | HB1 | 0.00 | 24.00 | 1.00 | 0.00 | 0.0 | 2 | 1 | 2D-NOESY |
| 970 | V3 | 3 | HA | P7 | 7 | HD2 | 0.00 | 51.00 | 2.40 | 0.00 | 0.0 | 5 | 0 | 2D-NOESY |
| 848 | R2 | 2 | HG1 | I5 | 5 | HD1 | 0.00 | 120.00 | 5.80 | 0.00 | 0.0 | 2 | 5 | 2D-NOESY |
| 644 | P7 | 7 | HB1 | R2 | 2 | HD1 | 0.00 | 13.00 | 0.34 | 0.00 | 0.0 | 2 | 1 | 2D-NOESY |
| 795 | D1 | 1 | HB2 | I5 | 5 | HG11 | 0.00 | 16.00 | 0.75 | 0.00 | 0.0 | 5 | 0 | 2D-NOESY |
| 1005 | Y4 | 4 | HN | F8 | 8 | HE1 | 0.00 | 29.00 | 0.73 | 0.00 | 0.0 | 0 | 1 | 2D-NOESY |
| 625 | H6 | 6 | HE1 | R2 | 2 | HG1 | 0.00 | 34.00 | 1.50 | 0.00 | 0.0 | 2 | 1 | 2D-NOESY |
| 799 | V3 | 3 | HG11 | I5 | 5 | HG11 | 0.00 | 730.00 | 37.00 | 0.00 | 0.0 | 5 | 2 | 2D-NOESY |
| 1009 | I5 | 5 | HN | F8 | 8 | HE1 | 0.00 | 88.00 | 4.30 | 0.00 | 0.0 | 0 | 1 | 2D-NOESY |
| 758 | H9 | 9 | HE1 | I5 | 5 | HA | 0.00 | 16.00 | 0.74 | 0.00 | 0.0 | 0 | 0 | 2D-NOESY |
| 548 | Y4 | 4 | HA | D1 | 1 | HB2 | 0.00 | 27.00 | 1.20 | 0.00 | 0.0 | 5 | 1 | 2D-NOESY |
| 892 | R2 | 2 | HB1 | H6 | 6 | HB1 | 0.00 | 19.00 | 0.90 | 0.00 | 0.0 | 5 | 1 | 2D-NOESY |
| 823 | H6 | 6 | HE1 | I5 | 5 | HG12 | 0.00 | 48.00 | 2.70 | 0.00 | 0.0 | 4 | 0 | 2D-NOESY |
| 622 | H6 | 6 | HB1 | R2 | 2 | HG1 | 0.00 | 20.00 | 1.00 | 0.00 | 0.0 | 2 | 1 | 2D-NOESY |
| 724 | R2 | 2 | HB1 | Y4 | 4 | HA | 0.00 | 180.00 | 10.00 | 0.00 | 0.0 | 5 | 1 | 2D-NOESY |
| 553 | I5 | 5 | HB | D1 | 1 | HB2 | 0.00 | 11.00 | 0.59 | 0.00 | 0.0 | 5 | 0 | 2D-NOESY |
| 929 | Y4 | 4 | HN | P7 | 7 | HB1 | 0.00 | 12.00 | 0.70 | 0.00 | 0.0 | 5 | 0 | 2D-NOESY |
| 1064 | I5 | 5 | HA | H9 | 9 | HD2 | 0.00 | 8.40 | 0.46 | 0.00 | 0.0 | 0 | 0 | 2D-NOESY |
| 836 | D1 | 1 | HB2 | I5 | 5 | HG21 | 0.00 | 15.00 | 0.88 | 0.00 | 0.0 | 5 | 2 | 2D-NOESY |
| 1116 | F8 | 8 | HZ | H9 | 9 | HN | 0.00 | 30.00 | 2.00 | 0.00 | 0.0 | 1 | 0 | 2D-NOESY |
| 696 | Y4 | 4 | HE1 | V3 | 3 | HN | 0.00 | 15.00 | 0.94 | 0.00 | 0.0 | 0 | 1 | 2D-NOESY |
| 1141 | P7 | 7 | HA | L10 | 10 | HB1 | 0.00 | 31.00 | 2.30 | 0.01 | 0.0 | 0 | 2 | 2D-NOESY |
| 629 | P7 | 7 | HD2 | R2 | 2 | HG1 | 0.00 | 18.00 | 1.20 | 0.01 | 0.0 | 2 | 1 | 2D-NOESY |
| 843 | H9 | 9 | HE1 | I5 | 5 | HG21 | 0.00 | 26.00 | 1.40 | 0.01 | 0.0 | 0 | 2 | 2D-NOESY |
| 1140 | H6 | 6 | HN | L10 | 10 | HB1 | 0.00 | 3.70 | 0.26 | 0.01 | 0.0 | 0 | 2 | 2D-NOESY |

-continued

| | | | | | | | | | | | |
|---|---|---|---|---|---|---|---|---|---|---|---|
| 1134 | Y4 | 4 | HE1 | L10 | 10 | HB1 | 0.00 | 7.70 | 0.49 | 0.01 | 0.0 | 5 | 5 | 2D-NOESY |
| 934 | H9 | 9 | HB1 | P7 | 7 | HB1 | 0.00 | 47.00 | 3.90 | 0.01 | 0.0 | 5 | 0 | 2D-NOESY |
| 793 | D1 | 1 | HA | I5 | 5 | HG11 | 0.00 | 29.00 | 2.30 | 0.01 | 0.0 | 5 | 0 | 2D-NOESY |
| 731 | P7 | 7 | HB2 | Y4 | 4 | HD1 | 0.00 | 82.00 | 6.60 | 0.01 | 0.0 | 5 | 1 | 2D-NOESY |
| 682 | F8 | 8 | HZ | V3 | 3 | HG21 | 0.00 | 7.40 | 0.62 | 0.01 | 0.0 | 0 | 2 | 2D-NOESY |
| 885 | H9 | 9 | HD2 | H6 | 6 | HA | 0.00 | 41.00 | 2.90 | 0.01 | 0.0 | 0 | 0 | 2D-NOESY |
| 723 | D1 | 1 | HA | Y4 | 4 | HA | 0.00 | 41.00 | 4.00 | 0.01 | 0.0 | 5 | 0 | 2D-NOESY |
| 847 | D1 | 1 | HB2 | I5 | 5 | HD1 | 0.00 | 28.00 | 2.70 | 0.01 | 0.0 | 5 | 2 | 2D-NOESY |
| 733 | D1 | 1 | HA | Y4 | 4 | HE1 | 0.00 | 66.00 | 5.10 | 0.01 | 0.0 | 5 | 1 | 2D-NOESY |
| 675 | P7 | 7 | HB1 | V3 | 3 | HG21 | 0.00 | 12.00 | 1.20 | 0.01 | 0.0 | 5 | 2 | 2D-NOESY |
| 628 | P7 | 7 | HD1 | R2 | 2 | HG1 | 0.00 | 18.00 | 1.70 | 0.01 | 0.0 | 2 | 1 | 2D-NOESY |
| 709 | P7 | 7 | HD1 | V3 | 3 | HN | 0.00 | 0.50 | 0.05 | 0.01 | 0.0 | 1 | 0 | 2D-NOESY |
| 971 | V3 | 3 | HN | P7 | 7 | HD2 | 0.00 | 9.40 | 0.95 | 0.01 | 0.0 | 5 | 0 | 2D-NOESY |
| 895 | R2 | 2 | HG1 | H6 | 6 | HB2 | 0.00 | 14.00 | 1.30 | 0.01 | 0.0 | 2 | 1 | 2D-NOESY |
| 512 | I5 | 5 | HG21 | D1 | 1 | HA | 0.00 | 22.00 | 2.30 | 0.01 | 0.0 | 5 | 2 | 2D-NOESY |
| 819 | R2 | 2 | HD1 | I5 | 5 | HG12 | 0.00 | 15.00 | 1.40 | 0.01 | 0.0 | 2 | 1 | 2D-NOESY |
| 1137 | H6 | 6 | HA | L10 | 10 | HB1 | 0.00 | 8.80 | 0.77 | 0.01 | 0.0 | 0 | 2 | 2D-NOESY |
| 888 | L10 | 10 | HB1 | H6 | 6 | HA | 0.00 | 8.70 | 0.77 | 0.01 | 0.0 | 5 | 2 | 2D-NOESY |
| 1153 | P7 | 7 | HD2 | L10 | 10 | HD11 | 0.00 | 11.00 | 1.20 | 0.01 | 0.0 | 0 | 2 | 2D-NOESY |
| 626 | H6 | 6 | HN | R2 | 2 | HG1 | 0.00 | 11.00 | 1.30 | 0.01 | 0.0 | 2 | 1 | 2D-NOESY |
| 1139 | H6 | 6 | HD2 | L10 | 10 | HB1 | 0.00 | 7.70 | 0.78 | 0.01 | 0.0 | 0 | 2 | 2D-NOESY |
| 967 | L10 | 10 | HN | P7 | 7 | HD1 | 0.00 | 7.10 | 0.84 | 0.02 | 0.0 | 5 | 0 | 2D-NOESY |
| 902 | D1 | 1 | HA | H6 | 6 | HE1 | 0.00 | 3.40 | 0.36 | 0.02 | 0.0 | 4 | 0 | 2D-NOESY |
| 982 | I5 | 5 | HG12 | F8 | 8 | HA | 0.00 | 8.80 | 1.10 | 0.02 | 0.0 | 5 | 0 | 2D-NOESY |
| 1142 | P7 | 7 | HB1 | L10 | 10 | HB1 | 0.00 | 23.00 | 2.70 | 0.02 | 0.0 | 0 | 2 | 2D-NOESY |
| 935 | L10 | 10 | HA | P7 | 7 | HB1 | 0.00 | 15.00 | 1.90 | 0.02 | 0.0 | 5 | 0 | 2D-NOESY |
| 818 | R2 | 2 | HA | I5 | 5 | HG12 | 0.00 | 29.00 | 3.70 | 0.02 | 0.0 | 5 | 0 | 2D-NOESY |
| 695 | Y4 | 4 | HD1 | V3 | 3 | HN | 0.00 | 19.00 | 2.30 | 0.02 | 0.0 | 0 | 1 | 2D-NOESY |
| 1143 | P7 | 7 | HD1 | L10 | 10 | HB1 | 0.00 | 12.00 | 1.10 | 0.02 | 0.0 | 0 | 2 | 2D-NOESY |
| 623 | H6 | 6 | HB2 | R2 | 2 | HG1 | 0.00 | 12.00 | 1.30 | 0.02 | 0.0 | 2 | 1 | 2D-NOESY |
| 511 | I5 | 5 | HG11 | D1 | 1 | HA | 0.00 | 19.00 | 2.30 | 0.02 | 0.0 | 5 | 0 | 2D-NOESY |
| 4 | 6 | | N | 6 | | HN | 1 | | O | 0.00 | 10.00 | 0.73 | 0.02 | 0.0 | 0 | 16 | HBOND |
| 1020 | H9 | 9 | HE1 | F8 | 8 | HN | 0.00 | 14.00 | 1.30 | 0.02 | 0.0 | 1 | 0 | 2D-NOESY |
| 620 | I5 | 5 | HN | R2 | 2 | HG1 | 0.00 | 34.00 | 4.30 | 0.02 | 0.0 | 2 | 1 | 2D-NOESY |
| 998 | I5 | 5 | HG11 | F8 | 8 | HD1 | 0.00 | 29.00 | 4.00 | 0.02 | 0.0 | 0 | 1 | 2D-NOESY |
| 1138 | H6 | 6 | HB2 | L10 | 10 | HB1 | 0.00 | 9.60 | 0.98 | 0.02 | 0.0 | 0 | 2 | 2D-NOESY |
| 797 | R2 | 2 | HD1 | I5 | 5 | HG11 | 0.00 | 14.00 | 1.60 | 0.02 | 0.0 | 2 | 1 | 2D-NOESY |
| 964 | H9 | 9 | HA | P7 | 7 | HD1 | 0.00 | 27.00 | 3.90 | 0.02 | 0.0 | 5 | 0 | 2D-NOESY |
| 669 | D1 | 1 | HB1 | V3 | 3 | HG21 | 0.00 | 120.00 | 16.00 | 0.02 | 0.0 | 5 | 2 | 2D-NOESY |
| 509 | I5 | 5 | HB | D1 | 1 | HA | 0.00 | 11.00 | 1.50 | 0.02 | 0.0 | 5 | 0 | 2D-NOESY |
| 1154 | P7 | 7 | HD2 | L10 | 10 | HD21 | 0.00 | 8.60 | 1.10 | 0.02 | 0.0 | 0 | 2 | 2D-NOESY |
| 796 | R2 | 2 | HA | I5 | 5 | HG11 | 0.00 | 29.00 | 4.30 | 0.02 | 0.0 | 5 | 0 | 2D-NOESY |
| 876 | R2 | 2 | HB1 | H6 | 6 | HA | 0.00 | 16.00 | 2.00 | 0.02 | 0.0 | 5 | 1 | 2D-NOESY |
| 1150 | P7 | 7 | HB1 | L10 | 10 | HD21 | 0.00 | 16.00 | 2.40 | 0.03 | 0.0 | 0 | 2 | 2D-NOESY |
| 979 | I5 | 5 | HB | F8 | 8 | HA | 0.00 | 8.60 | 1.40 | 0.03 | 0.0 | 5 | 0 | 2D-NOESY |
| 803 | P7 | 7 | HB1 | I5 | 5 | HG11 | 0.00 | 31.00 | 5.20 | 0.03 | 0.0 | 5 | 0 | 2D-NOESY |
| 551 | Y4 | 4 | HN | D1 | 1 | HB2 | 0.00 | 19.00 | 3.20 | 0.03 | 0.0 | 5 | 0 | 2D-NOESY |
| 997 | I5 | 5 | HB | F8 | 8 | HD1 | 0.00 | 28.00 | 5.00 | 0.03 | 0.0 | 0 | 1 | 2D-NOESY |
| 621 | H6 | 6 | HA | R2 | 2 | HG1 | 0.00 | 13.00 | 2.10 | 0.03 | 0.0 | 2 | 1 | 2D-NOESY |
| 697 | I5 | 5 | HB | V3 | 3 | HN | 0.00 | 2.40 | 0.40 | 0.03 | 0.0 | 1 | 0 | 2D-NOESY |
| 824 | P7 | 7 | HB1 | I5 | 5 | HG12 | 0.00 | 30.00 | 5.30 | 0.03 | 0.0 | 5 | 0 | 2D-NOESY |
| 15 | 3D | | 8 | N | 3D | | 9 | N | 130.00 | 36.00 | 130.00 | 0.03 | 0.0 | 0 | 0 | TDIHEDRALS |
| 508 | Y4 | 4 | HE1 | D1 | 1 | HA | 0.00 | 40.00 | 5.10 | 0.03 | 0.1 | 5 | 1 | 2D-NOESY |
| 834 | D1 | 1 | HA | I5 | 5 | HG21 | 0.00 | 13.00 | 2.30 | 0.04 | 0.0 | 5 | 2 | 2D-NOESY |
| 969 | R2 | 2 | HG1 | P7 | 7 | HD2 | 0.00 | 7.10 | 1.20 | 0.04 | 0.0 | 2 | 1 | 2D-NOESY |
| 668 | P7 | 7 | HD2 | V3 | 3 | HG11 | 0.00 | 19.00 | 3.50 | 0.04 | 0.0 | 5 | 2 | 2D-NOESY |
| 756 | F8 | 8 | HD1 | I5 | 5 | HA | 0.00 | 23.00 | 4.40 | 0.04 | 0.0 | 0 | 1 | 2D-NOESY |
| 11 | 3J | | 1 | HA | 3J | | 1 | HB1 | 13.00 | 1.00 | 13.00 | 0.04 | 0.0 | 0 | 1 | JCOUP |
| 933 | H6 | 6 | HE1 | P7 | 7 | HB1 | 0.00 | 16.00 | 3.10 | 0.04 | 0.0 | 4 | 0 | 2D-NOESY |
| 981 | I5 | 5 | HG11 | F8 | 8 | HA | 0.00 | 5.30 | 1.00 | 0.04 | 0.0 | 5 | 0 | 2D-NOESY |
| 932 | I5 | 5 | HG12 | P7 | 7 | HB1 | 0.00 | 27.00 | 5.30 | 0.04 | 0.0 | 5 | 0 | 2D-NOESY |
| 487 | L10 | 10 | HD11 | L10 | 10 | HA | 1200.00 | 460.00 | 1100.00 | 0.04 | 0.1 | 0 | 5 | 2D-NOESY |
| 737 | P7 | 7 | HB2 | Y4 | 4 | HE1 | 0.00 | 120.00 | 23.00 | 0.04 | 0.0 | 5 | 1 | 2D-NOESY |
| 5 | 3D | | 5 | C | 3D | | 6 | C | −93.00 | 46.00 | −97.00 | 0.04 | 0.1 | 0 | 0 | TDIHEDRALS |
| 1113 | P7 | 7 | HD1 | H9 | 9 | HN | 0.00 | 3.10 | 0.62 | 0.05 | 0.1 | 0 | 0 | 2D-NOESY |
| 879 | V3 | 3 | HN | H6 | 6 | HA | 0.00 | 8.40 | 1.70 | 0.05 | 0.1 | 5 | 0 | 2D-NOESY |
| 226 | Y4 | 4 | HB1 | V3 | 3 | HG21 | 270.00 | 110.00 | 270.00 | 0.05 | 0.1 | 5 | 5 | 2D-NOESY |
| 531 | I5 | 5 | HG12 | D1 | 1 | HB1 | 0.00 | 3.90 | 0.79 | 0.05 | 0.1 | 5 | 0 | 2D-NOESY |
| 1149 | P7 | 7 | HB1 | L10 | 10 | HD11 | 0.00 | 12.00 | 2.50 | 0.05 | 0.1 | 0 | 2 | 2D-NOESY |
| 1144 | P7 | 7 | HD2 | L10 | 10 | HB1 | 0.00 | 9.10 | 1.50 | 0.05 | 0.3 | 0 | 2 | 2D-NOESY |
| 883 | F8 | 8 | HD1 | H6 | 6 | HA | 0.00 | 41.00 | 9.40 | 0.06 | 0.1 | 0 | 1 | 2D-NOESY |
| 728 | D1 | 1 | HA | Y4 | 4 | HD1 | 0.00 | 33.00 | 7.60 | 0.06 | 0.1 | 5 | 1 | 2D-NOESY |
| 1068 | P7 | 7 | HD1 | H9 | 9 | HD2 | 0.00 | 26.00 | 4.70 | 0.06 | 0.2 | 0 | 0 | 2D-NOESY |
| 999 | I5 | 5 | HG12 | F8 | 8 | HD1 | 0.00 | 18.00 | 4.20 | 0.06 | 0.1 | 0 | 1 | 2D-NOESY |
| 828 | F8 | 8 | HD1 | I5 | 5 | HG12 | 0.00 | 18.00 | 4.20 | 0.06 | 0.1 | 0 | 1 | 2D-NOESY |
| 574 | I5 | 5 | HG12 | R2 | 2 | HA | 0.00 | 15.00 | 3.70 | 0.06 | 0.1 | 5 | 0 | 2D-NOESY |
| 530 | I5 | 5 | HG11 | D1 | 1 | HB1 | 0.00 | 3.90 | 0.85 | 0.06 | 0.1 | 5 | 0 | 2D-NOESY |
| 1126 | P7 | 7 | HB2 | L10 | 10 | HA | 0.00 | 10.00 | 2.40 | 0.06 | 0.1 | 5 | 0 | 2D-NOESY |
| 403 | F8 | 8 | HB1 | P7 | 7 | HB1 | 110.00 | 48.00 | 110.00 | 0.06 | 0.1 | 5 | 1 | 2D-NOESY |

-continued

| | | | | | | | | | | | | |
|---|---|---|---|---|---|---|---|---|---|---|---|---|
| 898 | R2 | 2 | HG1 | H6 | 6 | HD2 | 0.00 | 24.00 | 5.20 | 0.06 | 0.1 | 2 | 1 2D-NOESY |
| 938 | L10 | 10 | HN | P7 | 7 | HB1 | 0.00 | 10.00 | 2.50 | 0.06 | 0.1 | 5 | 0 2D-NOESY |
| 690 | D1 | 1 | HB2 | V3 | 3 | HN | 0.00 | 4.00 | 0.96 | 0.07 | 0.1 | 1 | 0 2D-NOESY |
| 1127 | F8 | 8 | HN | L10 | 10 | HA | 0.00 | 17.00 | 4.40 | 0.07 | 0.1 | 5 | 0 2D-NOESY |
| 839 | V3 | 3 | HN | I5 | 5 | HG21 | 0.00 | 45.00 | 12.00 | 0.07 | 0.1 | 5 | 2 2D-NOESY |
| 729 | D1 | 1 | HB2 | Y4 | 4 | HD1 | 0.00 | 10.00 | 2.00 | 0.07 | 0.7 | 5 | 1 2D-NOESY |
| 980 | I5 | 5 | HD1 | F8 | 8 | HA | 0.00 | 16.00 | 4.20 | 0.08 | 0.1 | 5 | 2 2D-NOESY |
| 643 | I5 | 5 | HG12 | R2 | 2 | HD1 | 0.00 | 6.50 | 1.40 | 0.08 | 0.3 | 2 | 1 2D-NOESY |
| 681 | F8 | 8 | HE1 | V3 | 3 | HG21 | 0.00 | 6.30 | 1.50 | 0.08 | 0.3 | 0 | 5 2D-NOESY |
| 959 | V3 | 3 | HN | P7 | 7 | HD1 | 0.00 | 5.00 | 1.20 | 0.08 | 0.5 | 5 | 0 2D-NOESY |
| 525 | V3 | 3 | HA | D1 | 1 | HB1 | 0.00 | 23.00 | 6.50 | 0.08 | 0.2 | 5 | 0 2D-NOESY |
| 878 | V3 | 3 | HG11 | H6 | 6 | HA | 0.00 | 21.00 | 6.00 | 0.09 | 0.1 | 5 | 2 2D-NOESY |
| 825 | P7 | 7 | HD1 | I5 | 5 | HG12 | 0.00 | 40.00 | 12.00 | 0.09 | 0.2 | 5 | 0 2D-NOESY |
| 983 | I5 | 5 | HG21 | F8 | 8 | HA | 0.00 | 16.00 | 4.70 | 0.09 | 0.1 | 5 | 2 2D-NOESY |
| 1054 | P7 | 7 | HB1 | H9 | 9 | HB1 | 0.00 | 25.00 | 7.80 | 0.10 | 0.2 | 5 | 1 2D-NOESY |
| 254 | V3 | 3 | HG21 | Y4 | 4 | HB1 | 250.00 | 100.00 | 270.00 | 0.10 | 0.4 | 5 | 5 2D-NOESY |
| 906 | V3 | 3 | HN | H6 | 6 | HE1 | 0.00 | 7.10 | 1.60 | 0.10 | 0.7 | 4 | 0 2D-NOESY |
| 138 | P7 | 7 | HA | F8 | 8 | HE1 | 130.00 | 55.00 | 130.00 | 0.10 | 0.6 | 0 | 1 2D-NOESY |
| 913 | L10 | 10 | HA | H6 | 6 | HE1 | 0.00 | 3.70 | 1.00 | 0.10 | 0.5 | 4 | 0 2D-NOESY |
| 674 | H6 | 6 | HE1 | V3 | 3 | HG21 | 0.00 | 71.00 | 16.00 | 0.11 | 1.0 | 4 | 2 2D-NOESY |
| 1007 | I5 | 5 | HG11 | F8 | 8 | HE1 | 0.00 | 25.00 | 8.10 | 0.11 | 0.3 | 0 | 1 2D-NOESY |
| 402 | F8 | 8 | HA | P7 | 7 | HB1 | 92.00 | 37.00 | 82.00 | 0.11 | 0.4 | 5 | 0 2D-NOESY |
| 884 | F8 | 8 | HE1 | H6 | 6 | HA | 0.00 | 26.00 | 7.20 | 0.12 | 1.2 | 0 | 1 2D-NOESY |
| 689 | D1 | 1 | HB1 | V3 | 3 | HN | 0.00 | 3.20 | 1.00 | 0.12 | 0.3 | 1 | 0 2D-NOESY |
| 838 | V3 | 3 | HB | I5 | 5 | HG21 | 0.00 | 60.00 | 20.00 | 0.13 | 0.3 | 5 | 2 2D-NOESY |
| 911 | P7 | 7 | HB2 | H6 | 6 | HE1 | 0.00 | 8.20 | 2.80 | 0.13 | 0.3 | 4 | 0 2D-NOESY |
| 290 | Y4 | 4 | HB1 | I5 | 5 | HG11 | 38.00 | 17.00 | 35.00 | 0.13 | 0.5 | 5 | 1 2D-NOESY |
| 617 | Y4 | 4 | HB1 | R2 | 2 | HG1 | 0.00 | 33.00 | 11.00 | 0.13 | 0.7 | 2 | 3 2D-NOESY |
| 463 | P7 | 7 | HB2 | F8 | 8 | HA | 100.00 | 41.00 | 110.00 | 0.13 | 0.4 | 5 | 0 2D-NOESY |
| 112 | P7 | 7 | HB1 | F8 | 8 | HN | 170.00 | 66.00 | 180.00 | 0.13 | 0.4 | 1 | 0 2D-NOESY |
| 905 | R2 | 2 | HG1 | H6 | 6 | HE1 | 0.00 | 4.70 | 1.50 | 0.14 | 0.8 | 2 | 1 2D-NOESY |
| 757 | F8 | 8 | HE1 | I5 | 5 | HA | 0.00 | 27.00 | 8.90 | 0.14 | 0.7 | 0 | 1 2D-NOESY |
| 725 | P7 | 7 | HB1 | Y4 | 4 | HA | 0.00 | 6.20 | 2.30 | 0.15 | 0.4 | 5 | 0 2D-NOESY |
| 1008 | I5 | 5 | HG12 | F8 | 8 | HE1 | 0.00 | 24.00 | 8.80 | 0.15 | 0.4 | 0 | 1 2D-NOESY |
| 1021 | L10 | 10 | HB1 | F8 | 8 | HN | 0.00 | 3.50 | 1.30 | 0.15 | 0.4 | 0 | 2 2D-NOESY |
| 491 | H9 | 9 | HB1 | L10 | 10 | HA | 190.00 | 74.00 | 190.00 | 0.15 | 0.8 | 5 | 1 2D-NOESY |
| 485 | L10 | 10 | HA | H9 | 9 | HB1 | 190.00 | 75.00 | 190.00 | 0.15 | 0.7 | 5 | 1 2D-NOESY |
| 1114 | P7 | 7 | HD2 | H9 | 9 | HN | 0.00 | 1.90 | 0.70 | 0.16 | 0.6 | 1 | 0 2D-NOESY |
| 904 | R2 | 2 | HA | H6 | 6 | HE1 | 0.00 | 2.40 | 0.76 | 0.16 | 1.4 | 4 | 0 2D-NOESY |
| 699 | I5 | 5 | HG12 | V3 | 3 | HN | 0.00 | 1.30 | 0.48 | 0.16 | 0.6 | 1 | 0 2D-NOESY |
| 899 | V3 | 3 | HN | H6 | 6 | HD2 | 0.00 | 16.00 | 5.80 | 0.16 | 0.8 | 4 | 0 2D-NOESY |
| 730 | P7 | 7 | HB1 | Y4 | 4 | HD1 | 0.00 | 23.00 | 9.20 | 0.17 | 0.6 | 5 | 1 2D-NOESY |
| 243 | I5 | 5 | HG21 | Y4 | 4 | HA | 480.00 | 190.00 | 440.00 | 0.17 | 0.8 | 5 | 5 2D-NOESY |
| 3 | 3D | 3 | C | 3D | 4 | C | −120.00 | 60.00 | −95.00 | 0.17 | 0.5 | 0 | 0 TDIHEDRALS |
| 455 | I5 | 5 | HN | P7 | 7 | HD2 | 30.00 | 12.00 | 28.00 | 0.17 | 1.2 | 5 | 1 2D-NOESY |
| 37 | I5 | 5 | HG21 | Y4 | 4 | HD1 | 340.00 | 140.00 | 330.00 | 0.17 | 0.9 | 5 | 11 2D-NOESY |
| 624 | H6 | 6 | HD2 | R2 | 2 | HG1 | 0.00 | 14.00 | 5.20 | 0.17 | 0.8 | 2 | 1 2D-NOESY |
| 1012 | P7 | 7 | HD1 | F8 | 8 | HE1 | 0.00 | 21.00 | 7.90 | 0.17 | 1.0 | 0 | 1 2D-NOESY |
| 910 | P7 | 7 | HB1 | H6 | 6 | HE1 | 0.00 | 7.60 | 3.10 | 0.18 | 0.6 | 4 | 0 2D-NOESY |
| 1069 | P7 | 7 | HD2 | H9 | 9 | HD2 | 0.00 | 16.00 | 5.30 | 0.20 | 2.4 | 0 | 0 2D-NOESY |
| 6 | 10 | N | 10 | HN | 1 | O | 0.00 | 20.00 | 8.10 | 0.20 | 1.1 | 0 | 15 HBOND |
| 21 | 3J | 3 | HA | 3J | 3 | HN | 8.00 | 0.50 | 8.00 | 0.21 | 1.2 | 0 | 0 JCOUP |
| 348 | I5 | 5 | HG21 | H6 | 6 | HA | 140.00 | 55.00 | 160.00 | 0.22 | 2.0 | 5 | 5 2D-NOESY |
| 958 | R2 | 2 | HG1 | P7 | 7 | HD1 | 0.00 | 4.10 | 1.70 | 0.23 | 2.2 | 2 | 1 2D-NOESY |
| 673 | H6 | 6 | HB1 | V3 | 3 | HG21 | 0.00 | 14.00 | 6.80 | 0.23 | 0.8 | 5 | 2 2D-NOESY |
| 154 | F8 | 8 | HD1 | H9 | 9 | HN | 39.00 | 15.00 | 33.00 | 0.24 | 1.9 | 1 | 1 2D-NOESY |
| 49 | V3 | 3 | HG21 | Y4 | 4 | HE1 | 110.00 | 42.00 | 120.00 | 0.24 | 2.4 | 5 | 5 2D-NOESY |
| 962 | F8 | 8 | HA | P7 | 7 | HD1 | 0.00 | 27.00 | 13.00 | 0.24 | 0.8 | 5 | 0 2D-NOESY |
| 510 | I5 | 5 | HD1 | D1 | 1 | HA | 0.00 | 22.00 | 9.90 | 0.24 | 1.2 | 5 | 2 2D-NOESY |
| 344 | H6 | 6 | HD2 | H6 | 6 | HA | 320.00 | 130.00 | 300.00 | 0.25 | 1.6 | 4 | 0 2D-NOESY |
| 114 | P7 | 7 | HG1 | F8 | 8 | HN | 77.00 | 31.00 | 86.00 | 0.25 | 3.6 | 1 | 1 2D-NOESY |
| 996 | I5 | 5 | HA | F8 | 8 | HD1 | 0.00 | 9.20 | 4.40 | 0.25 | 1.1 | 0 | 1 2D-NOESY |
| 390 | F8 | 8 | HD1 | P7 | 7 | HA | 310.00 | 120.00 | 340.00 | 0.25 | 2.3 | 0 | 1 2D-NOESY |
| 3 | 3J | 5 | HA | 3J | 5 | HN | 8.60 | 0.40 | 8.60 | 0.25 | 3.6 | 0 | 0 J15DEGC |
| 13 | 3D | 6 | N | 3D | 7 | N | 120.00 | 16.00 | 120.00 | 0.26 | 2.7 | 0 | 0 TDIHEDRALS |
| 3 | 3J | 5 | HA | 3J | 5 | HN | 8.60 | 0.40 | 8.60 | 0.26 | 2.9 | 0 | 0 J5DEGC |
| 462 | P7 | 7 | HB1 | F8 | 8 | HA | 70.00 | 28.00 | 82.00 | 0.26 | 1.5 | 5 | 0 2D-NOESY |
| 3 | 3J | 5 | HA | 3J | 5 | HN | 8.50 | 0.40 | 8.60 | 0.26 | 4.6 | 0 | 0 JCOUP |
| 125 | P7 | 7 | HA | F8 | 8 | HD1 | 300.00 | 120.00 | 340.00 | 0.26 | 2.5 | 0 | 1 2D-NOESY |
| 366 | H6 | 6 | HE1 | H6 | 6 | HB2 | 62.00 | 31.00 | 48.00 | 0.26 | 1.2 | 4 | 0 2D-NOESY |
| 665 | D1 | 1 | HB1 | V3 | 3 | HG11 | 0.00 | 77.00 | 37.00 | 0.26 | 1.8 | 5 | 2 2D-NOESY |
| 228 | Y4 | 4 | HE1 | V3 | 3 | HG21 | 100.00 | 42.00 | 120.00 | 0.26 | 2.8 | 5 | 5 2D-NOESY |
| 212 | Y4 | 4 | HN | V3 | 3 | HB | 170.00 | 71.00 | 200.00 | 0.27 | 2.6 | 5 | 0 2D-NOESY |
| 8 | 3D | 8 | C | 3D | 9 | C | −100.00 | 42.00 | −81.00 | 0.28 | 1.2 | 1 | 0 TDIHEDRALS |
| 526 | V3 | 3 | HB | D1 | 1 | HB1 | 0.00 | 23.00 | 11.00 | 0.28 | 2.2 | 5 | 0 2D-NOESY |
| 877 | R2 | 2 | HG1 | H6 | 6 | HA | 0.00 | 4.20 | 2.10 | 0.29 | 1.6 | 2 | 1 2D-NOESY |
| 909 | I5 | 5 | HG12 | H6 | 6 | HE1 | 0.00 | 5.10 | 2.70 | 0.29 | 1.4 | 4 | 0 2D-NOESY |
| 738 | H9 | 9 | HE1 | Y4 | 4 | HE1 | 0.00 | 15.00 | 5.90 | 0.30 | 5.6 | 0 | 1 2D-NOESY |
| 694 | Y4 | 4 | HB1 | V3 | 3 | HN | 0.00 | 3.20 | 1.70 | 0.30 | 1.9 | 0 | 1 2D-NOESY |

-continued

| | | | | | | | | | | | |
|---|---|---|---|---|---|---|---|---|---|---|---|
| 1010 | H6 | 6 | HA | F8 | 8 | HE1 | 0.00 | 16.00 | 7.20 | 0.31 | 8.0 | 0 | 1 | 2D-NOESY |
| 109 | F8 | 8 | HE1 | F8 | 8 | HN | 21.00 | 8.40 | 21.00 | 0.32 | 4.6 | 1 | 1 | 2D-NOESY |
| 332 | Y4 | 4 | HA | I5 | 5 | HD1 | 330.00 | 130.00 | 300.00 | 0.32 | 3.6 | 3 | 2 | 2D-NOESY |
| 30 | 3J | 3 | HA | 3J | 3 | HN | 8.00 | 0.40 | 8.00 | 0.33 | 2.9 | 0 | 0 | JCOUP |
| 908 | I5 | 5 | HG11 | H6 | 6 | HE1 | 0.00 | 4.80 | 2.70 | 0.33 | 1.8 | 4 | 0 | 2D-NOESY |
| 678 | P7 | 7 | HD2 | V3 | 3 | HG21 | 0.00 | 12.00 | 6.40 | 0.33 | 2.2 | 5 | 7 | 2D-NOESY |
| 349 | P7 | 7 | HB1 | H6 | 6 | HA | 63.00 | 25.00 | 76.00 | 0.34 | 2.5 | 5 | 0 | 2D-NOESY |
| 8 | 3J | 3 | HA | 3J | 3 | HN | 7.90 | 0.40 | 8.00 | 0.34 | 3.5 | 0 | 0 | J5DEGC |
| 405 | F8 | 8 | HE1 | P7 | 7 | HB1 | 44.00 | 18.00 | 47.00 | 0.34 | 13.0 | 0 | 1 | 2D-NOESY |
| 693 | Y4 | 4 | HA | V3 | 3 | HN | 0.00 | 4.10 | 2.20 | 0.34 | 2.6 | 1 | 0 | 2D-NOESY |
| 407 | H9 | 9 | HN | P7 | 7 | HB1 | 41.00 | 20.00 | 32.00 | 0.34 | 2.7 | 5 | 1 | 2D-NOESY |
| 101 | I5 | 5 | HG21 | H6 | 6 | HE1 | 25.00 | 10.00 | 22.00 | 0.34 | 3.1 | 4 | 5 | 2D-NOESY |
| 1 | 3J | 3 | HA | 3J | 3 | HN | 8.10 | 0.40 | 8.00 | 0.34 | 3.2 | 0 | 0 | J5DEGC |
| 688 | D1 | 1 | HA | V3 | 3 | HN | 0.00 | 9.80 | 5.10 | 0.35 | 3.6 | 1 | 2 | 2D-NOESY |
| 253 | V3 | 3 | HG11 | Y4 | 4 | HB1 | 160.00 | 63.00 | 140.00 | 0.35 | 6.6 | 5 | 5 | 2D-NOESY |
| 58 | P7 | 7 | HD2 | Y4 | 4 | HE1 | 420.00 | 170.00 | 350.00 | 0.36 | 6.3 | 5 | 1 | 2D-NOESY |
| 972 | Y4 | 4 | HN | P7 | 7 | HD2 | 0.00 | 11.00 | 6.20 | 0.37 | 3.5 | 5 | 0 | 2D-NOESY |
| 211 | V3 | 3 | HN | V3 | 3 | HB | 410.00 | 170.00 | 320.00 | 0.37 | 3.3 | 5 | 0 | 2D-NOESY |
| 53 | H6 | 6 | HN | Y4 | 4 | HE1 | 220.00 | 87.00 | 190.00 | 0.37 | 4.1 | 5 | 1 | 2D-NOESY |
| 8 | 3J | 3 | HA | 3J | 3 | HN | 7.90 | 0.40 | 8.00 | 0.38 | 4.8 | 0 | 0 | JCOUP |
| 616 | Y4 | 4 | HA | R2 | 2 | HG1 | 0.00 | 19.00 | 11.00 | 0.38 | 5.5 | 2 | 1 | 2D-NOESY |
| 698 | I5 | 5 | HG11 | V3 | 3 | HN | 0.00 | 0.95 | 0.55 | 0.38 | 3.2 | 1 | 0 | 2D-NOESY |
| 23 | 3J | 5 | HA | 3J | 5 | HN | 8.30 | 0.50 | 8.60 | 0.38 | 7.0 | 0 | 0 | JCOUP |
| 6 | 3D | 6 | C | 3D | 7 | C | −71.00 | 16.00 | −61.00 | 0.39 | 2.1 | 0 | 0 | TDIHEDRALS |
| 931 | I5 | 5 | HB | P7 | 7 | HB1 | 0.00 | 14.00 | 8.40 | 0.41 | 3.0 | 5 | 0 | 2D-NOESY |
| 1 | 3J | 3 | HA | 3J | 3 | HN | 8.10 | 0.40 | 8.00 | 0.41 | 5.1 | 0 | 0 | J15DEGC |
| 141 | L10 | 10 | HA | F8 | 8 | HE1 | 190.00 | 81.00 | 210.00 | 0.42 | 9.6 | 0 | 1 | 2D-NOESY |
| 322 | H6 | 6 | HD2 | I5 | 5 | HG21 | 180.00 | 71.00 | 160.00 | 0.42 | 6.5 | 4 | 2 | 2D-NOESY |
| 225 | Y4 | 4 | HA | V3 | 3 | HG21 | 200.00 | 79.00 | 140.00 | 0.43 | 3.0 | 5 | 2 | 2D-NOESY |
| 52 | I5 | 5 | HG21 | Y4 | 4 | HE1 | 240.00 | 95.00 | 200.00 | 0.43 | 5.1 | 5 | 11 | 2D-NOESY |
| 670 | D1 | 1 | HB2 | V3 | 3 | HG21 | 0.00 | 22.00 | 14.00 | 0.44 | 3.7 | 5 | 2 | 2D-NOESY |
| 488 | F8 | 8 | HD1 | L10 | 10 | HA | 110.00 | 45.00 | 84.00 | 0.44 | 4.7 | 0 | 1 | 2D-NOESY |
| 900 | P7 | 7 | HB1 | H6 | 6 | HD2 | 0.00 | 38.00 | 23.00 | 0.44 | 3.9 | 4 | 0 | 2D-NOESY |
| 24 | 3J | 9 | HA | 3J | 9 | HB1 | 19.00 | 1.50 | 18.00 | 0.44 | 4.9 | 0 | 2 | J5DEGC |
| 573 | D1 | 1 | HB1 | R2 | 2 | HA | 0.00 | 43.00 | 29.00 | 0.45 | 3.1 | 5 | 0 | 2D-NOESY |
| 1145 | P7 | 7 | HG1 | L10 | 10 | HB1 | 0.00 | 23.00 | 9.10 | 0.45 | 31.0 | 0 | 5 | 2D-NOESY |
| 180 | R2 | 2 | HD1 | R2 | 2 | HA | 350.00 | 170.00 | 360.00 | 0.46 | 5.1 | 4 | 1 | 2D-NOESY |
| 1115 | P7 | 7 | HG1 | H9 | 9 | HN | 0.00 | 6.10 | 3.70 | 0.46 | 7.0 | 1 | 1 | 2D-NOESY |
| 91 | P7 | 7 | HD1 | H6 | 6 | HD2 | 170.00 | 70.00 | 180.00 | 0.46 | 7.3 | 4 | 0 | 2D-NOESY |
| 894 | R2 | 2 | HB1 | H6 | 6 | HB2 | 0.00 | 2.00 | 1.10 | 0.46 | 7.8 | 5 | 1 | 2D-NOESY |
| 9 | 3J | 5 | HA | 3J | 5 | HN | 8.50 | 0.30 | 8.60 | 0.46 | 16.0 | 0 | 0 | J15DEGC |
| 155 | F8 | 8 | HE1 | H9 | 9 | HN | 7.20 | 2.90 | 9.10 | 0.47 | 3.7 | 1 | 2 | 2D-NOESY |
| 11 | 3J | 3 | HA | 3J | 3 | HN | 7.80 | 0.40 | 8.00 | 0.48 | 8.2 | 0 | 0 | J5DEGC |
| 613 | D1 | 1 | HB2 | R2 | 2 | HG1 | 0.00 | 33.00 | 22.00 | 0.48 | 3.8 | 2 | 1 | 2D-NOESY |
| 334 | Y4 | 4 | HD1 | I5 | 5 | HD1 | 180.00 | 71.00 | 200.00 | 0.49 | 15.0 | 5 | 5 | 2D-NOESY |
| 12 | 3J | 1 | HA | 3J | 1 | HB1 | 4.50 | 0.50 | 4.70 | 0.50 | 9.3 | 0 | 0 | JCOUP |
| 57 | P7 | 7 | HD1 | Y4 | 4 | HE1 | 460.00 | 180.00 | 400.00 | 0.50 | 8.3 | 5 | 1 | 2D-NOESY |
| 336 | H6 | 6 | HN | I5 | 5 | HD1 | 610.00 | 240.00 | 460.00 | 0.50 | 7.5 | 5 | 2 | 2D-NOESY |
| 497 | H9 | 9 | HA | L10 | 10 | HB1 | 160.00 | 64.00 | 200.00 | 0.50 | 6.0 | 0 | 2 | 2D-NOESY |
| 237 | V3 | 3 | HG11 | Y4 | 4 | HA | 120.00 | 51.00 | 87.00 | 0.52 | 5.9 | 5 | 2 | 2D-NOESY |
| 338 | H6 | 6 | HB2 | I5 | 5 | HD1 | 150.00 | 59.00 | 110.00 | 0.52 | 6.6 | 5 | 2 | 2D-NOESY |
| 852 | P7 | 7 | HB1 | I5 | 5 | HD1 | 0.00 | 33.00 | 22.00 | 0.52 | 6.0 | 5 | 2 | 2D-NOESY |
| 7 | 3D | 7 | C | 3D | 8 | C | −110.00 | 52.00 | −150.00 | 0.53 | 4.0 | 0 | 0 | TDIHEDRALS |
| 930 | I5 | 5 | HA | P7 | 7 | HB1 | 0.00 | 9.20 | 6.60 | 0.53 | 4.2 | 5 | 0 | 2D-NOESY |
| 90 | I5 | 5 | HG21 | H6 | 6 | HD2 | 330.00 | 130.00 | 370.00 | 0.54 | 8.6 | 4 | 5 | 2D-NOESY |
| 2 | 3 | N | 3 | HN | 1 | O | 0.00 | 10.00 | 4.60 | 0.54 | 22.0 | 0 | 16 | HBOND |
| 25 | 3J | 10 | HA | 3J | 10 | HN | 7.10 | 0.50 | 7.30 | 0.55 | 7.8 | 0 | 0 | JCOUP |
| 307 | H6 | 6 | HD2 | I5 | 5 | HG12 | 43.00 | 17.00 | 47.00 | 0.55 | 12.0 | 4 | 0 | 2D-NOESY |
| 259 | I5 | 5 | HG21 | Y4 | 4 | HB1 | 300.00 | 120.00 | 220.00 | 0.55 | 5.5 | 5 | 11 | 2D-NOESY |
| 461 | F8 | 8 | HE1 | F8 | 8 | HA | 210.00 | 84.00 | 150.00 | 0.55 | 5.0 | 0 | 1 | 2D-NOESY |
| 113 | P7 | 7 | HB2 | F8 | 8 | HN | 150.00 | 60.00 | 190.00 | 0.57 | 6.5 | 1 | 0 | 2D-NOESY |
| 291 | Y4 | 4 | HD1 | I5 | 5 | HG11 | 40.00 | 16.00 | 49.00 | 0.58 | 16.0 | 5 | 1 | 2D-NOESY |
| 92 | P7 | 7 | HD2 | H6 | 6 | HD2 | 290.00 | 120.00 | 240.00 | 0.59 | 16.0 | 4 | 0 | 2D-NOESY |
| 1 | 3J | 3 | HA | 3J | 3 | HN | 8.20 | 0.40 | 8.00 | 0.59 | 11.0 | 0 | 0 | JCOUP |
| 419 | Y4 | 4 | HD1 | P7 | 7 | HD1 | 120.00 | 49.00 | 97.00 | 0.60 | 7.6 | 5 | 1 | 2D-NOESY |
| 16 | 3J | 1 | HA | 3J | 1 | HB1 | 5.00 | 0.50 | 4.70 | 0.61 | 12.0 | 0 | 0 | J5DEGC |
| 8 | 3J | 3 | HA | 3J | 3 | HN | 7.90 | 0.30 | 8.00 | 0.61 | 11.0 | 0 | 0 | J15DEGC |
| 31 | 3J | 5 | HA | 3J | 5 | HN | 8.30 | 0.40 | 8.60 | 0.62 | 19.0 | 0 | 0 | JCOUP |
| 179 | R2 | 2 | HG1 | R2 | 2 | HA | 730.00 | 290.00 | 510.00 | 0.64 | 8.1 | 4 | 1 | 2D-NOESY |
| 15 | 3J | 1 | HA | 3J | 1 | HB2 | 8.30 | 0.50 | 8.20 | 0.64 | 21.0 | 0 | 0 | J5DEGC |
| 50 | I5 | 5 | HN | Y4 | 4 | HE1 | 300.00 | 120.00 | 210.00 | 0.64 | 8.9 | 5 | 1 | 2D-NOESY |
| 196 | R2 | 2 | HB1 | R2 | 2 | HD1 | 1200.00 | 470.00 | 880.00 | 0.65 | 12.0 | 4 | 3 | 2D-NOESY |
| 16 | 3J | 3 | HA | 3J | 3 | HB | 7.80 | 0.50 | 7.60 | 0.66 | 18.0 | 0 | 0 | JCOUP |
| 23 | 3J | 6 | HA | 3J | 6 | HB1 | 4.70 | 0.50 | 4.80 | 0.67 | 16.0 | 0 | 0 | J5DEGC |
| 238 | V3 | 3 | HG21 | Y4 | 4 | HA | 210.00 | 86.00 | 140.00 | 0.67 | 6.9 | 5 | 2 | 2D-NOESY |
| 34 | I5 | 5 | HN | Y4 | 4 | HD1 | 1200.00 | 470.00 | 810.00 | 0.67 | 9.9 | 5 | 1 | 2D-NOESY |
| 316 | Y4 | 4 | HD1 | I5 | 5 | HG21 | 190.00 | 74.00 | 130.00 | 0.68 | 8.8 | 5 | 5 | 2D-NOESY |
| 10 | 3J | 5 | HA | 3J | 5 | HN | 8.30 | 0.40 | 8.60 | 0.68 | 20.0 | 0 | 0 | JCOUP |
| 1112 | P7 | 7 | HB1 | H9 | 9 | HN | 0.00 | 3.50 | 2.80 | 0.68 | 7.9 | 1 | 0 | 2D-NOESY |

-continued

| | | | | | | | | | | | | |
|---|---|---|---|---|---|---|---|---|---|---|---|---|
| 18 | 3J | 6 | HA | 3J | 6 | HB1 | 4.90 | 0.50 | 4.80 | 0.69 | 23.0 | 0 | 0 | JCOUP |
| 880 | Y4 | 4 | HN | H6 | 6 | HA | 0.00 | 13.00 | 11.00 | 0.69 | 9.1 | 3 | 0 | 2D-NOESY |
| 317 | Y4 | 4 | HE1 | I5 | 5 | HG21 | 120.00 | 48.00 | 90.00 | 0.69 | 12.0 | 5 | 5 | 2D-NOESY |
| 399 | Y4 | 4 | HE1 | P7 | 7 | HB1 | 32.00 | 13.00 | 34.00 | 0.69 | 17.0 | 5 | 1 | 2D-NOESY |
| 914 | L10 | 10 | HB1 | H6 | 6 | HE1 | 0.00 | 4.80 | 3.20 | 0.70 | 29.0 | 0 | 2 | 2D-NOESY |
| 7 | 3J | 10 | HA | 3J | 10 | HN | 7.20 | 0.40 | 7.30 | 0.70 | 11.0 | 0 | 0 | J5DEGC |
| 172 | R2 | 2 | HB1 | D1 | 1 | HA | 190.00 | 76.00 | 140.00 | 0.70 | 12.0 | 5 | 1 | 2D-NOESY |
| 10 | 3J | 10 | HA | 3J | 10 | HN | 7.20 | 0.40 | 7.30 | 0.70 | 11.0 | 0 | 0 | J5DEGC |
| 13 | 3J | 10 | HA | 3J | 10 | HN | 7.20 | 0.40 | 7.30 | 0.71 | 11.0 | 0 | 0 | J5DEGC |
| 184 | V3 | 3 | HG21 | R2 | 2 | HA | 140.00 | 57.00 | 99.00 | 0.71 | 11.0 | 5 | 2 | 2D-NOESY |
| 481 | H9 | 9 | HE1 | H9 | 9 | HB1 | 140.00 | 56.00 | 100.00 | 0.72 | 11.0 | 0 | 1 | 2D-NOESY |
| 126 | P7 | 7 | HB2 | F8 | 8 | HD1 | 260.00 | 100.00 | 190.00 | 0.72 | 11.0 | 0 | 1 | 2D-NOESY |
| 429 | H6 | 6 | HD2 | P7 | 7 | HD1 | 160.00 | 63.00 | 180.00 | 0.72 | 20.0 | 4 | 0 | 2D-NOESY |
| 7 | R2 | 2 | HG1 | V3 | 3 | HN | 11.00 | 4.70 | 11.00 | 0.74 | 12.0 | 2 | 1 | 2D-NOESY |
| 13 | 3J | 1 | HA | 3J | 1 | HB2 | 8.40 | 0.50 | 8.20 | 0.74 | 34.0 | 0 | 0 | JCOUP |
| 7 | 3J | 10 | HA | 3J | 10 | HN | 7.40 | 0.40 | 7.30 | 0.76 | 17.0 | 0 | 0 | J15DEGC |
| 221 | V3 | 3 | HN | V3 | 3 | HG21 | 430.00 | 180.00 | 290.00 | 0.77 | 12.0 | 5 | 2 | 2D-NOESY |
| 373 | I5 | 5 | HG21 | H6 | 6 | HB2 | 290.00 | 120.00 | 190.00 | 0.77 | 10.0 | 5 | 5 | 2D-NOESY |
| 801 | H6 | 6 | HB2 | I5 | 5 | HG11 | 0.00 | 26.00 | 22.00 | 0.78 | 9.4 | 5 | 0 | 2D-NOESY |
| 357 | Y4 | 4 | HE1 | H6 | 6 | HB1 | 420.00 | 170.00 | 390.00 | 0.79 | 15.0 | 5 | 1 | 2D-NOESY |
| 10 | 3D | 3 | N | 3D | 4 | N | 130.00 | 36.00 | 160.00 | 0.80 | 11.0 | 0 | 0 | TDIHEDRALS |
| 340 | P7 | 7 | HA | I5 | 5 | HD1 | 150.00 | 60.00 | 110.00 | 0.81 | 15.0 | 5 | 2 | 2D-NOESY |
| 1006 | I5 | 5 | HB | F8 | 8 | HE1 | 0.00 | 11.00 | 9.70 | 0.81 | 12.0 | 0 | 1 | 2D-NOESY |
| 86 | I5 | 5 | HA | H6 | 6 | HD2 | 320.00 | 130.00 | 240.00 | 0.81 | 18.0 | 4 | 0 | 2D-NOESY |
| 614 | V3 | 3 | HA | R2 | 2 | HG1 | 0.00 | 53.00 | 47.00 | 0.82 | 11.0 | 2 | 1 | 2D-NOESY |
| 335 | Y4 | 4 | HE1 | I5 | 5 | HD1 | 160.00 | 63.00 | 110.00 | 0.83 | 13.0 | 5 | 5 | 2D-NOESY |
| 450 | H6 | 6 | HD2 | P7 | 7 | HD2 | 210.00 | 83.00 | 240.00 | 0.84 | 20.0 | 4 | 0 | 2D-NOESY |
| 2 | 3J | 4 | HA | 3J | 4 | HN | 8.00 | 0.40 | 7.90 | 0.84 | 21.0 | 0 | 0 | JCOUP |
| 223 | R2 | 2 | HA | V3 | 3 | HG21 | 150.00 | 62.00 | 99.00 | 0.84 | 13.0 | 5 | 2 | 2D-NOESY |
| 217 | Y4 | 4 | HB1 | V3 | 3 | HG11 | 220.00 | 88.00 | 140.00 | 0.88 | 20.0 | 5 | 5 | 2D-NOESY |
| 55 | H6 | 6 | HB1 | Y4 | 4 | HE1 | 510.00 | 200.00 | 390.00 | 0.88 | 22.0 | 5 | 1 | 2D-NOESY |
| 22 | 3J | 6 | HA | 3J | 6 | HB1 | 20.00 | 1.50 | 21.00 | 0.89 | 20.0 | 0 | 2 | J5DEGC |
| 289 | Y4 | 4 | HA | I5 | 5 | HG11 | 120.00 | 48.00 | 75.00 | 0.89 | 12.0 | 5 | 0 | 2D-NOESY |
| 446 | I5 | 5 | HG21 | P7 | 7 | HD2 | 150.00 | 58.00 | 93.00 | 0.90 | 15.0 | 5 | 5 | 2D-NOESY |
| 421 | I5 | 5 | HN | P7 | 7 | HD1 | 46.00 | 18.00 | 29.00 | 0.90 | 13.0 | 5 | 1 | 2D-NOESY |
| 104 | P7 | 7 | HD2 | H6 | 6 | HE1 | 34.00 | 13.00 | 23.00 | 0.90 | 18.0 | 4 | 0 | 2D-NOESY |
| 81 | H6 | 6 | HN | H6 | 6 | HD2 | 550.00 | 220.00 | 400.00 | 0.92 | 25.0 | 4 | 1 | 2D-NOESY |
| 672 | R2 | 2 | HG1 | V3 | 3 | HG21 | 0.00 | 29.00 | 27.00 | 0.92 | 13.0 | 2 | 5 | 2D-NOESY |
| 17 | 3J | 5 | HA | 3J | 5 | HB | 7.90 | 0.50 | 7.90 | 0.92 | 44.0 | 0 | 0 | JCOUP |
| 5 | 3J | 8 | HA | 3J | 8 | HN | 6.70 | 0.40 | 6.90 | 0.93 | 43.0 | 0 | 0 | JCOUP |
| 2 | 3J | 4 | HA | 3J | 4 | HN | 7.70 | 0.40 | 7.90 | 0.94 | 26.0 | 0 | 0 | J15DEGC |
| 102 | H6 | 6 | HN | H6 | 6 | HE1 | 40.00 | 16.00 | 25.00 | 0.95 | 18.0 | 4 | 1 | 2D-NOESY |
| 292 | Y4 | 4 | HE1 | I5 | 5 | HG11 | 17.00 | 6.80 | 22.00 | 0.95 | 26.0 | 5 | 1 | 2D-NOESY |
| 1117 | L10 | 10 | HA | H9 | 9 | HN | 0.00 | 6.50 | 6.00 | 0.98 | 19.0 | 1 | 0 | 2D-NOESY |
| 287 | I5 | 5 | HA | I5 | 5 | HG11 | 380.00 | 150.00 | 230.00 | 0.99 | 14.0 | 5 | 0 | 2D-NOESY |
| 1014 | L10 | 10 | HN | F8 | 8 | HE1 | 0.00 | 28.00 | 26.00 | 0.99 | 20.0 | 0 | 1 | 2D-NOESY |
| 2 | 3D | 2 | C | 3D | 3 | C | -100.00 | 34.00 | -130.00 | 1.00 | 16.0 | 0 | 0 | TDIHEDRALS |
| 367 | Y4 | 4 | HE1 | H6 | 6 | HB2 | 580.00 | 230.00 | 430.00 | 1.00 | 31.0 | 5 | 0 | 2D-NOESY |
| 4 | 3D | 4 | C | 3D | 5 | C | -100.00 | 24.00 | -120.00 | 1.00 | 16.0 | 0 | 0 | TDIHEDRALS |
| 305 | H6 | 6 | HN | I5 | 5 | HG12 | 230.00 | 91.00 | 130.00 | 1.00 | 16.0 | 5 | 0 | 2D-NOESY |
| 4 | V3 | 3 | HG21 | V3 | 3 | HN | 19.00 | 7.50 | 14.00 | 1.00 | 26.0 | 1 | 2 | 2D-NOESY |
| 826 | P7 | 7 | HD2 | I5 | 5 | HG12 | 0.00 | 11.00 | 11.00 | 1.00 | 19.0 | 5 | 0 | 2D-NOESY |
| 677 | P7 | 7 | HD1 | V3 | 3 | HG21 | 0.00 | 6.00 | 5.90 | 1.00 | 20.0 | 5 | 2 | 2D-NOESY |
| 9 | 3D | 2 | N | 3D | 3 | N | 140.00 | 36.00 | 100.00 | 1.00 | 19.0 | 0 | 0 | TDIHEDRALS |
| 32 | V3 | 3 | HG11 | Y4 | 4 | HD1 | 180.00 | 70.00 | 220.00 | 1.00 | 24.0 | 5 | 5 | 2D-NOESY |
| 961 | Y4 | 4 | HN | P7 | 7 | HD1 | 0.00 | 6.30 | 6.10 | 1.10 | 25.0 | 5 | 0 | 2D-NOESY |
| 32 | 3J | 5 | HG11 | 3J | 5 | HB | 5.80 | 1.00 | 6.70 | 1.10 | 33.0 | 0 | 0 | JCOUP |
| 907 | Y4 | 4 | HN | H6 | 6 | HE1 | 0.00 | 9.40 | 8.90 | 1.10 | 32.0 | 4 | 0 | 2D-NOESY |
| 128 | H9 | 9 | HN | F8 | 8 | HD1 | 280.00 | 110.00 | 330.00 | 1.10 | 55.0 | 0 | 1 | 2D-NOESY |
| 347 | I5 | 5 | HB | H6 | 6 | HA | 47.00 | 19.00 | 27.00 | 1.10 | 19.0 | 5 | 0 | 2D-NOESY |
| 845 | D1 | 1 | HA | I5 | 5 | HD1 | 0.00 | 10.00 | 9.90 | 1.10 | 24.0 | 5 | 2 | 2D-NOESY |
| 3 | V3 | 3 | HG11 | V3 | 3 | HN | 51.00 | 29.00 | 24.00 | 1.10 | 22.0 | 1 | 2 | 2D-NOESY |
| 546 | R2 | 2 | HB1 | D1 | 1 | HB2 | 0.00 | 20.00 | 20.00 | 1.10 | 19.0 | 3 | 1 | 2D-NOESY |
| 24 | 3J | 8 | HA | 3J | 8 | HN | 6.50 | 0.50 | 6.90 | 1.10 | 48.0 | 0 | 0 | JCOUP |
| 2 | 3J | 4 | HA | 3J | 4 | HN | 7.60 | 0.40 | 7.90 | 1.20 | 41.0 | 0 | 0 | J5DEGC |
| 153 | F8 | 8 | HB1 | H9 | 9 | HN | 70.00 | 28.00 | 41.00 | 1.20 | 29.0 | 1 | 1 | 2D-NOESY |
| 276 | Y4 | 4 | HE1 | I5 | 5 | HA | 170.00 | 67.00 | 96.00 | 1.20 | 25.0 | 5 | 1 | 2D-NOESY |
| 384 | I5 | 5 | HG21 | P7 | 7 | HA | 370.00 | 150.00 | 210.00 | 1.20 | 26.0 | 5 | 5 | 2D-NOESY |
| 333 | Y4 | 4 | HB1 | I5 | 5 | HD1 | 250.00 | 99.00 | 140.00 | 1.20 | 26.0 | 5 | 5 | 2D-NOESY |
| 281 | H6 | 6 | HD2 | I5 | 5 | HA | 390.00 | 150.00 | 240.00 | 1.20 | 34.0 | 5 | 0 | 2D-NOESY |
| 356 | H6 | 6 | HE1 | H6 | 6 | HB1 | 89.00 | 36.00 | 50.00 | 1.20 | 24.0 | 4 | 0 | 2D-NOESY |
| 136 | H6 | 6 | HN | F8 | 8 | HE1 | 180.00 | 77.00 | 100.00 | 1.20 | 25.0 | 0 | 3 | 2D-NOESY |
| 23 | 3J | 6 | HA | 3J | 6 | HB2 | 8.10 | 0.50 | 8.00 | 1.20 | 47.0 | 0 | 0 | J5DEGC |
| 103 | P7 | 7 | HD1 | H6 | 6 | HE1 | 20.00 | 8.00 | 24.00 | 1.20 | 61.0 | 4 | 0 | 2D-NOESY |
| 960 | Y4 | 4 | HA | P7 | 7 | HD1 | 0.00 | 11.00 | 12.00 | 1.20 | 22.0 | 5 | 0 | 2D-NOESY |
| 5 | 3J | 8 | HA | 3J | 8 | HN | 6.60 | 0.40 | 6.90 | 1.20 | 64.0 | 0 | 0 | J15DEGC |
| 471 | P7 | 7 | HB2 | F8 | 8 | HB1 | 250.00 | 100.00 | 140.00 | 1.20 | 19.0 | 5 | 1 | 2D-NOESY |
| 95 | H6 | 6 | HA | H6 | 6 | HE1 | 36.00 | 14.00 | 41.00 | 1.20 | 89.0 | 4 | 0 | 2D-NOESY |
| 195 | R2 | 2 | HA | R2 | 2 | HD1 | 290.00 | 120.00 | 360.00 | 1.30 | 58.0 | 4 | 1 | 2D-NOESY |

-continued

| | | | | | | | | | | | |
|---|---|---|---|---|---|---|---|---|---|---|---|
| 30 | V3 | 3 | HA | Y4 | 4 | HD1 | 770.00 | 310.00 | 430.00 | 1.30 | 25.0 | 5 | 3 | 2D-NOESY |
| 420 | Y4 | 4 | HE1 | P7 | 7 | HD1 | 320.00 | 130.00 | 400.00 | 1.30 | 70.0 | 5 | 1 | 2D-NOESY |
| 40 | P7 | 7 | HD1 | Y4 | 4 | HD1 | 170.00 | 69.00 | 97.00 | 1.30 | 30.0 | 5 | 1 | 2D-NOESY |
| 6 | 3J | 9 | HA | 3J | 9 | HN | 7.20 | 0.40 | 7.10 | 1.30 | 56.0 | 0 | 0 | J15DEGC |
| 130 | L10 | 10 | HA | F8 | 8 | HD1 | 150.00 | 61.00 | 84.00 | 1.30 | 26.0 | 0 | 1 | 2D-NOESY |
| 41 | P7 | 7 | HD2 | Y4 | 4 | HD1 | 160.00 | 66.00 | 110.00 | 1.30 | 31.0 | 5 | 1 | 2D-NOESY |
| 304 | Y4 | 4 | HE1 | I5 | 5 | HG12 | 39.00 | 16.00 | 22.00 | 1.30 | 31.0 | 5 | 1 | 2D-NOESY |
| 351 | P7 | 7 | HG1 | H6 | 6 | HA | 270.00 | 110.00 | 390.00 | 1.30 | 29.0 | 5 | 1 | 2D-NOESY |
| 850 | V3 | 3 | HN | I5 | 5 | HD1 | 0.00 | 44.00 | 49.00 | 1.30 | 31.0 | 3 | 2 | 2D-NOESY |
| 108 | F8 | 8 | HD1 | F8 | 8 | HN | 150.00 | 62.00 | 85.00 | 1.30 | 31.0 | 1 | 1 | 2D-NOESY |
| 218 | Y4 | 4 | HD1 | V3 | 3 | HG11 | 170.00 | 67.00 | 220.00 | 1.30 | 40.0 | 5 | 5 | 2D-NOESY |
| 460 | F8 | 8 | HD1 | F8 | 8 | HA | 1400.00 | 560.00 | 750.00 | 1.40 | 29.0 | 0 | 1 | 2D-NOESY |
| 43 | Y4 | 4 | HN | Y4 | 4 | HE1 | 260.00 | 110.00 | 150.00 | 1.40 | 36.0 | 5 | 1 | 2D-NOESY |
| 7 | 3J | 10 | HA | 3J | 10 | HN | 7.60 | 0.40 | 7.30 | 1.40 | 72.0 | 0 | 0 | JCOUP |
| 17 | 3J | 1 | HA | 3J | 1 | HB2 | 8.70 | 0.50 | 8.20 | 1.40 | 98.0 | 0 | 0 | J5DEGC |
| 54 | H6 | 6 | HA | Y4 | 4 | HE1 | 1300.00 | 510.00 | 700.00 | 1.40 | 46.0 | 5 | 1 | 2D-NOESY |
| 372 | I5 | 5 | HG12 | H6 | 6 | HB2 | 46.00 | 20.00 | 23.00 | 1.40 | 31.0 | 5 | 0 | 2D-NOESY |
| 350 | P7 | 7 | HB2 | H6 | 6 | HA | 110.00 | 42.00 | 55.00 | 1.40 | 30.0 | 5 | 0 | 2D-NOESY |
| 12 | 3D | 5 | N | 3D | 6 | N | 120.00 | 18.00 | 140.00 | 1.40 | 37.0 | 0 | 0 | TDIHEDRALS |
| 441 | Y4 | 4 | HD1 | P7 | 7 | HD2 | 99.00 | 39.00 | 110.00 | 1.40 | 180.0 | 5 | 1 | 2D-NOESY |
| 38 | H6 | 6 | HN | Y4 | 4 | HD1 | 250.00 | 100.00 | 150.00 | 1.40 | 45.0 | 5 | 1 | 2D-NOESY |
| 118 | H6 | 6 | HN | F8 | 8 | HD1 | 680.00 | 270.00 | 370.00 | 1.40 | 37.0 | 0 | 3 | 2D-NOESY |
| 841 | P7 | 7 | HB1 | I5 | 5 | HG21 | 0.00 | 22.00 | 25.00 | 1.40 | 31.0 | 5 | 2 | 2D-NOESY |
| 615 | V3 | 3 | HB | R2 | 2 | HG1 | 0.00 | 17.00 | 20.00 | 1.40 | 28.0 | 2 | 1 | 2D-NOESY |
| 56 | H6 | 6 | HB2 | Y4 | 4 | HE1 | 710.00 | 290.00 | 430.00 | 1.40 | 48.0 | 5 | 1 | 2D-NOESY |
| 912 | F8 | 8 | HE1 | H6 | 6 | HE1 | 0.00 | 23.00 | 19.00 | 1.50 | 160.0 | 0 | 1 | 2D-NOESY |
| 5 | 3J | 8 | HA | 3J | 8 | HN | 6.50 | 0.40 | 6.90 | 1.50 | 91.0 | 0 | 0 | J5DEGC |
| 418 | Y4 | 4 | HB1 | P7 | 7 | HD1 | 47.00 | 20.00 | 22.00 | 1.50 | 34.0 | 5 | 1 | 2D-NOESY |
| 294 | H6 | 6 | HA | I5 | 5 | HG11 | 11.00 | 6.90 | 19.00 | 1.50 | 41.0 | 5 | 0 | 2D-NOESY |
| 486 | L10 | 10 | HB1 | H9 | 9 | HB1 | 340.00 | 140.00 | 500.00 | 1.50 | 51.0 | 5 | 5 | 2D-NOESY |
| 1 | 3D | 1 | C | 3D | 2 | C | −85.00 | 26.00 | −110.00 | 1.50 | 93.0 | 0 | 0 | TDIHEDRALS |
| 318 | H6 | 6 | HN | I5 | 5 | HG21 | 730.00 | 290.00 | 380.00 | 1.50 | 34.0 | 5 | 2 | 2D-NOESY |
| 229 | I5 | 5 | HN | V3 | 3 | HG21 | 170.00 | 67.00 | 85.00 | 1.50 | 35.0 | 5 | 2 | 2D-NOESY |
| 495 | F8 | 8 | HD1 | L10 | 10 | HB1 | 32.00 | 13.00 | 45.00 | 1.50 | 73.0 | 0 | 5 | 2D-NOESY |
| 442 | Y4 | 4 | HE1 | P7 | 7 | HD2 | 250.00 | 100.00 | 350.00 | 1.50 | 72.0 | 5 | 1 | 2D-NOESY |
| 849 | V3 | 3 | HB | I5 | 5 | HD1 | 0.00 | 77.00 | 92.00 | 1.60 | 56.0 | 3 | 2 | 2D-NOESY |
| 470 | P7 | 7 | HB1 | F8 | 8 | HB1 | 210.00 | 86.00 | 110.00 | 1.60 | 37.0 | 5 | 1 | 2D-NOESY |
| 216 | Y4 | 4 | HN | V3 | 3 | HG11 | 580.00 | 230.00 | 300.00 | 1.60 | 38.0 | 5 | 2 | 2D-NOESY |
| 19 | 3J | 6 | HA | 3J | 6 | HB2 | 8.30 | 0.50 | 8.00 | 1.60 | 92.0 | 0 | 0 | JCOUP |
| 157 | H9 | 9 | HA | H9 | 9 | HD2 | 600.00 | 240.00 | 330.00 | 1.60 | 69.0 | 0 | 0 | 2D-NOESY |
| 326 | I5 | 5 | HN | I5 | 5 | HD1 | 780.00 | 320.00 | 390.00 | 1.60 | 38.0 | 5 | 2 | 2D-NOESY |
| 339 | H6 | 6 | HD2 | I5 | 5 | HD1 | 160.00 | 62.00 | 210.00 | 1.60 | 78.0 | 4 | 2 | 2D-NOESY |
| 31 | V3 | 3 | HB | Y4 | 4 | HD1 | 210.00 | 84.00 | 100.00 | 1.60 | 40.0 | 5 | 1 | 2D-NOESY |
| 25 | 3J | 10 | HA | 3J | 10 | HB1 | 21.00 | 1.50 | 19.00 | 1.60 | 43.0 | 0 | 2 | J5DEGC |
| 401 | H6 | 6 | HN | P7 | 7 | HB1 | 540.00 | 220.00 | 790.00 | 1.60 | 46.0 | 5 | 1 | 2D-NOESY |
| 359 | I5 | 5 | HG21 | H6 | 6 | HB1 | 320.00 | 130.00 | 160.00 | 1.60 | 40.0 | 5 | 5 | 2D-NOESY |
| 425 | I5 | 5 | HG21 | P7 | 7 | HD1 | 190.00 | 78.00 | 93.00 | 1.70 | 46.0 | 5 | 5 | 2D-NOESY |
| 808 | F8 | 8 | HE1 | I5 | 5 | HG11 | 0.00 | 6.50 | 8.10 | 1.70 | 54.0 | 0 | 1 | 2D-NOESY |
| 224 | Y4 | 4 | HN | V3 | 3 | HG21 | 840.00 | 340.00 | 420.00 | 1.70 | 55.0 | 5 | 2 | 2D-NOESY |
| 494 | L10 | 10 | HN | L10 | 10 | HB1 | 870.00 | 350.00 | 410.00 | 1.70 | 44.0 | 0 | 2 | 2D-NOESY |
| 472 | H9 | 9 | HN | F8 | 8 | HB1 | 790.00 | 320.00 | 410.00 | 1.70 | 54.0 | 5 | 1 | 2D-NOESY |
| 288 | Y4 | 4 | HN | I5 | 5 | HG11 | 26.00 | 10.00 | 13.00 | 1.70 | 50.0 | 5 | 0 | 2D-NOESY |
| 321 | H6 | 6 | HB2 | I5 | 5 | HG21 | 170.00 | 69.00 | 85.00 | 1.70 | 44.0 | 5 | 2 | 2D-NOESY |
| 51 | I5 | 5 | HA | Y4 | 4 | HE1 | 200.00 | 79.00 | 96.00 | 1.70 | 45.0 | 4 | 1 | 2D-NOESY |
| 391 | F8 | 8 | HE1 | P7 | 7 | HA | 89.00 | 36.00 | 130.00 | 1.70 | 71.0 | 0 | 1 | 2D-NOESY |
| 445 | I5 | 5 | HG12 | P7 | 7 | HD2 | 26.00 | 12.00 | 11.00 | 1.80 | 51.0 | 5 | 0 | 2D-NOESY |
| 14 | 3J | 1 | HA | 3J | 1 | HB1 | 5.30 | 0.50 | 4.70 | 1.80 | 72.0 | 0 | 0 | J5DEGC |
| 137 | I5 | 5 | HG21 | F8 | 8 | HE1 | 170.00 | 68.00 | 84.00 | 1.80 | 62.0 | 0 | 11 | 2D-NOESY |
| 105 | F8 | 8 | HA | H6 | 6 | HE1 | 33.00 | 13.00 | 18.00 | 1.80 | 78.0 | 0 | 1 | 2D-NOESY |
| 501 | F8 | 8 | HE1 | L10 | 10 | HD11 | 140.00 | 57.00 | 78.00 | 1.80 | 72.0 | 0 | 5 | 2D-NOESY |
| 6 | 3J | 9 | HA | 3J | 9 | HN | 7.40 | 0.40 | 7.10 | 1.80 | 130.0 | 0 | 0 | J5DEGC |
| 378 | P7 | 7 | HG1 | P7 | 7 | HA | 1100.00 | 450.00 | 520.00 | 1.80 | 48.0 | 5 | 1 | 2D-NOESY |
| 353 | P7 | 7 | HD2 | H6 | 6 | HA | 1600.00 | 650.00 | 700.00 | 1.80 | 44.0 | 5 | 0 | 2D-NOESY |
| 303 | Y4 | 4 | HD1 | I5 | 5 | HG12 | 93.00 | 37.00 | 44.00 | 1.80 | 48.0 | 5 | 1 | 2D-NOESY |
| 691 | R2 | 2 | HD1 | V3 | 3 | HN | 3.70 | 2.40 | 6.70 | 1.90 | 75.0 | 1 | 1 | 2D-NOESY |
| 400 | H6 | 6 | HA | P7 | 7 | HB1 | 180.00 | 72.00 | 76.00 | 1.90 | 51.0 | 5 | 0 | 2D-NOESY |
| 323 | P7 | 7 | HA | I5 | 5 | HG21 | 240.00 | 95.00 | 110.00 | 1.90 | 56.0 | 5 | 2 | 2D-NOESY |
| 314 | Y4 | 4 | HA | I5 | 5 | HG21 | 330.00 | 130.00 | 150.00 | 1.90 | 55.0 | 5 | 2 | 2D-NOESY |
| 368 | I5 | 5 | HN | H6 | 6 | HB2 | 130.00 | 76.00 | 28.00 | 1.90 | 53.0 | 4 | 1 | 2D-NOESY |
| 9 | 3J | 4 | HA | 3J | 4 | HN | 7.50 | 0.40 | 7.90 | 1.90 | 100.0 | 0 | 0 | J5DEGC |
| 9 | 3J | 4 | HA | 3J | 4 | HN | 7.50 | 0.40 | 7.90 | 2.00 | 110.0 | 0 | 0 | JCOUP |
| 255 | I5 | 5 | HN | Y4 | 4 | HB1 | 1500.00 | 590.00 | 650.00 | 2.00 | 57.0 | 5 | 1 | 2D-NOESY |
| 671 | R2 | 2 | HD1 | V3 | 3 | HG21 | 0.00 | 19.00 | 23.00 | 2.00 | 170.0 | 4 | 5 | 2D-NOESY |
| 361 | P7 | 7 | HG1 | H6 | 6 | HB1 | 160.00 | 66.00 | 73.00 | 2.00 | 67.0 | 5 | 1 | 2D-NOESY |
| 496 | F8 | 8 | HE1 | L10 | 10 | HB1 | 60.00 | 24.00 | 86.00 | 2.00 | 120.0 | 0 | 5 | 2D-NOESY |
| 191 | R2 | 2 | HA | R2 | 2 | HG1 | 340.00 | 140.00 | 510.00 | 2.00 | 110.0 | 4 | 1 | 2D-NOESY |
| 431 | H6 | 6 | HN | P7 | 7 | HD1 | 350.00 | 140.00 | 160.00 | 2.00 | 56.0 | 5 | 1 | 2D-NOESY |
| 262 | P7 | 7 | HD1 | Y4 | 4 | HB1 | 53.00 | 21.00 | 22.00 | 2.00 | 62.0 | 5 | 1 | 2D-NOESY |
| 175 | V3 | 3 | HG11 | D1 | 1 | HB1 | 77.00 | 31.00 | 37.00 | 2.00 | 70.0 | 5 | 2 | 2D-NOESY |

-continued

| | | | | | | | | | | | |
|---|---|---|---|---|---|---|---|---|---|---|---|
| 236 | V3 | 3 | HB | Y4 | 4 | HA | 110.00 | 44.00 | 45.00 | 2.00 | 56.0 | 5 | 0 | 2D-NOESY |
| 143 | L10 | 10 | HD11 | F8 | 8 | HE1 | 370.00 | 150.00 | 160.00 | 2.10 | 72.0 | 0 | 11 | 2D-NOESY |
| 12 | 3J | 4 | HA | 3J | 4 | HN | 7.40 | 0.40 | 7.90 | 2.10 | 120.0 | 0 | 0 | J5DEGC |
| 371 | I5 | 5 | HG11 | H6 | 6 | HB2 | 58.00 | 24.00 | 22.00 | 2.10 | 66.0 | 5 | 0 | 2D-NOESY |
| 209 | Y4 | 4 | HE1 | V3 | 3 | HA | 160.00 | 65.00 | 69.00 | 2.10 | 64.0 | 5 | 1 | 2D-NOESY |
| 452 | H6 | 6 | HN | P7 | 7 | HD2 | 380.00 | 150.00 | 160.00 | 2.10 | 65.0 | 5 | 1 | 2D-NOESY |
| 208 | Y4 | 4 | HD1 | V3 | 3 | HA | 660.00 | 260.00 | 270.00 | 2.20 | 74.0 | 5 | 1 | 2D-NOESY |
| 235 | V3 | 3 | HA | Y4 | 4 | HA | 520.00 | 210.00 | 210.00 | 2.20 | 71.0 | 5 | 1 | 2D-NOESY |
| 275 | Y4 | 4 | HD1 | I5 | 5 | HA | 390.00 | 160.00 | 160.00 | 2.20 | 73.0 | 5 | 1 | 2D-NOESY |
| 82 | H6 | 6 | HA | H6 | 6 | HD2 | 720.00 | 290.00 | 300.00 | 2.20 | 74.0 | 4 | 0 | 2D-NOESY |
| 306 | H6 | 6 | HA | I5 | 5 | HG12 | 47.00 | 19.00 | 19.00 | 2.20 | 74.0 | 5 | 0 | 2D-NOESY |
| 937 | L10 | 10 | HD21 | P7 | 7 | HB1 | 0.00 | 1.70 | 2.40 | 2.20 | 90.0 | 0 | 2 | 2D-NOESY |
| 320 | H6 | 6 | HB1 | I5 | 5 | HG21 | 170.00 | 70.00 | 71.00 | 2.20 | 77.0 | 5 | 2 | 2D-NOESY |
| 352 | P7 | 7 | HD1 | H6 | 6 | HA | 1700.00 | 720.00 | 660.00 | 2.20 | 70.0 | 5 | 0 | 2D-NOESY |
| 430 | H6 | 6 | HE1 | P7 | 7 | HD1 | 55.00 | 22.00 | 24.00 | 2.20 | 83.0 | 4 | 0 | 2D-NOESY |
| 315 | Y4 | 4 | HB1 | I5 | 5 | HG21 | 200.00 | 81.00 | 77.00 | 2.30 | 78.0 | 5 | 5 | 2D-NOESY |
| 132 | L10 | 10 | HD11 | F8 | 8 | HD1 | 200.00 | 79.00 | 80.00 | 2.30 | 82.0 | 0 | 11 | 2D-NOESY |
| 286 | I5 | 5 | HN | I5 | 5 | HG11 | 330.00 | 130.00 | 130.00 | 2.30 | 78.0 | 5 | 0 | 2D-NOESY |
| 193 | Y4 | 4 | HD1 | R2 | 2 | HG1 | 52.00 | 21.00 | 21.00 | 2.30 | 93.0 | 0 | 3 | 2D-NOESY |
| 387 | H6 | 6 | HD2 | P7 | 7 | HA | 78.00 | 31.00 | 30.00 | 2.40 | 89.0 | 4 | 0 | 2D-NOESY |
| 345 | Y4 | 4 | HD1 | H6 | 6 | HA | 120.00 | 48.00 | 170.00 | 2.40 | 220.0 | 5 | 1 | 2D-NOESY |
| 1011 | P7 | 7 | HB1 | F8 | 8 | HE1 | 0.00 | 31.00 | 47.00 | 2.40 | 97.0 | 0 | 1 | 2D-NOESY |
| 424 | I5 | 5 | HG12 | P7 | 7 | HD1 | 30.00 | 12.00 | 12.00 | 2.40 | 89.0 | 5 | 0 | 2D-NOESY |
| 194 | Y4 | 4 | HE1 | R2 | 2 | HG1 | 40.00 | 16.00 | 51.00 | 2.40 | 200.0 | 0 | 3 | 2D-NOESY |
| 398 | Y4 | 4 | HD1 | P7 | 7 | HB1 | 25.00 | 9.80 | 9.20 | 2.50 | 99.0 | 5 | 1 | 2D-NOESY |
| 383 | Y4 | 4 | HE1 | P7 | 7 | HA | 80.00 | 32.00 | 30.00 | 2.50 | 93.0 | 5 | 1 | 2D-NOESY |
| 337 | H6 | 6 | HA | I5 | 5 | HD1 | 230.00 | 91.00 | 83.00 | 2.50 | 88.0 | 5 | 2 | 2D-NOESY |
| 443 | I5 | 5 | HB | P7 | 7 | HD2 | 70.00 | 34.00 | 17.00 | 2.50 | 88.0 | 5 | 0 | 2D-NOESY |
| 444 | I5 | 5 | HG11 | P7 | 7 | HD2 | 32.00 | 14.00 | 11.00 | 2.50 | 90.0 | 5 | 0 | 2D-NOESY |
| 213 | V3 | 3 | HN | V3 | 3 | HG11 | 1400.00 | 540.00 | 500.00 | 2.50 | 92.0 | 5 | 2 | 2D-NOESY |
| 252 | V3 | 3 | HB | Y4 | 4 | HB1 | 180.00 | 73.00 | 67.00 | 2.50 | 89.0 | 5 | 1 | 2D-NOESY |
| 20 | 3J | 3 | HA | 3J | 3 | HB | 8.30 | 0.50 | 7.60 | 2.50 | 160.0 | 0 | 0 | J5DEGC |
| 1146 | F8 | 8 | HN | L10 | 10 | HB1 | 0.00 | 3.70 | 5.70 | 2.50 | 98.0 | 0 | 2 | 2D-NOESY |
| 477 | L10 | 10 | HB1 | H9 | 9 | HA | 550.00 | 220.00 | 200.00 | 2.50 | 88.0 | 5 | 2 | 2D-NOESY |
| 395 | P7 | 7 | HD1 | P7 | 7 | HB1 | 470.00 | 190.00 | 170.00 | 2.50 | 89.0 | 5 | 0 | 2D-NOESY |
| 396 | P7 | 7 | HD2 | P7 | 7 | HB1 | 400.00 | 160.00 | 140.00 | 2.50 | 91.0 | 5 | 0 | 2D-NOESY |
| 736 | P7 | 7 | HB1 | Y4 | 4 | HE1 | 0.00 | 23.00 | 34.00 | 2.50 | 120.0 | 5 | 1 | 2D-NOESY |
| 346 | Y4 | 4 | HE1 | H6 | 6 | HA | 500.00 | 200.00 | 700.00 | 2.60 | 250.0 | 5 | 1 | 2D-NOESY |
| 505 | F8 | 8 | HE1 | L10 | 10 | HD21 | 290.00 | 120.00 | 140.00 | 2.60 | 130.0 | 0 | 8 | 2D-NOESY |
| 183 | V3 | 3 | HG11 | R2 | 2 | HA | 500.00 | 200.00 | 180.00 | 2.60 | 100.0 | 5 | 2 | 2D-NOESY |
| 324 | P7 | 7 | HD1 | I5 | 5 | HG21 | 140.00 | 58.00 | 48.00 | 2.60 | 100.0 | 5 | 2 | 2D-NOESY |
| 936 | L10 | 10 | HD11 | P7 | 7 | HB1 | 0.00 | 1.70 | 2.50 | 2.60 | 130.0 | 0 | 2 | 2D-NOESY |
| 308 | I5 | 5 | HN | I5 | 5 | HG21 | 880.00 | 350.00 | 300.00 | 2.70 | 100.0 | 5 | 2 | 2D-NOESY |
| 341 | P7 | 7 | HD1 | I5 | 5 | HD1 | 130.00 | 53.00 | 45.00 | 2.70 | 100.0 | 5 | 2 | 2D-NOESY |
| 853 | P7 | 7 | HG1 | I5 | 5 | HD1 | 0.00 | 28.00 | 43.00 | 2.70 | 160.0 | 3 | 5 | 2D-NOESY |
| 375 | P7 | 7 | HG1 | H6 | 6 | HB2 | 170.00 | 67.00 | 59.00 | 2.70 | 110.0 | 5 | 1 | 2D-NOESY |
| 256 | I5 | 5 | HB | Y4 | 4 | HB1 | 170.00 | 68.00 | 59.00 | 2.70 | 100.0 | 5 | 1 | 2D-NOESY |
| 804 | P7 | 7 | HD1 | I5 | 5 | HG11 | 0.00 | 7.20 | 12.00 | 2.70 | 130.0 | 5 | 0 | 2D-NOESY |
| 805 | P7 | 7 | HD2 | I5 | 5 | HG11 | 0.00 | 6.70 | 11.00 | 2.70 | 120.0 | 5 | 0 | 2D-NOESY |
| 325 | P7 | 7 | HD2 | I5 | 5 | HG21 | 130.00 | 53.00 | 46.00 | 2.70 | 110.0 | 5 | 2 | 2D-NOESY |
| 886 | H9 | 9 | HE1 | H6 | 6 | HA | 0.00 | 4.10 | 5.40 | 2.70 | 300.0 | 0 | 0 | 2D-NOESY |
| 192 | V3 | 3 | HN | R2 | 2 | HG1 | 140.00 | 59.00 | 230.00 | 2.70 | 220.0 | 4 | 1 | 2D-NOESY |
| 342 | P7 | 7 | HD2 | I5 | 5 | HD1 | 140.00 | 58.00 | 47.00 | 2.80 | 120.0 | 5 | 2 | 2D-NOESY |
| 35 | I5 | 5 | HG11 | Y4 | 4 | HD1 | 150.00 | 59.00 | 49.00 | 2.80 | 110.0 | 5 | 1 | 2D-NOESY |
| 39 | H6 | 6 | HA | Y4 | 4 | HD1 | 510.00 | 210.00 | 170.00 | 2.80 | 120.0 | 5 | 1 | 2D-NOESY |
| 413 | P7 | 7 | HA | P7 | 7 | HD1 | 510.00 | 200.00 | 170.00 | 2.80 | 110.0 | 5 | 0 | 2D-NOESY |
| 215 | R2 | 2 | HA | V3 | 3 | HG11 | 550.00 | 220.00 | 180.00 | 2.80 | 120.0 | 5 | 2 | 2D-NOESY |
| 726 | P7 | 7 | HD2 | Y4 | 4 | HB1 | 0.00 | 15.00 | 24.00 | 2.80 | 180.0 | 5 | 1 | 2D-NOESY |
| 293 | H6 | 6 | HN | I5 | 5 | HG11 | 78.00 | 34.00 | 130.00 | 2.90 | 140.0 | 5 | 0 | 2D-NOESY |
| 456 | H9 | 9 | HE1 | P7 | 7 | HD2 | 16.00 | 6.40 | 7.30 | 2.90 | 160.0 | 0 | 0 | 2D-NOESY |
| 139 | P7 | 7 | HB2 | F8 | 8 | HE1 | 160.00 | 66.00 | 50.00 | 2.90 | 120.0 | 0 | 1 | 2D-NOESY |
| 178 | V3 | 3 | HG11 | D1 | 1 | HB2 | 96.00 | 39.00 | 32.00 | 2.90 | 130.0 | 5 | 2 | 2D-NOESY |
| 33 | 3J | 5 | HG12 | 3J | 5 | HB | 8.00 | 0.60 | 7.70 | 2.90 | 240.0 | 0 | 0 | JCOUP |
| 842 | P7 | 7 | HG1 | I5 | 5 | HG21 | 0.00 | 31.00 | 52.00 | 3.00 | 180.0 | 3 | 5 | 2D-NOESY |
| 261 | H6 | 6 | HA | Y4 | 4 | HB1 | 130.00 | 53.00 | 40.00 | 3.00 | 130.0 | 5 | 1 | 2D-NOESY |
| 965 | H9 | 9 | HE1 | P7 | 7 | HD1 | 11.00 | 4.40 | 5.50 | 3.00 | 170.0 | 0 | 0 | 2D-NOESY |
| 436 | P7 | 7 | HA | P7 | 7 | HD2 | 420.00 | 170.00 | 130.00 | 3.00 | 120.0 | 5 | 0 | 2D-NOESY |
| 437 | P7 | 7 | HB1 | P7 | 7 | HD2 | 480.00 | 190.00 | 140.00 | 3.00 | 130.0 | 5 | 0 | 2D-NOESY |
| 134 | F8 | 8 | HA | F8 | 8 | HE1 | 620.00 | 250.00 | 190.00 | 3.00 | 120.0 | 0 | 3 | 2D-NOESY |
| 249 | R2 | 2 | HG1 | Y4 | 4 | HB1 | 35.00 | 14.00 | 11.00 | 3.00 | 140.0 | 4 | 3 | 2D-NOESY |
| 233 | Y4 | 4 | HD1 | Y4 | 4 | HA | 2500.00 | 980.00 | 750.00 | 3.00 | 130.0 | 5 | 1 | 2D-NOESY |
| 414 | P7 | 7 | HB1 | P7 | 7 | HD1 | 590.00 | 240.00 | 170.00 | 3.10 | 140.0 | 5 | 0 | 2D-NOESY |
| 248 | Y4 | 4 | HE1 | Y4 | 4 | HB1 | 1500.00 | 580.00 | 420.00 | 3.10 | 140.0 | 4 | 3 | 2D-NOESY |
| 47 | R2 | 2 | HG1 | Y4 | 4 | HE1 | 170.00 | 67.00 | 51.00 | 3.10 | 160.0 | 0 | 3 | 2D-NOESY |
| 5 | R2 | 2 | HA | V3 | 3 | HN | 260.00 | 100.00 | 80.00 | 3.10 | 160.0 | 1 | 0 | 2D-NOESY |
| 6 | R2 | 2 | HB1 | V3 | 3 | HN | 50.00 | 20.00 | 16.00 | 3.10 | 150.0 | 1 | 1 | 2D-NOESY |
| 36 | I5 | 5 | HG12 | Y4 | 4 | HD1 | 150.00 | 60.00 | 44.00 | 3.10 | 140.0 | 5 | 1 | 2D-NOESY |
| 222 | V3 | 3 | HA | V3 | 3 | HG21 | 2300.00 | 940.00 | 710.00 | 3.10 | 130.0 | 5 | 2 | 2D-NOESY |
| 171 | D1 | 1 | HA | D1 | 1 | HA | 74000.00 | 30000.00 | 21000.00 | 3.10 | 140.0 | 5 | 0 | 2D-NOESY |

| | | | | | | | | | | | | |
|---|---|---|---|---|---|---|---|---|---|---|---|---|
| 115 | P7 | 7 | HD1 | F8 | 8 | HN | 76.00 | 30.00 | 23.00 | 3.10 | 130.0 | 1 | 0 | 2D-NOESY |
| 25 | Y4 | 4 | HN | Y4 | 4 | HD1 | 1700.00 | 670.00 | 500.00 | 3.20 | 150.0 | 5 | 1 | 2D-NOESY |
| 370 | I5 | 5 | HB | H6 | 6 | HB2 | 96.00 | 40.00 | 25.00 | 3.20 | 150.0 | 5 | 0 | 2D-NOESY |
| 250 | V3 | 3 | HN | Y4 | 4 | HB1 | 130.00 | 51.00 | 35.00 | 3.20 | 150.0 | 5 | 1 | 2D-NOESY |
| 214 | V3 | 3 | HA | V3 | 3 | HG11 | 2300.00 | 920.00 | 640.00 | 3.20 | 150.0 | 5 | 2 | 2D-NOESY |
| 502 | H9 | 9 | HA | L10 | 10 | HD11 | 150.00 | 61.00 | 240.00 | 3.30 | 270.0 | 0 | 2 | 2D-NOESY |
| 423 | I5 | 5 | HG11 | P7 | 7 | HD1 | 50.00 | 21.00 | 12.00 | 3.30 | 150.0 | 5 | 0 | 2D-NOESY |
| 489 | F8 | 8 | HE1 | L10 | 10 | HA | 160.00 | 66.00 | 260.00 | 3.30 | 380.0 | 0 | 2 | 2D-NOESY |
| 257 | I5 | 5 | HG11 | Y4 | 4 | HB1 | 130.00 | 51.00 | 35.00 | 3.30 | 150.0 | 5 | 1 | 2D-NOESY |
| 319 | H6 | 6 | HA | I5 | 5 | HG21 | 280.00 | 110.00 | 74.00 | 3.30 | 160.0 | 5 | 2 | 2D-NOESY |
| 881 | I5 | 5 | HG11 | H6 | 6 | HA | 0.00 | 10.00 | 19.00 | 3.30 | 170.0 | 3 | 0 | 2D-NOESY |
| 202 | V3 | 3 | HG21 | V3 | 3 | HA | 2800.00 | 1100.00 | 710.00 | 3.40 | 170.0 | 5 | 2 | 2D-NOESY |
| 19 | 3J | 2 | HA | 3J | 2 | HB2 | 6.80 | 0.50 | 5.90 | 3.40 | 180.0 | 0 | 0 | J5DEGC |
| 181 | V3 | 3 | HN | R2 | 2 | HA | 6200.00 | 2500.00 | 1600.00 | 3.40 | 170.0 | 5 | 0 | 2D-NOESY |
| 483 | F8 | 8 | HE1 | H9 | 9 | HB1 | 150.00 | 60.00 | 41.00 | 3.40 | 160.0 | 0 | 3 | 2D-NOESY |
| 127 | P7 | 7 | HG1 | F8 | 8 | HD1 | 250.00 | 100.00 | 67.00 | 3.40 | 160.0 | 0 | 3 | 2D-NOESY |
| 464 | H9 | 9 | HN | F8 | 8 | HA | 1000.00 | 420.00 | 1400.00 | 3.40 | 570.0 | 5 | 0 | 2D-NOESY |
| 241 | I5 | 5 | HG11 | Y4 | 4 | HA | 300.00 | 120.00 | 75.00 | 3.40 | 160.0 | 5 | 0 | 2D-NOESY |
| 242 | I5 | 5 | HG12 | Y4 | 4 | HA | 270.00 | 110.00 | 65.00 | 3.40 | 160.0 | 5 | 0 | 2D-NOESY |
| 174 | V3 | 3 | HN | D1 | 1 | HB1 | 81.00 | 32.00 | 22.00 | 3.40 | 160.0 | 5 | 0 | 2D-NOESY |
| 116 | P7 | 7 | HD2 | F8 | 8 | HN | 77.00 | 31.00 | 20.00 | 3.40 | 170.0 | 1 | 0 | 2D-NOESY |
| 260 | H6 | 6 | HN | Y4 | 4 | HB1 | 190.00 | 77.00 | 51.00 | 3.40 | 170.0 | 5 | 1 | 2D-NOESY |
| 451 | H6 | 6 | HE1 | P7 | 7 | HD2 | 88.00 | 35.00 | 23.00 | 3.50 | 170.0 | 4 | 0 | 2D-NOESY |
| 474 | L10 | 10 | HA | F8 | 8 | HB1 | 97.00 | 39.00 | 25.00 | 3.50 | 170.0 | 5 | 1 | 2D-NOESY |
| 282 | P7 | 7 | HD2 | I5 | 5 | HA | 140.00 | 57.00 | 36.00 | 3.50 | 180.0 | 5 | 0 | 2D-NOESY |
| 379 | P7 | 7 | HD1 | P7 | 7 | HA | 660.00 | 260.00 | 170.00 | 3.50 | 170.0 | 5 | 0 | 2D-NOESY |
| 380 | P7 | 7 | HD2 | P7 | 7 | HA | 530.00 | 210.00 | 130.00 | 3.50 | 180.0 | 5 | 0 | 2D-NOESY |
| 119 | F8 | 8 | HA | F8 | 8 | HD1 | 3100.00 | 1300.00 | 750.00 | 3.60 | 190.0 | 0 | 1 | 2D-NOESY |
| 199 | Y4 | 4 | HE1 | R2 | 2 | HD1 | 210.00 | 86.00 | 88.00 | 3.60 | 210.0 | 0 | 3 | 2D-NOESY |
| 201 | V3 | 3 | HG11 | V3 | 3 | HA | 2700.00 | 1100.00 | 640.00 | 3.60 | 190.0 | 5 | 2 | 2D-NOESY |
| 432 | F8 | 8 | HD1 | P7 | 7 | HD1 | 76.00 | 31.00 | 18.00 | 3.60 | 190.0 | 0 | 1 | 2D-NOESY |
| 240 | I5 | 5 | HB | Y4 | 4 | HA | 510.00 | 210.00 | 120.00 | 3.60 | 180.0 | 5 | 0 | 2D-NOESY |
| 186 | Y4 | 4 | HD1 | R2 | 2 | HA | 83.00 | 33.00 | 20.00 | 3.60 | 190.0 | 5 | 1 | 2D-NOESY |
| 187 | Y4 | 4 | HE1 | R2 | 2 | HA | 81.00 | 33.00 | 21.00 | 3.60 | 220.0 | 5 | 1 | 2D-NOESY |
| 234 | Y4 | 4 | HE1 | Y4 | 4 | HA | 630.00 | 250.00 | 150.00 | 3.60 | 190.0 | 5 | 1 | 2D-NOESY |
| 327 | I5 | 5 | HA | I5 | 5 | HD1 | 2900.00 | 1200.00 | 670.00 | 3.60 | 190.0 | 5 | 2 | 2D-NOESY |
| 490 | H9 | 9 | HA | L10 | 10 | HA | 420.00 | 170.00 | 96.00 | 3.70 | 190.0 | 5 | 0 | 2D-NOESY |
| 160 | F8 | 8 | HN | H9 | 9 | HD2 | 110.00 | 45.00 | 28.00 | 3.70 | 220.0 | 0 | 0 | 2D-NOESY |
| 142 | L10 | 10 | HB1 | F8 | 8 | HE1 | 400.00 | 160.00 | 86.00 | 3.70 | 190.0 | 0 | 5 | 2D-NOESY |
| 392 | H9 | 9 | HN | P7 | 7 | HA | 170.00 | 68.00 | 39.00 | 3.70 | 200.0 | 5 | 1 | 2D-NOESY |
| 504 | F8 | 8 | HD1 | L10 | 10 | HD21 | 140.00 | 57.00 | 220.00 | 3.70 | 550.0 | 0 | 8 | 2D-NOESY |
| 44 | Y4 | 4 | HA | Y4 | 4 | HE1 | 760.00 | 320.00 | 150.00 | 3.70 | 200.0 | 5 | 1 | 2D-NOESY |
| 131 | L10 | 10 | HB1 | F8 | 8 | HD1 | 200.00 | 81.00 | 45.00 | 3.80 | 200.0 | 0 | 5 | 2D-NOESY |
| 302 | Y4 | 4 | HB1 | I5 | 5 | HG12 | 150.00 | 59.00 | 30.00 | 3.80 | 210.0 | 5 | 1 | 2D-NOESY |
| 15 | 3J | 2 | HA | 3J | 2 | HB2 | 6.90 | 0.50 | 5.90 | 3.80 | 230.0 | 0 | 0 | JCOUP |
| 122 | I5 | 5 | HG21 | F8 | 8 | HD1 | 170.00 | 70.00 | 38.00 | 3.80 | 210.0 | 0 | 11 | 2D-NOESY |
| 258 | I5 | 5 | HG12 | Y4 | 4 | HB1 | 140.00 | 58.00 | 30.00 | 3.80 | 210.0 | 5 | 1 | 2D-NOESY |
| 433 | F8 | 8 | HE1 | P7 | 7 | HD1 | 34.00 | 14.00 | 7.90 | 3.80 | 210.0 | 0 | 1 | 2D-NOESY |
| 204 | R2 | 2 | HB1 | V3 | 3 | HA | 220.00 | 90.00 | 47.00 | 3.80 | 200.0 | 5 | 1 | 2D-NOESY |
| 449 | H6 | 6 | HB2 | P7 | 7 | HD2 | 680.00 | 270.00 | 140.00 | 3.90 | 220.0 | 5 | 0 | 2D-NOESY |
| 4 | 3J | 6 | HA | 3J | 6 | HN | 6.40 | 0.80 | 7.80 | 3.90 | 340.0 | 0 | 0 | J15DEGC |
| 479 | H9 | 9 | HN | H9 | 9 | HB1 | 2300.00 | 920.00 | 490.00 | 3.90 | 220.0 | 5 | 1 | 2D-NOESY |
| 18 | 3J | 2 | HA | 3J | 2 | HB1 | 6.80 | 0.50 | 5.90 | 3.90 | 250.0 | 0 | 0 | J5DEGC |
| 428 | H6 | 6 | HB2 | P7 | 7 | HD1 | 550.00 | 220.00 | 110.00 | 3.90 | 220.0 | 5 | 0 | 2D-NOESY |
| 268 | I5 | 5 | HG21 | I5 | 5 | HA | 5900.00 | 2400.00 | 1200.00 | 3.90 | 220.0 | 5 | 5 | 2D-NOESY |
| 369 | I5 | 5 | HA | H6 | 6 | HB2 | 490.00 | 200.00 | 100.00 | 3.90 | 210.0 | 5 | 0 | 2D-NOESY |
| 427 | H6 | 6 | HB1 | P7 | 7 | HD1 | 640.00 | 260.00 | 130.00 | 3.90 | 210.0 | 5 | 0 | 2D-NOESY |
| 279 | H6 | 6 | HB1 | I5 | 5 | HA | 430.00 | 170.00 | 84.00 | 4.00 | 230.0 | 5 | 0 | 2D-NOESY |
| 271 | V3 | 3 | HG21 | I5 | 5 | HA | 410.00 | 160.00 | 83.00 | 4.00 | 220.0 | 5 | 5 | 2D-NOESY |
| 882 | I5 | 5 | HG12 | H6 | 6 | HA | 0.00 | 9.70 | 19.00 | 4.00 | 260.0 | 3 | 0 | 2D-NOESY |
| 301 | Y4 | 4 | HA | I5 | 5 | HG12 | 320.00 | 130.00 | 65.00 | 4.00 | 220.0 | 5 | 0 | 2D-NOESY |
| 484 | L10 | 10 | HN | H9 | 9 | HB1 | 2400.00 | 980.00 | 460.00 | 4.00 | 230.0 | 5 | 1 | 2D-NOESY |
| 422 | I5 | 5 | HB | P7 | 7 | HD1 | 110.00 | 44.00 | 20.00 | 4.00 | 230.0 | 5 | 0 | 2D-NOESY |
| 198 | Y4 | 4 | HD1 | R2 | 2 | HD1 | 130.00 | 51.00 | 28.00 | 4.00 | 250.0 | 0 | 3 | 2D-NOESY |
| 448 | H6 | 6 | HB1 | P7 | 7 | HD2 | 830.00 | 330.00 | 170.00 | 4.00 | 230.0 | 5 | 0 | 2D-NOESY |
| 239 | I5 | 5 | HN | Y4 | 4 | HA | 6200.00 | 2500.00 | 1200.00 | 4.10 | 240.0 | 5 | 0 | 2D-NOESY |
| 280 | H6 | 6 | HB2 | I5 | 5 | HA | 570.00 | 230.00 | 100.00 | 4.10 | 240.0 | 5 | 0 | 2D-NOESY |
| 364 | H6 | 6 | HN | H6 | 6 | HB2 | 1400.00 | 580.00 | 240.00 | 4.10 | 240.0 | 5 | 0 | 2D-NOESY |
| 415 | P7 | 7 | HB2 | P7 | 7 | HD1 | 660.00 | 260.00 | 130.00 | 4.10 | 230.0 | 5 | 0 | 2D-NOESY |
| 459 | F8 | 8 | HA | F8 | 8 | HA | 20000.00 | 8200.00 | 3800.00 | 4.10 | 240.0 | 5 | 0 | 2D-NOESY |
| 266 | I5 | 5 | HG11 | I5 | 5 | HA | 1200.00 | 490.00 | 230.00 | 4.10 | 230.0 | 5 | 0 | 2D-NOESY |
| 358 | I5 | 5 | HA | H6 | 6 | HB1 | 460.00 | 180.00 | 84.00 | 4.20 | 240.0 | 5 | 0 | 2D-NOESY |
| 376 | P7 | 7 | HD1 | H6 | 6 | HB2 | 720.00 | 290.00 | 110.00 | 4.20 | 250.0 | 5 | 0 | 2D-NOESY |
| 4 | 3J | 6 | HA | 3J | 6 | HN | 6.40 | 0.80 | 7.80 | 4.20 | 390.0 | 0 | 0 | J5DEGC |
| 274 | Y4 | 4 | HB1 | I5 | 5 | HA | 450.00 | 180.00 | 81.00 | 4.20 | 250.0 | 5 | 1 | 2D-NOESY |
| 354 | H6 | 6 | HN | H6 | 6 | HB1 | 1200.00 | 480.00 | 220.00 | 4.20 | 240.0 | 5 | 0 | 2D-NOESY |
| 2 | V3 | 3 | HB | V3 | 3 | HN | 83.00 | 33.00 | 15.00 | 4.20 | 260.0 | 1 | 0 | 2D-NOESY |
| 807 | F8 | 8 | HD1 | I5 | 5 | HG11 | 0.00 | 2.00 | 4.00 | 4.20 | 280.0 | 0 | 1 | 2D-NOESY |
| 300 | Y4 | 4 | HN | I5 | 5 | HG12 | 62.00 | 25.00 | 11.00 | 4.20 | 240.0 | 5 | 0 | 2D-NOESY |

-continued

| | | | | | | | | | | | |
|---|---|---|---|---|---|---|---|---|---|---|---|
| 386 | H6 | 6 HA | P7 | 7 HA | 420.00 | 170.00 | 76.00 | 4.20 | 250.0 | 5 | 0 | 2D-NOESY |
| 14 | 3J | 2 HA | 3J | 2 HB1 | 6.90 | 0.50 | 5.90 | 4.30 | 310.0 | 0 | 0 | JCOUP |
| 309 | I5 | 5 HA | I5 | 5 HG21 | 3200.00 | 1300.00 | 520.00 | 4.30 | 260.0 | 5 | 2 | 2D-NOESY |
| 298 | I5 | 5 HA | I5 | 5 HG12 | 1300.00 | 530.00 | 220.00 | 4.30 | 260.0 | 5 | 0 | 2D-NOESY |
| 26 | Y4 | 4 HA | Y4 | 4 HD1 | 4300.00 | 1700.00 | 750.00 | 4.30 | 260.0 | 5 | 1 | 2D-NOESY |
| 389 | F8 | 8 HB1 | P7 | 7 HA | 810.00 | 320.00 | 140.00 | 4.30 | 260.0 | 5 | 1 | 2D-NOESY |
| 454 | F8 | 8 HE1 | P7 | 7 HD2 | 48.00 | 19.00 | 8.30 | 4.40 | 290.0 | 0 | 1 | 2D-NOESY |
| 210 | I5 | 5 HN | V3 | 3 HA | 300.00 | 120.00 | 42.00 | 4.40 | 270.0 | 5 | 0 | 2D-NOESY |
| 447 | H6 | 6 HA | P7 | 7 HD2 | 4400.00 | 1800.00 | 700.00 | 4.40 | 270.0 | 5 | 0 | 2D-NOESY |
| 267 | I5 | 5 HG12 | I5 | 5 HA | 1400.00 | 560.00 | 220.00 | 4.40 | 270.0 | 5 | 0 | 2D-NOESY |
| 374 | P7 | 7 HB2 | H6 | 6 HB2 | 83.00 | 35.00 | 10.00 | 4.40 | 270.0 | 5 | 0 | 2D-NOESY |
| 362 | P7 | 7 HD1 | H6 | 6 HB1 | 890.00 | 360.00 | 130.00 | 4.40 | 270.0 | 5 | 0 | 2D-NOESY |
| 251 | V3 | 3 HA | Y4 | 4 HB1 | 1000.00 | 420.00 | 160.00 | 4.50 | 280.0 | 5 | 1 | 2D-NOESY |
| 363 | P7 | 7 HD2 | H6 | 6 HB1 | 1200.00 | 480.00 | 170.00 | 4.50 | 280.0 | 5 | 0 | 2D-NOESY |
| 273 | Y4 | 4 HA | I5 | 5 HA | 730.00 | 290.00 | 110.00 | 4.50 | 280.0 | 5 | 0 | 2D-NOESY |
| 182 | V3 | 3 HB | R2 | 2 HA | 630.00 | 250.00 | 98.00 | 4.50 | 280.0 | 5 | 0 | 2D-NOESY |
| 377 | P7 | 7 HD2 | H6 | 6 HB2 | 1000.00 | 420.00 | 140.00 | 4.50 | 280.0 | 5 | 0 | 2D-NOESY |
| 438 | P7 | 7 HB2 | P7 | 7 HD2 | 740.00 | 300.00 | 110.00 | 4.50 | 280.0 | 5 | 0 | 2D-NOESY |
| 1051 | P7 | 7 HB1 | H9 | 9 HA | 0.00 | 7.60 | 16.00 | 4.50 | 300.0 | 5 | 0 | 2D-NOESY |
| 547 | R2 | 2 HG1 | D1 | 1 HB2 | 0.00 | 11.00 | 22.00 | 4.60 | 350.0 | 2 | 1 | 2D-NOESY |
| 245 | Y4 | 4 HB1 | Y4 | 4 HB1 | 39000.00 | 15000.00 | 5400.00 | 4.60 | 300.0 | 5 | 3 | 2D-NOESY |
| 453 | F8 | 8 HD1 | P7 | 7 HD2 | 120.00 | 48.00 | 17.00 | 4.60 | 300.0 | 0 | 1 | 2D-NOESY |
| 206 | Y4 | 4 HA | V3 | 3 HA | 660.00 | 270.00 | 93.00 | 4.60 | 300.0 | 5 | 0 | 2D-NOESY |
| 482 | F8 | 8 HN | H9 | 9 HB1 | 190.00 | 79.00 | 19.00 | 4.60 | 300.0 | 5 | 1 | 2D-NOESY |
| 278 | H6 | 6 HA | I5 | 5 HA | 560.00 | 220.00 | 75.00 | 4.60 | 300.0 | 5 | 0 | 2D-NOESY |
| 277 | H6 | 6 HN | I5 | 5 HA | 4500.00 | 1800.00 | 560.00 | 4.70 | 320.0 | 5 | 0 | 2D-NOESY |
| 469 | P7 | 7 HA | F8 | 8 HB1 | 1000.00 | 420.00 | 140.00 | 4.70 | 310.0 | 5 | 1 | 2D-NOESY |
| 107 | F8 | 8 HD1 | H6 | 6 HE1 | 65.00 | 26.00 | 9.20 | 4.70 | 330.0 | 0 | 1 | 2D-NOESY |
| 406 | H9 | 9 HE1 | P7 | 7 HB1 | 34.00 | 13.00 | 5.00 | 4.70 | 340.0 | 0 | 0 | 2D-NOESY |
| 297 | I5 | 5 HN | I5 | 5 HG12 | 900.00 | 360.00 | 120.00 | 4.70 | 310.0 | 5 | 0 | 2D-NOESY |
| 140 | P7 | 7 HG1 | F8 | 8 HE1 | 190.00 | 76.00 | 23.00 | 4.80 | 320.0 | 0 | 3 | 2D-NOESY |
| 426 | H6 | 6 HA | P7 | 7 HD1 | 5100.00 | 2000.00 | 660.00 | 4.80 | 320.0 | 5 | 0 | 2D-NOESY |
| 1013 | H9 | 9 HN | F8 | 8 HE1 | 0.00 | 43.00 | 91.00 | 4.80 | 490.0 | 0 | 1 | 2D-NOESY |
| 270 | V3 | 3 HB | I5 | 5 HA | 160.00 | 63.00 | 18.00 | 4.80 | 330.0 | 5 | 0 | 2D-NOESY |
| 176 | D1 | 1 HB2 | D1 | 1 HB2 | 28000.00 | 11000.00 | 3200.00 | 4.90 | 340.0 | 5 | 0 | 2D-NOESY |
| 475 | L10 | 10 HB1 | F8 | 8 HB1 | 220.00 | 88.00 | 21.00 | 4.90 | 340.0 | 5 | 5 | 2D-NOESY |
| 46 | R2 | 2 HB1 | Y4 | 4 HE1 | 380.00 | 150.00 | 45.00 | 4.90 | 340.0 | 5 | 3 | 2D-NOESY |
| 207 | Y4 | 4 HB1 | V3 | 3 HA | 1500.00 | 580.00 | 160.00 | 4.90 | 340.0 | 5 | 1 | 2D-NOESY |
| 394 | P7 | 7 HB1 | P7 | 7 HB1 | 9800.00 | 3900.00 | 1000.00 | 5.00 | 350.0 | 5 | 0 | 2D-NOESY |
| 173 | D1 | 1 HB1 | D1 | 1 HB1 | 29000.00 | 12000.00 | 3000.00 | 5.00 | 350.0 | 5 | 0 | 2D-NOESY |
| 197 | V3 | 3 HN | R2 | 2 HD1 | 110.00 | 46.00 | 170.00 | 5.00 | 1400.0 | 4 | 1 | 2D-NOESY |
| 246 | Y4 | 4 HN | Y4 | 4 HB1 | 3400.00 | 1400.00 | 350.00 | 5.00 | 360.0 | 5 | 1 | 2D-NOESY |
| 385 | H6 | 6 HN | P7 | 7 HA | 6100.00 | 2500.00 | 580.00 | 5.10 | 370.0 | 5 | 1 | 2D-NOESY |
| 111 | P7 | 7 HA | F8 | 8 HN | 1300.00 | 520.00 | 130.00 | 5.10 | 360.0 | 1 | 0 | 2D-NOESY |
| 809 | F8 | 8 HZ | I5 | 5 HG11 | 0.00 | 2.00 | 4.20 | 5.10 | 700.0 | 0 | 0 | 2D-NOESY |
| 412 | P7 | 7 HD1 | P7 | 7 HD1 | 8700.00 | 3500.00 | 770.00 | 5.20 | 380.0 | 5 | 0 | 2D-NOESY |
| 200 | V3 | 3 HA | V3 | 3 HA | 38000.00 | 15000.00 | 3000.00 | 5.20 | 380.0 | 5 | 0 | 2D-NOESY |
| 435 | P7 | 7 HD2 | P7 | 7 HD2 | 9200.00 | 3700.00 | 800.00 | 5.20 | 380.0 | 5 | 0 | 2D-NOESY |
| 507 | V3 | 3 HB | D1 | 1 HA | 0.00 | 23.00 | 51.00 | 5.20 | 470.0 | 5 | 0 | 2D-NOESY |
| 473 | L10 | 10 HN | F8 | 8 HB1 | 330.00 | 130.00 | 22.00 | 5.30 | 390.0 | 5 | 1 | 2D-NOESY |
| 465 | F8 | 8 HN | F8 | 8 HB1 | 4000.00 | 1600.00 | 290.00 | 5.40 | 400.0 | 5 | 1 | 2D-NOESY |
| 397 | Y4 | 4 HB1 | P7 | 7 HB1 | 40.00 | 16.00 | 2.80 | 5.40 | 410.0 | 5 | 1 | 2D-NOESY |
| 476 | L10 | 10 HN | H9 | 9 HA | 4200.00 | 1700.00 | 300.00 | 5.40 | 410.0 | 5 | 0 | 2D-NOESY |
| 263 | I5 | 5 HA | I5 | 5 HA | 33000.00 | 13000.00 | 1800.00 | 5.50 | 430.0 | 5 | 0 | 2D-NOESY |
| 612 | D1 | 1 HA | R2 | 2 HG1 | 0.00 | 70.00 | 160.00 | 5.50 | 580.0 | 2 | 1 | 2D-NOESY |
| 296 | I5 | 5 HG12 | I5 | 5 HG12 | 8900.00 | 3600.00 | 570.00 | 5.50 | 420.0 | 5 | 0 | 2D-NOESY |
| 33 | V3 | 3 HG21 | Y4 | 4 HD1 | 220.00 | 88.00 | 420.00 | 5.60 | 540.0 | 5 | 5 | 2D-NOESY |
| 205 | Y4 | 4 HN | V3 | 3 HA | 9200.00 | 3700.00 | 400.00 | 5.70 | 450.0 | 5 | 0 | 2D-NOESY |
| 404 | F8 | 8 HD1 | P7 | 7 HB1 | 85.00 | 34.00 | 160.00 | 5.80 | 1100.0 | 0 | 1 | 2D-NOESY |
| 4 | 3J | 6 HA | 3J | 6 HN | 6.00 | 0.80 | 7.80 | 5.90 | 690.0 | 0 | 0 | JCOUP |
| 11 | 3D | 4 N | 3D | 5 N | 120.00 | 14.00 | 150.00 | 6.00 | 550.0 | 0 | 0 | TDIHEDRALS |
| 524 | R2 | 2 HG1 | D1 | 1 HB1 | 0.00 | 8.70 | 23.00 | 6.90 | 770.0 | 2 | 1 | 2D-NOESY |
| 295 | H6 | 6 HD2 | I5 | 5 HG11 | 24.00 | 9.40 | 46.00 | 7.30 | 1300.0 | 4 | 0 | 2D-NOESY |
| 14 | 3D | 7 N | 3D | 8 N | 150.00 | 28.00 | 220.00 | 7.40 | 790.0 | 0 | 0 | TDIHEDRALS |
| 21 | 3J | 5 HA | 3J | 5 HB | 9.20 | 0.50 | 7.90 | 8.20 | 1300.0 | 0 | 0 | J5DEGC |
| 227 | Y4 | 4 HD1 | V3 | 3 HG21 | 200.00 | 79.00 | 420.00 | 8.50 | 1200.0 | 5 | 5 | 2D-NOESY |
| 499 | L10 | 10 HN | L10 | 10 HD11 | 140.00 | 57.00 | 310.00 | 9.00 | 1500.0 | 0 | 2 | 2D-NOESY |
| 500 | F8 | 8 HD1 | L10 | 10 HD11 | 98.00 | 39.00 | 220.00 | 13.00 | 4500.0 | 0 | 8 | 2D-NOESY |
| 164 | L10 | 10 HB1 | H9 | 9 HD2 | 87.00 | 35.00 | 190.00 | 13.00 | 4800.0 | 0 | 2 | 2D-NOESY |
| 506 | H9 | 9 HA | L10 | 10 HD21 | 87.00 | 38.00 | 240.00 | 21.00 | 9700.0 | 0 | 2 | 2D-NOESY |

EXAMPLE 4

Prediction of the Bioactive Conformation

The bioactive conformation for a ligand molecule is its protein-bound conformation and is highly sought-after for its usefulness in Computer-Aided Molecular Design processes (which are used throughout the Pharmaceutical industry in the development of new drugs). In particular, knowledge of the bioactive conformation is very important to lead optimisation and hit identification. Typically, proteins bind to a ligand molecule in a conformation very close to the global free energy minimum conformation in aqueous solution [45]. The mean dynamic 3D structure in aqueous solution that is determined using the methodology according to the present invention is equivalent to this global free energy minimum conformation. Therefore the mean dynamic 3D structure determined for a molecule using this methodology is an excellent predictor for the molecule's bioactive conformation, and the methodology is therefore of considerable usefulness to Computer-Aided Molecular Design processes. Shown in Table 3 below are several examples for different kinds of molecules where the mean dynamic 3D structure determined with this methodology has accurately predicted the bioactive conformation.

TABLE 3

RMSD values (for all heavy atoms) of the bioactive conformation compared to the mean dynamic 3D structure determined with the methodology according to the present invention.

| Molecule | PDB code for bioactive conformation | RMSD of mean dynamic 3D structure vs bioactive (Å) |
| --- | --- | --- |
| Hyaluronan | 2JCQ | 1.8 |
| Amikacin | 2G5Q | 1.1 |
| Streptomycin | 1NTB | 0.9 |
| Lisinopril | 1O86 | 0.7 |
| Enalaprilat | 1UZE | 0.6 |

A particular Computer-Aided Molecular Design technique that would clearly benefit from the near identity of the mean dynamic 3D structure in aqueous solution to the bioactive conformation is Ligand-Based Drug Design.

EXAMPLE 5

Improved Rationality in Medicinal Chemistry

Comparison of the dynamic 3D structures of lisinopril and AngiotensinI obtained using the methods of the present invention revealed areas where lisinopril does not optimally mimic the natural ligand's or bioactive conformation's shape and electrostatic properties.

Using this previously unobtainable information allowed the selection of appropriate modifications to the chemical structure of lisinopril to be realised that would remove flexibilities that were perceived to be disadvantageous to binding energies. In the absence of this 3D-dynamic information, the rationale for such modifications would not have been apparent even to an expert in the field.

One of these suggested modifications (inclusion of a bridging group) anticipated structural features of the next-generation ACE-inhibitor benazeprilat (see FIG. 32) which were independently arrived at via the traditional time-consuming processes of interative rounds of screening, SAR analysis and medicinal chemistry. It is clear from this result that dynamic 3D structures produced according to the present invention can be used to greatly aid lead optimisation decisions by medicinal chemists.

REFERENCES

1 Leach, A. (2001) In Molecular Modelling: Principles and Applications. Second Edition. pp. 2-3, Pearson Education EMA
2 Andreev, Y. G., Lightfoot, P. and Bruce, P. G. (1997) A general Monte Carlo approach to structure solution from powder-diffraction data. Journal of Applied Crystallography. 30, 294-305
3 Allinger, N. L. (1977) Conformational analysis. 130. MM2-hydrocarbon force-field utilizing v1 and v2 torisional terms. Journal of the American Chemical Society. 99, 8127-8134
4 Mandl, F. (1998) In Statistical physics. Second edition. pp. 31-67, Wiley
5 Raeside, D. E. (1976) Monte-Carlo principles and applications. Physics in Medicine and Biology. 21, 181-197
6 Farrow, N. A., Muhandiram, R., Singer, A. U., Pascal, S. M., Kay, C. M., Gish, G., Shoelson, S. E., Pawson, T., Formankay, J. D. and Kay, L. E. (1994) Backbone dynamics of a free and a phosphopeptide-complexed SRC homology-2 domain studied by $^{15}$N-NMR relaxation. Biochemistry. 33, 5984-6003
7 Almond, A., Bunkenborg, J., Franch, T., Gotfredsen, C. H. and Duus, J. O. (2001) Comparison of aqueous molecular dynamics with NMR relaxation and residual dipolar couplings favors internal motion in a mannose oligosaccharide. Journal of the American Chemical Society. 123, 4792-4802
8 Almond, A., DeAngelis, P. L. and Blundell, C. D. (2005) Dynamics of hyaluronan oligosaccharides revealed by 15N relaxation. Journal of the American Chemical Society. 127, 1086-1087
9 Mackeen, M., Almond, A., Cumpstey, I., Enis, S. C., Kupce, E., Butters, T. D., Fairbanks, A. J., Dwek, R. A. and Wormald, M. R. (2006) The importance of including local correlation times in the calculation of inter-proton distances from NMR measurements: ignoring local correlation times leads to significant errors in the conformational analysis of the Glc alpha 1-2Glc alpha linkage by NMR spectroscopy. Organic and Biomolecular Chemistry. 4, 2241-2246
10 Noggle, J. H. and Schirmer, R. E. (1971) The nuclear Overhauser effect: chemical applications. Academic Press, New York
11 Lipari, G. and Sazbo, A. (1982) Model-free approach to the interpretation of nuclear magnetic resonance relaxation in macromolecules. 1. Theory and range of validity. Journal of the American Chemical Society. 104, 4546-4559
12 Günter, H. (1994) In NMR spectroscopy: basic principles, concepts and applications in chemistry. Second edition. pp. 115-117, John Wiley & sons, New York
13 Prestegard, J. H., Al-Hashimi, H. M. and Tolman, J. R. (2000) NMR structures of biomolecules using field oriented media and residual dipolar couplings. Quarterly Reviews of Biophysics. 33, 371-424
14 Sykes, P. (1986) In A guidebook to mechanism in organic chemistry. pp. 4-5, Wiley, New York
15 Sykes, P. (1986) In A guidebook to mechanism in organic chemistry. p. 7, Wiley, New York
16 Campbell, I. D. and Sheard, B. (1987) Protein-structure determination by NMR. Trends in Biotechnology. 5, 302-306
17 Friebolin, H. (1991) In Basic one- and two-dimensional NMR spectroscopy. pp. 139-154, VCH, Weinheim.
18 Friebolin, H. (1991) In Basic one- and two-dimensional NMR spectroscopy. pp. 181-287, VCH, Weinheim.
19 Friebolin, H. (1991) In Basic one- and two-dimensional NMR spectroscopy. pp. 231-287, VCH, Weinheim.
20 Friebolin, H. (1991) In Basic one- and two-dimensional NMR spectroscopy. pp. 289-303, VCH, Weinheim.
21 Liu, M. L., Mao, X. A., Ye, C. H., Huang, H., Nicholson, J. K. and Lindon, J. C. (1998) Improved WATERGATE pulse sequences for solvent suppression in NMR spectroscopy. Journal of Magnetic Resonance. 132, 125-129

22 Griesinger, C., Sorensen, O. W. and Ernst, R. R. (1987) Practical aspects of the E-COSY technique—measurement of scalar spin-spin coupling-constants in peptides. Journal of Magnetic Resonance. 75, 474-492

23 Kuboniwa, H., Grzesiek, S., Delaglio, F. and Bax, A. (1994) Measurement of HNHα J-couplings in calcium-free calmodulin using new 2D and 3D water-flip-back methods. Journal of Biomolecular NMR. 4, 871-878

24 Almond, A., DeAngelis, P. L. and Blundell, C. D. (2006) Hyaluronan: The local solution conformation determined by NMR and computer modeling is close to a contracted left-handed 4-fold helix. Journal of Molecular Biology. 358, 1256-1269

25 Friebolin, H. (1991) In Basic one- and two-dimensional NMR spectroscopy. pp. 161-178, VCH, Weinheim.

26 Poveda, A., Asensio, J. L., MartinPastor, M. and JimenezBarbero, J. (1997) Solution conformation and dynamics of a tetrasaccharide related to the Lewis(X) antigen deduced by H-1 NMR NOESY, ROESY, and T-ROESY measurements. Carbohydrate Research. 300, 3-10

27 Friebolin, H. (1991) In Basic one- and two-dimensional NMR spectroscopy. pp. 111-127, VCH, Weinheim.

28 Lemieux, R. U., Fraser, R. R. and Stevens, J. D. (1962) Observations on Karplus curve in relation to conformation of 1,3-dioxolane ring. Canadian Journal of Chemistry-Revue Canadienne De Chimie. 40, 1955

29 Haasnoot, C. A. G., Deleeuw, F. A. A. M. and Altona, C. (1980) The Relationship between Proton-Proton NMR Coupling-Constants and Substituent Electronegativities 0.1. An Empirical Generalization of the Karplus Equation. Tetrahedron. 36, 2783-2792

30 Deprez-Poulain, R. and Deprez, B. (2004) Facts, figures and trends in lead generation. Current Topics in Medicinal Chemistry. 4, 569-580

31 Banerji, S., Wright, A. J., Noble, M., Mahoney, D. J., Campbell, I. D., Day, A. J. and Jackson, D. G. (2007) Structures of the CD44-hyaluronan complex provide insight into a fundamental carbohydrate-protein interaction. Nature Structural & Molecular Biology. 14, 234-239

32 Alonso, H., Andrey, A. A. and Bliznyuk, J. E. (2006) Docking and molecular dynamics simulations in drug design. Medical Research Reviews. 26, 531-568

33 Blundell, C. D. and Almond, A. (2006) Enzymatic and chemical methods for the generation of pure hyaluronan oligosaccharides with both odd and even numbers of monosaccharide units. Analytical Biochemistry. 353, 236-247

34 Blundell, C. D., DeAngelis, P. L., Day, A. J. and Almond, A. (2004) Use of N-15-NMR to resolve molecular details in isotopically-enriched carbohydrates: sequence-specific observations in hyaluronan oligomers up to decasaccharides. Glycobiology. 14, 999-1009

35 Blundell, C. D., Reed, M. A. C. and Almond, A. (2006) Complete assignment of hyaluronan oligosaccharides up to hexasaccharides. Carbohydrate Research. 341, 2803-2815

36 Blundell, C. D., DeAngelis, P. L. and Almond, A. (2006) Hyaluronan: the absence of amide-carboxylate hydrogen bonds and the chain conformation in aqueous solution are incompatible with stable secondary and tertiary structure models. Biochemical Journal. 396, 487-498

37 Mobli, M. and Almond, A. (2007) N-Acetylated amino sugars: the dependence of NMR $^3J_{HNH2}$-couplings on conformation, dynamics and solvent. Organic and Biomolecular Chemistry. 5, 2243-2251

38 Johnson, L. N. (1966) The crystal structure of N-acetyl-alpha-D-glucosamine. Acta Crystallographica. 21, 885-891

39 Perez, C., Lohr, F., Ruterjans, H. and Schmidt, J. M. (2001) Self-consistent Karplus parametrization of (3)J couplings depending on the polypeptide side-chain torsion chi(1). Journal of the American Chemical Society. 123, 7081-7093

40 Schubert, M., Labudde, D., Oschkinat, H. and Schmieder, P. (2002) A software tool for the prediction of Xaa-Pro peptide bond conformations in proteins based on C-13 chemical shift statistics. Journal of Biomolecular NMR. 24, 149-154

41 Natesh, R., Schwager, S. L. U., Sturrock, E. D. and Acharya, K. R. (2003) Crystal structure of the human angiotensin-converting enzyme-lisinopril complex. Nature. 421, 551-554

42 Cornilescu, G., Delaglio, F. and Bax, A. (1999) Protein backbone angle restraints from searching a database for chemical shift and sequence homology. Journal of Biomolecular NMR, 13: 289-302, 1999

43 Blundell, C. D. and Almond, A. (2007) Temperature dependencies of amide $^1$H- and $^{15}$N-chemical shifts in hyaluronan oligosaccharides. Magnetic Resonance in Chemistry 45: 430-433

44 Cierpicki, T. and Otlewski, J. (2001) Amide proton temperature coefficients as hydrogen bond indicators in proteins. Journal of Biomolecular NMR 21(3):249-61

45 Bostrom, J., Norrby, P. & Liljefors, T. (1998) Conformational energy penalties of protein-bounds ligands. Journal of Computer-Aided Molecular Design, 12: 383-396

46 Mobli, M., Nilsson, M., Almond, A. (2008) The structural plasticity of heparan sulphate NA-domains and hence their role in mediating multivalent interactions is confirmed by high-accuracy $^{15}$N-NMR relaxation studies. Glycoconjugate Journal 25: 401-414

The invention claimed is:

1. A method for generating an ensemble of discrete molecular structures representing a range of three-dimensional shapes of a solvated molecule, the molecule comprising a plurality of bonds each having an associated mean dihedral angle, wherein at least one bond is a rotatable bond having an associated distribution of dihedral angles, the method comprising:

receiving a set of internal coordinates of the molecule, said internal coordinates comprising a predefined mean dihedral angle for each bond; then assigning a probability distribution function to each bond, the probability distribution function comprising a predefined variability of the dihedral angle for said bond with respect to said predefined mean dihedral angle, the probability distribution function independent of experimental data for the solvated molecule; and then generating an ensemble of structures by implementing the set of internal coordinates and the assigned probability distribution functions by varying said dihedral angle for each bond according to said predefined dihedral angle variability; and then analyzing the ensemble of structures as a group, wherein all of the preceding steps are performed on a computer, and wherein the predefined variability of the dihedral angle for a rotatable bond is non-zero and corresponds to the associated distribution of dihedral angles.

2. The method according to claim 1, wherein the predefined variability of the dihedral angle is zero when a bond links first and second atoms and:
  the first and second atoms are linked via a double covalent bond, a triple covalent bond or when the first and second atoms are incorporated into an aromatic ring structure; or
  one of the first and second atoms is a hydrogen atom or a halogen atom; or
  first and second atoms are incorporated into a three or four-membered ring structure.

3. The method according to claim 1, wherein the predefined variability of the dihedral angle is non-zero and exhibits a unimodal variability of bond angles when a bond links first and second atoms via a single covalent bond and:
  a. one of the first and second atoms is linked to a third atom via a double or triple covalent bond; or
  b. the first and second atoms are oxygen atoms.

4. The method according to claim 1, wherein the predefined variability of the dihedral angle is non-zero and exhibits a bimodal variability of bond angles when a bond links first and second atoms and:
  the first and second atoms are incorporated into a five or six-membered saturated alicyclic ring structure; or
  a. the first and second atoms are linked via a single covalent bond and one of the first and second atoms is $sp^3$-hybridised and the other of the first and second atoms is $sp^2$-hybridised; or
  b. the first and second atoms are linked via a single covalent bond and said single covalent bond is conjugated to at least one further double covalent bond in the molecule.

5. The method according to claim 1, wherein said data indicating variability of said bond comprises data indicating that the variability of the bond is non-zero and exhibits a trimodal variability of bond angles when the first and second atoms are linked via a single covalent bond and:
  a. both of the first and second atoms are tetravalent and $sp^3$-hybridised; or
  b. one of the first and second atoms are $sp^3$-hybridised and the other of the first and second atoms is an oxygen atom.

6. The method according to claim 1, wherein the method further comprises predicting at least one experimental parameter from said generated ensemble of three-dimensional structures of said molecule.

7. The method according to claim 6, wherein the method further comprises a comparison of said at least one predicted experimental parameter to at least one further parameter derived from at least one physical experiment.

8. The method according to claim 7, wherein the method further comprises:
  determining an agreement function based on said comparison;
  generating further data representing a further ensemble of three-dimensional structures of said molecule;
  predicting at least one further experimental parameter from said further generated ensemble of three-dimensional structures of said molecule;
  comparing said at least one further predicted experimental parameter to said at least one parameter derived from at least one physical experiment;
  determining a further agreement function based on said comparison of the at least one further experimental parameter to said at least one parameter derived from at least one physical experiment; and
  generating data indicating the ensemble having the best agreement function.

9. The method according to claim 1, wherein the method further comprises predicting at least two experimental parameters from said generated ensemble of three-dimensional structures of said molecule.

10. The method according to claim 9, wherein the method further comprises a comparison of said at least two predicted experimental parameters to at least two further parameters derived from at least two physical experiments.

11. The method according to claim 10, wherein said at least two physical experiments provide data indicative of the three-dimensional structures of said molecule sampled over different time periods or over different ranges of movement of said molecule.

12. The method according to claim 1, wherein said molecule is selected from the group consisting of an organic molecule, a peptide, a carbohydrate, an antibiotic, a nucleic acid, a lipid, a metabolite, drug molecule, a protein, hyaluronan, lisinospril and AngiotensinI.

13. A method for generating data representing an optimised ensemble of three-dimensional structures of a molecule selected from a plurality of ensembles of three-dimensional structures of said molecule, wherein each ensemble is generated according to the method according to claim 1.

14. A method for predicting NMR data using an ensemble of three-dimensional structures of a molecule generated using the method according to claim 1.

15. A method for simulating a conformation of a molecule, such as a ligand molecule when bound to its intended target by generating an ensemble of three-dimensional structures of said molecule using the method according to claim 1.

16. Use of an ensemble of three-dimensional structures of a molecule, such as a ligand molecule generated according to the method set out in claim 1 to simulate a conformation of said molecule when bound to its intended target.

17. A method for simulating a bioactive conformation of a molecule selected from the group consisting of a peptide molecule, a carbohydrate molecule and a drug molecule by generating an ensemble of three-dimensional structures of said molecule using the method according to claim 1.

18. The method according to claim 1, wherein an ensemble of three-dimensional structures of a molecule selected from the group consisting of a peptide molecule, a carbohydrate molecule and a drug molecule is generated to simulate a bioactive conformation of said molecule.

19. A method for simulating the hydrogen bond occupancy in a molecule by generating an ensemble of three-dimensional structures of said peptide molecule using the method according to claim 1.

20. Use of an ensemble of three-dimensional structures of a molecule generated according to a method set out in claim 1 to simulate the hydrogen bond occupancy of said molecule.

21. A non-transitory computer readable medium comprising executable instructions configured to cause a computer to carry out the method according to claim 1.

22. A method for simulating the variability of the three-dimensional structure of a molecule, the molecule comprising a plurality of bonds each having an associated mean dihedral angle, wherein at least one bond is a rotatable bond having an associated distribution of dihedral angles, the method comprising:

receiving a set of internal coordinates of the molecule, said internal coordinates comprising a predefined mean dihedral angle for each bond; then assigning a probability distribution function to each bond, the probability distribution function comprising a predefined variability of the dihedral angle for said bond with respect to said predefined mean dihedral angle, the probability distribution function independent of experimental data for the solvated molecule; then simulating the variability of the three-dimensional structure of the molecule by implementing the set of internal coordinates and the assigned probability distribution functions by varying said dihedral angle for each bond according to said predefined dihedral angle variability; and then generating an ensemble of structures based upon said simulating; and then analyzing the ensemble of structures as a group, wherein all of the preceding steps are performed on a computer, and wherein the predefined variability of the dihedral angle for a rotatable bond is non-zero.

23. A non-transitory computer readable medium comprising executable instructions usable to generate an ensemble of three-dimensional structures of a molecule and to analyze the ensemble of three-dimensional structures of the molecule as a group, the molecule comprising a plurality of bonds, wherein at least one bond is a rotatable bond having an associated distribution of dihedral angles, the medium comprising a set of internal coordinates of the molecule, said internal coordinates comprising a predefined mean dihedral angle for each bond, and a probability distribution function for each bond, said probability distribution function comprising a predefined variability of the dihedral angle for said bond with respect to said predefined mean dihedral angle, wherein the predefined variability of the dihedral angle for a rotatable bond is non-zero and corresponds to the associated distribution of dihedral angles and wherein the probability distribution function independent of experimental data for the solvated molecule.

* * * * *